(12) United States Patent
Coghlan et al.

(10) Patent No.: US 7,411,072 B2
(45) Date of Patent: Aug. 12, 2008

(54) TRICYCLIC STEROID HORMONE NUCLEAR RECEPTOR MODULATORS

(75) Inventors: Michael Joseph Coghlan, Fishers, IN (US); Jonathan Edward Green, Avon, IN (US); Timothy Alan Grese, Indianapolis, IN (US); Prabhakar Kondaji Jadhav, Zionsville, IN (US); Donald Paul Matthews, Indianapolis, IN (US); Mitchell Irvin Steinberg, Indianapolis, IN (US); Kevin Robert Fales, Avon, IN (US); Michael Gregory Bell, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 521 days.

(21) Appl. No.: 10/517,010

(22) PCT Filed: Jun. 13, 2003

(86) PCT No.: PCT/US03/16213

§ 371 (c)(1),
(2), (4) Date: Dec. 3, 2004

(87) PCT Pub. No.: WO2004/052847

PCT Pub. Date: Jun. 24, 2004

(65) Prior Publication Data

US 2006/0063759 A1    Mar. 23, 2006

Related U.S. Application Data

(60) Provisional application No. 60/391,992, filed on Jun. 26, 2002.

(51) Int. Cl.
*A01N 43/52* (2006.01)
*C07D 235/04* (2006.01)
(52) U.S. Cl. .................................. 548/305.1; 514/395
(58) Field of Classification Search ................ None
See application file for complete search history.

(56) References Cited

U.S. PATENT DOCUMENTS

| | | | |
|---|---|---|---|
| 3,205,264 A | 9/1965 | Tristram et al. |
| 3,351,588 A | 11/1967 | Davis et al. |
| 3,519,621 A | 7/1970 | Humber et al. |
| 3,859,356 A | 1/1975 | Houlihan et al. |
| 4,282,233 A | 8/1981 | Vilani |
| 4,963,450 A | 10/1990 | Miyazaki et al. |
| 4,999,363 A | 3/1991 | Oshima et al. |
| 5,024,912 A | 6/1991 | Neishi et al. |
| 5,093,210 A | 3/1992 | Ohta et al. |
| 5,151,545 A | 9/1992 | McCarthy et al. |
| 5,378,701 A | 1/1995 | Ohshima et al. |
| 5,726,325 A | 3/1998 | Yoshida et al. |
| 6,289,190 B1 | 9/2001 | Amamiya et al. |
| 6,362,188 B1 | 3/2002 | Guzi et al. |
| 2007/0037788 A1* | 2/2007 | Gavardinas et al. ..... 514/210.21 |

FOREIGN PATENT DOCUMENTS

| | | |
|---|---|---|
| EP | 0 549 352 | 3/2000 |
| GB | 1 001 822 | 8/1965 |
| GB | 1 043 158 | 9/1966 |
| GB | 1 242 096 | 8/1971 |
| GB | 1 501 321 | 2/1978 |
| JP | 01161245 | 6/1989 |
| JP | 02032358 | 2/1990 |
| JP | 02113258 | 4/1990 |
| JP | 04046352 | 2/1992 |
| JP | 05002278 | 1/1993 |
| JP | 05281765 | 10/1993 |
| JP | 09101200 | 4/1997 |
| JP | 2001089680 | 4/2001 |
| WO | WO 97/11071 | 3/1997 |
| WO | WO 99/33786 | 7/1999 |
| WO | WO 00/06137 | 2/2000 |
| WO | WO 00/59884 | 10/2000 |
| WO | WO 01/95892 | 12/2001 |
| WO | WO 02/09759 | 2/2002 |
| WO | WO 02/17895 | 3/2002 |
| WO | WO 02/096893 | 12/2002 |

OTHER PUBLICATIONS

Treibs et al., caplus an 1951:8622.*
Werner, et al., "Imidazoline derivatives with antiarrhytmic activity," Journal of Medicinal Chemistry, vol. 10, No. 4, pp. 575-582; XP002283810 (1967).

(Continued)

*Primary Examiner*—Kamal Saeed
*Assistant Examiner*—Sun Jae Y Loewe
(74) *Attorney, Agent, or Firm*—Alexander Wilson

(57) ABSTRACT

The present invention relates to methods of treating pathological disorders susceptible to steroid hormone nuclear receptor modulation comprising administering to a patient in need thereof an effective amount of a compound of the formula:

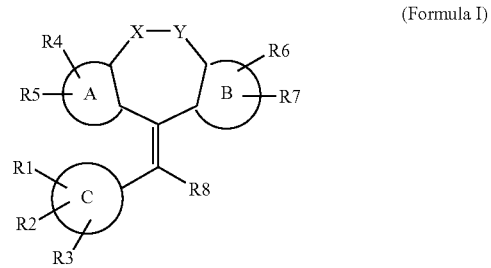

(Formula I)

or a pharmaceutically acceptable salt thereof. In addition, the present invention provides novel pharmaceutical compounds of Formula I, including the pharmaceutically acceptable salts thereof, as well as pharmaceutical compositions which comprise as an active ingredient a compound of Formula I.

7 Claims, No Drawings

OTHER PUBLICATIONS

Gadient, et al., "Uber neuartige tricyclische Thiazepin- und Thiepin-Derivate," Helvetica Chimica ACTA, vol. 45, No. 6, pp. 1860-1870; XP002283811 (1962).

Villani, et al, "Derivatives of 12, 11-dihydro-5H-dibenzo'a,d!cycloheptene and related compounds. II" Journal of Medicinal Chemistry, vol. 7, No. 4, pp. 457-460; XP002283812 (1964).

Bille-Same, et al., "Fulvenes et ethylenes thermochromes. LXXII. (1) Observations dans la serie du dibenzo'a,d!cyclohepta'1,4!diene," Bulletin De La Societe Chimique De France, No. 11, pp. 4212-4214; XP002283813 (1972).

Cordi, et al., "Synthesis and structure-activity of 4(5)-(2-2-diphenylethyl)imidazoles as new alpha2-adrenoreceptor agonists," European Journal of Medicinal Chemistry, vol. 25, No. 7, pp. 557-568; XP002283814 (1990).

Cheng, et al., "Synthesis and structure-activity relationships of 9-substituted acridines as endothelin-A receptor antagonists," Biorganic & MedicinalChemistry Letters, vol. 6, No. 24, pp. 2999-3002; XP002283815 (1996).

Bastian, et al., "4H-Benzo '4,5!cyclohepta'1,2-b!thiophene," Helvetica Chimica ACTA, vol. 49, pp. 214-234; XP002263672 (1966).

Daich, et al., "On the synthesis and reactivity of 4,10-dihydrobenzo'b!thieno-'2,3-e!thiepin-10-acetic acid and 5,10-dihydrobenzo e!thieno'2,3-b!thiepin-10-acetic acid," Journal of Heterocyclic Chemistry, vol. 29, No. 7, pp. 1789-1795; XP002283816 (1992).

Polman, et al., "Photoaddition of aromatic ketones to some arylacetylenes; formation of alpha,beta-unsaturated ketones and aldehyde," Recueil Des Travaux Chimiques Des Pays-Bas, vol. 92, pp. 845-854; XP008031504 (1973).

Wittig, et al., "Uber Ringerweiterung und Ringverengerung auf der Basis von Ylidisomerisationen," Justus Liebigs Annalen Der Chemie, vol. 594, pp. 89-118; XP008031512 (1955).

Davis, et al., "New psychotropic agents. VIII. Analogues of amitriptyline containing the normeperidine group," Journal of Medicinal Chemistry, vol. 10, No. 4, pp. 627-635; XP002284192 (1967).

R. G. Micetich, "Lithiation of five-membered heteroaromatic compounds. The methyl substitued 1,2-azoles, oxadiazoles, and thiadiazoles," Canadian Journal of Chemistry, vol. 48, No. 13, pp. 2006-2015 (1970).

Bergmann, et al., "Fulvenes and Thermochromic Ethylenes. Part 57. The Wittig-Horner Reaction with Fulvene Ketones and Related Ketones," Synthesis, vol. 2, No. 4, pp. 183-189 (1970).

Fox, et al., "Synthetic Antigonadotropines. II," J. Med. Chem, vol. 7, No. 6, pp. 790-792 (1964).

Boris, et al., "Antigonadotrophic Activity of Some Substituted Triphenylethlene Derivatives," Arch. Intern. Pharmacodyn, vol. 151, No. 3-4, pp. 475-489 (1964).

Bergmann, et al., "Fulvenes and Thermochromic Ethylenes. XXXIII. Polycyclic Derivataives of Heptafulvene," J. Org. Chem, vol. 28, No. 12, pp. 3341-3343 (1963).

Rabinovitz, J. Chem. Soc., Perkin Transactions 2: Physical Organic Chemistry, vol. 12, pp. 1836-1838 (1972).

* cited by examiner

TRICYCLIC STEROID HORMONE NUCLEAR RECEPTOR MODULATORS

This is the national phase application, under 35 USC 371, for PCT/US2003/016213, filed 13 Jun. 2003, which claims the benefit, under 35 USC 119(e), of US provisional application 60/391,992, filed 26 Jun. 2002.

BACKGROUND OF THE INVENTION

Nuclear hormone receptors are an evolutionarily conserved class of intracellular receptor proteins which have been termed "ligand dependent transcription factors". Evans et al., SCIENCE, 240: 889 (1988). The nuclear hormone receptor gene superfamily encodes structurally-related receptor proteins for glucocorticoids (e.g. cortisol, corticosterone, cortisone), androgens, mineralocorticoids (e.g. aldosterone), progestins, estrogen, and thyroid hormone. Also included within this superfamily of nuclear receptors are receptor proteins for vitamin D, retinoic acid, 9-cis retinoic acid, as well as those receptors for which no cognate ligands have been identified ("orphan receptors") Ribeiro et al., Annual Rev. Med., 46:443-453 (1995). Steroid hormone receptors represent a subset of the nuclear hormone receptor superfamily. So named according to the cognate ligand which complexes with the receptor in its native state, the steroid hormone nuclear receptors include the glucocorticoid receptor (GR), the androgen receptor (AR), the mineralocorticoid receptor (MR), the estrogen receptor (ER), and the progesterone receptor (PR). Tenbaum et al., Int. J. Biochem. Cell. Bio., 29(12):1325-1341(1997).

In contrast to membrane bound receptors, nuclear hormone receptors encounter their respective ligands following entry of the ligand into the cell. Once ligand binding occurs, the ligand-receptor complex modulates transcription of target genes within the cell nucleus. For example, most ligand-free nuclear receptors are bound in a complex with heat shock proteins (hsps) in the cytoplasm. Following entry of circulating hormone into the cell, binding elicits a conformational change in the receptor, dissociating the receptor from the hsp. The ligand bound receptors translocate to the nucleus, where they act as monomers as well as hetero-and homodimers in binding to particular hormone response elements (HREs) in the promoter regions of target genes. The HRE-receptor complex then, in turn, regulates transcription of proximally-located genes. (see Ribeiro et al., supra). On the other hand, thyroid hormone receptors (TRs) and other non-steroid receptors such as vitamin D receptor (VDR) and retinoic acid receptors (RAR) are bound to their respective HRE in the absence of hsps and/or cognate ligand. Hormones released from the circulation enter the cell, binding in the nucleus to these receptors which, in turn, hetero-dimerize to other nuclear receptors such as 9-cis retinoic acid (RXR). As with the steroid hormone nuclear receptors, following ligand binding, the ligand-bound receptor complex again regulates transcription of neighboring genes.

Mineralocorticoids and glucocorticoids exert profound influences on a multitude of physiological functions by virtue of their diverse roles in growth, development, and maintenance of homeostasis. The actions are mediated by the MR and GR which share approximately 94% homology in their respective DNA binding regions, and approximately 57% homology in their respective ligand-binding domains. Kino et al., J. of Endocrinology, 169, 437-445 (2001). In visceral tissues, such as the kidney and the gut, MR regulates sodium retention, potassium excretion, and water balance in response to aldosterone. In addition, MR expression in the brain appears to play a role in the control of neuronal excitability, in the negative feedback regulation of the hypothalamic-pituitary-adrenal axis, and in the cognitive aspects of behavioral performance. Castren et al., J. of Neuroendocrinology, 3, 461-466;(1993). GR, which is ubiquitously expressed in almost all tissues and organ systems, is crucial for the integrity of central nervous system function and the maintenance of cardiovascular, metabolic, and immune homeostasis. Kino et al., J. of Endocrinology, 169, 437-445 (2001).

Elevations in aldosterone levels, or excess stimulation of mineralocorticoid receptors, are linked to several pathological disorders or pathologic disease states including, Conn's Syndrome, primary and secondary hyperaldosteronism, increased sodium retention, increased magnesium and potassium excretion (diuresis), increased water retention, hypertension (isolated systolic and combined systolic/diastolic), arrhythmias, myocardial fibrosis, myocardial infarction, Bartter's Syndrome, and disorders associated with excess catecholamine levels. Hadley, M. E., ENDOCRINOLOGY, $2^{nd}$ Ed., pp. 366-381, (1988); and Brilla et al., Journal of Molecular and Cellular Cardiology, 25 (5), pp.563-575 (1993). Additionally, elevated aldosterone levels have been increasingly implicated with congestive heart failure (CHF). In CHF, the failing heart triggers hormonal mechanisms in other organs in response to the attending reductions in blood flow and blood pressure seen with CHF. In particular, the kidney activates the renin-angiotensin-aldosterone system (RAAS) causing an increase in aldosterone production by the adrenals which, in turn, promotes water and sodium retention, potassium loss, and further edema Although historically it was believed that aldosterone participated in the etiology of CHF only as a result of its salt retaining effects, several recent studies have implicated elevated aldosterone levels with events in extra-adrenal tissues and organs, such as myocardial and vascular fibrosis, direct vascular damage, and baroreceptor dysfunction. Pitt et al., New Eng. J. Med., 341:709-717 (1999). These findings are particularly significant since angiotensin converting enzyme (ACE) inhibitors, which were once thought to completely abolish aldosterone production, are now believed to only transiently suppress aldosterone production which has been shown to occur in extra-adrenal tissues including the heart and vasculature. Weber, New Eng. J. Med., 341:753-755 (1999); Fardella and Miller, Annu. Rev. Nutr., 16:443-470 (1996).

The involvement of aldosterone acting via MR in CHF was confirmed in the recently completed RALES (Randomized Aldactone Evaluation Study) study. Pitt et al., New Eng. J. Med., 341:709-717 (1999). The RALES study demonstrated that the use of Aldactone™ (spironolactone), a well-known competitive MR antagonist, in combination with standard CHF therapy, reduced cardiac related mortality by 30% and frequency of hospitalization by 35% in patients suffering from advanced CHF. However, spironolactone therapy has also been associated with attending side effects such as gastric bleeding, diarrhea, azotemia, hyperchloremic metabolic acidosis an type-4 renal tubule acidosis, nausea, gynecomastia, erectile dysfunction, hyperkalemia, and irregular menses. Thus, the mineralocorticoid receptor represents a viable target for CHF therapy either alone or in combination with conventional CHF therapies such as vasodilators (ACE inhibitors), inotropics (digoxin), diuretics, or beta blockers. Molecules, preferably non-steroids, which bind to the mineralocorticoid receptor and modulate receptor activity without the attending side effects of current therapies would be particularly desirable.

Finally, published international PCT application WO 02/17895 discloses that aldosterone antagonists are useful in the treatment of subjects suffering from one or more cognitive dysfunctions including, but not limited to psychoses, cognitive disorders (such as memory disturbances), mood disorders (such as depression and bipolar disorder), anxiety disorders, and personality disorders. In particular, Smythe et al., *Pharm. Biochem and Behav.*, (1997); 56(3); 507-513 and Young et al, *Arch. Gen. Psychiatry*, (2003); 60; 24-28, respectively, report that mineralocorticoid receptors, and modulation of MR activity, are involved in anxiety and major depression. In addition, Sasano et al., *Anticancer Research*, 17; 2001-2007 (1997) reports that expression of MR may be related to differentiation of breast carcinomas. Thus MR modulators may also have utility in treating cancer, particularly of the breast.

Glucocorticoids (e.g. cortisol, corticosterone, and cortisone), and the glucocorticoid receptor, have also been implicated in the etiology of a variety of pathological disorders or pathologic disease states. For example, cortisol hyposecretion is implicated in the pathogenesis of Addison's Disease and may result in muscle weakness, increased melanin pigmentation of the skin, weight loss, hypotension, and hypoglycemia. On the other hand, excessive or prolonged secretion of glucocorticoids has been correlated to Cushing's Syndrome and may also result in obesity, hypertension, glucose intolerance, hyperglycemia, diabetes mellitus, osteoporosis, polyuria, and polydipsia Hadley, M. E., ENDOCRINOLOGY, $2^{nd}$ Ed., pp. 366-381, (1988). Further, Coghlan et al., U.S. Pat. No. 6,166,013, issued Dec. 26, 2000, discloses that GR selective agents could modulate GR activity and, thus, be useful in the treatment of inflammation, tissue rejection, auto-immunity, malignancies such as leukemias and lymphomas, Cushing's syndrome, acute adrenal insufficiency, congenital adrenal hyperplasia, rheumatic fever, polyarteritis nodosa, granulomatous polyarteritis, inhibition of myeloid cell lines, immune proliferation/apoptosis, HPA axis suppression and regulation, hypercortisolemia, modulation of the Th1/Th2 cytokine balance, chronic kidney disease, stroke and spinal cord injury, hypercalcemia, hypergylcemia, acute adrenal insufficiency, chronic primary adrenal insufficiency, secondary adrenal insufficiency, congenital adrenal hyperplasia, cerebral edema, thrombocytopenia, and Little's syndrome. Coghlan et al. also discloses that GR modulators are especially useful in disease states involving systemic inflammation such as inflammatory bowel disease, systemic lupus erythematosus, polyartitis nodosa, Wegener's granulomatosis, giant cell arthritis, rheumatoid arthritis, osteoarthritis, hay fever, allergic rhinitis, urticaria, angioneurotic edema, chronic obstructive pulmonary disease, asthma, tendonitis, bursitis, Crohn's disease, ulcerative colitis, autoimmune chronic active hepatitis, organ transplantation, hepatitis, and cirrhosis; and that GR modulating compounds have been used as immunostimulants, repressors, and as wound healing and tissue repair agents.

In addition, Coghlan et al. discloses that GR modulators have also found use in a variety of topical diseases such as inflammatory scalp alopecia, panniculitis, psoriasis, discoid lupus erythematosus, inflamed cysts, atopic dermatitis, pyoderma gangrenosum, pemphigus vulgaris, bullous pemphigoid, systemic lupus erythematosus, dermatomyositis, eosinophilic fasciitis, relapsing polychondritis, inflammatory vasculitis, sarcoidosis, Sweet's disease, type 1 reactive leprosy, capillary hemangiomas, contact dermatitis, atopic dermatitis, lichen planus, exfoliative dermatitis, erythema nodosum, acne, hirsutism, toxic epidermal necrolysis, erythema multiform, and cutaneous T-cell lymphoma.

Finally, GR Modulators may also have utility in treating respiratory disorders, such as emphysema, and neuroinflammatory disorders, such as multiple sclerosis and Alzheimer's Disease.

Thus, it is clear that a ligand which has affinity for steroid hormone nuclear receptors, and particularly for MR and/or GR, could be used to modulate (i.e. repress, antagonize, agonize, partially antagonize, partially agonize) receptor activity and target gene expression, thereby influencing a multitude of physiological functions related to alterations in steroid hormone levels and/or steroid hormone receptor activity. In this regard, such ligands could be useful to treat a wide range of pathological disorders susceptible to steroid hormone nuclear receptor modulation.

Several art references disclose tricyclic derivative molecules useful as, inter alia, photographic coupling and developing agents, thromboxane A2 modulators, and as histamine H2 antagonists. Further, tricyclic-derivative compounds have also been disclosed as having pharmacological utility as, inter alia, antidepressants and anti-inflammatory agents. Surprisingly, however, and in accordance with the present invention, applicants have discovered a series of tricyclic compounds, particularly dibenzosuberane, dibenzoxapine, dibenzazapine, and dibenzthiepine derivatives, with affinity for steroid hormone nuclear receptors, and particularly for MR and GR. Such compounds could modulate receptor activity and, thus, have utility in treating pathological disorders related to alterations in steroid hormone level and/or to alterations in steroid hormone nuclear receptor activity. As a further embodiment, the present invention also provides a novel series of novel non-steroidal tricyclic compounds that exhibit steroid hormone nuclear receptor affinity and modulating activity. Such methods and compounds could address a long felt and continuing need for safe and effective pharmaceutical interventions without the attending side effects of steroidal-type agents. The treatment of steroid hormone related disorders is hereby furthered.

The following references describe examples of the state of the art as it relates to the present invention.

U.S. Pat. No. 4,282,233 discloses tricyclic molecules (i.e. Loratadine (Claritin™) as H2 antagonists.

U.S. Pat. No. 4,999,363 (and family members) discloses tricyclic molecules as thromboxane A2 antagonists.

U.S. Pat. Nos. 5,378,701 and 5,478,840 and 5,607,955 disclose tricyclic molecules as angiotensin II antagonists.

U.S. Pat. No. 6,362,188 B1 discloses tricyclic molecules as farnesyl protein transferase inhibitors.

Published International PCT Application WO 99/33786 discloses tricyclic propanamide derivative molecules as anti-inflammatory agents.

Published International PCT Application WO 96/19458 and U.S. Pat. Nos. 5,696,130; 5,994,544; 6,017,924, and 6,121,450 disclose quinoline derivative analogs as steroid hormone receptor modulators.

Published International PCT Application WO 00/06137 and U.S. Pat. No. 6,166,013 disclose triphenylmethane compounds as glucocorticoid receptor modulators.

U.S. Pat. No. 6,147,066 discloses anti-mineralocorticoid receptor compounds for use in treating drug withdrawal syndrome.

U.S. Pat. Nos. 6,008,210 and 6,093,708 disclose spirolactone compounds, such as spironolactone and epoxymexrenone, with affinity for the mineralocorticoid receptor for use in the treatment of myocardial fibrosis.

U.S. Pat. No. 5,024,912 discloses 5H Dibenzo (A,D) cycloheptenylidene and 5H Dibenzo (A,D) cycloheptanylidene derivatives as electrophotographic photosensitive agents.

U.S. Pat. Nos. 4,741,976, 4,539,507, 5,093,210, and 5,166,022 disclose the use of tricyclic molecules in electroluminescent devices.

SUMMARY OF THE INVENTION

The present invention is directed to the discovery that the tricyclic compounds of the present invention, as defined below, are modulators of steroid hormone nuclear receptors. Accordingly, the present invention provides a method of treating a pathological disorder susceptible to steroid hormone nuclear receptor modulation comprising administering to a patient in need thereof an effective amount of a compound of the formula:

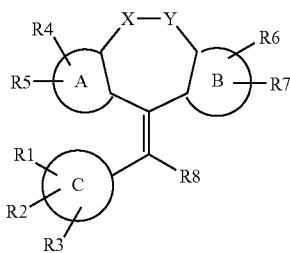

Formula I wherein,

A, B, and C each independently represent an aryl, heterocycle, or benzofused-heterocyclic ring;

X and Y together represent —$CH_2$—$CH_2$—, —CH=CH—, —$CH_2$—O—, —O—$CH_2$—, —O—$CH_2$—, —$CH_2$—S—, —S—$CH_2$—, —$CH_2$—SO—, —SO—$CH_2$—, —$CH_2$—$SO_2$—, —$SO_2$—$CH_2$—, —$CH_2$—$NR^{10}$—, —$NR^{10}$—$CH_2$—, —$NR^{10}$—CO—, —CO—$NR^{10}$—, or a group of the formula

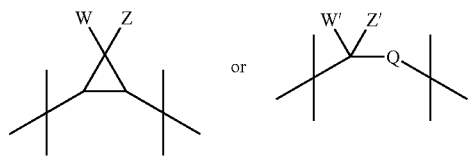

wherein W and Z each independently represent hydrogen, fluoro, or chloro; W' and Z' each independently represent hydrogen, fluoro, chloro, or methyl; and Q represents NH, O, S, or $CH_2$;

"$\text{---}$" represents a single or double bond;

$R^1$ represents hydrogen, halo, hydroxy, cyano, nitro, amino, oxo, ($C_1$-$C_6$)alkyl, ($C_1$-$C_6$)alkoxy, hydroxy($C_1$-$C_6$)alkyl, hydroxy($C_1$-$C_6$)alkoxy, ($C_2$-$C_6$)alkenyl, ($C_2$-$C_6$)alkynyl, $CH_2NH_2$, halo($C_1$-$C_6$)alkyl, halo($C_1$-$C_6$)alkoxy, C($CF_3$)$_2$OH, $SO_2NH_2$, $SO_2NR^9R^{10}$, $SO_2R^{11}$, $NHSO_2R^{11}$, $N(CH_3)SO_2CH_3$, $NR^9R^{10}$, $CH_2NH(OH)$, $CH_2NH(SO_2R^{11})$, $NHCOR^{12}$, $COR^{12}$, $CHNR^{13}$, $OR^{14}$, $SR^{14}$, ($C_3$-$C_7$)cycloalkyl, aryl, substituted aryl, ($C_1$-$C_4$)alkyl-aryl, ($C_1$-$C_4$)alkyl-substituted aryl, heterocycle, substituted heterocycle, ($C_1$-$C_4$)alkyl-heterocycle, or ($C_1$-$C_4$)alkyl-substituted heterocycle;

provided that where "C" represents an aryl group, $R^1$ is other than oxo, ($C_2$-$C_6$)alkenyl, or ($C_2$-$C_6$)alkynyl;

$R^2$ through $R^8$ each independently represent hydrogen, halo, hydroxy, cyano, nitro, amino, ($C_1$-$C_6$)alkyl, ($C_1$-$C_6$)alkoxy, hydroxy($C_1$-$C_6$)alkyl, hydroxy($C_1$-$C_6$)alkoxy, ($C_2$-$C_6$)alkenyl, ($C_2$-$C_6$)alkynyl, $CH_2NH_2$, halo($C_1$-$C_6$)alkyl, halo($C_1$-$C_6$)alkoxy, C($CF_3$)$_2$OH, $SO_2NH_2$, $SO_2NR^9R^{10}$, $SO_2R^{11}$, $NHSO_2R^{11}$, $NR^9R^{10}$, $CH_2NH(OH)$, $CH_2NH(SO_2R^{11})$, $NHCOR^{12}$, $COR^{12}$, $CHNR^{13}$, $OR^{14}$, $SR^{14}$, ($C_3$-$C_7$)cycloalkyl, aryl, substituted aryl, ($C_1$-$C_4$)alkyl-($C_1$-$C_6$)alkoxy, ($C_1$-$C_4$)alkyl-aryl, ($C_1$-$C_4$)alkyl-substituted aryl, heterocycle, substituted heterocycle, ($C_1$-$C_4$)alkyl-heterocycle, or ($C_1$-$C_4$)alkyl-substituted heterocycle;

provided that where "A", "B", or "C" represents an aryl group, each of $R^2$ through $R^7$ is other than ($C_2$-$C_6$)alkenyl or ($C_2$-$C_6$)alkynyl;

$R^9$ represents independently at each occurrence cyano, ($C_1$-$C_6$)alkyl, ($C_1$-$C_6$)alkoxy, ($C_1$-$C_4$)alkyl-($C_1$-$C_6$)alkoxy, halo($C_1$-$C_6$)alkyl, hydroxy($C_1$-$C_6$)alkyl, ($C_3$-$C_7$)cycloalkyl, NH—($C_1$-$C_6$)alkylamine, N,N—($C_1$-$C_6$)dialkylamine, aryl, substituted aryl, ($C_1$-$C_4$)alkyl-aryl, ($C_1$-$C_4$)alkyl-substituted aryl, heterocycle, substituted heterocycle, ($C_1$-$C_4$)alkyl-heterocycle, or ($C_1$-$C_4$)alkyl-substituted heterocycle;

$R^{10}$ represents independently at each occurrence hydrogen or ($C_1$-$C_6$)alkyl or $R^9$ and $R^{10}$ together with the nitrogen atom to which they are attached, form a substituted or unsubstituted heterocycle group;

$R^{11}$ represents independently at each occurrence amino, ($C_1$-$C_6$)alkyl, ($C_1$-$C_6$)alkoxy, halo($C_1$-$C_6$)alkyl, ($C_3$-$C_7$)cycloalkyl, aryl, substituted aryl, ($C_1$-$C_4$)alkyl-aryl, ($C_1$-$C_4$)alkyl-substituted aryl, heterocycle, substituted heterocycle, ($C_1$-$C_4$)alkyl-heterocycle, or ($C_1$-$C_4$)alkyl-substituted heterocycle;

$R^{12}$ represents independently at each occurrence hydrogen, amino, ($C_1$-$C_6$)alkyl, hydroxy($C_1$-$C_6$)alkyl, halo($C_1$-$C_6$)alkyl, ($C_1$-$C_6$)alkoxy, ($C_1$-$C_6$)alkyl-($C_1$-$C_6$)alkoxy, ($C_3$-$C_7$)cycloalkyl, NH—($C_1$-$C_6$)alkylamine, N,N—($C_1$-$C_6$)dialkylamine, aryl, substituted aryl, ($C_1$-$C_4$)alkyl-aryl, ($C_1$-$C_4$)alkyl-substituted aryl, heterocycle, substituted heterocycle, ($C_1$-$C_4$)alkyl-heterocycle, or ($C_1$-$C_4$)alkyl-substituted heterocycle;

$R^{13}$ represents independently at each occurrence OH, ($C_1$-$C_6$)alkyl, ($C_3$-$C_7$)cycloalkyl, aryl, heterocycle, or a substituted aryl or heterocycle;

$R^{14}$ represents independently at each occurrence ($C_3$-$C_7$)cycloalkyl, aryl, substituted aryl, acyl, ($C_1$-$C_4$)alkyl-aryl, ($C_1$-$C_4$)alkyl-substituted aryl, heterocycle, substituted heterocycle, ($C_1$-$C_4$)alkyl-heterocycle, ($C_1$-$C_4$)alkyl-substituted heterocycle, or ($C_1$-$C_4$)alkyl-($C_3$-$C_7$)cycloalkyl;

or a pharmaceutically acceptable salt thereof.

Examples of such disorders include Conn's Syndrome, primary and secondary hyperaldosteronism, increased sodium retention, increased magnesium and potassium excretion (diuresis), increased water retention, hypertension (isolated systolic and combined systolic/diastolic), arrhythmias, myocardial fibrosis, myocardial infarction, Bartter's Syndrome, disorders associated with excess catecholamine levels, diastolic and systolic congestive heart failure (CHF), peripheral vascular disease, diabetic nephropathy, cirrhosis with edema and ascites, esophageal varicies, Addison's Disease, muscle weakness, increased melanin pigmentation of the skin, weight loss, hypotension, hypoglycemia, Cushing's Syndrome, obesity, hypertension, glucose intolerance, hyperglycemia, diabetes mellitus, osteoporosis, polyuria, polydipsia, inflammation, autoimmune disorders, tissue rejection associated with organ transplant, malignancies such as leukemias and lymphomas, acute adrenal insufficiency, congenital adrenal hyperplasia, rheumatic fever, polyarteritis nodosa, granulomatous polyarteritis, inhibition of myeloid cell lines, immune proliferation/apoptosis, HPA axis suppression and regulation, hypercortisolemia, modulation of the Th1/Th2 cytokine balance, chronic kidney disease, stroke and spinal cord injury, hypercalcemia, hypergylcemia, acute adrenal insufficiency, chronic primary adrenal insufficiency, secondary adrenal insufficiency, congenital adrenal hyperplasia, cerebral edema, thrombocytopenia, and Little's syndrome, systemic inflammation, inflammatory bowel disease, systemic lupus erythematosus, discoid lupus erythematosus, polyartitis nodosa, Wegener's granulomatosis, giant cell arthritis, rheumatoid arthritis, osteoarthritis, hay fever, allergic rhinitis, contact dermatitis, atopic dermatitis, exfoliative dermatitis, urticaria, angioneurotic edema, chronic obstructive pulmonary disease, asthma, tendonitis, bursitis, Crohn's disease, ulcerative colitis, autoimmune chronic active hepatitis, hepatitis, cirrhosis, inflammatory scalp alopecia, panniculitis, psoriasis, inflamed cysts, pyoderma gangrenosum, pemphigus vulgaris, bullous pemphigoid, dermatomyositis, eosinophilic fasciitis, relapsing polychondritis, inflammatory vasculitis, sarcoidosis, Sweet's disease, type 1 reactive leprosy, capillary hemangiomas, lichen planus, erythema nodosum, acne, hirsutism, toxic epidermal necrolysis, erythema multiform, cutaneous T-cell lymphoma, emphysema, Alzheimer's Disease, and multiple sclerosis.

As a particular aspect, the present invention provides a method of treating a pathological disorder susceptible to mineralocorticoid or glucocorticoid receptor modulation comprising administering to a patient in need thereof an effective amount of a compound of Formula I, as described more fully herein and above. As a more particular aspect, the present invention provides a method of treating a pathological disorder susceptible to mineralocorticoid or glucocorticoid receptor antagonism comprising administering to a patient in need thereof an effective amount of a compound of Formula I, as described herein and above. As an even more particular aspect, the present invention provides a method of treating systolic and/or diastolic congestive heart failure or inflammation or rheumatoid arthritis comprising administering to a patient in need thereof an effective amount of a compound of Formula I, as described herein and above.

Certain of the tricyclic compounds corresponding to Formula I are believed to be novel and, thus, to constitute another embodiment of the present invention. As such, the present invention also provides a novel compound of Formula I:

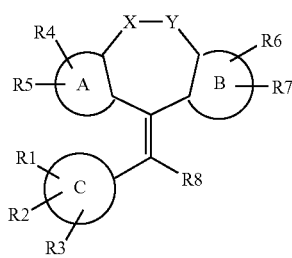

Formula I wherein,

A, B, and C each independently represent an aryl, heterocycle, or benzofused heterocyclic ring;

X and Y together represent —CH$_2$—CH$_2$—, —CH=CH—, —CH$_2$—O—, —O—CH$_2$—, —CH$_2$—S—, —S—CH$_2$—, —CH$_2$—SO—, —SO—CH$_2$—, —CH$_2$—SO$_2$—, —SO$_2$CH$_2$—, —CH$_2$—NR$^{10}$—, —NR$^{10}$—CH$_2$—, —NR$^{10}$—CO—, —CO—NR$^{10}$—, or a group of the formula

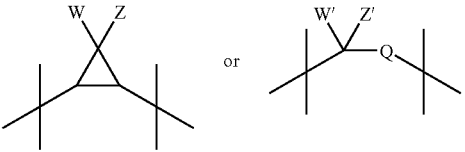

wherein W and Z each independently represent hydrogen, fluoro, or chloro; W' and Z' each independently represent hydrogen, fluoro, chloro, or methyl; and Q represents NH, O, S, or CH$_2$;

"$\equiv$" represents a single or double bond;

R$^1$ represents halo, hydroxy, cyano, nitro, amino, oxo, (C$_1$-C$_6$)alkyl, (C$_1$-C$_6$)alkoxy, hydroxy(C$_1$-C$_6$)alkyl, hydroxy(C$_1$-C$_6$)alkoxy, (C$_2$-C$_6$)alkenyl, (C$_2$-C$_6$)alkynyl, CH$_2$NH$_2$, halo(C$_1$-C$_6$)alkyl, halo(C$_1$-C$_6$)alkoxy, C(CF$_3$)$_2$OH, SO$_2$NH$_2$, SO$_2$NR$^9$R$^{10}$, SO$_2$R$^{11}$, NHSO$_2$R$^{11}$, N(CH$_3$)SO$_2$CH$_3$, NR$^9$R$^{10}$, CH$_2$NH(OH), CH$_2$NH(SO$_2$R$^{11}$), NHCOR$^{12}$, COR$^{12}$, CHNR$^{13}$, OR$^{14}$, SR$^{14}$, (C$_3$-C$_7$)cycloalkyl, aryl, substituted aryl, (C$_1$-C$_4$)alkyl-aryl, (C$_1$-C$_4$)alkyl-substituted aryl, heterocycle, substituted heterocycle, (C$_1$-C$_4$)alkyl-heterocycle, or (C$_1$-C$_4$)alkyl-substituted heterocycle;

provided that where "C" represents an aryl group, R$^1$ is other than oxo, (C$_2$-C$_6$)alkenyl, or (C$_2$-C$_6$)alkynyl;

further provided that where "C" represents a benzofused-heterocycle then R$^1$ may also represent hydrogen;

R$^2$ through R$^8$ each independently represent hydrogen halo, hydroxy, cyano, nitro, amino, (C$_1$-C$_6$)alkyl, (C$_1$-C$_6$)alkoxy, hydroxy(C$_1$-C$_6$)alkyl, hydroxy(C$_1$-C$_6$)alkoxy, (C$_2$-C$_6$)alkenyl, (C$_2$-C$_6$)alkynyl, CH$_2$NH$_2$, halo(C$_1$-C$_6$)alkyl, halo(C$_1$-C$_6$)alkoxy, C(CF$_3$)$_2$OH, SO$_2$NH$_2$, SO$_2$NR$^9$R$^{10}$, SO$_2$R$^{11}$, NHSO$_2$R$^{11}$, NR$^9$R$^{10}$, CH$_2$NH(OH), CH$_2$NH(SO$_2$R$^{11}$), NHCOR$^{12}$, COR$^{12}$, CHNR$^{13}$, OR$^{14}$, SR$^{14}$, (C$_3$-C$_7$)cycloalkyl, aryl, substituted aryl, (C$_1$-C$_4$)alkyl-aryl, (C$_1$-C$_4$)alkyl-(C$_1$-C$_6$)alkoxy, (C$_1$-C$_4$)alkyl-substituted aryl, heterocycle, substituted heterocycle, (C$_1$-C$_4$)alkyl-heterocycle, or (C$_1$-C$_4$)alkyl-substituted heterocycle;

provided that where "A", "B", or "C" represents an aryl group, each of R$^2$ through R$^7$ is other than (C$_2$-C$_6$)alkenyl or (C$_2$-C$_6$)alkynyl;

further provided that where "C" represents a phenyl ring and R$^1$ represents halo then at least one of R$^2$ and R$^3$ is other than hydrogen, (C$_1$-C$_6$)alkyl, aryl, substituted aryl, (C$_1$-C$_4$)alkyl-aryl, (C$_1$-C$_4$)alkyl-substituted aryl, CHF$_2$, or CF$_3$;

further provided that where "C" represents a six-membered ring and R$^1$ represents cyano, amino, NR$^9$R$^{10}$, or NHCOCH$_3$ and R$^2$ and R$^3$ are each hydrogen, then R$^1$ is not bound at the 4-position of said six-membered ring;

further provided that where "C" represents a six-membered ring and R$^1$ represents nitro, and R$^2$ and R$^3$ are each hydrogen, then R$^1$ is not bound at the 2, 4, or 6-position of said six-membered ring;

R$^9$ represents independently at each occurrence cyano, (C$_1$-C$_6$)alkyl, (C$_1$-C$_6$)alkoxy, (C$_1$-C$_4$)alkyl-(C$_1$-C$_6$)alkoxy, halo(C$_1$-C$_6$)alkyl, hydroxy(C$_1$-C$_6$)alkyl, (C$_3$-C$_7$)cycloalkyl, NH—(C$_1$-C$_6$)alkylamine, N,N—(C$_1$-C$_6$)dialkylamine, aryl, substituted aryl, (C$_1$-C$_4$)alkyl-aryl, (C$_1$-C$_4$)alkyl-substituted aryl, heterocycle, substituted heterocycle, (C$_1$-C$_4$)alkyl-heterocycle, or (C$_1$-C$_4$)alkyl-substituted heterocycle;

$R^{10}$ represents independently at each occurrence hydrogen or $(C_1-C_6)$alkyl or $R^9$ and $R^{10}$ together with the nitrogen atom to which they are attached, form a substituted or unsubstituted heterocycle group;

$R^{11}$ represents independently at each occurrence amino, $(C_1-C_6)$alkyl, $(C_1-C_6)$alkoxy, halo$(C_1-C_6)$alkyl, $(C_3-C_7)$cycloalkyl, aryl, substituted aryl, $(C_1-C_4)$alkyl-aryl, $(C_1-C_4)$alkyl-substituted aryl, heterocycle, substituted heterocycle, $(C_1-C_4)$alkyl-heterocycle, or $(C_1-C_4)$alkyl-substituted heterocycle;

$R^{12}$ represents independently at each occurrence hydrogen, amino, $(C_1-C_6)$alkyl, hydroxy$(C_1-C_6)$alkyl, halo$(C_1-C_6)$alkyl, $(C_1-C_6)$alkoxy, $(C_1-C_6)$alkyl-$(C_1-C_6)$alkoxy, $(C_3-C_7)$cycloalkyl, NH—$(C_1-C_6)$allylamine, N,N—$(C_1-C_6)$dialkylamine, aryl, substituted aryl, $(C_1-C_4)$alkyl-aryl, $(C_1-C_4)$alkyl-substituted aryl, heterocycle, substituted heterocycle, $(C_1-C_4)$alkyl-heterocycle, or $(C_1-C_4)$alkyl-substituted heterocycle;

$R^{13}$ represents independently at each occurrence OH, $(C_1-C_6)$alkyl, $(C_3-C_7)$cycloalkyl, aryl, heterocycle, or a substituted aryl or heterocycle;

$R^{14}$ represents independently at each occurrence $(C_3-C_7)$cycloalkyl, aryl, substituted aryl, acyl, $(C_1-C_4)$alkyl-aryl, $(C_1-C_4)$alkyl-substituted aryl, heterocycle, substituted heterocycle, $(C_1-C_4)$alkyl-heterocycle, $(C_1-C_4)$alkyl-substituted heterocycle, or $(C_1-C_4)$alkyl-$(C_3-C_7)$cycloalkyl;

or a pharmaceutically acceptable salt thereof

In another embodiment, the present invention provides a method of treating a pathological disorder susceptible to steroid hormone nuclear receptor modulation comprising administering to a patient in need thereof an effective amount of a novel compound of Formula I, or a pharmaceutically acceptable salt thereof, as described more fully herein and above. Examples of such disorders include Conn's Syndrome, primary and secondary hyperaldosteronism, increased sodium retention, increased magnesium and potassium excretion (diuresis), increased water retention, hypertension (isolated systolic and combined systolic/diastolic), arrhythmias, myocardial fibrosis, myocardial infarction, Bartter's Syndrome, disorders associated with excess catecholamine levels, diastolic and systolic congestive heart failure (CHF), peripheral vascular disease, diabetic nephropathy, cirrhosis with edema and ascites, esophageal varicies, Addison's Disease, muscle weakness, increased melanin pigmentation of the skin, weight loss, hypotension, hypoglycemia, Cushing's Syndrome, obesity, hypertension, glucose intolerance, hyperglycemia, diabetes mellitus, osteoporosis, polyuria, polydipsia, inflammation, autoimmune disorders, tissue rejection associated with organ transplant, malignancies such as leukemias and lymphomas, acute adrenal insufficiency, congenital adrenal hyperplasia, rheumatic fever, polyarteritis nodosa, granulomatous polyarteritis, inhibition of myeloid cell lines, immune proliferation/apoptosis, HPA axis suppression and regulation, hypercortisolemia, modulation of the Th1/Th2 cytokine balance, chronic kidney disease, stroke and spinal cord injury, hypercalcemia, hypergylcemia, acute adrenal insufficiency, chronic primary adrenal insufficiency, secondary adrenal insufficiency, congenital adrenal hyperplasia, cerebral edema, thrombocytopenia, and Little's syndrome, systemic inflammation, inflammatory bowel disease, systemic lupus erythematosus, discoid lupus erythematosus, polyartitis nodosa, Wegener's granulomatosis, giant cell arthritis, rheumatoid arthritis, osteoarthritis, hay fever, allergic rhinitis, contact dermatitis, atopic dermatitis, exfoliative dermatitis, urticaria, angioneurotic edema, chronic obstructive pulmonary disease, asthma, tendonitis, bursitis, Crohn's disease, ulcerative colitis, autoimmune chronic active hepatitis, hepatitis, cirrhosis, inflammatory scalp alopecia, panniculitis, psoriasis, inflamed cysts, pyoderma gangrenosum, pemphigus vulgaris, bullous pemphigoid, dermatomyositis, eosinophilic fasciitis, relapsing polychondritis, inflammatory vasculitis, sarcoidosis, Sweet's disease, type 1 reactive leprosy, capillary hemangiomas, lichen planus, erythema nodosum, acne, hirsutism, toxic epidermal necrolysis, erythema multiform, and cutaneous T-cell lymphoma.

As a particular aspect, the present invention provides a method of treating a pathological disorder susceptible to mineralocorticoid or glucocorticoid receptor modulation comprising administering to a patient in need thereof an effective amount of a novel compound of Formula I, as described herein and above. More particularly, the present invention provides a method of treating a pathological disorder susceptible to mineralocorticoid or glucocorticoid receptor antagonism comprising administering to a patient in need thereof an effective amount of a novel compound of Formula I, as described herein and above. As an even more particular aspect, the present invention provides a method of treating systolic and/or diastolic congestive heart failure or inflammation comprising administering to a patient in need thereof an effective amount of a novel compound of Formula I, as described herein and above.

In addition, the present invention also provides a method of modulating a steroid hormone nuclear receptor comprising administering to a patient in need thereof an effective amount of a compound of Formula I, or a pharmaceutically acceptable salt thereof More particularly, the present invention provides a method of modulating MR or GR comprising administering to a patient in need thereof an effective amount of a compound of Formula I, or a pharmaceutically acceptable salt thereof, as described herein and above. As an even more particular aspect, the present invention provides a method of modulating MR or GR comprising administering to a patient in need thereof an effective amount of a novel compound of Formula I, as described herein and above. More particular still, the present invention provides a method of antagonizing MR or GR comprising administering to a patient in need thereof an effective amount of a compound of Formula I, or a novel compound of Formula I, all as described herein and above.

In addition, the present invention provides pharmaceutical compositions of compounds of Formula I, including any pharmaceutically acceptable salts and hydrates thereof, comprising a compound of Formula I in combination with a pharmaceutically acceptable carrier, diluent or excipient. More particularly, the present invention provides pharmaceutical compositions comprising a novel compound of Formula I in combination with a pharmaceutically acceptable carrier, diluent or excipient. This invention also encompasses novel intermediates, and processes for the synthesis of the compounds of Formula I.

The present invention also provides the use of a compound of Formula I, or a pharmaceutically acceptable salt thereof, for the manufacture of a medicament for treating a pathological disorder susceptible to steroid hormone nuclear receptor modulation. More particularly, the present invention provides the use of a novel compound of Formula I, or a pharmaceutically acceptable salt thereof, for the manufacture of a medicament for treating a pathological disorder susceptible to steroid hormone nuclear receptor modulation. As an even more particular aspect, the present invention provides the use of a novel compound of Formula I for the manufacture of a medicament for treating congestive heart failure or inflammation.

DETAILED DESCRIPTION OF THE INVENTION

The present invention provides compounds with affinity for steroid hormone nuclear receptors, particularly MR and/or GR, which could be used to modulate (i.e. repress, antagonize, agonize, partially antagonize, partially agonize) receptor activity and gene expression, thereby influencing physiological functions related to steroid hormone levels and/or steroid hormone receptor activity. In this regard, such ligands are believed to be useful in treating or preventing a multitude of pathological disorders susceptible to steroid hormone nuclear receptor modulation. Thus, methods for the treatment or prevention of pathological disorders susceptible to steroid hormone nuclear receptor modulation constitute an important embodiment of the present invention. As a particular aspect, the present invention provides compounds useful as mineralocorticoid or glucocorticoid receptor modulators. As a more particular aspect, the present invention provides compounds useful as mineralocorticoid or glucocorticoid receptor antagonists. In addition, certain of the compounds of Formula I are believed to be novel which constitute yet another important embodiment of the present invention.

As will be understood by the skilled artisan, some of the compounds useful for the methods of the present invention may be available for prodrug formulation. As used herein, the term "prodrug" refers to a compound of Formula I which has been structurally modified such that in vivo the prodrug is converted, for example, by hydrolytic, oxidative, reductive, or enzymatic cleavage, into the parent molecule ("drug") as given by Formula I. Such prodrugs may be, for example, metabolically labile ester derivatives of the parent compound where said parent molecule bears a carboxylic acid group. Conventional procedures for the selection and preparation of suitable prodrugs are well known to one of ordinary skill in the art. Conversely, some compounds of Formula I may be suitable as antedrugs. "Antedrugs" are themselves pharmacologically active agents, containing metabolically labile functional groups, that upon administration are subsequently deactivated in vivo. Lee et al., *Arch. Pharm. Res.*, 25(2); 111-136 (2002) provides a discussion of such antedrugs and their utility.

It is also understood that many of the steroid hormone nuclear receptor modulators of the present invention may exist as pharmaceutically acceptable salts and, as such, pharmaceutically acceptable salts are therefore included within the scope of the present invention. The term "pharmaceutically acceptable salt" as used herein, refers to salts of the compounds of Formula I, which are substantially non-toxic to living organisms. Typical pharmaceutically acceptable salts include those salts prepared by reaction of the compounds of the present invention with a pharmaceutically acceptable mineral or organic acid or an organic or inorganic base. Such salts are known as acid addition and base addition salts. It is further understood by the skilled reader that salt forms of pharmaceutical compounds are commonly used because they are often more readily crystallized, or more readily purified, than are the free bases. In all cases, the use of the pharmaceutical compounds of the present invention as salts is contemplated in the description herein. Hence, it is understood that where compounds of Formula I are capable of forming salts, the pharmaceutically acceptable salts and isoforms thereof are encompassed in the names provided herein.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, bromide, iodide, hydroiodide, dihydroiodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4dioate, hexyne-1,6-dioate, benzoate, chlorobenzoate, methylbenzoate, hydroxybenzoate, methoxybenzoate, phthalate, xylenesulfonate, phenyl acetate, phenyl propionate, phenyl butyrate, citrate, lactate, α-hydroxybutyrate, glycolate, tartrate, methanesulfonate, propanesulfonate, naphthalene-1-sulfonate, napthalene-2-sulfonate, mandelate and the like. Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to one of two stereoisomers whose molecules are non-superimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers". The terms "racemate", "racemic mixture" or "racemic modification" refer to a mixture of equal parts of enantiomers.

The compounds of the present invention may have one or more chiral centers and may, therefore, exist in a variety of stereoisomeric configurations. As a consequence of these chiral centers the compounds of the present invention may occur as racemates, mixtures of enantiomers, and as individual enantiomers as well as diastereomers and mixtures of diastereomers. All such racemates, enantiomers, and diastereomers are within the scope of the present invention. Enantiomers of the compounds provided by the present invention can be resolved, for example, by one of ordinary skill in the art using standard techniques such as those described by J. Jacques, et al., "Enantiomers, Racemates, and Resolutions", John Wiley and Sons, Inc., 1981.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond from the chiral carbon toward the lowest priority group. The term "S" (sinister) refers to that configuration of a chiral center with a counterclockwise relationship of group priorities (highest to second lowest) when viewed along the bond from the chiral carbon toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103-120.

The specific stereoisomers and enantiomers of compounds of Formula I can be prepared by one of ordinary skill in the art utilizing well known techniques and processes, such as those disclosed by Eliel and Wilen, "Stereochemistry of Organic Compounds", John Wiley & Sons, Inc., 1994, Chapter 7; Separation of Stereoisomers, Resolution, Racemization; and by Collet and Wilen, "Enantiomers, Racemates, and Resolutions", John Wiley & Sons, Inc., 1981. For example, specific stereoisomers and enantiomers can be prepared by stereospecific syntheses using enantiomerically and geometrically pure, or enantiomerically or geometrically enriched starting materials. In addition, the specific stereoisomers and enantiomers can be resolved and recovered by techniques such as chromatography on chiral stationary phases, enzymatic resolution or fractional recrystallization of addition salts formed by reagents used for that purpose.

As will be appreciated by one of ordinary skill in the art, molecules containing a carbon-carbon double bond may exist as geometric isomers. Two methods are commonly used to designate the specific isomers, the "cis-trans" method and the "E and Z" method depending on whether the groups attached to each of the ethylene carbons are the same or different. A discussion of geometric isomerism and the naming of specific isomers is found in March, "Advanced Organic Chemistry", John Wiley & Sons, 1992, Chapter 4. All such geometric isomers, as well as mixtures of individual isomers, are contemplated and provided by the present invention.

Where used herein, the term "Pg" refers to a suitable oxygen or nitrogen protecting group. Suitable oxygen or nitrogen protecting groups, as used herein, refers to those groups intended to protect or block the oxygen or nitrogen group against undesirable reactions during synthetic procedures. Whether the term "Pg", as used herein, represents an oxygen protecting group or a nitrogen protecting group will be readily apparent to the ordinarily skilled artisan. The suitability of the oxygen or nitrogen protecting group used will depend upon the conditions that will be employed in subsequent reaction steps wherein protection is required, and is well within the knowledge of one of ordinary skill in the art.

Commonly used nitrogen protecting groups are disclosed in Greene, "Protective Groups In Organic Synthesis, 3$^{rd}$ Edition" (John Wiley & Sons, New York (1999)). Suitable nitrogen protecting groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, .alpha.-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, .alpha,.alpha.-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, triphenylmethyl, benzyloxymethyl and the like; and silyl groups such as trimethylsilyl and the like. Commonly used oxygen protecting groups are also disclosed in Greene (supra). Suitable oxygen protecting groups comprise alkyl groups such as methyl, ethyl, and the like; silyl groups such as t-butyldimethylsilyl, t-butyldiphenylsilyl, triisopropylsilyl, and the like, with t-butyldimethylsilyl being preferred. Other commonly used oxygen protecting groups include benzyl, 4-nitrophenyl methyl, benzoyl, and the like.

As used herein the term "$(C_1-C_4)$alkyl" refers to a straight or branched, monovalent, saturated aliphatic chain of 1 to 4 carbon atoms and includes, but is not limited to methyl, ethyl, n-propyl, isopropyl, n-butyl, isobutyl and the like.

As used herein the term "$(C_1-C_6)$alkyl" refers to a straight or branched, monovalent, saturated aliphatic chain of 1 to 6 carbon atoms and includes, but is not limited to methyl, ethyl, n-propyl, isopropyl, n-butyl, isobutyl, t-butyl, n-pentyl, n-hexyl, and the like. It is understood that the term "$(C_1-C_4)$alkyl" is included within the definition of "$(C_1-C_6)$alkyl".

As used herein the term "$(C_1-C_{10})$alkyl" refers to a straight or branched, monovalent, saturated aliphatic chain of 1 to 10 carbon atoms and includes, but is not limited to methyl, ethyl, propyl, isopropyl, n-butyl, isobutyl, tertiary butyl, pentyl, isopentyl, hexyl, 2,3-dimethyl-2-butyl, heptyl, 2,2-dimethyl-3-pentyl, 2-methyl-2-hexyl, octyl, 4-methyl-3-heptyl and the like. It is understood that the terms "$(C_1-C_4)$alkyl" and "$(C_1-C_6)$alkyl" are included within the definition of "$(C_1-C_{10})$alkyl".

As used herein, the terms "Me", "Et", "Pr", "i-Pr", "Bu" and "t-Bu" refer to methyl, ethyl, propyl, isopropyl, butyl and tert-butyl respectively.

As used herein, the term "$(C_1-C_4)$alkoxy" refers to an oxygen atom bearing a straight or branched, monovalent, saturated aliphatic chain of 1 to 4 carbon atoms and includes, but is not limited to methoxy, ethoxy, n-propoxy, isopropoxy, n-butoxy, and the like. As used herein the term "$(C_1-C_6)$alkoxy" refers to an oxygen atom bearing a straight or branched, monovalent, saturated aliphatic chain of 1 to 6 carbon atoms and includes, but is not limited to methoxy, ethoxy, n-propoxy, isopropoxy, n-butoxy, n-pentoxy, n-hexoxy, and the like. It is understood that the term "$(C_1-C_4)$alkoxy" is included within the definition of "$(C_1-C_6)$alkoxy".

As used herein, the term "hydroxy$(C_1-C_4)$alkyl" refers to a straight or branched, monovalent, saturated aliphatic chain of 1 to 4 carbon atoms bearing a hydroxyl group attached to one of the carbon atoms. As used herein, the term "hydroxy$(C_1-C_6)$alkyl" refers to a straight or branched, monovalent, saturated aliphatic chain of 1 to 6 carbon atoms bearing a hydroxyl group attached to one of the carbon atoms. It is understood that the term "hydroxy$(C_1-C_4)$alkyl" is included within the definition of "hydroxy$(C_1-C_6)$alkyl". As used herein, the term "hydroxy$(C_1-C_4)$alkoxy" refers to an oxygen atom bearing a straight or branched, monovalent, saturated aliphatic chain of 1 to 4 carbon atoms, further bearing a hydroxyl group attached to one of the carbon atoms. As used herein, the term "hydroxy$(C_1-C_6)$alkoxy" refers to an oxygen atom bearing a straight or branched, monovalent, saturated aliphatic chain of 1 to 6 carbon atoms, further bearing a hydroxyl group attached to one of the carbon atoms. It is understood that the term "hydroxy$(C_1-C_4)$alkoxy" is included within the definition of "hydroxy$(C_1-C_6)$alkoxy".

As used herein, the term "$(C_1-C_6)$alkyl-$(C_1-C_6)$alkoxy" refers to a straight or branched, monovalent, saturated aliphatic chain of 1 to 6 carbon atoms which has a $(C1-C_6)$ alkoxy group attached to the aliphatic chain. The term "$(C_1-C_4)$alkyl-$(C_1-C_6)$alkoxy" refers to a straight or branched, monovalent, saturated aliphatic chain of 1 to 4 carbon atoms which has a $(C_1-C_6)$alkoxy group attached to the aliphatic chain. It is understood that the term "$(C_1-C_4)$alkyl-$(C_1-C_6)$alkoxy" is included within the definition of "$(C_1-C_6)$alkyl- "(C₁-C₆)alkoxy". "(C₁-C₆)alkoxymethylene" refers to a methylene group bearing a (C₁-C₆)alkoxy group. "(C₁-C₆)alkoxy (C₁-C₆)alkoxy-methylene refers to a methylene group bearing a (C₁-C₆)alkoxy group which, in turn, bears an additional (C₁-C₆)alkoxy group attached to the aliphatic chain.

As used herein, the terms "halo", "halide" or "hal" of "Hal" refer to a chlorine, bromine, iodine or fluorine atom, unless otherwise specified herein.

As used herein, the term "halo(C₁-C₄)alkyl" refers to a straight or branched, monovalent, saturated aliphatic chain of 1 to 4 carbon atoms bearing one or more halo groups attached to one or more of the carbon atoms. As used herein, the term "halo(C₁-C₆)alkyl" refers to a straight or branched, monovalent, saturated aliphatic chain of 1 to 6 carbon atoms bearing one or more halo groups attached to one or more of the carbon atoms. It is understood that the term "halo(C₁-C₄)alkyl" is included within the definition of "halo(C₁-C₆)alkyl". Typical examples of "halo(C₁-C₆)alkyl" include CF₃, CHF₂, CH₂F, and the like. As used herein, the term "halo(C₁-C₄)alkoxy" refers to an oxygen atom bearing a straight or branched, monovalent, saturated aliphatic chain of 1 to 4 carbon atoms, further bearing one or more halo groups attached to one or more of the carbon atoms. As used herein, the term "halo(C₁-C₆)alkoxy" refers to an oxygen atom bearing a straight or branched, monovalent, saturated aliphatic chain of 1 to 6 carbon atoms, further bearing one or more halo groups attached to one or more of the carbon atoms. It is understood that the term "halo(C₁-C₄)alkoxy" is included within the definition of "halo(C₁-C₆)alkoxy". Typical examples of "halo (C₁-C₆)alkoxy" include OCF₃, OCHF₂, OCH₂F, and the like.

As used herein the term "(C₂-C₆)alkenyl" refers to a straight or branched, monovalent, unsaturated aliphatic chain having from two to six carbon atoms and having a double bond. Typical (C₂-C₆)alkenyl groups include ethenyl (also known as vinyl), 1-methylethenyl, 1-methyl-1-propenyl, 1-butenyl, 1-hexenyl, 2-methyl-2-propenyl, 1-propenyl, 2-propenyl, 2-butenyl, 2-pentenyl, and the like.

As used herein the term "(C₂-C₆)alkynyl" refers to a straight or branched, monovalent, unsaturated aliphatic chain having from two to six carbon atoms and having a triple bond.

As used herein, the term "acyl" refers to a hydrogen or a (C₁-C₆)alkyl group attached to a carbonyl group. Typical acyl groups include formyl, acetyl, propionyl, butyryl, valeryl, and caproyl.

As used herein, the term "aryl" refers to a monovalent carbocyclic group containing one or more fused or non-fused phenyl rings and includes, for example, phenyl, 1- or 2-naphthyl, 1,2-dihydronaphthyl, 1,2,3,4-tetrahydronaphthyl, and the like. The term "substituted aryl" refers to an aryl group substituted with one to three moieties, preferably one or two, chosen from the group consisting of acyl, halogen, hydroxy, cyano, nitro, amino, (C₁-C₆)alkyl, (C₁-C₄)alkylsulfonyl, halo (C₁-C₆)alkyl, (C₁-C₆)alkoxy, halo(C₁-C₆)alkoxy, (C₁-C₆) alkylthio, (C₃-C₇)cycloalkyl, (C₁-C₄)alkyl-(C₃-C₇)cycloalkyl, aryl, (C₁-C₄)alkyl-aryl, heterocycle, (C₁-C₄)alkyl-heterocycle, (C₁-C₄)alkoxy-heterocycle, (C₁-C₆) alkoxycarbonyl, N,N(C₁-C₆)dialkylamine, NH(C₁-C₆) alkylamine, NHSO₂(C₁-C₄)alkyl, (C₁-C₄)alkyl-N,N—(C₁-C₆)dialkylamine, (C₁-C₄)alkoxy-N,N—(C₁-C₆) dialkylamine difluoromethyl, difluoromethoxy, trifluoromethyl, trifluoromethoxy, CF₂CF₃, benzoyl, phenoxy, or an aryl or heterocycle group further substituted with one to two moieties selected from the group consisting of:

(C₁-C₄)alkyl,
(C₃-C₇)cycloalkyl,
halo,
hydroxy,
(C₁-C₄)alkoxy,
CF₃,
OCF₃,
CHF₂,
OCHF₂,
CF₂CF₃,
cyano,
nitro,
amino,
NH(C₁-C₄)alkylamine, and
N,N—(C₁-C₄)dialkylamine;

As used herein, the term "(C₁-C₆)alkyl-aryl" refers to a straight or branched, monovalent, saturated aliphatic chain of 1 to 6 carbon atoms which has an aryl group attached to the aliphatic chain. "(C₁-C₄)alkyl-aryl" refers to a straight or branched, monovalent, saturated aliphatic chain of 1 to 4 carbon atoms which has an aryl group attached to the aliphatic chain. It is understood that the term "(C₁-C₄)alkyl-aryl" is included within the definition of "(C₁-C₆)alkyl-aryl. Examples of "(C₁-C₆)alkyl-aryl" include the following:

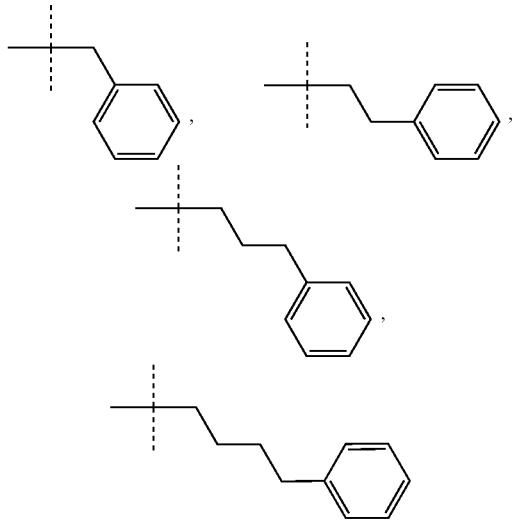

and the like.

As used herein, the term "(C₁-C₄)alkyl-substituted aryl" refers to a straight or branched, monovalent, saturated aliphatic chain of 1 to 4 carbon atoms which has a substituted aryl group, as described above, attached to the aliphatic chain. Examples of "(C₁-C₄)alkyl-substituted aryl" include methylbenzyl, phenylbenzyl, nitrobenzyl, methoxybenzyl, chlorobenzyl, bromobenzyl, dimethlybenzyl, aminobenzyl, dichlorobenzyl, and the like.

As used herein, the term "aryl(C₁-C₆)alkoxy" refers to an oxygen atom bearing a straight or branched, monovalent, saturated aliphatic chain of 1 to 6 carbon atoms wherein said aliphatic chain, in turn, bears an aryl group.

As used herein the term "(C₃-C₁₀)cycloalkyl" refers to a saturated hydrocarbon ring structure composed of one or more fused or unfused rings containing from three to ten carbon atoms. Typical (C₃-C₁₀)cycloalkyl groups include cyclopropyl, cyclobutyl, cyclopentyl, cyclohexyl, cycloheptyl, cyclooctyl, adamantanyl, and the like. "(C₃-C₇)cycloalkyl" refers to a saturated hydrocarbon ring structure composed of one or more fused or unfused rings containing from three to seven carbon atoms. It is understood that the definition of "(C₃-C₇)cycloalkyl" is included within the definition of "($C_3$-$C_{10}$)cycloalkyl". The term "substituted ($C_3$-$C_7$)cycloalkyl" refers to a "($C_3$-$C_7$)cycloalkyl group substituted with one or two moieties chosen from the group consisting of halogen, hydroxy, cyano, nitro, amino, ($C_1$-$C_6$) alkyl, ($C_1$-$C_6$)alkoxy, ($C_1$-$C_4$)alkyl-($C_3$-$C_{10}$)cycloalkyl, ($C_1$-$C_4$)alkyl-aryl, ($C_1$-$C_6$)alkoxycarbonyl, N,N($C_1$-$C_6$)dialkylamine, NH($C_1$-$C_6$)alkylamine, ($C_1$-$C_4$)alkyl-N,N—$C_1$-$C_6$dialkylamine, difluoromethyl, difluoromethoxy, trifluoromethyl, and trifluoromethoxy.

As used herein, the term "($C_1$-$C_4$)alkyl-($C_3$-$C_7$)cycloalkyl" refers to a straight or branched, monovalent, saturated aliphatic chain of 1 to 4 carbon atoms which has a ($C_3$-$C_7$)cycloalkyl attached to the aliphatic chain. Included within the term "($C_1$-$C_4$)alkyl-($C_3$-$C_7$)cycloalkyl" are the following:

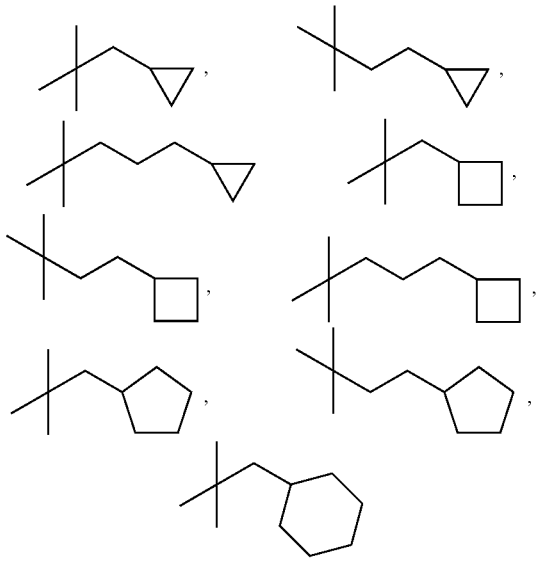

and the like. As used herein, the term "($C_1$-$C_4$)alkyl-substituted ($C_3$-$C_7$)cycloalkyl" refers to a straight or branched, monovalent, saturated aliphatic chain of 1 to 4 carbon atoms bearing a substituted ($C_3$-$C_7$)cycloalkyl group attached to the aliphatic chain.

As used herein the term "($C_3$-$C_7$)cycloalkoxy" refers to an oxygen atom bearing a saturated hydrocarbon ring structure composed of one or more fused or unfused rings containing from three to seven carbon atoms.

As used herein, the term "($C_1$-$C_6$) alkoxycarbonyl" refers to a carbonyl group having a ($C_1$-$C_6$)alkyl group attached to the carbonyl carbon through an oxygen atom. Examples of this group include t-butoxycarbonyl, methoxycarbonyl, ethoxycarbonyl and the like. It is understood that the term "($C_1$-$C_4$) alkoxycarbonyl" is included within the definition of "($C_1$-$C_6$) alkoxycarbonyl".

As used herein the term "heterocycle" refers to a saturated or unsaturated, five- or six-membered ring, which contains one to four heteroatoms selected from the group consisting of oxygen, sulfur, and nitrogen. It is understood that the remaining atoms are carbon and that the heterocycle may be attached at any point which provides for a stable structure. Examples of heterocycle groups include thiophenyl, furyl, tetrahydrofuryl, pyrrolyl, imidazolyl, pyrrazolyl, thiazolyl, thiazolidinyl, isothiazolyl, oxazolyl, isoxazolyl, triazolyl, thiadiazolyl, oxadiazolyl, tetrazolyl, pyridyl, pyridinyl, pyrimidyl, pyrazinyl, pyridiazinyl, triazinyl, imidazolyl, dihydropyrimidyl, tetrahydropyrimdyl, pyrrolidinyl, piperidinyl, piperazinyl, pyrazolidinyl, pyrimidinyl, imidazolidimyl, morpholinyl, pyranyl, thiomorpholinyl, and the like. As used herein, the term "benzofused heterocyclic ring" or "benzofused heterocycle" refers to a saturated or unsaturated, five- or six-membered ring, which contains one to four heteroatoms selected from the group consisting of oxygen, sulfur, and nitrogen, and which is fused to a phenyl group. Representative "benzofused heterocyclic rings" include benzooxazole, benzoimidazole, benzimidazole, benzofuran, benzothiophene, benzothiazole, azaindole, and indole.

The term "substituted heterocycle" represents a heterocycle group substituted with one or two moieties chosen from the group consisting of acyl, halogen, hydroxy, cyano, nitro, amino, ($C_1$-$C_6$)alkyl, ($C_1$-$C_4$)alkylsulfonyl, halo($C_1$-$C_6$) alkyl, ($C_1$-$C_6$)alkoxy, halo($C_1$-$C_6$)alkoxy, ($C_1$-$C_6$)alkylthio, ($C_3$-$C_7$)cycloalkyl, ($C_1$-$C_4$)alkyl-($C_3$-$C_7$)cycloalkyl, aryl, ($C_1$-$C_4$)alkyl-aryl, heterocycle, ($C_1$-$C_4$)alkyl-heterocycle, ($C_1$-$C_4$)alkoxy-heterocycle, ($C_1$-$C_6$)alkoxycarbonyl, N,N ($C_1$-$C_6$)dialkylamine, NHCOCH$_3$, NH($C_1$-$C_6$)alkylamine, NHSO$_2$($C_1$-$C_4$)alkyl, ($C_1$-$C_4$)alkyl-N,N—$C_1$-$C_6$dialkylamine, ($C_1$-$C_4$)alkoxy-N,N—$C_1$-$C_6$dialkylamine, difluoromethyl, difluoromethoxy, trifluoromethyl, trifluoromethoxy, CF$_2$CF$_3$, or an aryl or heterocycle group further substituted with one to two moieties selected from the group consisting of:

($C_1$-$C_4$)alkyl,
($C_3$-$C_7$)cycloalkyl,
halo,
hydroxy,
($C_1$-$C_4$)alkoxy,
CF$_3$,
OCF$_3$,
CHF$_2$,
OCHF$_2$,
CF$_2$CF$_3$,
cyano,
nitro,
amino,
NH($C_1$-$C_4$)alkylamine, and
N,N—($C_1$-$C_4$)dialkylamine;

Examples of substituted heterocycle include methylisoxazole, dimethylisoxazole, methylimidazole, trifluoromethyl imidazole, pyridinyl thiophene, and the like. The term "substituted benzofused heterocycle" represents a benzofused heterocycle group substituted with one or two moieties chosen from the group consisting of acyl, halogen, hydroxy, cyano, nitro, amino, ($C_1$-$C_6$)alkyl, halo($C_1$-$C_6$)alkyl, or ($C_1$-$C_6$)alkoxy.

As used herein, the term "($C_1$-$C_4$)alkyl-heterocycle" refers to a straight or branched, monovalent, saturated aliphatic chain of 1 to 4 carbon atoms which has a heterocycle group attached to the aliphatic chain. Examples of "($C_1$-$C_4$)alkyl-heterocycle" include:

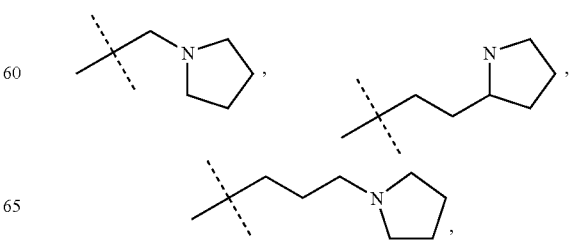

-continued

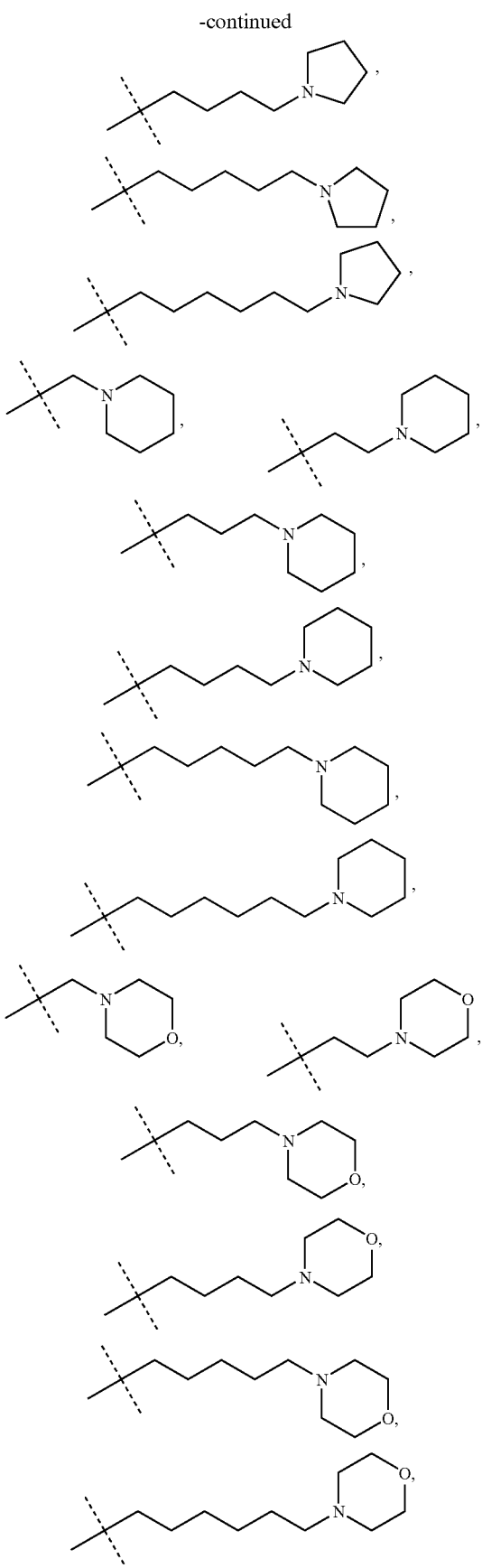

-continued

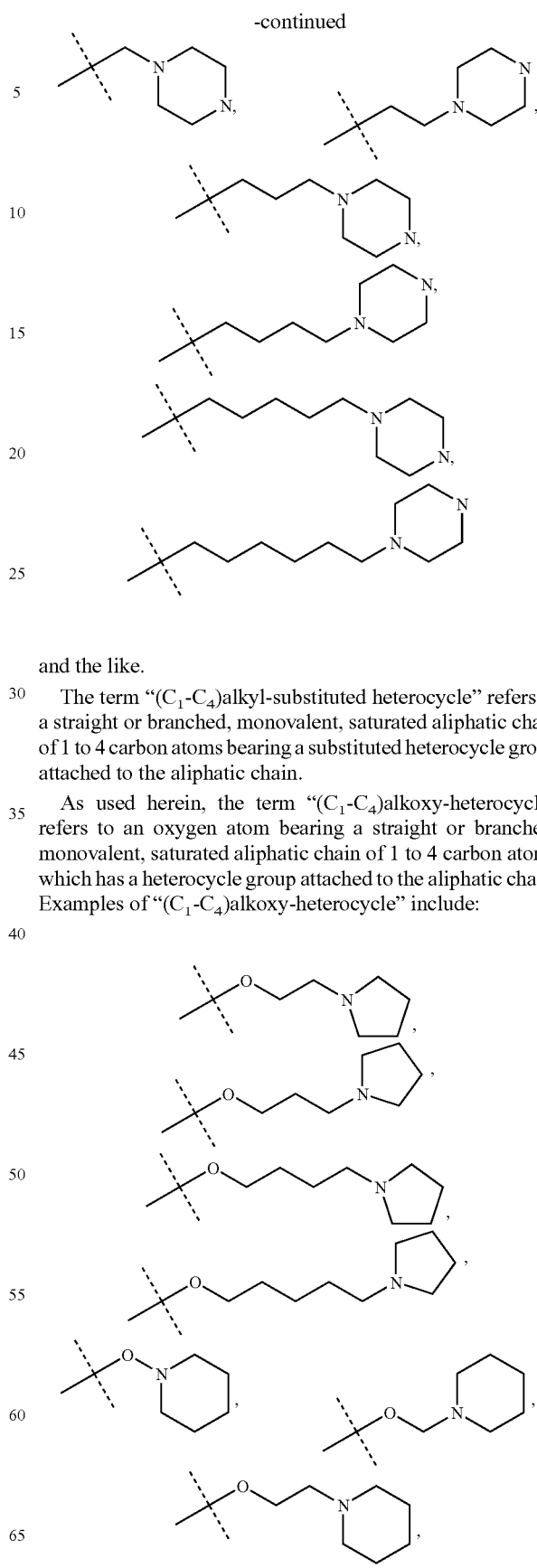

and the like.

The term "$(C_1-C_4)$alkyl-substituted heterocycle" refers to a straight or branched, monovalent, saturated aliphatic chain of 1 to 4 carbon atoms bearing a substituted heterocycle group attached to the aliphatic chain.

As used herein, the term "$(C_1-C_4)$alkoxy-heterocycle" refers to an oxygen atom bearing a straight or branched, monovalent, saturated aliphatic chain of 1 to 4 carbon atoms which has a heterocycle group attached to the aliphatic chain. Examples of "$(C_1-C_4)$alkoxy-heterocycle" include:

-continued

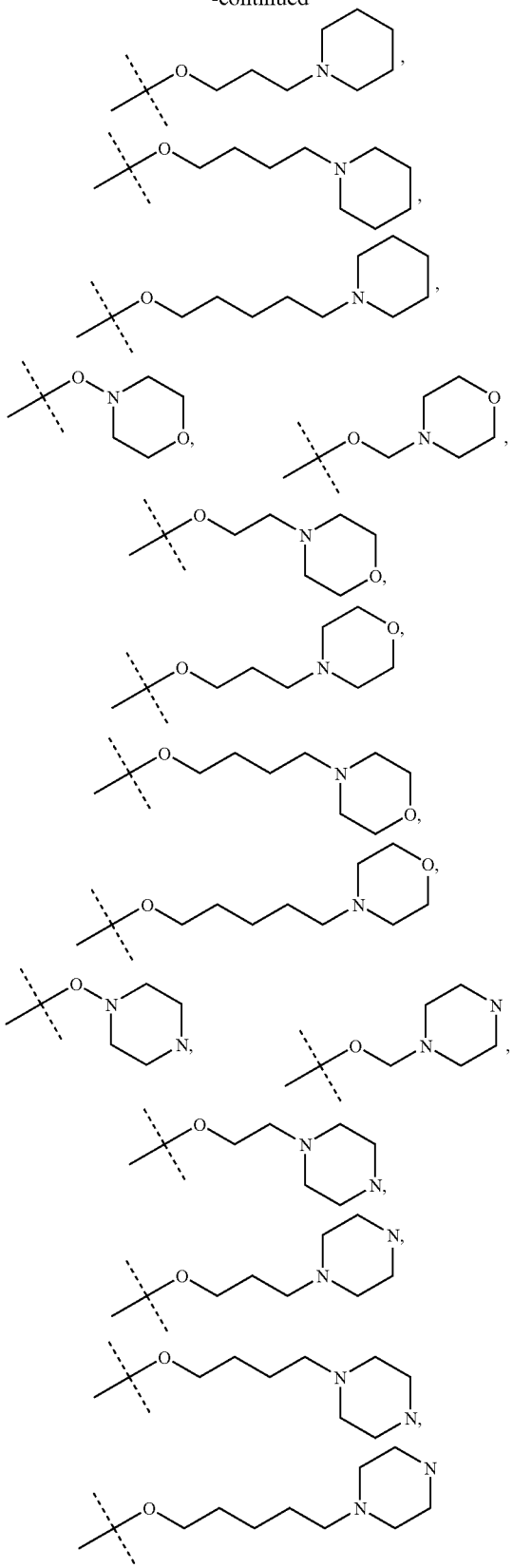

and the like.

The term "($C_1$-$C_4$)alkoxy-substituted heterocycle" refers to a straight or branched, monovalent, saturated aliphatic chain of 1 to 4 carbon atoms bearing a substituted heterocycle group attached to the aliphatic chain.

As used herein the term "NH($C_3$-$C_7$)cycloalkyl" refers to an amino group substituted with a saturated hydrocarbon ring structure composed of one or more fused or unfused rings containing from three to seven carbon atoms.

As used herein the term "N,N—($C_1$-$C_6$)dialkylamine" refers to a nitrogen atom substituted with two straight or branched, monovalent, saturated aliphatic chains of 1 to 6 carbon atoms. Included within the term "N,N—($C_1$-$C_6$)dialkylamine" are —N(CH$_3$)$_2$, —N(CH$_2$CH$_3$)$_2$, —N(CH$_2$CH$_2$CH$_3$)$_2$, —N(CH$_2$CH$_2$CH$_2$CH$_3$)$_2$, and the like. "NH—($C_1$-$C_6$) alkylamine" refers to a nitrogen atom substituted with a straight or branched, monovalent, saturated aliphatic chains of 1 to 6 carbon atoms.

As used herein the term "($C_1$-$C_6$)alkyl-N,N—$C_1$-$C_6$dialkylamine" refers to straight or branched, monovalent, saturated aliphatic chain of 1 to 6 carbon atoms which has an N,N—($C_1$-$C_6$)dialkylamine attached to the aliphatic chain. Included within the term "($C_1$-$C_6$)alkyl-N,N—($C_1$-$C_6$)dialkylamine" are the following:

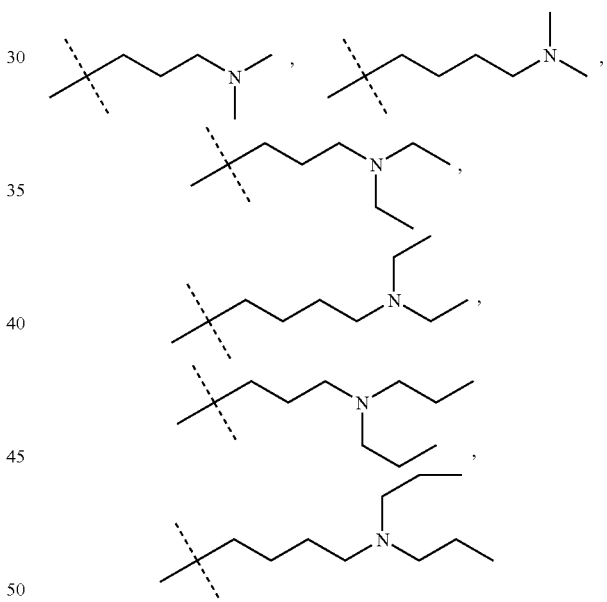

and the like.

As used herein the term "($C_1$-$C_6$)alkoxy-N,N—($C_1$-$C_6$) dialkylamine" refers to an oxygen atom bearing a straight or branched, monovalent, saturated aliphatic chain of 1 to 6 carbon atoms which has an N,N—$C_1$-$C_6$ dialkylamine attached to the aliphatic chain. Included within the term "$C_1$-$C_6$ alkoxy-N,N—($C_1$-$C_6$)dialkylamine" are the following:

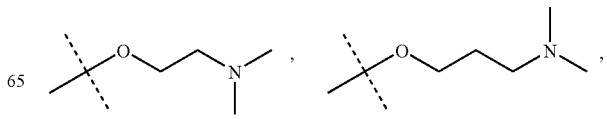

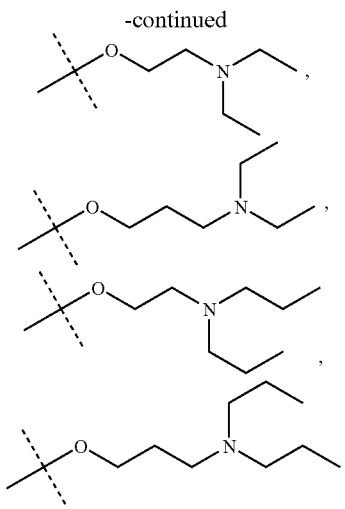

and the like.

The compounds of the present invention have an aryl, heterocycle, or benzofused-heterocycle ring (ring "C" of Formula I) attached to the tricyclic core. Each of these ring structures, in turn, may be singularly or multiply substituted as denoted in Formula I. As a consequence, a uniform method of numbering is needed to denote the positions on the rings where substitution occurs or may occur. As such, where ring "C" is a five-membered ring, the following numbering pattern is used to denote the positions on the ring where substitution occurs, or may occur

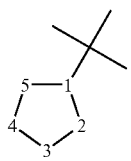

Where ring "C" is a six-membered ring, the following numbering pattern is used to denote the positions on the ring where substitution occurs, or may occur

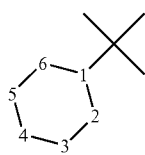

As stated, the compounds of the present invention may have a benzofused-heterocycle ring (ring "C" of Formula I) attached to the tricyclic core. Each of these ring structures, in turn, may be singularly or multiply substituted as denoted in Formula I. More particularly, where ring "C" is a benzofused-heterocycle, ring "C" attaches to the tricyclic core of Formula I through the phenyl portion of the bicyclic system and the substituents $R^1$-$R^3$ attach to ring "C" through the heteroatom containing portion of the bicyclic ring system. This particular configuration of ring "C", when "C" represents a benzofuzed heterocycle, in relation to the tricyclic core of Formula I and the substituents $R^1$-$R^3$ is given by the following:

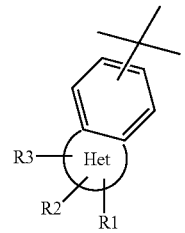

Representative examples where ring "C" is a benzofused-heterocycle include benzoimidazole, benzothiazole, benzooxazole, benzothiadiazole, indazole, indole, oxindole, and benzimidazole.

Representative examples where ring "C" is a benzofused-heterocycle and at least one of $R^1$-$R^3$ is other than hydrogen, include benzoimidazole, benzothiazolone, benzooxazolone, indoline, N-methylbenzoimidazolone, N-ethylbenzoimidazolone, N-propylbenzoimidazolone, N-isopropylbenzoimidazolone, N-isobutylbenzoimidazolone, N-trifluoroethylbenzoimidazolone, N-phenylbenzoimidazolone, N-pyridinylbenzoimidazolone, N-imidazolylbenzoimidazolone, N-thiazolylbenzoimidazolone, N-oxazolylbenzoimidazolone, N-morpholinoethylbenzoimidazolone, N-morpholinopropylbenzoimidazolone, N-methylpiperazinylethylbenzoimidazolone, N-(1-piperdinyl)ethylbenzoimidazolone, N-(1-pyrrolidinyl)ethylbenzoimidazolone, N-(1-piperdin-4-yl)ethylbenzoimidazolone, N-(1-methylpiperdin-4-yl)benzoimidazolone, N-(1-pyrrolidin-3-yl)benzoimidazolone, and N-(1-methylpyrrolidin-3-yl)benzoimidazolone, and the like.

The designation "◂▬" refers to a bond that protrudes forward out of the plane of the page.

The designation "⋯⋯" refers to a bond that protrudes backward out of the plane of the page.

As used herein, the term "steroid hormone nuclear receptor modulator" refers to those nuclear hormone receptor ligands which bind to any one of GR, MR, AR, ER, or PR, of the larger class of nuclear hormone receptors, and either agonize, antagonize, partially agonize, partially antagonize, or repress the receptor's activity.

As used herein the term "mineralocorticoid receptor" or "MR" refers to the mineralocorticoid receptor subtype, of the larger class of nuclear hormone receptors, which binds the mineralocorticoid hormone aldosterone, as its cognate ligand. The term "mineralocorticoid receptor modulator" or "mineralocorticoid modulator" or "MR modulator" as used herein, refers to those nuclear hormone receptor ligands which bind to the mineralocorticoid receptor subtype and modulate (i.e. agonize, antagonize, partially agonize, partially antagonize, or repress) the receptor activity. As a particular embodiment, the present invention provides antagonists of MR activity.

As used herein the term "glucocorticoid receptor" or "GR" refers to the glucocorticoid receptor subtype, of the larger class of nuclear hormone receptors, which binds the glucocorticoid hormones cortisol, corticosterone, or cortisone as its cognate ligand. The term "glucocorticoid receptor modulator" or "glucocorticoid modulator" or "GR modulator", as used herein, refers to those nuclear hormone receptor ligands which bind to the glucocorticoid receptor subtype and modulate (i.e. agonize, antagonize, partially agonize, partially antagonize, or repress) the receptor activity.

As used herein, the term "disorder susceptible to steroid hormone nuclear receptor modulation" refers to any pathological disorder, of any origin, known or believed to be responsive to administration of a modulator (i.e. agonist, antagonist, partial agonist, or partial antagonist) of a steroid hormone nuclear receptor. Such pathological disorders include Conn's Syndrome, primary and secondary hyperaldosteronism, increased sodium retention, increased magnesium and potassium excretion (diuresis), increased water retention, hypertension (isolated systolic and combined systolic/diastolic), arrhythmias, myocardial fibrosis, myocardial infarction, Bartter's Syndrome, disorders associated with excess catecholamine levels, diastolic and systolic congestive heart failure (CHF), peripheral vascular disease, diabetic nephropathy, cirrhosis with edema and ascites, esophageal varicies, Addison's Disease, muscle weakness, increased melanin pigmentation of the skin, weight loss, hypotension, hypoglycemia, Cushing's Syndrome, obesity, hypertension, glucose intolerance, hyperglycemia, diabetes mellitus, osteoporosis, polyuria, polydipsia, inflammation, autoimmune disorders, tissue rejection associated with organ transplant, malignancies such as leukemias and lymphomas, acute adrenal insufficiency, congenital adrenal hyperplasia, rheumatic fever, polyarteritis nodosa, granulomatous polyarteritis, inhibition of myeloid cell lines, immune proliferation/apoptosis, HPA axis suppression and regulation, hypercortisolemia, modulation of the Th1/Th2 cytokine balance, chronic kidney disease, stroke and spinal cord injury, hypercalcemia, hypergylcemia, acute adrenal insufficiency, chronic primary adrenal insufficiency, secondary adrenal insufficiency, congenital adrenal hyperplasia, cerebral edema, thrombocytopenia, and Little's syndrome, systemic inflammation, inflammatory bowel disease, systemic lupus erythematosus, discoid lupus erythematosus, polyartitis nodosa, Wegener's granulomatosis, giant cell arthritis, rheumatoid arthritis, osteoarthritis, hay fever, allergic rhinitis, contact dermatitis, atopic dermatitis, exfoliative dermatitis, urticaria, angioneurotic edema, chronic obstructive pulmonary disease, asthma, tendonitis, bursitis, Crohn's disease, ulcerative colitis, autoimmune chronic active hepatitis, hepatitis, cirrhosis, inflammatory scalp alopecia, panniculitis, psoriasis, inflamed cysts, pyoderma gangrenosum, pemphigus vulgaris, bullous pemphigoid, dermatomyositis, eosinophilic fasciitis, relapsing polychondritis, inflammatory vasculitis, sarcoidosis, Sweet's disease, type 1 reactive leprosy, capillary hemangiomas, lichen planus, erythema nodosum, acne, hirsutism, toxic epidermal necrolysis, erythema multiform, cutaneous T-cell lymphoma, emphysema, Alzheimer's Disease, and multiple sclerosis.

As used herein the term "congestive heart failure" (CHF) or "congestive heart disease" refers to a disease state of the cardiovascular system whereby the heart is unable to efficiently pump an adequate volume of blood to meet the requirements of the body's tissues and organ systems. Typically, CHF is characterized by left ventricular failure (systolic dysfunction) and fluid accumulation in the lungs, with the underlying cause being attributed to one or more heart or cardiovascular disease states including coronary artery disease, myocardial infarction, hypertension, diabetes, valvular heart disease, and cardiomyopathy. The term "diastolic congestive heart failure" refers to a state of CHF characterized by impairment in the ability of the heart to properly relax and fill with blood. Conversely, the term "systolic congestive heart failure" refers to a state of CHF characterized by impairment in the ability of the heart to properly contract and eject blood.

As appreciated by one of skill in the art, pathological disorders may present as a "chronic" condition, or an "acute" episode. The term "chronic", as used herein, means a condition of slow progress and long continuance. As such, a chronic condition is treated when it is diagnosed and treatment continued throughout the course of the disease. Conversely, the term "acute" means an exacerbated event or attack, of short course, followed by a period of remission. Thus, the treatment of pathological disorders contemplates both acute events and chronic conditions. In an acute event, compound is administered at the onset of symptoms and discontinued when the symptoms disappear. As described above, a chronic condition is treated throughout the course of the disease.

As used herein the term "patient" refers to a mammal, such a mouse, gerbil, guinea pig, rat, dog or human. It is understood, however, that the preferred patient is a human. As used herein, the terms "treating", "treatment", or "to treat" each mean to alleviate symptoms, eliminate the causation of resultant symptoms either on a temporary or permanent basis, and to prevent, slow the appearance, or reverse the progression or severity of resultant symptoms of the named disorder. As such, the methods of this invention encompass both therapeutic and prophylactic administration.

As used herein the term "effective amount" refers to the amount or dose of the compound, upon single or multiple dose administration to the patient, which provides the desired effect in the patient under diagnosis or treatment. An effective amount can be readily determined by the attending diagnostician, as one skilled in the art, by the use of known techniques and by observing results obtained under analogous circumstances. In determining the effective amount or dose of compound administered, a number of factors are considered by the attending diagnostician, including, but not limited to: the species of mammal; its size, age, and general health; the degree of involvement or the severity of the disease involved, the response of the individual patient; the particular compound administered; the mode of administration; the bioavailability characteristics of the preparation administered; the dose regimen selected; the use of concomitant medication; and other relevant circumstances.

A typical daily dose will contain from about 0.01 mg/kg to about 100 mg/kg of each compound used in the present method of treatment. Preferably, daily doses will be about 0.05 mg/kg to about 50 mg/kg, more preferably from about 0.1 mg/kg to about 25 mg/kg.

Oral administration is a preferred route of administering the compounds employed in the present invention whether administered alone, or as a combination of compounds capable of acting as a mineralocorticoid receptor modulator. Oral administration, however, is not the only route, nor even the only preferred route. Other preferred routes of administration include transdermal, percutaneous, pulmonary, intravenous, intramuscular, intranasal, buccal, sublingual, or intrarectal routes. Where the steroid hormone nuclear receptor modulator is administered as a combination of compounds, one of the compounds may be administered by one route, such as oral, and the other may be administered by the transdermal, percutaneous, pulmonary, intravenous, intramuscular, intranasal, buccal, sublingual, or intrarectal route, as particular circumstances require. The route of administration may be varied in any way, limited by the physical properties of the compounds and the convenience of the patient and the caregiver.

The compounds employed in the present invention may be administered as pharmaceutical compositions and, therefore, pharmaceutical compositions incorporating compounds of Formula I, and more particularly the novel compounds of Formula I, are important embodiments of the present invention. Such compositions may take any physical form that is pharmaceutically acceptable, but orally administered pharmaceutical compositions are particularly preferred. Such pharmaceutical compositions contain, as an active ingredient, an effective amount of a compound of Formula I, including the pharmaceutically acceptable salts and hydrates thereof, which effective amount is related to the daily dose of the compound to be administered. Each dosage unit may contain the daily dose of a given compound, or may contain a fraction of the daily dose, such as one-half or one-third of the dose. The amount of each compound to be contained in each dosage unit depends on the identity of the particular compound chosen for the therapy, and other factors such as the indication for which it is given. The pharmaceutical compositions of the present invention may be formulated so as to provide quick, sustained, or delayed release of the active ingredient after administration to the patient by employing well known procedures.

The following discussion provides typical procedures for preparing pharmaceutical compositions incorporating the compounds of the present invention However, the following is in no way intended to limit the scope of the pharmaceutical compositions provided by the present invention.

Compositions are preferably formulated in a unit dosage form, each dosage containing from about 1 to about 500 mg of each compound individually or in a single unit dosage form, more preferably about 5 to about 300 mg (for example 25 mg). The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

The inert ingredients and manner of formulation of the pharmaceutical compositions are conventional. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches and suspensions. In general, compositions contain from about 0.5% to about 50% of the compounds in total, depending on the desired doses and the type of composition to be used. The amount of the compound, however, is best defined as the "effective amount", that is, the amount of each compound which provides the desired dose to the patient in need of such treatment. The activity of the compounds employed in the present invention do not depend on the nature of the composition, hence, the compositions are chosen and formulated solely for convenience and economy.

Capsules are prepared by mixing the compound with a suitable diluent and filling the proper amount of the mixture in capsules. The usual diluents include inert powdered substances such as starches, powdered cellulose especially crystalline and microcrystalline cellulose, sugars such as fructose, mannitol and sucrose, grain flours, and similar edible powders.

Tablets are prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

Tablets are often coated with sugar as a flavor and sealant. The compounds may also be formulated as chewable tablets, by using large amounts of pleasant-tasting substances such as mannitol in the formulation, as is now well-established practice. Instantly dissolving tablet-like formulations are also now frequently used to assure that the patient consumes the dosage form, and to avoid the difficulty in swallowing solid objects that bothers some patients.

A lubricant is often necessary in a tablet formulation to prevent the tablet and punches from sticking in the die. The lubricant is chosen from such slippery solids as talc, magnesium and calcium stearate, stearic acid and hydrogenated vegetable oils.

Tablet disintegrators are substances which swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethylcellulose, for example, may be used, as well as sodium lauryl sulfate.

Enteric formulations are often used to protect an active ingredient from the strongly acid contents of the stomach. Such formulations are created by coating a solid dosage form with a film of a polymer which is insoluble in acid environments, and soluble in basic environments. Exemplary films are cellulose acetate phthalate, polyvinyl acetate phthalate, hydroxypropyl methylcellulose phthalate and hydroxypropyl methylcellulose acetate succinate.

When it is desired to administer the compound as a suppository, the usual bases may be used. Cocoa butter is a traditional suppository base, which may be modified by addition of waxes to raise its melting point slightly. Water-miscible suppository bases comprising, particularly, polyethylene glycols of various molecular weights are in wide use, also.

Transdermal patches have become popular recently. Typically they comprise a resinous composition in which the drugs will dissolve, or partially dissolve, which is held in contact with the skin by a film which protects the composition. Many patents have appeared in the field recently. Other, more complicated patch compositions are also in use, particularly those having a membrane pierced with innumerable pores through which the drugs are pumped by osmotic action.

It is understood by one of ordinary skill in the art that the procedures as described above can also be readily applied to a method of treating pathological disorders susceptible to steroid hormone nuclear receptor modulation, and particularly congestive heart failure.

Particular Aspects of the Methods and Uses of the Invention

The following list sets out several groupings of particular substituents and particular variables for compounds of Formula I. It will be understood that certain methods and uses as described herein, employing compounds of Formula I having such particular substituents or variables, represent particular aspects of the methods and uses of the present invention. It will be further understood that each of these groupings of particular substituents and particular variables may be combined with other provided groupings, to create still additional particular aspects of the methods and uses of the present invention.

Thus, a particular aspect of the methods and uses of the present invention is one wherein the compound to be administered is a compound of Formula I, wherein:
(a) "A" represents phenyl, pyridine, pyrimidine, pyrazine, thiophene, oxazole, imidazole, or thiazole;
(b) "A" represents a ring selected from the following

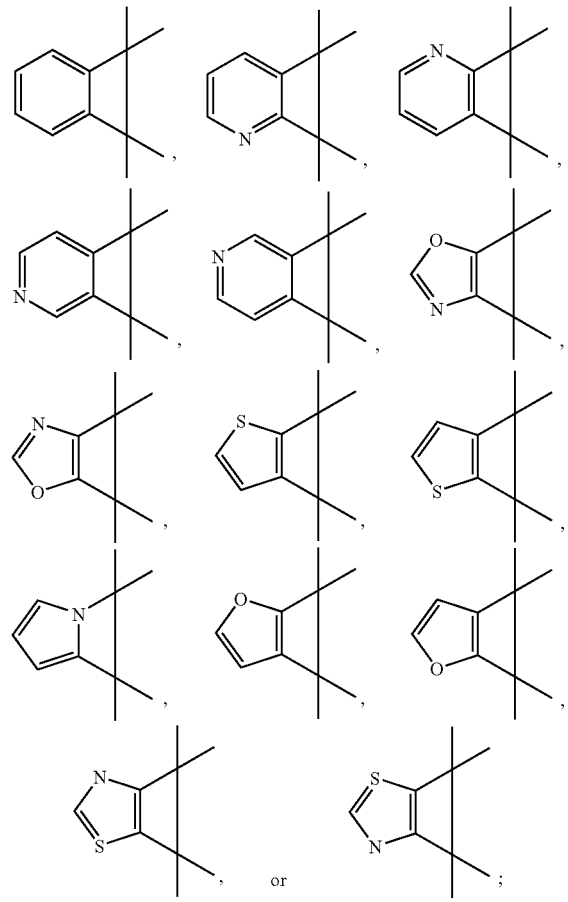

(c) "A" represents the following

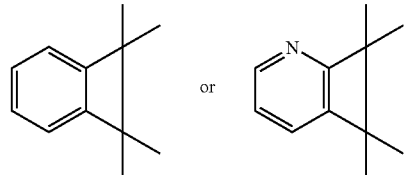

(d) "A" represents (e)

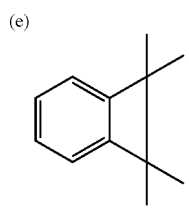

(e) "B" represents phenyl, pyridine, pyrimidine, pyrazine, thiophene, oxazole, imidazole, or thiazole;
(f) "B" represents an aryl or heterocyclic ring selected from the following

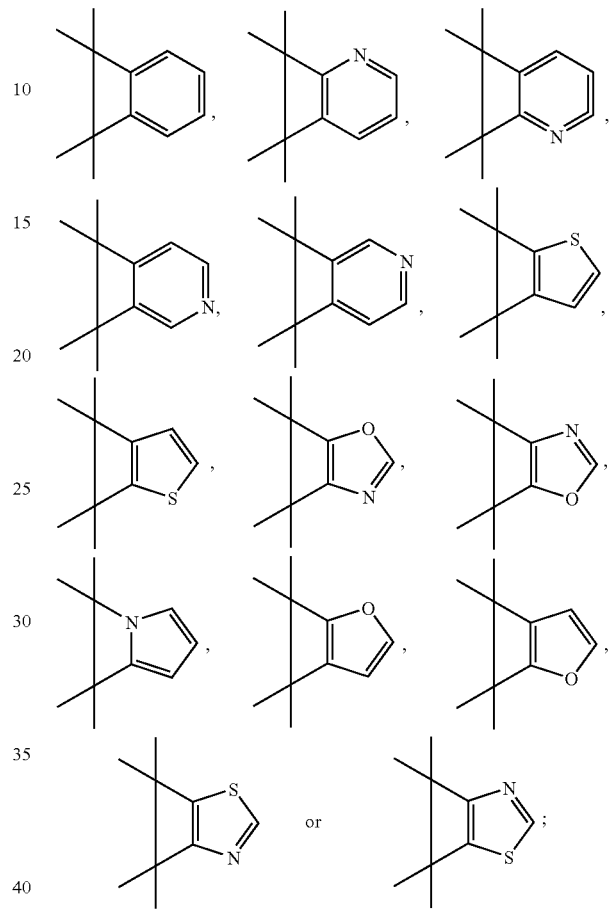

(g) "B" represents the following

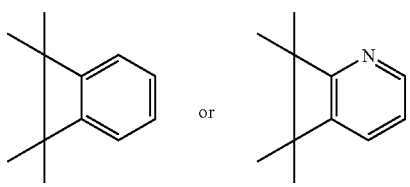

(h) "B" represents

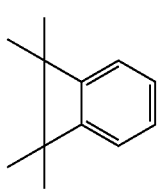

(i) C represents an aryl, heterocycle, or benzofused heterocycle selected from the following (j) C represents the following
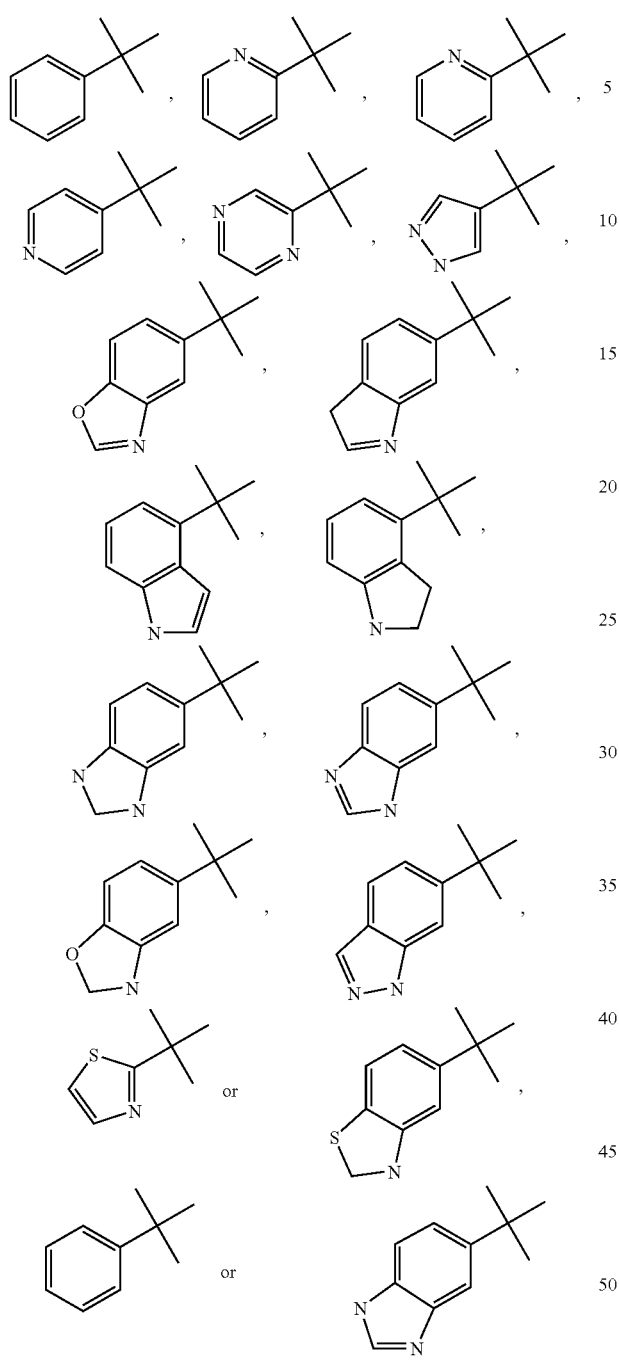
"C" represents a benzofused heterocycle having a non-hydrogen substituent at at least one of R1-R3, wherein said benzofused heterocycle having a non-hydrogen substituent is given by the following:
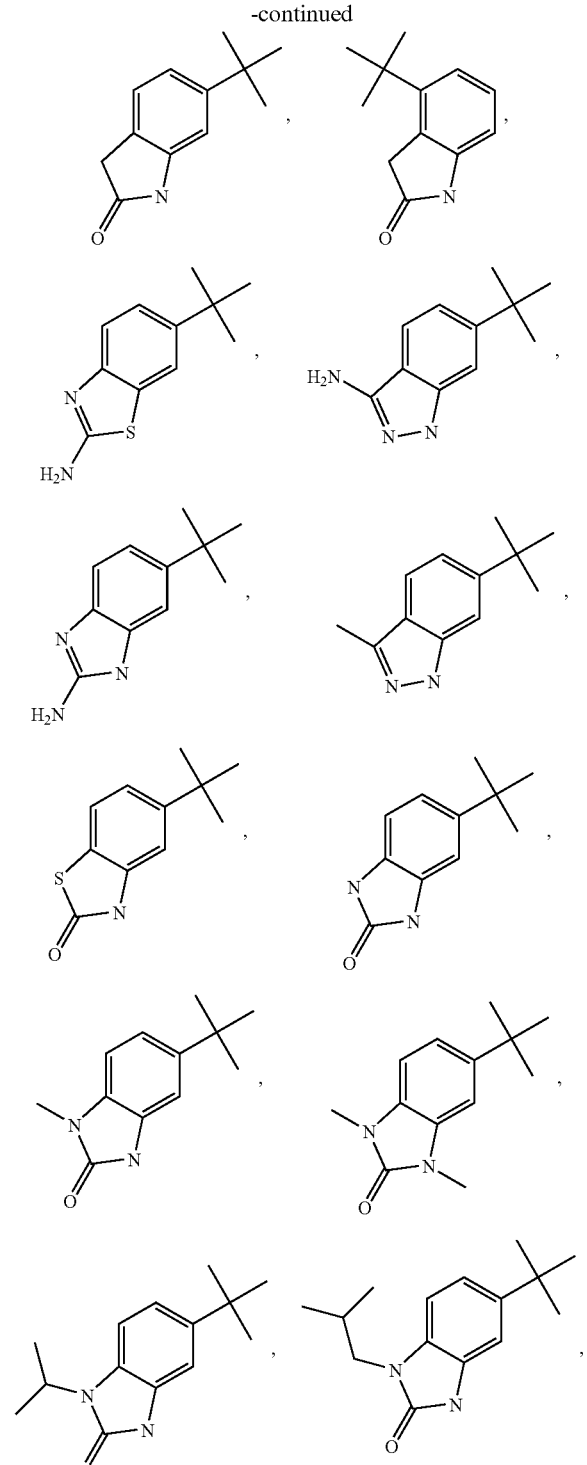

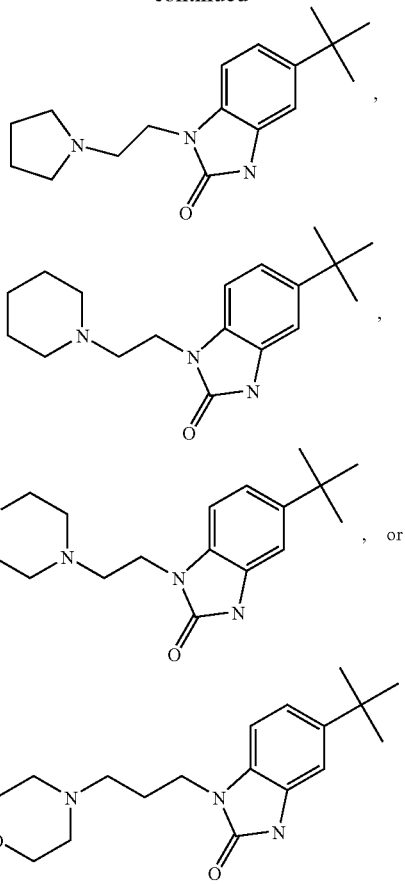

(1) "C" represents a benzofused heterocycle having a non-hydrogen substituent at at least one of R1-R3, wherein said benzofused heterocycle having a non-hydrogen substituent is given by the following:

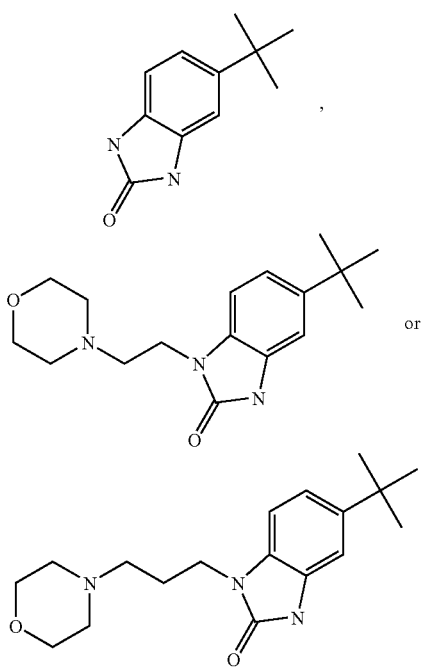

(m.) X—Y represents —$CH_2$—$CH_2$—, —$CH_2$—O—, —O—$CH_2$—, —$CH_2$—S—, —S—$CH_2$—, —$NR^{10}$—CO—, —CO—$NR^{10}$—, —$CH_2$—$NR^{10}$—, —$NR^{10}$—$CH_2$—, —CH=CH—, or a group of the formula

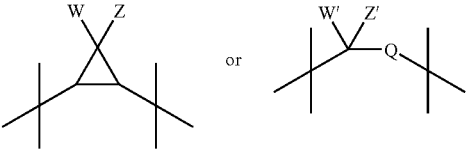

wherein W and Z each represent hydrogen, fluoro, or chloro; and W' and Z' each represent hydrogen, fluoro, chloro, or methyl, and Q represents NH, O, S, or $CH_2$;

(n) X—Y represents —$CH_2$—$CH_2$—, —$CH_2$—O—, —CH=CH—, or a group of the formula

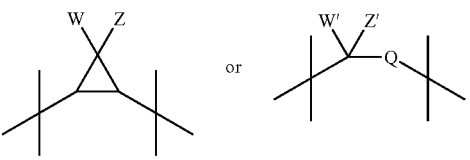

wherein W and Z each represent hydrogen, fluoro, or chloro; and W' and Z' each represent fluoro, chloro, or methyl, and Q represents NH, O, S, or $CH_2$;

(o) X—Y represents —O—$CH_2$—, —$CH_2$—S—, —S—$CH_2$—, —$NR^{10}$—CO—, —CO—$NR^{10}$—, —$CH_2$—$NR^{10}$—, or —$NR^{10}$—$CH_2$—;

(p) X—Y represents —$CH_2$—$CH_2$—;

(q) X—Y represents —$CH_2$—O—;

(r) X—Y represents —O—$CH_2$—;

(s) X—Y represents —$CH_2$—S—;

(t) X—Y represents —S—$CH_2$—;

(u) X—Y represents —$NR^{10}$—CO—;

(v) X—Y represents —$NR^{10}$—CO— wherein R10 represents hydrogen or methyl;

(w) X—Y represents —CO—$NR^{10}$—;

(x) X—Y represents —CO—$NR^{10}$— wherein R10 represents hydrogen or methyl;

(y) X—Y represents —$CH_2$—$NR^{10}$—;

(z) X—Y represents —$CH_2$—$NR^{10}$— wherein R10 represents hydrogen or methyl;

(aa) X—Y represents —$NR^{10}$—$CH_2$—;

(bb) X—Y represents —$NR^{10}$—$CH_2$— wherein R10 represents hydrogen or methyl;

(cc) X—Y represents —CH=CH—;

(dd) "$\equiv$" represents a double bond.

Additional particular aspects of the methods and uses of the present invention are those wherein the compound to be administered is a compound of Formula I, wherein $R^1$ is as follows:

(a) $R^1$ represents hydrogen, halo, hydroxy, cyano, nitro, amino, oxo, ($C_1$-$C_6$)alkyl, ($C_1$-$C_6$)alkoxy, hydroxy($C_1$-$C_6$)alkyl, hydroxy($C_1$-$C_6$)alkoxy, ($C_2$-$C_6$)alkenyl, ($C_2$-$C_6$)alkynyl, $CH_2NH_2$, halo($C_1$-$C_6$)alkyl, halo($C_1$-$C_6$)alkoxy, $SO_2NH_2$, $SO_2NR^9R^{10}$, $SO_2R^{11}$, NH $SO_2R^{11}$, N($CH_3$)$SO_2CH_3$, $CH_2NH(SO_2R^{11})$, $NR^9R^{10}$, $NHCOR^{12}$, $COR^{12}$, $CHNR^{13}$, $OR^{14}$, $SR^{14}$, $C_3$-$C_7$)cycloalkyl, heterocycle, ($C_1$-$C_4$)alkyl-heterocycle, or substituted heterocycle, provided that where "C" represents an aryl group then $R^1$ is other than oxo, $(C_2$-$C_6)$alkenyl, or $(C_2$-$C_6)$alkynyl;

(b) $R^1$ represents $SO_2R^{11}$, $N(CH_3)SO_2CH_3$, $OR^{14}$, $SR^{14}$, $(C_3$-$C_7)$cycloalkyl, $(C_1$-$C_4)$alkyl-heterocycle or oxo provided "C" does not represent an aryl group when $R^1$ is oxo;

(c) $R^1$ represents hydrogen, halo, hydroxy, cyano, nitro, amino, $(C_1$-$C_6)$alkyl, $(C_1$-$C_6)$alkoxy, hydroxy$(C_1$-$C_6)$alkyl, hydroxy$(C_1$-$C_6)$alkoxy, $(C_2$-$C_6)$alkenyl, $(C_2$-$C_6)$alkynyl, $CH_2NH_2$, halo$(C_1$-$C_6)$alkyl, halo$(C_1$-$C_6)$alkoxy, $SO_2NH_2$, $SO_2NR^9R^{10}$, $NHSO_2R^{11}$, $CH_2NH(SO_2R^{11})$, $NR^9R^{10}$, $NHCOR^{12}$, $COR^{12}$, $CHNR^{13}$, heterocycle, substituted heterocycle, provided that where "C" represents an aryl group then $R^1$ is other than $(C_2$-$C_6)$alkenyl or $(C_2$-$C_6)$alkynyl;

(d) $R^1$ represents halo, hydroxy, cyano, amino, $(C_1$-$C_6)$alkyl, $(C_1$-$C_6)$alkoxy, hydroxymethyl, $CH_2NH_2$, $CHF_2$, $CF_3$, $OCHF_2$, $OCF_3$, $SO_2NH_2$, $SO_2NR^9R^{10}$, $NHSO_2R^{11}$, $CH_2NH(SO_2R^{11})$, $NR^9R^{10}$, $NHCOR^{12}$, $COR^{12}$, $CHN(OH)$, heterocycle, substituted heterocycle;

Further particular aspects are those methods and uses wherein the compound to be administered is a compound of Formula I wherein $R^1$ is as follows:

(a) $R^1$ represents halo;
(b) $R^1$ represents bromo, chloro, or fluoro;
(c) $R^1$ represents hydroxy attached at the 3, 4, or 5 position of ring "C" when "C" represents a six-membered ring;
(d) $R^1$ represents cyano;
(e) $R^1$ represents amino;
(f) $R^1$ represents oxo provided "C" does not represent an aryl group;
(g) $R^1$ represents methyl, ethyl, propyl, or isopropyl;
(h) $R^1$ represents methyl;
(i) $R^1$ represents methoxy or ethoxy;
(j) $R^1$ represents methoxy;
(k) $R^1$ represents hydroxymethyl;
(l) $R^1$ represents aminomethyl;
(m) $R^1$ represents difluoromethyl, trifluoromethyl, difluoromethoxy, or trifluoromethoxy;
(n) $R^1$ represents difluoromethyl, trifluoromethyl, or difluoromethoxy,
(o) $R^1$ represents sulfonamido;
(p) $R^1$ represents $SO_2NR^9R^{10}$;
(q) $R^1$ represents $SO_2NR^9R^{10}$, wherein $R^9$ represents $(C_1$-$C_6)$alkyl, $(C_1$-$C_6)$alkoxy, $(C_1$-$C_4)$alkyl-$(C_1$-$C_6)$alkoxy, halo$(C_1$-$C_6)$alkyl, $(C_3$-$C_7)$cycloalkyl, aryl, substituted aryl, $(C_1$-$C_4)$alkyl-aryl, $(C_1$-$C_4)$alkyl-substituted aryl, heterocycle, substituted heterocycle, $(C_1$-$C_4)$alkyl-heterocycle, or $(C_1$-$C_4)$alkyl-substituted heterocycle and $R^{10}$ represents hydrogen or methyl, or $R^9$ and $R^{10}$ together with the nitrogen to which they are attached form a substituted or unsubstituted heterocycle;
(r) $R^1$ represents $SO_2NR^9R^{10}$, wherein $R^9$ represents $(C_1$-$C_6)$alkyl, $(C_1$-$C_4)$alkyl-$(C_1$-$C_6)$alkoxy, halo$(C_1$-$C_6)$alkyl, $(C_3$-$C_7)$cycloalkyl, aryl, $(C_1$-$C_4)$alkyl-aryl, heterocycle and $R^{10}$ represents hydrogen or methyl, or $R^9$ and $R^{10}$ together with the nitrogen to which they are attached form a substituted or unsubstituted heterocycle;
(s) $R^1$ represents N-(methyl)-sulfonamido, N-(ethyl)-sulfonamido, N,N-(dimethyl)sulfonamido, N-(propyl)sulfonamido, N-(benzyl)-sulfonamido, N-(2-methoxyethyl)sulfonamido, morpholino-sulfonyl, N-(phenyl)-sulfonamido, N-(cyclopropyl)-sulfonamido, 4-(4trifluoromethyl-phenyl)-piperidinyl sulfonamido, or N-(2,2,2-trifluoro-ethyl)-sulfonamido;

(t) $R^1$ represents $SO_2R^{11}$ wherein $R^{11}$ represents amino, $(C_1$-$C_6)$alkyl, or morpholino;
(u) $R^1$ represents $SO_2R^{11}$ wherein $R^{11}$ represents methyl;
(v) $R^1$ represents NH $SO_2R^{11}$;
(w) $R^1$ represents NH $SO_2R^{11}$ wherein $R^{11}$ represents amino, $(C_1$-$C_6)$alkyl, halo$(C_1$-$C_6)$alkyl, $(C_1$-$C_6)$alkoxy, $(C_3$-$C_7)$cycloalkyl, aryl, substituted aryl, heterocycle, or substituted heterocycle;
(x) $R^1$ represents NH $SO_2R^{11}$ wherein $R^{11}$ represents amino, $(C_1$-$C_6)$alkyl, $(C_1$-$C_6)$alkoxy, $(C_3$-$C_7)$cycloalkyl, aryl, substituted aryl, heterocycle, or substituted heterocycle;
(y) $R^1$ represents NH $SO_2R^{11}$ wherein $R^{11}$ represents $(C_1$-$C_6)$alkyl, $(C_1$-$C_6)$alkoxy, $(C_3$-$C_7)$cycloalkyl, NH—$(C_1$-$C_6)$alkylamine, aryl, substituted aryl, heterocycle, or substituted heterocycle;
(z) $R^1$ represents NH $SO_2R^{11}$ wherein $R^{11}$ represents methyl, ethyl, propyl, isopropyl, butyl, or 2-methyl propyl;
(aa) $R^1$ represents NH $SO_2R^{11}$ wherein $R^{11}$ represents methyl;
(bb) $R^1$ represents NH $SO_2R^{11}$ wherein $R^{11}$ represents methyl and wherein said NH $SO_2R^{11}$ group is attached at the 3, 4, or 5 position of ring "C" when "C" represents a six-membered ring.
(cc) $R^1$ represents NH $SO_2R^{11}$ wherein $R^{11}$ represents methyl and wherein said NH $SO_2R^{11}$ group is attached at the 3 or 5 position of ring "C" when "C" represents a six-membered ring.
(dd) $R^1$ represents NH $SO_2R^{11}$ wherein $R^{11}$ represents trifluoromethyl or difluoromethyl;
(ee) $R^1$ represents NH $SO_2R^{11}$ wherein $R^{11}$ represents cyclopropyl;
(ff) $R^1$ represents NH $SO_2R^{11}$ wherein $R^{11}$ represents phenyl;
(gg) $R^1$ represents NH $SO_2R^{11}$ wherein $R^{11}$ represents phenyl substituted one to two times with a substituent individually selected from the group consisting of methyl, methoxy, chloro, fluoro, and trifluoromethyl;
(hh) $R^1$ represents NH $SO_2R^{11}$ wherein $R^{11}$ represents 4-methylphenyl, 4-fluorophenyl, 4-chlorophenyl, 4-methoxyphenyl, 3,4-dichlorophenyl, or 3-trifluoromethylphenyl;
(ii) $R^1$ represents NH $SO_2R^{11}$ wherein $R^{11}$ represents heterocycle;
(jj) $R^1$ represents NH $SO_2R^{11}$ wherein $R^{11}$ represents thiophene or imidazole;
(kk) $R^1$ represents NH $SO_2R^{11}$ wherein $R^{11}$ represents substituted heterocycle;
(ll) $R^1$ represents NH $SO_2R^{11}$ wherein $R^{11}$ represents substituted imidazole, isoxazole, thiazole, or thiophene;
(mm) $R^1$ represents NH $SO_2R^{11}$ wherein $R^{11}$ represents substituted imidazole, isoxazole, or thiophene;
(nn) $R^1$ represents NH $SO_2R^{11}$ wherein $R^{11}$ represents 1,2-dimethyl-1H imidazole, 3,5-dimethylisoxazole, 1-methyl-1H imidazole, or 5-pyridin-2-yl-thiophene, or a group of the formula:

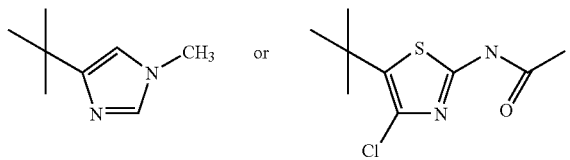

(oo) $R^1$ represents NH $SO_2R^{11}$ wherein $R^{11}$ represents 1,2-dimethyl-1H imidazole, 3,5-dimethylisoxazole, 1-methyl-1H imidazole, or 5-pyridin-2-yl-thiophene;
(pp) $R^1$ represents N(CH3)SO2CH3;
(qq) $R^1$ represents $CH_2NHSO_2CH_3$
(rr) $R^1$ represents $NR^9R^{10}$;
(ss) $R^1$ represents $NR^9R^{10}$, wherein $R^9$ represents $(C_1$-$C_6)$ alkyl or cyano and $R^{10}$ represents hydrogen or methyl;
(tt) $R^1$ represents $NR^9R^{10}$, wherein $R^9$ represents $(C_1$-$C_6)$ alkyl and $R^{10}$ represents hydrogen or methyl;
(uu) $R^1$ represents methylamine or dimethylamine;
(vv) $R^1$ represents $NHCOR^{12}$;
(ww) $R^1$ represents $NHCOR^{12}$ wherein $R^{12}$ represents H, amino, $(C_1$-$C_6)$alkyl, $(C_1$-$C_6)$alkoxy, hydroxy$(C_1$-$C_6)$ alkyl, $(C_1$-C)alkyl-$(C_1$-$C_6)$alkoxy, halo$(C_1$-$C_6)$alkyl, NH-methylamine,NH-ethylamine, or heterocycle;
(xx) $R^1$ represents $NHCOR^{12}$ wherein $R^{12}$represents H, amino, $(C_1$-$C_6)$alkyl, or heterocycle;
(yy) $R^1$ represents $NHCOR^{12}$ wherein $R^{12}$ represents H, amino,methyl, trifluoromethyl, hydroxymethyl, methoxymethyl,
(zz) $R^1$ represents $NHCOR^{12}$ wherein $R^{12}$ represents NH-methylamine, NH-ethylamine, or N,N-dimethylamine;
(aaa) $R^1$ represents acetamido, isonicotinamido, or $NHCONH_2$;
(bbb) $R^1$ represents $COR^{12}$;
(ccc) $R^1$ represents $COR^{12}$ wherein $R^{12}$ represents H, amino, $(C_1$-$C_6)$alkyl, $(C_1$-$C_6)$alkoxy, hydroxy$(C_1$-$C_6)$ alkyl;
(ddd) $R^1$ represents $COR^{12}$ wherein $R^{12}$ represents H, amino, $(C_1$-$C_6)$alkyl, or heterocycle;
(eee) $R^1$ represents $COR^{12}$ wherein $R^{12}$ represents $(C_1$-$C_6)$ alkoxy or hydroxy$(C_1$-$C_6)$alkyl;
(fff) $R^1$ represents CHO, $CONH_2$;
(ggg) $R^1$ represents $COOCH_3$;
(hhh) $R^1$ represents $COCH_2OH$;
(iii) $R^1$ represents $CONH(CH_3)$ or $CONH(CH_2CH_3)$;
(jjj) $R^1$ represents $OR^{14}$ wherein $R^{14}$ represents $(C_1$-C) alkyl-heterocycle or acetyl;
(kkk) $R^1$ represents $OR^{14}$ wherein $R^{14}$ represents acetyl;
(lll) $R^1$ represents $OR^{14}$ wherein $R^{14}$ represents a group of the formula

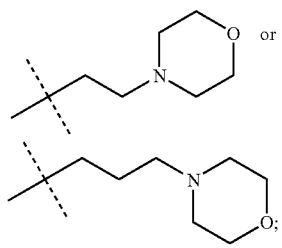

(mmm) $R^1$ represents $OR^{14}$ wherein $R^{14}$ represents a group of the formula

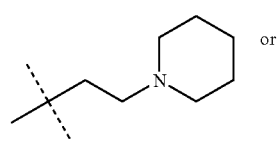

-continued

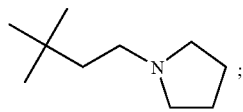

(nnn) $R^1$ represents $SR^{14}$ wherein $R^{14}$ represents methyl;
(ooo) $R^1$ represents cyclopropyl;
(ppp) $R^1$ represents heterocycle;
(qqq) $R^1$ represents pyrazine, pyridine, pyrazole, imidazole, or isoxazole;
(rrr) $R^1$ represents pyrazin-2-yl, pyridin-2-yl, 1H pyrazol-5yl, or pyridin-3-yl;
(sss) $R^1$ represents substituted heterocycle;
(ttt) $R^1$ represents substituted pyrazine, substituted pyridine, substituted pyrazole, substituted imidazole, or substituted isoxazole; or
(uuu) $R^1$ represents 4-trifluoromethyl-1H imidazolyl, 3,5-dimethyl isoxazolyl.
(aaaa) $R^1$ represents (C1-$C_4$)alkyl-heterocycle;
(bbbb) $R^1$ represents a group of the formula

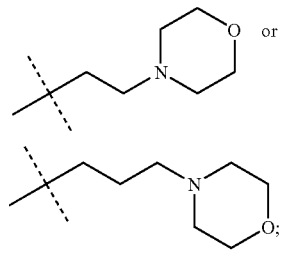

Additional particular aspects of the methods and uses of the present invention are those wherein the compound to be administered is a compound of Formula I, wherein $R^2$ is as follows:

(a) $R^2$ represents hydrogen, halo, hydroxy, cyano, amino, $(C_1$-$C_6)$alkyl, $(C_1$-$C_6)$alkoxy, hydroxymethyl, $CH_2NH_2$, halo$(C_1$-$C_6)$alkyl, halo$(C_1$-$C_6)$alkoxy, $SO_2NH_2$, $SO_2NR^9R^{10}$, NH $SO_2R^{11}$, $CH_2NH(SO_2R^{11})$, $NR^9R^{10}$, $NHCOR^{12}$, $COR^{12}$, CHN(OH), $(C_3$-$C_7)$cycloalkyl, heterocycle, $(C_1$-$C_4)$alkyl-heterocycle, or substituted heterocycle;
(b) $R^2$ represents hydrogen, $(C_3$-$C_7)$cycloalkyl, or $(C_1$-$C_4)$ alkyl-heterocycle;
(c) $R^2$ represents hydrogen, halo, hydroxy, cyano, amino, $(C_1$-$C_6)$alkyl, $(C_1$-$C_6)$alkoxy, hydroxymethyl, $CH_2NH_2$, halo$(C_1$-$C_6)$alkyl, halo$(C_1$-$C_6)$alkoxy, $SO_2NH_2$, $SO_2NR^9R^{10}$, NH $SO_2R^{11}$, $CH_2NH(SO_2R^{11})$, $NR^9R^{10}$, $NHCOR^{12}$, $COR^{12}$, CHN(OH), heterocycle, or substituted heterocycle;
(d) $R^2$ represents hydrogen, halo, hydroxy, $(C_1$-$C_6)$alkyl, $(C_1$-$C_6)$alkoxy, $CHF_2$, $CF_3$, $OCHF_2$, or $OCF_3$;

Further particular aspects are those methods and uses wherein the compound to be administered is a compound of Formula I wherein $R^2$ is as follows:

(a) $R^2$ represents halo;
(b) $R^2$ represents cyclopropyl, or a group of the formula

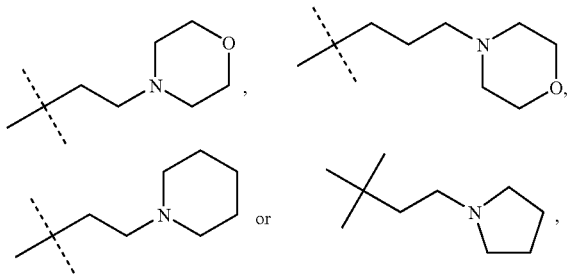

(c) $R^2$ represents cyclopropyl;
(d) $R^2$ represents a group of the formula

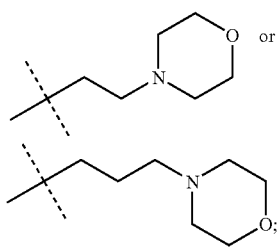

(e) $R^2$ represents a group of the formula

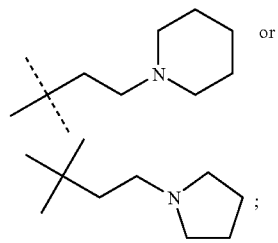

(f) $R^2$ represents bromo, chloro, or fluoro;
(g) $R^2$ represents hydroxy,
(h) $R^2$ represents $(C_1-C_6)$alkyl;
(i) $R^2$ represents methyl, isopropyl, or 2-methylpropyl;
(j) $R^2$ represents methyl;
(k) $R^2$ represents $(C_1-C_6)$alkoxy,
(l) $R^2$ represents methoxy;
(m) $R^2$ represents $CHF_2$, $CF_3$, $OCHF_2$, or $OCF_3$; or
(n) $R^2$ represents hydrogen.

Additional particular aspects of the methods and uses of the present invention are those wherein the compound to be administered is a compound of Formula I, wherein $R^3$ is as follows:
(a) $R^3$ represents hydrogen, halo, hydroxy, cyano, amino, $(C_1-C_6)$alkyl, $(C_1-C_6)$alkoxy, hydroxymethyl, $CH_2NH_2$, halo$(C_1-C_6)$alkyl, halo$(C_1-C_6)$alkoxy, $SO_2NH_2$, $SO_2NR^9R^{10}$, NH $SO_2R^{11}$, $CH_2NH(SO_2R^{11})$, $NR^9R^{10}$, $NHCOR^{12}$, $COR^{12}$, CHN(OH), heterocycle, or substituted heterocycle;
(b) $R^3$ represents hydrogen, halo, or $(C_1-C_6)$alkyl;
(c) $R^3$ represents halo;
(d) $R^3$ represents bromo, chloro, of fluoro;
(e) $R^3$ represents $(C_1-C_6)$alkyl;
(f) $R^3$ represents methyl; or
(g) $R^3$ represents hydrogen.

Additional particular aspects of the methods and uses of the present invention are those wherein the compound to be administered is a compound of Formula I, wherein $R^4$ through $R^7$ are as follows:
(a) $R^4$ through $R^7$ each independently represent hydrogen, halo, hydroxy, cyano, amino, $(C_1-C_6)$alkyl, $(C_1-C_6)$alkoxy, hydroxymethyl, $CH_2NH_2$, $CHF_2$, $CF_3$, $OCH_2$, $OCF_3$, $SO_2NH_2$, $SO_2CH_3$, $SO_2NR^9R^{11}$, NH $SO_2R^{11}$, $CH_2NH(SO_2R^{11})$, $NR^9R^{10}$, $NHCOR^{12}$, $COR^{12}$, CHN(OH), $OR^{14}$, $SR^{14}$, aryl, heterocycle, or substituted heterocycle;
(b) $R^4$ through $R^7$ each independently represent hydrogen, $SO_2NH_2$, $SO_2CH_3$, $OR^{14}$, $SR^{14}$, or aryl;
(c) $R^4$ through $R^7$ each independently represent hydrogen, halo, hydroxy, cyano, amino, $(C_1-C_6)$alkyl, $(C_1-C_6)$alkoxy, hydroxymethyl, $CH_2NH_2$, $CHF_2$, $CF_3$, $OCHF_2$, $OCF_3$, $SO_2NH_2$, $SO_2NR^9R^{10}$, NH $SO_2R^{11}$, $CH_2NH(SO_2R^{11})$, $NR^9R^{10}$, $NHCOR^{12}$, $COR^{12}$, CHN(OH), heterocycle, or substituted heterocycle;
(d) $R^4$ through $R^7$ each independently represent hydrogen, halo, hydroxy, $(C_1-C_6)$alkyl, $(C_1-C_6)$alkoxy, or $OR^{14}$.

Further particular aspects are those methods and uses wherein the compound to be administered is a compound of Formula I wherein $R^4$ through $R^7$ are as follows:
(a) $R^4$ through $R^7$ each independently represent halo;
(b) $R^4$ through $R^7$ each independently represent bromo, chloro, or fluoro;
(c) $R^4$ through $R^7$ each independently represent hydroxy;
(d) $R^4$ through $R^7$ each independently represent $(C_1-C_6)$alkyl;
(e) $R^4$ through $R^7$ each independently represent methyl, ethyl, isopropyl, or 2-methylpropyl
(f) $R^4$ through $R^7$ each independently represent methyl;
(g) $R^4$ through $R^7$ each independently represent $(C_1-C_6)$alkoxy;
(h) $R^4$ through $R^7$ each independently represent methoxy, methylethoxy, ethoxy, or propyloxy;
(i) $R^4$ through $R^7$ each independently represent methoxy;
(j) $R^4$ through $R^7$ each independently represent $OR^{14}$;
(k) $R^4$ through $R^7$ each independently represent $OR^{14}$ wherein $R^{14}$ represents $(C_1-C_4)$alkyl-aryl, $(C_1-C_4)$alkyl-substituted aryl, $(C_1-C_4)$alkyl-heterocycle, or $(C_1-C_4)$alkyl-$(C_3-C_7)$cycloalkyl;
(l) $R^4$ through $R^7$ each independently represent $OR^{14}$ wherein $R^{14}$ cyclopropylmethyl, benzyl, phenylethyl, methoxyphenyl ethyl or a group of the formula

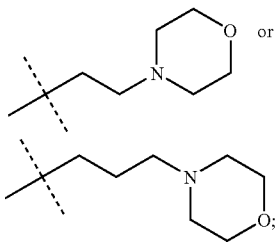

(m) $R^4$ through $R^7$ each independently represent a group of the formula

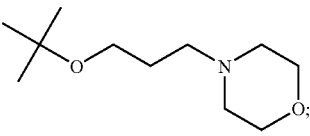

(n) $R^4$ through $R^7$ each independently represent cyclopropylmethoxy;
(o) $R^4$ through $R^7$ each independently represent trifluoromethyl, difluoromethyl, trifluoromethoxy, or difluoromethoxy;
(p) $R^4$ through $R^7$ each independently represent cyano, or amino;
(q) $R^4$ through $R^7$ each independently represent hydroxymethyl or aminomethyl;
(r) $R^4$ through $R^7$ each independently represent $SO_2NH_2$, $SO_2CH_3$, or $SCH_3$;
(s) $R^4$ through $R^7$ each independently represent $NHCOR^{12}$ or $COR^{12}$;
(t) $R^4$ through $R^7$ each independently represent $NHCOR^{12}$ or $COR^{12}$ wherein $R^{12}$ represents independently at each occurrence hydrogen, amino, methyl, or methoxy;
(u) $R^4$ through $R^7$ each independently represent phenyl;
(v) $R^4$ through $R^7$ each independently represent NH $SO_2R^{11}$;
(w) $R^4$ through $R^7$ each independently represent NH $SO_2R^{11}$ wherein $R^{11}$ represents $(C_1-C_6)$alkyl;
(x) $R^4$ through $R^7$ each independently represent NH $SO_2CH_3$;
(y) $R^4$ through $R^7$ each independently represent $NR^9R^{10}$;
(z) $R^4$ through $R^7$ each independently represent $NR^9R^{10}$ wherein $R^9$ represents methyl and $R^{10}$ represent methyl;
(aa) $R^4$ through $R^7$ each independently represent hydrogen.

Still additional particular aspects of the methods and uses of the present invention are those wherein the compound to be administered is a compound of Formula I, wherein $R^4$ and $R^6$ are as follows:

(a) $R^4$ and $R^6$ each independently represent hydrogen, halo, hydroxy, cyano, amino, $(C_1-C_6)$alkyl, $(C_1-C_6)$alkoxy, halo$(C_1-C_6)$alkyl, hydroxymethyl, $CH_2NH_2$, $SO_2NH_2$, $SO_2CH_3$, NH $SO_2R^{11}$, $NR^9R^{10}$, $NHCOR^{12}$, $COR^{12}$, $OR^{14}$, $SR^{14}$, or aryl;
(b) $R^4$ and $R^6$ each independently represent hydrogen, halo, hydroxy, cyano, amino, methyl, ethyl, propyl, isopropyl, methoxy, ethoxy, propyloxy, methylethoxy, difluoromethyl, trifluoromethyl, hydroxymethyl, $SO_2CH_3$, NH $SO_2R^{11}$ wherein R11 represents $(C_1-C_6)$alkyl, $NR^9R^{10}$ wherein $R^9$ and $R^{10}$ represents $(C_1-C_6)$alkyl, $NHCOR^{12}$ wherein $R^{12}$ represents $(C_1-C_6)$alkyl; $COR^{12}$ wherein R12 represents hydrogen, amino, or $(C_1-C_6)$alkoxy; $OR^{14}$ wherein $R^{14}$ represents $(C_1-C_4)$alkyl-$(C_3-C_7)$cycloalkyl, $(C_1-C_4)$alkyl-aryl, $(C_1-C_4)$allyl-substituted aryl, or $(C_1-C_4)$alkyl-heterocycle; $SR^{14}$ wherein $R^{14}$ represents $(C_1-C_6)$alkyl; or aryl;
(c) $R^4$ and $R^6$ each independently represent chloro, bromo, or fluoro;
(d) $R^4$ and $R^6$ each independently represent hydroxy;
(e) $R^4$ and $R^6$ each independently represent cyano, or amino;
(f) $R^4$ and $R^6$ each independently represent methyl, ethyl, propyl, or isopropyl;
(g) $R^4$ and $R^6$ each independently represent methoxy, ethoxy, propyloxy, or methylethoxy;
(h) $R^4$ and $R^6$ each independently represent difluromethyl, trifluoromethyl, or hydroxymethyl;
(i) $R^4$ and $R^6$ each independently represent $SO_2CH_3$;
(j) $R^4$ and $R^6$ each independently represent NH $SO_2CH_3$;
(k) $R^4$ and $R^6$ each independently represent dimethylamine;
(l) $R^4$ and $R^6$ each independently represent CHO, $CONH_2$, or $COOCH_3$;
(m) $R^4$ and $R^6$ each independently represent $OR^{14}$ wherein $R^{14}$ represents $(C_1-C_4)$alkyl-$(C_3-C_7)$cycloalkyl, $(C_1-C_4)$alkyl-aryl, $(C_1-C_4)$alkyl-substituted aryl, or $(C_1-C_4)$alkyl-heterocycle;
(n) $R^4$ and $R^6$ each independently represent $OR^{14}$ wherein $R^{14}$ represents cyclopropylmethyl, phenylethyl, methoxyphenyl ethyl, or a group of the formula

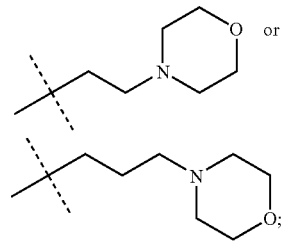

(o) $R^4$ and $R^6$ each independently represent cyclopropylmethoxy,
(p) $R^4$ and $R^6$ each independently represent a group of the formula

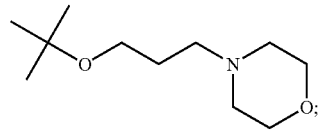

(q) $R^4$ and $R^6$ each independently represent $SCH_3$;
(r) $R^4$ and $R^6$ each independently represent phenyl; or
(s) $R^4$ and $R^6$ each independently represent hydrogen.

Still additional particular aspects of the methods and uses of the present invention are those wherein the compound to be administered is a compound of Formula I, wherein $R^5$ and $R^7$ are as follows:

(a) $R^5$ and $R^7$ each independently represent hydrogen, hydroxxy, halo, $(C_1-C_6)$alkyl, or $(C_1-C_6)$alkoxy;
(b) $R^5$ and $R^7$ each independently represent hydroxy;
(c) $R^5$ and $R^7$ each independently represent chloro, bromo, or fluoro;
(d) $R^5$ and $R^7$ each independently represent methyl, or methoxy; or
(e) $R^5$ and $R^7$ each independently represent hydrogen.

Yet additional particular aspects of the methods and uses of the present invention are those wherein the compound to be administered is a compound of Formula I, wherein $R^8$ is as follows:

(a) $R^8$ represents hydrogen, halo, $(C_1-C_6)$alkyl, hydroxy $(C_1-C_6)$alkyl, $(C_1-C_4)$alkyl -$(C_1-C_6)$alkoxy, $COR^{12}$, $(C_3-C_7)$cycloalkyl, aryl or substituted aryl;
(b) $R^8$ represents bromo, chloro, or fluoro;
(c) $R^8$ represents methyl, ethyl, propyl, isopropyl, or 2-methylpropyl;
(d) $R^8$ represents hydroxymethyl;
(e) $R^8$ represents $(C_1-C_4)$alkyl -$(C_1-C_6)$alkoxy;

(f) R⁸ represents methoxymethyl;
(g) R⁸ represents $COR^{12}$ wherein $R^{12}$ represents methoxy, ethoxy, hydroxyamethyl, or methoxymethyl;
(h) R⁸ represents $(C_3-C_7)$cycloalkyl;
(i) R⁸ represents phenyl, methoxyphenyl, methylphenyl, or phenyl-phenyl; or
(j) R⁸ represents hydrogen.

In addition, it will be understood that a most particular aspect of the methods and uses of the present invention are those wherein the compound to be administered is any compound of Formula I exemplified herein.

Particular Aspects of the Novel Compounds of the Invention

As discussed previously, certain compounds of Formula I are believed to be novel and, thus, to represent another embodiment of the present invention. The following list sets out several groupings of particular substituents and particular variables of the novel compounds of Formula I. It will be understood that novel compounds of Formula I having such particular substituents and variables represent particular aspects of the present invention. It will be further understood that each of these groupings may be combined with other provided groupings, to create still additional particular aspects of the present invention.

Thus, a particular aspect of the novel compounds of Formula I is one wherein:
(a) "A" represents phenyl, pyridine, pyrimidine, pyrazine, thiophene, oxazole, imidazole, or thiazole;
(b) "A" represents a ring selected from the following (c) "A" represents the following

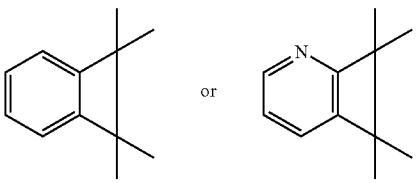

(d) "A" represents

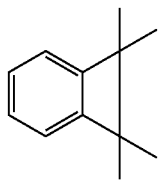

(f) "B" represents phenyl, pyridine, pyrimidine, pyrazine, thiophene, oxazole, imidazole, or thiazole;
(g) "B" represents an aryl or heterocyclic ring selected from the following

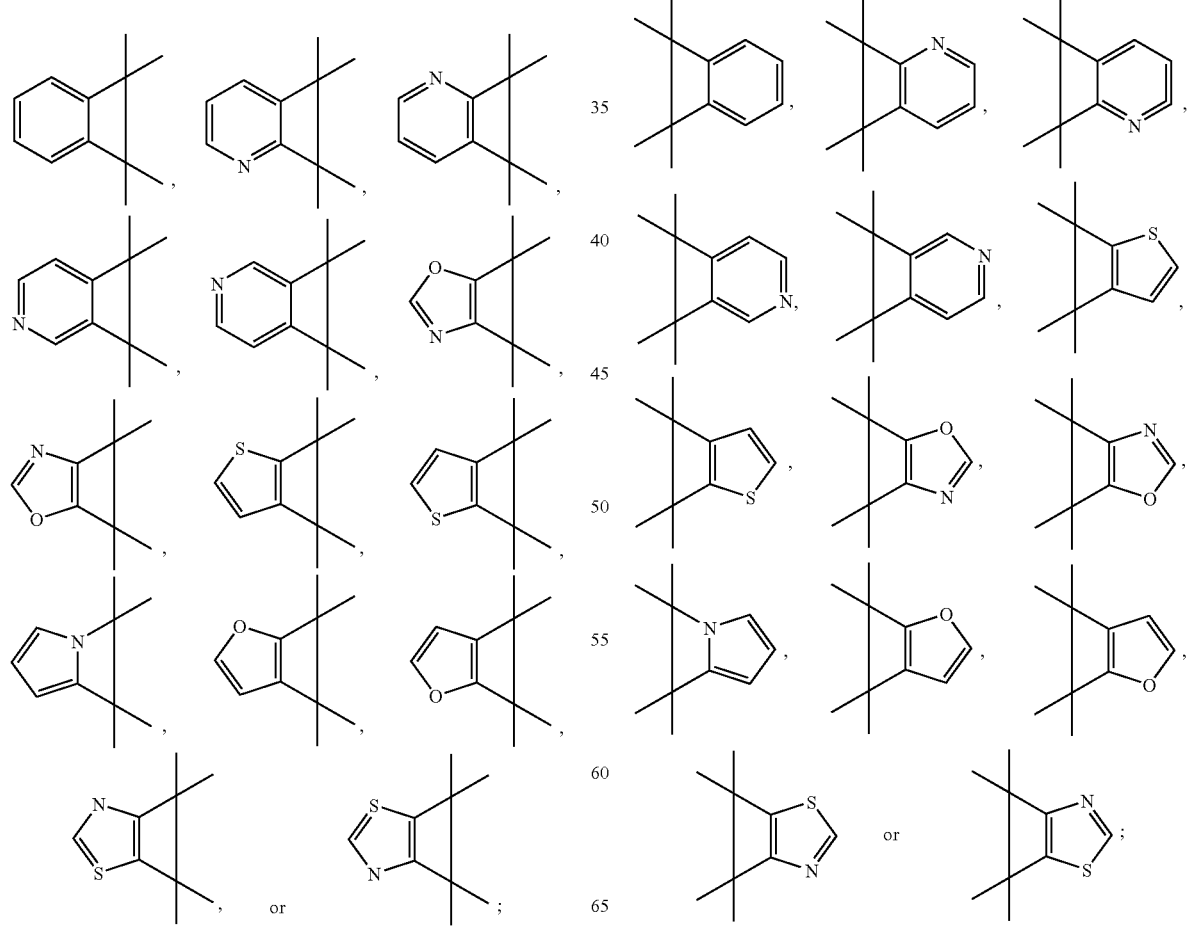

(h) "B" represents the following

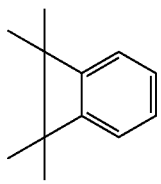 or 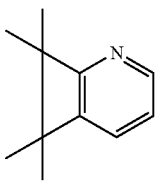

(i) "B" represents

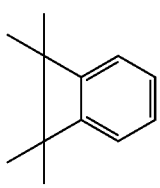

(j) "C" represents an aryl, heterocycle, or benzofused heterocycle selected from the following

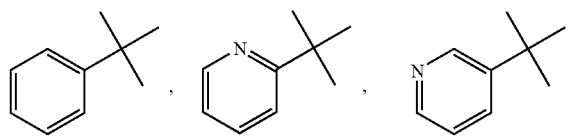

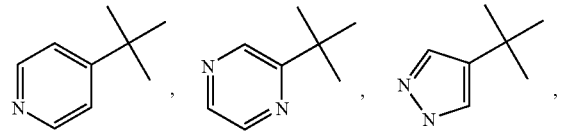

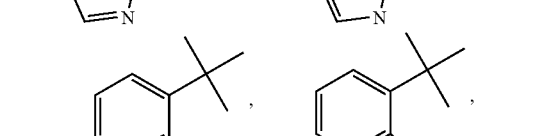

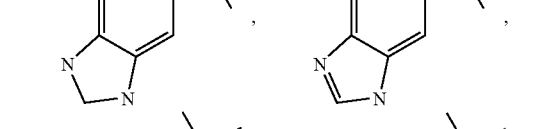

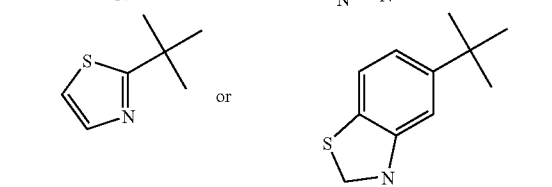

(j) "C" represents the following

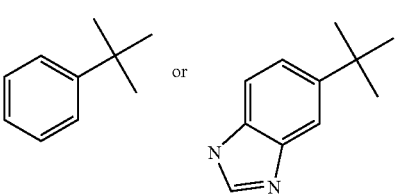

(k) "C" represents a benzofused heterocycle having a non-hydrogen substituent at at least one of R1-R3, wherein said benzofused heterocycle having a non-hydrogen substituent is given by the following:

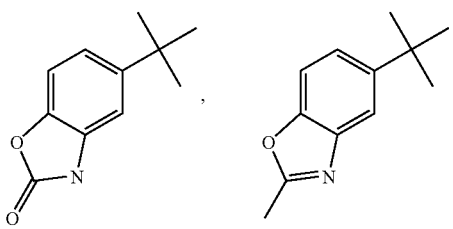

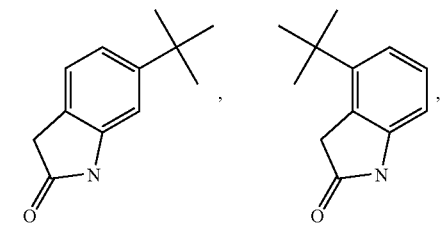

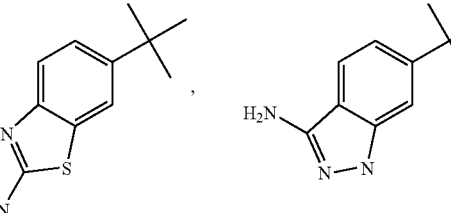

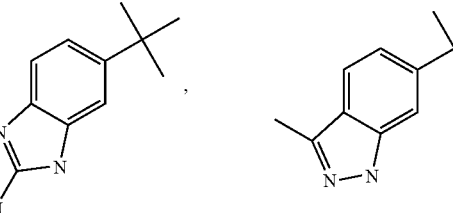

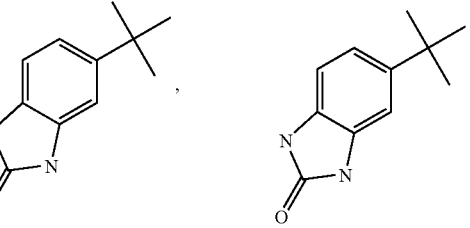

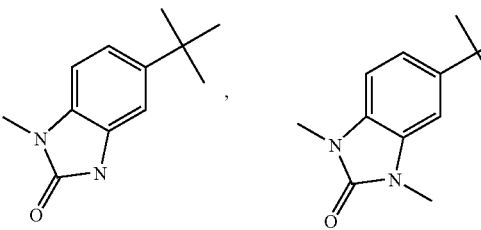

-continued

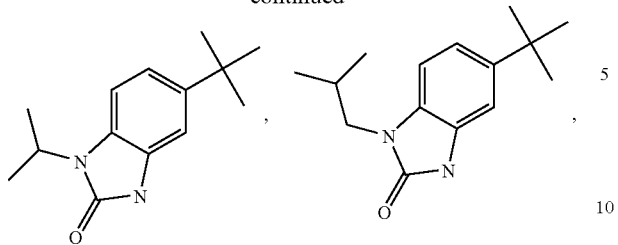

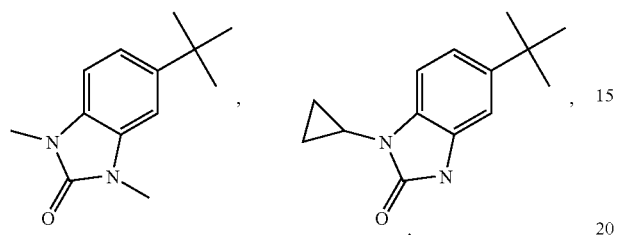

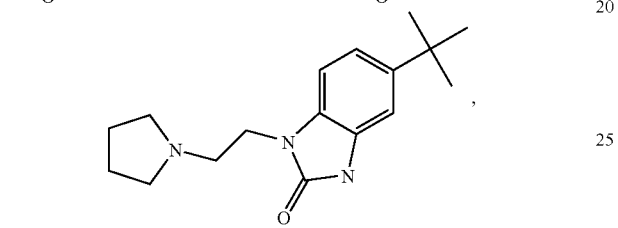

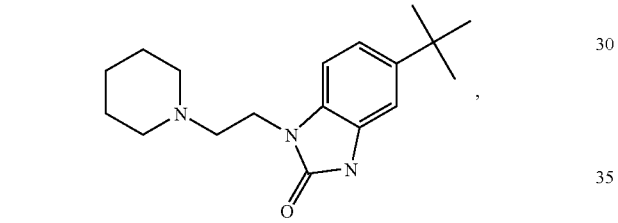

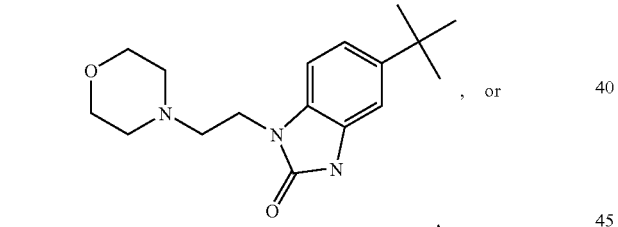

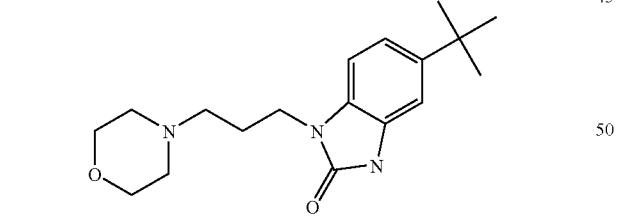, or (p) "C" represents a benzofused heterocycle having a non-hydrogen substituent at at least one of R1-R3, wherein said benzofused heterocycle having a non-hydrogen substituent is given by the following:

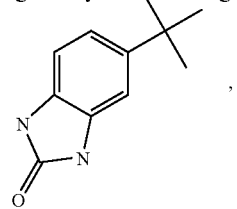,

-continued

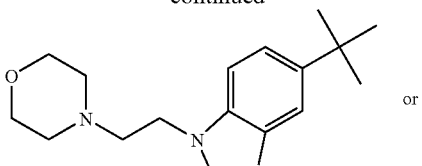 or

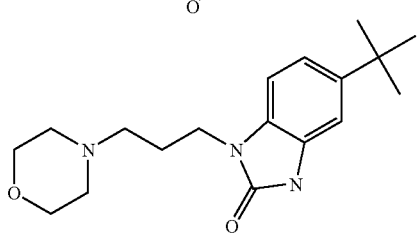

(m) X—Y represents —$CH_2$—$CH_2$—, —$CH_2$—O—, —O—$CH_2$—, —$CH_2$—S—, —S—$CH_2$—, —$NR^{10}$—CO—, —CO—$NR^{10}$—, —$CH_2$—$NR^{10}$—, —$NR^{10}$—$CH_2$—, —CH=CH—, or a group of the formula

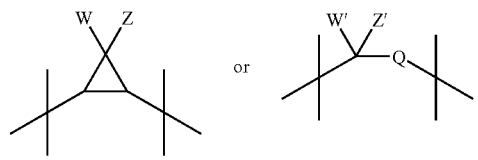

wherein W and Z each represent hydrogen, fluoro, or chloro; and W' and Z' each represent hydrogen, fluoro, chloro, or methyl, and Q represents NH, O, S, or $CH_2$;

(n) X—Y represents —$CH_2$—$CH_2$—, —$CH_2$—O—, —CH=CH—, or a group of the formula

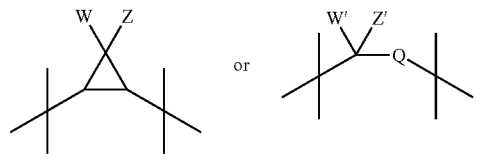

wherein W and Z each represent hydrogen, fluoro, or chloro; and W' and Z' each represent fluoro, chloro, or methyl, and Q represents NH, O, S, or $CH_2$;

(o) X—Y represents —O—$CH_2$—, —$CH_2$—S—, —S—$CH_2$—, —$NR^{10}$—CO—, —CO—$NR^{10}$—, —$CH_2$—$NR^{10}$—, or —$NR^{10}$—$CH_2$—;

(p) X—Y represents —$CH_2$—$CH_2$—;
(q) X—Y represents —$CH_2$—O—;
(r) X—Y represents —O—$CH_2$—;
(s) X—Y represents —$CH_2$—S—;
(t) X—Y represents —S—$CH_2$—;
(u) X—Y represents —$NR^{10}$—CO—;
(v) X—Y represents —$NR^{10}$—CO— wherein R10 represents hydrogen or methyl;
(w) X—Y represents —CO—$NR^{10}$—;
(x) X—Y represents —CO—$NR^{10}$— wherein R10 represents hydrogen or methyl;
(y) X—Y represents —$CH_2$—$NR^{10}$—;

(z) X—Y represents —CH$_2$—NR$^{10}$— wherein R10 represents hydrogen or methyl;
(aa) X—Y represents —NR$^{10}$—CH$_2$—;
(bb) X—Y represents —NR$^{10}$—CH$_2$— wherein R10 represents hydrogen or methyl;
(cc) X—Y represents —CH=CH—;
(dd) "$\text{---}$" represents a double bond;

Additonal particular aspects of the novel compounds of the present invention are those wherein the novel compound is a compound of Formula I, wherein R$^1$ is as follows:

(a) R$^1$ represents halo, hydroxy, cyano, nitro, amino, oxo, (C$_1$-C$_6$)alkyl, (C$_1$-C$_6$)alkoxy, hydroxy(C$_1$-C$_6$)alkyl, hydroxy(C$_1$-C$_6$)alkoxy, (C$_2$-C$_6$)alkenyl, (C$_2$-C$_6$)alkynyl, CH$_2$NH$_2$, halo(C$_1$-C$_6$)alkyl, halo(C$_1$-C$_6$)alkoxy, SO$_2$NH$_2$, SO$_2$NR$^9$R$^{10}$, SO$_2$R$^{11}$, NHSO$_2$R$^{11}$, N(CH$_3$)SO$_2$CH$_3$, CH$_2$NH(SO$_2$R$^{11}$), NR$^9$R$^{10}$, NHCOR$^{12}$, COR$^{12}$, CHNR$^{13}$, OR$^{14}$, SR$^{14}$, (C$_3$-C$_7$)cycloalkyl, heterocycle, (C$_1$-C$_4$)alkyl-heterocycle, or substituted heterocycle, provided that where "C" represents an aryl group then R$^1$ is other than oxo, (C$_2$-C$_6$)alkenyl or (C$_2$-C$_6$)alkynyl; further provided that where "C" represents a phenyl ring and R$^1$ represents halo then at least one of R$^2$ and R$^3$ is other than hydrogen, (C$_1$-C$_6$)alkyl, aryl, substituted aryl, (C$_1$-C$_4$)alkyl-aryl, (C$_1$-C$_4$)alkyl-substituted aryl, CHF$_2$, or CF$_3$; further provided that where "C" represents a benzo-fused heterocycle then R$^1$ may also represent hydrogen further provided that where "C" represents a six-membered ring and R$^1$ represents cyano, amino, NR$^9$R$^{10}$, or NHCOCH$_3$ and R$^2$ and R$^3$ are each hydrogen, then R$^1$ is not bound at the 4-position of said six-membered ring; further provided that where "C" represents a six-membered ring and R$^1$ represents nitro, and R$^2$ and R$^3$ are each hydrogen, then R$^1$ is not bound at the 2, 4, or 6-position of said six-membered ring;

(b) R$^1$ represents SO$_2$R$^{11}$, N(CH$_3$)SO$_2$CH$_3$, OR$^{14}$, SR$^{14}$, (C$_3$-C$_7$)cycloalkyl, (C$_1$-C$_4$)alkyl-heterocycle or oxo provided "C" does not represent an aryl group when R$^1$ is oxo;

(c) R$^1$ represents halo, hydroxy, cyano, nitro, amino, (C$_1$-C$_6$)alkyl, (C$_1$-C$_6$)alkoxy, hydroxy(C$_1$-C$_6$)alkyl, hydroxy(C$_1$-C$_6$)alkoxy, (C$_2$-C$_6$)alkenyl, (C$_2$-C$_6$)alkynyl, CH$_2$NH$_2$, halo(C$_1$-C$_6$)alkyl, halo(C$_1$-C$_6$)alkoxy, SO$_2$NH$_2$, SO$_2$NR$^9$R$^{10}$, NHSO$_2$R$^{11}$, CH$_2$NH(SO$_2$R$^{11}$), NR$^9$R$^{10}$, NHCOR$^{12}$, COR$^{13}$, CHNR$^{13}$, heterocycle, or substituted heterocycle, provided that where "C" represents an aryl group then R$^1$ is other than (C$_2$-C$_6$)alkenyl or (C$_2$-C$_6$)alkynyl; further provided that where "C" represents a phenyl ring and R$^1$ represents halo then at least one of R$^2$ and R$^3$ is other than hydrogen, (C$_1$-C$_6$)alkyl, aryl, substituted aryl, (C$_1$-C$_4$)alkyl-aryl, (C$_1$-C$_4$)alkyl-substituted aryl, CHF$_2$, or CF$_3$; further provided that where "C" represents a benzo-fused heterocycle then R$^1$ may also represent hydrogen further provided that where "C" represents a six-membered ring and R$^1$ represents cyano, amino, NR$^9$R$^{10}$, or NHCOCH$_3$ and R$^2$ and R$^3$ are each hydrogen, then R$^1$ is not bound at the 4-position of said six-membered ring; further provided that where "C" represents a six-membered ring and R$^1$ represents nitro, and R$^2$ and R$^3$ are each hydrogen, then R$^1$ is not bound at the 2, 4, or 6-position of said six-membered ring;

(d) R$^1$ represents halo, hydroxy, cyano, amino, (C$_1$-C$_6$)alkyl, (C$_1$-C$_6$)alkoxy, hydroxymethyl, CH$_2$NH$_2$, CHF$_2$, CF$_3$, OCHF$_2$, OCF$_3$, SO$_2$NH$_2$, SO$_2$NR$^9$R$^{10}$, NHSO$_2$R$^{11}$, CH$_2$NH(SO$_2$R$^{11}$), NR$^9$R$^{10}$, NHCOR$^{12}$, COR$^{12}$, CHN(OH), heterocycle, substituted heterocycle, provided that where "C" represents a phenyl ring and R$^1$ represents halo then at least one of R$^2$ and R$^3$ is other than hydrogen, (C$_1$-C$_6$)alkyl, aryl, substituted aryl, (C$_1$-C$_4$)alkyl-aryl, (C$_1$-C$_4$)alkyl-substituted aryl, CHF$_2$, or CF$_3$; further provided that where "C" represents a benzo-fused heterocycle then R$^1$ may also represent hydrogen;

further provided that where "C" represents a six-membered ring and R$^1$ represents cyano, amino, NR$^9$R$^{10}$, or NHCOCH$_3$ and R$^2$ and R$^3$ are each hydrogen, then R$^1$ is not bound at the 4-position of said six-membered ring;

Further particular aspects are those methods and uses wherein the compound to be administered is a compound of Formula I wherein R$^1$ is as follows:

(a) R$^1$ represents halo provided that where "C" represents a phenyl ring then at least one of R$^2$ and R$^3$ is other than hydrogen, (C$_1$-C$_6$)alkyl, aryl, substituted aryl, (C$_1$-C$_4$)alkyl-aryl, (C$_1$-C$_4$)alkyl-substituted aryl, CHF$_2$, or CF$_3$;

(b) R$^1$ represents bromo, chloro, or fluoro provided that where "C" represents a phenyl ring then at least one of R$^2$ and R$^3$ is other than hydrogen, (C$_1$-C$_6$)alkyl, aryl, substituted aryl, (C$_1$-C$_4$)alkyl-aryl, (C$_1$-C$_4$)alkyl-substituted aryl, CHF$_2$, or CF$_3$;

(c) R$^1$ represents hydroxy attached at the 3, 4, or 5 position of ring "C" when "C" represents a six-membered ring;

(d) R$^1$ represents cyano provided that where "C" represents a six-membered ring and R$^2$ and R$^3$ are each hydrogen, then R$^1$ is not bound at the 4-position of said six-membered ring;

(e) R$^1$ represents amino provided that where "C" represents a six-membered ring and R$^2$ and R$^3$ are each hydrogen, then R$^1$ is not bound at the 4-position of said six-membered ring;

(f) R$^1$ represents oxo provided "C" does not represent an aryl group;

(g) R$^1$ represents methyl, ethyl, propyl, or isopropyl;

(h) R$^1$ represents methyl;

(i) R$^1$ represents methoxy or ethoxy, (j) R$^1$ represents methoxy;

(k) R$^1$ represents hydroxymethyl;

(l) R$^1$ represents aminomethyl;

(m) R$^1$ represents difluoromethyl, trifluoromethyl difluoromethoxy, or trifluoromethoxy, (n) R$^1$ represents difluoromethyl, trifluoromethyl, or difluoromethoxy;

(o) R$^1$ represents sulfonamido;

(p) R$^1$ represents SO$_2$NR$^9$R$^{10}$;

(q) R$^1$ represents SO$_2$NR$^9$R$^{10}$, wherein R$^9$ represents (C$_1$-C$_6$)alkyl, (C$_1$-C$_6$)alkoxy, (C$_1$-C$_4$)alkyl-(C$_1$-C$_6$)alkoxy, halo(C$_1$-C$_6$)alkyl, (C$_3$-C$_7$)cycloalkyl, aryl, substituted aryl, (C$_1$-C$_4$)alkyl-aryl, (C$_1$-C$_4$)alkyl-substituted aryl, heterocycle, substituted heterocycle, (C$_1$-C$_4$)alkyl-heterocycle, or (C$_1$-C$_4$)alkyl-substituted heterocycle and R$^{10}$ represents hydrogen or methyl, or R$^9$ and R$^{10}$ together with the nitrogen to which they are attached form a substituted or unsubstituted heterocycle;

(r) R$^1$ represents SO$_2$NR$^9$R$^{10}$, wherein R$^9$ represents (C$_1$-C$_6$)alkyl, (C$_1$-C$_4$)alkyl-(C$_1$-C$_6$)alkoxy, halo(C$_1$-C$_6$)alkyl, (C$_3$-C$_7$)cycloalkyl, aryl, (C$_1$-C$_4$)alkyl-aryl, heterocycle and R$^{10}$ represents hydrogen or methyl, or R$^9$ and R$^{10}$ together with the nitrogen to which they are attached form a substituted or unsubstituted heterocycle;

(s) R$^1$ represents N-(methyl)-sulfonamido, N-(ethyl)-sulfonamido, N,N-(dimethyl) sulfonamido, N-(propyl) sulfonamido, N-(benzyl)-sulfonamido, N-(2-methoxy ethyl) sulfonamido, morpholino-sulfonyl, N-(phenyl)-sulfonamido, N-(cyclopropyl)-sulfonamido, 4-(4-trifluoromethyl-phenyl)-piperidinyl sulfonamido, or N-(2,2,2-trifluoro-ethyl)-sulfonamido;

(t) $R^1$ represents $SO_2R^{11}$ wherein $R^{11}$ represents amino, $(C_1-C_6)$alkyl, or morpholino;

(u) $R^1$ represents $SO_2R^{11}$ wherein $R^{11}$ represents methyl;

(v) $R^1$ represents NH $SO_2R^{11}$;

(w) $R^1$ represents NH $SO_2R^{11}$ wherein $R^{11}$ represents amino, halo$(C_1-C_6)$alkyl, $(C_1-C_6)$alkyl, $(C_1-C_6)$alkoxy, $(C_3-C_7)$cycloalkyl, aryl, substituted aryl, heterocycle, or substituted heterocycle;

(x) $R^1$ represents NH $SO_2R^{11}$ wherein $R^{11}$ represents amino, $(C_1-C_6)$alkyl, $(C_1-C_6)$alkoxy, $(C_3-C_7)$cycloalkyl, aryl, substituted aryl, heterocycle, or substituted heterocycle;

(y) $R^1$ represents NH $SO_2R^{11}$ wherein $R^{11}$ represents $(C_1-C_6)$alkyl, $(C_1-C_6)$alkoxy, $(C_3-C_7)$cycloalkyl, aryl, substituted aryl, heterocycle, or substituted heterocycle;

(z) $R^1$ represents NH $SO_2R^{11}$ wherein $R^{11}$ represents methyl, ethyl, propyl, isopropyl, butyl, or 2-methyl propyl;

(aa) $R^1$ represents NH $SO_2R^{11}$ wherein $R^{11}$ represents methyl;

(bb) $R^1$ represents NH $SO_2R^{11}$ wherein $R^{11}$ represents methyl and wherein said NH $SO_2R^{11}$ group is attached at the 3, 4, or 5 position of ring "C" when "C" represents a six-membered ring.

(cc) $R^1$ represents NH $SO_2R^{11}$ wherein $R^{11}$ represents methyl and wherein said NH $SO_2R^{11}$ group is attached at the 3 or 5 position of ring "C" when "C" represents a six-membered ring.

(dd) $R^1$ represents NH $SO_2R^{11}$ wherein $R^{11}$ represents trifluoromethyl or difluoromethyl;

(ee) $R^1$ represents NH $SO_2R^{11}$ wherein $R^{11}$ represents cyclopropyl;

(ff) $R^1$ represents NH $SO_2R^{11}$ wherein $R^{11}$ represents phenyl;

(gg) $R^1$ represents NH $SO_2R^{11}$ wherein $R^{11}$ represents phenyl substituted one to two times with a substituent individually selected from the group consisting of methyl, methoxy, chloro, fluoro, and trifluoromethyl;

(h) $R^1$ represents NH $SO_2R^{11}$ wherein $R^{11}$ represents 4-methylphenyl, 4-fluorophenyl, 4-chlorophenyl, 4-methoxyphenyl, 3,4-dichlorophenyl, or 3-trifluoromethylphenyl;

(ii) $R^1$ represents NH $SO_2R^{11}$ wherein $R^{11}$ represents heterocycle;

(jj) $R^1$ represents NH $SO_2R^{11}$ wherein $R^{11}$ represents thiophene or imidazole;

(kk) $R^1$ represents NH $SO_2R^{11}$ wherein $R^{11}$ represents substituted heterocycle;

(ll) $R^1$ represents NH $SO_2R^{11}$ wherein $R^{11}$ represents substituted imidazole, isoxazole, thiazole or thiophene;

(mm) $R^1$ represents NH $SO_2R^{11}$ wherein $R^{11}$ represents substituted imidazole, isoxazole, or thiophene;

(nn) $R^1$ represents NH $SO_2R^{11}$ wherein $R^{11}$ represents 1,2-dimethyl-1H imidazole, 3,5-dimethylisoxazole, 1-methyl-1H imidazole, or 5-pyridin-2-yl-thiophene, or a group of the formula:

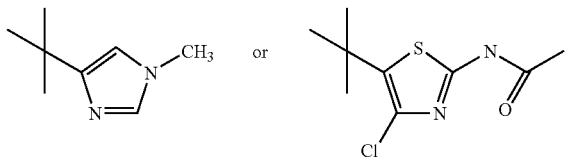

(oo) $R^1$ represents NH $SO_2R^{11}$ wherein $R^{11}$ represents 1,2-dimethyl-1H imidazole, 3,5-dimethylisoxazole, 1-methyl-1H imidazole, or 5-pyridin-2-yl-thiophene;

(pp) $R^1$ represents N(CH3)SO2CH3;

(qq) $R^1$ represents $CH_2NHSO_2CH_3$ (rr) $R^1$ represents $NR^9R^{10}$ provided that where "C" represents a six-membered ring and $R^2$ and $R^3$ are each hydrogen, then $R^1$ is not bound at the 4-position of said six-membered ring;

(ss) $R^1$ represents $NR^9R^{10}$, wherein $R^9$ represents $(C_1-C_6)$alkyl or cyano and $R^{10}$ represents hydrogen or methyl provided that where "C" represents a six-membered ring and $R^2$ and $R^3$ are each hydrogen, then $R^1$ is not bound at the 4-position of said six-membered ring;

(tt) $R^1$ represents $NR^9R^{10}$, wherein $R^9$ represents $(C_1-C_6)$alkyl and $R^{10}$ represents hydrogen or methyl provided that where "C" represents a six-membered ring and $R^2$ and $R^3$ are each hydrogen, then $R^1$ is not bound at the 4-position of said six-membered ring;

(uu) $R^1$ represents $NR^9R^{10}$, wherein $R^9$ represents $(C_1-C_6)$alkyl and $R^{10}$ represents hydrogen or methyl provided that where "C" represents a six-membered ring and $R^2$ and $R^3$ are each hydrogen, then $R^1$ is not bound at the 4-position of said six-membered ring;

(vv) $R^1$ represents methylamine or dimethylamine, provided that where "C" represents a six-membered ring and $R^2$ and $R^3$ are each hydrogen, then $R^1$ is not bound at the 4-position of said six-membered ring;

(ww) $R^1$ represents $NHCOR^{12}$ provided that where "C" represents a six-membered ring and $R^2$ and $R^3$ are each hydrogen, then $R^1$ is not bound at the 4-position of said six-membered ring when $R^1$ represents $NHCOCH_3$;

(xx) $R^1$ represents $NHCOR^{12}$ wherein $R^{12}$ represents H, amino, $(C_1-C_6)$alkyl, $(C_1-C_6)$alkoxy, hydroxy$(C_1-C_6)$alkyl, $(C_1-C)$alkyl-$(C_1-C_6)$alkoxy, halo$(C_1-C_6)$alkyl, NH-methylamine, NH-ethylamine, or heterocycle, provided that where "C" represents a six-membered ring and $R^2$ and $R^3$ are each hydrogen, then $R^1$ is not bound at the 4-position of said six-membered ring when $R^1$ represents $NHCOCH_3$;

(yy) $R^1$ represents $NHCOR^{12}$ wherein $R^{12}$ represents H, amino, $(C_1-C_6)$alkyl, or heterocycle provided that where "C" represents a six-membered ring and $R^2$ and $R^3$ are each hydrogen, then $R^1$ is not bound at the 4-position of said six-membered ring when $R^1$ represents $NHCOCH_3$;

(zz) $R^1$ represents $NHCOR^{12}$ wherein $R^{12}$ represents H, amino, methyl, trifluoromethyl, hydroxymethyl, methoxymethyl, provided that where "C" represents a six-membered ring and $R^2$ and $R^3$ are each hydrogen, then $R^1$ is not bound at the 4-position of said six-membered ring when $R^1$ represents $NHCOCH_3$;

(aaa) $R^1$ represents $NHCOR^{12}$ wherein $R^{12}$ represents NH-methylamine, NH-ethylamine, or N,N-dimethylamine;

(bbb) $R^1$ represents $NHCOCH_3$, isonicotinamido, or $NHCONH_2$ provided that where "C" represents a six-membered ring and $R^2$ and $R^3$ are each hydrogen, then $R^1$ is not bound at the 4-position of said six-membered ring when $R^1$ represents $NHCOCH_3$;
(ccc) $R^1$ represents $COR^{12}$;
(ddd) $R^1$ represents $COR^{12}$ wherein $R^{12}$ represents H, amino, $(C_1-C_6)$alkyl, $(C_1-C_6)$alkoxy, hydroxy$(C_1-C_6)$alkyl;
(eee) $R^1$ represents $COR^{12}$ wherein $R^{12}$ represents H, amino, $(C_1-C_6)$alkyl, or heterocycle;
(fff) $R^1$ represents $COR^{12}$ wherein $R^{12}$ represents $(C_1-C_6)$alkoxy or hydroxy$(C_1-C_6)$alkyl;
(ggg) $R^1$ represents CHO, $CONH_2$;
(hhh) $R^1$ represents $COOCH_3$;
(iii) $R^1$ represents $COCH_2OH$;
(jjj) $R^1$ represents $CONH(CH_3)$ or $CONH(CH_2CH_3)$;
(kkk) $R^1$ represents $OR^{14}$ wherein $R^{14}$ represents $(C_1-C)$alkyl-heterocycle or acetyl;
(lll) $R^1$ represents $OR^{14}$ wherein $R^{14}$ represents acetyl;
(mmm) $R^1$ represents $OR^{14}$ wherein $R^{14}$ represents a group of the formula

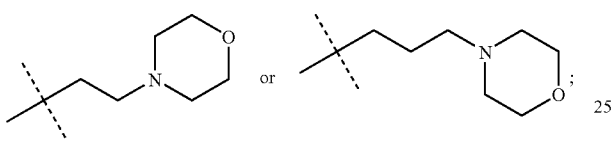

(nnn) $R^1$ represents $OR^{14}$ wherein $R^{14}$ represents a group of the formula

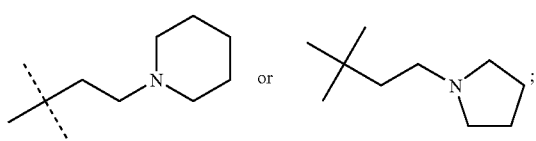

(ooo) $R^1$ represents $SR^{14}$ wherein $R^{14}$ represents methyl;
(ppp) $R^1$ represents cyclopropyl;
(qqq) $R^1$ represents heterocycle;
(rrr) $R^1$ represents pyrazine, pyridine, pyrazole, imidazole, or isoxazole;
(sss) $R^1$ represents pyrazin-2-yl, pyridin-2-yl, 1H pyrazol-5yl, or pyridin-3-yl;
(ttt) $R^1$ represents substituted heterocycle;
(uuu) $R^1$ represents substituted pyrazine, substituted pyridine, substituted pyrazole, substituted imidazole, or substituted isoxazole; or
(vvv) $R^1$ represents 4-trifluoromethyl-1H imidazolyl, 3,5-dimethyl isoxazolyl.
(www) $R^1$ represents $(C1-C_4)$alkyl-heterocycle;
(xxx) $R^1$ represents a group of the formula

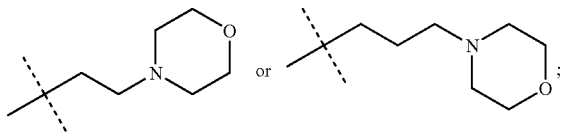

Additional particular aspects of the novel compounds of the present invention are those wherein the compound of Formula I is one wherein $R^2$ is as follows:
(a) $R^2$ represents hydrogen, halo, hydroxy, cyano, amino, $(C_1-C_6)$alkyl, $(C_1-C_6)$alkoxy, hydroxymethyl, $CH_2NH_2$, halo$(C_1-C_6)$alkyl, halo$(C_1-C_6)$alkoxy, $SO_2NH_2$, $SO_2NR^9R^{10}$, $NH\,SO_2R^{11}$, $CH_2NH(SO_2R^{11})$, $NR^9R^{10}$, $NHCOR^{12}$, $COR^{12}$, $CHN(OH)$, $(C_3-C_7)$cycloalkyl, heterocycle, $(C_1-C_4)$alkyl-heterocycle, or substituted heterocycle;
(b) $R^2$ represents hydrogen, $(C_3-C_7)$cycloalkyl, or $(C_1-C_4)$alkyl-heterocycle;
(c) $R^2$ represents hydrogen, halo, hydroxy, cyano, amino, $(C_1-C_6)$alkyl, $(C_1-C_6)$alkoxy, hydroxymethyl, $CH_2NH_2$, halo$(C_1-C_6)$alkyl, halo$(C_1-C_6)$alkoxy, $SO_2NH_2$, $SO_2NR^9R^{10}$, $NH\,SO_2R^{11}$, $CH_2NH(SO_2R^{11})$, $NR^9R^{10}$, $NHCOR^{12}$, $COR^{12}$, $CHN(OH)$, heterocycle, or substituted heterocycle;
(d) $R^2$ represents hydrogen, halo, hydroxy, $(C_1-C_6)$alkyl, $(C_1-C_6)$alkoxy, $CHF_2$, $CF_3$, $OCHF_2$, or $OCF_3$;

Further particular aspects are those novel compounds wherein the compound of Formula I is one wherein $R^2$ is as follows:
(a) $R^2$ represents halo;
(b) $R^2$ represents cyclopropyl, or a group of the formula

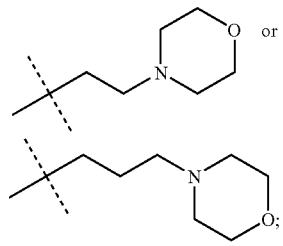

(c) $R^2$ represents cyclopropyl;
(d) $R^2$ represents a group of the formula

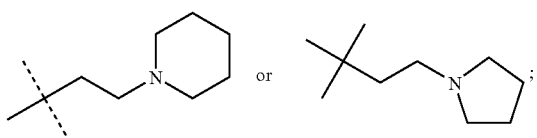

(e) $R^2$ represents a group of the formula

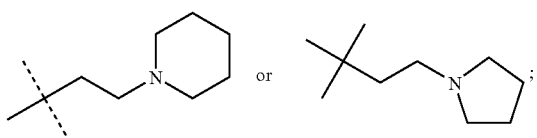

(f) $R^2$ represents bromo, chloro, or fluoro;
(g) $R^2$ represents hydroxy;
(h) $R^2$ represents $(C_1-C_6)$alkyl;
(i) $R^2$ represents methyl, isopropyl, or 2-methylpropyl;
(j) $R^2$ represents methyl;
(k) $R^2$ represents $(C_1-C_6)$alkoxy,
(l) $R^2$ represents methoxy,
(m) $R^2$ represents $CHF_2$, $CF_3$, $OCHF_2$, or $OCF_3$; or
(n) $R^2$ represents hydrogen.

Additional particular aspects of the novel compounds of the present invention are those wherein the compound of Formula I is one wherein $R^3$ is as follows:

(a) $R^3$ represents hydrogen, halo, hydroxy, cyano, amino, $(C_1-C_6)$alkyl, $(C_1-C_6)$alkoxy, hydroxymethyl, $CH_2NH_2$, halo$(C_1-C_6)$alkyl, halo$(C_1-C_6)$alkoxy, $SO_2NH_2$, $SO_2NR^9R^{10}$, NH $SO_2R^{11}$, $CH_2NH(SO_2R^{11})$, $NR^9R^{10}$, $NHCOR^{12}$, $COR^{12}$, CHN(OH), heterocycle, or substituted heterocycle;

(b) $R^3$ represents hydrogen, halo, or $(C_1-C_6)$alkyl;

(c) $R^3$ represents halo;

(d) $R^3$ represents bromo, chloro, of fluoro;

(e) $R^3$ represents $(C_1-C_6)$alkyl;

(f) $R^3$ represents methyl; or (g) $R^3$ represents hydrogen.

Additional particular aspects of the novel compounds of the present invention are those wherein the compound of Formula I is one wherein $R^4$ through $R^7$ are as follows:

(a) $R^4$ through $R^7$ each independently represent hydrogen, halo, hydroxy, cyano, amino, $(C_1-C_6)$alkyl, $(C_1-C_6)$alkoxy, hydroxymethyl, $CH_2NH_2$, $CHF_2$, $CF_3$, $OCHF_2$, $OCF_3$, $SO_2NH_2$, $SO_2CH_3$, $SO_2NR^9R^{10}$, NH $SO_2R^{11}$, $CH_2NH(SO_2R^{11})$, $NR^9R^{10}$, $NHCOR^{12}$, $COR^{12}$, CHN(OH), $OR^{14}$, $SR^{14}$, aryl, heterocycle, or substituted heterocycle;

(b) $R^4$ through $R^7$ each independently represent hydrogen, $SO_2NH_2$, $SO_2CH_3$, $OR^{14}$, $SR^{14}$, or aryl;

(c) $R^4$ through $R^7$ each independently represent hydrogen, halo, hydroxy, cyano, amino, $(C_1-C_6)$alkyl, $(C_1-C_6)$alkoxy, hydroxymethyl, $CH_2NH_2$, $CHF_2$, $CF_3$, $OCHF_2$, $OCF_3$, $SO_2NH_2$, $SO_2NR^9R^{10}$, NH $SO_2R^{11}$, $CH_2NH(SO_2R^{11})$, $NR^9R^{10}$, $NHCOR^{12}$, $COR^{12}$, CHN(OH), heterocycle, or substituted heterocycle;

(c) $R^4$ through $R^7$ each independently represent hydrogen, halo, hydroxy, $(C_1-C_6)$alkyl, $(C_1-C_6)$alkoxy, or $OR^{14}$;

Further particular aspects are those compounds of Formula I wherein $R^4$ through $R^7$ are as follows:

(a) $R^4$ through $R^7$ each independently represent halo;

(b) $R^4$ through $R^7$ each independently represent bromo, chloro, or fluoro;

(c) $R^4$ through $R^7$ each independently represent hydroxy;

(d) $R^4$ through $R^7$ each independently represent $(C_1-C_6)$alkyl;

(e) $R^4$ through $R^7$ each independently represent methyl, ethyl, isopropyl, or 2-methylpropyl;

(f) $R^4$ through $R^7$ each independently represent methyl;

(g) $R^4$ through $R^7$ each independently represent $(C_1-C_6)$alkoxy;

(h) $R^4$ through $R^7$ each independently represent methoxy, methylethoxy, ethoxy, or propyloxy;

(i) $R^4$ through $R^7$ each independently represent methoxy;

(j) $R^4$ through $R^7$ each independently represent $OR^{14}$;

(k) $R^4$ through $R^7$ each independently represent $OR^{14}$ wherein $R^{14}$ represents $(C_1-C_4)$alkyl-aryl, $(C_1-C_4)$alkyl-substituted aryl, $(C_1-C_4)$alkyl-heterocycle, or $(C_1-C_4)$alkyl-$(C_3-C_7)$cycloalkyl;

(l) $R^4$ through $R^7$ each independently represent $OR^{14}$ wherein $R^{14}$ cyclopropylmethyl, benzyl, phenylethyl, methoxyphenyl ethyl or a group of the formula

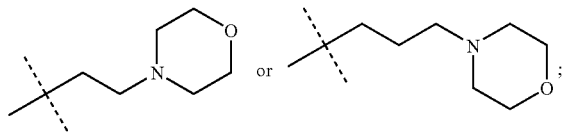

(m) $R^4$ through $R^7$ each independently represent a group of the formula

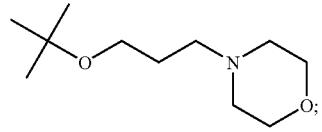

(n) $R^4$ through $R^7$ each independently represent cyclopropylmethoxy;

(o) $R^4$ through $R^7$ each independently represent trifluoromethyl, difluoromethyl, trifluoromethoxy, or difluoromethoxy, (p) $R^4$ through $R^7$ each independently represent cyano, or amino;

(q) $R^4$ through $R^7$ each independently represent hydroxymethyl, or aminomethyl;

(r) $R^4$ through $R^7$ each independently represent $SO_2NH_2$, $SO_2CH_3$, or $SCH_3$;

(s) $R^4$ through $R^7$ each independently represent $NHCOR^{12}$ or $COR^{12}$;

(t) $R^4$ through $R^7$ each independently represent $NHCOR^{12}$ or $COR^{12}$ wherein $R^{12}$ represents independently at each occurrence amino, methyl, or methoxy;

(u) $R^4$ through $R^7$ each independently represent phenyl;

(v) $R^4$ through $R^7$ each independently represent NH $SO_2R^{11}$;

(w) $R^4$ through $R^7$ each independently represent NH $SO_2R^{11}$ wherein $R^{11}$ represents $(C_1-C_6)$alkyl;

(x) $R^4$ through $R^7$ each independently represent NH $SO_2CH_3$;

(y) $R^4$ through $R^7$ each independently represent $NR^9R^{10}$;

(z) $R^4$ through $R^7$ each independently represent $NR^9R^{10}$ wherein $R^9$ represents methyl and $R^{10}$ represent methyl;

(aa) $R^4$ through $R^7$ each independently represent hydrogen.

Still additional particular aspects of the novel compounds of the present invention are those wherein the compound is a compound of Formula I, wherein $R^4$ and $R^6$ are as follows:

(a) $R^4$ and $R^6$ each independently represent hydrogen, halo, hydroxy, cyano, amino, $(C_1-C_6)$alkyl, $(C_1-C_6)$alkoxy, halo$(C_1-C_6)$alkyl, hydroxymethyl, $CH_2NH_2$, $SO_2NH_2$, $SO_2CH_3$, NH $SO_2R^{11}$, $NR^9R^{10}$, $NHCOR^{12}$, $COR^{12}$, $OR^{14}$, $SR^{14}$, or aryl;

(b) $R^4$ and $R^6$ each independently represent hydrogen, halo, hydroxy, cyano, amino, methyl, ethyl, propyl, isopropyl, methoxy, ethoxy, propyloxy, methylethoxy, difluromethyl, trifluoromethyl, hydroxymethyl, $SO_2CH_3$, NH $SO_2R^{11}$ wherein R11 represents $(C_1-C_6)$alkyl, $NR^9R^{10}$ wherein $R^9$ and $R^{10}$ represents $(C_1-C_6)$alkyl, $NHCOR^{12}$ wherein $R^{12}$ represents $(C_1-C_6)$alkyl; $COR^{12}$ wherein R12 represents hydrogen, amino, or $(C_1-C_6)$alkoxy; $OR^{14}$ wherein $R^{14}$ represents $(C_1-C_4)$alkyl-$(C_3-C_7)$cycloalkyl, $(C_1-C_4)$alkyl-aryl, $(C_1-C_4)$alkyl-substituted aryl, or $(C_1-C_4)$alkyl-heterocycle; $SR^{14}$ wherein $R^{14}$ represents $(C_1-C_6)$alkyl; or aryl;

(c) $R^4$ and $R^6$ each independently represent chloro, bromo, or fluoro;
(d) $R^4$ and $R^6$ each independently represent hydroxy,
(e) $R^4$ and $R^6$ each independently represent cyano, or amino;
(f) $R^4$ and $R^6$ each independently represent methyl, ethyl, propyl, or isopropyl;
(g) $R^4$ and $R^6$ each independently represent methoxy, ethoxy, propyloxy, or methylethoxy;
(h) $R^4$ and $R^6$ each independently represent difluoromethyl, trifluoromethyl, or hydroxymethyl;
(i) $R^4$ and $R^6$ each independently represent $SO_2CH_3$;
(j) $R^4$ and $R^6$ each independently represent $NH\,SO_2CH_3$;
(k) $R^4$ and $R^6$ each independently represent dimethylamine;
(l) $R^4$ and $R^6$ each independently represent CHO, $CONH_2$, or $COOCH_3$;
(m) $R^4$ and $R^6$ each independently represent $OR^{14}$ wherein $R^{14}$ represents $(C_1-C_4)$alkyl-$(C_3-C_7)$cycloalkyl, $(C_1-C_4)$ alkyl-aryl, $(C_1-C_4)$alkyl-substituted aryl, or $(C_1-C_4)$ alkyl-heterocycle;
(n) $R^4$ and $R^6$ each independently represent $OR^{14}$ wherein $R^{14}$ represents cyclopropylmethyl, phenylethyl, methoxyphenyl ethyl, or a group of the formula

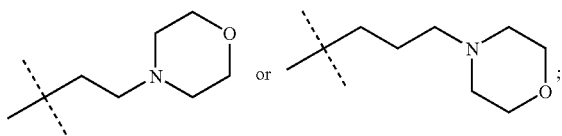

(o) $R^4$ and $R^6$ each independently represent cyclopropylmethoxy;
(p) $R^4$ and $R^6$ each independently represent a group of the formula

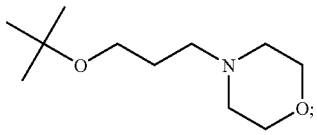

(q) $R^4$ and $R^6$ each independently represent $SCH_3$; and
(r) $R^4$ and $R^6$ each independently represent phenyl;
(s) $R^4$ and $R^6$ each independently represent hydrogen;

Still additional particular aspects of the novel compounds of the present invention are those wherein the compound is a compound of Formula L wherein $R^5$ and $R^7$ are as follows:
(a) $R^5$ and $R^7$ each independently represent hydrogen, hydroxy, halo, $(C_1-C_6)$alkyl, or $(C_1-C_6)$alkoxy;
(b) $R^5$ and $R^7$ each independently represent hydroxy;
(c) $R^5$ and $R^7$ each independently represent chloro, bromo, or fluoro;
(d) $R^5$ and $R^7$ each independently represent methyl, or methoxy;
(e) $R^5$ and $R^7$ each independently represent hydrogen;

Yet additional particular aspects of the novel compounds of the present invention are those wherein the compound of Formula I is one wherein $R^8$ is as follows:
(a) $R^8$ represents hydrogen, halo, $(C_1-C_6)$alkyl, hydroxy $(C_1-C_6)$allyl, $(C_1-C_4)$alkyl —$(C_1-C_6)$alkoxy, $COR^{12}$, $(C_3-C_7)$cycloalkyl, aryl or substituted aryl;
(b) $R^8$ represents bromo, chloro, or fluoro;

(c) $R^8$ represents methyl, ethyl, propyl, isopropyl, or 2-methylpropyl;
(d) $R^8$ represents hydroxymethyl;
(e) $R^8$ represents $(C_1-C_4)$alkyl-$(C_1-C_6)$alkoxy;
(f) $R^8$ represents methoxymethyl;
(g) $R^8$ represents $COR^{12}$ wherein $R^{12}$ represents methoxy, ethoxy, hydroxyamethyl, or methoxymethyl;
(h) $R^8$ represents $(C_3-C_7)$cycloalkyl;
(i) $R^8$ represents phenyl, methoxyphenyl, methylphenyl, or phenyl-phenyl;
(j) $R^8$ represents hydrogen.

In addition, it will be understood that a most particular aspect of the novel compounds of the present invention are those wherein the compound is any novel compound of Formula I exemplified herein.

Compounds of the present invention, including novel compounds, can be further divided into sections as represented by Formulas I(a) through I(g) below. As such, methods and uses employing compounds of Formula I(a)-I(g), as well as novel compounds of Formula I(a)-I(g), represent more particular aspects of the present invention. Section 1, as given by Formula I(a), contains derivatives of Formula I having substitution on the "C" ring but not on the "A" or "B" rings. Section 2, as given by Formula I(b), contains derivatives of Formula I having substitution on the "C" ring and further on the "A" and/or "B" rings. Section 3, as given by Formula I(c), contains derivatives of Formula I wherein the "C" ring further represents a heterocyclic or benzofused heterocyclic. Section 4, as given by Formula I(d), contains derivatives of Formula I wherein the "A" and/or "B" ring further represents a heterocyclic ring. Section 5, as given by Formula I(e), contains derivatives of Formula I wherein the bridge depicted by —X—Y— represents a fused cyclopropyl structure. Section 6, as given by Formula I(f), contains derivatives of Formula I wherein the bridge depicted by —X—Y— contains a heteroatom or heteroatom containing group at either the X or Y position. Finally, Section 7, as given by Formula I(g), contains derivatives of Formula I wherein $R^8$ is other than hydrogen and the bridge depicted by —X—Y— contains either a heteroatom or heteroatom containing group at either the X or Y position or both X and Y are $CH_2$.

Formula I(a)

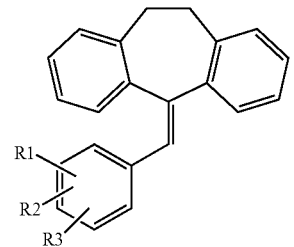

wherein
"═" represents a double bond;
$R^1$ represents hydrogen, halo, hydroxy, cyano, nitro, amino, $(C_1-C_6)$alkyl, $(C_1-C_6)$alkoxy, halo$(C_1-C_6)$alkyl, hydroxy$(C_1-C_6)$alkyl, halo$(C_1-C_6)$alkoxy, $SO_2NR^9R^{10}$, $SO_2R^{11}$, $NHSO_2R^{11}$, $CH_2NHSO_2R^{11}$, $N(CH_3)SO_2R^{11}$, $NR^9R^{10}$, $NHCOR^{12}$, $COR^{12}$, $CH_2NH_2$, $SR^{14}$, heterocycle, or substituted heterocycle;
$R^2$ represents hydrogen, halo, hydroxy, $(C_1-C_6)$alkyl, $(C_1-C_6)$alkoxy, or halo$(C_1-C_6)$alkyl;
$R^3$ represents hydrogen or halo;

R⁹ represents independently at each occurrence cyano, (C₁-C₆)alkyl, (C₁-C₄)alkyl-(C₁-C₆)alkoxy, halo(C₁-C₆)alkyl, (C₃-C₇)cycloalkyl, aryl, or (C₁-C₄)alkyl-aryl;

R¹⁰ represents independently at each occurrence hydrogen or (C₁-C₆)alkyl, or R⁹ and R¹⁰ together with the nitrogen to which they are attached form a substituted or unsubstituted heterocycle R¹¹ represents independently at each occurrence amino, (C₁-C₆)alkyl, halo(C₁-C₆)alkyl, NH—(C₁-C₆)alkylamine, N,N—(C₁-C₆)dialkylamine, aryl, substituted aryl, heterocycle, or substituted heterocycle;

R¹² represents independently at each occurrence H, amino, (C₁-C₆)alkyl, or heterocycle; and R¹⁴ represents (C₁-C₆)alkyl.

Formula I(b)

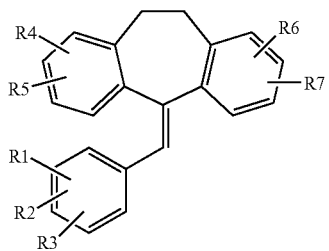

wherein
"---" represents a double bond;
R¹ represents hydrogen, halo, hydroxy, cyano, amino, (C₁-C₆)alkyl, (C₁-C₆)alkoxy, halo(C₁-C₆)alkyl, halo(C₁-C₆)alkoxy, NHSO₂R¹¹, NR⁹R¹⁰, CH₂NH(SO₂R¹¹), NHCOR¹², COR¹², OR¹⁴;

R² represents hydrogen or halo;

R³ represents hydrogen;

R⁴ and R⁶ each independently represent hydrogen, halo, hydroxy, cyano, amino, (C₁-C₆)alkyl, (C₁-C₆)alkoxy, halo(C₁-C₆)alkyl, NHSO₂R¹¹, NR⁹R¹⁰, NHCOR¹², COR¹², OR¹⁴, SO₂R¹¹, SR¹⁴, aryl, or heterocycle;

R⁵ and R⁷ each independently represent hydrogen, halo, hydroxy, or (C₁-C₆)alkoxy, R⁹ represents independently at each occurrence cyano or (C₁-C₆)alkyl;

R¹⁰ represents independently at each occurrence hydrogen or (C₁-C₆)alkyl;

R¹¹ represents independently at each occurrence amino, (C₁-C₆)alkyl, halo(C₁-C₆)alkyl, NH—(C₁-C₆)alkylamine, N,N—(C₁-C₆)dialkylamine, aryl, substituted aryl, heterocycle, or substituted heterocycle;

R¹² represents independently at each occurrence H, amino, (C₁-C₆)alkyl, (C₁-C₆)alkoxy, hydroxy(C₁-C₆)alkyl, (C₁-C)alkyl-(C₁-C₆)alkoxy, halo(C₁-C₆)alkyl, NH-methylamine, NH-dimethylamine, NH-ethylamine, or heterocycle; and R¹⁴ represents independently at each occurrence (C₁-C₆)alkyl, (C₁-C₄)alkyl-aryl, (C₁-C₄)alkyl-substituted aryl, (C₁-C₄)alkyl-heterocycle, or (C₁-C₄)alkyl-(C₃-C₇)cycloalkyl.

Formula I(c)

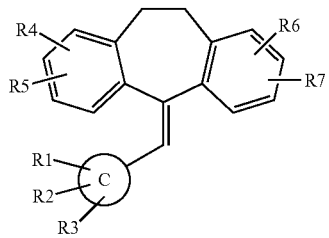

wherein
"---" represents a double bond
"C" represents a heterocycle or benzofused heterocycle ring;

R¹ represents hydrogen, halo, hydroxy, amino, oxo, (C₁-C₆)alkyl, (C₁-C₆)alkoxy, NHSO₂R¹¹, or (C₁-C₄)alkyl-heterocycle;

R² represents hydrogen, halo, (C₁-C₆)alkyl, (C₃-C₇)cycloalkyl, heterocycle, or (C₁-C₄)alkyl-heterocycle;

R3 represents hydrogen;

R4 and R6 each independently represent hydrogen, halo, hydroxy, cyano, ammo, (C₁-C₆)alkyl, (C₁-C₆)alkoxy, or halo(C₁-C₆)alkyl;

R5 and R7 each independently represent hydrogen, halo, hydroxy, (C₁-C₆)alkyl, or (C₁-C₆)alkoxy; and R11 represents (C₁-C₆)alkyl.

Formula I(d)

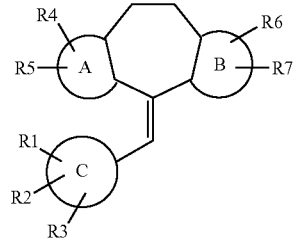

wherein
"A" and "B", each independently represent phenyl or a heterocycle, provided at least one of "A" and "B" is a heterocycle;

"C" is as previously defined;

"---" represents a double bond

R¹ represents hydrogen, halo, hydroxy, amino, oxo, (C₁-C₆)alkyl, (C₁-C₆)alkoxy, halo(C₁-C₆)alkyl, NHSO₂R¹¹, NHCOR¹², COR¹², (C₃-C₇)cycloalkyl, heterocycle, or (C₁-C₄)alkyl-heterocycle, provided that when "C" represents aryl then R1 is other than oxo;

R² represents hydrogen, halo, hydroxy, (C₁-C₆)alkyl, or (C₃-C₇)cycloalkyl;

R³ represents hydrogen;

R⁴ and R⁶ each independently represent hydrogen, halo, hydroxy, cyano, amino, (C₁-C₆)alkyl, (C₁-C₆)alkoxy, halo(C₁-C₆)allyl, or NHCOR¹²;

R⁵ and R⁷ each independently represent hydrogen or halo;

R¹¹ represents (C₁-C₆)alkyl or aryl; and

R¹² represents independently at each occurrence (C₁-C₆)alkyl or (C₁-C₆)alkoxy.

Formula I(e)

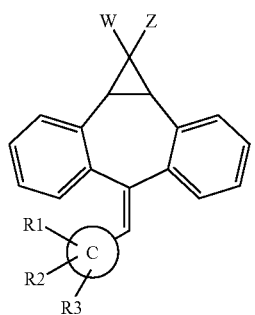

Wherein

W and Z each independently represent hydrogen, fluoro, or chloro

"$=$" represents a double bond

"C" represents phenyl or benzofused heterocycle;

$R^1$ represents hydrogen, hydroxy, amino, oxo, or $NHSO_2R^{11}$, provided that when "C" represents aryl then R1 is other than oxo;

$R^2$ and $R^3$ each represent hydrogen; and $R^{11}$ represents $(C_1-C_6)$alkyl.

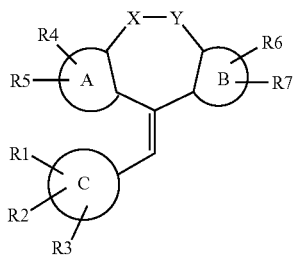

Formula I(f)

wherein

"$=$" represents a double bond;

"A" and "B" represent phenyl or heterocycle and "C" is as previously defined;

X and Y together represent —$CH_2$—O—, —O—$CH_2$—, —$CH_2$—S—, —S—$CH_2$—, —$CH_2$SO—, —SO—$CH_2$—, —$CH_2$—$SO_2$—, —$SO_2$—$CH_2$—, —$CH_2NR^{10}$—, —$NR^{10}$—$CH_2$—, —$NR^{10}$—CO—, or —CO—$NR^{10}$—, wherein $R^{10}$ is as previously defined;

$R^1$ represents hydrogen, halo, hydroxy, amino, oxo, $(C_1-C_6)$alkyl, $(C_1-C_6)$alkoxy, halo$(C_1-C_6)$alkyl, hydroxy$(C_1-C_6)$alkyl, $NHSO_2R^{11}$, $CH_2NH(SO_2R^{11})$, $NHCOR^{12}$, $COR^{12}$, $OR^{14}$, $(C_3-C_7)$cycloalkyl, or $(C_1-C_4)$alkyl-heterocycle, provided that when "C" represents aryl then R1 is other than oxo;

$R^2$ represents hydrogen, halo, $(C_1-C_6)$alkyl, $(C_3-C_7)$cycloalkyl, heterocycle, or $(C_1-C_4)$alkyl-heterocycle;

$R^3$ represents hydrogen, or $(C_1-C_6)$alkyl;

$R^4$ and $R^6$ each independently represent hydrogen, halo, $(C_1-C_6)$alkyl, $(C_1-C_6)$alkoxy, halo$(C_1-C_6)$alkyl, or $COR^{12}$; and $R^5$ and $R^7$ each independently represent hydrogen, halo, $(C_1-C_6)$alkyl, or $(C_1-C_6)$alkoxy.

$R^{10}$ represents independently at each occurrence hydrogen $(C_1-C_6)$alkyl;

$R^{11}$ represents independently at each occurrence $(C_1-C_6)$alkyl, halo$(C_1-C_6)$alkyl, aryl, substituted aryl, or $(C_3-C_7)$cycloalkyl;

$R^{12}$ represents independently at each occurrence $(C_1-C_6)$alkyl, $(C_1-C_6)$alkoxy, NH-methylamine, NH-dimethylamine, or NH-ethylamine; and $R^{14}$ represents acetyl.

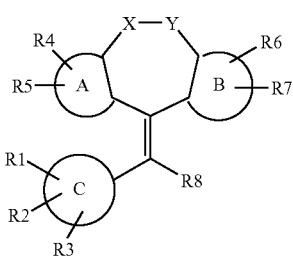

Formula I(g)

wherein

"$=$" represents a double bond;

"A" and "B" represent phenyl or heterocycle and "C" is as defined previously,

X and Y together represent —$CH_2$—O—, —O—$CH_2$—, —$CH_2$—S—, —S—$CH_2$—, —$CH_2$SO—, —SO—$CH_2$—, —$CH_2$$SO_2$—, —$SO_2$—$CH_2$—, —$CH_2$—$NR^{10}$—, —$NR^{10}$—$CH_2$—, —$NR^{10}$—CO—, or —CO—$NR^{10}$—;

R1 represents hydrogen, halo, hydroxy, amino, oxo, and $NHSO_2R^{11}$, provided that when "C" represents aryl then R1 is other than oxo;

R2 and R3 each individually represent hydrogen or halo;

R4 and R6 each independently represent hydrogen, halo, $(C_1-C_6)$alkyl, $(C_1-C_6)$alkoxy, or $OR^{14}$;

R5 and R7 each independently represent hydrogen or halo;

R8 represents halo, $(C_1-C_6)$alkyl, $(C_1-C_6)$alkoxy, hydroxy $(C_1-C_6)$alkyl, $(C_1-C_4)$alkyl-$(C_1-C_6)$alkoxy, $COR^{12}$, aryl, or substituted aryl;

$R^{10}$ represents hydrogen or $(C_1-C_6)$alkyl;

$R^{11}$ represents $(C_1-C_6)$alkyl;

$R^{12}$ represents $(C_1-C_6)$alkoxy, and $R^{14}$ represents $(C_1-C_4)$alklyl-$(C_3-C_7)$cycloalkyl.

Further particular aspects of the methods and uses employing compounds of Formula I(a)-I(g) are provided by the groupings of particular substituents and particular variables, as set forth above, for the methods and uses employing compounds of Formula I, generally. Further particular aspects of the novel compounds of Formula I(a)-I(g) are provided by the groupings of particular substituents and particular variables, as set forth above, for the novel compounds of Formula I, generally.

All of the compounds of Formula I, including the novel compounds of Formula I, can be can be chemically prepared, for example, by following the synthetic routes set forth in the Schemes below. However, the following discussion is not intended to be limiting to the scope of the present invention in any way. For example, the specific synthetic steps for the routes described for the synthesis of compounds of a particular section herein, may be combined in different ways, or in conjunction with steps from different schemes, to prepare additional compounds of Formula I or compounds of a different section. For example, the conditions described in Scheme VII, Step C may be employed to synthesize the final products of many of the compounds of Formula I including, for example, derivatives wherein the bridge depicted by —X—Y— contains a heteroatom or heteroatom containing group at either the X or Y position.

All substituents, unless otherwise indicated, are as previously defined. The reagents and starting materials are readily available to one of ordinary skill in the art. For example, certain reagents or starting materials can be prepared by one of ordinary skill in the art following procedures disclosed in J. Prakt. Chem. 333 (4) (1991); J. Marsh, Advanced Organic Chemistry (4$^{th}$ edition); J. Med. Chem. (1990); J. S. Buck and W. S. Ide, Organic Synthesis Coll. Vol. II, 622-623, (1943) J. P. Wolfe and S. L. Buchwald, Organic Synthesis, (78) 23-31 (2000); Tetrahedron Letters, 39 (51) 9365-9368 (1998); F. Kurzer, Organic Synthesis, Coll. Vol. (IV) 49 (1963); and Synthetic Communications, 1129-1135 (1991). Additional reagents, starting materials, or useful procedures may be found in M Kurokawa, F Sato, Y Masuda, T Yoshida and Y Ochi, Chem. Pharm. Bull., 39; 10; (1991) 2564-5273, Y Ohishi, H Yoshitaka, M Mitsuo, T Mukai, K Kimura, M Nagahara, Chem. Pharm. Bull., 38; 4; (1990) 1066-1068, Inman, Raiford, JACS; 56 (1934) 1586-1587, Clark, Pessolano, JACS; 80 (1958) 1662, P. Bollinger, P. Cooper.; H. U. Gubler, A. Leutwiler, T. Payne Helv. Chim. Acta ;73; (1990);1 197, G. Vassilikogiannakis, M. Hatzimarinaki, M. Orfanapoulos J. Org Chem., 65, 8180; Y. Girard, J. G. Atkinson, P. C. Belanger, J. J. Fuentes, J. Rokach, C. S. Rooney, D. C.

Remy, C. A. Hunt *J. Org. Chem.*, 48; (1983); 3220, D. S. Matteson, D. Majumder *Organometallics*, 2; (1983); 230; *Journal of Heterocyclic Chemistry*, 73; (1971) *Journal of Medicinal Chemistry*, 33;

(1990); 3095, *Journal of Organic Chemistry*, 60; (1995); 7508, Bergmann, E. D., Solomonovici, A., *Synthesis*, (1970); 183-189, Poirier et al., *Org. Letters*, 3; 23; (2001); 3795-3798, Spanish Patent ES2092957 A1(1996); Brown, C., et al., *J. Chem. Soc.*, Perkin Trans., 3007 (1982); Deck, L. M., et al., *Org. Prep. Proceed. Int.*, 22(4); 495-500, (1990); Lee, J. C., et al., *Synth. Comm.*, 25(9), 1367-1370 (1995); Ho, Z. C., et al., *Tetrahedron*, 52(41), 13189-13200 (1996); M Murata, T Takashi, S Watanabe and Y Yusuru, *J. Org. Chem.*; 65 (1) 164-168 (2000); and T. Ishiyama, M. Murata, N. Miyaura, *J. Org. Chem.*, 60(23), 7508-7510 (1995). Other necessary reagents and starting material may be made by procedures which are selected from standard techniques of organic and heterocyclic chemistry, techniques which are analogous to the syntheses of known structurally similar compounds, and the procedures described in the Examples below, including any novel procedures.

Scheme I provides procedures for the synthesis of compounds of Formula I wherein the bond represented by "$\equiv$" attached to the tricyclic core is a double bond and at least one of $R^1$ through $R^3$ is, for example, an N-substituted- or unsubstituted-sulfonamido group.

In Scheme I, Step B, the anion of the methyl sulfate ester of formula (2) is first generated using an appropriate base, such as n-butyl-Li, sec-butyl-Li, or t-butyl-Li at about −78 to 25° C., in an inert solvent such as THF. For a general discussion of anion formation see J. Marsh, Advanced Organic Chemistry (4$^{th}$ edition) 606-610. After generation of the anion is complete, a tricyclic, for example substituted or unsubstituted dibenzcsubzranc (formula (3)) dibenzosuberone (formula (10)), is added. During acidic work-up, the carbinol dehydrates to the olefin and the sulfate ester hydrolyzes to the corresponding sulfonic acid to provide the compound of formula (4).

In Scheme I, Step C, using thionyl chloride and following methods well known to one of ordinary skill in the art, the sulfonic acid is converted to the corresponding sulfonyl chloride of formula (5). Inert solvents, such as methylene chloride, may be used and a catalytic amount of N,N-dimethylformamide increases the reaction rate. (J. Marsh, Advanced Organic Chemistry (4$^{th}$ ed.); 499) provides a detailed description and additional literature references.

In Scheme I, Step D, the sulfonyl chloride is reacted with an excess of a substituted or unsubstituted amine, at about 10 to 60° C. for 2 to 24 hours, in an inert solvent such as THF, dioxane or methylene chloride (which may contain an acid scavenger such as pyridine or triethylamine) to provide the compound of Formula I, wherein at least one of $R^1$ through $R^3$

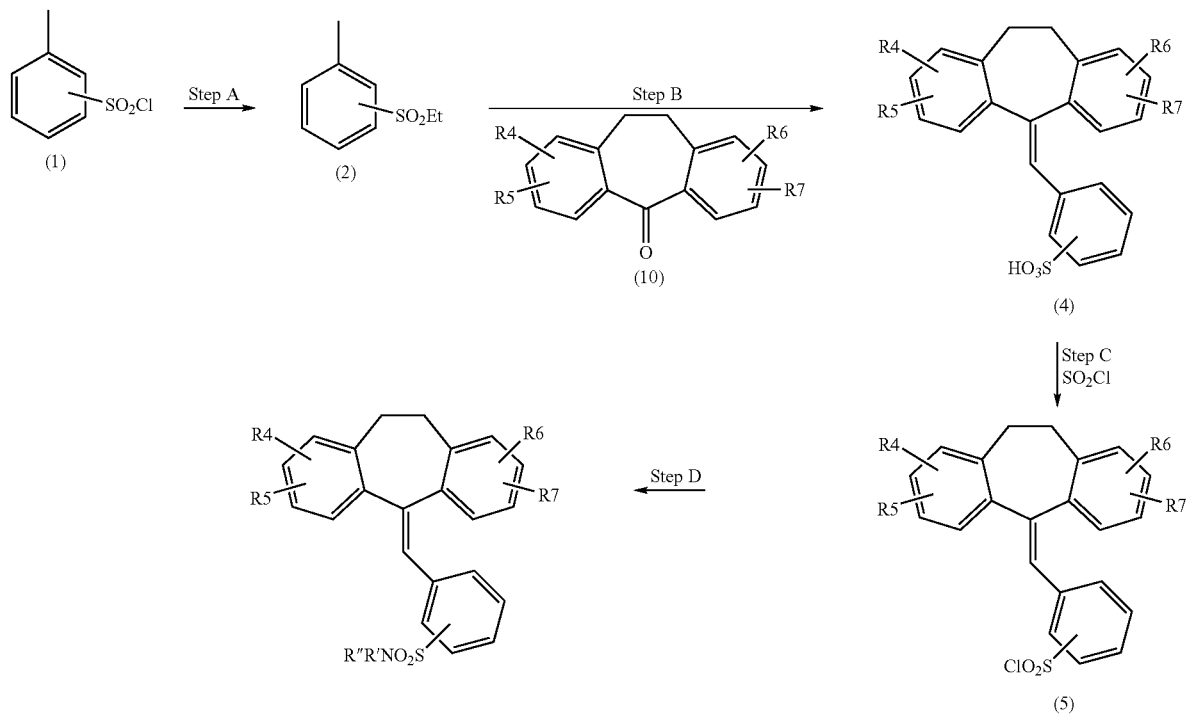

Scheme I

In Scheme I, Step A, a substituted or unsubstituted toluenesulfonyl chloride derivative of formula (1) is reacted with an excess of ethanol in an inert solvent such as dioxane at about 0 to 50° C. for about 10 to 48 hours, according to a procedure similar to that in J. Prakt. Chem. 333 (4) (1991). The HCl produced is neutralized in situ with a base, such as triethylamine or pyridine, with the progress of the reaction being followed by tlc. After work-up, the crude product can be purified using silica gel to give sulfate ester of formula (2).

is, for example, an N-substituted- or unsubstituted-sulfonamido group. The product can then be purified using standard techniques such silica gel chromatography, eluting with suitable eluent such as ethyl acetate and hexane.

Scheme II provides procedures for the synthesis of compounds of Formula I wherein the bond represented by "$\equiv$" attached to the tricyclic core is a double bond and at least one of $R^1$ through $R^3$ is, for example, halo or (C1-C4) alkoxy.

Scheme II

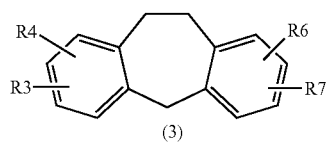 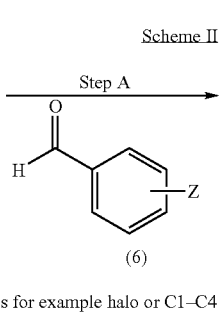 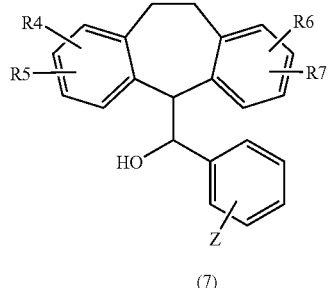

(Z is for example halo or C1–C4 alkoxy)

Formula I
(at least one of $R^1$–$R^3$ is Z;
Z is halo or C1–C4 alkoxy)

In Scheme II, Step A, the lithium anion of dibenzosuberane is first generated using an appropriate base such as n-butyl-Li, sec-butyl-Li, or t-butyl-Li at about −78 to 25° C. in an inert solvent such as THF, diethyl ether, or diglyme, for about 0.5-5 hours. After anion generation is complete, the solution is cooled to about −25 to 10° C. and a solution of an unsubstituted or substituted benzaldehyde derivative of formula (6) is added and the corresponding carbinol of formula (7) is isolated.

In Scheme II, Step B, the carbinol is dehydrated to the corresponding olefin derivative using 1-25% concentrated $H_2SO_4$ in glacial acetic acid at a temperature of about 25 to 100° C., for about 1 to 24 hours. The product of Formula I, wherein at least one of $R^1$ through $R^3$ is; for example, halo or ($C_1$-$C_4$)alkoxy, can then be purified using standard techniques such silica gel chromatography, eluting with suitable eluent such as ethyl acetate and hexane.

Scheme III provides procedures for the synthesis of compounds of Formula I wherein the bond represented by "⸗" attached to the tricyclic core is a double bond and at least one of $R^1$ through $R^3$ is, for example, hydroxy, difluoromethoxy, trifluoromethoxy, and the like Scheme III

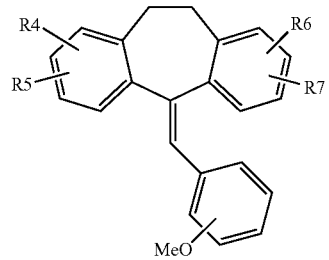

Formula I
(at least one of $R^1$–$R^3$ is OMe)

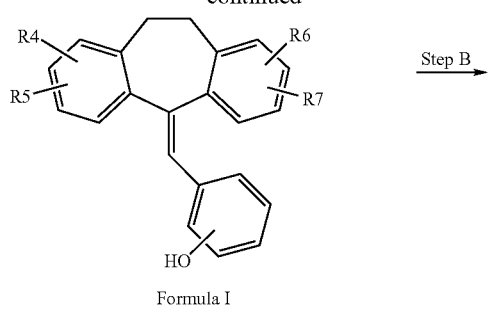

Formula I
(at least one of $R^1$–$R^3$ is OH)

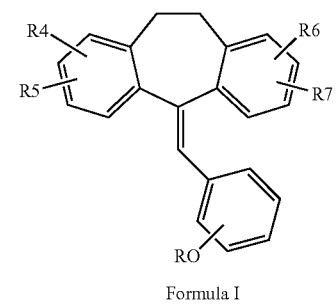

Formula I
(at least one of $R^1$–$R^3$ is OR;
R is for example $CHF_2$ or $CF_3$)

In Scheme III, Step A, a compound of Formula L wherein at least one of $R^1$ through $R^3$ is methoxy, is readily converted to a phenol derivative by treatment with either pyridine hydrochloride or boron tribromide. For a more detailed discussion of the formation of phenols from methyl ethers see J. Marsh, Advanced Organic Chemistry (4th edition) 433-434.

In Scheme III, Step B, the phenol derivative of Formula I may be converted, for example, to a fluoromethoxy derivative using standard procedures as detailed in J. Med. Chem. 1230-1241 (1990). The products of Formula I can all be purified using standard techniques known in the art, such as silica gel chromatography with a suitable eluent such as ethyl acetate and hexane.

Schemes IV(a)-IV(d) provide yet additional procedures for the synthesis of compounds of Formula I wherein the bond represented by "═" attached to the tricyclic core is a double bond. For example, Scheme IV(a) provides procedures for synthesizing compounds of Formula I wherein at least one of R1 through $R^3$ is a heterocyclic group.

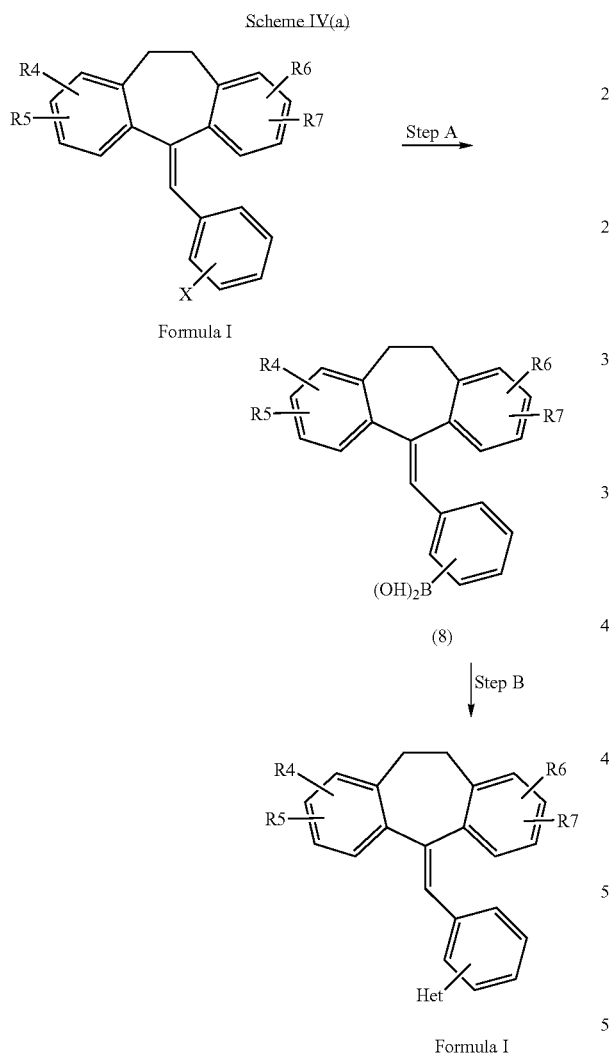

In Scheme IV(a), Step A, the lithium anion of the aryl halide derivative of Formula I (at least one of $R^1$ through $R^3$ is halo) is first generated by dissolving the aryl halide derivative in a suitable solvent such as THF, diethyl ether, or dioxane, cooling to a temperature of about −78 to −25° C., followed by addition of an appropriate base such as n-butyl-Li, sec-butyl-Li, or t-butyl-Li. The reaction is stirred for about 10 to 45 minutes to generate the anion. The boronic acid derivatives of formula (8) are prepared by quenching the anion of Formula I with triisopropyl borate followed by acidic hydrolysis.

In Scheme IV(a), Step B, following procedures well known in the art, the compound of formula (8) is treated under standard conditions with a compound of the general formula Het-Hal, (wherein Het is a heterocyclic moiety and Hal is bromo, chloro, or iodo) to provide the compound of Formula I wherein at least one of $R^1$ through $R^3$ is a heterocyclic moiety.

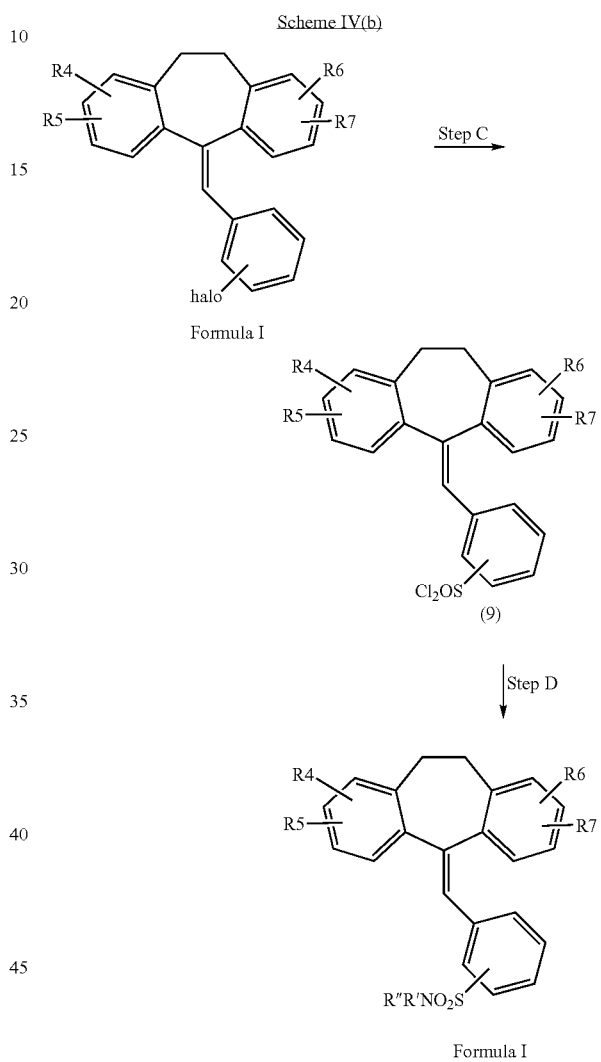

In Scheme IV(a), Step C, the lithium anion of the aryl bromide derivative of Formula I (at least one of $R^1$ through $R^3$ is halo) is first generated by dissolving the aryl halide derivative in a suitable solvent such as THF, diethyl ether, or dioxane, cooling to a temperature of about −78 to −25° C., followed by addition of an appropriate base such as n-butyl-Li, sec-butyl-Li, or t-butyl-Li. The reaction is stirred for about 10 to 45 minutes to generate the anion. Using standard techniques, the aryl sulfonyl chloride of formula (9) is prepared by quenching the aryl halide anion with sulfuryl chloride.

In Scheme IV(b), Step D, the aryl sulfonyl chloride derivative of formula (9) is treated with N-substituted- or unsubstituted- amines, as previously described in Scheme I above, to provide the compound of Formula I, wherein at least one of $R^1$ through $R^3$ is, for example, an N-substituted- or unsubstituted sulfonamide. The product can then be purified using standard techniques such silica gel chromatography, eluting with suitable eluent such as ethyl acetate and hexane.

Scheme IV(c)

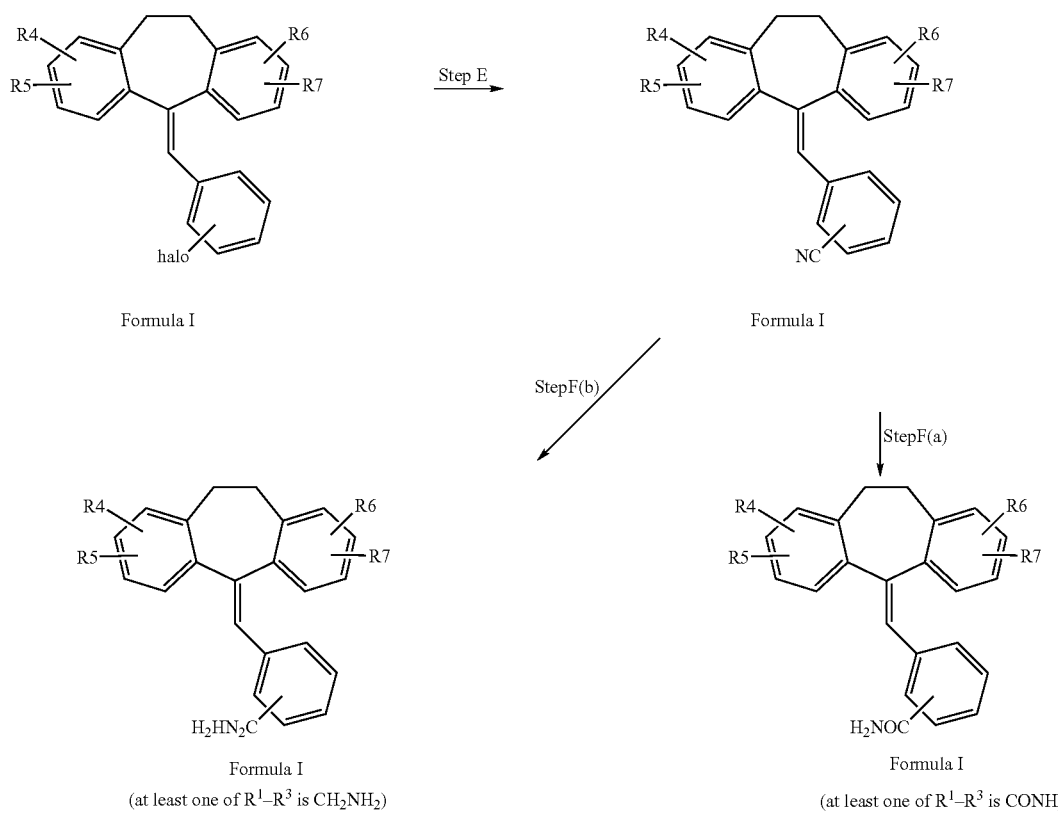

In Scheme IV(c), Step E, the aryl halide derivative is dissolved in a suitable solvent, such as N-methylpyrrolidinone (NMP), and sparged with nitrogen for 5-15 minutes. Solid CuCN and CuI are added and the reaction is heated to a temperature ranging from about 100 to 150° C. for 1 to 24 hour. The reaction is then cooled and shaken with aqueous ferric chloride and ethyl acetate, to provide the benzonitrile derivative of Formula I. The product can then be purified using standard techniques such silica gel chromatography, eluting with suitable eluent such as ethyl acetate and hexane.

In Scheme IV(c), Step F(a), the benzonitrile is first dissolved in a suitable solvent, such as DMSO, then solid $K_2CO_3$ is added, followed by about 30% $H_2O_2$. The reaction is stirred for about 3 hours followed by quenching with water. The product of Formula I, wherein at least one of $R^1$ through $R^3$ is, for example $COR^{12}$ is then collected and dried under vacuum.

Alternatively, in Step F(b), the benzonitrile may be reduced to the corresponding aminomethyl. For example, the corresponding nitrile is first dissolved in diethyl ether. Lithium aluminum hydride is then added and the reaction is stirred at room temperature for 1-24 h. The reaction is quenched by using procedures known in the art and as described in Fieser and Fieser, Reagents for Organic Synthesis, Vol. 1 pp 581-595. The inorganic solids are then filtered and washed with ether. After drying ($MgSO_4$) and concentration, the crude compound is obtained wherein at least one of R1 through R3 is aminomethyl. Further purification can be accomplished using column chromatography with the appropriate solvents.

Scheme IV(d) provides procedures for the synthesis of compounds of Formula I wherein at least one of $R^1$ through $R^3$ is, for example, a fluoromethyl, hydroxy, or an oxime.

Scheme IV(d)

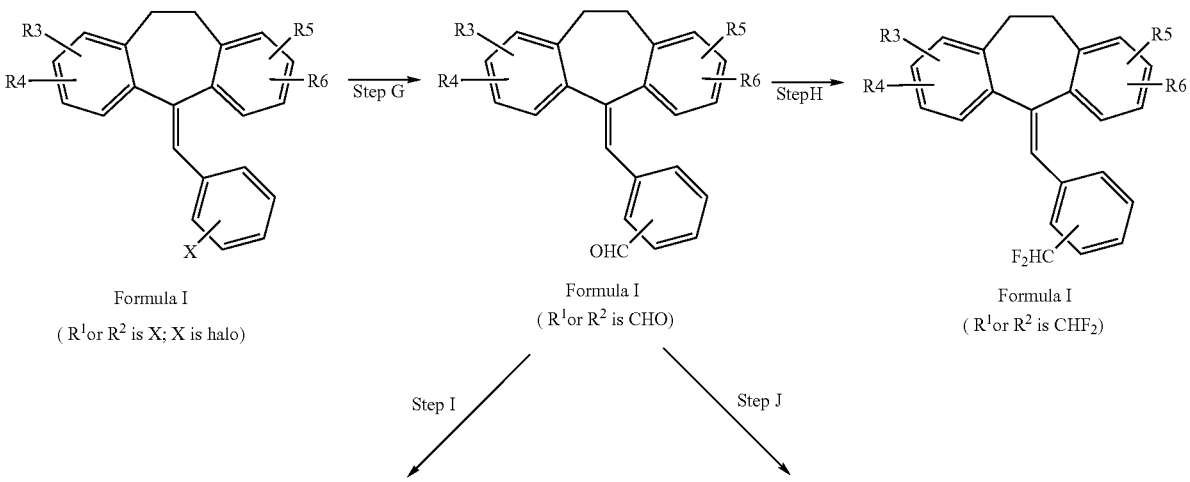

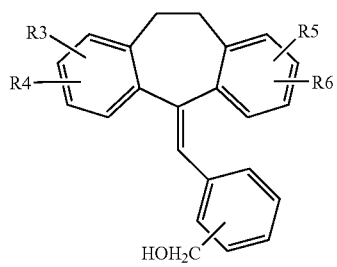

Formula I
($R^1$or $R^2$ is CH$_2$OH)

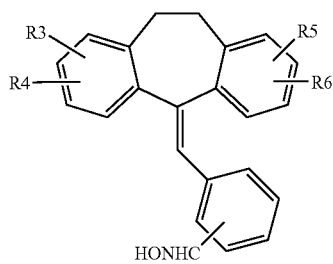

Formula I
(R is CHNR$^{12}$ or R2 is CHNR$^{12a}$)

In Scheme IV(d), Step G, the lithium anion of the aryl halide derivative of Formula I is first generated by dissolving the aryl bromide derivative in a suitable solvent such as THF, diethyl ether, or dioxane, cooling to a temperature of about −78 to −25° C., followed by addition of an appropriate base such as n-butyl-Li, sec-butyl-Li, or t-butyl-Li. The reaction is stirred for about 10 to 45 minutes to generate the anion. Using standard techniques, the aldehyde derivative of Formula I (at least one of $R^1$ through $R^3$ is CHO) is then generated by reacting the anion with N,N-dimethylformamide.

In Scheme IV(d), Step H, the aldehyde derivative is converted into a fluoromethyl derivative by dissolving in dichloromethane and treating with 1 to 5 equivalents of a fluorinating agent such as diethylamino sulfur trifluoride (DAST) and stirring at about 10 to 50° C. for 5 to 48 hours.

In Scheme IV(d), Step I, using standard procedures, the aldehyde derivatives of Formula I (at least one of $R^1$ through $R^3$ is CHO) are reduced to the corresponding alcohol derivatives by reaction with sodium borohydride in ethanol.

In Scheme IV(d), Step J, using methods as described in J. S. Buck and W. S. Ide, Organic Synthesis Coil. Vol. II, 622-623, (1943) the aldehyde derivative of Formula I is converted to the corresponding oxime derivative of Formula I under standard conditions.

The Formula I products of Steps G, H, I and J, may all be purified using standard techniques such silica gel chromatography, eluting with a suitable eluent such as ethyl acetate and hexane.

Schemes V(a)-V(b) provide procedures for the synthesis of various N-substituted- and unsubstituted-amine derivatives of Formula I (at least one of $R^1$ through $R^3$ is, for example, amino, N-substituted amino, or N,N-disubstituted amino) wherein the bond represented by "═" attached to the tricyclic core is a double bond.

Scheme V(a)

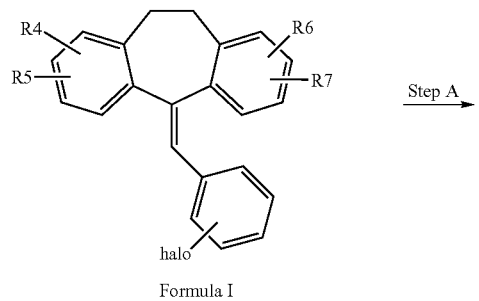

Formula I

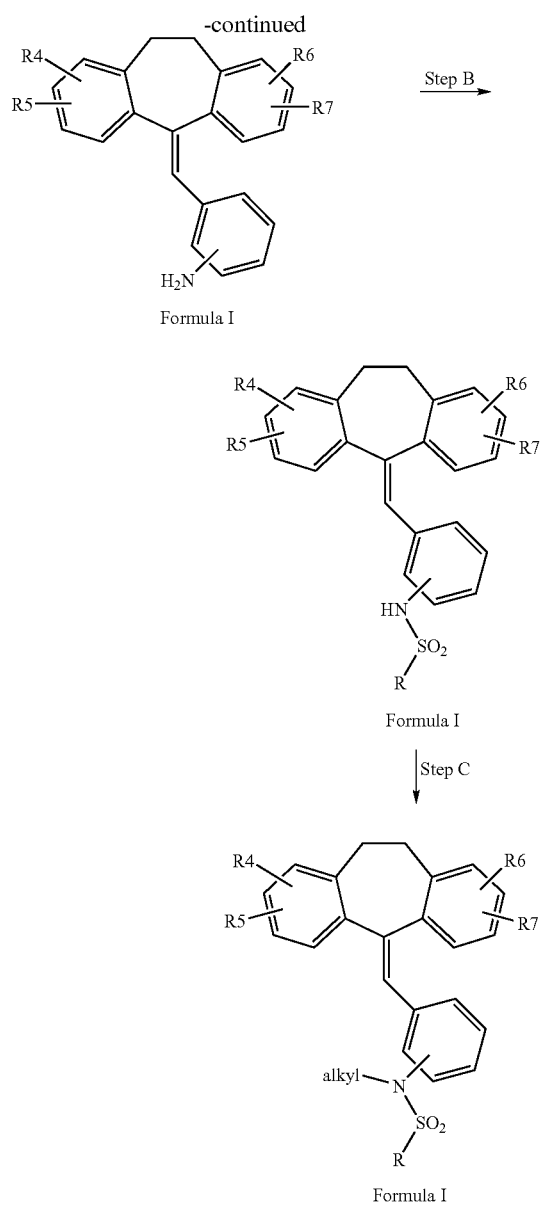

In Scheme V(a), Step A, the halo derivative of Formula I, prepared as described previously in Scheme II, is converted to an arylamine derivative using procedures as described in J. P. Wolfe and S. L. Buchwald, Organic Synthesis, Vol 78 23-31 (2000). After work-up, the crude imine is hydrolyzed to the amine using aqueous hydrochloric acid in tetrahydrofuran. The amines are purified by trituration with toluene/hexane or using silica gel chromatography, eluting with ethyl acetate and hexane.

In Scheme V(a), Step B, the amine derivative of Formula I is converted to a substituted-amine derivative by reaction with a sulfonyl chloride in pyridine at a temperature of about 10 to 50° C. for about 5 to 48 hours. The crude product of Formula I wherein at least one of $R^1$ through $R^3$ is, for example an N-[sulfonyl]-amino moiety can then be purified using silica gel chromatograph, eluting with a mixture of ethyl acetate and hexane.

In Scheme V(a), Step C, the N-[sulfonyl]-amines maybe converted to disubstituted-amine derivatives according to procedures as detailed in Tetrahedron Letters, 39(51)9365-9368 (1998). The anion is generated using sodium hydride in N,N-dimethylformamide at temperatures ranging from about 0 to 30° C. for about 0.25 to 2 hours. After addition of excess iodomethane, the reaction is stirred at room temperature for about 1 to 24 hours and then the crude product of Formula I, wherein at least one of $R^1$ through $R^3$ is, for example, a disubstituted N,N-[alkyl, sulfonyl]-amine can then be purified using silica gel chromatograph, eluting with a mixture of ethyl acetate and hexane.

In Scheme V(b), Step D, the amine derivative of Formula I prepared as described in Scheme V(a), above, is converted to the corresponding urea using procedures as described by F. Kurzer, Organic Synthesis, Coll. Vol. (IV) 49 (1963). For example, a compound of Formula I, wherein at least one of $R^1$ is $NH_2$ is combined with HOAc and water. A solution of sodium cyanate in water is then added to the mixture of the amine derivative. The reaction is stirred at room temperature for about 2 hours and then poured into water. The compound of Formula I, wherein at least one of $R^1$ through $R^3$ is, for example $NRCONH_2$ is then extracted with EtOAc, dry ($MgSO_4$) and concentrated to provide crude product. The crude product may then be purified by standard techniques such as silica gel chromatography, eluting with a mixture of ethyl acetate and hexane. (Alternatively in Step D, the amine derivative of Formula I is converted into an amide derivative of Formula L by reacting with an acid halide in pyridine at about 10 to 50° C. for about 5 to 48 hours. The crude product of can then be purified using silica gel chromatography, eluting with a mixture of ethyl acetate and hexane).

In Scheme V(b), Step E, the amine derivative of Formula I is mono- or di-alkylated using standard procedures well known to those of ordinary skill in the art. For a detailed descriptions of such methods, see Synthetic Communications, 1129-1135 (1991). The crude products of Formula I, wherein at least one of $R^1$ through $R^3$ is, for example NH—

Scheme V(b)

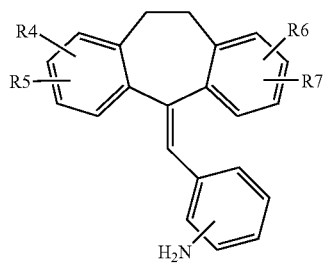

Formula I

Step D

Step E

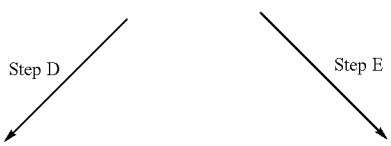

Formula I

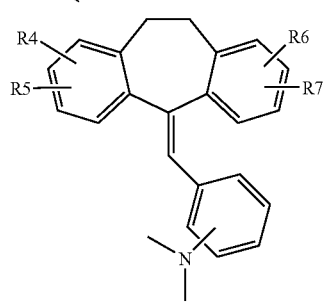

Formula I ($R^1$ or $R^2$ is N,N-($C_1$–$C_4$)dialkylamine)

(C1-C4) alkylamine or N,N—(C1-C4)dialkylamine, can then be purified using silica gel chromatography, eluting with a mixture of ethyl acetate and hexane.

To provide compounds of Formula I wherein the bond represented by "⸗" attached to the dibenzosuberane core is a single bond, the olefin moiety of the compounds of Formula I, prepared according to Schemes I-V above, can be readily reduced using a catalyst such as palladium on carbon (5 to 10%) in a solvent such as ethanol or methanol. The pressure of hydrogen used may vary from atmospheric to 60 psi. The reaction is performed at temperatures ranging from about 20 to 50° C. for 1 to 20 hours. For more details on hydrogenation of olefins, see H. O. House, Modern Synthetic Reactions, $2^{nd}$ edition, pp. 1-34 (1972).

Schemes VI provides yet additional procedures for the synthesis of compounds of Formula I. Scheme VI is particularly useful where at least one of $R^1$ through $R^3$ is, for example, nitro or amino; wherein X and Y represent —CH=CH—; and wherein the bond represented by "⸗" attached to the tricyclic core is a double bond.

Scheme VI

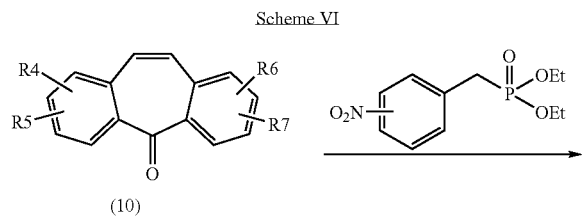

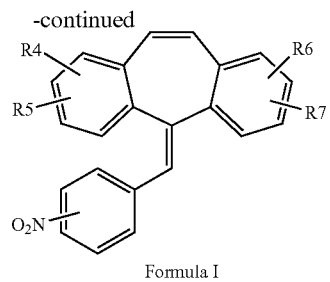

Formula I (at least one of $R^1$–$R^3$ is nitro)

In Scheme VI, the phosphonate of structure (11) is first dissolved in a suitable solvent, such as DMF, DMSO or acetonitrile at room temperature under an inert atmosphere. An appropriate base, such as sodium hydride, is then added. After stirring from 0.5 to 6 hours, the dibenzosuberone- or dibenzosuberenone-derivative of structure (10), dissolved in a suitable solvent such as DMF, is then added. The reaction is stirred for about 6 to 24 hours and then quenched with aqueous HCl. The product, wherein at least one of R1 through R3 is, for example nitro, is then extracted into EtOAc, dried (MgSO$_4$) and concentrated. The product is purified using column chromatography, eluted with EtOAc/hexanes. (For a more detailed discussion of this Horner-Enunons procedure, see J. Marsh, Advanced Organic Chemistry ($4^{th}$ edition) pp 959-960 and references cited therein).

Scheme VII provides procedures for the synthesis of compounds of Formula I employing Suzuki coupling conditions. In particular, the procedures of Scheme VII are useful for synthesizing compounds of Formula I wherein a heterocyclic or substituted heterocyclic ring is attached to the tricyclic core of Formula I; and wherein the bond represented by "⸗" attached to the tricyclic core is a double bond.

Scheme VII

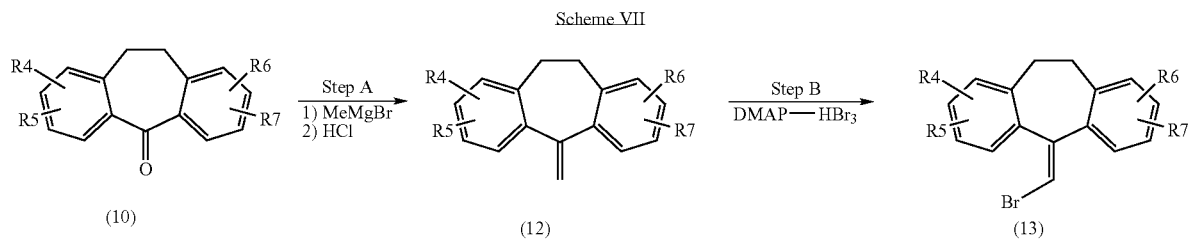

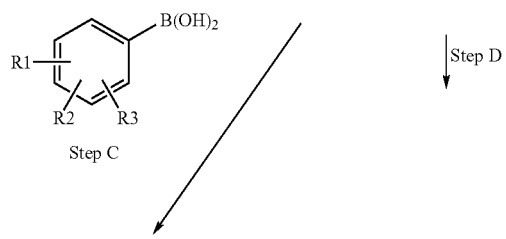

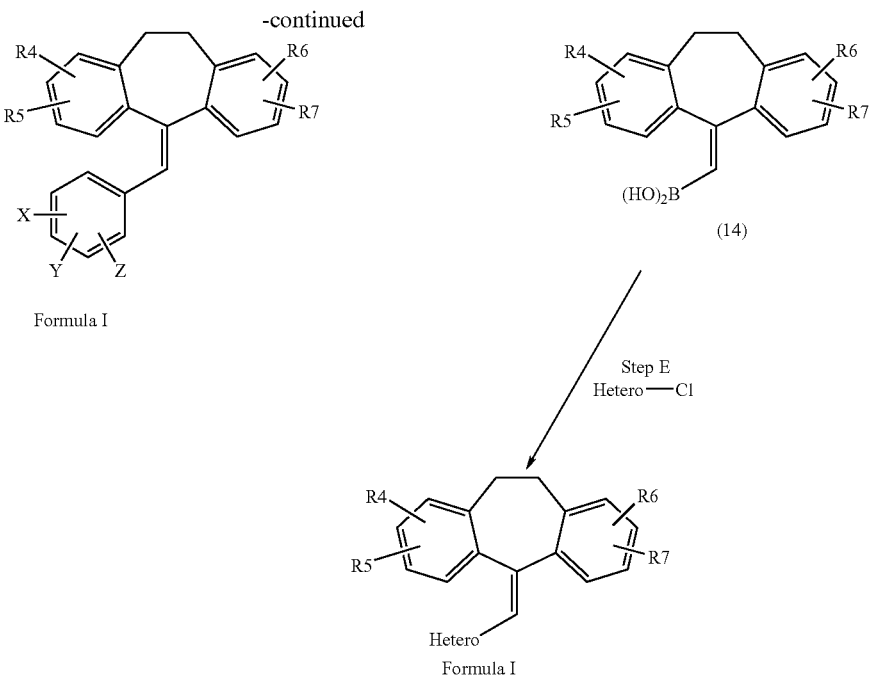

In Scheme VII, Step A, the dibenzosuberone derivative (10) is dissolved in an appropriate solvent such as diethyl ether, dioxane or tetrahydrofuran and 1 to 5 equivalents of methylmagnesium bromide is added. After 2-24 hours, the intermediate carbinol derivative is converted to the exomethylene derivative by cooling to 0° C. and adding HCl. After stirring for about 1-18 hours, the reaction is shaken with EtOAc and water. The organic solution is dried (MgSO$_4$) and concentrated. The crude product of structure (12) is purified by short path column chromatography (silica gel, hexane containing EtOAc).

In Step B, the compound of structure (12) is dissolved in a solvent such as methylene chloride, chloroform, carbon tetrachloride or 1,2-dichloroethane and treated with a slight excess of dimethylaminopyridine tribromide. The reaction is stirred at room temperature for about 1-24 hours. The excess brominating reagent is quenched with Na$_2$SO$_3$ and the reaction is partitioned between water and organic solvent. The solvent is dried (Na$_2$SO$_4$) and concentrated under reduced pressure to yield the crude product of structure (13). The crude compound of structure (13) is purified by short path column chromatography (silica gel, hexane containing EtOAc).

In Step D, derivatives of structure (14) are prepared by adding t-BuLi portionwise (exotherm) to a solution of the vinyl bromide (13) in dry TEF at −78° C. under N$_2$. The reaction is stirred at −78° C. for 45 min and trimethyl borate is then added. The reaction is warmed to room temperature and stirred for about an additional 30 min. The mixture is then concentrate using standard procedures, ethylene glycol and toluene are added, and the reaction refluxed overnight. The reaction is then cooled to room temperature, the layers separated and the ethylene glycol layer extracted with toluene, the toluene layers are then combined and concentrated to provide the compound of structure (14). The crude product (14) can then be purified by silica gel chromatography eluting with ethyl acetate:hexanes:triethylamine.

In Step C, the vinyl bromide of structure (13) and aryl boronic acid are mixed in dioxane. 2.0M aqueous Na$_2$CO$_3$ is then added and the reaction sparged with N$_2$ for 5 min. Pd(PPh$_3$)$_4$ is added and the reaction vial immediately sealed. The reaction is heated to about t 70-100° C. for about 8-24 h. The reaction is then quenched with H$_2$O and the product of Formula I extracted into CH$_2$Cl$_2$. After drying (Na$_2$SO$_4$) and concentration, the crude product is purified using chromatography on silica gel, eluting with ethyl acetate/hexanes to obtain the purified product of Formula I.

In Step E, a mixture of the vinyl borate of structure (14), a substituted or unsubstituted chloroheterocycle, cesium fluoride and [1,1'-bis(diphenylphosphino)-ferrocene]dichloropalladium (II) (1:1 complex with CH$_2$Cl$_2$) in dioxane is heated at about 50-100° C. for about 12-72 h. The solvent is removed using a stream of nitrogen and the resulting residue is shaken with H$_2$O and CH$_2$Cl$_2$ and loaded onto a Varian ChemElut CE1005 solid-phase extraction cartridge. Elute with CH$_2$Cl$_2$, and concentrate using standard procedure to obtain the crude product of Formula I, wherein a heterocycle or substituted heterocycle is attached to the tricyclic core. The crude product can then be purified by mass-guided reverse-phase HPLC to obtain the purified product of Formula I. Alternatively, in Step E, a mixture of vinyl borate (14), a substituted or unsubstituted chloroheterocycle, K$_2$CO$_3$ and ethanol is sparged with N$_2$ for 10 min. Pd(PPh$_3$)$_4$ is then added and the reaction sealed immediately. The reaction is heated at about 70-100° C. for about 12-72 h. The mixture is then concentrated under N$_2$, then H$_2$O (1 mL) and ethyl acetate (1 mL) are added. The residue is load onto a Varian ChemElut CE1005 solid-phase extraction cartridge. Elute with ethyl acetate, collect, and concentrate the crude reaction. The crude product can then be purified on silica gel, eluting with ethyl acetate/hexanes to obtain the pure product of Formula I wherein a substituted or unsubstituted heterocycle is attached to the tricyclic core.

Scheme VIII provides yet additional procedures for the synthesis of compounds of Formula I, particularly those wherein rings A and/or B are heterocyclic rings.

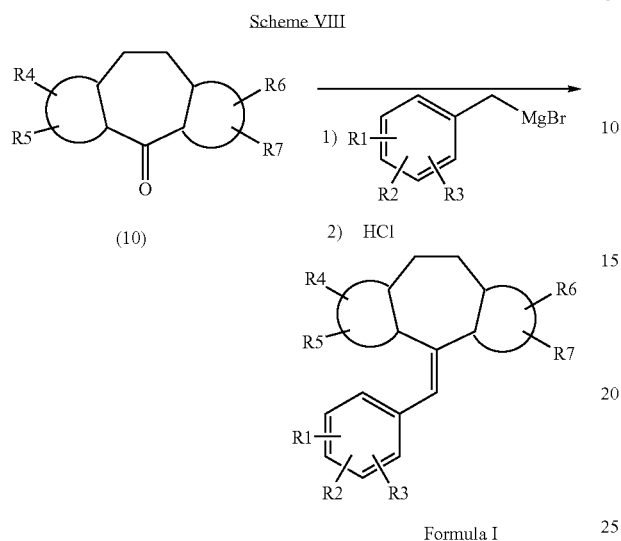

In Scheme VIII, a solution of the appropriate substituted or unsubstituted benzyl magnesium bromide in TIF is added to a solution of (10) in THF under Ar. The resulting solution is stirred for about 1-24 h at about 25° C. before quenching with saturated, aqueous ammonium chloride. The mixture is filtered and the magnesium salts washed with diethyl ether. The filtrate is then with water and brine, dried ($Na_2SO_4$), and concentrated under reduced pressure. The resulting tertiary alcohol can then be purified by column chromatography (hexanes/ethyl acetate).

The crude carbinol is dissolved in $CHCl_3$ and concentrated hydrochloric acid is then added. The resulting dark solution is stirred for 2 h at about 25° C. Water and $CHCl_3$ are added, the layers separated, and the organic layer washed successively with saturated, aqueous sodium bicarbonate and brine. The crude product of Formula I is then dried ($MgSO_4$) and concentrated via rotary evaporation. The crude material may then be purified by flash chromatograpy(hexanes/ethyl acetate) to provide the purified final product of Formula I (wherein A and/or B are, for example, heterocyclic rings).

Additional Schemes for the Synthesis of Compounds of the Invention:

Scheme IX provides procedures useful for the synthesis of compounds of Formula I wherein the "C" ring represents an N-substituted benzimidazole derivative.

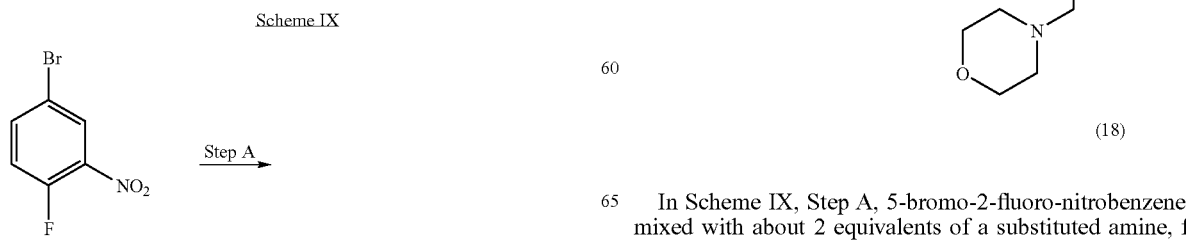

In Scheme IX, Step A, 5-bromo-2-fluoro-nitrobenzene is mixed with about 2 equivalents of a substituted amine, for example 4-(2-aminoethyl)morpholine, in THF. The reaction is stirred at room temperature for about 18 h. The THF is removed under reduced pressure and the residue partitioned between water and ethyl acetate. The organic layer is dried (MgSO4) and concentrated to provide compound of structure (15).

In Scheme IX, Step B, the compound of structure (15) is dissolved in ethyl acetate or THF and 5% Pt/C (sulfided) is added. The slurry is placed under 60 psi hydrogen gas at room temperature for about 8 h. The reaction is then filtered and concentrated to provide, for example, the compound of structure (16) as a dark red oil. Compound (16) may then be purified, for example by using a short plug of silica gel and 10% 2N NH3 in MeOH/dichloromethane.

In Scheme IX, Step C, the compound of structure (16) is mixed with NaHCO3, water, and methanol. Slowly, phenyl chloroformate (about 1.5 equivalents) is added and the reaction is stirred for about 1 h at room temperature. 5N NaOH (about 1.5 equivalents) is then added and the reaction is stirred overnight at room temperature. The solid of structure (17) is collected by vacuum filtration and washed with methanol.

In Scheme IX, Step D, under a blanket of nitrogen, a solution of compound (17) in THF is cooled to about 5° C. and 3N ethylmagnesium bromide is added. After about ½ h, the reaction is cooled to about −72° C. and slowly 1.7M t-BuLi is added. The reaction is allowed to warm to about −55° C., then trimethyl borate is added and the reaction is allowed to stir at room temperature overnight. 5N HCl is then added and the reaction stirred for about 4 h. The pH is adjusted to about 6-7 and the crude boronic acid is extracted into ethyl acetate, dried and concentrated to give the crude acid which is then slurried with toluene and pinacol is added. The reaction is heated briefly and stirred overnight. Ethyl acetate and aqueous NaHCO3 are added, the organics extracted with water and the dried MgSO4) organic layer is evaporated to give the purified product of compound (18).

Schemes X-XIII provide procedures useful for the synthesis of compounds of Formula I wherein the "A" and/or "B" ring represents a heterocyclic ring, which may be substituted or unsubstituted. Also, Scheme X demonstrates an alternative procedure to that described in Scheme VII, Step A for converting the ketone moiety to a methylene by use of the Tebbe reagent.

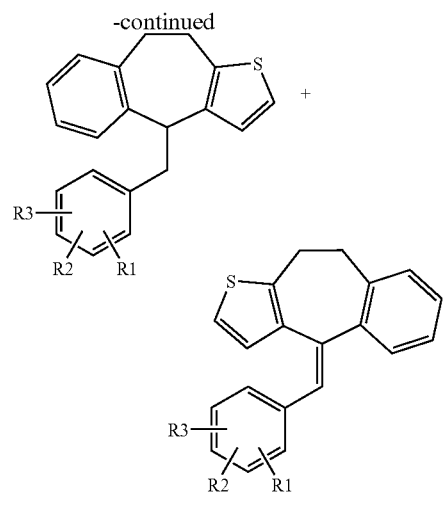

Formula I

In Scheme X, Step A, to a solution of, for example, 9,10-dihydro-1-thia-benzo[f]azulene-4-one (see P. Bollinger, P. Cooper.; H. U. Gubler, A. Leutwiler, T. Payne *Helv. Chim. Acta*. 1990, 73, 1197) at about −40° C. is added about 3 equiv of a 0.5 M solution of Tebbe reagent in toluene and about 3 equiv of pyridine in THF (0.1 M) under Ar. The resulting mixture is stirred for about 2 h then allowed to warm to 0° C. over ca. 30 min period before diluting with diethyl ether. 5 N sodium hydroxide is then added carefully until bubbling ceases, then solid Na$_2$SO$_4$, and the reaction stirred for about 1 h. The mixture is then filtered through Celite®, then the filtrate by rotary evaporation. The crude residue of compound (19) may then be purified by standard techniques such as column chromatography (hexanes) to give the purified product of structure (19).

In Scheme X, Steps B and C, the compound of structure (19) may be treated according to the procedures as described in Scheme VII, Steps B and C to provide the compound of Formula I.

Scheme X

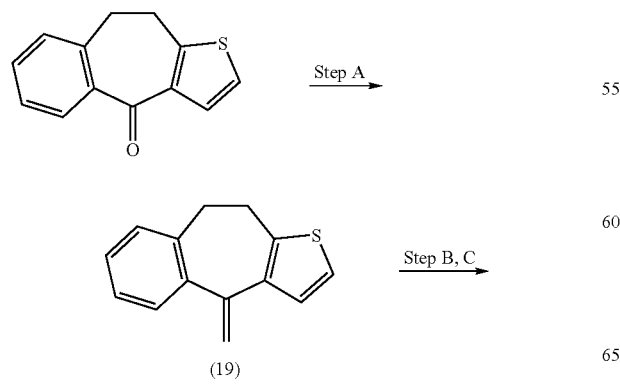

Scheme XI

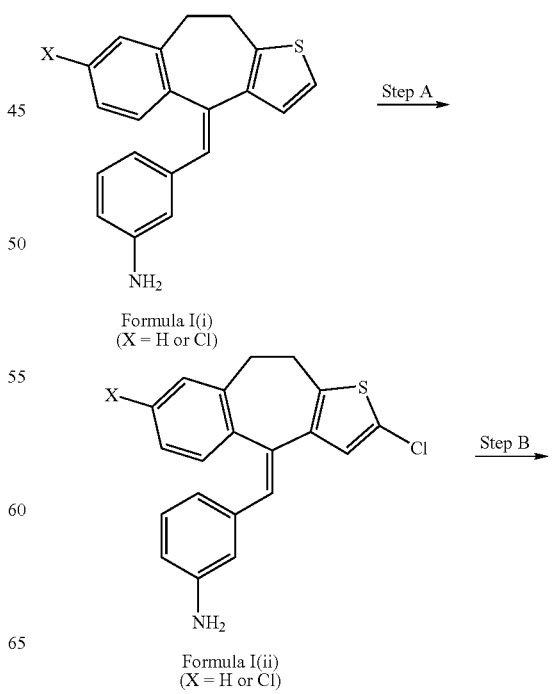

Formula I(i)
(X = H or Cl)

Formula I(ii)
(X = H or Cl)

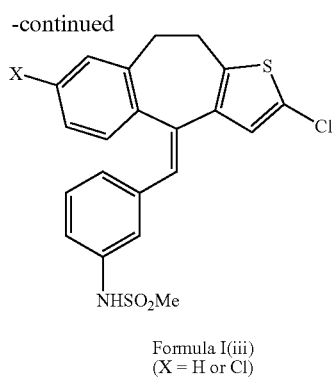

Formula I(iii)
(X = H or Cl)

In Scheme XI, procedures for the synthesis of compounds of Formula I wherein "A" or "B" represents a chlorothiophene are provided. In Scheme XI, Step A, about 2 equiv of n-BuLi-hexanes is added dropwise to a solution of a compound of Formula I(i), for example 3-(9,10-Dihydro-1-thia-benzo[f]azulenylidenemethyl)-phenylamine, in THF at about 0° C. under Ar. The resultant dark solution is stirred for about 1 h before adding about 2.5 equiv of hexachloroethane in THF. The reaction is stirred for about 2 h, quenched with excess water, and acidified to neutral pH. The aqueous layer is extracted with diethyl ether (3×) and then dried (MgSO$_4$), and the combined organic layers are concentrated under reduced pressure. The crude product (formula I(ii)) may then be purifed using standard techniques, such as by column chromatography to give the 2-chlorothiophene derivative compound.

In Scheme XI, Step B, the amino group of Ring "C" may be treated according to procedures as described in Scheme V(a), Step B to provide further methanesulfonamide derivatives of Formula I(iii).

Scheme XIII provides procedures for the synthesis of derivatives of Formula I wherein Ring "A" and or "B" represents a methylated heterocycle, particularly a methylated thiazole. In Scheme XII, Step A, add about 1.2 equiv of n-BuLi-hexanes dropwise to a solution of compound (20) (4methylene-9,10 dihydro4H-3-thia-1-aza-benzo[f]azulene) in THF at about −78° C. under Ar. The resultant dark green solution is stirred for about 5 min before adding about 1.2 equiv of iodomethane in THF. The reaction is allowed to warm and stirred at room temperature for about 18 h before quenching with excess water. The layers are separated and the aqueous layer extracted with, for example, diethyl ether (3×) and then dried (MgSO$_4$. The combined organic layers may then be concentrated under reduced pressure and the product (Structure (21))used in the next step without further purification.

In Scheme XII, Steps B and C, the compound of structure (21) is treated according to procedures as described Scheme VII, Steps B and C to provide the compound of Formula I wherein Ring "A" and or "B" represents a methylated heterocycle.

Scheme XIII

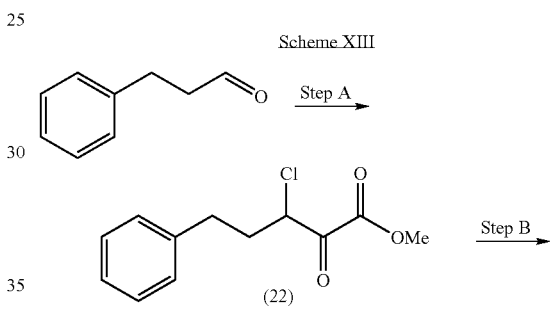

Scheme XII

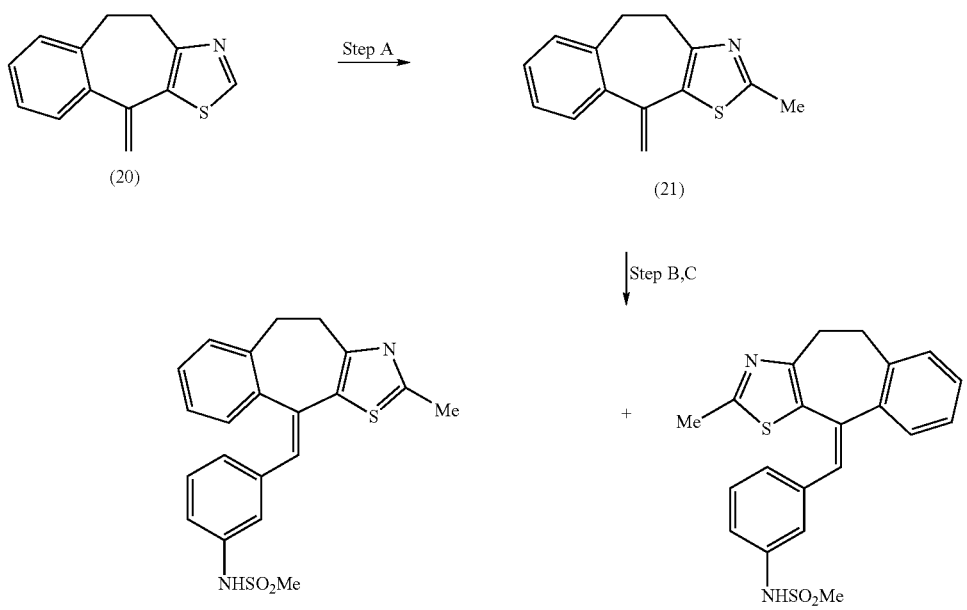

Formula I

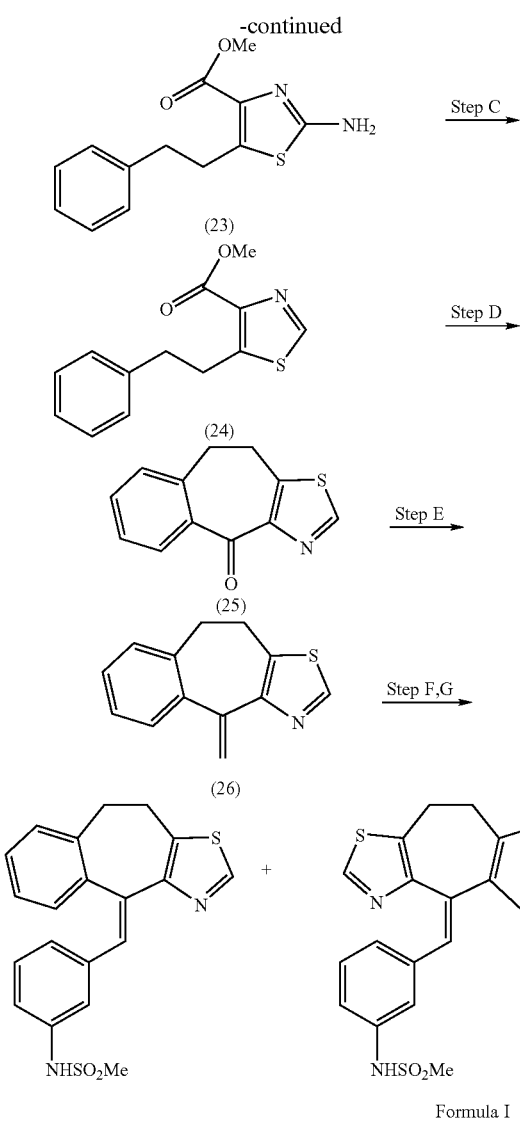

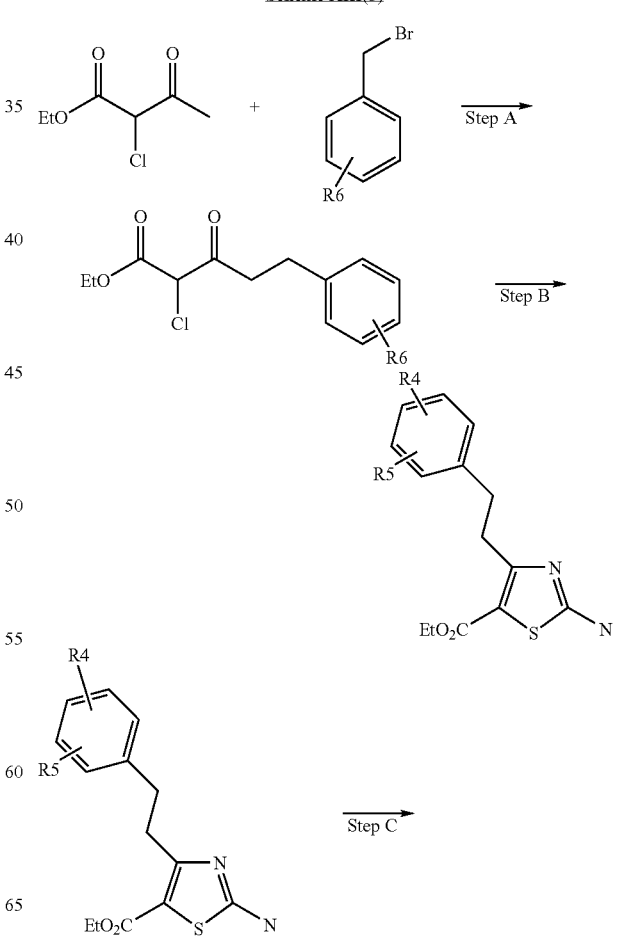

stirred and heated to about 140° C. for about 24 h and then about 150° C. for about 5 h. Carefully the hot mixture is added to ice-cold aqueous sodium hydroxide. The reaction is then extracted, for example with EtOAc, and the combined organic layers washed with brine, dried (MgSO$_4$), and concentrated under reduced pressure. The crude residue of structure(25) may then be purified by standard techniques, such as by column chromatography (10% to 50% EtOAc:hexanes) to provide the purified compound of structure (25).

In Scheme XIII, Step E, the compound of structure(25) is treated according to procedures as described in Scheme VII, Step A to provide compound of structure (26).

In Scheme XIII, Steps F and G, the compound of structure (26) is treated according to procedures as described Scheme VII, Steps B and C to provide the compound of Formula I wherein Ring "A" and or "B" represents a thiazole ring.

Alternatively, the desired starting thiazole ketone can be prepared as as shown in Scheme XIII(b), below. In step A, 2-chloro-3-oxo-butyric acid ethyl ester in THF is treated with first NaH (1 equivalent) then n-BuLi (1 equivalent) while the temperature is held at about 60 to –10° C. and then the appropriately substituted benzyl bromide added. In Step B, the intermediate 2-chloro-3-oxo-5-phenyl-pentanoic acid ethyl ester derivative is reacted with thiourea in refluxing ethanol for 1-24 hours. This ester can be cyclized using PPA and heating at from 160-250° C. for 1-15 hours. As described in Scheme XIII(a), Step C , the amino moiety can be converted to —H. This intermediate ketone can be converted to final products as in Scheme XIII(a), Steps E, F and G.

Scheme XIII(b)

Scheme XIII provides additional procedures for the synthesis of compounds of Formula I wherein Ring "A" and or "B" represents a thiazole. In Scheme XIII, Step A, a flask is charged with equimolar methyl dichloroacetate and 3-phenyl-prionaldehyde in diethyl ether. The solution is cooled to about 0° C. and about 1 equiv of sodium methoxide in methanol is added over a 1 h period. The mixture is vigourously stirred for about 2 h at about 0 C and then allow to warm to room temperature before adding brine. The layers are separated, dried (MgSO$_4$) and the organic concentrated to give the crude residue of compound (22).

In Scheme XIII, Step B, reflux the compound of structure (22) and thiourea in MeOH for about 4 h, then basify with ammonia-MeOH and add brine. The reaction is then extract with, for example ethyl acetate, then the combined organic layers are washed with brine, dried(MgSO$_4$), and concentrated under reduced pressure to give the compound of structure (23).

In Scheme XIII, Step C, about one equiv of the compound of structure (23) and about 3 equiv of isoamyl nitrite in THF are refluxed for about 3 h. Evaporate The volatile components are evaporated to provide the compound of structure (24).

In Scheme XIII, Step D, a thick slurry of the compound of structure (24) and polyphosphoric acid (PPA) is rapidly

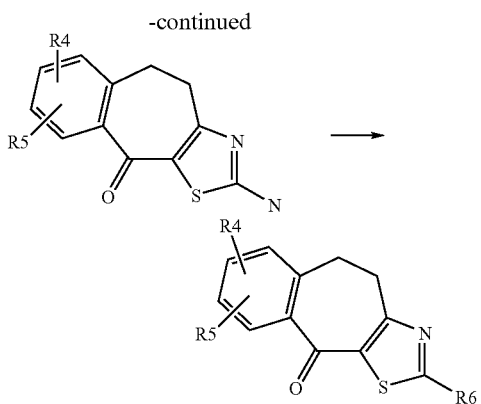

Scheme XIV provides additional procedures for the synthesis of compounds of Formula I wherein ring "A" and or "B" is substituted.

Scheme XIV

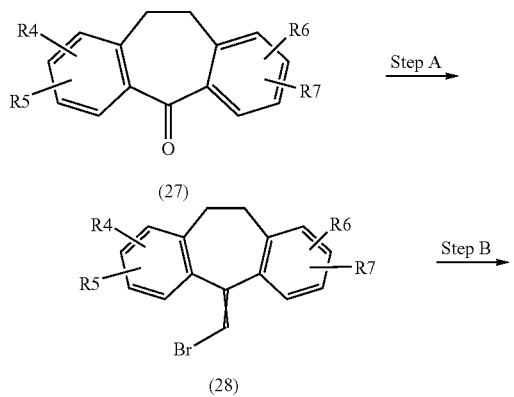

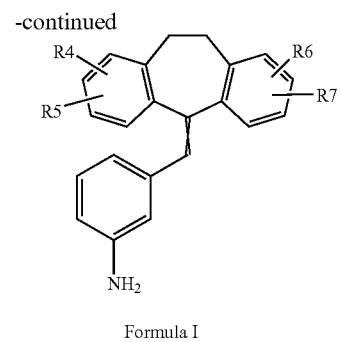

Formula I

In Scheme XIV, Step A, a mixture of 2-3 equiv of bromomethyltriphenylphosphonium bromide (see G. Vassilikogiannakis, M. Hatzimarinaki, M. Orfanapoulos *J. Org. Chem.*, 65, 8180) in THF (0.5 M) is cooled to about −78° C. and about 2-3 equiv of LiHMDS-THF is added dropwise to give a bright yellow mixture. The reaction is stirred for about 1 h at about −78° C. and then for about 10 min at 0° C. The mixture is re-cooled to about −78° C. and the compound of structure (27) is added. The dark mixture to is allowed to warm to room temperature and stirred for about 3.5 h before adding saturated, aqueous saturated ammonium chloride and diluting with pentane. The mixture is filtered through celite, the filtrate concentrated under reduced pressure, and purifed by standard techniques such as column chromatography (1% to 2% to 3% to 5% EtOAc:hexanes) to give the compound of structure (28) as a 1:1 mixture of geometric isomers.

In Scheme XIV, Step B, the compound of structure (28) is treated according to procedures as described in Scheme VII, Step C to provide the compound of Formula I.

Scheme XV provides additional procedures for the synthesis of compounds of Formula I wherein ring "A" and or "B" represents a heterocyclic ring and additionally shows methodology to prepare useful intermediate vinyl borate ester derivatives.

Scheme XV

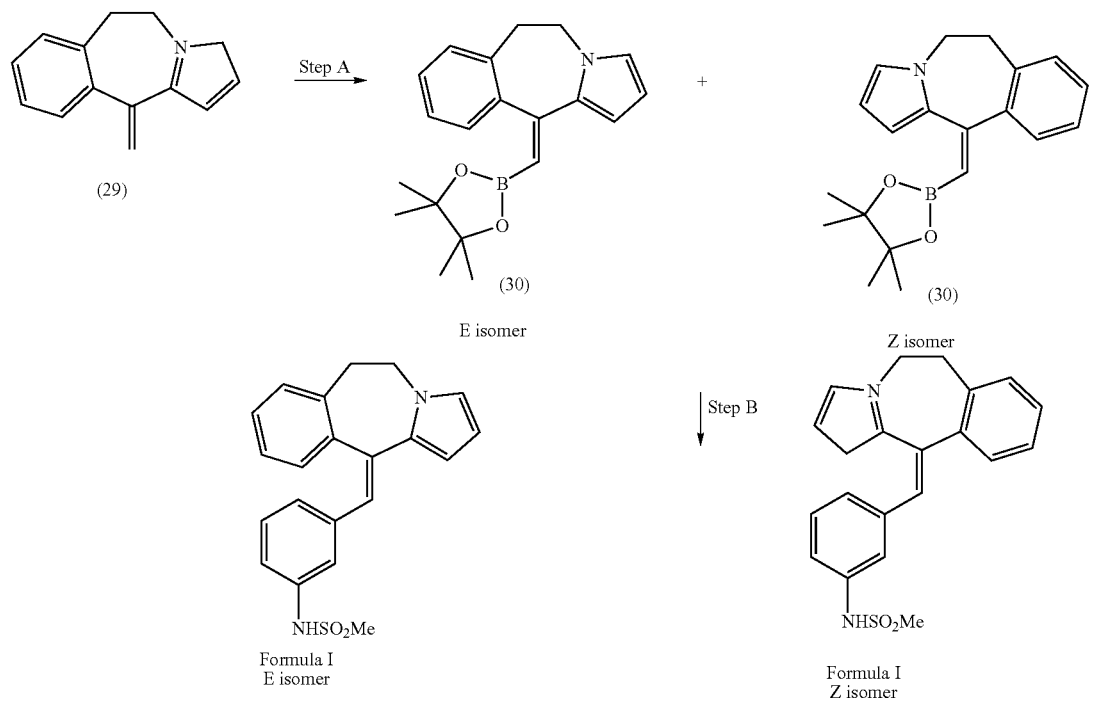

In Scheme XV, Step A, about one equiv of, for example, 5,6-dihydro-benzo[d]pyrrolo[1,2-a]azepin-11-one (structure (29))(see Y. Girard, J. G. Atkinson, P. C. Belanger, J. J. Fuentes, J. Rokach, C. S. Rooney, D. C. Remy, C. A. Hunt *J. Org. Chem.* 1983, 48, 3220) in THF is added to a solution of about 2.5 equiv of pinicol lithio(trimethylsilyl)methaneboronate (see D. S. Matteson, D. Majumder *Organometallics* 1983, 2, 230), about 1 equiv TMEDA, about 2.5 equiv of tetramethylpiperidine (TMP), and THF at about −78° C. The solution is allowed to warm to room temperature and stirred for about 3.5 h before quenching with excess water. The reaction is extracted with Et$_2$O (4×), dried (MgSO$_4$) and concentrated under reduced pressure. The crude residue may then be purified by standard techniques such as column chromatography (5% to 10% EtOAc:hexanes) to give the pure E-isomer and Z-isomer of structure (30).

In Scheme XV, Step B, the compound of structure (30) is treated according to procedures as described in Scheme VII, Step C to provide the E and Z isomer of the compound of Formula I.

Scheme XVI provides yet additional procedures for synthesizing compounds of Formula I wherein ring "A" and or "B" represents a heterocyclic ring.

In Scheme XVI, Step A, diisopropylamine is dissolved in dry tetrahydrofuran and the resulting mixture cooled to about −78° C. Butyllithium is then added and the reaction mixture is warmed to about 0° C. then a fine slurry of 2-methyl-nicotinic acid in THF (25 mL) is added portionwise during about 10 min. The resulting slurry is stirred for about 1 h, then 3-fluorobenzyl bromide is added and the mixture is stirred for about 5 min. The reaction is quenched with water and extracted with diethyl ether. The pH of the aqueous layer is adjusted to about 3.1 with concentrated aqueous hydrochloric acid solution. The resulting slurry is treated with ethyl acetate and stirred to dissolve all solids. The layers are separated and the aqueous layer extracted with ethyl acetate. Concentrate the combined extracts are then concentrated to dryness to provide the compound of structure (31).

In Scheme XVI, Step B, the compound of Structure (31) is combined with polyphosphoric acid (about 100 g) and heated to about 160° C. for about 6 h. The reaction mixture is allowed to slowly cool over 12 h, then reheated to about 160° C. and poured into ice. The transfer is completed using water and the pH of the aqueous mixture adjusted to about 8.0 with 50% aqueous sodium hydroxide solution. The product of structure

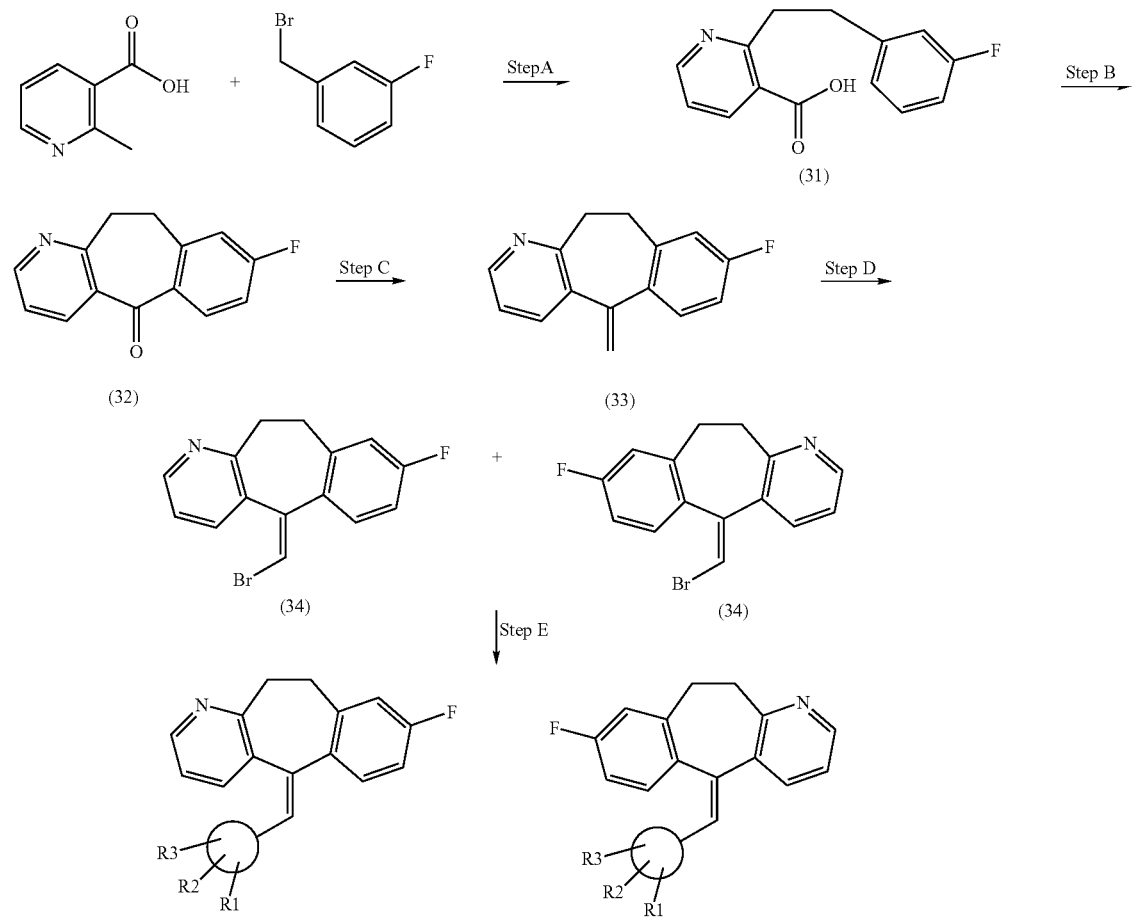

Scheme XVI

Formula 1

(32) is extracted with methylene chloride. The combined organic extracts are dried with magnesium sulfate, filtered and concentrated. The compound of structure (32) may then be purified using standard techniques such as flash chromatography (25% ethyl acetate/hexanes to 50% ethyl acetate/hexanes) to provide the purified product of the compound of structure (32). (See *Journal of Heterocyclic Chemistry* 1971, 73).

In Scheme XVI, Step C, a mixture of compound (32) and dry THF is chilled to about 0° C. This mixture is treated with methyl magnesium bromide, the cooling removed, and the mixture is stirred at room temperature for about 15 min. The reaction is quenched, while cooling with an ice-water bath, by adding saturated aqueous ammonium chloride solution (50 mL). The layers are separated and the aqueous layer extracted with methylene chloride (2×50 mL). The combined organic layers are dried with magnesium sulfate, filtered, and concentrated to provide the intermediate product of structure (33) as a thick crude oil. Without further purification, this residue is dissolved in a solution of sulfuric acid in acetic acid (3% by volume, 50 mL) and the mixture stirred at room temperature for about 12-18 h. The reaction mixture is concentrated to remove excess solvent and the resulting orange residue dissolved in 1N aqueous sodium hydroxide solution (25 mL) and ethyl acetate (50 mL). the pH of the resulting mixture is adjusted to about 8 with 5N aqueous sodium hydroxide solution. The layers are separted, and the aqueous extracted with ethyl acetate (2×50 mL). The combined organic layers are dried with magnesium sulfate, filtered, and concentrated to provide the compound of structure (33).

In Scheme XVI, Step D, the compound of structure (33) is treated according to procedures as described in Scheme VI, Step B, to provide E and Z isomer of compound (34).

In Scheme XVI, Step E, the compound of structure (34) is treated according to procedures as described in Scheme VII, Step C to provide the E and Z isomer of the compound of Formula I.

Scheme XVII provides yet additional procedures for synthesizing compounds of Formula I wherein ring "A" and or "B" represents a heterocyclic ring and wherein the bridge depicted by —X—Y— contains a heteroatom or heteroatom containing group at either the X or Y position.

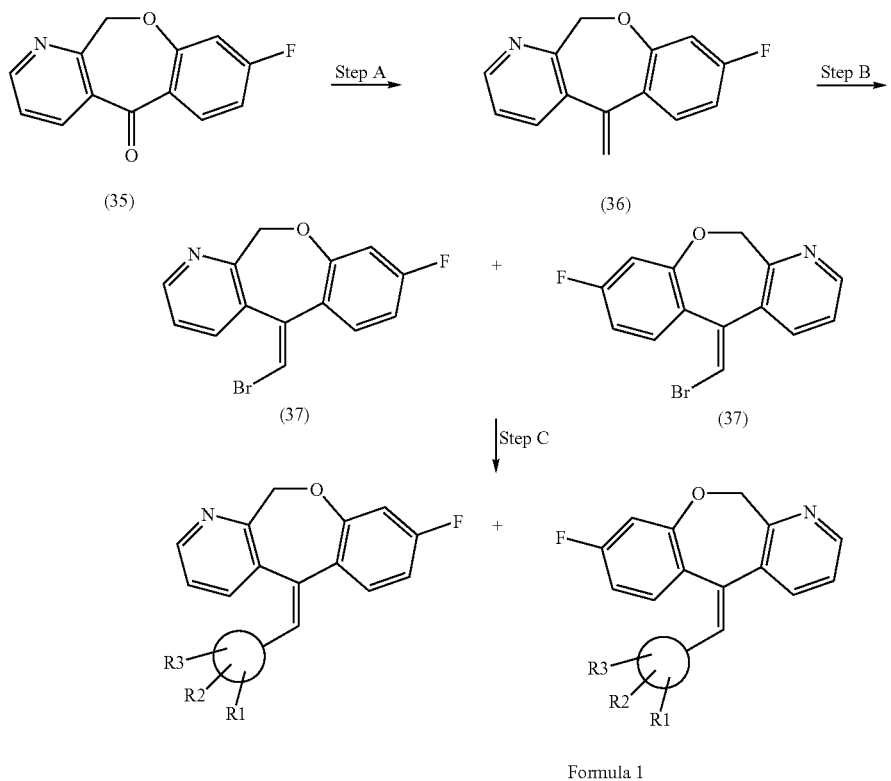

Scheme XVII

Formula 1

In Scheme XVII, Step A, the compound of structure (35), for example, (8-fluoro-11H-10-oxa-1-aza-dibenzo[a,d]cyclohepten-5-one) (see *Journal of Medicinal Chemistry* 1990, 33, 3095) and anhydrous tetrahydrofuran (25 mL) are combined and the solution cooled to about 0° C. Tebbe reagent (0.5M/L solution in toluene) is then added, cooling is removed, and the mixture stirred for about 10 min. The reaction is quenched by adding saturated aqueous Rochelle's salt solution and the biphasic mixture stirred rapidly for about 10 min. The layers are then separated and the aqueous layer extracted with ethyl acetate. The combined organic layers are dried with magnesium sulfate, filtered and concentrated. The crude product of compound (36) may then be purified using standard techniques such as flash chromatography (25% ethyl acetate/hexanes) to provide the purified product of structure (36).

In Scheme XVII, Step B, the compound of structure (36) is treated according to procedures as described in Scheme VII, Step B, to provide E and Z isomer of compound (37).

In Scheme XVII, Step C, the compound of structure (37) is treated according to procedures as described in Scheme VII, Step C to provide the E and Z isomer of the compound of Formula I.

Scheme XVIII provides general procedures for the synthesis of compounds of Formula I wherein ring "A" and or "B" is contains an ether moeity

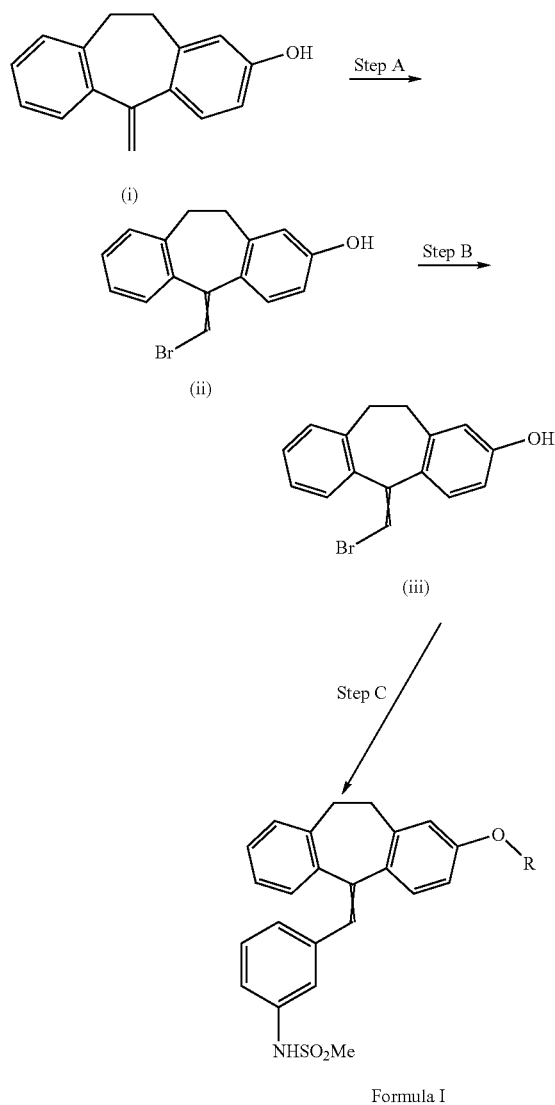

In Scheme XVIII, Step A, the compound of structure (i) (5-methylene-10,11-dihydro-5H-dibenzo[a,d]cyclohepten-2-ol), prepared from commercially available 2-hydroxy-10,11-dihydro-dibenzo[a,d]cyclohepten-5-one using procedures as described Scheme VII, Step A, is treated under conditions as described in Scheme VII, Step B to provide the compound of structure (ii) (5-bromomethylene-10,11-dihydro-5H-dibenzo[a,d]cyclohepten-2-ol)

In Scheme XVIII, Step B, 2.5 equivalents of PS-TBD Resin (commercially available: Argonaut Technologies) is added to a fritted vessel. The bottom of the vessel is capped and about 1.0 equivalent of 5-bromomethylene-10,11-dihydro-5H-dibenzo[a,d]cyclohepten-2-ol in acetonitrile is added. About 0.8 equivalents of the appropriate alkyl halide in acetonitrile is then added and the top of the vessel is capped and the vessel rotated for about 48-96 hours. The vessel is then uncapped and the filtrate collected into a screw-cap vial. The resin is washed with acetonitrile followed by dichloromethane. The filtrate is combined with the washings and concentrate under vacuum.

In Scheme XVIII, Step C, into the screw capped vial containing the bromomethylene ether, about 1.2 equivalents of potassium carbonate and about 1.1 equivalents of, for example, N-[3-(4,4,5,5-tetramethyl-[1,3,2]-dioxaboronan-2-yl)-phenyl]-methanesulfonamide, is added. The solution is purged with nitrogen for about 5 min. then about 0.1 equivalents of palladium tetrakis(triphenylphosphine) is added into the vial. The vial is capped and heated to about 90-100° C. for about 16 hours with continuous stirring. The reaction is then loaded onto Chem-Elute column (Varian Sample Prep) primed with water and the column is eluted with ethyl acetate. The filtrate is then concentrated under vacuum and may be purified by standard techniques such as silica gel chromatography.

Determination of Biological Activity

To demonstrate that compounds of the present invention have affinity for steroid hormone nuclear receptors, and thus have the capacity to modulate steroid hormone nuclear receptors, soluble MR and GR binding assays are performed. All ligands, radioligands, solvents, and reagents employed in the binding assays are readily available from commercial sources, or can be readily synthesized by the ordinarily skilled artisan.

Mineralocorticoid Receptor Binding Assay:

The full length human MR gene is cloned from a human kidney or human brain cDNA library. Briefly, using synthetic oligonucleotide primers (Eli Lilly and Company, Indianapolis) directed to nucleotides 20-54 and 3700-3666 of the human MR, polymerase chain reaction (PCR) is performed under standard conditions using a human cDNA library. The PCR reaction is performed in a final volume of 50 µl containing about 1 µl of a 50× stock solution of polymerase; about 1 µl of a 50× stock solution of dNTP; about 5 µl of an appropriate PCR buffer; about 1 µl of each primer; about 51 µl of a H. kidney or H. brain cDNA library; and about 36 µl of water. The reaction is allowed to denature for about 30 seconds at 95 degrees Celsius, anneal for about 30 seconds at 55 degrees Celsius, and extend for about 5 minutes at 72 degrees Celsius, the sequence being repeated for a total of about 35 cycles. The desired PCR product (3.68 Kb) is confirmed by gel electrophoresis and subsequently cut from the gel and stored at about −20 degrees Celsius until extraction. To extract the cDNA product from the agarose gel, the QIAEX II Gel Extraction protocol (QIAGEN, Inc.) is employed according to the manufacturer's instructions. Following extraction, the MR cDNA is cloned into an appropriate cloning vector (Zero Blunt TOPO PCR Cloning Kit Invitrogen, Inc.) and a pAcHLT-baculovirus transfer vector (B.D./Pharminogen), then expressed in SF9 insect cells, essentially according to manufacturer's instructions. Sf9 cells are grown at a scale where gram quantity cell pellets are obtained for subsequent use in the MR binding assay. Harvested cell pellets are lysed by repeated freeze-thaw cycles (about 4) in a suitable lysis buffer then centrifuged at about $1 \times 10^3$ G (with the supernatant being saved for future assays).

MR binding assays are performed in a final total volume of about 250 µl containing about 20-25 µg of protein and 0.5 nM of [$^3$H]-aldosterone plus varying concentrations of test compound or vehicle. The assay binding buffer consists of 30 mM sodium molybdate, 30 mM of TRIS-HCl, 5 mM sodium phosphate, 5 mM sodium pyrophosphate, and about 10% glycerol, pH=7.5.

Briefly, assays are prepared at RT in 96-well Falcon 3072 plates, each well containing 210 µl of binding buffer, 10 µl of [$^3$H] -aldosterone, 10 µl of test compound/vehicle, and 20 µl of the resuspended receptor protein extract. Incubations are carried out at 4 degrees Celsius with shaking for about 16 hours. 200 µl aliquots of each incubation are filtered onto Millipore HA 0.45 micron 96-well filter plates, pre-moistened with cold 30 mM TRIS-HCl. The filter plates are suctioned dry with vacuum and immediately washed 3× with cold 30 mM TRIS-HCl. The plates are then punched out and the amount of receptor-ligand complex is determined by liquid scintillation counting using 4 ml of Ready Protein Plus™ liquid scintillation cocktail.

$IC_{50}$ values (defined as the concentration of test compound required to decrease [$^3$H]-aldosterone binding by 50%/o) are then determined. Ki values for each respective test compound can then be calculated by application of the Cheng-Prusoff equation as described in Cheng et al., Relationship Between The Inhibition Constant (Ki) and The Concentration of Inhibitor Which Causes 50% Inhibition ($IC_{50}$) of an Enzymatic Reaction, Biochem. Pharmacol., 22: 3099-31088; (1973).

Glucocorticoid Receptor Binding Assay:

To demonstrate the GR modulating potency of compounds of the present invention the following source of glucocorticoid receptor is employed. A549 human lung epithelial cells (ATCC) are grown at a scale where gram quantity cell pellets are obtained. Harvested cell pellets are washed twice in cold phosphate buffered saline, centrifuged, and resuspended in cold assay binding buffer. The assay binding buffer consists of 10% glycerol, 50 mM Tris-HCl (pH7.2), 75 mM sodium chloride, 1.5 mM magnesium chloride, 1.5 mM EDTA, and 10 mM sodium molybdate. Cell suspensions were lysed via sonication, centrifuged, and the "extract" supernatant is snap frozen and stored at −80 C until needed.

GR binding assays are performed in a final volume of 140 ul containing 50-200 ug of A549 cell extract and 1.86 nM [$^3$H]-dexamethasone (Amersham) plus varying concentrations of test compound or vehicle. Briefly, assays are prepared at RT in 96-well Fisher 3356 plates, each well containing 100 ul of A549 cell extract, 20 ul of [$^3$H]-dexamethasone, and 20 ul of test compound/vehicle. Incubations are carried out at 4 degrees Celsius for 16 hours. After incubation, 70 ul of 3× dextran-coated charcoal solution is added to each reaction, mixed, and incubated for 8 minutes at RT. 3×-dextran-coated charcoal solution consists of 250 ml assay binding buffer, 3.75 g Norit A charcoal (Sigma), and 1.25 g dextran T-70 (Amersham). Charcoal/unbound radioligand complexes are removed by centrifugation of the plate and 140 ul of supernatant from each well is transferred to another 96 well Optiplate (Packard Instruments). 200 ul of Microscint-20 scinillant (Packard Instruments) is added to each well and amount of receptor bound radioligand is determined using Packard Instruments TopCount instrument.

$IC_{50}$ values, defined as the concentration of test compound required to decrease [$^3$H-dexamethasone binding by 50%, are then determined. Ki values for each respective test compound can then be calculated by application of the Cheng-Prusoff equation as described in Cheng et al., Relationship Between The Inhibition Constant (Ki) and The Concentration of Inhibitor Which Causes 50% Inhibition ($IC_{50}$) of an Enzymatic Reaction, Biochem. Pharmacol., 22: 3099-31088; (1973).

Binding assay protocols for PR, AR, and ER, similar to those described above for MR and GR, can be readily designed by the ordinarily skilled artisan. U.S. Pat. No. 6,166,013 provides examples of such protocols. Representative compounds of the present invention have a Ki in the MR or GR binding assay of ≦50 µM. Table I (see infra.) provides MR and GR binding data for a representative sample of the exemplified compounds of the present invention.

To demonstrate the ability of compounds of the present invention to modulate the activity of a steroid hormone receptor (i.e. either agonize, antagonize, partially agonize, or partially antagonize), bioassays are performed which detect modulation of target gene expression in cells transiently transfected with a nuclear receptor protein and a hormone response element-reporter gene construct. The solvents, reagents, and ligands employed in the functional assay are readily available from commercial sources, or can be synthesized by one of ordinary skill in the art.

Functional Assay of Mineralocorticoid Receptor Modulation:

For the MR transient transfection assay, COS-7 cells are transfected with full length human MR and a 2×GRE-luciferase gene construct. Following transfection, the ability of test compounds to modulate expression of the luciferase reporter gene product is monitored. Briefly, on day one, COS cells are harvested from cell culture plates using standard procedures such as treatment with Trypsin-EDTA (GIBCO BRL). Culture medium is then added to the cells and the cell-medium mixture is plated in 96-well plates coated with poly-(d)-lysine (approximately $3 \times 10^4$ cells/well). Cells are grown for about 4 hours then transfected with Fugene-6 reagent with plasmids containing human MR, previously cloned into pc.DNA 3.1 expression vector, and 2×GRE-reporter gene construct (GRE-luciferase), previously cloned into pTAL-luc vector. Transfection is carried out in DMEM with 5% fetal calf serum, charcoal treated. 24 hours later cells are exposed to various concentrations of aldosterone in the presence and absence of test compound and incubated for an additional 24 hours. The reaction is terminated by the addition of lysis buffer followed by luciferin (luciferase substrate). Luciferase expression, as an indicator of ligand induced MR transactivation, is monitored by chemiluminescence measured using a microtiter plate luminometer (MLX). The kinetic inhibition constant ($K_b$ or $K_p$) can then be determined by analysis of dose-response curves for aldosterone, in the presence and absence of test compound, using standard techniques.

TABLE I

Mineralocorticoid and Glucocorticoid Receptor Binding Assay Values

| Example No. | MR Ki (nM) | GR Ki (nM |
|---|---|---|
| 206(a) | +++ | +++ |
| 262 | +++ | +++ |
| 197(a) | +++ | +++ |
| 125 | +++ | +++ |
| 267 | +++ | +++ |

TABLE I-continued

Mineralocorticoid and Glucocorticoid Receptor Binding Assay Values

| Example No. | MR Ki (nM) | GR Ki (nM) |
|---|---|---|
| 199(a) | +++ | +++ |
| 199(b) | +++ | +++ |
| 207 | +++ | +++ |
| 274 | +++ | +++ |
| 141 | +++ | +++ |
| 182 | +++ | +++ |
| 184(a) | +++ | +++ |
| 181(a) | +++ | +++ |
| 268 | +++ | +++ |
| 208(b) | +++ | +++ |
| 50 | +++ | +++ |
| 208(a) | +++ | +++ |
| 162 | +++ | +++ |
| 183 | +++ | +++ |
| 205(b) | +++ | +++ |
| 187 | +++ | +++ |
| 206(b) | +++ | +++ |
| 184(b) | +++ | +++ |
| 188(a) | +++ | +++ |
| 214 | +++ | +++ |
| 205(a) | +++ | +++ |
| 211(a) | +++ | +++ |
| 222(a) | +++ | +++ |
| 178 | +++ | +++ |
| 163 | +++ | +++ |
| 200(a) | +++ | +++ |
| 91 | +++ | +++ |
| 200(b) | +++ | +++ |
| 185(b) | +++ | ++ |
| 191 | +++ | +++ |
| 258 | +++ | +++ |
| 201 | +++ | +++ |
| 161 | +++ | +++ |
| 189 | +++ | +++ |
| 161(b) | +++ | +++ |
| 90 | +++ | +++ |
| 48 | +++ | +++ |
| 253 | +++ | +++ |
| 75 | +++ | +++ |
| 208(c) | +++ | +++ |
| 92 | +++ | +++ |
| 57 | +++ | +++ |
| 49 | +++ | +++ |
| 186 | +++ | +++ |
| 192 | +++ | +++ |
| 198(a) | +++ | +++ |
| 215 | +++ | +++ |
| 223 | +++ | + |
| 149 | +++ | +++ |
| 112 | +++ | +++ |
| 221(a) | +++ | +++ |
| 155 | +++ | +++ |
| 216 | +++ | +++ |
| 263 | +++ | ++ |
| 188(b) | +++ | +++ |
| 86 | +++ | +++ |
| 202 | +++ | ++ |
| 171 | +++ | +++ |
| 185(a) | +++ | +++ |
| 205(c) | +++ | +++ |
| 261 | +++ | +++ |
| 167 | +++ | +++ |
| 173(a) | +++ | +++ |
| 126 | +++ | +++ |
| 181(b) | +++ | +++ |
| 254 | +++ | +++ |
| 81 | +++ | + |
| 1 | +++ | +++ |
| 65 | +++ | + |
| 251 | +++ | +++ |
| 153 | +++ | ++ |
| 45 | +++ | ++ |
| 177 | +++ | ++ |
| 71 | +++ | +++ |
| 151 | +++ | ++ |
| 157 | +++ | ++ |
| 193 | +++ | +++ |
| 74 | +++ | +++ |
| 231 | +++ | +++ |
| 121 | +++ | + |
| 175 | +++ | + |
| 105 | +++ | +++ |
| 272 | +++ | + |
| 54 | +++ | +++ |
| 211(b) | +++ | ++ |
| 271 | +++ | +++ |
| 133 | +++ | ++ |
| 5 | +++ | +++ |
| 135 | +++ | + |
| 229 | +++ | ++ |
| 132 | +++ | ++ |
| 4 | +++ | ++ |
| 198(b) | +++ | ++ |
| 129 | +++ | +++ |
| 62 | +++ | + |
| 221(b) | +++ | +++ |
| 72 | +++ | + |
| 104 | +++ | +++ |
| 259 | +++ | + |
| 128 | +++ | ++ |
| 108 | +++ | +++ |
| 110 | +++ | +++ |
| 145 | +++ | +++ |
| 245 | +++ | + |
| 130 | +++ | + |
| 2 | +++ | +++ |
| 95 | +++ | ++ |
| 93 | +++ | +++ |
| 70 | +++ | ++ |
| 253 | +++ | + |
| 106 | +++ | +++ |
| 228 | +++ | ++ |
| 114 | +++ | +++ |
| 116 | +++ | +++ |
| 220 | +++ | + |
| 170(b) | +++ | +++ |
| 118 | +++ | +++ |
| 85 | +++ | +++ |
| 224 | +++ | +++ |
| 47 | +++ | ++ |
| 80 | +++ | +++ |
| 94 | +++ | +++ |
| 210 | +++ | ++ |
| 78 | +++ | ++ |
| 69 | +++ | +++ |
| 194 | +++ | +++ |
| 107 | +++ | NT |
| 236 | +++ | +++ |
| 87 | +++ | +++ |
| 31 | +++ | + |
| 35 | +++ | +++ |
| 27 | +++ | ++ |
| 64 | +++ | +++ |
| 117 | +++ | +++ |
| 148 | +++ | ++ |
| 120 | +++ | + |
| 60 | +++ | + |
| 259 | +++ | + |
| 249 | +++ | +++ |
| 113 | +++ | +++ |
| 212 | +++ | ++ |
| 225 | +++ | + |
| 152 | +++ | + |
| 219 | +++ | ++ |
| 154 | +++ | ++ |
| 42 | +++ | + |
| 6 | +++ | +++ |
| 256 | +++ | ++ |

TABLE I-continued

Mineralocorticoid and Glucocorticoid Receptor Binding Assay Values

| Example No. | MR Ki (nM) | GR Ki (nM) |
|---|---|---|
| 180 | +++ | ++ |
| 84 | +++ | + |
| 225 | +++ | NT |
| 143 | +++ | + |
| 217 | +++ | + |
| 96 | +++ | + |
| 68 | +++ | +++ |
| 169 | +++ | +++ |
| 255 | +++ | +++ |
| 173(b) | +++ | + |
| 196 | +++ | +++ |
| 137 | +++ | ++ |
| 168 | +++ | ++ |
| 99 | +++ | ++ |
| 82 | +++ | ++ |
| 218 | +++ | ++ |
| 131 | +++ | + |
| 166 | +++ | + |
| 52 | +++ | + |
| 77 | +++ | +++ |
| 32 | +++ | ++ |
| 79 | +++ | +++ |
| 109 | +++ | +++ |
| 170(a) | +++ | ++ |
| 174 | +++ | ++ |
| 195(a) | +++ | ++ |
| 233 | +++ | + |
| 227 | +++ | ++ |
| 88 | +++ | ++ |
| 244 | +++ | + |
| 237 | +++ | + |
| 73 | +++ | ++ |
| 76 | ++ | +++ |
| 3 | ++ | ++ |
| 230 | ++ | + |
| 264 | ++ | + |
| 41 | ++ | + |
| 699 | +++ | +++ |
| 700 | +++ | +++ |
| 521 | +++ | +++ |
| 522 | +++ | +++ |
| 363 | +++ | +++ |
| 364 | +++ | +++ |
| 498 | +++ | ++ |
| 499 | +++ | +++ |
| 703 | +++ | +++ |
| 287 | +++ | +++ |
| 365 | +++ | +++ |
| 366 | +++ | +++ |
| 367 | +++ | + |
| 368 | +++ | + |
| 369 | +++ | + |
| 447 | +++ | +++ |
| 448 | +++ | + |
| 449 | +++ | + |
| 500 | +++ | +++ |
| 501 | +++ | +++ |
| 502 | +++ | +++ |
| 370 | +++ | ++ |
| 371 | +++ | +++ |
| 372 | +++ | ++ |
| 465 | +++ | ++ |
| 466 | +++ | ++ |
| 373 | +++ | + |
| 374 | +++ | +++ |
| 375 | +++ | +++ |
| 722 | +++ | +++ |
| 723 | +++ | +++ |
| 376 | +++ | +++ |
| 377 | +++ | + |
| 301 | +++ | +++ |
| 302 | +++ | +++ |
| 450 | +++ | +++ |
| 451 | +++ | + |
| 334 | +++ | +++ |
| 335 | +++ | +++ |
| 452 | +++ | ++ |
| 378 | +++ | ++ |
| 379 | +++ | + |
| 524 | +++ | +++ |
| 503 | +++ | +++ |
| 303 | +++ | +++ |
| 380 | +++ | ++ |
| 453 | +++ | ++ |
| 336 | +++ | + |
| 504 | +++ | +++ |
| 337 | ++ | |
| 338 | +++ | ++ |
| 339 | +++ | +++ |
| 454 | +++ | +++ |
| 481 | +++ | +++ |
| 407 | +++ | +++ |
| 408 | +++ | +++ |
| 409 | +++ | +++ |
| 410 | +++ | +++ |
| 304 | +++ | +++ |
| 340 | +++ | +++ |
| 341 | +++ | +++ |
| 558 | +++ | |
| 342 | +++ | +++ |
| 488 | +++ | +++ |
| 525 | +++ | +++ |
| 526 | +++ | + |
| 527 | +++ | + |
| 528 | +++ | ++ |
| 529 | +++ | + |
| 530 | +++ | +++ |
| 531 | +++ | +++ |
| 532 | +++ | ++ |
| 533 | +++ | ++ |
| 534 | +++ | + |
| 535 | ++ | + |
| 305 | +++ | ++ |
| 306 | +++ | ++ |
| 278 | +++ | |
| 381 | +++ | +++ |
| 286 | +++ | + |
| 382 | +++ | +++ |
| 559 | +++ | +++ |
| 307 | +++ | ++ |
| 455 | +++ | + |
| 456 | +++ | + |
| 411 | +++ | +++ |
| 412 | +++ | ++ |
| 347 | +++ | +++ |
| 348 | +++ | +++ |
| 308 | +++ | + |
| 309 | +++ | ++ |
| 578 | +++ | + |
| 739 | +++ | +++ |
| 580 | +++ | + |
| 581 | +++ | + |
| 740 | +++ | +++ |
| 582 | +++ | + |
| 330 | +++ | +++ |
| 583 | +++ | + |
| 584 | ++ | + |
| 585 | +++ | + |
| 586 | +++ | + |
| 587 | +++ | + |
| 279 | +++ | + |
| 383 | +++ | +++ |
| 560 | +++ | ++ |
| 536 | +++ | +++ |
| 588 | +++ | +++ |
| 589 | +++ | +++ |
| 310 | +++ | ++ |
| 483(a) | +++ | +++ |

TABLE I-continued

Mineralocorticoid and Glucocorticoid Receptor Binding Assay Values

| Example No. | MR Ki (nM) | GR Ki (nM) |
|---|---|---|
| 483(b) | +++ | +++ |
| 280 | +++ | ++ |
| 457 | +++ | +++ |
| 349 | +++ | +++ |
| 537 | +++ | + |
| 458 | +++ | +++ |
| 311 | +++ | +++ |
| 312 | +++ | +++ |
| 313 | +++ | |
| 314 | +++ | +++ |
| 413 | +++ | +++ |
| 414 | +++ | +++ |
| 467 | +++ | +++ |
| 538 | +++ | +++ |
| 331 | | +++ |
| 332 | | +++ |
| 627 | +++ | +++ |
| 628 | +++ | +++ |
| 468 | +++ | +++ |
| 469 | +++ | +++ |
| 470 | +++ | + |
| 471 | +++ | +++ |
| 290 | +++ | ++ |
| 291 | +++ | +++ |
| 659 | ++ | + |
| 629 | +++ | +++ |
| 630 | +++ | +++ |
| 315 | +++ | + |
| 350 | +++ | +++ |
| 316 | +++ | +++ |
| 351 | +++ | +++ |
| 317 | +++ | + |
| 318 | +++ | ++ |
| 741 | +++ | +++ |
| 539 | +++ | +++ |
| 540 | +++ | +++ |
| 541 | +++ | ++ |
| 542 | +++ | + |
| 543 | +++ | + |
| 544 | +++ | ++ |
| 292 | +++ | +++ |
| 459 | +++ | ++ |
| 293 | +++ | +++ |
| 631 | +++ | ++ |
| 611 | +++ | |
| 294 | +++ | + |
| 660 | +++ | +++ |
| 604 | +++ | ++ |
| 783 | +++ | +++ |
| 384 | +++ | +++ |
| 632 | +++ | +++ |
| 633 | +++ | +++ |
| 385 | +++ | ++ |
| 561 | +++ | ++ |
| 352 | +++ | +++ |
| 295 | +++ | +++ |
| 296 | +++ | + |
| 545 | +++ | + |
| 661 | +++ | +++ |
| 662 | +++ | +++ |
| 634 | +++ | +++ |
| 635 | +++ | ++ |
| 281 | +++ | + |
| 297 | +++ | + |
| 386 | +++ | +++ |
| 387 | +++ | +++ |
| 636 | +++ | +++ |
| 637 | +++ | +++ |
| 663 | +++ | +++ |
| 664 | +++ | +++ |
| 665 | +++ | +++ |
| 415 | +++ | +++ |
| 416 | +++ | +++ |
| 417 | +++ | +++ |
| 418 | +++ | ++ |
| 460 | +++ | ++ |
| 461 | +++ | +++ |
| 462 | +++ | ++ |
| 605 | +++ | +++ |
| 606 | +++ | +++ |
| 562 | +++ | +++ |
| 669 | +++ | +++ |
| 343 | ++ | +++ |
| 484(a) | ++ | +++ |
| 590 | +++ | ++ |
| 840 | +++ | +++ |
| 793 | +++ | +++ |
| 794 | +++ | +++ |
| 795 | +++ | +++ |
| 796 | +++ | +++ |
| 388 | +++ | +++ |
| 389 | +++ | +++ |
| 753 | +++ | +++ |
| 344 | +++ | +++ |
| 463 | +++ | + |
| 464 | +++ | + |
| 638 | +++ | ++ |
| 612 | +++ | + |
| 742 | +++ | +++ |
| 743 | +++ | +++ |
| 744 | +++ | +++ |
| 745 | +++ | +++ |
| 390 | +++ | +++ |
| 391 | +++ | +++ |
| 472 | +++ | + |
| 473 | +++ | + |
| 797 | +++ | +++ |
| 798 | +++ | +++ |
| 639 | +++ | + |
| 319 | +++ | +++ |
| 704 | +++ | +++ |
| 705 | +++ | +++ |
| 799 | +++ | +++ |
| 800 | +++ | +++ |
| 724 | +++ | +++ |
| 725 | +++ | +++ |
| 801 | +++ | +++ |
| 802 | +++ | +++ |
| 670 | +++ | +++ |
| 671 | +++ | +++ |
| 672 | +++ | +++ |
| 673 | +++ | +++ |
| 674 | +++ | +++ |
| 675 | +++ | +++ |
| 676 | +++ | +++ |
| 681 | +++ | +++ |
| 682 | +++ | +++ |
| 754 | | +++ |
| 726 | +++ | +++ |
| 727 | +++ | +++ |
| 728 | +++ | +++ |
| 729 | +++ | +++ |
| 392 | +++ | +++ |
| 393 | +++ | +++ |
| 320 | +++ | +++ |
| 321 | +++ | +++ |
| 353 | +++ | +++ |
| 640 | +++ | +++ |
| 549 | +++ | + |
| 484(b) | +++ | +++ |
| 482 | +++ | +++ |
| 546 | +++ | +++ |
| 547 | +++ | +++ |
| 746 | +++ | +++ |
| 747 | +++ | +++ |
| 748 | +++ | +++ |
| 755 | +++ | +++ |
| 322 | +++ | +++ |

TABLE I-continued

Mineralocorticoid and Glucocorticoid Receptor Binding Assay Values

| Example No. | MR Ki (nM) | GR Ki (nM) |
|---|---|---|
| 323 | +++ | +++ |
| 324 | | ++ |
| 563 | +++ | +++ |
| 564 | +++ | +++ |
| 838 | +++ | +++ |
| 839 | +++ | +++ |
| 706 | +++ | +++ |
| 707 | +++ | +++ |
| 708 | +++ | +++ |
| 709 | +++ | +++ |
| 565 | +++ | + |
| 683 | +++ | +++ |
| 684 | +++ | +++ |
| 550 | +++ | +++ |
| 551 | +++ | +++ |
| 771 | +++ | +++ |
| 772 | +++ | +++ |
| 325 | +++ | +++ |
| 641 | +++ | ++ |
| 642 | +++ | ++ |
| 643 | +++ | + |
| 730 | +++ | +++ |
| 731 | +++ | +++ |
| 732 | +++ | +++ |
| 733 | +++ | +++ |
| 609 | +++ | ++ |
| 591 | +++ | + |
| 592 | +++ | + |
| 712 | +++ | +++ |
| 607 | +++ | ++ |
| 326 | +++ | +++ |
| 327 | +++ | +++ |
| 773 | +++ | +++ |
| 774 | +++ | +++ |
| 841 | +++ | +++ |
| 842 | +++ | +++ |
| 566 | +++ | + |
| 593 | +++ | + |
| 749 | +++ | +++ |
| 750 | +++ | +++ |
| 623 | +++ | +++ |
| 624 | +++ | +++ |
| 734 | +++ | +++ |
| 735 | +++ | +++ |
| 715 | +++ | ++ |
| 775 | +++ | +++ |
| 776 | +++ | +++ |
| 803 | +++ | +++ |
| 804 | +++ | +++ |
| 594 | +++ | +++ |
| 595 | +++ | +++ |
| 817 | +++ | +++ |
| 818 | +++ | +++ |
| 298 | +++ | + |
| 299 | +++ | ++ |
| 644 | +++ | ++ |
| 645 | +++ | |
| 805 | +++ | +++ |
| 806 | +++ | +++ |
| 300 | +++ | ++ |
| 807 | +++ | +++ |
| 808 | +++ | +++ |
| 596 | +++ | + |
| 836 | +++ | +++ |
| 837 | +++ | +++ |
| 809 | +++ | +++ |
| 810 | +++ | +++ |
| 419 | +++ | +++ |
| 420 | +++ | +++ |
| 421 | +++ | +++ |
| 597 | +++ | +++ |
| 598 | +++ | +++ |
| 613 | +++ | +++ |
| 552 | +++ | +++ |
| 553 | +++ | +++ |
| 777 | +++ | +++ |
| 778 | +++ | +++ |
| 345 | +++ | + |
| 346 | +++ | + |
| 827 | +++ | +++ |
| 828 | +++ | +++ |
| 829 | +++ | +++ |
| 830 | +++ | +++ |
| 831 | +++ | +++ |
| 832 | +++ | +++ |
| 422 | +++ | +++ |
| 811 | +++ | +++ |
| 812 | +++ | +++ |
| 423 | +++ | +++ |
| 424 | +++ | +++ |
| 736 | +++ | +++ |
| 737 | +++ | +++ |
| 738 | +++ | +++ |
| 779 | +++ | +++ |
| 625 | +++ | |
| 618 | +++ | |
| 646 | +++ | ++ |
| 784 | +++ | +++ |
| 785 | +++ | +++ |
| 786 | +++ | +++ |
| 608 | +++ | + |
| 614 | +++ | ++ |
| 554 | +++ | ++ |
| 780 | +++ | +++ |
| 813 | +++ | +++ |
| 814 | +++ | +++ |
| 617 | +++ | +++ |
| 647 | +++ | ++ |
| 819 | +++ | +++ |
| 820 | +++ | +++ |
| 821 | +++ | +++ |
| 822 | +++ | +++ |
| 752 | +++ | +++ |
| 436 | +++ | ++ |
| 787 | +++ | +++ |
| 788 | +++ | +++ |
| 789 | +++ | +++ |
| 790 | +++ | +++ |
| 833 | +++ | +++ |
| 823 | +++ | +++ |
| 824 | +++ | +++ |
| 719 | +++ | |
| 843 | | |
| 815 | +++ | |
| 816 | +++ | |
| 791 | +++ | |
| 792 | +++ | |
| 756 | +++ | |
| 425 | +++ | |
| 426 | +++ | |
| 781 | +++ | |
| 782 | +++ | |
| 825 | +++ | |
| 826 | +++ | |
| 485(a) | | |
| 329 | | +++ |
| 440 | +++ | + |
| 489 | +++ | + |
| 602 | +++ | +++ |
| 603 | +++ | +++ |
| 284 | +++ | |
| 285 | +++ | |
| 506 | +++ | +++ |
| 355 | +++ | +++ |
| 356 | +++ | +++ |
| 357 | +++ | +++ |
| 509 | +++ | +++ |
| 358 | +++ | +++ |

TABLE I-continued

Mineralocorticoid and Glucocorticoid Receptor Binding Assay Values

| Example No. | MR Ki (nM) | GR Ki (nM) |
|---|---|---|
| 761 | +++ | +++ |
| 762 | +++ | +++ |
| 763 | +++ | +++ |
| 764 | +++ | +++ |
| 765 | +++ | +++ |
| 476 | +++ | +++ |
| 443 | +++ | + |
| 649 | +++ | + |
| 512 | +++ | +++ |
| 619 | +++ | +++ |
| 620 | +++ | +++ |
| 555 | +++ | +++ |
| 556 | +++ | +++ |
| 396 | +++ | +++ |
| 397 | +++ | + |
| 557 | +++ | +++ |
| 721 | +++ | +++ |
| 571 | +++ | +++ |
| 572 | +++ | +++ |
| 573 | +++ | +++ |
| 656 | +++ | +++ |
| 400 | +++ | +++ |
| 445 | +++ | + |
| 574 | +++ | +++ |
| 577 | +++ | +++ |
| 687 | +++ | +++ |
| 361 | +++ | +++ |
| 401 | +++ | +++ |
| 437 | +++ | ++ |
| 626 | +++ | + |
| 519 | +++ | +++ |
| 520 | +++ | +++ |
| 769 | +++ | +++ |
| 770 | +++ | +++ |
| 403 | +++ | +++ |
| 404 | +++ | +++ |
| 689 | | +++ |
| 692 | +++ | +++ |
| 693 | +++ | +++ |
| 694 | +++ | +++ |
| 695 | +++ | +++ |
| 696 | +++ | +++ |
| 405 | +++ | +++ |
| 406 | +++ | +++ |
| 496 | +++ | +++ |
| 497 | +++ | +++ |
| 477 | +++ | + |

Legend:
"+" represents a value of ≦10,000 nM
"++" represents a value of ≦1,000 nM
"+++" represents a value of ≦500 nM
"−−" indicates the value was not determined The following preparations and examples further illustrate the invention and represent typical synthesis of the compounds of Formula I, including any novel compounds, as described generally above. The reagents and starting materials are readily available to, or may be readily synthesized by, one of ordinary skill in the art. As used herein, the following terms have the meanings indicated: "i.v." refers to intravenously, "p.o." refers to orally; "i.p." refers to intraperitoneally, "eq" or "equiv." refers to equivalents; "g" refers to grams; "mg" refers to milligrams; "L" refers to liters; "mL" refers to milliliters; "µL" refers to microliters; "mol" refers to moles; "mmol" refers to millimoles; "psi" refers to pounds per square inch; "mm Hg" refers to millimeters of mercury; "min" refers to minutes; "h" or "hr" refers to hours; "C" refers to degrees Celsius; "TLC" refers to thin layer chromatography, "HPLC" refers to high performance liquid chromatography; "$R_f$" refers to retention factor; "$R_t$" refers to retention time; "δ" refers to part per million down-field from tetramethylsilane; "THF" refers to tetrahydrofuran; "DMF" refers to N,N-dimethylformamide; "DMSO" refers to dimethyl sulfoxide; "aq" refers to aqueous; "EtOAc" refers to ethyl acetate; "iPrOAc" refers to isopropyl acetate; "MeOH" refers to methanol; "MTBE" refers to tert-butyl methyl ether; "PPh$_3$" refers to triphenylphosphine; "DEAD" refers to diethyl azodicarboxylate; "RT" refers to room temperature; "Pd—C" refers to palladium over carbon; NaBH(OAc)$_3$ refers to sodium triacetoxyborohydride; "Bn" refers to benzyl; "BnNH$_2$" refers to benzyl amine; H$_2$ refers to hydrogen; "$K_i$" refers to the dissociation constant of an enzyme-antagonist complex and serves as an index of ligand binding; and "ID$_{50}$" and "ID$_{100}$" refer to doses of an administered therapeutic agent which produce, respectively, a 50% and 100% reduction in a physiological response.

Instrumental Analysis

Unless otherwise indicated, $^1$H NMR spectra are recorded on a either a 300 MHz or 400 MHz Varian spectrometer at ambient temperature. Data are reported as follows: chemical shift in ppm from internal standard tetramethylsilane on the δ scale, multiplicity (b=broad, s=singlet, d=doublet, t=triplet, q=quartet, qn=quintet and m=multiplet), integration, coupling constant (Hz) and assignment. Positive and negative electrospray mass spectral data are obtained on a Micromass Platform LCZ equipped with an autosampler. Analytical thin layer chromatography is performed on EM Reagent 0.25-mm silica gel 60-F plates. Visualization is accomplished with UV light. HPLC analysis is performed on an Agilent 1100 Series HPLC using an acetonitrile/0.03M phosphate buffer (80/20) as the mobile phase using an Agilent Eclipse XDB-C8 analytical 4.6×150 mm 5-micron column. Melting points are determined on a Mettler Toledo PP62 melting point apparatus. GC-MS data are obtained on an Agilent HP6890 GC using a HP-5MS (30 m, 0.25 mm i.d., 0.25 µm film) column.

Section 1 (derivatives of Formula I having substitution on the "C" ring but not on the "A" or "B" rings.)

PREPARATION 1

2-(10,11-Dihydro-dibenzo[a,d]cyclohepten-5-ylidenemethyl)-benzenesulfonyl chloride

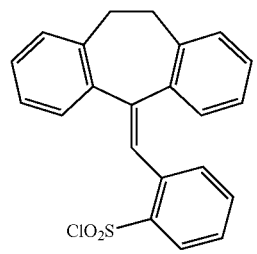

A. Preparation of 2-(10,11-Dihydro-dibenzo[a,d]cyclohepten-5-ylidenemethyl)-benzenesulfonic acid (LY622781, ER0-A01318-26B)

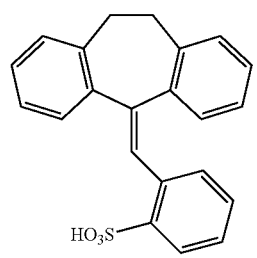

1. Treat a mixture of o-toluenesulfonyl chloride (22 g, 115 mmol) in dioxane (200 mL) with triethylamine (28 mL, 200 mmol) and cool to 10° C. Add ethanol (50 mL) and allow the reaction to warm to room temperature. After 18 h, acidify the reaction and remove most of the solvent under reduced pressure. Partition the residue between water/EtOAc. Dry the organic layer with $MgSO_4$ and concentrate to give 22.6 g colorless oil. Purify using flash chromatography (10% EtOAc/hexane) to give 7.4 g of pure ester. $^1$H NMR (CDCl3) δ1.50 (t, 3H), 2.64 (s, 3H), 4.08 (q, 2H), 7.34 (m, 2H), 7.50 (t, 1H), 7.96 (d, 2H). (Literature ref: J. Prakt. Chem. 333 (4) 625-635 (1991).

2. Under a blanket of nitrogen, cool (6.4 g, 32 mmol) toluene-2-sulfonic acid ethyl ester in THF (140 mL) to –70° C. Add n-butyllithium (1.6M, 22.5 mL, 36 mmol) slowly. An orange solid forms. After 20 minutes, add a solution of dibenzosuberone (6.32 g, 30 mmol) in THF (15 mL). Allow warming to room temperature and stir for 2 h. Concentrate to remove most of the THF and dissolve the residue in EtOAc and shake vigorously with 5N HCl for 5 minutes. Dry the organic layer ($MgSO_4$) and concentrate to give 10.8 g crude product as a dark red oil. Purify the crude product by flash chromatography (300 g silica gel, 5% HOAc/EtOAc) to give crude sulfonic acid. Remove residual HOAc by repeatedly azeotroping with toluene to yield 910 mg orange solid. $^1$H NMR (DMSO-d6) δ2.80-3.44 (br m, 4H), 6.54 (d, 1H), 6.78-7.76 (m,12H); MS (ES) 361 (M−1).

B. Preparation of 2-(10,11 -Dihydro-dibenzo[a,d]cyclohepten-5-ylidenemethyl)-benzenesulfonyl chloride (ER0-A01318-30)

Treat a mixture of 2-(10,11-dihydro dibenzo[a,d]cyclohepten-5-ylidenemethyl)-benzenesulfonic acid (710 mg, 2 mmol) in thionyl chloride (10 mL) with 5 drops DMF and reflux for 40 minutes. TLC (10% EtOAc/hexane) shows a new higher $R_f$ material and no starting material. The material is then concentrated to give 760 mg crude sulfonyl chloride, which is used without further purification. (Note: To confirm the structure, a small aliquot is reacted with methylamine. The MS (ES) of the corresponding sulfonamide is readily detected).

Following the procedures essentially as described in Preparation 1 above, and using the appropriately substituted arylsulfonyl chloride, the following sulfonyl chlorides were prepared:

PREPARATION 2

2-(10,11-Dihydro-dibenzo[a,d]cyclohepten-5-ylidenemethyl)-5-methyl-benzenesulfonyl chloride

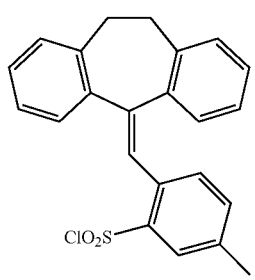

To confirm the structure, a small aliquot is reacted with methylamine. The MS (ES) of the corresponding sulfonamide is readily detected.

PREPARATION 3

4-Chloro-2-(10,11-dihydrodibenzo[a,d]cyclohepten-5-ylidenemethyl)-5-methyl-benzenesulfonyl chloride

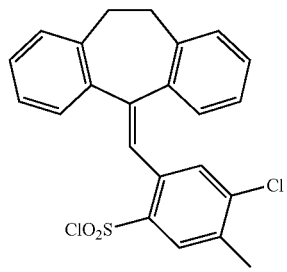

To confirm the structure, a small aliquot is reacted with methylamine. The MS (ES) of the corresponding sulfonamide is readily detected

PREPARATION 4

3-(10,11-Dihydro-dibenzo[a,d]cyclohepten-5-ylidenemethyl)-benzenesulfonyl chloride

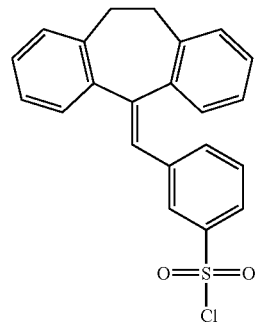

To confirm the structure, a small aliquot is reacted with methylamine. The MS (ES) of the corresponding sulfonamide is readily detected

EXAMPLE 1

3-(10,11-Dihydro-dibenzo[a,d]cyclohepten-5-ylidenemethyl)-N-methyl-benzenesulfonamide

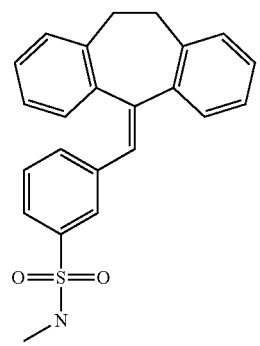

Treat a solution of 3-(10,11-dihydro-dibenzo[a,d]cyclohepten-5-ylidenemethyl)-benzenesulfonyl chloride (95 mg, 0.25 mmol) in THF (2 mL) with methylamine (300 □L 40% aqueous solution, 3.5 mmol) at room temperature. Stir reaction overnight at room temperature, then concentrate under a stream of $N_2$. Take residue up in 2 mL $CH_2Cl_2$ and shake with 2 mL 1N HCl. Load the biphasic solution onto a Varian ChemElut 1005 solid-phase extraction column and elute with 10-15 mL $CH_2Cl_2$. Collect organics and concentrate under $N_2$ stream. Purify via silica gel chromatography (1:3 ethyl acetate:hexanes) to afford 45 mg (48%) of yellow solid, mp 153.9° C. $^1$H NMR (CDCl$_3$) δ 2.48 (s, 3H), 2.79-3.61 (br m, 4H), 4.19 (br s, 1H), 6.78-7.63 (m, 13H); MS (ES) 376 (M+H). HPLC shows 94% purity.

Following the procedures essentially as described in Example 1 above, reaction of the appropriate sulfonyl chloride from Preparations 1-4 and the appropriate amine gives the following compounds:

EXAMPLE 2

2-(10,11-Dihydro-dibenzo[a,d]cyclohepten-5-ylidenemethyl)-5,N-dimethyl-benzenesulfonamide

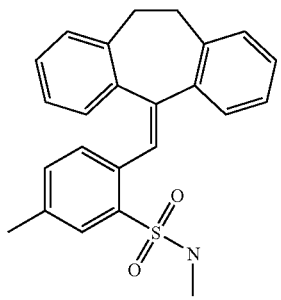

Prepared in 49% from the sulfonyl chloride (500 mg, 1.27 mmol) and methanesulfonyl chloride to give white needles (EtOH), mp 174.9° C. $^1$H NMR δ 2.36 (s, 3H), 2.77 (d, 3H), 3.29 (br s, 4H), 4.51 (q, 1H), 6.73-7.29 M, 10H), 7.58 (m, 1H), 7.82 (s, 1H); MS (ES) 390 (M+1). HPLC shows 99.6% purity.

EXAMPLE 3

2-(10,11-Dihydro-dibenzo[a,d]cyclohepten-5-ylidenemethyl)-benzenesulfonamide

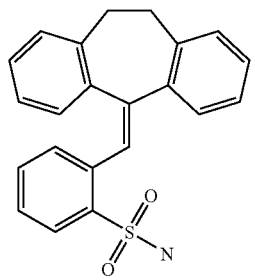

Prepared in 18% yield as a white solid, $^1$H NMR (CDCl$_3$) δ 3.29 (br s, 4H), 4.97 (br s, 2H), 6.76-7.65 (m, 13H); MS (ES) 361 (M−1).

EXAMPLE 4

2-(10,11-Dihydro-dibenzo[a,d]cyclohepten-5-ylidenemethyl)-N-methyl-benzenesulfonamide

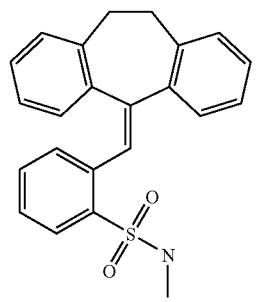

Prepared in 16% yield as a white solid, mp 149° C., MS (ES) 376 (M+1), 374 (M−1).

EXAMPLE 5

2-(10,11-Dihydro-dibenzo[a,d]cyclohepten-5-ylidenemethyl)-N,N-dimethyl-benzenesulfonamide

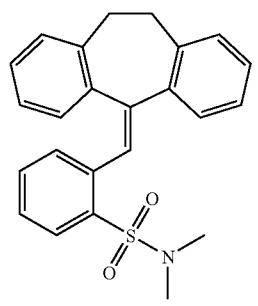

Prepared in 28% yield as a white solid, $^1$HNMR (CDCl$_3$) δ 2.90(s, 6H), 3.18 (br S, 4), 6.79-7.95 (m, 13H); MS (ES) 390 (M+1).

EXAMPLE 6

2-(10,11-Dihydro-benzo[a,d]cyclohepten-5-ylidenemethyl)-N-propyl-benzenesulfonamide

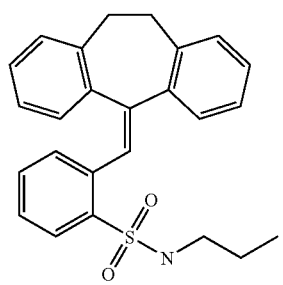

Prepared in 23% yield as a white solid, mp 155.6° C., ¹H NMR (CDCl₃) δ 0.98 (t, 3H), 1.61 (q, 2H), 3.05 (q, 2H), 3.30 (br s, 4H), 4.57 (br t, 1H), 6.78-7.42 (m, 13H); MS (ES) 404 (M+1), 402 (M−1).

EXAMPLE 7

2-(10,11-Dihydro-dibenzo[a,d]cyclohepten-5-ylidenemethyl)-N-(2-methoxy-ethyl)-benzenesulfonamide

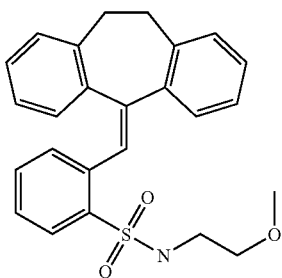

Prepared in 10% yield to give a white solid. ¹H NMR (CDCl₃) δ 2.85-3.70 (m, 11H), 5.13 (br t, 1H), 6.84-8.01 (m, 13H); MS (ES) 420 (M+H), 418 (M−H).

EXAMPLE 8

4-[2-(10,11-Dihydro-dibenzo[a,d]cyclohepten-5-ylidenemethyl)-benzenesulfonyl]-morpholine

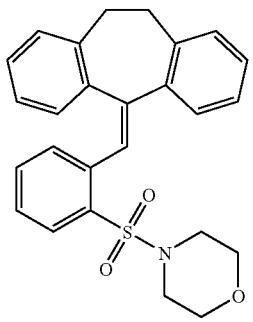

Prepared in 29% yield as a white solid, mp 139.3° C. ¹H NMR (CDCl₃) δ 2.76-3.89 (m, 12H), 6.57-7.93 (m, 13H). MS (ES) 432 (M+H).

EXAMPLE 9

4-Chloro-2-(10,11-dihydro-dibenzo[a,d]cyclohepten-5-ylidenemethyl)-5-methyl-benzenesulfonamide

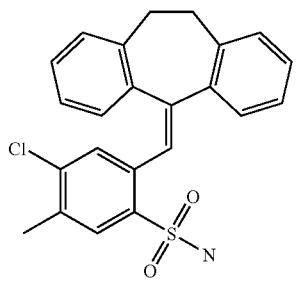

MS (ES) 408 (M−H). HPLC shows 81% purity.

EXAMPLE 10

4-Chloro-2-(10,11-dihydro-dibenzo[a,d]cyclohepten-5-ylidenemethyl)-5,N,N-trimethylbenzenesulfonamide

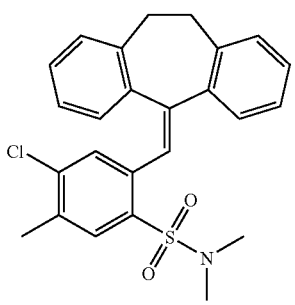

White solid, mp 199.9° C. ¹HNMR (CDCl₃) δ 2.36 (s, 3H), 2.95 (s, 6H), 2.98-3.66 (br m, 4H), 6.79-7.80 (m, 11H); MS (ES) 438 (M+H), 436 (M−H.; HPLC shows 98% purity.

EXAMPLE 11

4-Chloro-2-(10,11-dihydro-dibenzo[a,d]cyclohepten-5-ylidenemethyl)-5-methyl-N-propyl-benzenesulfonamide

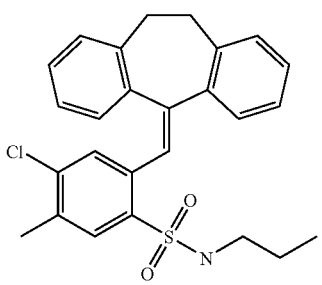

White solid. MS (ES) 452 (M+H), 450 (M−H). HPLC shows 97% purity.

EXAMPLE 12

4-[4-Chloro-2-(10,11-dihydro-dibenzo[a,d]cyclohepten-5-ylidenemethyl)-5-methyl-benzenesulfonyl]-morpholine

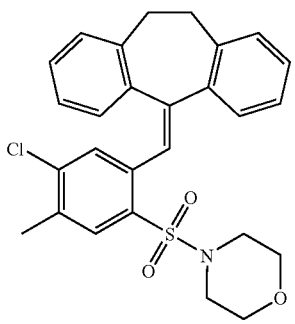

White solid, mp 194.7° C. ¹H NMR (CDCl₃) δ 2.20 (s, 3H), 2.65-3.67 (m, 12H), 6.63-7.60 (m, 11H); MS (ES) 480 (M+H). HPLC shows 98% purity.

EXAMPLE 13

2-[2-(2-Ethyl-phenyl)-penta-1,4-dienyl]-5-methyl-N-phenyl-benzenesulfonamide; compound with propene

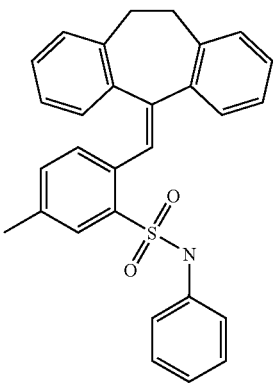

White solid, mp 220.4° C. $^1$H NMR (CDCl$_3$) δ 2.31 (s, 3H), 2.85-3.60 (br m, 4H), 4.54 (br t, 1H), 6.10-7.84 (m, 17H); MS (ES) 452 (M+H), 450 (M−H). HPLC shows 93% purity.

EXAMPLE 14

N-Cyclopropyl-2-(10,11-dihydro-dibenzo[a,d]cyclohepten-5-ylidenemethyl)-5-methyl-benzenesulfonamide

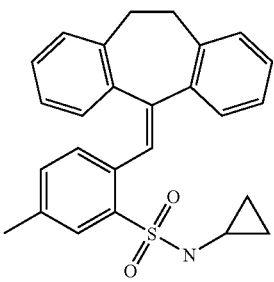

White solid, mp 160.8° C. MS (ES) 416 (M+H), 414 (M−H). HPLC shows 86% purity.

EXAMPLE 15

N-Benzyl-2-(10,11-dihydro-dibenzo[a,d]cyclohepten-5-ylidenemethyl)-5-methyl-benzenesulfonamide

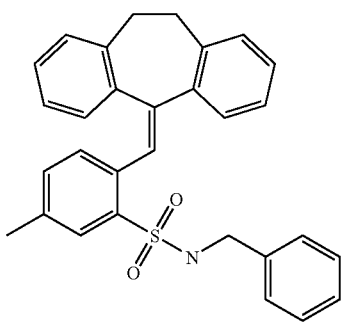

Colorless oil, slowly crystallized, mp 138.3° C. $^1$H NMR (CDCl$_3$) δ 2.34 (s, 3H), 2.87-3.69 (br s, 4H), 4.28 (d, 2H), 4.82 (br t, 1H), 6.70-7.85 (m, 17H); MS (ES) 464 (M−H). HPLC shows 96% purity.

EXAMPLE 16

1-[2-(10,11-Dihydro-dibenzo[a,d]cyclohepten-5-ylidenemethyl)-5-methyl-benzenesulfonyl]-4-(4-trifluoromethyl-phenyl)-piperidine

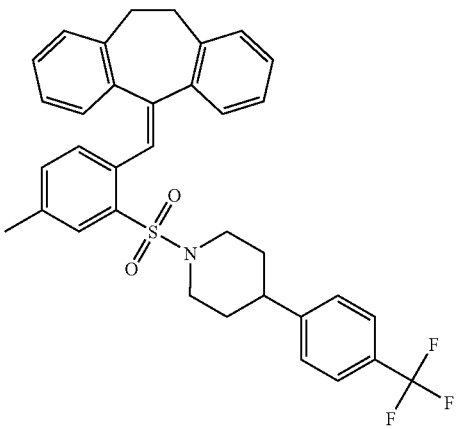

White foam. MS (ES) 588 (M+H). HPLC shows 96% purity.

EXAMPLE 17

2-(10,11-Dihydro-dibenzo[a,d]cyclohepten-5-ylidenemethyl)-N-ethyl-5-methyl-benzenesulfonamide

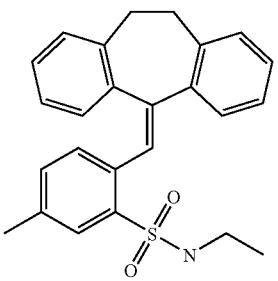

White foam, mp 172.4° C. MS (ES) 402 (M−H). HPLC shows 95% purity.

EXAMPLE 18

2-(10,11-Dihydro-dibenzo[a,d]cyclohepten-5-ylidenemethyl)-5-methyl-benzenesulfonamide

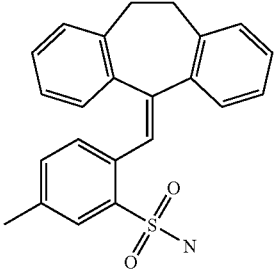

$^1$H NMR (CDCl$_3$) δ2.38 (s, 3H), 2.80-3.80 (br m, 4H), 6.77-7.92 (m, 12H); MS (ES) 375 (M−H. HPLC shows 78% purity.

EXAMPLE 19

2-(10,11-Dihydro-dibenzo[a,d]cyclohepten-5-ylidenemethyl)-5,N,N-trimethyl-benzenesulfonamide

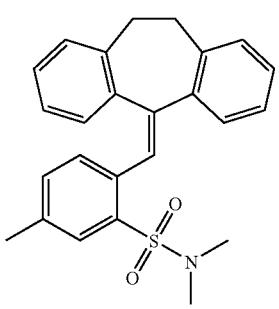

White solid, mp 186.6° C. MS (ES) 404 (M+H).

EXAMPLE 20

2-(10,11-Dihydro-dibenzo[a,d]cyclohepten-5-ylidenemethyl)-5-methyl-N-propyl-benzenesulfonamide

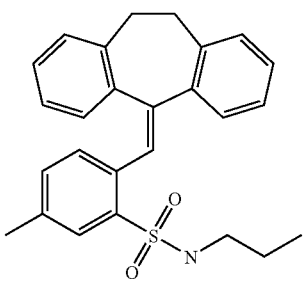

White solid, mp 149.8° C. MS (S) 418 (M+H), 416 (M−H). HPLC shows 96% purity.

EXAMPLE 21

2-(10,11-Dihydro-dibenzo[a,d]cyclohepten-5-ylidenemethyl)-N-(2-methoxy-ethyl)-5-methyl-benzenesulfonamide

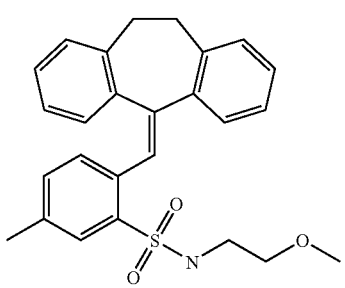

$^1$H NMR (CDCl$_3$) δ 2.33 (s, 3H), 2.85-3.20 (m, 1H), 5.12 (br t, 1H), 6.61-7.33 (m, 12H); MS (ES) 434 (M+H), 432 (M−H). HPLC shows 98% purity.

EXAMPLE 22

4-[2-(10,11-Dihydro-dibenzo[a,d]cyclohepten-5-ylidenemethyl)-5-methyl-benzenesulfonyl]-morpholine

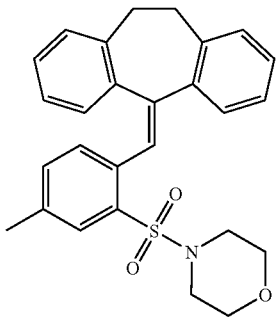

White solid, mp 157.2° C. $^1$H NMR (CDCl$_3$) δ 2.35 (s, 3H), 2.85-4.00 (m, 12H), 6.72-7.75 (m, 12H); MS (ES) 446 (M+H). HPLC shows 95% purity.

EXAMPLE 23

2-(10,11-Dihydro-dibenzo[a,d]cyclohepten-5-ylidenemethyl)-5-methyl-N-(2,2,2-trifluoro-ethyl)-benzenesulfonamide

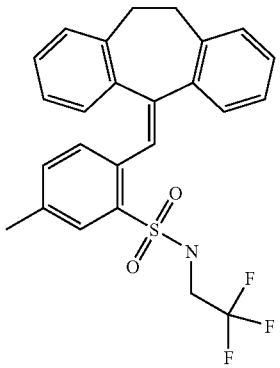

White needles, mp 100.7° C. $^1$H NMR (CDCl$_3$) δ 2.35 (s, 3H), 3.0-3.6 (br s, 4H), 3.76 (m, 2H), 5.05 (br t, 1H), 6.75-7.62 (m, 11H), 7.78 (s, 1H); MS (ES) 457 (M+H), 456 (M−H). HPLC shows 99% purity.

EXAMPLE 24

3-(10,11-Dihydro-dibenzo[a,d]cyclohepten-5-ylidenemethyl)-benzenesulfonamide

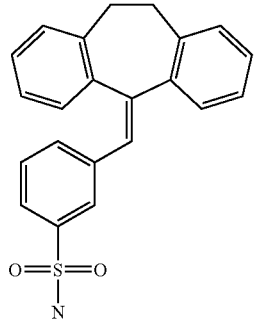

White crystalline solid, mp 204.0° C. $^1$H NMR (DMSO-d$_6$) δ 2.77-3.45 (br m, 4H), 6.81-7.68 (br m, 15H); MS (ES) 384 (M+Na). HPLC shows 98% purity.

EXAMPLE 25

3-(10,11-Dihydro-dibenzo[a,d]cyclohepten-5-yliden-emethyl)-N,N-dimethyl-benzenesulfonamide

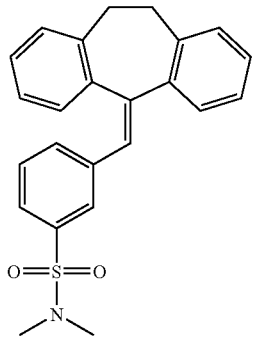

White crystalline solid, mp 167.3° C. ¹H NMR (CDCl₃) δ 2.54 (s, 6H), 2.80-3.64 (br m, 4H), 6.86 (s, 1H), 6.91-7.56 (m, 12H); MS (ES) 390 (M+H). HPLC shows 96% purity.

EXAMPLE 26

4-[3-(10,11-Dihydro-dibenzo[a,d]cyclohepten-5-ylidenemethyl)-benzenesulfonyl]-morpholine

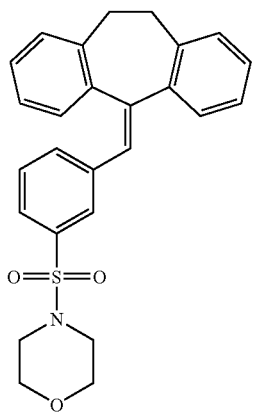

Off-white crystalline solid. ¹H NMR (CDCl₃) δ 2.73 (m, 4H), 2.82-3.63 (br m, 4H), 3.70 (m, 4H), 6.86 (s, 1H), 6.92-7.51 (m, 12H); MS (ES) 432 (M+H). HPLC shows 96% purity.

EXAMPLE 27

4-(10,11-Dihydro-dibenzo[a,d]cyclohepten-5-yliden-emethyl)-N-methyl-benzenesulfonamide

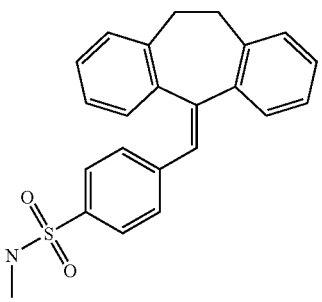

White solid, mp 189.7° C. ¹H NMR (CDCl₃) δ 2.65 (d, 3H), 2.81-3.65 (br m, 4H), 4.23 (br m, 1H), 6.85 (s, 1H), 6.94-7.67 (m, 12H); MS (ES) 376 (+H), 374 (M−H). HPLC shows 98% purity.

PREPARTION 5

(3-Bromo-phenyl)-(10,11-dihydro-5H-dibenzo[a,d]cyclohepten-5-yl)-methanol

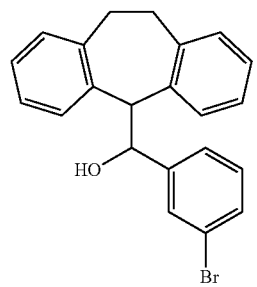

Under nitrogen, cool a THF (300 mL) solution of dibenzosuberane (23.9 g, 123 mmol) to 0° C. and add n-BuLi (1.6M, 90 mL, 144 mmol). Remove the cooling bath and the reaction stir at ambient temperature for 1 h. Cool the orange solution to 5° C. and add a solution of 3-bromobenzaldehyde (22.8 g, 123 mmol) in THF (100 mL). After 30 min., quench the reaction with saturated NH₄Cl (200 mL) and remove most of the THF under reduced pressure. Shake the residue with brine/EtOAc. Dry the organic layer (MgSO₄) and concentrate to give 49.2 g colorless oil. HPLC shows 86% purity. The compound is sufficiently pure to carry on to the next reaction. Purify a small portion on silica gel using EtOAc/hexane to give a colorless oil that rapidly crystallized, mp 93.9° C., ¹H NMR (CDCl3) δ3.00 (m,2H), 3.57 (m,2H), 3.94 (d,1H), 5.30 (d,1H), 6.38 (d,1H), 6.76-7.34 (m,12H); MS (EI) 360 (M−H₂O).

Using the procedures essentially as described in Preparation 5, and the appropriately substituted benzaldehyde, the following crude alcohol intermediates are made. Unless otherwise stated, these intermediate carbinols are not isolated or characterized, buth rather, used in the synthesis of compounds of Formula I without purther purification.

PREPARATION 6

(2-Bromo-phenyl)-(10,11-dihydro-5H-dibenzo[a,d]cyclohepten-5-yl)-methanol

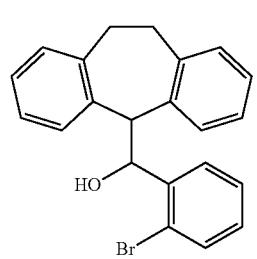

Light yellow solid, mp146.9° C. MS (FD) 361 (M−H₂O).

PREPARATION 7

(4-Bromo-phenyl)-(10,11-dihydro-5H-dibenzo[a,d]cyclohepten-5-yl)-methanol

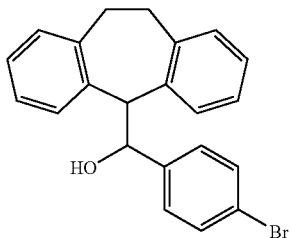

Viscous yellow oil, MS (EI) 360 (M–H$_2$O). HPLC (ISO80-10M) t=1.86 min.

PREPARATION 8

(2-Methoxy-phenyl)-(10,11-dihydro-5H-dibenzo[a,d]cyclohepten-5-yl)-methanol

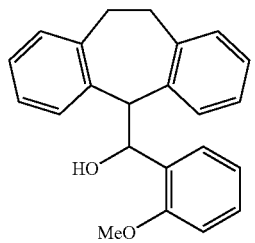

Pale yellow solid, mp113.1° C.

PREPARATION 9

(3-Methoxy-phenyl)-(10,11-dihydro-5H-dibenzo[a,d]cyclohepten-5-yl)-methanol

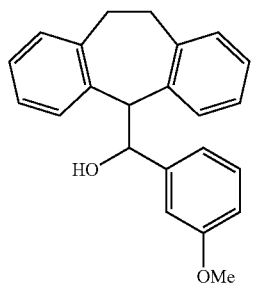

Pale yellow solid, mp132.1° C.

PREPARATION 10

(4-Methoxy-phenyl)-(10,11-dihydro-5H-dibenzo[a,d]cyclohepten-5-yl)-methanol

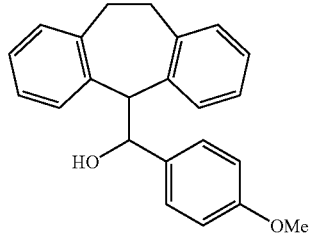

Pale yellow solid, mp103.1° C.

PREPARATION 11

(3-Bromo-4-methoxy-phenyl)-(10,11-dihydro-5H-dibenzo[a,d]cyclohepten-5-yl)-methanol

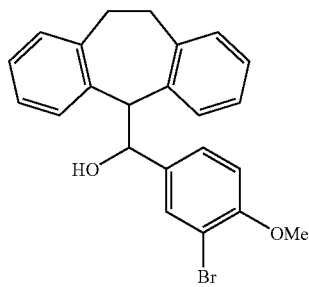

HPLC (ISO80-10M) t=1.75 min.

PREPARATION 12

(2,3-Dimethoxy-phenyl)-(10,11-dihydro-5H-dibenzo[a,d]cyclohepten-5-yl)-methanol

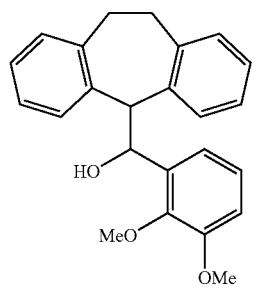

Used without further characterization or purification.

PREPARATION 13

(3,4Dimethoxy-phenyl)(10,11-dihydro-5H-dibenzo[a,d]cyclohepten-5-yl)-methanol

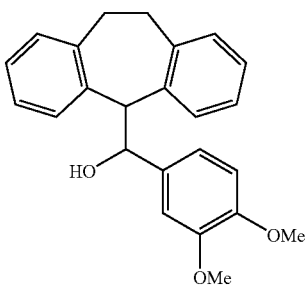

HPLC (ISO80-10M) t=1.43 min.

PREPARATION 14

(3-bromo-5-methoxy-phenyl)-(10,11-dihydro-5H-dibenzo[a,d]cyclohepten-5-yl)-methanol

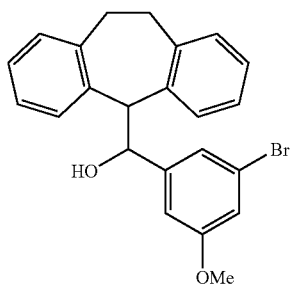

Used without further characterization or purification.

EXAMPLE 28

5-(3-Bromo-benzylidene)-10,11-dihydro-5H-dibenzo-[a,d]cycloheptene

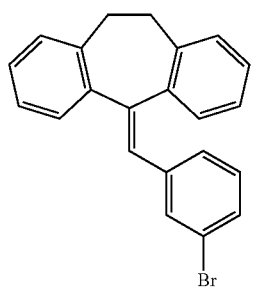

Add the crude product from Preparation 5 above (48.85 g, 129 mmol) to a premixed solution of HOAc (300 mL) and concentrated $H_2SO_4$ (6 mL). Reflux the solution for 2.5 h and then cool to ambient temperature. Shake the reaction with EtOAc (1 L)/water (1L). Wash the organic layer again with water and then 1N NaOH (2×). Dry the organic layer ($MgSO_4$) and concentrate to give 54 g crude product. Recrystallize from hexane to afford 26.6 g (57%)light tan crystals, mp 104.7° C., $^1$H NMR (CDCl3) δ2.97 (br d, 2H), 3.43 (br d, 2H), 6.50 (s, 1H), 6.86-7.47 (m, 12H); MS (FAB+) 360. HPLC shows 98.3% purity. Anal: Calcd. for $C_{22}H_{17}Br$: C, 73.14; H, 4.74. Found: C, 73.22; H, 4.84.

Following the procedures essentially as described in Example 28 above, reaction of the appropriate crude alcohol intermediate from Preparations 6-14 above, gives the following compounds:

EXAMPLE 29

5-(2-Bromo-benzylidene)-10,11-dihydro-5H-dibenzo-[a,d]cycloheptene

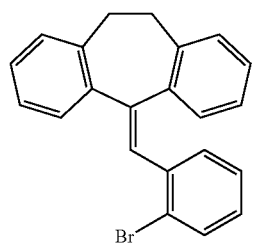

Recrystallize from hexane, mp 122.7° C., $^1$H NMR (CDCl3) δ 2.80-3.64 (br s, 4H), 6.60-7.20 (m, 11H), 7.45-7.57 (m,2H); MS (EI) 360.

EXAMPLE 30

5-(4-Bromo-benzylidene)-10,11-dihydro-5H-dibenzo-[a,d]cycloheptene

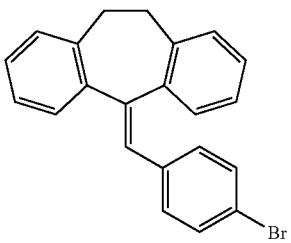

Viscous oil, $^1$H NMR (CDCl3) δ 2.80-3.64 (br m, 4H), 6.74-7.55 (m, 13H); MS (EI) 360. HPLC shows 96.4% purity.

EXAMPLE 31

5-(2-Methoxy-benzylidene)-10,11-dihydro-5H-dibenzo-[a,d]cycloheptene

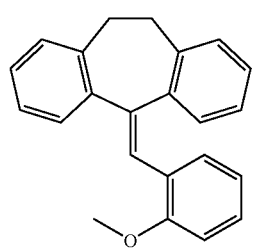

Recrystallize from hexane, mp 129.3° C., $^1$H NMR (CDCl3) δ 2.80-3.64 (br m, 4H), 3.86 (s, 3H), 6.59-7.58 (m, 13H). HPLC shows 100% purity.

EXAMPLE 32

5-(3-Methoxy-benzylidene)-10,11-dihydro-5H-dibenzo-[a,d]cycloheptene

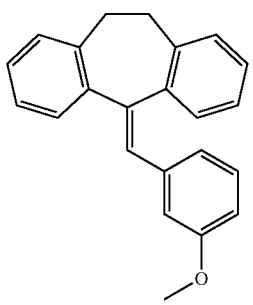

Triturate with hexane, mp 83.0° C.; ¹H NMR (CDCl3) δ 2.80-3.60 (m, 4H), 3.55 (s, 3H), 6.48-7.50 (m, 13H). HPLC shows 98.8% purity.

EXAMPLE 33

5-(4-Methoxy-benzylidene)-10,11-dihydro-5H-dibenzo-[a,d]cycloheptene

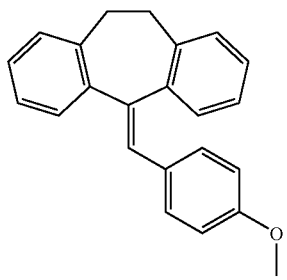

Purify on silica gel using $CH_2Cl_2$. Recrystallize from hexane/$CH_2Cl_2$, mp 116.8° C. ¹H NMR (CDCl3) δ 2.94 (br d, 2H), 3.46 (br d, 2H), 3.77 (s, 3H), 6.65-7.48 (m, 13H).

EXAMPLE 34

5-(3-Bromo-4-methoxy-benzylidene)-10,11-dihydro-5H-dibenzo[a,d]cycloheptene

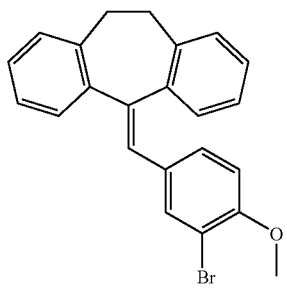

Recrystallize from hexane/toluene, mp 140.7° C. ¹H NMR (CDCl3) δ2.94 (br d, 2), 3.45 (br d, 2H), 3.83 (s, 3H), 6.64-7.48 (m, 12H). HPLC shows 95% purity.

EXAMPLE 35

5-2,3-Dimethoxy-benzylidene)-10,11-dihydro-5H-dibenzo[a,d]cycloheptene

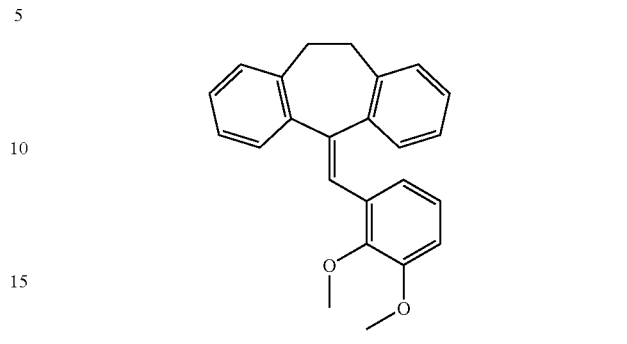

Purify on silica gel using EtOAc/hexane. Light yellow solid, mp 130.6° C. ¹H NMR (CDCl3) δ 2.94 (br d, 2H), 3.45 (br d, 2H), 3.82 (s, 3H), 3.95 (s, 3H), 6.27 (dd, 1H), 6.65-7.27 (m, 9H), 7.57, m, 1H); MS (ES) 343 (N+H). HPLC shows 91% purity.

EXAMPLE 36

5-(3,4-Dimethoxy-benzylidene)-10,11-dihydro-5H-dibenzo[a,d]cycloheptene

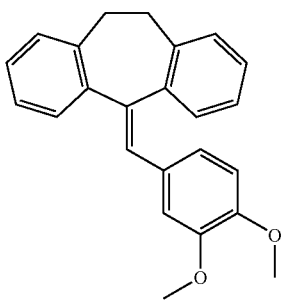

Purify on silica gel using EtOAc/hexane to give a white solid, mp 102.8° C. ¹H NMR (CDCl3) δ 2.80-3.60 (br dd, 4H), 3.42 (s, 3H), 3.83 (s, 3H), 6.42 (s, 1H), 6.72 (m, 3H), 7.06-7.47 (m, 8H). HPLC shows 97% purity.

EXAMPLE 40

5-(5-Bromo-2-methoxy-benzylidene)-10,11-dihydro-5H-dibenzo[a,d]cycloheptene

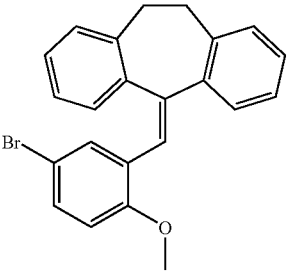

Following the procedures essentially as described for Preparation 5 and Example 28 above, using dibenzosuberane (15.0 g, 77.2 mmol) and 5-bromo-o-anisaldehyde (16.6 g, 77.2 mmol), recrystallization from boiling toluene/hexanes affords 19.78 g (65%) of the title compound as a tan solid. ¹H-NMR (CDCl₃) δ 2.76-3.70 (br m, 4H), 3.81 (s, 3H), 6.69 (d, 1H), 6.76 (d, 1H), 6.88-7.29 (m, 9H), 7.53 (m, 1H); HPLC shows 100% purity.

EXAMPLE 41

3-(10,11-Dihydro-dibenzo[a,d]cyclohepten-5-ylidenemethyl)-4-methoxy-phenylamine

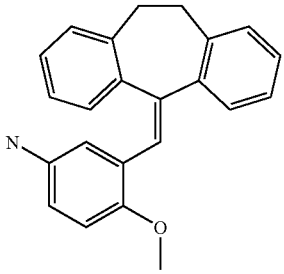

Following the procedures essentially as described in Example 86 below, and using 5-(5-bromo-2-methoxy-benzylidene)-10,11-dihydro-5H-dibenzo[a,d]cycloheptene (10.0 g, 25.56 mmol), affords 6.52 g (78%) of the title compound as a solid. MS (ES) 328 (M+H); HPLC shows 99% purity.

EXAMPLE 42

N-[3-(10,11-Dihydro-dibenzo[a,d]cyclohepten-5-ylidenemethyl)-4-methoxy-phenyl]-methanesulfonamide

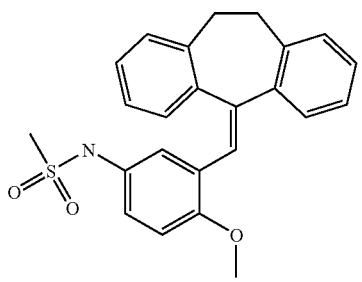

Following the procedures essentially as described in Example 90 below, and using 3-(10,11-dihydro-dibenzo[a,d]cyclohepten-5-ylidenemethyl)-4-methoxy-phenylamine (500 mg, 1.53 mmol), affords 398 mg (64%) of the title compound as a white foam. MS (ES) 423 (M+H), 404 (M−H); HPLC shows 100% purity.

EXAMPLE 45

N-[5-(10,11-Dihydro-dibenzo[a,d]cyclohepten-5-ylidenemethyl)-2-methyl-phenyl]-methanesulfonamide

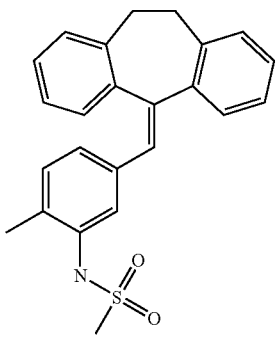

Following the procedure essentially as described for Example 219, below, and using 5-bromomethylene-10,11-dihydro-5H-dibenzo[a,d]cycloheptene (300 mg, 1.05 mmol) and (3-amino-4-methylphenyl)boronic acid hydrochloride (217 mg, 1.16 mmol), yields 245 mg (75%) 5-(10,11-dihydro-dibenzo[a,d]cyclohepten-5-ylidenemethyl)-2-methyl-phenylamine as a brown oil. Then, following procedures essentially as described in Example 90, below, and using 5-(10,11-dihydro-dibenzo[a,d]cyclohepten-5-ylidenemethyl)-2-methyl-phenylamine (100 mg, 0.321 mmol), affords 35 mg (28%) of the title compound as a colorless oil. MS (ES) 407 (M+NH$_4$), 388 (M−H); HPLC shows 98% purity.

EXAMPLE 46

N-(3-Bromo-4-methyl-phenyl)-methanesulfonamide

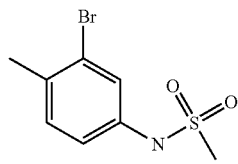

Following the procedures essentially as described for Example 90, below, and using 3-bromo-4-methylaniline (5.00 g, 26.9 mmol), recrystallzation from boiling toluene/hexanes affords 6.08 g (86%) of the title compound as a tan crystalline solid. MS (ES) 263 (M−H), HPLC shows 100% purity.

PREPARATION 15

N-[4-Methyl-3-(4,4,5,5-tetramethyl-[1,3,2]dioxaborolan-2-yl)-phenyl]-methanesulfonamide

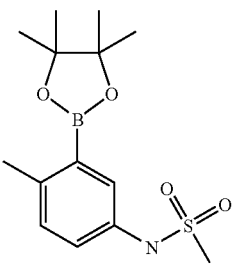

Mix N-(3-bromo-4-methyl-phenyl)-methanesulfonamide (500 mg, 1.89 mmol), bis(pinacolato)diboron (576 mg, 2.27 mmol), and potassium acetate (557 mg, 5.67 mmol) in DMSO (6 mL). Sparge solution with N$_2$ for 10 min, then add Pd(dppf)Cl$_2$ (1:1 complex with CH$_2$Cl$_2$, 154 mg, 0.189 mmol) and heat to 85° C. overnight. Cool reaction mixture to room temperature, dilute with ethyl acetate (100 mL), and wash organics four times with H$_2$O. Dry (MgSO$_4$) and concentrate organics to a brown oil. Chromatograph on silica gel (40 g), eluting with 20% to 40% ethyl acetate/hexanes affords 415 mg (71%) of the title compound as a colorless oil. MS (ES) 329 (M+NH$_4$), 310 (M−H); HPLC shows 96% purity.

EXAMPLE 47

N-[3-(10,11-Dihydro-dibenzo[a,d]cyclohepten-5-ylidenemethyl)-4-methyl-phenyl]-methanesulfonamide

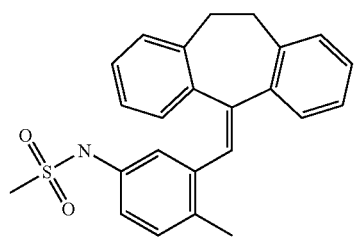

Following the procedures essentially as described in Example 219, below, and using N-[4-methyl-3-(4,4,5,5-tetramethyl-[1,3,2]dioxaborolan-2-yl)-phenyl]-methanesulfonamide (120 mg, 0.386 mmol) and 5-bromomethylene-10,11-dihydro-5H-dibenzo[a,d]cycloheptene (100 mg, 0.351 mmol) affords 83 mg (61%) of the title compound as a yellow solid. MS (ES) 407 (M+NH$_4$), 388 (M–H); HPLC shows 91% purity.

PREPARATION 16

N-(3-Bromo-2-methyl-phenyl)-methanesulfonamide

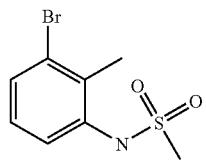

Following procedures essentially as described in Example 90, below, and using 2-methyl-3-bromoaniline (5.00 g, 26.87 mmol), recrystallization from boiling toluene/hexanes affords 6.77 g (95%) of the title compound as a light green solid. MS (ES) 263 (M–H); HPLC shows 100% purity.

PREPARATION 17

N-[2-Methyl-3-(4,4,5,5-tetramethyl-[1,3,2]dioxaborolan-2-yl)-phenyl]-methanesulfonamide

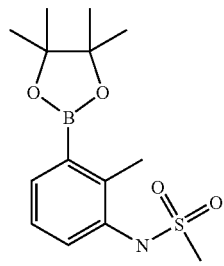

Mix N-(3-bromo-2-methyl-phenyl)-methanesulfonamide (500 mg, 1.89 mmol), bis(pinacolato)diboron (576 mg, 2.27 mmol), and potassium acetate (557 mg, 5.67 mmol) in DMSO (6 mL). Sparge solution with N$_2$ for 5 min, then add Pd(dppf)Cl$_2$ (1:1 complex with CH$_2$Cl$_2$, 154 mg, 0.189 mmol) and heat to 85° C. overnight. Cool reaction mixture to room temperature, dilute with ethyl acetate (100 mL), and wash organics three times with H$_2$O. Dry MgSO$_4$) and concentrate organics to a brown oil. Chromatograph on silica gel (40 g), eluting with 20% to 40% ethyl acetate/hexanes affords 458 mg (78%) of the title compound as a colorless oil. MS (ES) 310 (M–H); HPLC shows 76% purity.

EXAMPLE 48

N-[3-(10,11-Dihydro-dibenzo[a,d]cyclohepten-5-ylidenemethyl)-2-methyl-phenyl]-methanesulfonamide

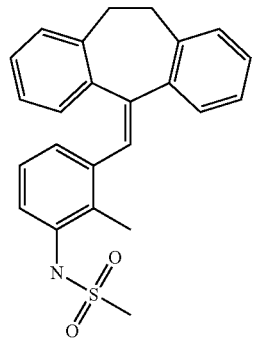

Following the procedures essentially as described in Example 219, below, and using N-[2-methyl-3-(4,4,5,5-tetramethyl-[1,3,2]dioxaborolan-2-yl)-phenyl]-methanesulfonamide (120 mg, 0.386 mmol) and 5-bromomethylene-10,11-dihydro-5H-dibenzo[a,d]cycloheptene (100 mg, 0.351 mmol), purification by UV-guided semi-preparatory reverse-phase HPLC affords 18 mg (13%) of the title compound as a yellow oil. MS (ES) 407 M+NH$_4$), 388 (M–H); HPLC shows 96% purity.

PREPARATION 18

5-Bromo-2-fluoro-phenylamine

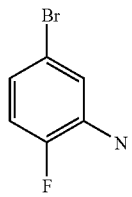

Dissolve 4-bromo-1-fluoro-2-nitrobenzene (5.00 g, 22.73 mmol) and SnCl$_2$ (dihydrate, 25.46 g, 113.6 mmol) in ethanol (100 mL) and heat to reflux overnight. Cool to room temperature and concentrate in-vacuo. Dissolve residue in ethyl acetate and basify with saturated aqueous NaHCO$_3$. Filter through a pad of Celite and extract filtrate with ethyl acetate. Dry (MgSO$_4$) and concentrate organics to a brown oil. Chromatograph on 90 g silica gel, eluting with 5% to 10% ethyl acetate/hexanes affords 2.85 g (66%) of the title compound as a tan oil. MS (ES) 191 (M+H); HPLC shows 99% purity.

PREPARATION 19

N-(5-Bromo-2-fluoro-phenyl)-methanesulfonamide

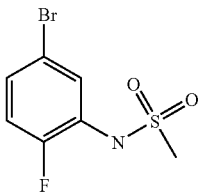

Dissolve 5-bromo-2-fluoro-phenylamine (1.40 g, 7.37 mmol), N,N-dimethylamino-4-pyridine (90 mg, 0.737 mmol), and methanesulfonyl chloride (1.69 g, 14.74 mmol) in CH2Cl2 (10 mL) and pyridine (10 mL). Stir under $N_2$ for 4 h and concentrate in-vacuo. Dilute residue with 1.00N aqueous HCl (20 mL) and extract into ethyl acetate. Dry (MgSO$_4$) and concentrate organics to a yellow solid. Dissolve in THF (20 mL) and add 1.0M tetrabutylammonium fluoride/THF (4.83 mL, 4.83 mmol). Heat to reflux for 3 h, then add H$_2$O and brine. Extract into ethyl acetate, then dry (MgSO$_4$) and concentrate organics to a white solid. Recrystallization from boiling toluene/hexanes affords 768 mg (39%) of the title compound as a white solid. MS (ES) 267 (M−H); HPLC shows 100% purity.

EXAMPLE 49

N-[5-(10,11-Dihydro-dibenzo[a,d]cyclohepten-5-ylidenemethyl)-2-fluoro-phenyl]-methanesulfonamide

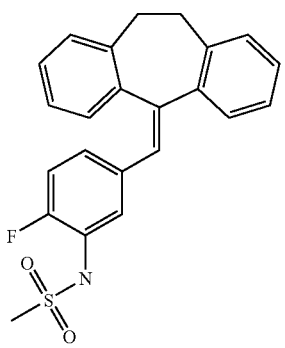

Following the procedures essentially as described in Example 219 (below) and using (10,11-dihydro-dibenzo[a,d]cyclohepten-5-ylidene)-boronic acid (0.197M in dioxane, 3.35 mL, 0.660 mmol) and N-(5-bromo-2-fluoro-phenyl)-methanesulfonamide (147 mg, 0.550 mmol) affords 141 mg (65%) of the title compound as a purple foam. MS (ES) 411 (M+NH4), 392 (M−H); HPLC shows 91% purity.

PREPARATION 20

N-(3-Fluoro-5-iodo-phenyl)-methanesulfonamide

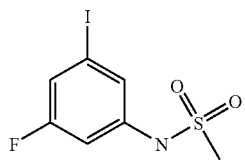

Dissolve 3-fluoro-5-iodoaniline (600 mg, 2.53 mmol) (prepared as described in published PCT International Application WO96/23783 A1, published Aug. 8, 1996), methanesulfonyl chloride (896 mg, 7.83 mmol), triethylamine (1.91 g, 18.9 mmol), and N,N-dimethylamino-4-pyridine (31 mg, 0.253 mmol) in CH$_2$Cl$_2$ (10 mL) and stir at room temperature overnight. Dilute with 1.00N aqueous HCl (20 mL) and extract into ethyl acetate. Dry (MgSO$_4$) and concentrate organics to a yellow solid. Dissolve solid in THF (50 mL) and add 1.0M tetrabutylammonium fluoride (2.8 mL). Heat to reflux for 3.5 h. Cool to room temperature, dilute with H$_2$O, and extract into ethyl acetate. Dry (MgSO$_4$) and concentrate organics. Chromatograph on silica gel (40 g), eluting with 20% to 35% ethyl acetate/hexanes affords 618 mg (78%) of the title compound as a white solid. MS (ES) 314 (M−H); HPLC shows 100% purity.

EXAMPLE 50

N-[3-(10,11-Dihydro-dibenzo[a,d]cyclohepten-5-ylidenemethyl)-5-fluoro-phenyl]-methanesulfonamide

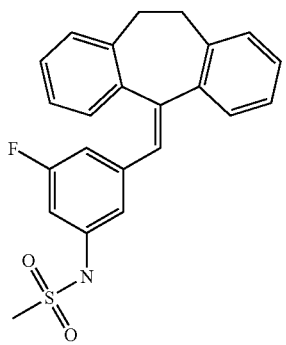

Following procedures essentially as described in Example 219, below, and using 10,11-dihydro-dibenzo[a,d]cyclohepten-5-ylidene)-boronic acid (0.198M in dioxane, 5.1 mL, 1.02 mmol) and N-(3-fluoro-5-iodo-phenyl)-methanesulfonamide (268 mg, 0.850 mmol), purification by UV-guided reverse-phase semi-preparatory HPLC affords 108 mg (32%) of the title compound as a colorless oil. MS (ES) 394 (M+H), 392 (M−H); HPLC shows 99% purity.

EXAMPLE 51

5-(3,5-Dimethoxy-benzylidene)-10,11-dihydro-5H-dibenzo[a,d]cycloheptene

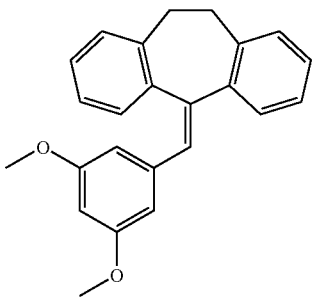

Following procedures essentially as described in Preparation 5 and Example 28, above, and using dibenzosuberone (2.00 g, 10.29 mmol) and 3,5-dimethoxybenzaldehyde (1.71 g, 10.29 mmol), affords 1.43 g (41%) of the title compound as a yellow foam. $^1$H-NMR (CDCl$_3$) δ 2.79-3.64 (br m, 4H), 3.55 (s, 6H), 6.20 (d, 2H), 6.25 (t, 1H), 6.72 (s, 1H), 7.06-7.30 (m, 7H), 7.48 (m, 1H); HPLC shows 99% purity.

EXAMPLE 52

5-(2,5-Dimethoxy-benzylidene)-10,11-dihydro-5H-dibenzo[a,d]cycloheptene

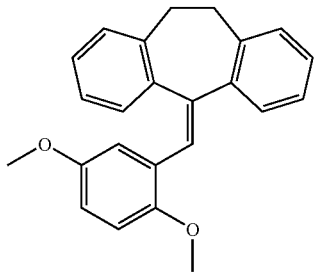

Following procedures essentially as described in Preparation 5 and Example 28, above, and using dibenzosuberone (2.00 g, 10.29 mmol) and 2,5-dimethoxybenzaldehyde (1.71 g, 10.29 mmol) affords 1.27 g (36%) of the title compound as a yellow solid. $^1$H-NMR (CDCl$_3$) δ 2.74-3.67 (br m, 4H), 3.34 (s, 3H), 3.83 (s, 3H), 6.27 (d, 1H), 6.65 (dd, 1H), 6.77 (d, 1H), 6.98-7.28 (m, 8H), 7.56 (dd, 1H); HPLC shows 99% purity.

EXAMPLE 53

5-(2,4-Dimethoxy-benzylidene)-10,11-dihydro-5H-dibenzo[a,d]cycloheptene

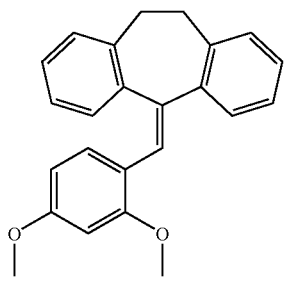

Following procedures essentially as described in Preparation 5 and Example 28, above, and using dibenzosuberone (2.00 g, 10.29 mmol) and 2,4-dimethoxybenzaldehyde (1.71 g, 10.29 mmol) affords 231 mg (7%) of the title compound as a white foam. $^1$H-NMR (CDCl$_3$) δ 2.70-3.67 (br m, 4H), 3.73 (s, 3H), 3.84 (s, 3H), 6.15 (dd, 1H), 6.41 (d, 1H), 6.61 (d, 1H), 6.9-7.27 (m, 8H), 7.56 (dd, 1H); HPLC shows 98% purity.

EXAMPLE 54

5-(10,11-Dihydro-dibenzo[a,d]cyclohepten-5-ylidenemethyl)-benzene-1,3-diol

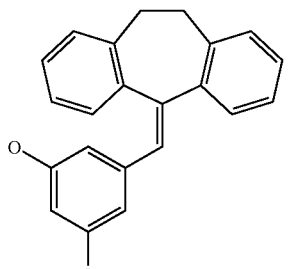

Following procedures essentially as described in Example 57, below, and using 5-(3,5-dimethoxy-benzylidene)-10,11-dihydro-5H-dibenzo[a,d]cycloheptene (664 mg, 1.94 mmol), affords 608 mg (99%) of the title compound as a colorless oil. $^1$H-NMR (CDCl$_3$) δ 2.73-3.62 (br m, 4H), 4.89 (br s, 2H), 6.07 (d, 2H), 6.14 (t, 1H), 6.64 (s, 1H), 7.04-7.28 (7H), 7.44 (m, 1H); HPLC shows 98% purity.

EXAMPLE 57

3-(10,11-Dihydro-dibenzo[a,d]cyclohepten-5-ylidenemethyl)-phenol

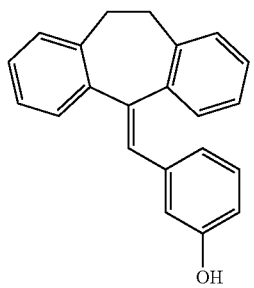

Stir a molten mixture of 5-(3-methoxy-benzylidene)-10,11-dihydro-5H-dibenzo[a,d]cycloheptene (1.11 g, 3.55 mmol) and pyridine hydrochloride (10 g, 87 mmol) at 215° C. for 40 min. Cool the reaction mixture to 100° C., dilute with 1N HCl, and extract with ethyl acetate. Dry organics (MgSO$_4$), filter, and concentrate to a brown oil containing the title compound. Purification via silica gel chromatography (1:6 ethyl acetate:hexanes) affords 940 mg (89%) of a tan oil. $^1$H NMR (CDCl$_3$) δ 2.76-3.63 (br m, 4H), 4.59 (s, 1H), 6.45 (s, 1H), 6.64 (m, 2H), 6.75 (s, 1H), 6.99-7.52 (m, 9H); MS (ES) 299 (M+H), 297 (M−H). HPLC shows 97% purity.

EXAMPLE 60 b -(10,11-Dihydro-dibenzo[a,d]cyclohepten-5-ylidenemethyl)-phenol

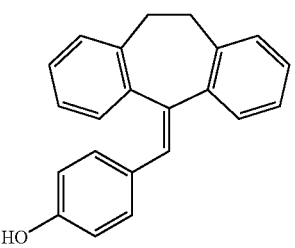

Following procedures essentially as described in Example 57, above, and using 5-(4-methoxy-benzylidene)-10,11-dihydro-5H-dibenzo[a,d]cycloheptene gives the title compound in 60% yield as a white crystalline solid, mp 56.9° C. $^1$H NMR (CDCl$_3$) δ 2.77-3.60 (br m, 4H), 4.71 (s, 1H), 6.62 (d, 2H), 6.73 (s, 1H), 6.92 (d, 2H), 7.02-7.50 (m, 8H); MS (ES) 297 (M−H). HPLC shows 97% purity.

EXAMPLE 62

4-(10,11-Dihydro-dibenzo[a,d]cyclohepten-5-ylidenemethyl)-benzene-1,2-diol

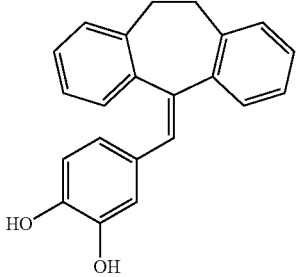

Following procedures essentially as described in Example 57, above, and using 5-(3,4-dimethoxy-benzylidene)-10,11dihydro-5H-dibenzo[a,d]cycloheptene gives the title compound in 79% yield as a brown foam, mp 138.0° C. $^1$H NMR (CDCl$_3$) δ 2.76-3.62 (br m, 4H), 4.84 (s, 1H), 5.07 (s, 1H), 6.47 (s, 1H), 6.55 (m, 11H); MS (ES) 313 (M−H). HPLC shows 95% purity.

EXAMPLE 63

2-Amino-4-(10,11-dihydro-dibenzo[a,d]cyclohepten-5-ylidenemethyl)-phenol

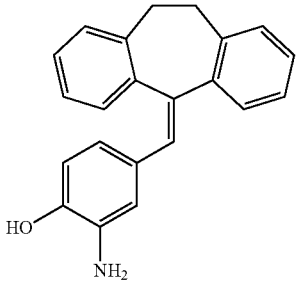

Following procedures essentially as described in Example 57, above, and using 5-(10,11-dihydro-dibenzo[a,d]cyclohepten-5-ylidenemethyl)-2-methoxy-phenylamine gives the title compound in 75% yield as a brown foam, mp 158.8° C. $^1$H NMR (CDCl$_3$) δ 2.72-4.45 (br 10 m, 61), 6.31-7.54 (br m, 13H). MS (ES) 314 (M+H), 312 (M−H). HPLC shows 98% purity.

EXAMPLE 64

N-[5-(10,11-Dihydro-dibenzo[a,d]cyclohepten-5-ylidenemethyl)-2-hydroxy-phenyl]-methanesulfonamide

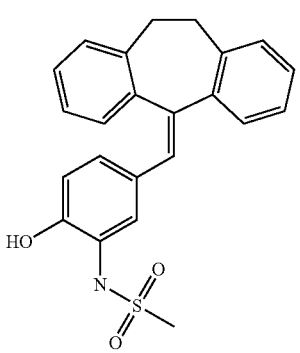

Cool a solution of N-[5-(10,11-dihydro-dibenzo[a,d]cyclohepten-5-ylidenemethyl)-2-methoxy-phenyl]-methanesulfonamide (100 mg, 0.247 mmol) in CH$_2$Cl$_2$ (5 mL) to 0° C. Add 23.3 □L (62 mg, 0.247 mmol) BBr$_3$ and warm up to room temperature. Stir for 20 min, then add 30.0 □L (79.5 mg, 0.317 mmol) more BBr$_3$. Stir at room temperature for 1 h, then dilute reaction with 90 mL saturated aqueous NaHCO$_3$. Stir overnight. Separate the layers, and extract the aqueous layer with CH$_2$Cl$_2$. Combine and dry organics (MgSO$_4$), filter, and concentrate to afford 94 mg (97%) of a white foam, mp 122.6° C. $^1$H NMR (CDCl$_3$) δ 2.70 (s, 3H), 2.79-3.59 (br m, 4H), 5.94 (s, 1H), 6.39 (s, 1H), 6.70-7.98 (m, 12H); MS (ES) 414 (M+Na), 390 (M−H). HPLC shows 99% purity.

EXAMPLE 65

5-(3-Difluoromethoxy-benzylidene)-10,11-dihydro-5H-dibenzo[a,d]cycloheptene

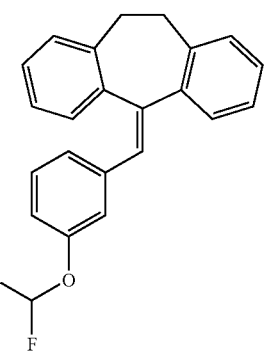

Add pellets of KOH (376 mg, 6.7 mmol) to a solution of 3-(10,11-dihydro-dibenzo[a,d]cyclohepten-5-ylidenemethyl)-phenol (200 mg, 0.67 mmol) in isopropanol (10 mL). Bubble chlorodifluoromethane (Freon 22) slowly into the reaction mixture for 2 h. Concentrate the reaction mixture, and take the residue up in 1N HCl. Extract into ethyl acetate, dry organics (MgSO$_4$), filter, and concentrate to a milky tan oil containing the title compound. Purify via silica gel chromatography (1:20 ethyl acetate:hexanes) to afford 108 mg (20%) of a white solid, mp 91.3° C. $^1$H NMR (CDCl$_3$) δ 2.66-3.56 (br m, 4H), 6.12 (t, 1H, J=80 Hz), 6.55-7.43 (m, 13H); MS (EI) 348. HPLC shows 97% purity.

EXAMPLE 66

5-(2-Difluoromethoxy-benzylidene)-10,11-dihydro-5H-dibenzo[a,d]cycloheptene

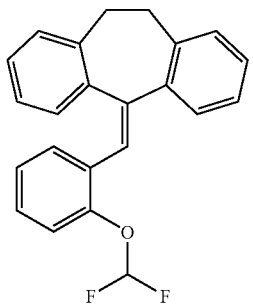

Following the procedures essentially as described in Example 65 above, 5-(2-difluoromethoxy-benzylidene)-10, 11-dihydro-5H-dibenzo[a,d]cycloheptene gives the title compound in 20% yield as a white solid, mp 81.1° C. $^1$H NMR (CDCl$_3$) δ 2.76-3.72 (br m, 4H), 6.57 (t, 1H, J=72 Hz), 6.75-7.57 (m, 13H); MS (EI) 348. HPLC shows 95% purity.

EXAMPLE 67

5-(4-Difluoromethoxy-benzylidene)-10,11-dihydro-5H-dibenzo[a,d]cycloheptene

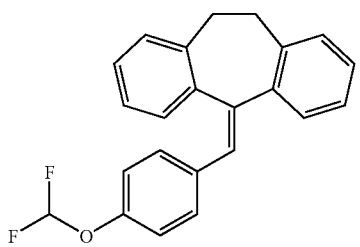

Following the procedures essentially as described in Example 65 above, 5-(4-difluoromethoxy-benzylidene)-10, 11-dihydro-5H-dibenzo[a,d]cycloheptene gives the title compound in 46% yield as a white solid, mp 65.8° C. $^1$H NMR (CDCl$_3$) δ 2.76-3.64 (br m, 4H), 6.44 (t, 1H, J=76 Hz), 6.76 (s, 1H), 6.84-7.50 (m, 12H); MS (EI) 348. HPLC shows 100% purity.

PREPARATION 21

3-(10,11-Dihydro-dibenzo[a,d]cyclohepten-5-yliden-emethyl)-benzenesulfonyl chloride

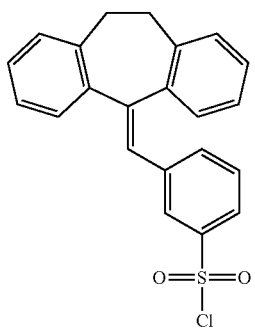

Under a blanket of nitrogen, cool 5-(3-bromo-benzylidene)-10,11-dihydro-5H-dibenzo-[a,d]cycloheptene (2.8 g, 7.75 mmol) in THF (40 mL) to −78° C. and add n-BuLi (1.6M, 5.8 mL, 9.3 mmol) via syringe. After 20 min, add sulfuryl chloride (800 μl, 10 mmol). The color lightened immediately. Quench the reaction with saturated NH$_4$Cl and mix the reaction with water/EtOAc. Dry (MgSO$_4$) and concentrate to give 2.7 g pale yellow oil. Purify on silica gel using a gradient of 100% hexane to 30% EtOAc/hexane to give 380 mg (13%) sulfonyl chloride. Stir a small aliquot with dimethylamine for several hours. MS (ES) gives the correct mass for the dimethylsulfonamide derivative.

PREPARATION 22

4-(10,11-Dihydro-dibenzo[a,d]cyclohepten-5-yliden-emethyl)-benzenesulfonyl chloride

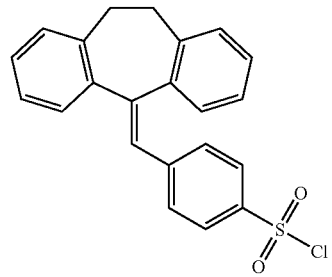

Prepared using Procedure E to give 142 mg (8%) sulfonyl chloride as a pale yellow oil.

EXAMPLE 68

4-(10,11-Dihydro-dibenzo[a,d]cyclohepten-5-yliden-emethyl)-benzaldehyde

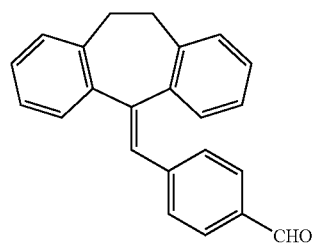

Under nitrogen, cool 5-(4-bromo-benzylidene)-10,11-dihydro-5H-dibenzo-[a,d]cycloheptene (2.2 g, 6.1 mmol) in THF (40 mL) to 65° C. and add n-BuLi (1.6 M, 5 mL, 8 mmol) via syringe. After 15 minutes, add DMF (1 mL, 14 mmol). After 1 h, the quench the reaction with saturated NH$_4$Cl and partition between water/EtOAc. Dry (MgSO$_4$) and concentrate to yield 1.8 g crude aldehyde. Purify on silica gel using hexane/EtOAc to give 940 mg colorless oil that slowly crystallized to give a white solid, mp 106.4° C.; $^1$H NMR (CDCl3) δ 2.80-3.60 (br dd, 4H), 6.84 (s, 1H), 6.92-7.63 (m, 12H), 9.90 (s, 1H); MS (EI) 310. HPLC shows 96% purity.

EXAMPLE 69

2-(10,11-Dihydro-dibenzo[a,d]cyclohepten-5-yliden-emethyl)-benzaldehyde

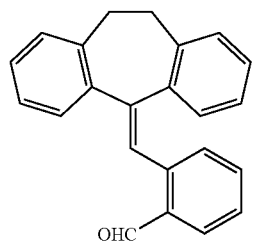

Following procedures essentially as described in Example 68, the title compound was prepared from the corresponding bromide derivative to give white crystals (hexane/EtOAc, 42%), mp 198.9° C. $^1$H NMR (CDCl3) δ 2.80-3.60 (br s, 4H), 6.67-7.86 (m, 13H), 10.42 (s,1H); MS (EI) 310. HPLC shows 97% purity.

EXAMPLE 70

3-(10,11-Dihydro-dibenzo[a,d]cyclohepten-5-ylidenemethyl)-benzaldehyde

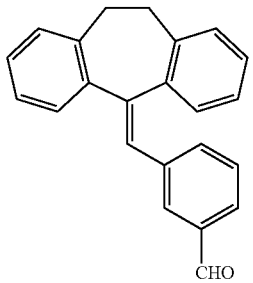

Following procedures essentially as described in Example 68 the title compound was isolated as a white solid (38%), mp 86.7° C. $^1$H NMR (CDCl3) δ2.80-3.60 (br dd, 4H), 6.84 (s, 1H), 6.93-7.65 (m, 12H), 9.81 (s, 1H); MS (EI) 310. HPLC shows 97% purity.

EXAMPLE 71

5-(2-Difluoromethyl-benzylidene)-10,11-dihydro-5H-dibenzo[a,d]cycloheptene

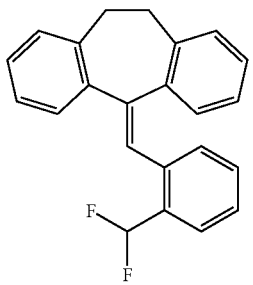

Dissolve 2-(10,11-dihydro-dibenzo[a,d]cyclohepten-5-ylidenemethyl)-benzaldehyde (100 mg, 0.32 mmol) in CH$_2$Cl$_2$ (3 mL) and add (diethylamino)sulfur trifluoride (DAST) (210≡l, 1.6 mmol). Stir the reaction overnight at ambient temperature. Shake the crude reaction with saturated NaHCO$_3$/CH$_2$Cl$_2$. Dry (MgSO$_4$) and concentrate to give 110 mg crude product. Purify on silica gel using hexane/CH$_2$Cl$_2$ to give 50 mg (47%) title compound as a white solid, mp. 13.3° C. $^1$H NMR (CDCl3) δ 2.80-3.60 (br s, 4H), 6.72-7.58 (m, 14H); MS (EI) 332. HPLC shows 98% purity.

EXAMPLE 72

5-(3-Difluoromethyl-benzylidene)-10,11-dihydro-5H-dibenzo[a,d]cycloheptene

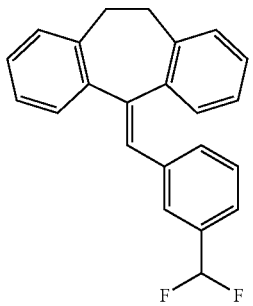

Following procedures essentially as described in Example 71, the title compound was prepared as a light yellow solid (39%), mp 92.5° C. $^1$H NMR (CDCl3) δ 2.96 (br d, 2H), 3.44 (br d, 2H), 6.45 (t, 1H, J=70 Hz), 6.80 (s, 1H), 6.94-7.33 (m, 11H), 7.48 (m, 1H); MS (EI) 332. HPLC shows 94% purity.

EXAMPLE 73

5-(4-Difluoromethyl-benzylidene)-10,11-dihydro-5H-dibenzo[a,d]cycloheptene

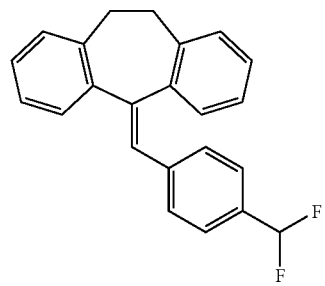

Following procedures essentially as described in Example 71, the title compound was prepared as a colorless oil (39%); $^1$H NMR (CDCl3) δ 2.80-3.60 (br dd, 4H), 6.47 (t, 1H, J=55 Hz), 6.72 (s, 1H), 6.87-7.24 (m, 11H), 7.42 (m, 1H); MS (EI) 332. HPLC shows 100% purity.

EXAMPLE 74

[2-(10,11-Dihydro-dibenzo[a,d]cyclohepten-5-ylidenemethyl)-phenyl]-methanol

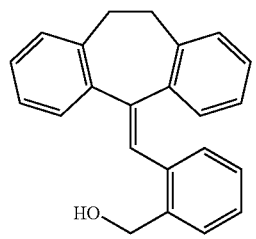

Treat a solution of 2-(10,11-dihydro-dibenzo[a,d]cyclohepten-5-ylidenemethyl)-benzaldehyde (125 mg, 0.4 mmol) in EtOH (4 mL) with NaBH$_4$ (30 mg, 0.8 mmol). After 4 h at room temperature, quench the reaction with 1N HCl and concentrate. Shake the residue en with water/EtOAc. Dry the organic layer (MgSO$_4$) and concentrate to give 130 mg crude product. Purify on silica gel (EtOAc/hexane) to give 90 mg (72%) colorless oil which slowly crystallized, mp 121.8° C. $^1$H NMR (CDCl3) δ 3.28 (br s, 4H), 4.85 (s, 2H), 6.77-7.60 (m, 13H; MS (EI) 312. HPLC shows 98% purity.

EXAMPLE 75

[3-(10,11-Dihydro-dibenzo[a,d]cyclohepten-5-ylidenemethyl)-phenyl]-methanol

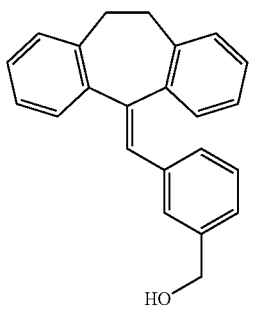

Following procedures essentially as described in Example 74, the title compound was obtained as a colorless oil which slowly crystallized. $^1$H NMR (CDCl3) δ 3.03 (br d, 2H), 3.47 (br d, 2H), 4.55 (s, 2H), 6.84 (s, 1H), 6.93-7.31 (m, 11H), 7.52 (m, 1H ); MS (EI) 312. HPLC shows 93% purity.

EXAMPLE 76

[4-(10,11-Dihydro-dibenzo[a,d]cyclohepten-5-ylidenemethyl)-phenyl]-methanol

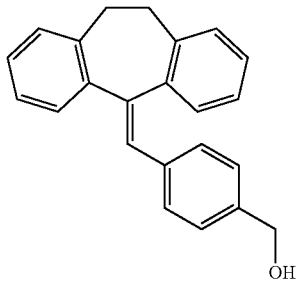

Following procedures essentially as described in Example 74, the title compound was obtained as a colorless oil (65%); $^1$H NMR (CDCl3) δ3.03 (br d, 2H), 3.47 (br d, 2H), 4.62 (s, 2H), 6.78 (s, 1H), 7.02-7.34 (m, 1111), 7.520 (m, 1H); MS (EI) 312.

EXAMPLE 77

2-(10,11-Dihydro-dibenzo[a,d]cyclohepten-5-ylidenemethyl)-benzaldehyde oxime

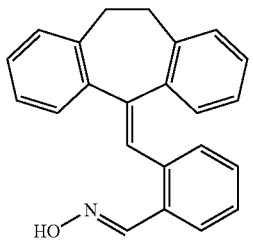

Dissolve 2-(10,11-dihydro-dibenzo[a,d]cyclohepten-5-ylidenemethyl)-benzaldehyde (110 mg,0.35 mmol) in EtOH (4 mL). In a separate flask, dissolve hydroxylamine hydrochloride (35 mg, 0.5 mmol) in water (1 mL). Add this solution the aldehyde solution and stir at room temperature for 18 h. Pour the reaction into water (300 mL) and extract the product into EtOAc. Dry (MgSO$_4$) and concentrate to give 140 mg crude product. Purity on silica gel using EtOAc/hexane to give 82 mg (72%) title compound as a white solid. $^1$H NMR (CDCl3) δ 3.31 (br s, 4H), 6.73-7.33 (m, 11H), 7.55 (m, 1H), 7.70 (dd, 1H), 8.58 (s, 1H); MS (ES) 326 (M+1), 324 (M−1). HPLC shows 98% purity.

EXAMPLE 78

3-(10,11-Dihydro-dibenzo[a,d]cyclohepten-5-ylidenemethyl)-benzaldehyde oxime

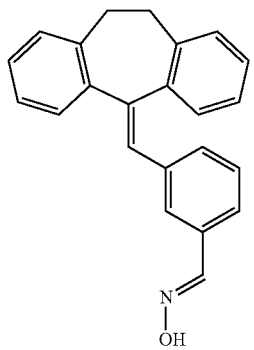

Following procedures essentially as described in Example 77, the title compound was prepared in 55% yield from 3-(10,11-dihydro-dibenzo[a,d]cyclohepten-5-ylidenemethyl)-benzaldehyde (50 mg, 0.161 mmol). $^1$H NMR (CDCl3) δ 2.92 (br d, 2H), 3.36 (br d, 2H), 6.72 (s, 1H), 6.87-7.43 (m, 12H), 7.87 (s, 1H); MS (ES) 326 (M+1).

EXAMPLE 79

4-(10,11-Dihydro-dibenzo[a,d]cyclohepten-5-ylidenemethyl)-benzaldehyde oxime

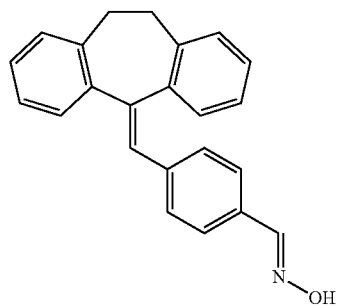

Following procedures essentially as described in Example 77, the title compound was prepared in 55% yield from 4-(10,11ihydro-dibenzo[a,d]cyclohepten-5-ylidenemethyl)-benzaldehyde (117 mg, 0.38 mmol). $^1$H NMR (CDCl3) δ 2.77 (br d, 2H), 3.21 (br d, 2H), 6.57 (s, 1H), 6.61-7.64 (m,12H), 7.82 (s, 1H); MS (ES) 326 (M+1). HPLC shows 97% purity.

EXAMPLE 80

2-(10,11-Dihydro-dibenzo[a,d]cyclohepten-5-yliden-emethyl)-benzonitrile

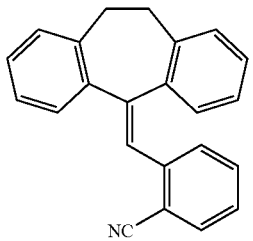

Sparge a mixture of 5-methylene-10,11-dihydro-5H-dibenzo[a,d]cycloheptene (2.0 g, 9.7 mmol) (prepared as described in Journal of Organic Chemistry, 53 (8) 1768-1774 (1988)), 2-bromobenzonitrile ((1.77 g, 9.7 mmol), NaOAc (1 g, 12 mmol) and dimethylacetamide (100 mL) with nitrogen for 15 minutes. Add Hermann catalyst (320 mg, 0.46 mmol) (Chem. Eur. J. 1357-1364 (1997)) and heat at 150° C. for 6 days. Cool the reaction and partition between water (1 L) and EtOAc (500 mL). Wash the organic layer with water (3×1L). Dry (MgSO$_4$) and concentrate under reduced pressure to give 3.3 g brown oil. Purify on silica gel using EtOAc/hexane 500 mg nitrile that is 81% pure by glc. Recrystallize (EtOH) to give 213 mg (7%) pale yellow plates, mp 185.4° C. $^1$H NMR (CDCl$_3$) δ 3.04 (br d, 2H), 3.47 (br s, 2H), 6.82-7.34 (m, 11H), 7.62 (m, 2H); MS (ES) 308 (M+1). HPLC shows 98% purity.

EXAMPLE 81

3-(10,11-Dihydro-dibenzo[a,d]cyclohepten-5-yliden-emethyl)-benzonitrile

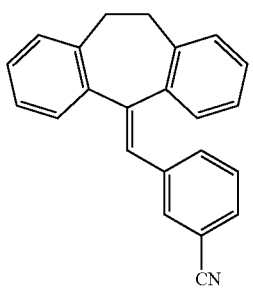

Purge a solution of 5-(3-bromo-benzylidene)-10,11-dihydro-5H-dibenzo-[a,d]cycloheptene (4.2 g, 11.6 mmol) in N-methylpyrrolidinone (80 mL) with nitrogen for 10 minutes. Add CuI (6.7 g, 35 mmol) and CuCN (3.1 g, 35 mmol) and heat to 130° C. After 1 hour, cool the reaction to ambient temperature and shake with aqueous FeCl$_3$ (200 mL) and EtOAc (200 mL). Wash the organic layer with water, dry with MgSO$_4$ and concentrate to obtain 6.4 g crude product. Purify on silica gel using EtOAc/hexane to obtain 2.55 g (71%) title compound as a white solid, mp 115.7° C. $^1$H NMR (CDCl$_3$) δ 3.02 (br d, 2H), 3.40 (br d, 2H), 6.77 (s, 1H), 6.93 (dd, 1H), 7.02-7.49 (m,11H); MS (EI) 307. HPLC shows 98% purity.

EXAMPLE 82

4-(10,11-Dihydro-dibenzo[a,d]cyclohepten-5-yliden-emethyl)-benzonitrile

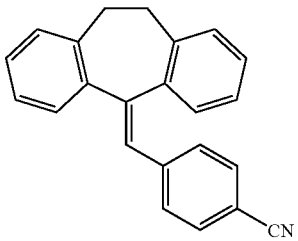

Following procedures essentially as described in Example 81and using 5-(4-bromo-benzylidene)-10,11-dihydro-5H-dibenzo-[a,d]cycloheptene (4.2 g, 11.6 mmol) gives 2.02 g (57%) as tan viscous oil. $^1$H NMR (CDCl$_3$) δ 3.06 (br d, 2H), 3.48 (br d, 2H), 6.85 (s, 1H), 6.98 (dd, 1H), 7.06-7.57 (m, 11H; MS (EI) 307. HPLC shows 97% purity.

EXAMPLE 83

2-(10,11-Dihydro-dibenzo[a,d]cyclohepten-5-yliden-emethyl)-benzamide

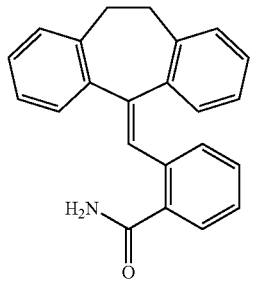

Dissolve 2-(10,11-dihydro-dibenzo[a,d]cyclohepten-5-ylidenemethyl)-benzonitrile (100 mg, 0.32 mmol) in DMSO (3 mL) and add solid K$_2$CO$_3$ (50 mg) followed by 30% H$_2$O$_2$ (100□1). Stir the reaction for 3 h. and quench by pouring into water. Collect the white solid and dry in a vacuum oven to yield 84 mg (81%). $^1$H NMR (DMSO-d$_6$) δ2.95 (br s, 2H), 3.38 (br s, 2H), 6.67-7.56 (m, 12H), 7.90 (s, 1H); MS (ES) 326 (M+1) (M−1). HPLC shows 95% purity.

EXAMPLE 84

3-(10,11-Dihydro-dibenzo[a,d]cyclohepten-5-yliden-emethyl)-benzamide

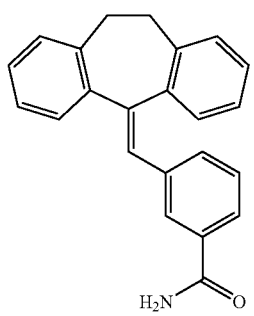

Following procedures essentially as described in Example 83 and starting with 3-(10,11-dihydro-dibenzo[a,d]cyclohepten-5-ylidenemethyl)-benzonitrile (480 mg, 1.56 mmol) gives 445 mg (88%) as an off-white solid. $^1$H NMR (DMSO-$d_6$) δ 2.95 (br s, 2H), 3.40 (br s, 2H), 6.85-7.54 (m, 10H), 7.61 (d, 1H), 7.72 (s, 1H), 7.84 (s, 1H); MS (ES) 326 (M+1), 324 (M−1). HPLC shows 94% purity.

EXAMPLE 85

4-(10,11-Dihydro-dibenzo[a,d]cyclohepten-5-ylidenemethyl)-benzamide

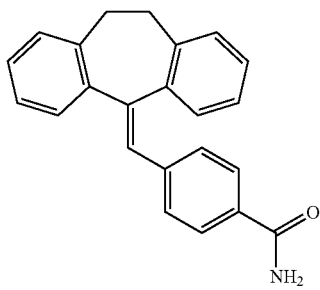

Following procedures essentially as described in Example 83 and starting with 4-(10,11-dihydro-dibenzo[a,d]cyclohepten-5-ylidenemethyl)-benzonitrile (230 mg, 0.75 mmol) gives 226 mg (93%) white powder. $^1$H NMR (DMSO-$d_6$) δ 2.95 (br s, 2H), 3.38 (br s, 2H), 6.82-7.54 (m, 11H), 7.67 (d, 1H), 7.87 (s, 1H); MS (ES) 326 (M+1). HPLC shows 96% purity.

EXAMPLE 86

3-(10,11-Dihydro-dibenzo[a,d]cyclohepten-5-ylidenemethyl)-phenylamine

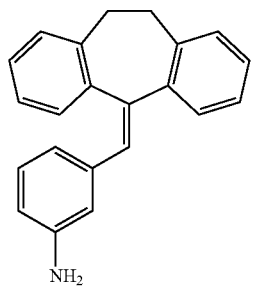

Dissolve 5-(3-bromo-benzylidene)-10,11-dihydro-5H-dibenzo[a,d]cycloheptene (3.00 g, 8.30 mmol) in toluene (75 mL) and add the following reagents: tris(dibenzylidineacetone)dipalladium(0) (380 mg, 0.415 mmol), racemic BINAP (517 mg, 0.830 mmol), sodium t-butoxide (1.12 g, 11.6 mmol), and benzophenone imine (3.48 mL, 3.76 g, 20.76 mmol). Heat the mixture to reflux overnight. Cool to room temperature and dilute with H$_2$O. Extract into ethyl acetate and dry organics (MgSO$_4$). Concentrate organics and take the residue up in a 1:1 mixture of THF and 1N HCl. After 2 h, extract into ethyl acetate and dry organics (MgSO$_4$). Concentrate to a brown solid containing the title compound. Boil the solid in a 5:1:0.1 mixture of toluene:ethyl acetate:THF. Cool the suspension to −26° C. and filter, collect 1.98 g (80%) of a white solid, mp 204.3° C. $^1$H NMR (DMSO-$d_6$) δ 2.90 (br s, 2H), 3.36 (br d, 2H), 6.77-7.51 (m, 15H); MS (ES) 298 (M+H). HPLC shows 99% purity.

EXAMPLE 87

2-(10,11-Dihydro-dibenzo[a,d]cyclohepten-5-ylidenemethyl)-phenylamine

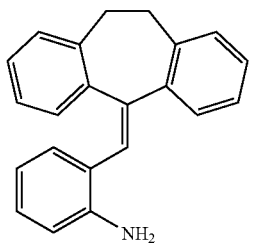

Following procedures essentially as described in Example 86, 5-(2-bromo-benzylidene)-10,11-dihydro-5H-dibenzo[a,d]cycloheptene gives the title compound in 85% yield as a yellow foam, mp 145.2° C. after purification using silica gel chromatography(75:24:1 hexanes:CH2Cl2:2M NH3/MeOH). $^1$H NMR (CDCl$_3$) δ 3.25 (br s, 4H), 3.80 (s, 2H), 6.45-7.51 (m, 13H); MS (ES) 298 (M+H). HPLC shows 95% purity.

EXAMPLE 88

4-(10,11-Dihydro-dibenzo[a,d]cyclohepten-5-ylidenemethyl)-phenylamine

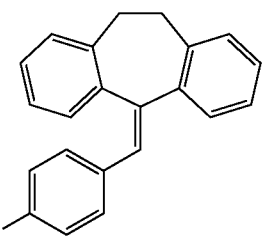

Following procedures essentially as described in Example 86, 5-(4-bromo-benzylidene)-10,11-dihydro-5H-dibenzo[a,d]cycloheptene gives the title compound in 54% yield as an orange solid, mp>250° C. after purification by triturating with hot CH$_2$Cl$_2$. $^1$H NMR (DMSO-$d_6$) δ 2.86 (br s, 2H), 3.32 (br d, 2H), 6.74 (s, 1H), 6.89-7.48 (m, 14H); MS (ES) 298 (M+H). HPLC shows 98% purity.

EXAMPLE 89

5-(10,11-Dihydro-dibenzo[a,d]cyclohepten-5-ylidenemethyl)-2-methoxy-phenylamine

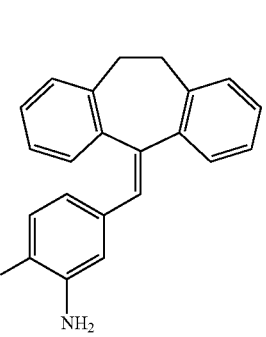

Following procedures essentially as described in Example 86, 5-(3-bromo-4-methoxy-benzylidene)-10,11-dihydro-5H-dibenzo[a,d]cycloheptene gives the title compound in 36% yield as a yellow foam, mp 62.7° C. after purification via silica gel chromatography (1:9 ethyl acetate:hexanes). $^1$H NMR (CDCl$_3$) δ 2.69-3.73 (br m, 6H), 3.80 (s, 3H), 6.36 (s, 1H), 6.48 (dd, 1H), 6.60 (d, 1H), 6.66 (s, 1H), 7.00-7.50 (m, 8H); MS (ES) 328 (M+H). HPLC shows 98% purity.

EXAMPLE 90

N-[3-(10,11-Dihydro-dibenzo[a,d]cyclohepten-5-ylidenemethyl)-phenyl]-methanesulfonamide

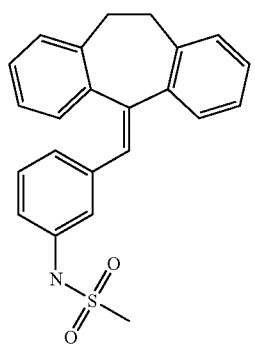

Dissolve 3-(10,11-dihydro-dibenzo[a,d]cyclohepten-5-ylidenemethyl)-phenylamine (400 mg, 1.34 mmol) in anhydrous pyridine (10 mL) and add methanesulfonyl chloride (616 mg, 416□L, 5.38 mmol). Stir overnight at room temperature, then concentrate. Take residue up in ethyl acetate and 1N HCl and separate the layers. Extract aqueous layer with ethyl acetate, combine organics, and dry (MgSO$_4$). Concentrate to a brown oil. Purify via silica gel chromatography (2:3 ethyl acetate:hexanes) to yield 350 mg (70%) of yellow foam, mp 66.3° C. $^1$H NMR (CDCl$_3$) δ 2.71 (s, 3H), 2.75-3.56 (br m, 4H), 6.09 (s, 1H), 6.64-7.43 (m, 13H); MS (ES) 398 (M+23), 374 (M−H). HPLC shows 96% purity.

EXAMPLE 91

Ethanesulfonic acid [3-(10,11-hydro-dibenzo[a,d]cyclohepten-5-ylidenemethyl)-phenyl]-amide

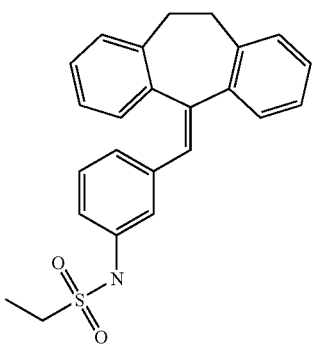

Following procedures essentially as described in Example 90, 3-(10,11-dihydro-dibenzo[a,d]cyclohepten-5-ylidenemethyl)-phenylamine and ethanesulfonyl chloride gives the title compound in 74% yield as a brown solid, mp 180.2° C. $^1$H NMR (CDCl$_3$) δ 1.25 (t, 3H), 2.80-3.60 (br m, 6H), 6.06 (br s, 1H), 6.71-7.51 (m, 13H); MS (ES) 412 (M+Na), 388 (M−H). HPLC shows 99% purity.

EXAMPLE 92

Propane-2-sulfonic acid [3-(10,11-dihydro-dibenzo[a,d]cyclohepten-5-ylidenemethyl)-phenyl]-amide

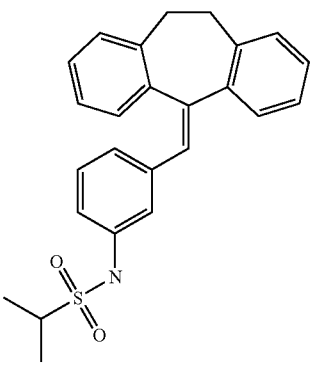

Following procedures essentially as described in Example 90, 3-(10,11-dihydro-dibenzo[a,d]cyclohepten-5-ylidenemethyl)-phenylamine and isopropylsulfonyl chloride gives the title compound in 22% yield as a white solid, mp 187.7° C. $^1$H NMR (CDCl$_3$) δ 1.28 (d, 6H), 2.80-3.60 (br m, 5H), 6.47 (s, 1H), 6.75-7.50 (m, 13H); MS (ES) 426 (M+Na), 402 (M−H). HPLC shows 94% purity.

EXAMPLE 93

N-[3-(10,11-Dihydrodibenzo[a,d]cyclohepten-5-ylidenemethyl)-phenyl]-benzenesulfonamide

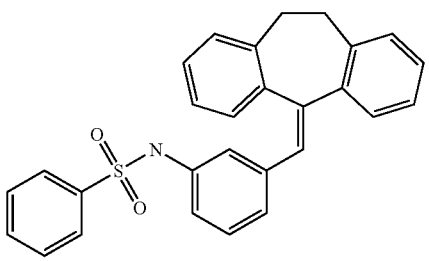

Following procedures essentially as described in Example 90, 2-(10,11-dihydro-dibenzo[a,d]cyclohepten-5-ylidenemethyl)-phenylamine and benzenesulfonyl chloride gives the title compound in 82% yield as a white solid, mp 121.9° C. $^1$H HMR (CDCl$_3$) δ 2.76-3.56 (br m, 4H), 6.64-7.77 (m, 19H); MS (ES) 460 (M+Na), 436 (M−H). HPLC shows 98% purity.

EXAMPLE 94

3,5-Dimethyl-isoxazole-4-sulfonic acid [3-(10,11-dihydro-dibenzo[a,d]cyclohepten-5-ylidenemethyl)-phenyl]-amide

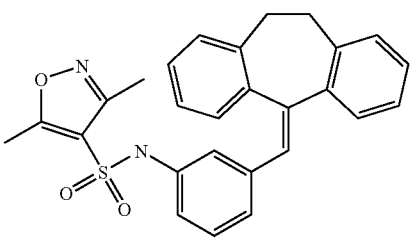

Following procedures essentially as described in Example 90, 2-(10,11-dihydro-dibenzo[a,d]cyclohepten-5-ylidenemethyl)-phenylamine and 3,5-dimethyl-isoxazole-4-sulfonyl chloride gives the title compound in 80% yield as a white solid, mp 149.3° C. ¹H NMR (CDCl₃) δ 2.21 (s, 3H), 2.40 (s, 3H), 2.77-3.54 (br m, 4H), 6.57 (s, 1H), 669 (d, 2H), 6.86-7.48 (m, 11H); MS (ES) 479 (M+Na) 455 (M–H). HPLC shows 95% purity.

EXAMPLE 95

1-Methyl-1H-imidazole-4-sulfonic acid [3-(10,11-dihydro-dibenzo[a,d]cyclohepten-5-ylidenemethyl)-phenyl]-amide

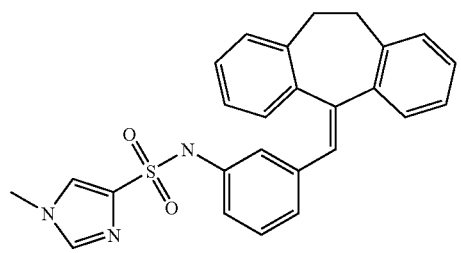

Following procedures essentially as described in Example 90, 2-(10,11-dihydro-dibenzo[a,d]cyclohepten-5-ylidenemethyl)-phenylamine and 1-methyl-1H-imidazole-4sulfonyl chloride gives the title compound in 40% yield as a white solid, mp 257.0° C. ¹H NMR (DMSO-d₆) δ 2.90 (br s, 2H), 3.35 (br s, 2H), 3.64 (s, 3H), 6.46 (d, 1H), 6.67 (s, 1H), 6.80-7.46 (m, 11H), 7.79 (d, 2H), 6.11 (s, 1H); MS (ES) 464 (M+Na). HPLC shows 100% purity.

EXAMPLE 96

1,2-Dimethyl-1H-imidazole-4sulfonic acid [3-(10,11-dihydro-dibenzo[a,d]cyclohepten-5-ylidenemethyl)-phenyl]-amide

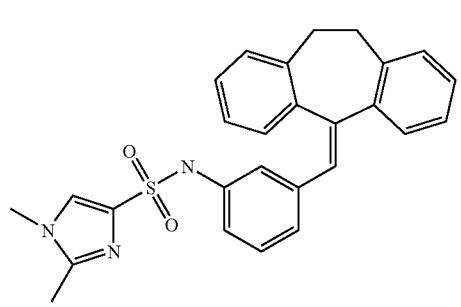

Following procedures essentially as described in Example 90, 2-(10,11-dihydro-dibenzo[a,d]cyclohepten-5-ylidenemethyl)-phenylamine and 1,2-dimethyl-1H-imidazole-4-sulfonyl chloride gives the title compound in 1% yield as a white solid. MS (ES) 456 (M+H). HPLC shows 100% purity.

EXAMPLE 97

N-[5-(10,11-Dihydro-dibenzo[a,d]cyclohepten-5-ylidenemethyl)-2-methoxy-phenyl]-methanesulfonamide

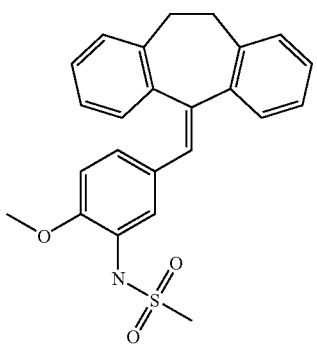

Following procedures essentially as described in Example 90-, 5-(10,11-dihydro-dibenzo[a,d]cyclohepten-5-ylidenemethyl)-2-methoxy-phenylamine and methanesulfonyl chloride gives the title compound in 77% yield as a tan foam, mp 192.1° C. ¹H NMR (CDCl₃) δ 2.74 (s, 3H), 2.80-4.61 (br m, 4H), 4.81 (s, 3H), 6.67-7.50 (m, 13H); MS (ES) 423 (M+NH₄), 404 (M–H). HPLC shows 100% purity.

EXAMPLE 99

N-[4-(10,11-Dihydro-dibenzo[a,d]cyclohepten-5-ylidenemethyl)-phenyl]-methanesulfonamide

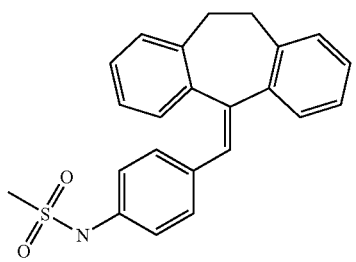

Following procedures essentially as described in Example 90, 4-(10,11-dihydro-dibenzo[a,d]cyclohepten-5-ylidenemethyl)-phenylamine and methanesulfonyl chloride gives the title compound in 48% yield as a tan solid, mp 210.7° C. ¹H NMR (CDCl₃) δ 2.72-3.58 (br m, 7H), 6.49 (s, 1H), 6.74 (s, 1H), 6.96-7.49 (m, 12H); MS (ES) 398 (M+Na), 374 (M–H). HPLC shows 98% purity.

EXAMPLE 104

Propane-1-sulfonic acid [3-(10,11-dihydro-dibenzo[a,d]cyclohepten-5-ylidenemethyl)-phenyl]-amide

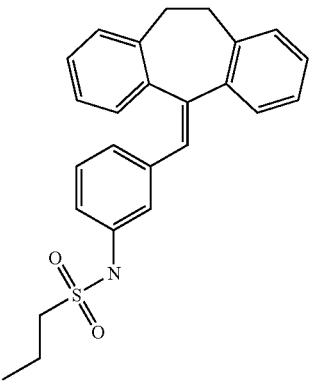

Following procedures essentially as described in Example 90, 3-(10,11-dihydro-dibenzo[a,d]cyclohepten-5-ylidenemethyl)-phenylamine (50 mg, 0.168 mmol) and 1-propanesulfonyl chloride (144 mg, 1.01 mmol) affords 34 mg (50%) of the title compound as a white foam. MS (ES) 426 M+Na), 402 (M−H); HPLC shows 99% purity.

EXAMPLE 105

Butane-1-sulfonic acid [3-(10,11-dihydro-dibenzo[a,d]cyclohepten-5-ylidenemethyl)-phenyl]-amide

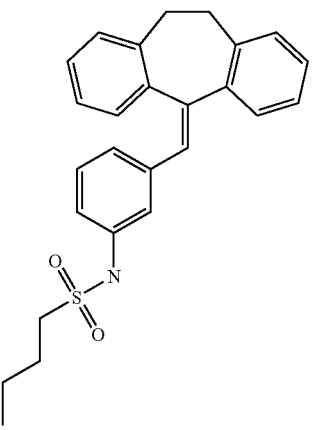

Following procedures essentially as described in Example 90, 3-(10,11-dihydro-dibenzo[a,d]cyclohepten-5-ylidenemethyl)-phenylamine (50 mg, 0.168 mmol) and 1-butanesulfonyl chloride (158 mg, 1.01 mmol) affords 41 mg (58%) of the title compound as a colorless oil. MS (ES) 440 (M+Na); HPLC shows 99% purity.

EXAMPLE 106

Ethanesulfonic acid [4-(10,11-dihydro-dibenzo[a,d]cyclohepten-5-ylidenemethyl)-phenyl]amide

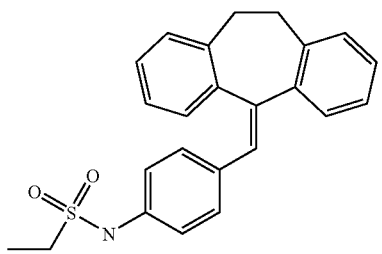

Following procedures essentially as described in Example 90,4-(10,11-dihydro-dibenzo[a,d]cyclohepten-5-ylidenemethyl)-phenylamine (100 mg, 0.336 mmol) and ethanesulfonyl chloride (129 mg, 1.01 mmol) affords 74 mg (57%) of the title compound as a colorless oil. MS (ES) 412 (M+Na), 388 (M−H); HPLC shows 97% purity.

EXAMPLE 107

Propane-2-sulfonic acid [4-(10,11-dihydro-dibenzo[a,d]cyclohepten-5-ylidenemethyl)-phenyl]-amide

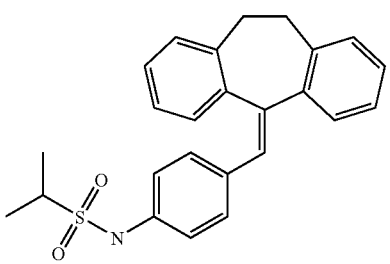

Following procedures essentially as described in Example 90, 4-(10,11-dihydro-dibenzo[a,d]cyclohepten-5-ylidenemethyl)-phenylamine (100 mg, 0.336 mmol) and 2-propanesulfonyl chloride (144 mg, 1.01 mmol) affords the title compound. MS (ES) 426 (M+Na), 402 (M−H); HPLC shows 93% purity.

EXAMPLE 108

Propane-1-sulfonic acid [4-(10,11-dihydro-dibenzo[a,d]cyclohepten-5-ylidenemethyl)-phenyl]-amide

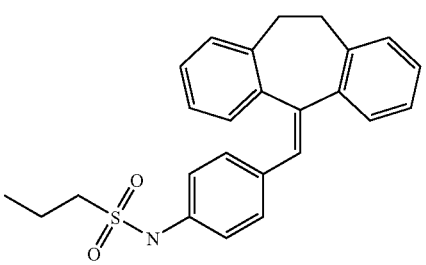

Following procedures essentially as described in Example 90, 4-(10,11-dihydro-dibenzo[a,d]cyclohepten-5-ylidenemethyl)-phenylamine (100 mg, 0.336 mmol) and 1-propanesulfonyl chloride (144 mg, 1.01 mmol) affords 69 mg (51%) of the title compound as a colorless oil. MS (ES) 426 (M+Na), 402 (M−H); HPLC shows 99% purity.

EXAMPLE 109

Butane-1-sulfonic acid [4-(10,11-dihydro-dibenzo[a,d]cyclohepten-5-ylidenemethyl)-phenyl]-amide

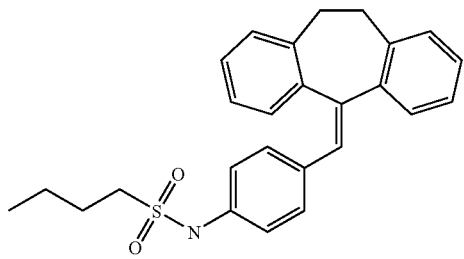

Following procedures essentially as described in Example 90, 4-(10,11-dihydro-dibenzo[a,d]cyclohepten-5-ylidenemethyl)-phenylamine (100 mg, 0.336 mmol) and 1-butanesulfonyl chloride (158 mg, 1.01 mmol) affords 88 mg (63%) of the title compound as a yellow oil. MS (ES) 440 (M+Na), 416 (H); HPLC shows 98% purity.

EXAMPLE 110

2-Methyl-propane-1-sulfonic acid [3-(10,11-dihydro-dibenzo[a,d]cyclohepten-5-ylidenemethyl)-phenyl]-amide

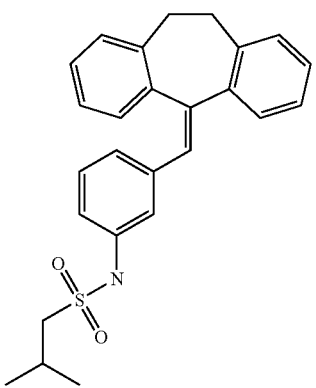

Following procedures essentially as described in Example 90, 3-(10,11-dihydro-dibenzo[a,d]cyclohepten-5-ylidenemethyl)-phenylamine (50 mg, 0.168 mmol) and 2-methyl-propane-1-sulfonyl chloride (53 mg, 0.336 mmol) (prepared as described in Quast, H., Synthesis (1974), (7), 489-90) affords 15 mg (21%) of the title compound as a brown oil. MS (ES) 435 (M+NH$_4$), 416 (M−H); HPLC shows 100% purity.

EXAMPLE 112

Dimethylsulfamic acid [3-(10,11-dihydro-dibenzo[a,d]cyclohepten-5-ylidenemethyl)-phenyl]-amide

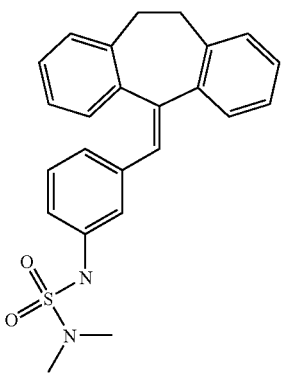

Following procedures essentially as described in Example 90, 3-(10,11-dihydro-dibenzo[a,d]cyclohepten-5-ylidenemethyl)-phenylamine (100 mg, 0.336 mmol) and dimethylsulfamoyl chloride (144 mg, 1.01 mmol) affords 92 mg (68%) of the title compound as a yellow oil. MS (ES) 427 (M+Na), 403 (M−H); HPLC shows 93% purity.

EXAMPLE 113

Dimethylsulfamic acid [4-(10,11-dihydro-dibenzo[a,d]cyclohepten-5-ylidenemethyl)-phenyl]-amide

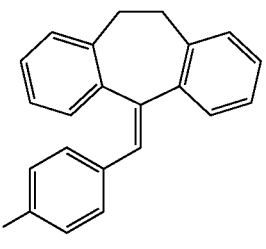

Following procedures essentially as described in Example 90, 4-(10,11-dihydro-dibenzo[a,d]cyclohepten-5-ylidenemethyl)-phenylamine (100 mg, 0.336 mmol) and dimethylsulfamoyl chloride (144 mg, 1.01 mmol) affords 83 mg (61%) of the title compound as a white solid. MS (ES) 427 (M+Na), 403 (M−H); HPLC shows 87% purity.

EXAMPLE 114

N-[3-(10,11-Dihydro-dibenzo[a,d]cyclohepten-5-ylidenemethyl)-phenyl]-acetamide

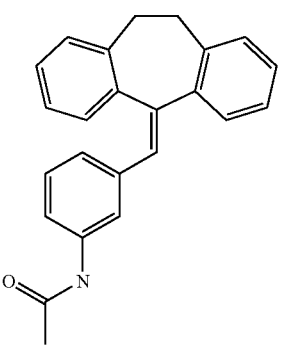

Following procedures essentially as described in Example 90, 3-(10,11-dihydro-dibenzo[a,d]cyclohepten-5-ylidenemethyl)-phenylamine and acetyl chloride give the title compound in 25% yield as a white solid. $^1$H NMR (CDCl3) δ 2.12 (s, 3H), 2.76-3.61 (br m, 4H), 6.71 (d, 1H), 6.75 (s, 1H), 6.96-7.50 (m, 13H); MS (ES) 340 (M+H). HPLC shows 100% purity.

EXAMPLE 115

N-[2-(10,11-Dihydro-dibenzo[a,d]cyclohepten-5-ylidenemethyl)-phenyl]-acetamide

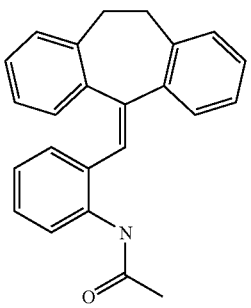

Following procedures essentially as described in Example 90, 2-(10,11-dihydro-dibenzo[a,d]cyclohepten-5-ylidenemethyl)-phenylamine and acetyl chloride give the title compound in 70% yield as a yellow solid, mp 189.7° C. $^1$H NMR (CDCl$_3$) δ 2.16 (s, 3H), 3.26 (br s, 4H), 6.78 (s, 1H), 6.84-7.50 (m, 11H), 7.82 (d, 1H); MS (ES) 340 (M+H) 338 (M−H). HPLC shows 94% purity.

EXAMPLE 116

N-[4-(10,11-Dihydro-dibenzo[a,d]cyclohepten-5-ylidenemethyl)-phenyl]-acetamide

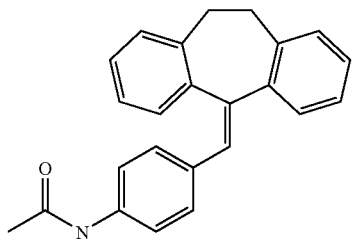

Following procedures essentially as described in Example 90, 4-(10,11-dihydro-dibenzo[a,d]cyclohepten-5-ylidenemethyl)-phenylamine and acetyl chloride give the title compound in 51% yield as an off-white solid, mp 134.8° C. $^1$H NMR (CDCl$_3$) δ 2.12 (s, 3H), 2.78-3.61 (br m, 4H), 6.75 (s, 1H), 6.95-7.52 (m, 13H); MS (ES) 340 (M+H). HPLC shows 95% purity.

EXAMPLE 117

N-[4-(10,11-Dihydro-dibenzo[a,d]cyclohepten-5-ylidenemethyl)-phenyl]-isonicotinamide

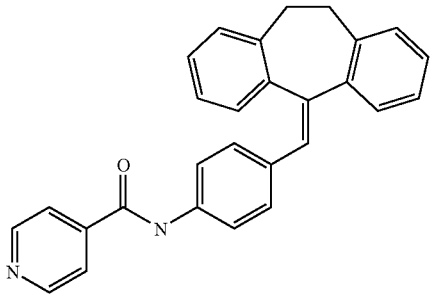

Following procedures essentially as described in Example 90, 4-(10,11-dihydro-dibenzo[a,d]cyclohepten-5-ylidenemethyl)-phenylamine and isonicotinoyl chloride give the title compound in 17% yield as a yellow solid, mp 252.1° C. $^1$H NMR (DMSO-d$_6$) δ 2.94 (br s, 2H), 3.87 (br s, 2H), 6.82 (s, 1H), 6.90-7.62 (m, 12H), 7.83 (d, 2H), 8.79 (d, 2H), 10.47 (s, 1H); MS (ES) 403 (M+H), 401 (M−H). HPLC shows 93% purity.

EXAMPLE 118

[3-(10,11-Dihydro-dibenzo[a,d]cyclohepten-5-ylidenemethyl)-phenyl]-methyl-amine

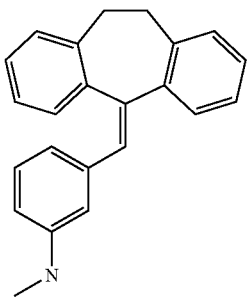

and

EXAMPLE 119

[3-(10,11-Dihydro-dibenzo[a,d]cyclohepten-5-ylidenemethyl)-phenyl]-dimethyl-amine

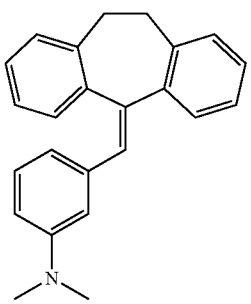

Using a procedure described in Syn. Comm. 1129-1135 (1991), dissolve 3-(10,11-dihydro-dibenzo[a,d]cyclohepten-5-ylidenemethyl)-phenylamine (100 mg, 0.336 mmol) in toluene (5 mL) and add (Bu)4NBr (2 mg, 0.006 mmol), K$_2$CO$_3$ (46 mg, 0.336), and NaOH (54 mg, 1.34 mmol). Stir for 1 h at 35° C., and then add Me$_2$SO$_4$ (33 L, 44 mg, 0.353 mmol). Stir for 2 h, then warm up to 55° C. Stir overnight, then add 20 L Me$_2$SO$_4$ (26 mg, 0.211 mmol). Stir at 55° C. for 6 h, then cool to room temperature. Dilute reaction with H$_2$O and ethyl acetate. Separate layers and extract aqueous layer with ethyl acetate. Combine organics, dry (MgSO$_4$), and concentrate to an oil containing the two title compounds. Separation and purification of the title compounds is effected via silica gel chromatography (1:19 ethyl acetate:hexanes).

[3-(10,11-Dihydro-dibenzo[a,d]cyclohepten-5-ylidenemethyl)-phenyl]-methyl-amine (Example 118) is obtained in 17% yield (18 mg) as a colorless oil. $^1$H NMR (CDCl$_3$) δ 2.59 (s, 3H), 2.70-3.65 (br m, 5H), 6.26 (s, 1H), 6.40 (d, 1H), 6.46 (d, 1H), 6.74 (s, 1H), 6.97-7.53 (m, 9H); MS (ES) 312 (M+H). HPLC shows 99% purity. [3-(10,11-Dihydro-dibenzo[a,d] cyclohepten-5-ylidenemethyl)-phenyl]-dimethyl-amine (Example 119) is obtained in 14% yield (15 mg) as a colorless oil. $^1$H NMR (CDCl$_3$) δ 2.62 (s, 6H), 2.68-3.58 (br m, 4H), 6.33 (s, 1H), 6.44 (m, 2H), 6.67 (s, 1H), 6.95-7.44 (m, 9H); MS (ES) 326 (M+H). HPLC shows 98% purity.

EXAMPLE 120

[2-(10,11-Dihydro-dibenzo[a,d]cyclohepten-5-ylidenemethyl)-phenyl]-methyl-amine

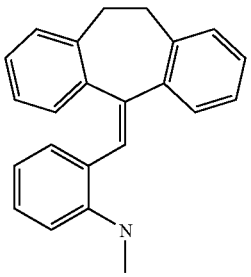

and

EXAMPLE 121

[2-(10,11-Dihydro-dibenzo[a,d]cyclohepten-5-ylidenemethyl)-phenyl]-dimethyl-amine

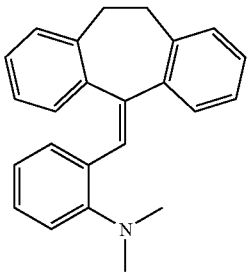

Following procedures essentially as described in Examples 118 and 119, 2-(10,11-dihydro-dibenzo[a,d]cyclohepten-5-ylidenemethyl)-phenylamine gives the title compounds.

[2-(10,11-Dihydro-dibenzo[a,d]cyclohepten-5-ylidenemethyl)-phenyl]-methyl-amine (Example 85) is obtained in 21% yield as a yellow oil. $^1$H NMR (CDCl$_3$) δ 2.91 (s, 3H), 3.26 (br s, 4H), 3.94 (br s, 1H), 6.47 (t, 1H), 6.62 (d, 1H), 6.70 (s, 1H), 6.71 (d, 1H), 6.86-7.51 (m, 9H); MS (ES) 312 (M+H). HPLC shows 98% purity. [2-(10,11-Dihydro-dibenzo[a,d]cyclohepten-5-ylidenemethyl)-phenyl]-dimethyl-amine (Example 86) is obtained in 16% yield as a colorless oil. $^1$H NMR (CDCl$_3$) δ6 2.96 (s, 6H), 3.24 (br s, 4H), 6.66 (m, 2H), 6.94-7.28 (m, 1OH), 7.57 (d, 1H); MS (ES) 326 (M+H). HPLC shows 96% purity.

EXAMPLE 122

[4-(10,11-Dihydro-dibenzo[a,d]cyclohepten-5-ylidenemethyl)-phenyl]-methyl-amine

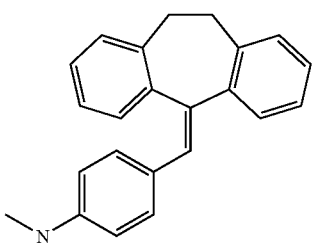

and

EXAMPLE 123

[4-(10,11-Dihydro-dibenzo[a,d]cyclohepten-5-ylidenemethyl)-phenyl]-dimethyl-amine

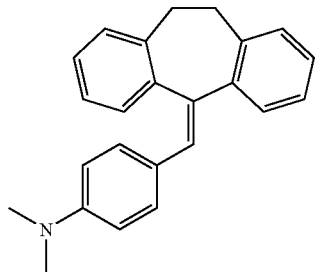

Following procedures essentially as described in Examples 118 and 119, 4-(10,11-dihydro-dibenzo[a,d]cyclohepten-5-ylidenemethyl)-phenylamine gives the title compounds.

[4-(10,11-Dihydro-dibenzo[a,d]cyclohepten-5-ylidenemethyl)-phenyl]-methyl-amine (Example 122) is obtained in 47% yield as a yellow solid. $^1$H NMR (CDCl$_3$) δ 2.66-3.55 (br m, 4H), 2.72 (s, 3H), 4.60 (s, 1H), 6.33 (d, 2H), 6.61 (s, 1H), 6.80 (d, 2H), 6.96-7.43 (m, 8H); MS (ES) 312 (M+H). HPLC shows 98% purity. [4-(10,11-Dihydro-dibenzo[a,d]cyclohepten-5-ylidenemethyl)-phenyl]-dimethyl-amine (Example 123) is obtained in 2% yield as a white solid. $^1$H NMR (CDCl$_3$) δπ2.71-3.65 (br m, 4H), 2.90 (s, 6H), 6.51 (d, 2H), 6.69 (s, 1H), 6.92 (d, 2H), 7.04-7.50 (m, 8H); MS (ES) 326 (M+H). HPLC shows 99% purity.

EXAMPLE 124

N-[3-(10,11-Dihydro-dibenzo[a,d]cyclohepten-5-ylidenemethyl)-phenyl]-N-methyl-methanesulfonamide

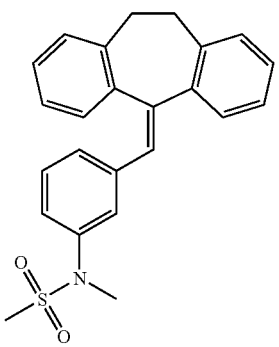

Dissolve N-[3-(10,11-dihydro-dibenzo[a,d]cyclohepten-5-ylidenemethyl)-phenyl]-methanesulfonamide (10 mg, 0.265 mmol) in DMF (4 mL) and add NaH (13 mg of a 60% suspension in mineral oil, 0.318 mmol). Stir at room temperature for 50 min, then add MeI (33 L, 75 mg, 0.530 mmol). Stir at room temp for 1 h. Dilute reaction mixture with H2O and ethyl acetate. Separate layers, and wash organics with H$_2$O. Dry organics (MgSO$_4$) and concentrate to 101 mg (100%) of a pale yellow solid, mp 124.2° C. $^1$H NMR (CDCl$_3$) δ 2.53 (s, 3H), 2.72-3.54 (br m, 4H), 6.74 (s, 1H), 6.78 (s, 1H), 6.91-7.43 (m, 11H); MS (ES) 412 (M+Na). HPLC shows 97% purity.

EXAMPLE 125

N-[3-(10,11-Dihydro-5H-dibenzo[a,d]cyclohepten-5-ylmethyl)-phenyl]-methanesulfonamide

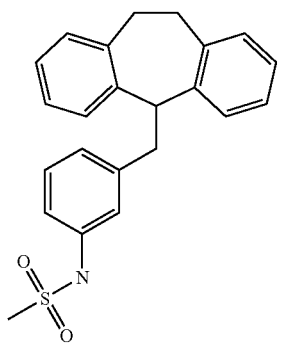

Dissolve N-[3-(10,11-dihydro-dibenzo[a,d]cyclohepten-5-ylidenemethyl)-phenyl]-methanesulfonamide (100 mg, 0.265) in ethanol (25 mL) and add 10% Pd/C (56 mg). Pressurize to 60 psi with H$_2$ and shake overnight at room temperature. Filter reaction through a pad of Celite and concentrate filtrate to 54 mg (54%) of white foam, mp 149.0° C. $^1$H NMR (CDCl$_3$) δ 2.70 (s, 3H), 2.98 (br q, 2H), 3.28 (d, 2H), 3.40 (br q, 2H), 4.11 (br s, 1H), 6.16 (s, 1H), 6.58 (s, 1H), 6.82-7.20 (m, 11H); MS (S) 395 (M+Na), 376 (M–H). HPLC shows 94% purity.

EXAMPLE 126

3-(10,11-Dihydro-5H-dibenzo[a,d]cyclohepten-5-ylmethyl)-phenol

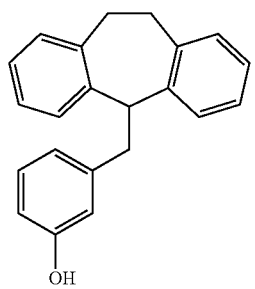

Following procedures similar to those as described in Example 125, 3-(10,11-Dihydro-dibenzo[a,d]cyclohepten-5-ylidenemethyl)-phenol and a H$_2$ balloon gave the title compound in 64% yield as a white solid, mp 76.6° C. $^1$H NMR (CDCl$_3$) δ 3.06 (br q, 2H), 3.33 (d, 2H), 3.47 (br q, 2H), 4.2 (br s, 1H), 4.74 (s, 1H), 6.40 (s, 1H), 6.39 (m, 2H), 6.96-7.17 (m, 9H); MS (ES) 299 (M–H). HPLC shows 93% purity.

EXAMPLE 127

[2-(10,11-Dihydro-dibenzo[a,d]cyclohepten-5-ylidenemethyl)-phenyl]-urea

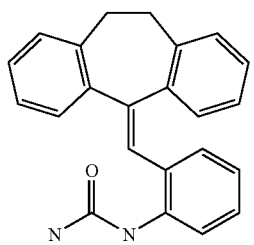

According to the procedure of F. Kurzer, Org. Syn. Coll. Vol (IV) 49 (1963), mix 2-(10,11-dihydro-dibenzo[a,d]cyclohepten-5-ylidenemethyl)-phenylamine ((133 mg, 0.54 mmol) with HOAc (4 mL) and water (2 mL). Dissolve sodium cyanate (80 mg, 1.2 mmol) in water (1 mL) and add this solution to the amine derivative. Stir the reaction at room temperature for 2 h. and then pour into water (100 mL). Extract the title compound into EtOAc, dry (MgSO$_4$) and concentrate to give 240 mg crude product. Purify on silica gel using EtOAc/hexane to give 150 mg (48%) product as a colorless oil. MS (ES) 341 (M+1), 339 (M–1). HPLC shows 96.6% purity.

EXAMPLE 128

[3-(10,11-Dihydro-dibenzo[a,d]cyclohepten-5-ylidenemethyl)-phenyl]-urea

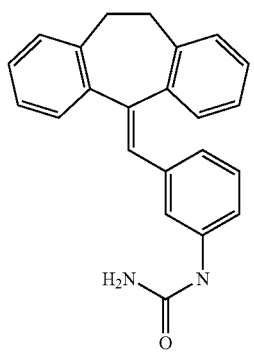

Following procedures essentially as described in Example 127 and using 3-(10,11-dihydro-dibenzo[a,d]cyclohepten-5-ylidenemethyl)-phenylamine (200 mg, 0.67 mmol) provides the title compound in 66% yield as a colorless oil. MS (ES) 341 (M+1), 339 (M–1). HPLC shows 100% purity.

EXAMPLE 129

[4-(10,11-Dihydro-dibenzo[a,d]cyclohepten-5-ylidenemethyl)-phenyl]-urea

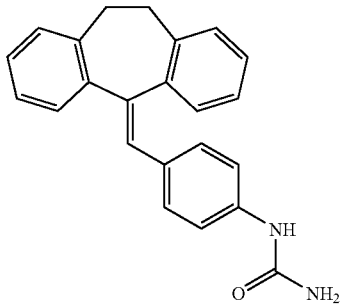

Following procedures essentially as described in Example 127 and using 4-(10,11-dihydro-dibenzo[a,d]cyclohepten-5-ylidenemethyl)-phenylamine (143 mg, 0.58 mmol) provides the title compound in 41% yield as a colorless oil. MS (ES) 341 (M+1), 339 (M−1). HPLC shows 100% purity.

EXAMPLE 130

5-(2-Methyl-benzylidene)-10,11-dihydro-5H-dibenzo[a,d]cycloheptene

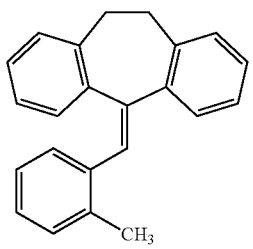

Combine 5-bromomethylene-10,11-dihydro-5H-dibenzo[a,d]cycloheptene (0.5 g, 1.75 mmol) and o-tolylboronic acid (0.238 g, 1.75 mmol) using procedures essentially as described in Example 219, below. Pass through a plug of silica gel equilibrated with hexanes. Concentrate the filtrate to give the title product: MS (m/e) 296 (M+); Analysis for $C_{23}H_{20}$: Calcd: C, 93.19 H, 6.80. Found: C, 93.42 H, 6.79.

EXAMPLE 131

5-(2-Methyl-benzyl)-10,11-dihydro-5H-dibenzo[a,d]cycloheptene

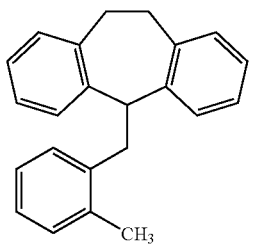

Add the 5-(2-methyl-benzylidene)-10,11-dihydro-5H-dibenzo [a,d]cycloheptene (0.19 g, 0.64 mmol) to a mixture of 10% Pd/C (0.075 g) suspended in absolute ethanol (4.0 mL) and ethyl acetate (2.0 mL) and hydrogenate under a balloon of hydrogen at room temperature and pressure. Stir for 17 h, remove the catalyst via filtration through a pad of Celite, evaporate the filtrate and pass through a plug of silica gel equilibrated with hexanes. Concentrate the filtrate to give the title product: MS (m/e) 298 (M+). Analysis for $C_{23}H_{22}$: Calcd: C, 91.99 H, 7.39. Found: C, 91.95 H, 7.39.

EXAMPLE 132

5-(3-Methyl-benzylidene)-10,11-dihydro-5H-dibenzo[a,d]cycloheptene

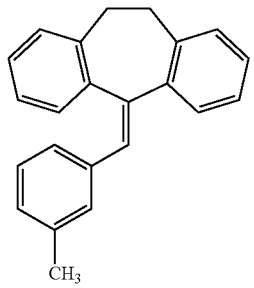

Combine 5-bromomethylene-10,11-dihydro-5H-dibenzo[a,d]cycloheptene (0.5 g, 1.75 mmol) and m-tolylboronic acid (0.238 g, 1.75 mmol) using procedures essentially as described in Example 219, below. Pass through a plug of silica gel equilibrated with hexanes. Concentrate the filtrate to give the title product: MS (m/e): 296 (M+); HPLC (ISO80-10M)) t=17.78 min (95%).

EXAMPLE 133

5-(3-Methyl-benzyl)-10,11-dihydro-5H-dibenzo[a,d]cycloheptene

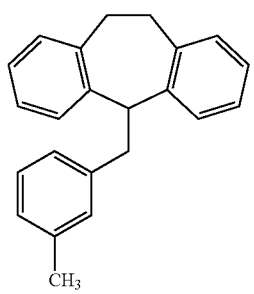

Add 5-(3-methyl-benzylidene)-10,11-dihydro-5H-dibenzo[a,d]cycloheptene (0.18 g, 0.61 mmol), to a mixture of 10% Pd/C (0.045 g) suspended in absolute ethanol (4.0 mL) and ethyl acetate (2.0 mL) and hydrogenate under a balloon of hydrogen at room temperature and pressure. Stir for 17 h, remove the catalyst via filtration through a pad of Celite. Evaporate the filtrate and pass through a plug of silica gel equilibrated with hexanes. Concentrated the filtrate to give the title product. MS (m/e): 298 (M+). HPLC (ISO80-10M) t=1.00 (98%).

EXAMPLE 134

5-(2-Trifluoromethyl-benzylidene)-10,11-dihydro-5H-dibenzo[a,d]cycloheptene

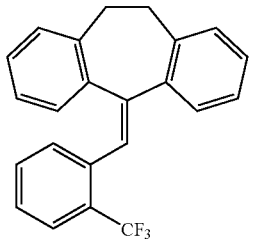

Combine 5-bromomethylene-10,11-dihydro-5H-dibenzo[a,d]cycloheptene (0.5 g, 1.75 mmol) and 2-(trifluoromethyl)phenyl boronic acid (0.33 g, 1.75 mmol) using procedures essentially as described in Example 219, below. Pass through a plug of silica gel equilibrated with hexanes. Concentrate the filtrate to give the title product. Analysis for $C_{23}H_{17}F_3$: Calcd: C, 78.84 H, 4.89; Found: C, 78.65 H, 4.96. HPLC (ISO80-10M)) t=16.67 min (99%).

EXAMPLE 135

5-(2-Trifluoromethyl-benzyl)-10,11-dihydro-5H-dibenzo[a,d]cycloheptene

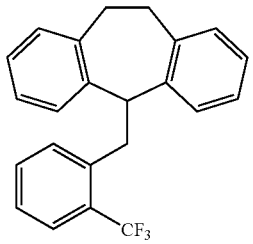

Add 5-(2-trifluoromethyl-benzylidene)-10,11-dihydro-5H-dibenzo[a,d]cycloheptene (0.16 g, 0.45 mmol) to a mixture of 10% Pd/C (0.075 g) suspended in absolute ethanol (4.0 mL) and ethyl acetate (2.0 mL) and hydrogenate under a balloon of hydrogen at room temperature and pressure. Stir for 17 h, remove the catalyst via filtration through a pad of Celite. Evaporate the filtrate and pass through a plug of silica gel equilibrated with hexanes. Concentrated the filtrate to give the title product. MS (m/e): 352 (M+). Analysis for $C_{23}H_{19}F_3$: Calcd: C, 78.39 H, 5.43. Found: C, 78.84 H, 5.11.

EXAMPLE 136

5-(3-Trifluoromethyl-benzylidene)-10,11-dihydro-5H-dibenzo[a,d]cycloheptene

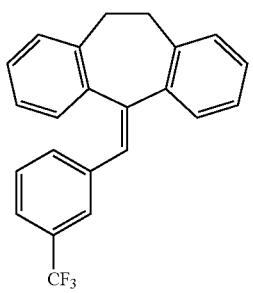

Combine 5-bromomethylene-10,11-dihydro-5H-dibenzo[a,d]cycloheptene (0.5 g, 1.75 mmol) and 3-(trifluoromethyl)phenyl boronic acid (0.33 g, 1.75 mmol) using procedures essentially as described in Example 219, below. Pass through a plug of silica gel equilibrated with hexanes. Concentrate the filtrate to give the title product. Analysis for $C_{23}H_{17}F_3$: Calcd: C, 78.84 H. 4.89; Found: C, 79.03.H, 5.03. HPLC (ISO80-10M)) t=16.30 min (98%).

EXAMPLE 137

5-(3-Trifluoromethyl-benzyl)-10,11-dihydro-5H-dibenzo[a,d]cycloheptene

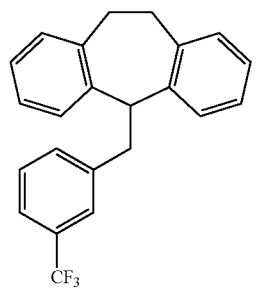

Add 5-(3-trifluoromethyl-benzylidene)-10,11-dihydro-5H-dibenzo[a,d]cycloheptene (0.145 g, 0.41 mmol), to a mixture of 10% Pd/C (0.04 g) suspended in absolute ethanol (4.0 mL) and ethyl acetate (4.0 mL) and hydrogenate under a balloon of hydrogen at room temperature and pressure. Stir for 17 h, remove the catalyst via filtration through a pad of Celite. Evaporate the filtrate and pass through a plug of silica gel equilibrated with hexanes. Concentrated the filtrate to give the title product. MS (m/e): 352 (M+); GC retention time=7.11 min.

EXAMPLE 138

5-(4-Trifluoromethyl-benzylidene)-10,11-dihydro-5H-dibenzo[a,d]cycloheptene

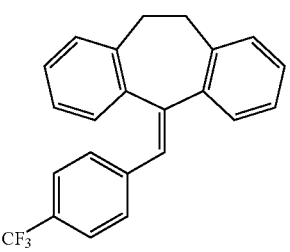

Combine 5-bromomethylene-10,11-dihydro-5H-dibenzo[a,d]cycloheptene (0.5 g, 1.75 mmol) and 4-(trifluoromethyl)phenyl boronic acid (0.33 g, 1.75 mmol using procedures essentially as described in Example 219, below. Pass through a plug of silica gel equilibrated with hexanes. Concentrate the filtrate to give the title product: MS (m/e): 350 (M+). HPLC (ISO80-10M)) t=17.32 min.

EXAMPLE 139

5-(4-Trifluoromethyl-benzyl)-10,11-dihydro-5H-dibenzo[a,d]cycloheptene

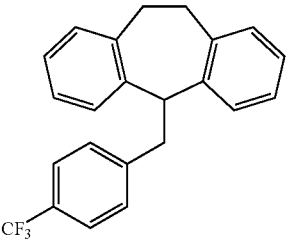

Add the 5-(4-trifluoromethyl-benzylidene)-10,11-dihydro-5H-dibenzo[a,d]cycloheptene (0.14 g, 0.45 mmol), to a mixture of 10% Pd/C (0.05 g) suspended in absolute ethanol (4.0 mL) and ethyl acetate (4.0 mL) and hydrogenate under a balloon of hydrogen at room temperature and pressure. Stir for 17 h, remove the catalyst via filtration through a pad of Celite. Evaporate the filtrate and pass through a plug of silica gel equilibrated with hexanes. Concentrate the filtrate to gives the title product. MS (m/e): 352 (M+); Analysis for $C_{23}H_{19}F_3$: Calcd: C, 78.39 H, 5.43. Found: C, 78.70 H, 5.16.

EXAMPLE 140

5-(3,5-Bis-trifluoromethyl-benzylidene)-10,11-dihydro-5H-dibenzo[a,d]cycloheptene

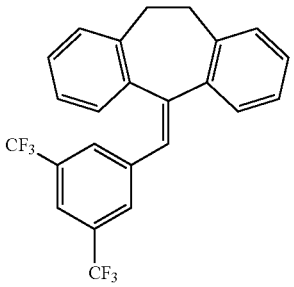

Combine 5-bromomethylene-10,11-dihydro-5H-dibenzo[a,d]cycloheptene (0.5 g, 1.75 mmol) and 3,5-bis (trifluoromethyl)phenyl boronic acid (0.449 g, 1.75 mmol) using procedures essentially as described in Example 219, below. Pass through a plug of silica gel equilibrated with hexanes. Concentrate the filtrate to give the title product. Analysis for $C_{24}H_{16}F_6$: Calcd: C, 68.90 H, 3.85. Found: C, 68.64 H, 3.80. HPLC (ISO80-10M)) t=5.64 min (98%).

EXAMPLE 141

5-(3,5-Bis-Trifluoromethyl-benzyl)-10,11-dihydro-5H-dibenzo[a,d]cycloheptene

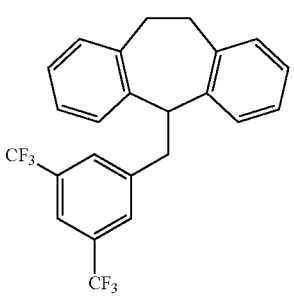

Add 5-(3,5-bis-trifluoromethyl-benzylidene)-10,11-dihydro-5H-dibenzo [a,d]cycloheptene (0.28 g, 0.67 mmol) to a mixture of 10% Pd/C (0.08 g) suspended in absolute ethanol (4.0 mL) and ethyl acetate (4.0 mL) and hydrogenate under a balloon of hydrogen at room temperature and pressure. Stir for 17 h, remove the catalyst via filtration through a pad of Celite. Evaporate the filtrate and pass through a plug of silica gel equilibrated with hexanes. Concentrate the filtrate to give the title product. MS (m/e): 420 (M+); Analysis for $C_{24}H_{18}F_6$: Calcd: C, 68.56 H, 4.31. Found: C, 68.55 H. 4.01.

EXAMPLE 142

5-Pyridin-2-yl-thiophene-2-sulfonic acid [4-(10,11-dihydro-dibenzo[a,d]cyclohepten-5-ylidenemethyl)-phenyl]-amide

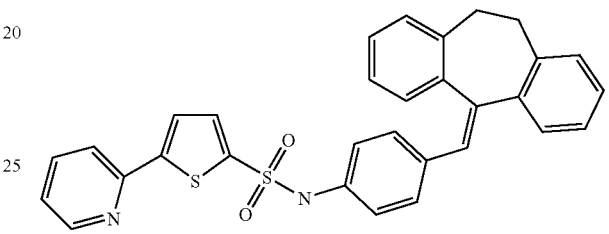

Prepared according to procedures essentially as described in Example 90, using 4-(10,11)-dihydro-dibenzo(a,d)cyclohepten-5-ylidene methyl phenylamine (297 mg, 1.0 mmol) and 5-pyridin-2-yl-thiophene-2-sulfonyl chloride (260 mg, 1.0 mmol) to give the title compound (HOW MUCH). Purify using column chromatography ethyl acetate/hexane to give 48 mg (10%) product. MS (ES) 521 (M+1), 519 (M−1). HPLC shows 97% purity.

EXAMPLE 143

1-Methyl-1H-imidazole-4-sulfonic acid [4-(10,11-dihydro-dibenzo[a,d]cyclohepten-5-ylidenemethyl)-phenyl]-amide

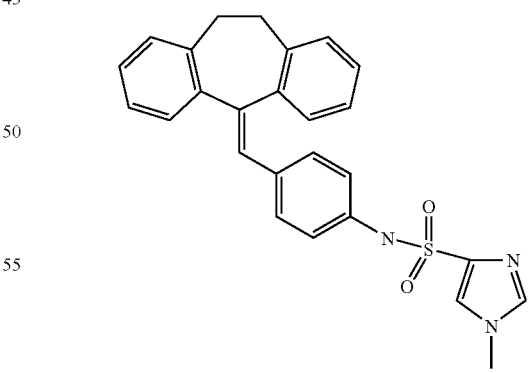

Prepared according to procedures essentially as described in Example 90, using 4-(10,11)-dihydro-dibenzo(a,d)cyclohepten-5-ylidene methyl phenylamine (297 mg, 1.0 mmol) and 1-methyl-1H-imidazole-4-sulfonyl chloride (180 mg, 1.0 mmol) to give the title compound 44 mg (10%) after being purified by mass guided reverse-phase HPLC. MS (ES) 442 (M+1). HPLC shows 97% purity.

EXAMPLE 144

3-(10,11-Dihydro-dibenzo[a,d]cyclohepten-5-ylidenemethyl)-benzylamine

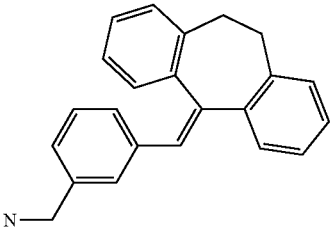

Dissolve 1.0 g (3.25 mmol) of the corresponding nitrile (prepared as described in Example 81) in diethyl ether (70 mL). Add lithium aluminum hydride (250 mg, 6.6 mmol) and stir at room temperature for 3 h. Quench the reaction by adding 8 drops water, 8 drops 5N NaOH and 16 drops water. Filter the inorganic solids and wash with ether. After drying ($MgSO_4$) and concentration, the title compound was obtained in 98% yield as a colorless oil, MS (ES) 312 (N+1). HPLC shows 98% purity.

EXAMPLE 145

N-[3-(10,11-Dihydro-dibenzo[a,d]cyclohepten-5-ylidenemethyl)-benzyl]-methanesulfonamide

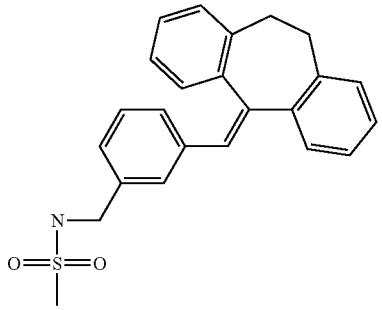

Following procedures essentially as described in Example 90, reaction of the benzylamine (70 mg, 0.225 mmol) prepared in Example 144 and methanesulfonyl chloride (52 □L, 0.68 mmol) affords 40 mg of the title compound in 46% yield as a colorless oil after purification using column chromatography (30% ethyl acetate/hexane). MS (ES) 388 (M−1). HPLC shows 97% purity.

EXAMPLE 146

2-[3-(10,11-Dihydro-dibenzo[a,d]cyclohepten-5-ylidenemethyl)-phenyl]-4-trifluoromethyl-1H-imidazole

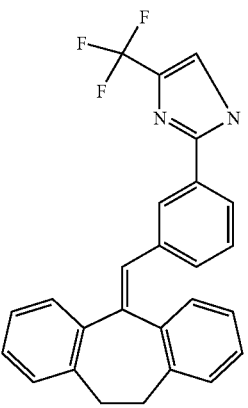

According to Matthews et al, J. Med. Chem. 33 317 (1990), mix 1,1-dibromo-1',1',1'-trifluoroacetone (216 mg, 0.8 mmol), NaOAc (112 mg, 1.4 mmol) and water (2 mL). Warm the solution at 60° C. for 0.5 h. Cool the solution in an ice bath and add 3-(10,11-dihydro-dibenzo[a,d]cyclohepten-5-ylidenemethyl)-benzaldehyde(145 mg,0.47 mmol) in methanol (2 mL) and concentrated $NH_4OH$ (2 mL) and stir overnight at room temperature. Concentrate and collect the solid. Purify by column chromatography (30% ethyl acetate/hexane) to give 19% title compound. MS (ES) 417 (M+1), 415 (M−1). HPLC shows 86% purity.

EXAMPLE 147

2-[4-(10,11-Dihydro-dibenzo[a,d]cyclohepten-5-ylidenemethyl)-phenyl]4-trifluoromethyl-1H-imidazole

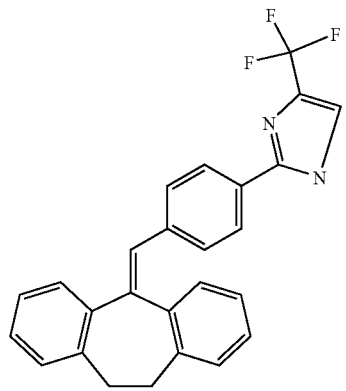

Prepare using procedures as described in Example 146 to give the title compound as a pale yellow powder, MS (ES) 417 (M+1), 415 (M−1). HPLC shows 95% purity.

EXAMPLE 148

5-(4-Fluoro-3-methoxy-benzylidene)-10,11-dihydro-5H-dibenzo[a,d]cycloheptene

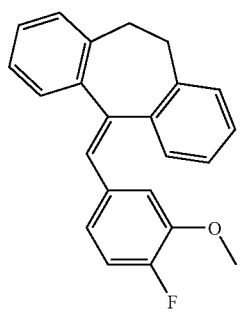

Following procedures essentially as described in Example 28 and using 4-fluoro-3-methoxybenzaldehyde (1.59 g, 10.3 mmol), dibenzosuberane (1.94 g, 10 mmol, provides 1.66 g of title compound in 49% yield as a light tan oil that slowly crystallized. HPLC shows 93% purity.

EXAMPLE 149

5-(10,11-Dihydro-dibenzo[a,d]cyclohepten-5-yliden-emethyl)-2-fluoro-phenol

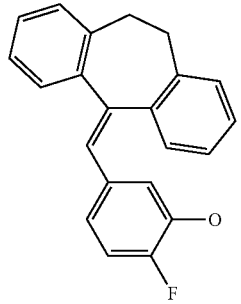

Demethylation of the corresponding methoxy derivative of Example 148 using the procedures as described in Example 57, provides 1.28 g (900%) of title compound as a pale tan oil. MS (ES) 315 (M−1). HPLC shows 95% purity.

EXAMPLE 150

5-(2-Fluoro-5-methoxy-benzylidene)-10,11-dihydro-5H-dibenzo[a,d]cycloheptene

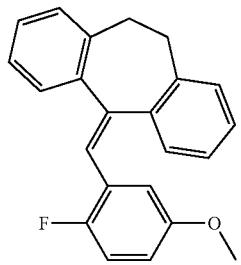

Following procedures essentially as described in Example 28 and using 2-fluoro-5-methoxybenzaldehyde (1.59 g, 10.3 mmol) and dibenzosuberane (1.94 g, 10 mmol), provides 210 mg of title compound as white crystals. mp 110.7° C. (hexane). HPLC shows 99% purity.

EXAMPLE 151

3-(10,11-Dihydro-dibenzo[a,d]cyclohepten-5-yliden-emethyl)-4-fluoro-phenol

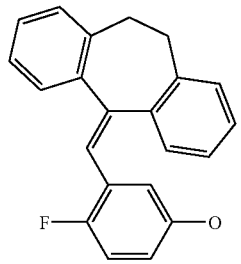

Demethylation of the corresponding methoxy derivative of Example 150 using the procedures as described in Example 57, provides 110 mg of title compound in 46% yield as a colorless oil. MS (ES) 315 (M−1). HPLC shows 94% purity.

EXAMPLE 152

5-(2-Fluoro-3-methoxy-benzylidene)-10,11-dihydro-5H-dibenzo[a,d]cycloheptene

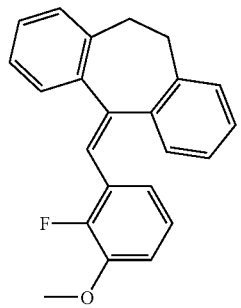

Following procedures essentially as described in Example 28 and using 2-fluoro-3-methoxybenzaldehyde (2.4 g, 15.4 mmol) and dibenzosuberane (3.0 g, 15.4 mmol), provides 1.5 g of title compound as white crystals. mp 148.9° C. HPLC shows 96% purity.

EXAMPLE 153

3-(10,11-Dihydro-dibenzo[a,d]cyclohepten-5-yliden-emethyl)-2-fluoro-phenol

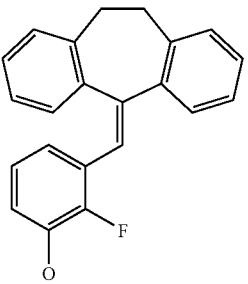

Demethylation of the corresponding methoxy derivative of Example 152 using the procedures as described in Example 57, provides 410 mg (47%) of title as light tan crystals, mp 143.2° C. MS (ES) 315 (M−1). HPLC shows 94% purity.

EXAMPLE 154

5-(3-Fluoro-5-methoxy-benzylidene)-10,11-dihydro-5H-dibenzo[a,d]cycloheptene

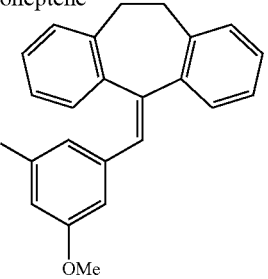

Following procedures essentially as described in Example 219, below, and using 3-fluoro-5-methoxyphenylboronic acid (300 mg, 1.76 mmol) and 5-bromomethylene-10,11-dihydro-5H-dibenzo[a,d]cycloheptene (450 mg, 1.6 mmol) provides 275 mg of title compound in 52% yield as a pale yellow oil. HPLC shows 97% purity.

EXAMPLE 155

3-(10,11-Dihydro-dibenzo[a,d]cyclohepten-5-ylidenemethyl)-5-fluoro-phenol

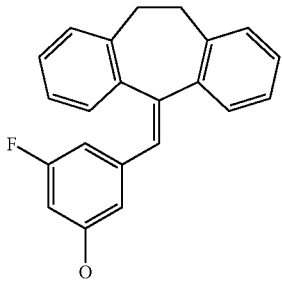

Demethylation of the corresponding methoxy derivative of Example 154 using BBr$_3$ provides the title compound in 62% yield as a colorless, viscous oil. MS (ES) 315(M−1). HPLC shows 94% purity.

EXAMPLE 156

5-(4-Chloro-3-methoxy-benzylidene)-10,11-dihydro-5H-dibenzo[a,d]cycloheptene

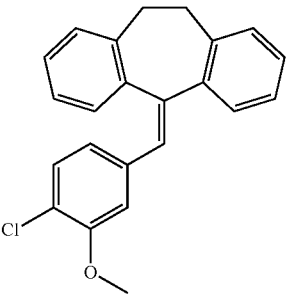

Following procedures essentially as described in Example 219, below, and using 4-chloro-5-methoxyphenylboronic acid (160 mg, 0.78 mmol) and 5-bromomethylene-10,11-dihydro-5H-dibenzo[a,d]cycloheptene (222 mg, 0.85 mmol) provides 80 mg of title compound in 23% yield as a colorless oil. HPLC shows 92% purity.

EXAMPLE 157

2-Chloro-5-(10,11-dihydro-dibenzo[a,d]cyclohepten-5-ylidenemethyl)-phenol

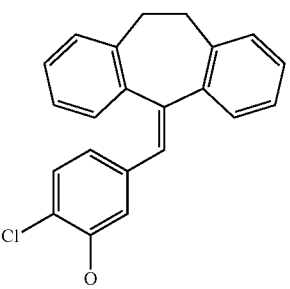

Demethylation of the corresponding methoxy derivative of Example 154 using BBr$_3$ provides the title compound in 42% yield as a colorless, oil. MS (ES) 333 (M+1), 331 (e).

PREPARATION 23

5-Methylene-10,11-dihydro-5H-dibenzo[a,d]cycloheptene

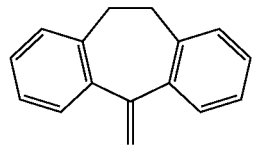

Add methylmagnesium bromide (3M solution in Et$_2$O, 48.0 mL, 144 mmol) dropwise to a cooled (0° C.) solution of dibenzosuberone (20.0 g, 96.03 mmol) in THF (140 mL) under N$_2$ (exothermic). Let solution warm up to room temperature and continue stirring for 2 h. Cool solution to 0° C. and quench with saturated aqueous NH$_4$Cl (exothermic, emits gas). Extract into ethyl acetate, dry organics (MgSO$_4$) and concentrate in-vacuo. Dissolve residue in 4N HCl/dioxane (40 mL) and stir at room temperature overnight. Concentrate and dilute with H$_2$O. Extract into ethyl acetate, dry organics (MgSO$_4$) and concentrate to a yellow oil. Purify crude product by loading onto a 30 g plug of silica gel and eluting with hexanes until eluent shows no UV activity. Combine and concentrate hexane washes to afford 16.72 g (84%) of the title compound as a white solid, mp 65.1° C. HPLC shows 98% purity.

PREPARATION 24

5-Bromomethylene-10,11-dihydro-5H-dibenzo[a,d]cycloheptene

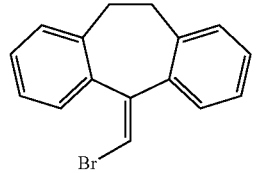

Dissolve 5-methylene-10,11-dihydro-5H-dibenzo[a,d]cycloheptene (10.00 g, 48.48 mmol) in CHCl$_3$ (125 mL) and add 4-(dimethylamino)pyridinium tribromide (19.35 g, 53.32 mmol). Stir at room temperature for 2.5 h and quench with saturated aqueous Na$_2$SO$_3$. Separate layers, wash organics with saturated aqueous NaHCO$_3$, then H$_2$O. The dried organics (MgSO$_4$) and concentrated to a yellow oil. Purify crude product by loading onto a 20 g plug of silica gel and eluting with hexanes until eluent shows no UV activity. Combine and concentrate hexane washes to afford 13.01 g (94%) of the title compound as a white solid, mp 73.6° C. HPLC shows 99% purity.

PREPARATION 25

(10,11-Dihydro-dibenzo[a,d]cyclohepten-5-ylidene)-boronic acid

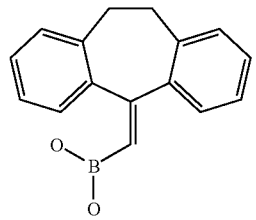

Add t-BuLi (1.7M in pentane, 36.3 mL, 61.71 mmol) portionwise (exotherm) to a solution of 5-bromomethylene-10,11-dihydro-5H-dibenzo[a,d]cycloheptene (8.00 g, 20.05 mmol) in dry THF (150 mL) at −78° C. under N$_2$. Stir at −78° C. for 45 min and add trimethyl borate (8.75 g, 84.15 mmol).

Warm to room temperature and stir for 30 min. Concentrate reaction mixture to a pale yellow gritty oil, add ethylene glycol (30 mL) and toluene (100 mL), and reflux overnight. Cool to room temperature, separate layers and extract ethylene glycol layer with toluene. Combine and concentrate toluene layers to a yellow oil. Purify by silica gel chromatography (40 g) eluting with 3:1:0.02 ethyl acetate:hexanes:triethylamine to afford 2.68 g (35%) of the title compound as a white foam. MS (ES) 249 (M−H); HPLC shows 91% purity.

EXAMPLE 158

5-(3-Nitro-benzylidene)-5H-dibenzo[a,d]cycloheptene

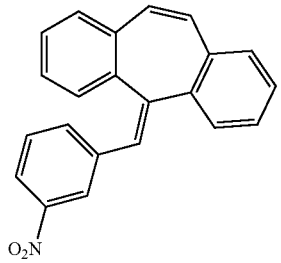

Dissolve the phosphonate [generate from heating 3-nitobenzyl bromide (786 mg, 3.6 mmol) in triethyl phosphite (0.62 ml, 3.6 mmol) at 80° C. for 12 h.] in DMF (10 ml) at RT under nitrogen atmosphere. To this mixture,.add sodium hydride (87.3 mg, 3.6 mmol) and stir for 1 h. Add dibenzosuberenone (250 mg, 1.2 mmol) in 2 ml of DMF and stir for 18 h. Partition the residue between 1N HCl/EtOAc. Dry (MgSO$_4$) and concentrate to give 121.6 mg of a pale yellow oil. $^1$H NMR (CDCl$_3$) δ7.84 (dt, 1H), 7.72 (t, 1H), 7.45 (d, 1H), 7.4-7.3 (m, 2H), 7.3-7.2 (m, 2H), 7.2-7.0 (m, 4H), 7.0-6.85 (m, 3H), 6.42 (s, 1H).

EXAMPLE 159

3-Dibenzo[a,d]cyclohepten-5-ylidenemethyl-phenylamine

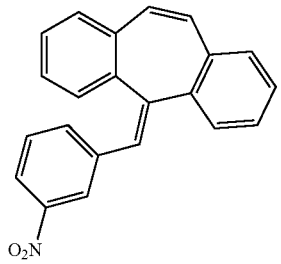

Dissolve 5-(3-nitro-benzylidene)-5H-dibenzo[a,d]cycloheptene (120 mg, 0.4 mmol) in absolute ethanol. Add (10 ml tin chloride (416 mg, 2.0 mmol) and heat to reflux. After 18 h, cool and partition between 1N NaOH/EtOAc. Dry the organic layers (MgSO$_4$) and concentrate to give 92.3 mg of a white solid. MS [EI+] 296 (M+H).

EXAMPLE 160

N-(3-Dibenzo[a,d]cyclohepten-5-ylidenemethyl-phenyl)-methanesulfonamide Dissolve 3-dibenzo[a,d]cyclohepten-5-ylidenemethyl-phenylamine (90 mg, 0.3 mmol) in 5 mL of

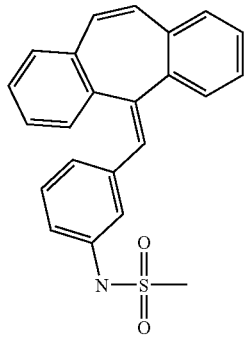

methylene chloride under a nitrogen atmosphere. Add pyridine (0.05 mL, 0.6 mmol) then methanesulfonyl chloride (0.03 mL, 0.3 mmol). Stir at room temperature for 12 h, then partition between water/methylene chloride and dry with MgSO$_4$. Concentrate to give 65.9 mg of a white solid. $^1$H NMR (CDCl$_3$) δ7.84 (d, 1H), 7.72 (s, 1H), 7.45 (d, 1H), 7.4-7.3 (m, 2H), 7.3-7.2 (m, 2H), 7.2-7.0 (m, 4H), 7.0-6.85 (m, 2H), 6.61 (m, 1H), 6.50 (s, 1H), 2.85 (s, 3H). MS [EI+] 374 (M+H)$^+$, 391 (M+18).

Section 2 (derivatives of Formula I having substitution on both the "C" ring and furtheron the "A" and/or "B" rings.)

EXAMPLE 161

N-[3-(2-Methoxy-10,11-dihydro-dibenzo[a,d]cyclohepten-5-ylidenemethyl)-phenyl]-methanesulfonamide (E-isomer and Z-isomer)

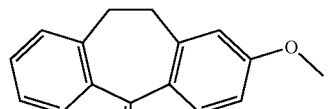

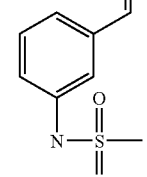

E-isomer

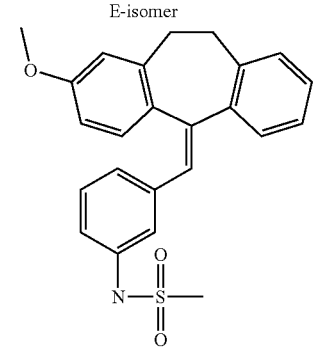

Z-isomer

Following the procedures essentially as described in Example 219, below, and using 5-bromomethylene-2-methoxy-10,11-dihydro-5H-dibenzo[a,d]cycloheptene (E/Z mixture, 700 mg, 2.22 mmol) Prepared from 2-methoxydibenzosuberone as described in Preparations 23 and 24) with 3-methanesulfonylaminophenylboronic acid (522 mg, 2.4 mmol) to give 485 mg (54%) of an E/Z mixture of isomers. Use UV guided reverse-phase HPLC with 1/1 acetonitrile/0.1% aqueous trifluoroacetic acid to separate the isomers. The E isomer comes off the column first. MS (ES) 406 (M+1), 404 (M−1). HPLC purity is 99.6%. The second isomer off the column is the Z-isomer, MS (ES) 406 (+l), 404 (M−1). HPLC purity is 98%.

EXAMPLE 162

N-[3-(2-Hydroxy-10,11-dihydro-dibenzo[a,d]cyclohepten-5-ylidenemethyl)-phenyl]-methanesulfonamide (E/Z Mixture)

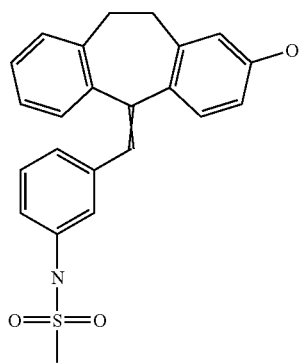

Demethylate the corresponding methoxy mixture of Example 161 using BBr₃ to give the title compound in 69% yield. MS (ES) 392 (M+1), 390 (M−1). HPLC shows 48% of the faster eluting isomer and 45% of the slower isomer.

EXAMPLE 163

Ethanesulfonic acid [3-(2-methoxy-10,11-dihydro-dibenzo[a,d]cyclohepten-5-ylidenemethyl)-phenyl]-amide (E/Z Mixture)

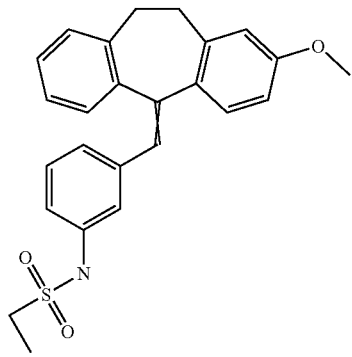

Following the procedures essentially as described in Example 219, below, and using 5-bromomethylene-2-methoxy-10,11dihydro-5H-dibenzo[a,d]cycloheptene (E/Z mixture, 97 mg, 0.31 mmol) with 3-ethanesulfonylaminophenylboronic acid (78 mg, 0.34 mmol) to give 57 mg (44%) of an E/Z mixture of the title compound. MS (ES) 420 (M+1) weak, 418 (M−1). HPLC shows 45% of the E isomer and 53% of the Z isomer.

EXAMPLE 165

N-[2-(2-Methoxy-10,11-dihydro-dibenzo[a,d]cyclohepten-5-ylidenemethyl)-phenyl]-methanesulfonamide (E/Z Mixture)

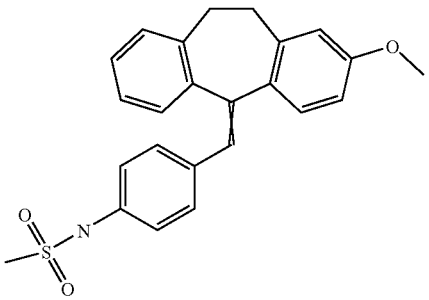

Following the procedures essentially as described in Example 219, below, and using 5-bromomethylene-2-methoxy-10,11-dihydro-5H-dibenzo[a,d]cycloheptene (E/Z mixture, 100 mg, 0.32 mmol) with 4-methanesulfonylaminophenylboronic acid (75 mg, 0.35 mmol) to give 35 mg (27%) of an E/Z mixture of the title compound. MS (ES) 406 (M+1), 404 (M−1). HPLC shows 53% of the E isomer and 44% of the Z isomer.

EXAMPLE 166

4-(2-Methoxy-10,11-dihydro-dibenzo[a,d]cyclohepten-5-ylidenemethyl)-phenylamine E/Z Mixture)

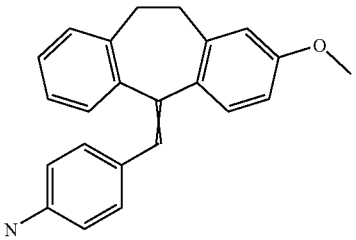

Isolate the title compound, which is derived from an impurity in the starting 4-methanesulfonylaminophenylboronic acid in the above reaction. MS (ES) 828 (M+1). HPLC shows 41% of the faster eluting isomer and 58% of the slower isomer.

EXAMPLE 167

3-(2-Methoxy-10,11-dihydro-dibenzo[a,d]cyclohepten-5-ylidenemethyl)-phenol

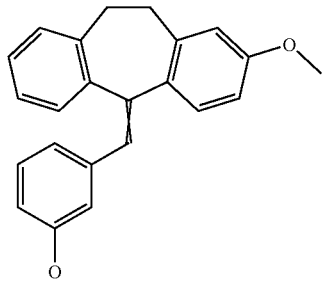

Following the procedures essentially as described in Example 219, below, and using 5-bromomethylene-2-methoxy-10,11-dihydro-5H-dibenzo[a,d]cycloheptene (E/Z mixture, 100 mg, 0.32 mmol) with 3-hydroxyphenylboronic acid (48 mg, 0.35 mmol) to give 43 mg (41%) of an E/Z mixture of the title compound as a tan foam. MS (ES) 327 (M−1). HPLC shows 42% of the E isomer and 55% of the Z isomer.

EXAMPLE 168

4-(2-Methoxy-10,11-dihydro-dibenzo[a,d]cyclohepten-5-ylidenemethyl)-phenol (E/Z Mixture)

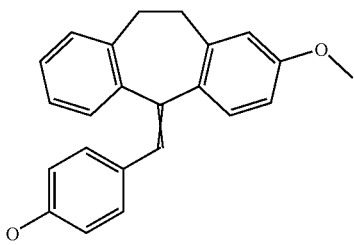

Following the procedures essentially as described in Example 219, below, and using 5-bromomethylene-2-methoxy-10,11-dihydro-5H-dibenzo[a,d]cycloheptene (E/Z mixture, 220 mg, 0.7 mmol) with 4-hydroxyphenylboronic acid (110 mg, 0.8 mmol) to give 117 mg (51%) of an E/Z mixture of the title compound as a tan foam. MS (ES) 327 (M−1). HPLC shows 40% of the E isomer and 54% of the Z isomer.

EXAMPLE 169

5-(4-Hydroxy-benzylidene)-10,11-dihydro-5H-dibenzo[a,d]cyclohepten-2-ol (E/Z Mixture)

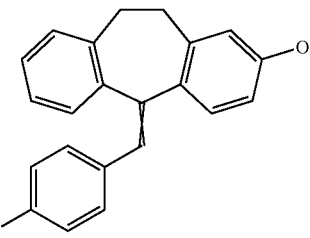

Demethylate the corresponding methoxy derivative mixture from Example 168 using BBr$_3$ to give the title compound in 80% yield. MS (ES) 315 (M+1), 313 (M−1). HPLC shows 44% of the faster eluting isomer and 52% of the slower isomer.

EXAMPLE 170 (a) AND (b)

N-[3-(2,3-Dimethoxy-10,11-dihydro-dibenzo[a,d]cyclohepten-5-ylidenemethyl)-phenyl]-methanesulfonamide (E-isomer) and N-[3-(2,3-Dimethoxy-10,11-dihydro-dibenzo[a,d]cyclohepten-5-ylidenemethyl)-phenyl]-methanesulfonamide (Z-isomer)

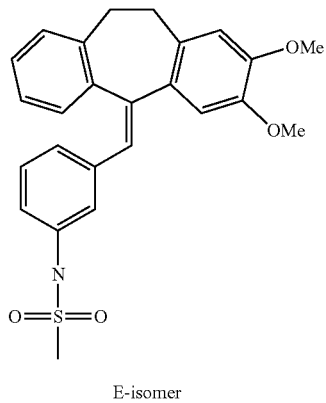

E-isomer

-continued

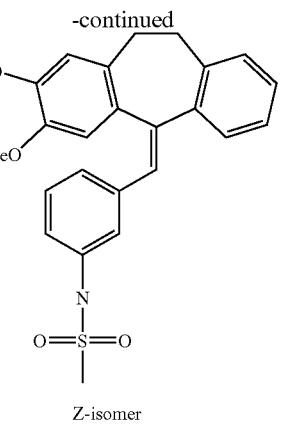

Z-isomer

Following procedures essentially as described in Example 239, below, the title compounds are prepared from the corresponding dimethoxydibenzosuberone and m-bromobenzylmagnesium bromide. These bromo derivatives are converted to the amino derivatives using procedures described in Example 86. The intermediate E and Z amines are reacted with methanesulfonyl chloride as described in Procedure M. The title compounds are purified on silica gel using 33% ethyl acetate/hexane to give 170 mg E/Z mixture. Use column chromatography (20% ethyl acetate/hexane) to give 50 mg of the E isomer (Example 170(a)); MS (ES) 434 (M−1), HPLC 92% and 35 mg of the Z isomer (Example 170(b)); MS (ES) 434 (M−1), HPLC 95%.

EXAMPLE 171

N-[3-(2,3-Dihydroxy-10,11-dihydro-dibenzo[a,d]cyclohepten-5-ylidenemethyl)-phenyl]-methanesulfonamide (E/Z Mixture)

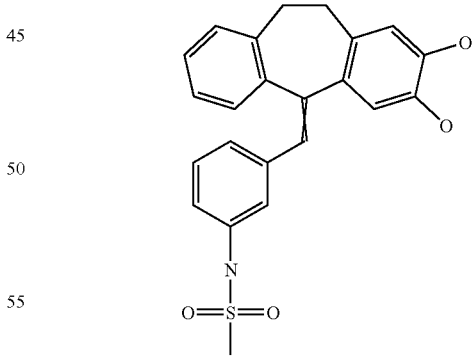

Demethylate N-[3-(2,3-dimethoxy-10,11-dihydro-dibenzo[a,d]cyclohepten-5-ylidenemethyl)-phenyl]-methanesulfonamide (60 mg, 0.14 mmol) form Example 170 using BBr$_3$ to give 53 mg (93%) the title compound as a tan semi-solid. MS (ES) 408 M+1), 406 (M−1). HPLC shows 47% faster eluting isomer and 53% slower isomer.

EXAMPLE 172

1-Chloro-5-(4-chloro-3-methoxy-benzylidene)-10,11-dihydro-5H-dibenzo[a,d]cycloheptene (mixture of E/Z isomers)

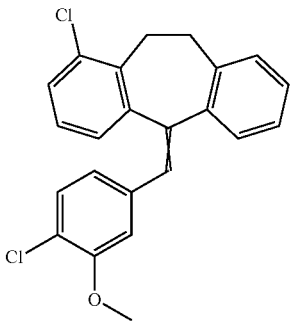

Following procedures essentially as described in Example 219, below, and using 4-chloro-3-methoxyphenylboronic acid (160 mg, 0.85 mmol) with 5-bromomethylene-1-chloro-10,11-dihydro-5H-dibenzo[a,d]cycloheptene (249 mg, 0.78 mmol) to give 440 mg crude product. Purify by chromatography to give 210 mg (71%) colorless oil. HPLC (ISO90-10M) shows 51% at t=7.62 min and 45% at t=9.86 min.

EXAMPLE 173

2-Chloro-5-(1-chloro-10,11-dihydro-dibenzo[a,d]cyclohepten-5-ylidenemethyl)-phenol (Z-isomer, LY2054560, ER0-A01846-65B) and 2-Chloro-5-(1-chloro-10,11-dihydro-dibenzo[a,d]cyclohepten-5-ylidenemethyl)-phenol (E-isomer)

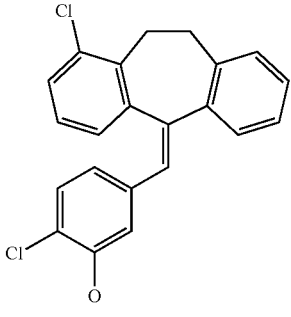
Z-isomer

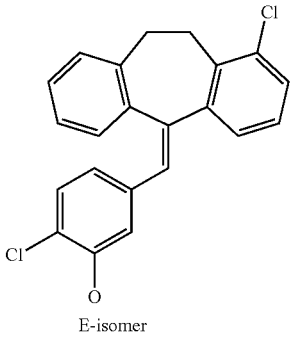
E-isomer

Demethylate 1-chloro-5-(4-chloro-3-methoxy-benzylidene)-10,11-dihydro-5H-dibenzo[a,d]cycloheptene (mixture of E/Z isomers) (215 mg, 0.56 mmol) from Example 172 using BBr$_3$. Separate the isomers using a chromatatron (2% EtOAc/hexane) to give 47 mg Z isomer. MS (S) 365 (M−1). HPLC shows 98% purity. The lower spot is the E isomer, 33 mg. MS (ES) 365 (M−1). HPLC shows 96% purity.

EXAMPLE 174

2-Chloro-5-(2-trifluoromethyl-benzylidene)-10,11-dihydro-5H-dibenzo[a,d]cycloheptene

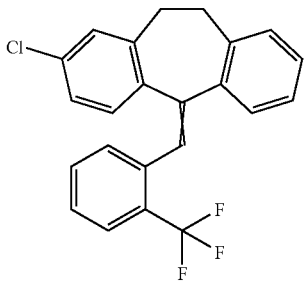

Following procedures essentially as described in Example 219, below, and using 2-(trifluoromethyl)phenylboronic acid (59 mg, 0.31 mmol) and 5-bromomethylene-2-chloro-10,11-dihydro-5H-dibenzo[a,d]cycloheptene (91 mg, 0.28 mmol) provides 97 mg (90%) title compound. GC/MS data: retention times in minutes (MS data for M$^+$·ion): 18.19 (384), 18.38(384)Mass Spec (EI+) 384

EXAMPLE 175

2-Chloro-5-(2-methyl-benzylidene)-10,11-dihydro-5H-dibenzo[a,d]cycloheptene

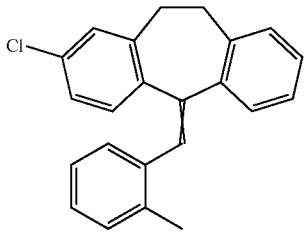

Following procedures essentially as described in Example 219, below, and using o-tolylboronic acid (91 mg, 0.67 mmol) and 5-bromomethylene-2-chloro-10,11-dihydro-5H-dibenzo[a,d]cycloheptene (178 mg, 0.56 mmol) provides the title compound. GC/MS data: retention times in minutes (MS data for M$^+$·ion): 19.62 (330), 19.83(330) Mass Spec (EI+) 330.

EXAMPLE 177

2-Chloro-5-(3-methyl-benzylidene)-10,11-dihydro-5H-dibenzo[a,d]cycloheptene

Following procedures essentially as described in Example 219, below, and using m-tolylboronic acid (61 mg, 0.45 mmol) and 5-bromomethylene-2-chloro-10,11-dihydro-5H-dibenzo[a,d]cycloheptene (119 mg, 0.37 mmol) provides the title compound. GC/MS data: retention times in minutes (MS data for M$^+$·ion): 19.60 (330), 19.95(330) Mass Spec (EI+) 330.

EXAMPLE 178

3-(2-Chloro-10,11-dihydro-dibenzo[a,d]cyclohepten-5-ylidenemethyl)-phenol

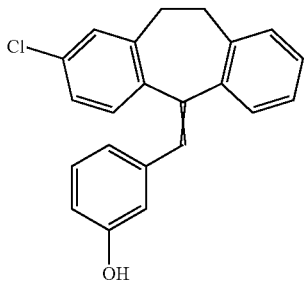

Following procedures essentially as described in Example 219, below, and using (3-hydroxyphenyl)boronic acid (108 mg, 0.78 mmol) and 5-bromomethylene-2-chloro-10,11-dihydro-5H-dibenzo[a,d]cycloheptene (209 mg, 0.65 mmol) provides the title compound. Mass Spec (EI+) 332.

EXAMPLE 179

2-Chloro-5-(4-trifluoromethyl-benzylidene)-10,11-dihydro-5H-dibenzo[a,d]cycloheptene

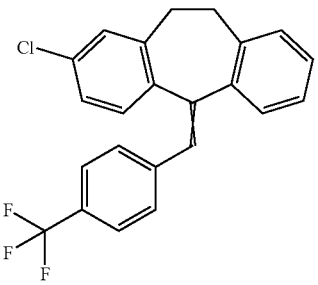

Following procedures essentially as described in Example 219, below, and using 4-(trifluoromethyl)phenylboronic acid (114 mg, 0.60 mmol) and 5-bromomethylene-2-chloro-10,11-dihydro-5H-dibenzo[a,d]cycloheptene (156 mg, 0.48 mmol) provides the title compound. GC/MS data: retention times in minutes (MS data for $M^{+}$·ion): 18.52 (384), 18.78 (384)Mass Spec (EI+) 384.

EXAMPLE 180

4-(2-Chloro-10,11-dihydro-dibenzo[a,d]cyclohepten-5-ylidenemethyl)-phenol

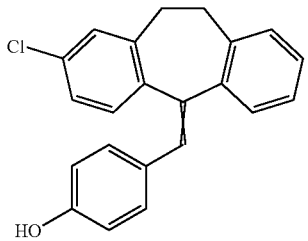

Following procedures essentially as described in Example 219, below, and using (4-hydroxyphenyl)boronic acid (55 mg, 0.40 mmol) and 5-bromomethylene-2-chloro-10,11-dihydro-5H-dibenzo[a,d]cycloheptene (103 mg, 0.32 mmol) provides the title compound. Mass Spec (EI+) 332.

EXAMPLE 181

3-(2-Chloro-10,11-dihydro-dibenzo[a,d]cyclohepten-5-ylidenemethyl)-phenol (Z-isomer) and 3-(2-Chloro-10,11-dihydro-dibenzo[a,d]cyclohepten-5-ylidenemethyl)-phenol (E-isomer)

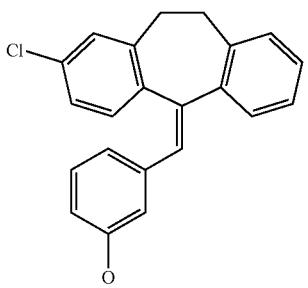

Z isomer

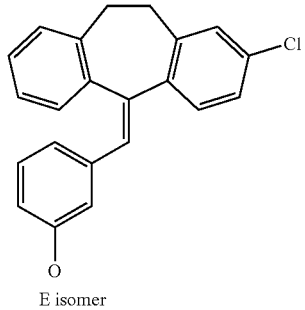

E isomer

Following procedures essentially as described in Example 219, below, and using 3-hydroxyphenylboronic acid (99 mg, 0.72 mmol) and 5-bromomethylene-10,11-dihydro-5H-2-chlorodibenzo[a,d]cycloheptene (209 mg, 0.65 mmol) (prepared from 2-chlorodibenzosuberone using procedures as described in Preparations 23 and 24) provides 90 mg Z isomer, MS (ES) 332, 334 (M+1), 331, 333 (M−1). HPLC shows 95% purity. The E isomer (51 mg) was isolated as a colorless oil, MS (ES) 332, 334 (M+1), 331, 333 (M−1). HPLC shows 99% purity.

EXAMPLE 182

N-[3-(2,8-Dichloro-10,11-dihydro-dibenzo[a,d]cyclohepten-5-ylidenemethyl)-phenyl]-methanesulfonamide

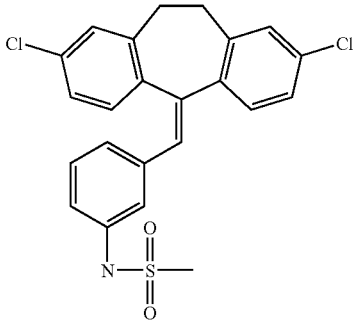

Following procedures essentially as described in Example 219, below, and using 3-methanesulfonamidophenylboronic acid (154 mg, 0.71 mmol) and 5-bromomethylene-10,11-dihydro-5H-2,8-dichlorodibenzo[a,d]cycloheptene (230 mg, 0.65 mmol) (prepared from 2,8-dichlorodibenzosuberone (M. R. Pavia et al, J. Med. Chem. (35) 4238-4248 (1992)) using procedures as described in Preparations 23 and 24) provides 164 mg (57%) title compound as a white solid, mp 182.4° C. MS (ES) 444 (M+1), 442 (M−1. HPLC shows 97% purity.

EXAMPLE 183

3-(2,8-Dichloro-10,11-dihydro-dibenzo[a,d]cyclo-hepten-5-ylidenemethyl)-phenol

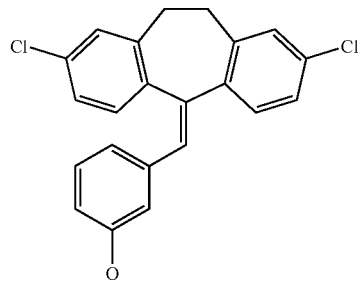

Following procedures essentially as described in Example 219, below, and using 3-hydroxyphenylboronic acid (98 mg, 0.71 mmol) and 5-bromomethylene-10,11-dihydro-5H-2,8-dichlorodibenzo[a,d]cycloheptene (230 mg, 0.65 mmol) (prepared from 2,8-dichlorodibenzosuberone (M. R. Pavia et al, J. Med. Chem. (35) 4238-4248 (1992)) using procedures as described in Preparations 23 and 24) provides 178 mg title compound in 75% yield as a pale yellow oil. MS (ES) 365 (M−1). HPLC shows 93% purity.

EXAMPLE 184

N-[3-(1-Fluoro-10,11-dihydro-dibenzo[a,d]cyclo-hepten-5-ylidenemethyl)-phenyl]-methanesulfona-mide (Z-isomer) and N-[3-(1-Fluoro-10,11-dihydro-dibenzo[a,d]cyclohepten-5-ylidenemethyl)-phenyl]-methanesulfonamide (E-isomer)

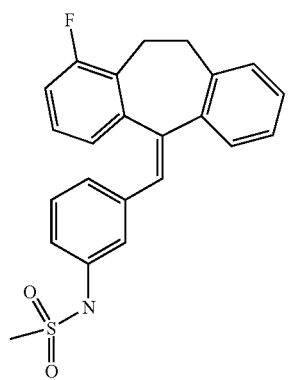

Z isomer

-continued

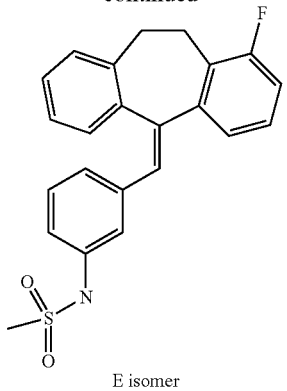

E isomer

Following procedures essentially as described in Example 219, below, and using 3-methanesulfonamidophenylboronic acid (388 mg, 1.8 mmol) and 5-bromomethylene-1-fluoro-10,11-dihydro-5H-dibenzo[a,d]cycloheptene (E/Z mixture, 500 mg, 1.65 mmol) (Prepared from 1-fluorodibenzosub-erone (Chem. Abstr. 70 106272a (1969) using procedures as described in Preparations 23 and 24) provides the title compound. Separate the isomers using column chromatography (gradient of 10% EtOAc/hexane to 25% EtOAc/hexane) to give 66 mg Z isomer as a white powder, mp 153.5° C., MS (ES) 392 (M−1). HPLC shows 100% purity. Isolate 18 mg E isomer as the slower moving spot, MS (ES) 392 (M−1). HPLC shows 97% purity.

EXAMPLE 185

3-(1-Fluoro-10,11-dihydro-dibenzo[a,d]cyclohepten-5-ylidenemethyl)-phenol (E-isomer) and 3-(1-Fluoro-10,11-dihydro-dibenzo[a,d]cyclohepten-5-ylidenemethyl)-phenol (Z-isomer)

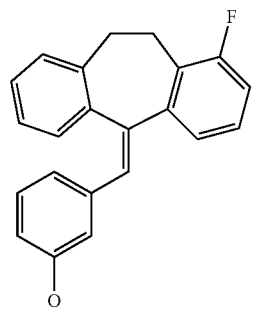

E-isomer

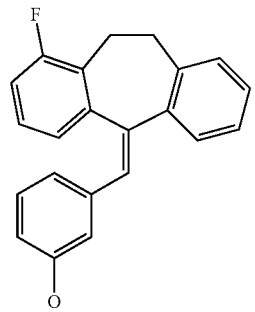

Z-isomer

Following procedures essentially as described in Example 219, below, and using 3-hydroxyphenylboronic acid (250 mg, 1.8 mmol) and 5-bromomethylene-1-fluoro-10,11-dihydro-5H-dibenzo[a,d]cycloheptene (E/Z mixture, 500 mg, 1.65 mmol) (Prepared from 1-fluorodibenzosuberone (Chem. Abstr. 70 106272a (1969) using procedures as described in Preparations 23 and 24) provides 750 mg crude product of the title compound. Separate the isomers using radial chromatography (hexane→3% EtOAc/hexane) to give 115 mg Z-isomer as a pale yellow foam, mp 119.9° C. MS (ES) 315 (M−1). HPLC shows>95% purity. The E-isomer is the slower moving material, 69 mg yellow foam, mp 158.1° C. MS (ES) 315 (M−1). HPLC shows 99% purity.

EXAMPLE 186

3-(1-Fluoro-10,11-dihydro-5H-dibenzo[a,d]cyclohepten-5-ylmethyl)-phenol

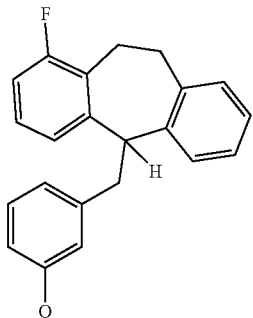

Dissolve 3-(1-fluoro-10,11-dihydro-dibenzo[a,d]cyclohepten-5-ylidenemethyl)-phenol (170 mg, 0.54 mmol) in EtOH (5 mL) and add 10% Pd/C (50 mg). Stir for 18 h under an atmosphere of hydrogen. Filter and concentrate. Purify the crude product using column chromatography (10% EtOAc/hexane→25% EtOAc/hexane) to give 98 mg (57%) product as a colorless oil. MS (ES) 317 (M−1). HPLC shows 99% purity.

EXAMPLE 187

N-[3-(1-Fluoro-10,11-dihydro-5H-dibenzo[a,d]cyclohepten-5-ylmethyl)-phenyl]-methanesulfonamide

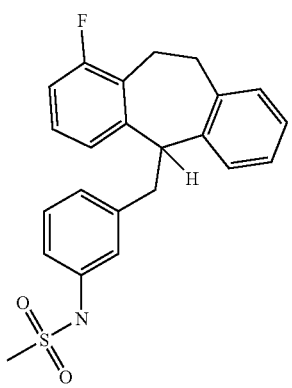

Dissolve 150 mg (0.38 mmol) N-[3-(1-fluoro-10,11-dihydro-dibenzo[a,d]cyclohepten-5-ylidenemethyl)-phenyl]-methanesulfonamide in EtOH (5 mL) and add 10% Pd/C (50 mg). Stir for 18 h under an atmosphere of hydrogen. Filter and concentrate. Purify the crude product using column chromatography (10% EtOAc/hexane→25% EtOAc/hexane) to give 6 mg product as a colorless oil. MS (ES) 394 (M−1). HPLC shows 99% purity.

EXAMPLE 188

N-[3-(3-Chloro-10,11-dihydro-dibenzo[a,d]cyclohepten-5-ylidenemethyl)-phenyl]-methanesulfonamide (Z-isomer) and N-[3-(3-Chloro-10,11-dihydro-dibenzo[a,d]cyclohepten-5-ylidenemethyl)-phenyl]-methanesulfonamide (E-isomer)

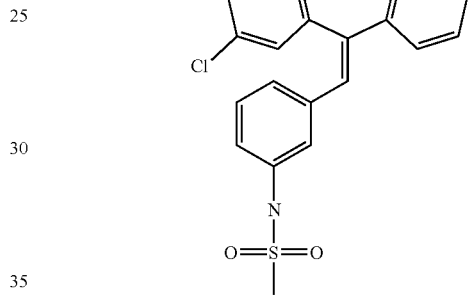

E-isomer

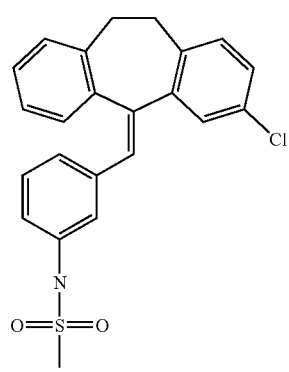

Z-isomer

Following procedures essentially as described in Example 219, below, and using 3-methanesulfonamidophenyl boronic acid (473 mg, 2.2 mmol) with 5-bromomethylene-3-chloro-10,11-dihydro-5H-dibenzo[a,d]cycloheptene (640 mg, 2 mmol) provides 1.17 crude product as a brown oil. Purify the crude product using column chromatography eluting with 5% EtOAc/hexane to 25% EtOAc/hexane to give 315 mg of the Z-isomer, mp 177.1° C., (MS (ES) 408 (M−1), HPLC 99% purity) and 115 mg E-isomer, mp 130.5° C., (MS (ES) 408 (M−1), HPLC 90% purity).

EXAMPLE 189

N-[3-(3-Chloro-10,11-dihydro-5H-dibenzo[a,d]cyclohepten-5-ylmethyl)-phenyl]-methanesulfonamide

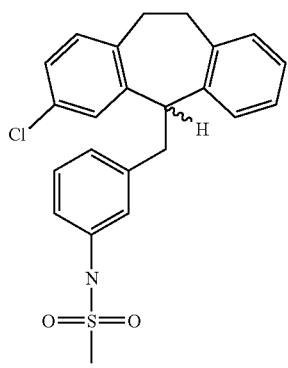

Dissolve N-[3-(3-chloro-10,11-dihydro-dibenzo[a,d]cyclohepten-5-ylidenemethyl)-phenyl]-methanesulfonamide (200 mg, 0.49 mmol) in EtOAc (30 mL) and add 5% Pt/C (150 mg). Stir for 18 h under an atmosphere of hydrogen. Add 5% Pt/C (200 mg). Stir for 24 h under an atmosphere of hydrogen. Filter and concentrate to give 140 mg crude product. Purify using reverse-phase UV guided HPLC to give 28 mg viscous tan oil, MS (ES) 410 (M−1). HPLC shows 99% purity.

EXAMPLE 190

3-(3-Chloro-10,11-dihydro-dibenzo[a,d]cyclohepten-5-ylidenemethyl)-phenol (Z-isomer) and 3-(3-Chloro-10,11-dihydro-dibenzo[a,d]cyclohepten-5-ylidenemethyl)-phenol (E-isomer)

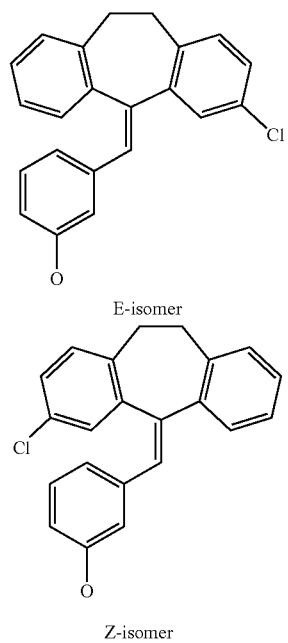

Following procedures essentially as described in Example 219, below, and using 3-hydroxyphenyl boronic acid (300 mg, 2.2 mmol) with 5-bromomethylene-3-chloro-10,11-dihydro-5H-dibenzo[a,d]cycloheptene (640 mg, 2 mmol) to give 880 mg crude product. Purify using reverse-phase UV guided HPLC (1/1 CH$_3$CN/0.1% TFA) to give 163 mg Z-isomer as a pink foam (HPLC shows 99% purity at t=4.96 min) and 43 mg E-isomer (MS (ES) 331 (M−1), HPLC shows 95% purity at t=5.22 min).

EXAMPLE 191

N-[3-(2,8-Dimethoxy-10,11-dihydro-dibenzo[a,d]cyclohepten-5-ylidenemethyl)-phenyl]-methanesulfonamide

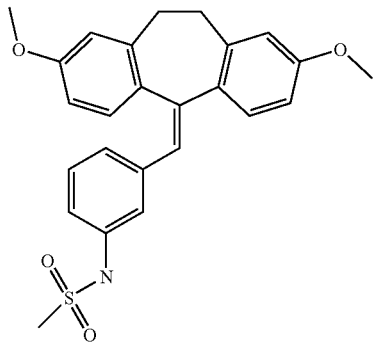

Following procedures essentially as described in Example 219, below, and using 3-methanesulfonamidophenyl boronic acid (473 mg, 2.2 mmol) with 5-bromomethylene-2,8-dimethoxy-10,11-dihydro-5H-dibenzo[a,d]cycloheptene (690 mg, 2 mmol) to give 1.3 g crude product. Purify the crude product using column chromatography eluting with 10% EtOAc/hexane to 30% EtOAc/hexane to give 340 mg (39%) product as a pale yellow solid, mp 109.6° C. MS (ES) 436 (M+1), 434 (M−1). HPLC shows 91% purity at t=3.11 min.

EXAMPLE 192

N-[3-(2,8-Dihydroxy-10,11-dihydro-dibenzo[a,d]cyclohepten-5-ylidenemethyl)-phenyl]-methanesulfonamide

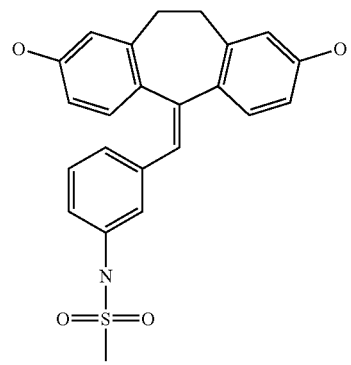

Demethylate N-[3-(2,8-dihydroxy-10,11-dihydro-dibenzo[a,d]cyclohepten-5-ylidenemethyl)-phenyl]-methanesulfonamide (112 mg, 0.26 mmol) with BBr$_3$. Purify on silica gel eluting with 25% EtOAc/hexane to 35% EtOAc/hexane to give 72 mg (68%) title compound as a colorless oil, MS (ES) 408 (M+1), 406 (M−1). HPLC shows 98% purity.

EXAMPLE 193

3-(2,8-Dimethoxy-10,11-dihydro-dibenzo[a,d]cyclo-hepten-5-ylidenemethyl)-phenol

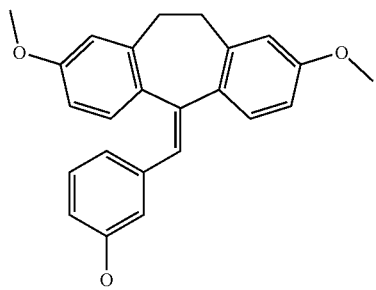

Following procedures essentially as described in Example 219, below, and using 3-hydroxyphenyl boronic acid (304 mg, 2.2 mmol) with 5-bromomethylene-2,8-dimethoxy-10,11-dihydro-5H-dibenzo[a,d]cycloheptene (690 mg, 2 mmol) to give 990 mg crude product. Purify the crude product using column chromatography eluting with 8% EtOAc/hexane to 25% EtOAc/hexane to give 240 mg (33%) product as a colorless oil. MS (ES) 357 (M−1). HPLC shows 99% purity at t=3.33 min.

EXAMPLE 194

5-(3-Hydroxy-benzylidene)-10,11-dihydro-5H-dibenzo[a,d]cycloheptene-2,8-diol

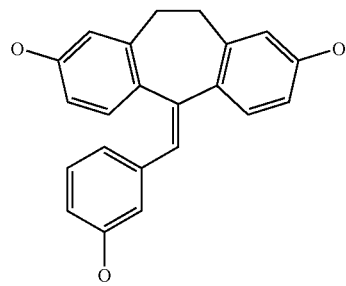

Demethylate 3-(2,8-dimethoxy-10,11-dihydro-dibenzo[a,d]cyclohepten-5-ylidenemethyl)-phenol (91 mg, 0.25 mmol) with BBr$_3$ to give crude title compound. Purify on silica gel eluting with 25% EtOAc/hexane to 35% EtOAc/hexane to give 80 mg (96%) as a light pink solid, MS (ES) 331 (m+1), 329 (M−1). HPLC shows 96% purity.

EXAMPLE 195

3-[2-(2-Morpholin-4-yl-ethoxy)-10,11-dihydro-dibenzo[a,d]cyclohepten-5-ylidenemethyl]-phenol (E-isomer) and 3-[2-(2-Morpholin-4-yl-ethoxy)-10,11-dihydro-dibenzo[a,d]cyclohepten-5-ylidenemethyl]-phenol (Z-isomer)

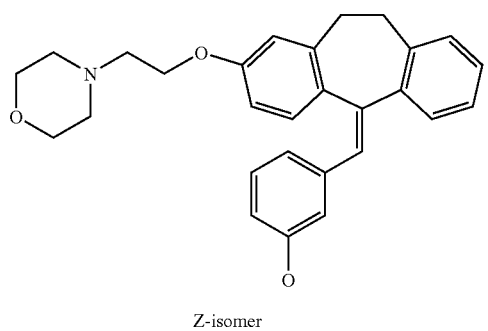

Z-isomer

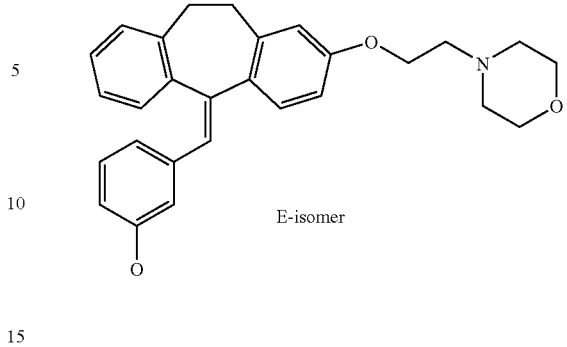

E-isomer

Following procedures essentially as described in Example 219, below, and using 4-[2-(5-bromomethylene-10,11-dihydro-5H-dibenzo[a,d]cyclohepten-2-yloxy)-ethyl]-morpholine (220 mg, 0.53 mmol) and 3-hydroxyphenylboronic acid (80 mg, (0.58 mmol). Attempted purification on silica gel eluting with 70% EtOAc/hexane to 100% EtOAc/hexane gave 136 mg of an E/Z mixture. Separate the isomers using UV guided reverse-phase using 34% CH$_3$CN/66% 0.1% aq. TFA. Pool the pure fractions and neutralize with aq. NaHCO$_3$. Concentrate to remove the organic solvent and extract the product into EtOAc. After drying (MgSO$_4$) and concentration, 40 mg of the E-isomer was obtained as a tan foam, MS (ES) 428 (M+1). HPLC 95% purity at t=1.88 min. Similarly, 7.2 mg of the Z-isomer was obtained as a viscous oil, MS (ES) 428 (M+1). HPLC 96% purity at t=2.27 min.

EXAMPLE 196

N-{3-[2-(2-Morpholin-4-yl-ethoxy)-10,11-dihydro-dibenzo[a,d]cyclohepten-5-ylidenemethyl]-phenyl}-methanesulfonamide

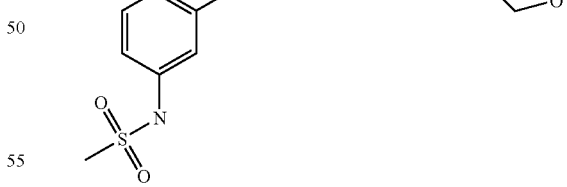

Following procedures essentially as described in Example 219, below, and using 4-[2-(5-bromomethylene-10,11-dihydro-5H-dibenzo[a,d]cyclohepten-2-yloxy)-ethyl]-morpholine (220 mg, 0.53 mmol) and 3-methanesulfonamidophenylboronic acid (125 mg, 0.58 mmol). Purification on silica gel eluting with EtOAc then EtOAc/1% MeOH/NH$_3$, gave 57 mg of pure E-isomer. MS (ES)505 (M+1), 503(M−1). HPLC shows 92% purity at t=1.79 min.

EXAMPLE 197

N-[3-(1,2-Dichloro-10,11-dihydro-dibenzo[a,d]cyclohepten-5-ylidenemethyl)-phenyl]-methanesulfonamide (Z-isomer) and N-[3-(1,2-Dichloro-10,11-dihydro-dibenzo[a,d]cyclohepten-5-ylidenemethyl)-phenyl]-methanesulfonamide (E-isomer)

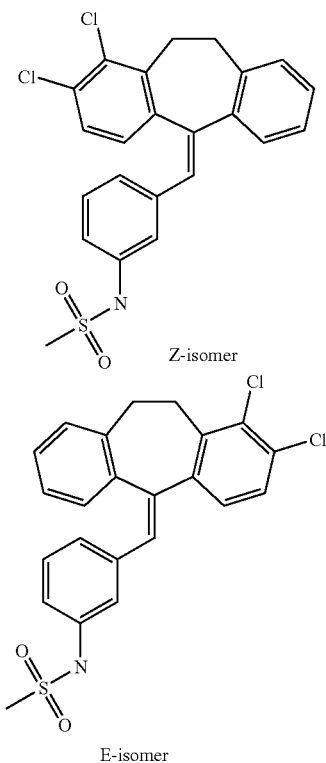

Z-isomer

E-isomer

Following procedures essentially as described in Example 219, below, and using 3-methanesulfonamidophenyl boronic acid (473 mg, 2.2 mmol) with 5-bromomethylene-1,2-dichloro-10,11-dihydro-5H-dibenzo[a,d]cycloheptene (700 mg, 2 mmol) to give 1.29 g crude product. Purify the crude product using column chromatography eluting with 10% EtOAc/hexane to 20% EtOAc/hexane, to give the Z-isomer, 330 mg yellow foam, mp 190.1° C., MS (ES) 442 (M−1). HPLC shows 98% purity at t=3.55 min. Continue to elute and obtain 126 mg E-isomer, mp 168.6° C., MS (ES) 442 (M−1). HPLC shows 97% purity at t=3.84 min.

EXAMPLE 198

3-(1,2-Dichloro-10,11-dihydro-dibenzo[a,d]cyclohepten-5-ylidenemethyl)-phenol (Z-isomer) and 3-(1,2-Dichloro-10,11-dihydro-dibenzo[a,d]cyclohepten-5-ylidenemethyl)-phenol (E-isomer)

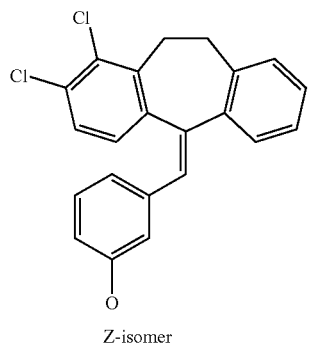

Z-isomer

-continued

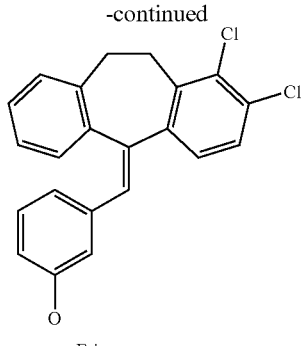

E-isomer

Following procedures essentially as described in Example 219, below, and using 3-hydroxyphenyl boronic acid (310 mg, 2.2 mmol) with 5-bromomethylene-1,2-dichloro-10,11-dihydro-5H-dibenzo[a,d]cycloheptene (700 mg, 2 mmol) to give 1.39 g crude product. Purify the crude product using column chromatography eluting with 5% EtOAc/hexane to 15% EtOAc/hexane to give the Z-isomer, 330 mg yellow foam, mp 67.6° C., MS (ES) 365 (M−1). HPLC shows 94% purity at t=4.05 min. Continue to elute and obtain 190 mg E-isomer, MS (ES) 365 (M−1). HPLC shows 94% purity at t=4.34 min

EXAMPLE 199

N-[3-(2-Fluoro-10,11-dihydro-dibenzo[a,d]cyclohepten-5-ylidenemethyl)-phenyl]-methanesulfonamide (Z-isomer) and N-[3-(2-Fluoro-10,11-dihydro-dibenzo[a,d]cyclohepten-5-ylidenemethyl)-phenyl]-methanesulfonamide (E-isomer)

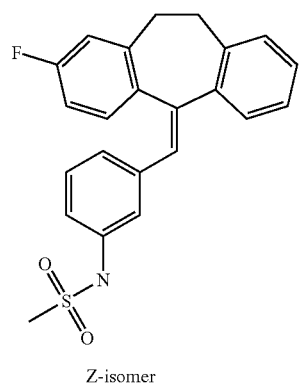

Z-isomer

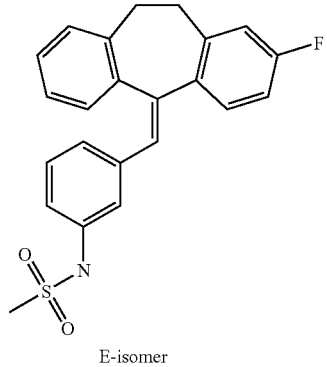

E-isomer

Following procedures essentially as described in Example 219, below, and using 3-methanesulfonamidophenyl boronic acid (596 mg, 2.77 mmol) with 5-bromomethylene-2-fluoro-10,11-dihydro-5H-dibenzo[a,d]cycloheptene (765 mg, 2.52 mmol) to give 1.49 g crude product. Purify the crude product using column chromatography (15% EtOAc/hexane→25% EtOAc/hexane) to give 212 mg Z-isomer as a colorless foam, mp 150.6° C. MS (ES) 392 (M−1). HPLC (ISO60-15M) shows 94% purity at t=12.34 min. Continue to elute and obtain 203 mg E-isomer as a white foam, mp 145.7° C. MS (ES) 392 (M−1). HPLC (ISO60-15M) shows 94% purity at t=11.86 min.

EXAMPLE 200

3-(2-Fluoro-10,11-dihydro-dibenzo[a,d]cyclohepten-5-ylidenemethyl)-phenol (Z-isomer) and 3-(2-Fluoro-10,11-dihydro-dibenzo[a,d]cyclohepten-5-ylidenemethyl)-phenol (E-isomer)

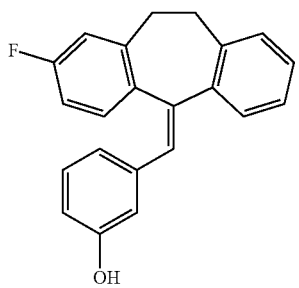

Z-isomer

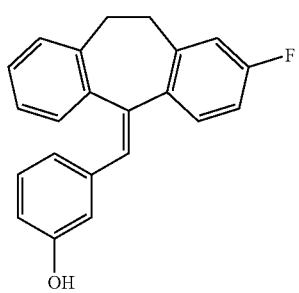

E-isomer

Following procedures essentially as described in Example 219, below, and using 3-hydroxyphenyl boronic acid (415 mg, 3.0 mmol) with 5-bromomethylene-2-fluoro-10,11-dihydro-5H-dibenzo[a,d]cycloheptene (825 mg, 2.72 mmol) to give 1.07 g crude product. Purify the crude product using column chromatography eluting with 5% EtOAc/hexane to 15% EtOAc/hexane to give 120 mg pure Z-isomer as a tan viscous oil, MS (ES) 315 (M−1). HPLC (IOS80-10M) shows 94% purity at t=4.02 min. Continue to elute and obtain 120 mg E-isomer as tan oil, MS (ES) 315 (M−1). HPLC (IOS80-10M) shows 94% purity at t=3.86 min.

EXAMPLE 201

N-[3-(1,9-Difluoro-10,11-dihydro-dibenzo[a,d]cyclohepten-5-ylidenemethyl)-phenyl]-methanesulfonamide

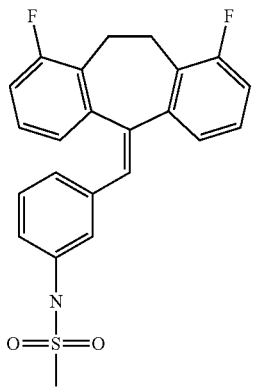

Following procedures essentially as described in Example 219, below, and using 3-methanesulfonamidophenyl boronic acid (592 mg, 2.75 mmol) and 5-bromomethylene-1,9-difluoro-10,11-dihydro-5H-dibenzo[a,d]cycloheptene (803 mg, 2.75 mmol), provides 1.52 g of the title compound crude product. The crude product is purified using column chromatography (15% EtOAc/hexane to 30% EtOAc/hexane) to give 690 mg (67%) white solid. MS (ES) 410 (M−1). HPLC (ISO90-10M) shows 92% purity at t=2.64 min.

EXAMPLE 202

3-(1,9-Difluoro-10,11-dihydro-dibenzo[a,d]cyclohepten-5-ylidenemethyl)-phenol

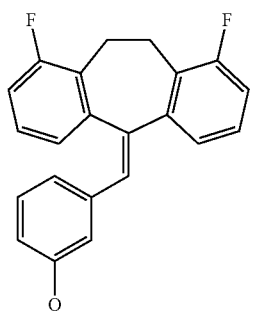

Following procedures essentially as described in Example 219, below, and using 3-hydroxyphenyl boronic acid (380 mg, 2.75 mmol) and 5-bromomethylene-1,9-difluoro-10,11-dihydro-5H-dibenzo[a,d]cycloheptene (803 mg, 2.75 mmol), provides to 1.04 g of the title compound as crude product. The crude product is purified using column chromatography eluting with 15% EtOAc/hexane to 30% EtOAc/hexane to give 500 mg (60%) product as a light yellow foam, mp 129.5° C. MS (ES) 333 (M−1). HPLC (ISO90-10M) shows 98% at t=2.90 min.

EXAMPLE 203

3-(1-Chloro-dibenzo[a,d]cyclohepten-5-ylidenem-ethyl)-phenylamine

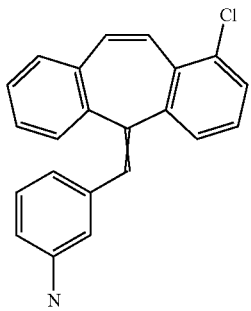

Heat a suspension of NaH (60% suspension in mineral oil, 49 mg, 1.2 mmol) in DMSO (6 mL) to 80° C. under $N_2$ until evolution of $H_2$ stops. Dissolve (3-nitro-benzyl)-phosphonic acid diethyl ester (prepared according to procedures as described in Okamoto et. al., Bull. Chem. Soc. Jpn. (1987), 60(1), 277-82) (338 mg, 1.2 mmol) in DMSO (1 mL) and add to reaction mixture. Add 1-chloro-10,11-dihydro-dibenzo[a,d]cyclohepten-5-one (prepared according to procedures as described in Humber et al., J. Med. Chem. (1978), 21(12), 1225-31) (200 mg, 0.824 mmol) at once and heat to 100° C. for 48 h. Cool to room temperature. Dilute reaction mixture with ethyl acetate (50 mL) and wash twice with $H_2O$. Dry ($MgSO_4$) and concentrate organics to a brown oil. Chromatograph on silica gel (10 g), eluting with 2% to 4% ethyl acetate/hexanes to afford a mixture of compounds. Dissolve this mixture in ethanol (10 mL) and add $SnCl_2$ (dihydrate, 508 mg, 2.25 mmol). Heat to reflux for 3 h and cool to room temperature. Concentrate reaction mixture, then dissolve residue in diethyl ether. Wash organics with $H_2O$, 1.00N aqueous NaOH, then twice with $H_2O$. Dry ($MgSO_4$) and concentrate organics to a yellow oil. Chromatograph on silica gel (10 g), eluting with 5% to 10% ethyl acetate/hexanes to afford 28 mg (10%) of the title compound as a colorless oil. MS (ES) 330 (M+H); HPLC reveals 36:64 mixture of geometric isomers—36% at 4.977 min, 64% at 5.218 min—overall 100% purity.

EXAMPLE 204

N-[3-(1-Chloro-dibenzo[a,d]cyclohepten-5-yliden-emethyl)-phenyl]-methanesulfonamide

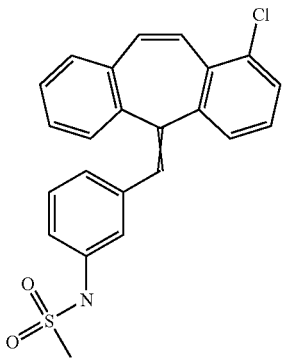

Following procedures essentially as described in Example 90, and using 3-(1-chloro-dibenzo[a,d]cyclohepten-5-ylidenemethyl)-phenylamine (63 mg, 0.190 mmol, affords 26 mg (33%) of the title compound as a white foam. MS (ES) 425 (M+N), 406 (M−H); HPLC reveals a mixture of geometric isomers—41% at 2.879 min, 59% at 2.985 min—overall 100% purity.

EXAMPLE 205(a), (b), AND (c)

N-[3-(1-Chloro-10,11-dihydro-dibenzo[a,d]cyclo-hepten-5-ylidenemethyl)-phenyl]-methanesulfona-mide

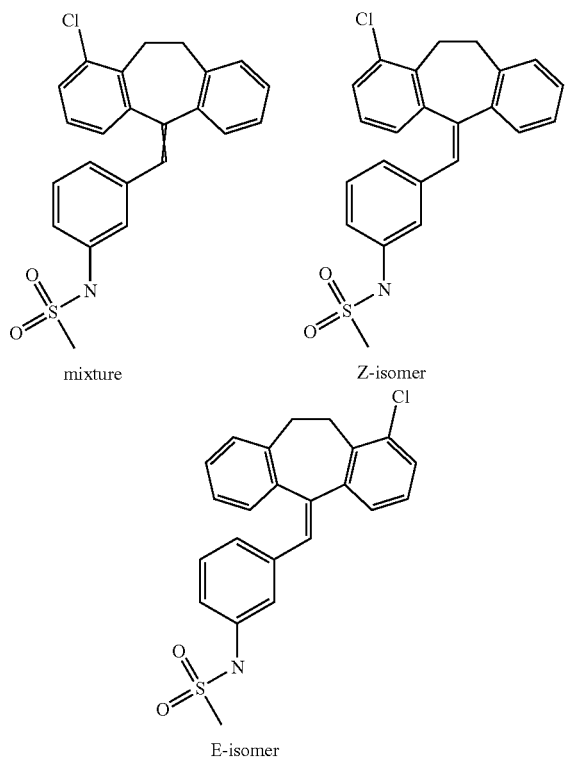

Following procedures essentially as described in Example 219, below, and using 5-bromomethylene-1-chloro-10,11-dihydro-5H-dibenzo[a,d]cycloheptene (100 mg, 0.313 mmol) and 3-methanesulfonylamino-phenylboronic acid (74 mg, 0.344 mmol), affords 102 mg (79%) of the title compound (Example 205(a)) as a mixture of geometric isomers. MS (ES) 408 (M−H); HPLC reveals a 57:43 mixture of geometric isomers—54% at 3.061 min, 40% at 3.197 min—overall 94% purity. Separate geometric isomers on a 1000 micron silica gel chromatatron rotor, (10% to 13% ethyl acetate/hexanes) to afford 22 mg (17%) of the Z-isomer of the title compound (Example 205(b), (MS (ES) 410 (M+H). HPLC shows 98% purity. Continue to elute to give 11 mg (9%) of the E-isomer of the title compound (Example 205(c)) (MS (ES) 410 (M+H), 408 (M−H); HPLC shows 94% purity).

EXAMPLE 206(a) AND (b)

N-[3-(2-Chloro-10,11-dihydro-dibenzo[a,d]cyclo-hepten-5-ylidenemethyl)-phenyl]-methanesulfona-mide (Z isomer and E isomer)

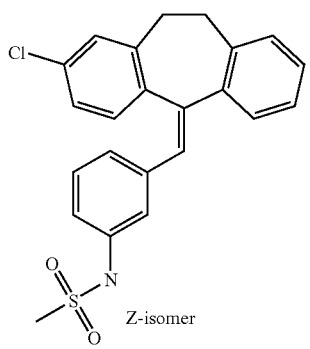

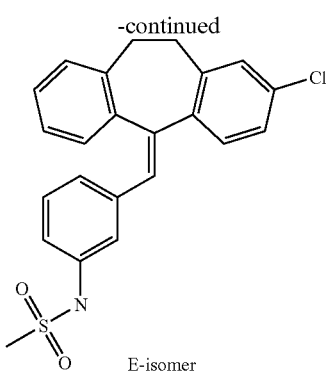

E-isomer

Following procedures essentially as described in Example 219, below, and using 5-bromomethylene-2-chloro-10,11-dihydro-5H-dibenzo[a,d]cycloheptene (100 mg, 0.313 mmol) and 3-methanesulfonylaminophenylboronic acid (74 mg, 0.344 mmol), affords 37 mg (29%) of the Z-isomer (Example 206(a)) of the title compound as a colorless oil (MS (ES) 408 (M−H). HPLC shows 99% purity. Continue to elute and obtain 23 mg (18%) of the E-isomer (Example (b)) of the title compound as a colorless oil (MS (ES) 408 (M−H); HPLC shows 92% purity).

EXAMPLE 207

N-[3-(2-Chloro-10,11-dihydro-5H-dibenzo[a,d]cycloheptenylmethyl)-phenyl]-methanesulfonamide

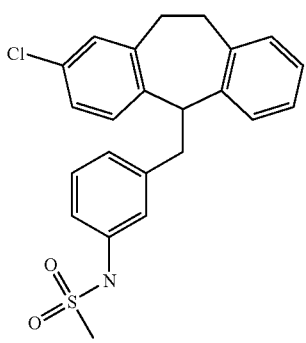

Dissolve N-[3-(2-chloro-10,11-dihydro-dibenzo[a,d]cyclohepten-5-ylidenemethyl)-phenyl]-methanesulfonamide (mixture of geometric isomers, 100 mg, 0.243 mmol) in ethanol (15 mL) and add 5% Pt/C (20 mg). Stir at room temperature under a H₂ balloon for 72 h. Filter reaction mixture through a pad of Celite, and concentrate filtrate to a colorless oil. Chromatograph on silica gel (10 g), eluting with 15% to 25% ethyl acetate/hexanes. Re-purify by UV-guided semi-preparatory reverse-phase HPLC to afford 44 mg (44%) of the title compound as a colorless oil. MS (ES) 429 (M+NH₄), 410 (M−H); HPLC shows 98% purity.

EXAMPLE 208(a), (b,) AND (c)

Ethanesulfonic acid [3-(1-chloro-10,11-dihydro-dibenzo[a,d]cyclohepten-5-ylidenemethyl)-phenyl]-amide

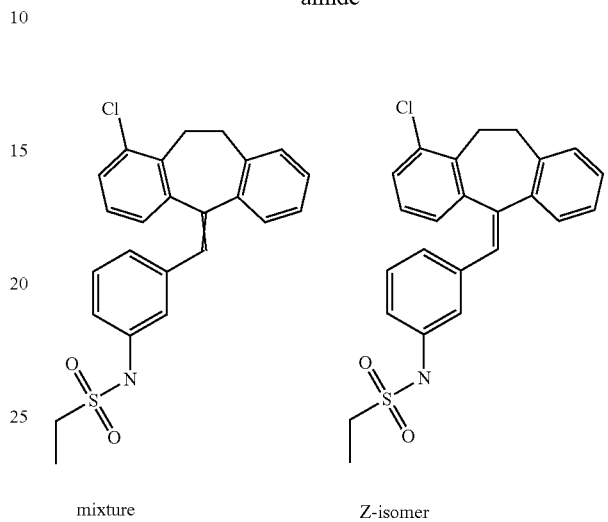

mixture    Z-isomer

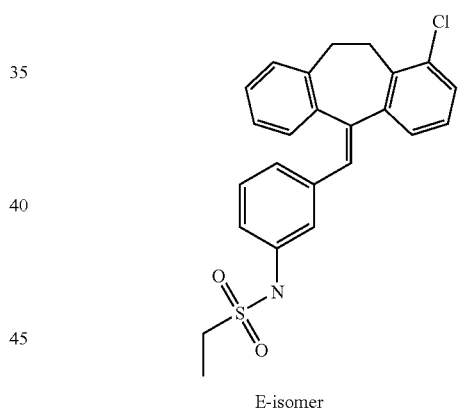

E-isomer

Following procedures essentially as described in Example 219, below, and using 5-bromomethylene-1-chloro-10,11-dihydro-5H-dibenzo[a,d]cycloheptene (100 mg, 0.313 mmol) and 3-ethanesulfonylaminophenylboronic acid (79 mg, 0.344 mmol), affords 112 mg (84%) of a mixture of geometric isomers of the title compound (Example 208(a)) as a yellow solid (MS (ES) 424 (M+H); HPLC shows 94% purity). Separate geometric isomers using a chromatatron rotor (10% ethyl acetate/hexanes) to afford 13 mg (10%) of the Z-isomer (Example 208(b)) of the title compound as a white solid, (MS (ES) 424 (M+H), 422 (M−H). HPLC shows 96% purity). Continue to elute and isolate 6 mg (5%) of the E-isomer (Example 208(c)) of the title compound as a white solid (MS (ES) 424 (M+H), 422 (M−H); HPLC shows 97% purity).

EXAMPLE 210

N-[4-(1-Chloro-10,11-dihydro-dibenzo[a,d]cyclohepten-5ylidenemethyl)-phenyl]-methanesulfonamide

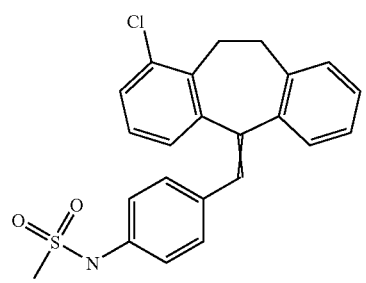

Following procedures essentially as described in Example 219, below, and using 5-bromomethylene-1-chloro-10,11-dihydro-5H-dibenzo[a,d]cycloheptene (100 mg, 0.313 mmol) and 4-methanesulfonylaminophenylboronic acid (74 mg, 0.344 mmol), affords 55 mg (43%) of a mixture of geometric isomers of the title compound as a brown oil. MS (ES) 408 (M–H); HPLC shows 96% purity.

EXAMPLE 211(a) AND (b)

3-(1-Chloro-10,11-dihydro-dibenzo[a,d]cyclohepten-5-ylidenemethyl)-phenol

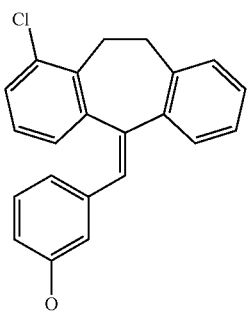

Z-isomer

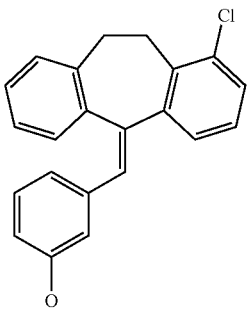

E-isomer

Following procedures essentially as described in Example 219, below, and using 5-bromomethylene-1-chloro-10,11-dihydro-5H-dibenzo[a,d]cycloheptene (100 mg, 0.313 mmol) and 3-hydroxyphenylboronic acid (47 mg, 0.344 mmol) affords 8 mg (8%) of the Z-isomer of the title compound (MS (ES) 331 (M–H). HPLC shows 95% purity. Continue to elute and isolate 27 mg (26%) of the E-isomer of the title compound, MS (ES) 331 (M–H). HPLC shows 97% purity.

EXAMPLE 212

4-(1-Chloro-10,11-dihydro-dibenzo[a,d]cyclohepten-5-ylidenemethyl)-phenol

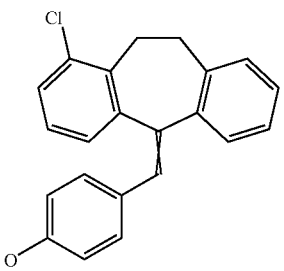

Following procedures essentially as described in Example 219, below, and using 5-bromomethylene-1-chloro-10,11dihydro-5H-dibenzo[a,d]cycloheptene (100 mg, 0.313 mmol) and 4-hydroxyphenylboronic acid (47 mg, 0.344 mmol), affords 84 mg (81%) of a mixture of geometric isomers of the title compound as a brown oil. MS (ES) 331 (M–H); HPLC shows 97% purity.

EXAMPLE 213

5-Bromomethylene-3-fluoro-10,11-dihydro-5H-dibenzo[a,d]cycloheptene

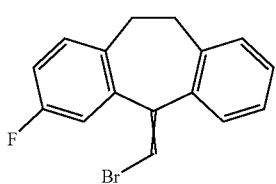

A. Following the procedures essentially as described in Preparation 23, using 3.84 g (16.97m) of 3-fluoro-10,11-dihydro-dibenzo[a,d]cyclohepten-5-one (prepared according to procedures as described in published PCT hit. Appl. WO 9856752 A1 19981217 (1998)) to obtain 2.88 g (75%) of 3-fluoro-5-methylene-10,11-dihydro-5H-dibenzo[a,d]cycloheptene as a white solid.

B. Following the procedures essentially as described in Preparations 24 and 25, 2.62 g (11.70 mmol) of the material from Step A, above, affords 3.152 g (89%) of a mixture of geometric isomers of the title compound as a yellow oil. MS [EI] 302,304; HPLC shows 99% purity.

EXAMPLE 214

N-[3-(3-Fluoro-10,11-dihydro-dibenzo[a,d]cyclo-hepten-5-ylidenemethyl)-phenyl]-methanesulfonamide

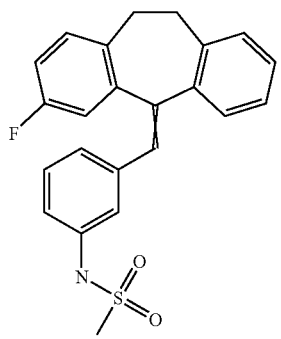

Following the procedures essentially as described in Example 219, below, and using 5-bromomethylene-3-fluoro-10,11-dihydro-5H-dibenzo[a,d]cycloheptene (200 mg, 0.660 mmol) and 3-methanesulfonylaminophenylboronic acid (156 mg, 0.726 mmol), affords 212 mg (82%) of a mixture of geometric isomers of the title compound as a yellow solid. MS (ES) 411 (M+NH$_4$), 392 (M−H); HPLC shows 98% purity.

EXAMPLE 215

3-(3-Fluoro-10,11-dihydro-dibenzo[a,d]cyclohepten-5-ylidenemethyl)-phenol

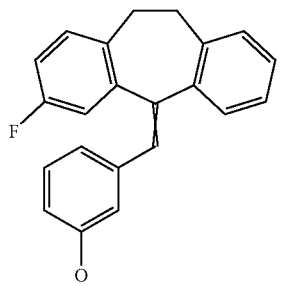

Following the procedures essentially as described in Example 219, below, and using 5-bromomethylene-3-fluoro-10,11-dihydro-5H-dibenzo[a,d]cycloheptene (200 mg, 0.660 mmol) and 3-hydroxyphenylboronic acid (100 mg, 0.726 mmol), affords 192 mg (92%) of a mixture of geometric isomers of the title compound as a yellow oil. MS (ES) 339 (M+Na), 315 (M−H); HPLC shows 95% purity.

Section 3 (derivatives of Formula I wherein the "C" ring further represents a heterocyclic or benzofused heterocyclic ring.)

EXAMPLE 216

5-(10,11-Dihydro-dibenzo[a,d]cyclohepten-5-ylidenemethyl)-3H-benzooxazol-2-one

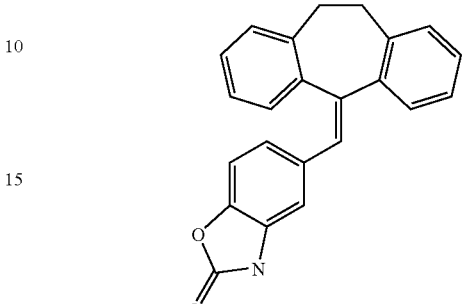

Add phenyl chloroformate (24 µL, 0.195 mmol) to a suspension of 2-amino-4-(10,11-dihydro-dibenzo[a,d]cyclohepten-5-ylidenemethyl)-phenol (61 mg, 0.195 mmol) (see Example 63) and NaHCO$_3$ (16 mg, 0.195 mmol) in water (5 mL) and methanol (10 mL). Stir for 30 min at room temperature and add aqueous NaOH (1.00N, 195 µL). Stir overnight and add aqueous HCl (1.00N, 195 µL). Extract with CH$_2$Cl$_2$, dry organics (MgSO$_4$), and concentrate to a brown oil containing the title compound. Purify on silica gel (10 g) eluting with 10% TO 35% ethyl acetate/hexanes, and then triturate with 50% CH$_2$Cl$_2$/hexanes to afford 8 mg (13%) of a white solid. MS (ES) 357 (M+NH$_4$), 338 (M−H); HPLC shows 94% purity.

EXAMPLE 217

5-(10,11-Dihydro-dibenzo[a,d]cyclohepten-5-ylidenemethyl)-benzooxazole

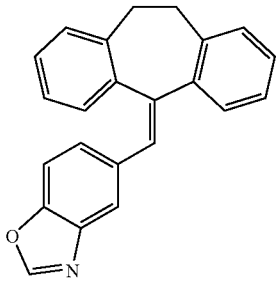

Dissolve 2-amino-4-(10,11-dihydro-dibenzo[a,d]cyclohepten-5-ylidenemethyl)-phenol (see Example 63) (60 mg, 0.191 mmol) in triethylorthoformate (3 mL) and heat to reflux for 4.5 h. Cool to room temperature and concentrate in-vacuo to a brown oil. Chromatograph on 10 g silica gel eluting with 5% to 25% ethyl acetate/hexanes to afford 52 mg (84%) of the title compound as a colorless oil; MS (ES) 324 (M+H), 322 (M−H), HPLC shows 94% purity.

EXAMPLE 218

5-(10,11-Dihydro-dibenzo[a,d]cyclohepten-5-yliden-emethyl)-2-methyl-benzooxazole

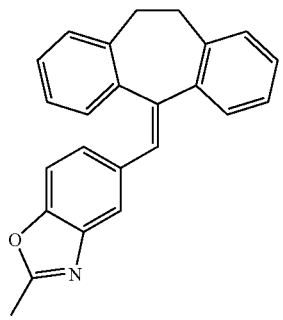

Dissolve 2-amino-4-(10,11-dihydro-dibenzo[a,d]cyclo-hepten-5-ylidenemethyl)-phenol (60 mg, 0.191 mmol) in triethylorthoacetate (5 mL) and heat to reflux for 4 h. Cool to room temperature and concentrate in-vacuo to a brown oil. Chromatograph on 10 g silica gel eluting with 5% to 25% ethyl acetate/hexanes to afford S 1mg (79%) of the title compound as a colorless oil. MS (ES) 338 (M+H); HPLC shows 98% purity.

EXAMPLE 219

6-(10,11-Dihydro-dibenzo[a,d]cyclohepten-5-yliden-emethyl)-1H-indole

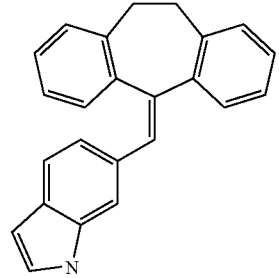

In a 1-dram vial, mix (10,11-dihydro-dibenzo[a,d]cyclo-hepten-5-ylidene)-boronic acid (100 mg, 0.400 mmol) and 6-bromoindole (86 mg, 0.440 mmol) in dioxane (2.5 mL) and 2.0M aqueous $Na_2CO_3$ (400 □L, 1.00 mmol). Sparge with $N_2$ for 5 min, add Pd(PPh$_3$)$_4$ (23 mg, 0.02 mmol), and immediately seal vial. Heat to 85° C. overnight, then concentrate under $N_2$. Add $H_2O$ (1 mL) and $CH_2Cl_2$ (1 mL) and load onto a Varian ChemElut CE1005 solid-phase extraction cartridge. Elute, collect, and concentrate 15 mL $CH_2Cl_2$ to obtain crude product. Chromatograph on silica gel (10 g), eluting with 0% to 25% ethyl acetate/hexanes to obtain 24 mg (19%) of the title compound as a colorless oil. $^1$H-NMR (CDCl$_3$) δ 2.75-3.60 (br m, 4H), 6.81 (s, 1H), 7.00-7.30 (m, 12H), 7.50 (m, 1H); HPLC shows 99% purity.

EXAMPLE 220

4-(10,11-Dihydro-dibenzo[a,d]cyclohepten-5-yliden-emethyl)-1H-indole

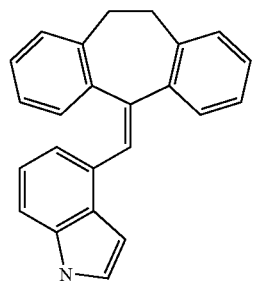

Following the procedures essentially as described in Example 219, 4-bromoindole (86 mg, 0.440 mmol) and (10,11-dihydro-dibenzo[a,d]cyclohepten-5-ylidene)-boronic acid (100 mg, 0.400 mmol) afford 6 mg (5%) of the title compound as a colorless oil. $^1$H-NMR (CDCl$_3$) δ 2.77-3.63 (br m, 4H), 6.79 (s, 1H), 6.97-7.29 (m, 12H), 7.49 (m, 1H). HPLC shows 96% purity.

PREPARATION 26

2-Oxo-2,3-dihydro-benzooxazole-5-boronic acid

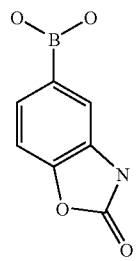

Add n-BuLi (1.6M in hexanes, 8.76 mL, 14.02 mmol) portionwise (exotherm) to a solution of 5-bromo-3H-ben-zooxazol-2-one (1.00 g, 4.67 mmol) in dry THF (28 mL) at −78° C. under $N_2$. Stir at −40° C. for 1 h and add trimethylborate (1.94 g, 18.68 mmol) at once. Warm up to room temperature overnight. Add 1N aqueous HCl (50 mL) and stir for 3 h at room temperature. Extract into ethyl acetate, dry (MgSO$_4$) and concentrate organics to a brown solid. Triturate with hexanes/toluene and collect 766 mg (92%) of the title compound as a brown powder. MS (ES) 179 (M+H), 177 (M−H); HPLC shows 80% purity.

EXAMPLE 221(a) AND (b)

1-Chloro-10,11-dihydro-dibenzo[a,d]cyclohepten-5-ylidenemethyl)-3H-benzooxazol-2-one (Z isomer and E isomer)

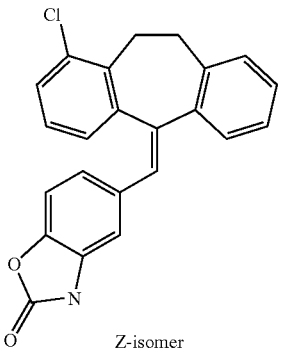

Z-isomer

-continued

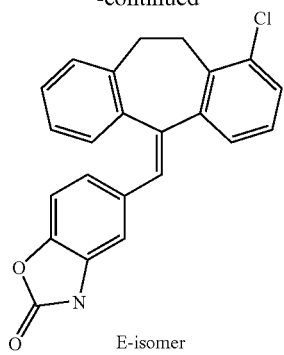
E-isomer

Following procedures essentially as described in Example 219 and using 5-bromomethylene-1-chloro-10,11-dihydro-5H-dibenzo[a,d]cycloheptene (200 mg, 0.630 mmol) and 2-oxo-2,3-dihydro-benzooxazole-5-boronic acid (134 mg, 0.750 mmol) provides 29 mg (12%) of the Z-isomer (Example 221(a)) of title compound as a tan solid (MS (ES) 372 (M–H); HPLC shows 99% purity) and 0 23 mg (10%) of the E-isomer (Example 221(b)) of the title compound as a tan solid. MS (ES) 372 (M–H); HPLC shows 97% purity.

EXAMPLE 222(a) AND (b)

5-(2-Chloro-10,11-dihydro-dibenzo[a,d]cyclohepten-5-ylidenemethyl)-3H-benzooxazol-2-one (Z isomer and E isomer)

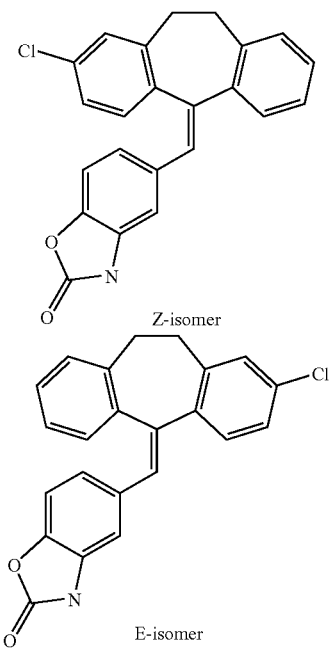

Following procedures essentially as described in Example 219 and using 5-bromomethylene-2-chloro-10,11-dihydro-5H-dibenzo[a,d]cycloheptene (200 mg, 0.630 mmol) and 2-oxo-2,3-dihydro-benzooxazole-5-boronic acid (134 mg, 0.750 mmol), provides the title compound. Purify by UV-guided semi-prep reverse-phase HPLC to obtain 14 mg (6%) of the Z-isomer (Example 222(a)) of title compound as a white solid (MS (ES) 391 (M+NH$_4$), 372 (M–H); HPLC shows 94% purity) and 5 mg (2%) of the E-isomer (Example 222(b)) of the title compound as a white solid. MS (ES) 391 (M+NH$_4$), 372 (M–H); HPLC shows 96% purity.

PREPARATION 27

5-Bromo-1,3-dihydro-benzoimidazol-2-one

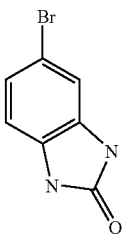

Add phenyl chloroformate (922 mg, 5.89 mmol) to a suspension of 4-bromo-benzene-1,2-diamine (1.00 g, 5.35 mmol) and NaHCO$_3$ (483 mg, 5.89 mmol) in methanol (20 mL) and H$_2$O (10 mL). Stir at room temperature for 3.5 h and add 1.00N aqueous NaOH (6 mL, 6.00 mmol). Stir overnight at room temperature and filter. Wash the filter cake with H$_2$O and dry in-vacuo overnight to obtain 386 mg (34%) of the title compound as a brown powder. MS (ES) 213,215 (M+H), 211,213 (M–H); HPLC shows 95% purity.

EXAMPLE 223

5-(10,11-Dihydro-dibenzo[a,d]cyclohepten-5-ylidenemethyl)-1,3-dihydro-benzoimidazol-2-one

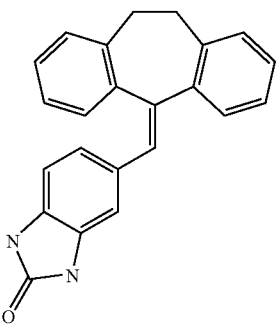

Following procedures essentially as described in Example 230, below, and using (10,11-dihydro-dibenzo[a,d]cyclohepten-5-ylidene)-boronic acid (0.0825M in toluene, 10 mL, 0.825 mmol) and 5-bromo-1,3-dihydro-benzoimidazol-2-one (117 mg, 0.550 mmol), provides the title compound. Purify by triturating with CH$_2$Cl$_2$ to obtain 85 mg (45%) of the title compound as a white powder. MS (ES) 339 (M+H), 337 (M–H); HPLC shows 93% purity.

PREPARATION 28

4-Bromo-1,3-dihydro-indol-2-one

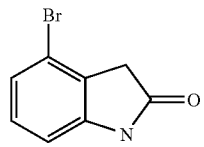

Add a solution of I$_2$ (2.62 g, 10.30 mmol) in DMF (10 mL) dropwise to a solution of 4-bromoindole (2.00 g, 10.20 mmol) and KOH (1.43 g, 25.5 mmol) in DMF (40 mL). Stir for 30 min at room temperature and add saturated aqueous Na$_2$SO$_3$. Stir at room temperature for 15 min, then dilute reaction mixture with ethyl acetate (100 mL). Wash organics three times with H$_2$O, dry organics (MgSO$_4$) and concentrate to a brown oil. Dissolve oil in 2-methoxyethanol (40 mL) and heat to 100° C. Add H$_3$PO$_4$ (9 mL) and heat to reflux for 48 h. Cool to room temperature and dilute with H$_2$O (75 mL). Extract into ethyl acetate, dry MgSO$_4$) and concentrate organics to a dark brown oil. Chromatograph on silica gel (90 g), eluting with 20% to 40% ethyl acetate/hexanes to afford 121 mg (6%) of the title compound as a tan solid. MS (ES) 212,214 (M+H), 210,212 (M–H); HPLC shows 76% purity.

EXAMPLE 224

4-(10,11-Dihydro-dibenzo[a,d]cyclohepten-5-ylidenemethyl)-1,3-dihydro-indol-2-one

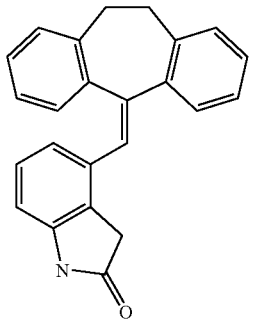

Following procedures essentially as described in Example 229 and using (10,11-dihydro-dibenzo[a,d]cyclohepten-5-ylidene)-boronic acid (0.0825M in toluene, 7.4Ml, 0.61 mmol) (concentrated to dryness before use in reaction). Add 4-bromo-1,3-dihydro-indol-2-one (108 mg, 0.510 mmol) to provide 37 mg (22%) of the title compound as a tan solid. MS (ES) 338 (M+H); HPLC shows 96% purity.

PREPARATION 29

2-(10,11-Dihydro-dibenzo[a,d]cyclohepten-5-ylidenemethyl)-phenylboronic acid

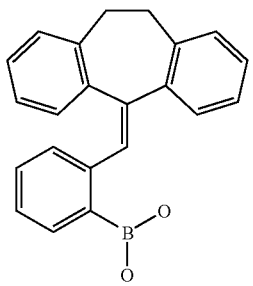

Add n-BuLi (1.6M in hexanes, 12.98 Ml, 20.76 mmol) portionwise (exothermic) to a solution of 5-(2-bromo-benzylidene)-10,11-dihydro-5H-dibenzo[a,d]cycloheptene (5.00 g, 13.84 mmol) in dry THF (50 Ml) at –78° C. under N$_2$. Let stir at –78° C. for 30 min, then add triisopropyl borate (5.21 g, 27.68 mmol) and warm up to room temperature overnight. Add 50 Ml 1.00N HCl and stir for 15 min. Extract into ethyl acetate, dry (MgSO$_4$) and concentrate organics to a brown foam. Recrystallize from boiling hexanes, then chromatograph on silica gel (40 g), eluting with 20% to 50% ethyl acetate/hexanes to afford the title compound as a white foam, mp 134.1° C. MS (ES) 325 (M–H); HPLC shows 82% purity.

EXAMPLE 225

2-[2-(10,11-Dihydro-dibenzo[a,d]cyclohepten-5-ylidenemethyl)-phenyl]-pyrazine

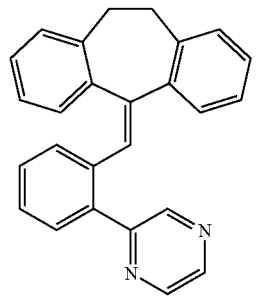

In a 1-dram vial, mix 2-(10,11-dihydro-dibenzo[a,d]cyclohepten-5-ylidenemethyl)-phenylboronic acid (100 mg, 0.307 mmol), chloropyrazine (69 mg, 0.460 mmol), cesium fluoride (94 mg, 0.614 mmol), and [1,1'-bis(diphenylphosphino)-ferrocene]dichloropalladium(II) (1:1 complex with CH$_2$C$_2$, 25 mg, 0.031 mmol) in dioxane (2 mL). Heat to 85° C. for 72 h, then remove solvent under nitrogen. Take up the resulting residue in H$_2$O (1 mL) and CH$_2$Cl$_2$ (1 mL) and load onto a Varian ChemElut CE1005 solid-phase extraction cartridge. Elute, collect, and concentrate 15 mL CH$_2$Cl$_2$ to obtain crude product. Purify by mass-guided reverse-phase HPLC to obtain 2.3 mg (2%) of the title compound. MS (ES) 361 (M+H); HPLC shows 93% purity.

EXAMPLE 226

4-[2-(10,11-Dihydro-dibenzo[a,d]cyclohepten-5-ylidenemethyl)-phenyl]-3,5-dimethyl-isoxazole

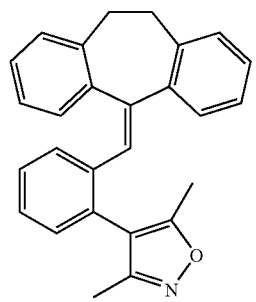

Following procedures essentially as described in Example 225 and using 2-(10,11-dihydro-dibenzo[a,d]cyclohepten-5-ylidenemethyl)-phenylboronic acid (100 mg, 307 mmol) and 4-bromo-3,5-dimethylisoxazole (81 mg, 0.460 mmol), provides the title compound in 2% yield. MS (ES) 378 (M+H); HPLC shows 94% purity.

EXAMPLE 227

2-[2-(10,11-Dihydro-dibenzo[a,d]cyclohepten-5-ylidenemethyl)-phenyl]-pyridine

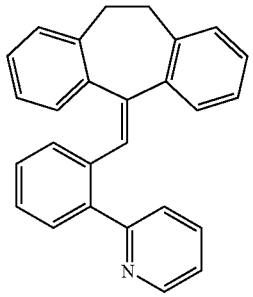

Following procedures essentially as described in Example 225 and using 2-(10,11-dihydro-dibenzo[a,d]cyclohepten-5-ylidenemethyl)-phenylboronic acid (100 mg, 0.307 mmol) and 2-chloropyridine (52 mg, 0.460 mmol), provides the title compound. Purify further via silica gel chromatography to obtain 14.7 mg (13%) of material that is 84% pure by HPLC. MS (S) 360 (M+H).

EXAMPLE 228

3-[2-(10,11-Dihydro-dibenzo[a,d]cyclohepten-5-ylidenemethyl)-phenyl]-pyridine

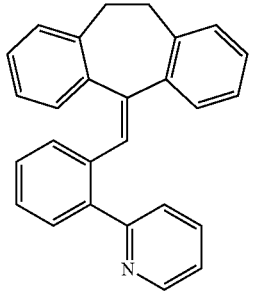

Following procedures essentially as described in Example 225 and using 2-(10,11-dihydro-dibenzo[a,d]cyclohepten-5-ylidenemethyl)-phenylboronic acid (100 mg, 0.307 mmol) and 3-bromopyridine (73 mg, 0.460 mmol) provides the title compound. Purify further via silica gel chromatography to obtain 14.9 mg (14%) of material that is 98% pure by HPLC. MS (ES) 360 (M+H).

EXAMPLE 229

5-[3-(10,11-Dihydro-dibenzo[a,d]cyclohepten-5-ylidenemethyl)-phenyl]-1H-pyrazole

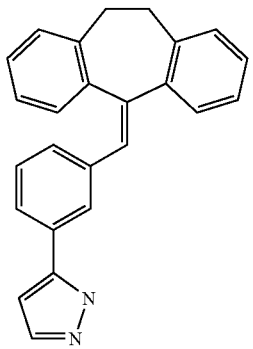

In a 6-dram vial mix (10,11-dihydro-dibenzo[a,d]cyclohepten-5-ylidene)-boronic acid (0.0825M in toluene, 10 mL, 0.825 mmol), 5-(3-bromo-phenyl)-1H-pyrazole (153 mg, 0.688 mmol), $K_2CO_3$ (570 mg, 4.125 mmol) and ethanol (5 mL). Sparge reaction mixture with $N_2$ for 10 min and add $Pd(PPh_3)_4$ (56 mg, 0.048 mmol). Seal vial immediately and heat to 85° C. for 72 h. Concentrate under $N_2$, then add $H_2O$ (1 mL) and ethyl acetate (1 mL). Load onto a Varian ChemElut CE1005 solid-phase extraction cartridge. Elute, collect, and concentrate 30 mL ethyl acetate. Chromatograph on 35 g silica gel, eluting with 25% to 35% ethyl acetate/hexanes. Re-purify by UV-guided semi-preparatory reverse-phase HPLC to afford 35 mg (15%) of the title compound as a milky white oil. MS (ES) 349 (M+H), 347 (M−H); HPLC shows 99% purity.

EXAMPLE 230

6-(10,11-Dihydro-dibenzo[a,d]cyclohepten-5-ylidenemethyl)-pyridin-2-ylamine

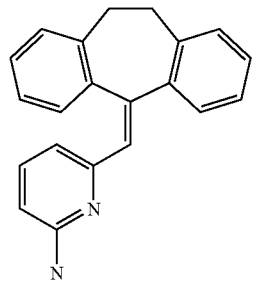

Following procedures essentially as described in Example 219 and using 2-amino-6-bromopyridine (95 mg, 0.550 mmol) and (10,11-dihydro-dibenzo[a,d]cyclohepten-5-ylidene)-boronic acid (0.197M in dioxane, 3.35 mL, 0.660 mmol), provides 98 mg (60%) of the title compound as a yellow oil. MS (ES) 299 (M+H); HPLC shows 97% purity.

EXAMPLE 231

N-[6-(10,11-Dihydro-dibenzo[a,d]cyclohepten-5-ylidenemethyl)-pyridin-2-yl]-methanesulfonamide

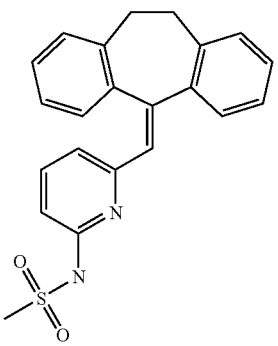

Mix 6-(10,11-dihydro-dibenzo[a,d]cyclohepten-5-ylidenemethyl)-pyridin-2-ylamine (70 mg, 0.235 mmol), triethylamine (68 μL, 0.470 mmol), N,N-dimethylaminopyridine (3 mg, 0.024 mmol), and methanesulfonyl chloride (19 μL, 0.247 mmol) in CH$_2$Cl$_2$ (2 mL). Stir at room temperature overnight and add 150 μL triethylamine and 40 μL methanesulfonyl chloride. Stir at room temperature for 6 h and add 1.00N aqueous HCl (1 mL). Load mixture onto a Varian ChemElut CE1005 solid-phase extraction cartridge, then elute, collect, and concentrate 45 mL CH$_2$Cl$_2$. Dissolve crude product in THF (5 mL), add 1.0M tetrabutylammonium fluoride (0.25 mL), and heat to reflux for 1 h. Cool to room temperature and dilute with H$_2$O and brine. Extract into ethyl acetate, dry (MgSO$_4$) and concentrate organics. Chromatograph on silica gel (10 g), eluting with 20% to 35% ethyl acetate/hexanes to afford 61 mg (69%) of the title compound as a yellow oil. MS (ES) 377 (M+H), 375 (M−H); BPLC shows 96% purity.

EXAMPLE 232

6-(10,11-Dihydro-dibenzo[a,d]cyclohepten-5-ylidenemethyl)-pyrazin-2-ylamine

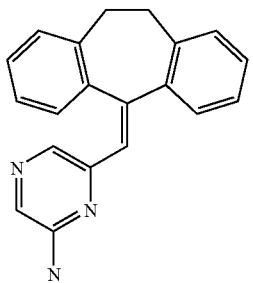

Following procedures essentially as described in Example 219 and using 2-amino-6-chloropyrazine (71 mg, 0.550 mmol) and (10,11-dihydro-dibenzo[a,d]cyclohepten-5-ylidene)-boronic acid (0.197M in dioxane, 3.35 mL, 0.660 mmol), provides the title compound. Purify by recrystallization (ethyl acetate/hexanes) to obtain 48 mg (29%) of the title compound as a yellow solid. MS (ES) 300 (M+H); HPLC shows 96% purity.

EXAMPLE 233

N-[6-(10,11-Dihydro-dibenzo[a,d]cyclohepten-5-ylidenemethyl)-pyrazin-2-yl]-methanesulfonamide

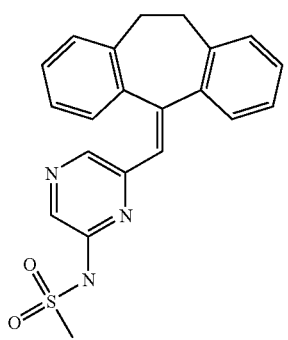

Mix 6-(10,11-dihydro-dibenzo[a,d]cyclohepten-5-ylidenemethyl)-pyrazin-2-ylamine (35 mg, 0.117 mmol), triethylamine (34 μL, 0.234 mmol), N,N-dimethylaminopyridine (2 mg, 0.018 mmol), and methanesulfonyl chloride (10 μL, 0.123 mmol) in CH$_2$Cl$_2$ (2 mL). Stir at room temperature overnight and add 150 μL triethylamine and 40 μL methanesulfonyl chloride. Stir at room temperature for 6 h and add 1.00N aqueous HCl (1 mL). Load mixture onto a Varian ChemElut CE1005 solid-phase extraction cartridge, then elute, collect, and concentrate 45 mL CH$_2$Cl$_2$. Dissolve crude product in THF (5 mL), add 1.0M tetrabutylammonium fluoride (0.30 mL), and heat to reflux for 1 h. Cool to room temperature and dilute with H$_2$O and brine. Extract into ethyl acetate, dry (MgSO$_4$) and concentrate organics. Chromatograph on silica gel (4 g), eluting with 20%→35% ethyl acetate/hexanes to afford 19 mg (43%) of the title compound as a white solid. MS (ES) 378 (M+H), 376 (M−H); HPLC shows 100% purity.

EXAMPLE 234

2-(10,11-Dihydro-dibenzo[a,d]cyclohepten-5-ylidenemethyl)-pyridin-4-ylamine

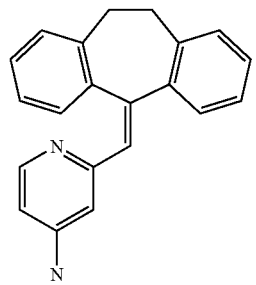

Following procedures essentially as described in Example 225 and using 4-amino-2-chloropyridine (216 mg, 1.68 mmol) and (10,11-dihydro-dibenzo[a,d]cyclohepten-5-ylidene)-boronic acid (0.197M in dioxane, 10.2 mL, 2.01 mmol), provides the title compound. Chromatograph on silica gel (35 g), eluting with 40% to 60% ethyl acetate/hexanes to afford 250 mg (42%) of the title compound as a brown oil. MS (ES) 299 (M+H). HPLC shows 98% purity.

EXAMPLE 235

N-[2-(10,11-Dihydro-dibenzo[a,d]cyclohepten-5-ylidenemethyl)-pyridin-4-yl]-methanesulfonamide

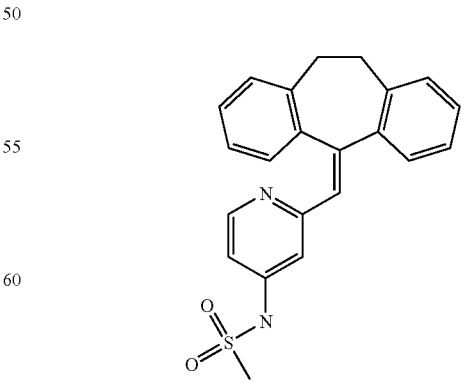

Mix 2-(10,11-dihydro-dibenzo[a,d]cyclohepten-5-ylidenemethyl)-pyridin-4-ylamine (176 mg, 0.590 mmol), triethylamine (600 μL, 4.13 mmol), N,N-dimethylaminopyridine (7 mg, 0.059 mmol), and methanesulfonyl chloride (137 μL, 1.769 mmol) in CH₂Cl₂ (10 mL). Stir at room temperature for 3 h and dilute with H₂O (15 mL). Extract into CH₂Cl₂, dry (MgSO₄) and concentrate organics. Dissolve crude product in THF (10 mL), add 1.0M tetrabutylammonium fluoride (0.89 mL), and heat to reflux for 4 h. Cool to room temperature and dilute with H₂O. Extract into ethyl acetate, dry (MgSO₄) and concentrate organics. Chromatograph on silica gel (10 g), eluting with 80% →90% ethyl acetate/hexanes to afford 150 mg (68%) of the title compound as a yellow foam. MS (ES) 377 (M+H), 375 (M−H); BPLC shows 96% purity.

EXAMPLE 236

5-(10,11-Dihydro-dibenzo[a,d]cyclohepten-5-ylidenemethyl)pyridin-3-ol

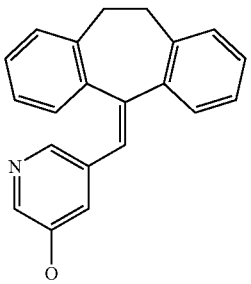

Following procedures essentially as described in Example 225 and using 5-chloro-2-pyridinol (77 mg, 0.591 mmol) and (10,11-dihydro-dibenzo[a,d]cyclohepten-5-ylidene)-boronic acid (0.197M in dioxane, 3.58 mL, 0.709 mmol), provides the title compound. Chromatograph on silica gel (10 g), eluting with 60% to 75% ethyl acetate/hexanes to give 40 mg of brown oil. Re-chromatograph on silica gel (5 g) eluting with 60% ethyl acetate/hexanes to afford 15 mg (8%) of the title compound as a brown oil. MS (ES) 300 (M+H), 298 (M−H); HPLC shows 95% purity.

EXAMPLE 237

4-(10,11-Dihydro-dibenzo[a,d]cyclohepten-5-ylidenemethyl)-1H-pyrazole

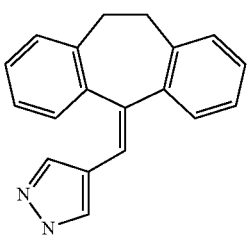

Following procedures essentially as described in Example 229 and using 4-iodopyrazole (107 mg, 0.55 mmol) and (10, 11-dihydro-dibenzo[a,d]cyclohepten-5-ylidene)-boronic acid (0.198M in dioxane, 4.2 mL, 0.825 mmol), provides 27 mg (18%) of the title compound as a colorless oil. MS (ES) 273 (M+H), 271 (M−H). HPLC shows 98% purity.

EXAMPLE 238

4-Benzylidene-9,10-hydro-4H-1-thia-benzo[f]azulene (E and Z Isomer)

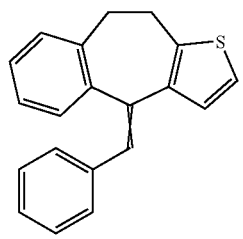

A. Add a 1.0 M solution of benzyl magnesium bromide (0.5 mL, 0.5 mmol) in THF to a solution of 9,10-dihydro-1-thia-benzo[f]azulene4-one (20.8 mg, 0.97 mmol) (prepared according to procedures of Bollinger, P.; Cooper, P.; Gubler, H. U.; Leutwiler, A.; Payne, T. *Helv. Chim. Acta* 1990, 73, 1197) in 1.0 mL of THF under Ar. Stir the resulting solution for 2 h at 25° C. before quenching with ca. 100 μL of saturated, aqueous ammonium chloride. Filter the mixture and wash the magnesium salts with copious amounts of diethyl ether. Wash the filtrate with 1-mL portions of water and brine, dry (Na₂SO₄) and concentrate under reduced pressure. The tertiary alcohol can be purified by column chromatography (9:1 hexanes:ethyl acetate).

B. Dissolve the crude oil in 1.5 mL of CHCl₃, add ca. 40 μL (2 drops) of concentrated hydrochloric acid, and then stir the resulting dark solution for 2 h at 25° C. Add 1 mL of water and 1 mL of CHCl₃, separate the layers, and wash the organic layer successively with 0.5-mL portions of saturated, aqueous sodium bicarbonate and brine. Dry (MgSO₄) and concentrate via rotary evaporation. Purify by flash chromatography (hexanes) to afford 6.7 mg (24%, 2 steps) of a white solid as a 2:1 mixture of E- and Z-isomers. MS (CI): 289 (M+1). ¹H NMR (CDCl₃, 400 MHz) δ 2.90-3.60 (m, 4 H), 6.53 (d, J=5.4 Hz, 1/3 H), 6.66 (s, 1/3 H), 6.86 (d, J=5.4 Hz, 1/3 H), 6.94 (s, 2/3 H), 7.01-7.34 (m, 10 H), 7.39-7.41 (m, 2/3 H); HPLC shows >95% purity: $t_R$=5.854 min (E+Z; 80:20 MeOH:H₂O to MeOH).

Section 4 (derivatives of Formula I wherein the "A" and/or "B" ring represents a heterocyclic ring.)

EXAMPLE 239

4-(2,4-Dichloro-benzylidene)-9,10-dihydro-4H-1-thia-benzo[f]azulene (Mixture of E and Z Isomers)

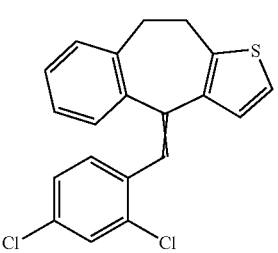

Following the procedures essentially as described in Example 238 and using 9,10-dihydro-1-thia-benzo[f]azulene-4-one (40.8 mg, 0.19 mmol) and 2,4-dichlorobenzyl magnesium chloride (0.575 mmol) in THF:diethyl provides, after dehydration, 30.0 mg (44%) of the title compound as a 3:1 mixture of E- and Z-isomers. $^1$H NMR (CDCl$_3$) δ 2.88-3.40 (m, 4 H), 6.26 (d, J=4.8 Hz, 1/4 H), 6.50 (d, J=8.2 Hz, 3/4 H); 6.63 (s, 1/4 H, Z), 6.74 (s, 3/4 H), 6.76 (td, J=8.6 Hz, 2.0 Hz, 3/4 H), 6.88 (td, J=8.2 Hz, 1.2 Hz, 3/4 H), 6.96 (s, 3/4 H), 6.95-6.98 (m, 1/4 H), 7.06 (d, J=4.8 Hz, 3/4 H), 7.08-7.20 (m, 14/4 H), 7.28 (d, J=2.0 Hz, 3/4 H), 7.34 (d, J=2.4 Hz, 1/4 H), 7.35-7.38 (m, 1/4 H); TLC shows 0.95% purity: R$_f$=0.20 (hexanes).

EXAMPLE 240

4-(3,5-Dimethyl-benzylidene)-9,10-dihydro-4H-1-thia-benzo[f]azulene (Mixture of E- and Z-Isomers)

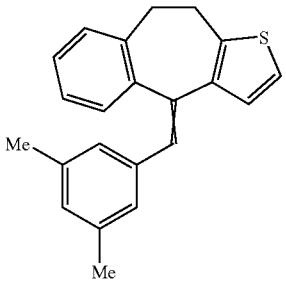

Following the procedures essentially as described in Example 238 and using 9,10-dihydro-1-thia-benzo[f]azulene-4-one (47.0 mg (0.22 mmol) and solution of 3,5-dimethylbenzyl magnesium bromide(0.650 mmol) in THF, provides, after dehydration, 39.6 mg (57%) of the title compound as a 1.6:1 mixture of E- and Z-isomers. MS (EI): 316 (M$^+$); $^1$H NMR (CDCl$_3$) δ 2.13 (s, 18/5 H), 2.24 (s, 12/5 H), 2.40-3.80 (m, 4 H), 6.54 (d, J=5.6 Hz, 2/5 H), 6.53-6.55 (m, 7/5 H), 6.74 (s, 3/5 H), 6.83-6.84 (m, 2/5 H), 6.86 (s, 3/5 H), 6.93 (s, 3/5 H), 7.01-7.02 (m, 1 H), 7.08 (app d, J=5.6 Hz, 2/5 H), 7.14 (app d, J=5.6 Hz, 2/5 H), 7.19-7.25 (m, 4 H), 7.30 (d, J=8.0 Hz, 3/5 H), 7.37-7.39 (m, 2/5 H).

EXAMPLE 241

E- and Z-4-Benzylidene-9,10-dihydro-4H-3-thia-benzo[f]azulene (Mixture of E- and Z-Isomers)

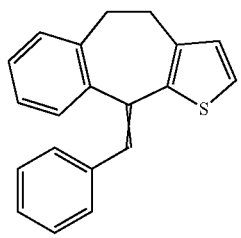

Following the procedures essentially as described in Example 238 and using 9,10-dihydro-3-thia-benzo[f]azulene-4-one (32.9 mg, 0.153 mmol) (prepared according to Hallberg, A.; Pedaja, P. *Tetrahedron* 1983, 39, 819) and solution of benzyl magnesium bromide (0.470 mmol) in THF, provides 15.1 mg (34%) of the title compound as a 4:1 mixture of E- and Z-isomers: MS (CI): 289 (M+1); $^1$H NMR (CDCl$_3$) δ 2.98-3.12 (m, 4 H), 6.61 (d, J=5.2 Hz, 1/5 H), 6.65 (s, 1/5 H); 6.66 (d, J=5.6 Hz, 4/5 H), 6.96 (s, 4/5 H), 6.97 (d, J=3.2 Hz, 4/5 H), 6.97 (d, J=3.2 Hz, 4/5 H), 6.96 (s, 38/5 H), 7.28-7.31 (m, 4/5 H).

EXAMPLE 242

4-(2,4-Dichloro-benzylidene)-9,10-dihydro-4H-3-thia-benzo[f]azulene (E- and Z-Isomers)

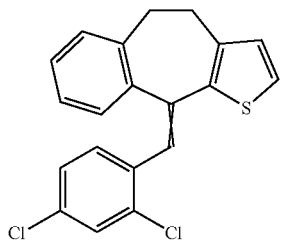

Following the procedures essentially as described in Example 238 and using 9,10-dihydro-3-thia-benzo[f]azulene-4-one (23.3 mg, 0.108 mmol) and solution of 2,4-dichlorobenzyl magnesium chloride (0.325 mmol) in THF provides, after dehydration, 12.5 mg (32%) of the title compound as a 3:1 mixture of E- and Z-isomers: $^1$H NMR (CDCl$_3$) δ 2.88-3.40 (m, 4 H), 6.26 (d, J=4.8 Hz, 1/4 H), 6.50 (d, J=8.2 Hz, 3/4 H); 6.63 (s, 1/4 H, Z), 6.74 (s, 3/4 H), 6.76 (td, J=8.6 Hz, 2.0 Hz, 3/4 H), 6.88 (td, J=8.2 Hz, 1.2 Hz, 3/4 H), 6.96 (s, 3/4 H), 6.95-6.98 (m, 15/4 H), 7.28 (d, J=2.0 Hz, 3/4 H), 7.34 (d, J=2.4 Hz, 1/4 H), 7.35-7.38 (m, 1/4 H); TLC shows >95% purity: R$_f$=0.20 hexanes).

EXAMPLE 243(a) AND (b)

E-N-[3-(9,10-Dihydro-1-thia-benzoazulen-4-ylidenemethyl)-phenyl]-methanesulfonamide (E-isomer) and Z-N-[3-(9,10-Dihydro-1-thia-benzoazulen-4-ylidenemethyl)-phenyl]-methanesulfonamide (Z-isomer)

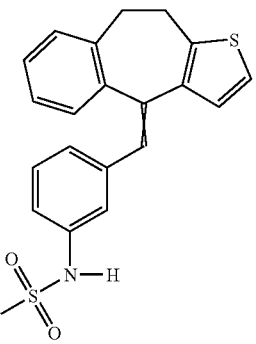

Following the procedures essentially as described in Example 219 and using 4-bromomethylene-9,10-dihydro-4H-1-thia-benzo[f]azulene (54.1 mg, 0.186 mmol) and 3-methylsulfonaminophenyl boronic acid (43.4 mg, 0.202 mmol), (prepared according to M. L. Quan, J. Wityak, C. Dominguez, J. V. Duncia, C. A. Kettner, C. D. Ellis, A. Y. Liauw, J. M. Park, J. B. Santella, R. M. Knabb, M. J. Thoolen, P. C. Weber and R. R. Wexler *Bioorg. Med. Chem. Lett.* 1997, 13, 1595), provides the title compound. Purify the crude residue by column chromatography (hexanes to 7:3 hexanes:ethyl acetate) to give 49.7 mg (ca. 70%) of the title compound as a 1:1 mixture of E- and Z-isomers. The isomers were separated via HPLC on a Waters Symmetry C18 5-μm 19-mm×300-mm semi-preparatory column using a 7:3 MeCN:H$_2$0 (0.1% TFA) eluent and were identified on the basis of the following spectroscopic properties. E-N-[3-(9,10-Dihydro-1-thia-benzoazulen-4-ylidenemethyl)-phenyl]-methanesulfonamide (Example 243)a)): MS (CI): 382 (M+1); $^1$H NMR (CDCl$_3$, 400 MHz) δ 2.78 (s, 3 H), 2.90-3.45 (m, 4 H), 6.12 (s, 1 H), 6.72 (app s, 1 H), 6.91 (s, NH, 1 H), 6.93-7.03 (m, 3 H), 7.10-7.23 (m, 4 H), 7.32 (d, J=7.8 Hz, 1 H); HPLC shows >95% purity: $t_R$=3.194 min (80:20 MeOH:H$_2$0 to MeOH). Z-N-[3-(9,10-Dihydro-1-thia-benzoazulen-4-ylidenemethyl)-phenyl]-methanesulfonamide (Example 243(b)): MS (CI): 382 (M+1); $^1$H NMR (CDCl$_3$, 400 MHz) δ 2.94 (s, 3 H), 3.24 (br s, 4 H), 6.50 (d, J=5.0 Hz, 1 H), 6.64 (s, 1H), 6.88 (d, J=5.0 Hz, 1 H), 7.08-7.18 (m, 3 H), 7.26-7.30 (m, 4 H), 7.38-7.40 (m, 1 H); HPLC shows >95% purity: $t_R$=3.194 min (80:20 MeOH:H$_2$0 to MeOH).

EXAMPLE 244

3-(8-Chloro-5,6-dihydro-benzo[5,6]cyclohepta[1,2-b]pyridin-11-ylidenemethyl)-phenol, (Z-isomer)

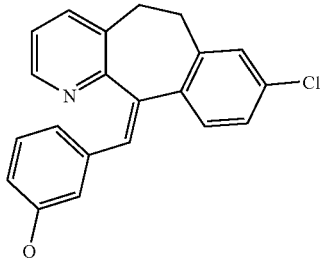

A. Prepare 11-(3-bromo-benzylidene)-8-chloro-6,11-dihydro-5H-benzo[5,6]cyclohepta[1,2-b]pyridine according to procedures essentially as described in Example 28 using m-bromobenzylmagnesium bromide (7.5 mmol)and 8-chloro-5,6-dihydro-benzo[5,6]cyclohepta[1,2-b]pyridin-11-one (600 mg, 2.5 mmol) in ether (25 mL). Separate the E and Z isomers by column chromatography (15% ethyl acetate/hexane).

B. Separately, convert each isomer to the hydroxyl derivative by using the following procedure: Mix 11-(3-bromobenzylidene)-8-chloro-6,11-dihydro-5H-benzo[5,6]cyclohepta[1,2-b]pyridine (500 mg, (1.26 mmol),pinacol diborane (416 mg, 1.64 mmol), KOAc (375 mg, 3.8 mmol) in DMSO (10 mL). Sparge with nitrogen for 10 minutes and then add Pd(dppf)Cl$_2$ (160 mg, 0.2 mmol) and heat at 80° C. for 4 h. Shake with water and ethyl acetate. Dry the organic layer (MgSO$_4$) and concentrate to give 650 mg crude product. Purify by column chromatography (15% ethyl acetate/hexane) to give 310 mg (56%) 8-chloro-11-[3-(4,4,5,5-tetramethyl-[1,3,2]dioxaborolan-2-yl)-benzylidene]-6,11-dihydro-5H-benzo[5,6]cyclohepta[1,2-b]pyridine. MS (ES) 444 (M+1). Purify by HPLC is 89%.

C. Mix 8-chloro-11-[3-(4,4,5,5-tetramethyl-[1,3,2]dioxaborolan-2-yl)-benzylidene]-6,11-dihydro-5H-benzo[5,6]cyclohepta[1,2-b]pyridine (300 mg, 0.68 mmol), HOAc (1 mL), water (1 mL), THF (5 mL) and 30% H$_2$O$_2$ (mL). Stir the reaction at RT for 4 h. Quench with aqueous Na$_2$S$_2$O$_3$ and extract the product into EtOAc. Dry (MgSO$_4$) and concentrate to give 250 mg crude product. Purify by column chromatography (15% ethyl acetate/hexane) to give 66 mg 3-(8-chloro-5,6-dihydro-benzo[5,6]cyclohepta[1,2-b]pyridin-11-ylidenemethyl)-phenol, Z-isomer as a white solid, mp 221.2° C. MS (ES) 334 (M+1), 332 (M−1). HPLC shows 99% purity.

EXAMPLE 245

3-(8-Chloro-5,6-dihydro-benzo[5,6]cyclohepta[1,2-b]pyridin-11-ylidenemethyl)-phenol, (E-isomer)

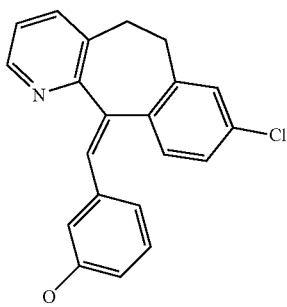

Prepared as described in Example 244, above, to provide 90 mg (57%) product as a white solid, mp>250° C. MS (ES) 334 (M+1), 332 (M−1). HPLC shows 94% purity.

EXAMPLE 246

N-[3-(8-Chloro-5,6-dihydro-benzo[5,6]cyclohepta[1,2-b]pyridin-11-ylidenemethyl)-phenyl]-methanesulfonamide(E isomer,)

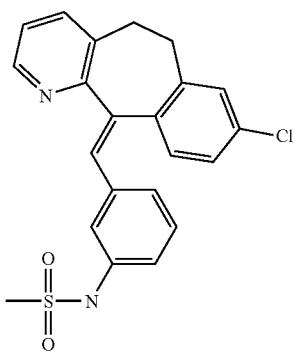

Following procedures as described in Example 219 and using 11-bromomethylene-8-chloro-6,11-dihydro-5H-benzo[5,6]cyclohepta[1,2-b]pyridine (E-isomer)(820 mg,2.56 mmol) and 3-methanesulfonylaminophenylboronic acid (605 mg,2.8 mmol), provides the title compound in 53% yield as a white foam after purification on silica gel using 50% EtOAc/ hexane. MS (ES) 411 (M+1), 409 9M−1). HPLC shows 97% purity.

EXAMPLE 247

N-[3-(2-Methyl-9,10-dihydro-1-oxa-3-aza-benzo[f] azulen-4-ylidenemethyl)-phenyl]-methanesulfonamide

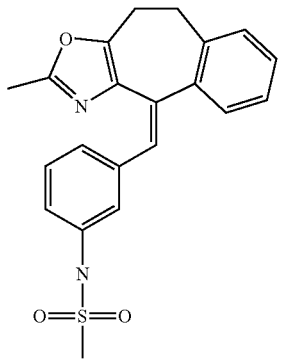

Prepare the corresponding ketone (2-methyl-9,10-dihydro-1-oxa-3-aza-benzo[f]azulen-4-one) as described by E. E. Galantay, et al, J. Med. Chem. (17) 1316-1327 (1974) and convert to the corresponding Z-isomer of the vinyl bromide using procedures essentially as described in Preparations 23 and 24. Then, following procedures essentially as described in Example 219, combine the ketone with 3-methanesulfonamidophenyl boronic acid (325 mg, 1.5 mmmol). Purify the crude product using column chromatography (30% EtOAc/ hexane to 50% EtOAc/hexane) to provide 180 mg (38%) Z-isomer as a light tan solid, mp 184.6° C., MS (ES) 381 (M+1), 379 (M−1). HPLC shows 94% purity at t=1.99 min.

EXAMPLE 248

3-(2-Methyl-9,10-dihydro-1-oxa-3-aza-benzo[f]azulen-4-ylidenemethyl)-phenol

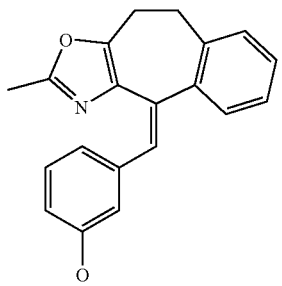

Prepare the corresponding ketone (2-methyl-9,10-dihydro-1-oxa-3-aza-benzo[f]azulen-4-one) as described by E. E. Galantay, et al, J. Med. Chem. (17) 1316-1327 (1974) and convert to the corresponding Z-isomer of the vinyl bromide using procedures essentially as described in Preparations 23 and 24. Then, following procedures essentially as described in Example 219, combine the ketone with 3-hydroxyphenyl boronic acid (207 mg, 1.5 mmmol). Purify the crude product using column chromatography (15% EtOAc/hexane to 30% EtOAc/hexane) to give 26 mg title compound, MS (ES) 304 (M+1). HPLC shows 93% purity at t=2.48 min.

EXAMPLE 249

(E)-N-[3-(5,6-Dihydro-benzo[5,6]cyclohepta[1,2-b] pyridin-11-ylidenemethyl)-phenyl]-methanesulfonamide (LY2076945, JN9-A01943-65)

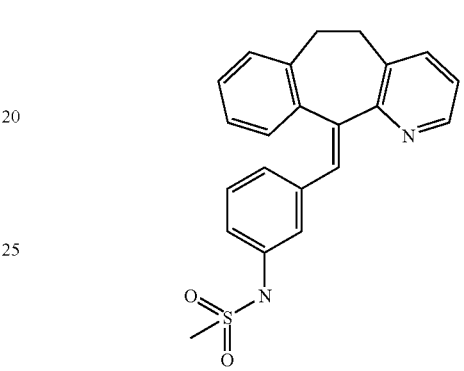

Following procedures essentially as described in Example 219, combine 11-bromomethylene-6,11-dihydro-5H-benzo [5,6]cyclohepta[1,2-b]pyridine (250 mg, 0.87 mmol) and 3-methanesulfonamide-phenyl boronic acid (244 mg, 1.1 mmol). Purify the product via flash chromatography, eluting the product with solutions of increasing concentrations of ethyl acetate in hexanes (10% to 50%). Combine product fractions, concentrate and dry to yield 190 mg (58%) of product as a white solid. LC/MS (APCI-pos): 377.1 (M+H). $^1$H NMR (CDCl$_3$, 400 MHz): δ8.49 (dd,1H), 7.42 (d,1H), 7.32 (s,1H), 7.29 (d,1H), 7.23-7.11 (m,3H), 7.01 (bd,3H), 6.94 (d,1H), 6.86 (s,2H), 3.6-2.9 (bm, 4H), 2.78 (s,3H).

EXAMPLE 250

(E)-3-(5,6-Dihydro-benzo[5,6]cyclohepta[1,2-b] pyridin-11-ylidenemethyl)-phenol

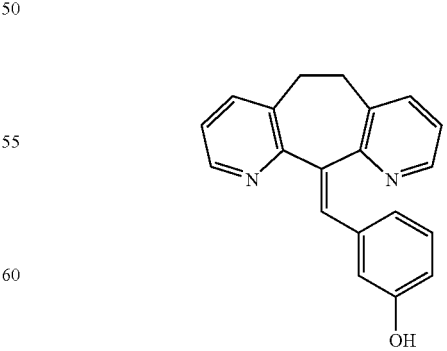

Following procedures essentially as described in Example 219, combine 11-bromomethylene-6,11-dihydro-5H-benzo [5,6]cyclohepta[1,2-b]pyridine (250 mg, 0.87 mmol) and

EXAMPLE 251

(Z)-N-[3-(10,11-Dihydro-benzo[4,5]cyclohepta[1,2-b]pyridin-5-ylidenemethyl)-phenyl]-methanesulfonamide

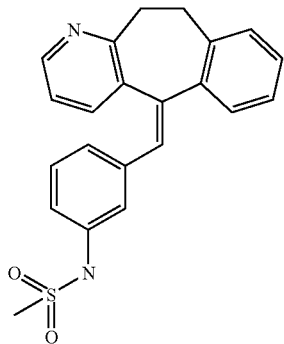

Following procedures essentially as described in Example 219, combine (Z)-5-bromomethylene-10,11-dihydro-benzo[4,5]cyclohepta[1,2-b]pyridine (153 mg, 0.53 mmol) with 3-methanesulfonamide-phenyl boronic acid (150 mg, 0.7 mmol). After work-up, purify the crude product by flash chromatography (10% ethyl acetate/hexanes to 25% ethyl acetate/hexanes to 50% ethyl acetate/hexanes) to provide 180 mg (90%) of purified product. LC/MS: 377.1 (M+H) 375 (M−H). Purity by LC/MS 95%.

EXAMPLE 252

(Z)-3-(10,11-Dihydro-benzo[4,5]cyclohepta[1,2-b]pyridin-5-ylidenemethyl)-phenol

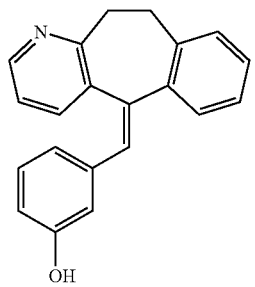

Following procedures essentially as described in Example 219, combine (Z)-5-bromomethylene-10,11-dihydro-benzo[4,5]cyclohepta[1,2-b]pyridine (153 mg, 0.53 mmol) 3-hydroxyphenyl boronic acid (85 mg, 0.59 mmol). After work-up, purify the crude product by flash chromatography (10% ethyl acetate/hexanes to 25% ethyl acetate/hexanes to 50% ethyl acetate/hexanes) to provide 68 mg (43%) of purified product.
LC/MS: (300.1 (M+H). Purity by HPLC is 95%.

EXAMPLE 253

(E)-N-[3-(10,11-Dihydro-benzo[4,5]cyclohepta[1,2-b]pyridin-5-ylidenemethyl)-phenyl]-methanesulfonamide

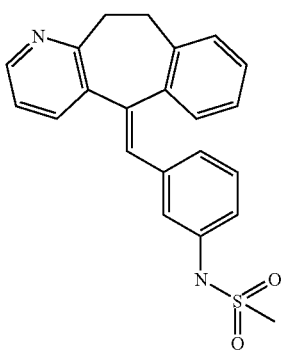

Following procedures essentially as described in Example 219, combine (E)-5-bromomethylene-10,11-dihydro-benzo[4,5]cyclohepta[1,2-b]pyridine (105 mg, 0.37 mmol) 3-methanesulfonamide-phenyl boronic acid (103 mg, 0.18 mmol). After work-up, purify the crude product by flash chromatography (10% ethyl acetate/hexanes to 25% ethyl acetate/hexanes to 50% ethyl acetate/hexanes) to provide 105 mg (76%) of purified product. LC/MS: 377.1 (M+H), 375 (M−H). Purity by LC/MS is 95%. $^1$HNMR (CDCl$_3$, 400 MHz): δ8.44 (dd,1H), 7.82 (dd,1H), 7.31 (d,2H), 7.26-7.14 (m,3H), 7.03 (dq,2H), 6.95 (dd,1H), 6.87 (d,1H), 6.80-6.77 (m,3H), 3.6-2.9 (bm,4H), 2.80 (s,3H).

EXAMPLE 254

(E)-3-(10,11-Dihydro-benzo[4,5]cyclohepta[1,2-b]pyridin-5-ylidenemethyl)-phenol

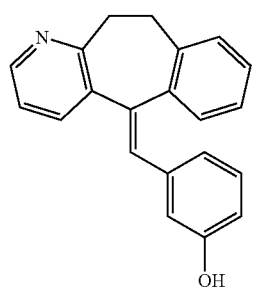

Following procedures essentially as described in Example 219, combine (E)-5-bromomethylene-10,11-dihydro-benzo[4,5]cyclohepta[1,2-b]pyridine (105 mg, 0.37 mmol) 3-hydroxyphenyl boronic acid (58 mg, 0.4 mmol). After work-up, purify the crude product by flash chromatography (10% ethyl acetate/hexanes to 25% ethyl acetate/hexanes to 50% ethyl acetate/hexanes) to provide 45 mg (41%) of purified product. LC/MS: 300.1 (M+H).
$^1$H NMR (CDCl$_3$, 400 MHz): δ8.25 (d,1H), 7.79 (d,1H), 7.18-7.12 (m,1H), 7.01-6.90 (m,5H), 6.68 (s,1H), 6.58 (dd, 1H), 6.54 (d,1H), 6.37 (s,1H), 3.5-2.6 (m,4H).

Section 5 (derivatives of Formula I wherein the bridge depicted by —X—Y— represents a fused cyclopropyl structure.)

---

(3-hydroxyphenyl) boronic acid (133 mg, 0.96 mmol). Purify to provide product 166 mg (63%) as an off-white solid. LC/MS: 300.1 (M+H). $^1$H NMR (DMSO, 400 MHz): δ9.22 (s,1H), 8.40 (d,1H), 7.49 (d,1H), 7.34 (d,1H), 7.24 (d,1H), 7.21 (d,3H), 7.15 (s,1H), 7.04 (t,1H), 6.92 (d,1H), 6.90 (d,1H), 6.52 (d,1H), 6.40-6.42 (m,2H), 3.4-2.8 (m,4H).

EXAMPLE 255

N-[3-(8,8-Difluoro-4-ylidine methyl-2,3,5,6-dibenzobicyclo[5.1.0]octane)-phenyl]-methanesulfonamide

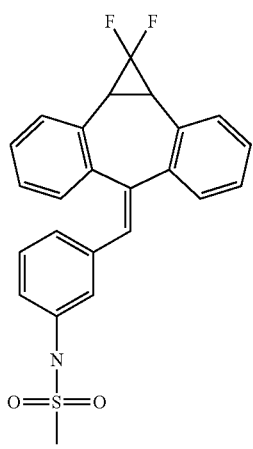

Following procedures essentially as described in Example 219 and using 8,8-difluoro-4-bromomethylene-2,3,5,6-dibenzobicyclo[5.1.0]octane (163 mg, 0.4 mmol) and 3-(methylsulfonamido)phenylboronic acid (116 mg, 0.54 mmol) to provide the title compound. Evaporate and purify on silica gel (methanol/dichloromethane) to obtain 99 mg (48%) of the title compound. Add ethyl acetate to obtain a crystalline material. MS (ES) 423 (M−1).

EXAMPLE 256

N-[3-(8,8-Difluoro-4-ylidine methyl-2,3,5,6-dibenzobicyclo[5.1.0]octane)-phenol

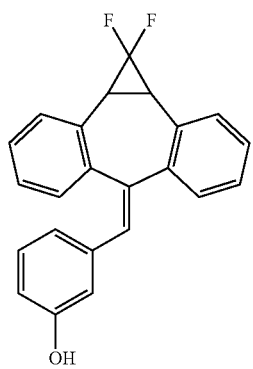

Following procedures essentially as described in Example 219 and using 8,8-difluoro-4-bromomethylene-2,3,5,6-dibenzobicyclo[5.1.0]octane (166 mg, 0.5 mmol) and (3-hydroxypheny)boronic acid (76 mg, 0.55 mmol). Purify with silica gel (ethyl acetate/hexanes) chromatography to obtain 103 mg (60%) foam. MS (ES) 346 (M−1).

EXAMPLE 257

N-[3-(4-Ylidine methyl-2,3,5,6-dibenzobicyclo[5.1.0]octane)-phenyl]-methanesulfonamide

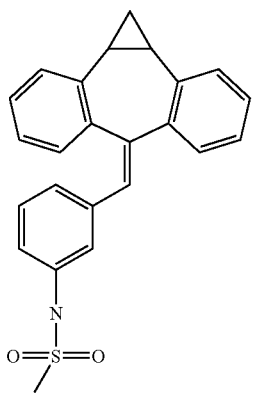

Following procedures essentially as described in Example 219 and using 4-bromomethylene-2,3,5,6-dibenzobicyclo[5.1.0]octane (208 mg, 0.7 mmol) and 3-(methylsulfonamido)phenylboronic acid (166 mg, 0.77 mmol) to provide the title compound. Purify on silica gel using methanol/dichloromethane and ethyl acetate/hexanes by radial chromatography. Obtain 83.5 mg (31%). MS (ES) 387 (M−1).

EXAMPLE 258

N-[3-(4-Ylidine methyl-2,3,5,6-dibenzobicyclo[5.1.0]octane)-phenol

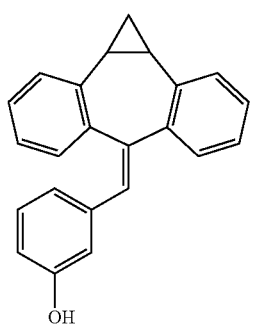

Following procedures essentially as described in Example 219 and using 4-bromomethylene-2,3,5,6-dibenzobicyclo[5.1.0]octane (208 mg, 0.7 mmol) and (3-hydroxypheny)boronic acid (106 mg, 0.77 mmol) to provide the title compound. Evaporate the reaction and add to a Celite cartridge using dichloromethane. Elute with dichloromethane. Evaporate the eluent and purify on silica gel ethyl acetate/hexanes chromatography to obtain 60 mg (28%) of the title compound as a foam. GC/MS t=21.49 min MW=310.

EXAMPLE 259

N-[3-(8,8-Dichloro-4-ylidene methyl-2,3,5,6-dibenzobicyclo[5.1.0]octane)-phenyl]-methanesulfonamide

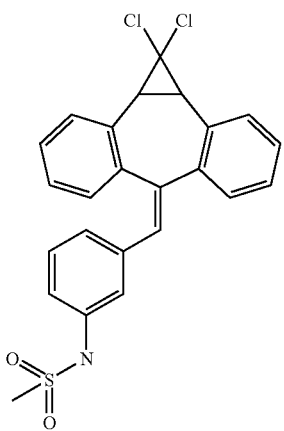

Following procedures essentially as described in Example 219, combine 8,8-Dichloro-4-bromomethylene-2,3,5,6-dibenzobicyclo[5.1.0]octane (160 mg, 0.44 mmol) and 3-methanesulfonamide-phenyl boronic acid (103 mg, 0.48 mmol to provide the title compound. Purify the product using radial chromatography eluting the product with solutions of increasing concentrations of ethyl acetate in hexanes (5, 10, 15, 20, and 25%). Combine product fractions, concentrate and dry to yield 120 mg (60%) of product as a white solid, mp 199-201° C. LC/MS (ES): 474 (M+NH$_4$$^+$), 456 (M$^+$).

EXAMPLE 260

N-[3-(8,8-Dichloroylidene methyl-2,3,5,6-dibenzobicyclo[5.1.0]octane)-phenol

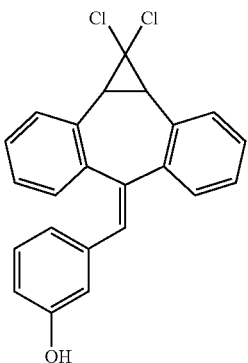

Following procedures essentially as described in Example 219, combine 8,8-dichloro-4-bromomethylene-2,3,5,6-dibenzobicyclo[5.1.0]octane (160 mg, 0.44 mmol) and (3-hydroxyphenyl)-boronic acid (70 mg, 0.4 mmol) to provide the title compound. Purify the product radial chromatography eluting the product with solutions of increasing concentrations of ethyl acetate in hexanes (5, 10, 15, and 20%). Combine product fractions, concentrate and dry to yield 59 mg (36%) of product as a white solid. LC/MS (ES$^+$): 397 (M+NH$_4$$^+$), 379 (M$^+$). $^1$H NMR (CDCl$_3$, 400 MHz): δ7.50 (d, 1H), 7.42 (d, 1H), 7.36 (dd, 1H), 7.35-7.26 (m, 3H), 7.12-7.02 (m, 3H), 6.72-6.62 (m, 3H), 6.55 (dd, 1H), 4.89 (s, 1H), 3.46 (d, 1H), 3.35 (d, 1H).

Section 6 (derivatives of Formula I wherein the bridge depicted by —X—Y— contains a heteroatom or heteroatom containing group at either the X or Y position.)

EXAMPLE 261

N-[3-(6-Oxo-5,6-dihydro-dibenzo[b,e]azepin-11-ylidenemethyl)-phenyl]-methanesulfonamide

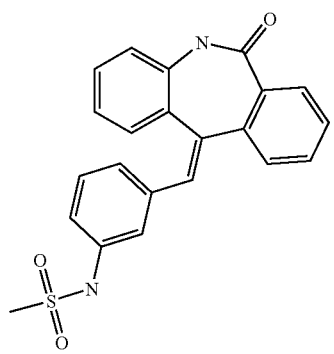

Following procedures essentially as described in Example 158 and using 5H-dibenzo[b,e]azepine-6,11-dione (97 mg, 0.31 mmol) and methanesulfonyl chloride (26 □L, 0.34 mmol), followed by procedures essentially as described in Example 90, 83 g of the title compound is provided in 68% yield as a white solid. $^1$H NMR (DMSO) δ10.54(s, 1H), 9.67 (s, 1H), 7.82 (d, 1H), 7.63 (t, 1H), 7.52 (d, 1H), 7.46 (m, 1H), 7.25 (m, 2H), 7.15 (m, 1H), 7.02 (s, 1H), 6.99 (d, 1H), 6.98 (m, 2H), 6.80 (m, 2H), 2.81 (s, 3H), MS [EI+] 391 (M+H).

EXAMPLE 262

N-[3-(11H-10-Thia-dibenzo[a,d]cyclohepten-5-ylidenemethyl)-phenyl]-methanesulfonamide(

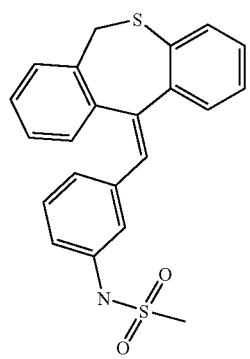

Dissolve 3-(11H-10-thia-dibenzo[a,d]cyclohepten-5-ylidenemethyl)-phenylamine (20 mg, 0.06 mmol) in 5 mL of methylene chloride under a nitrogen atmosphere. Then, following procedures essentially as described in Example 90 22.3 mg of the title compound is provided as a white solid. $^1$H NMR (CDCl$_3$) δ7.49 (m, 1H), 7.48 (d, 1H1), 7.35 (td, 1H), 7.25-7.15 (m, 2H), 7.15-7.10 (m, 2H), 7.10-6.95 (m, 3H), 6.87 (d, 1H), 6.79 (s, 1H), 6.24 (m, 1H), 6.10 (s, 1H), 5.00 (d, 1H), 3.55 (d, 1H), 2.80 (s, 3H). MS [EI+] 394 (M+H), 392

EXAMPLE 263

N-[3-(10-Oxo-10,11-dihydro-10$\lambda^4$-thia-dibenzo[a,d]cyclohepten-5-ylidenemethyl)-phenyl]-methanesulfonamide

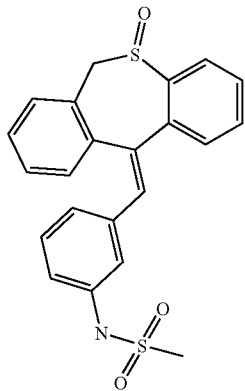

In 5 mL of acetonitrile add Fe(NO$_3$)$_3$·9H2O (5.1 mg, 0.013 mmol) and FeBr3 (1.9 mg, 0.006 mmol). Add N-[3-(11H-10-thia-dibenzo[a,d]cyclohepten-5-ylidenemethyl)-phenyl]-methanesulfonamide (50 mg, 0.13 mmol) and stir for 2 h at ambient temperature. Extract with methylene chloride, dry (MgSO$_4$) and concentrate. Purify by recrystallization from carbon tetrachloride to yield 13.6 mg of a yellow solid. $^1$H NMR (CDCl$_3$) δ7.85 (m, 1H), 7.57 (m, 1H), 7.55 (m, 1H), 7.35 (td, 1H), 7.25-7.15 (m, 2H), 7.10 (d, 1H), 7.02 (dd, 1H), 7.00-6.95 (m, 3H), 6.22 (s, 1H), 4.60 (b, 2H), 3.55 (d, 1H), 2.80 (s, 3H). MS [EI+] 410 (M+H)$^+$, 408 (M−H)$^−$. (M−H)

EXAMPLE 264

N-[3-(10,10-Dioxo-10,11-dihydro-10$\lambda^6$-thia-dibenzo[a,d]cyclohepten-5-ylidenemethyl)-phenyl]-Methanesulfonamide

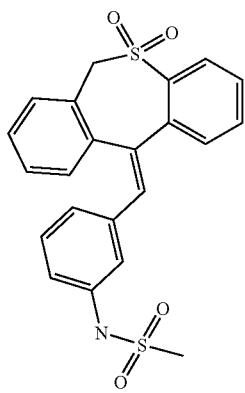

Dissolve N-[3-(10-oxo-10,11-dihydro-10$\lambda^4$-thia-dibenzo[a,d]cyclohepten-5-ylidenemethyl)-phenyl]-methanesulfonamide (35 mg, 0.085 mmol) in 5 mL of methylene chloride at ambient temperature. Add 300 mg of silica gel followed by t-butylperoxide (0.012 mL, 0.085 mmol). Stir overnight, filter and evaporate. Recrystallize from 1:1 ether:pentane to obtain 10.6 mg of the product as a yellow solid. $^1$H N (CDCl$_3$) δ8.91 (b, 1H), 7.85 (m, 1H), 7.57 (m, 1H), 7.55 (m, 1H), 7.35 (m, 1H), 7.25-7.15 (m, 2H), 7.10 (m, 1H), 7.02 (m, 1H), 7.00-6.95 (m, 1H), 6.30 (d, 2H), 6.15 (d, 1H), 5.25 (t, 1H), 4.40 (t, 1H), 2.80 (s, 311). MS [EI+] 424 (M−H).

EXAMPLE 265

11-(3-Nitro-benzylidene-6,11-dihydro-dibenzo[b,e]oxepine

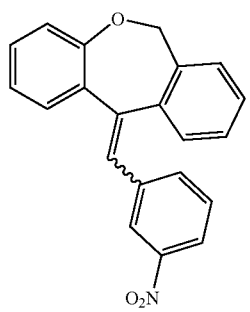

Following procedures as described in Example 229 combine 11-bromomethylene-6,11-dihydydro-dibenzo[b,e]oxepine (500 mg) with m-nitrophenyl boronic acid (290 mg). Flash chromatography eluting with 1:1 toluene:hexanes gave 310 g of a 3:1 mix of both isomers(54.4% yield). $^1$H NMR (400 MHz, CDCl$_3$) δ 7.96-7.94 (d, 11H), 7.87 (s, 1H), 7.52-7.47 (m, 2H), 7.37-7.16 (m, 5H), 7.00-6.95 (t, 3H), 6.85-6.83 (d, 1H).

EXAMPLE 266

3-(6H-Dibenzo[b,e]oxepin-1-ylidenemethyl)-phenylamine

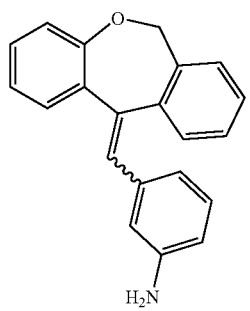

Dissolve 11-(3-Nitro-benzylidene-6,11-dihydro-dibenzo[b,e]oxepine (200 mg) in ethanol (10 mL) add tin chloride dihydrate (680 mg) and reflux for 5 h. Concentrate the reaction in vacuo, re-dissolve in ethyl acetate and wash with 1N sodium hydroxide solution. Separate the layers wash with brine and dry over sodium sulfate. Purity using filter chromatography eluting with 10% ethyl acetate:toluene to give 60 mg of product (56% yield).

MS m/z: 300 (M$^+$ 1).

EXAMPLE 267

N-[3-(6H-Dibenzo[b,e]oxepine-11-ylidenemethyl)-phenyl]-methanesulfonamide

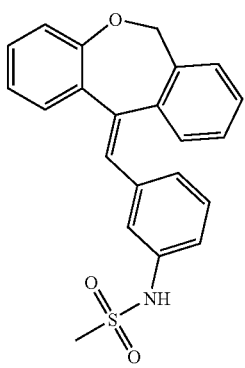

Following the procedures essentially as described in Example 90, the aniline of Example 266 (180 mg) is reacted with methanesulfonyl chloride (50L) to provide the title compound. Elute with 1-3-6% ethyl acetate:toluene (silica gel) over a step gradient to give 40 mg title product (17.6% yield) $^1$H NMR (400 MHz, CDCl$_3$) δ 7.5-7.46 (t, 2H), 7.34-7.30 (t, 1H), 7.21-7.15 (m, 3H), 7.06-6.9 (m, 5H), 6.83-6.80 (d, 1H), 6.76 (s, 1H), 6.16 (s, 1H), 2.8 (s, 3H).

MS m/z: 376.1 (M$^-$−1).

EXAMPLE 268

N-[3-(6H-Dibenzo[b,e]oxepin-11-ylidenemethyl)-phenyl]-methanesulfonamide

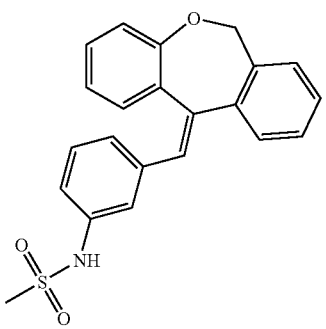

Following the procedures essentially as described in Example 90, the aniline of Example 266 (180 mg) is reacted with methanesulfonyl chloride (SOL) to provide 5 mg (2.2% yield) of the title compound. $^1$H NMR (400 MHz, CDCl$_3$) δ 7.48-7.45 (d, 1H), 7.41-7.37 (m, 1H), 7.34-7.32 (m, 2H), 7.20-7.17 (d, 1H), 7.15-6.99 (m, 5H), 6.90-6.88 (d, 1H), 6.67-6.61 (m, 2H), 6.26 (s, 1H), 5.33 (broad s, 2H), 2.87 (s, 3H).

MS m/z: 376.1 (M$^-$−1).

EXAMPLE 269

E-4-Methoxy-11-(3-nitro-benzylidene)-6,11-dihydro-dibenzo[b,e]oxepine

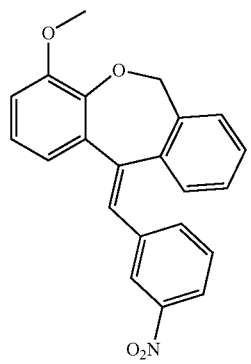

Following procedures essentially as described in Example 230, 11-bromomethylene-4-methoxy-6,11-dihydro-dibenzo[b,e]oxepine is combined with m-nitrophenyl boronic acid. The pure E isomer is isolated by recrystallization with hexanes and diethyl ether to give 311 mg of product (33% yield). $^1$H NMR (400 MHz, CDCl$_3$) δ 7.979-7.949 (d, 1H), 7.874 (s, 1H), 7.509-7.491 (d, 1H), 7.365-7.324 (t, 1H), 7.305-7.237 (m, 2H), 7.204-7.162 (t, 1H), 7.123-7.100 (d, 1H), 6.992-6.912 (m, 3H), 6.864-6.840 (d, 1H), 5.75 (broad s, 1H), 5.19 (broad s, 1H), 3.84 (s, 3H).

EXAMPLE 270

3-(4-Methoxy-6H-dibenzo[b,e]oxepin-11-ylidenemethyl)-phenylamine

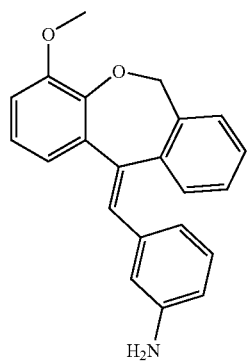

Prepare the title compound by SnCl$_2$ reduction of 4-methoxy-11-(3-nitro-benzylidene)-6,11-dihydro-dibenzo[b,e]oxepine (from Example 270) to provide 267 mg of product (93.7% yield). This material is used without further characterization.

EXAMPLE 271

N-[3-(4-Methoxy-6H-dibenzo[b,e]oxepin-11-ylidenemethyl)-phenyl]-methanesulfonamide

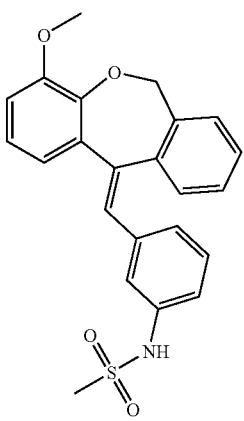

Following procedures essentially as described in Example 90, the title compound is prepared from 3-(4-Methoxy-6H-dibenzo[b,e]oxepin-11-ylidenemethyl)-phenylamine and methanesulfonyl chloride. Flash chromatography eluting with 5 to 10 to 20% ethyl acetate:toluene provides 198 mg product (60% yield) of the title final product.

$^1$H NMR (400 MHz, CDCl$_3$) δ 7.482-7.463 (d, 1H), 7.321-7.237 (m, 2H), 7.193-7.149 (t, 1H), 7.110-7.086(d, 1H), 7.035-6.973 (m, 2H), 6.936-6.881 (m, 3H), 6.840-6.815 (d, 1H), 6.763 (s, 1H), 6.127 (s, 1H), 3.83 (s, 3H), 2.80 (s, 3H). MS m/z: 406.1 (M$^-$−1).

EXAMPLE 272

7-Chloro-11-(3-nitro-benzylidene)-6,11-dihydro-dibenzo[b,e]oxepine

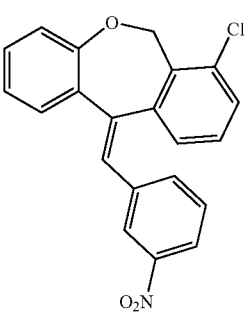

Following procedures essentially as described in Example 230, 11-bromomethylene-7-chloro-6,11-dihydro-dibenzo[b,e]oxepine is combined with m-nitrophenyl boronic acid to provide the title compound. The pure Z isomer is isolated by crystallization (diethyl ether) to give 1.4 g (31.7% yield) product. $^1$H NMR (400 MHz, CDCl$_3$) δ 8.038-8.017 (d, 1H), 7.976 (s, 1H), 7.511-7.491 (d, 1H), 7.431-7.410 (d, 1H), 7.369-7.253 (m, 3H), 7.160-7.121 (t, 1H), 7.041-7.005 (m, 2H), 6.928-6.919 (d, 1H), 6.908-6.898 (d, 1H), 5.60 (s, 2H).

EXAMPLE 273

3-(7-Chloro-6H-dibenzo[b,e]oxepin-11-ylidenemethyl)-phenylamine

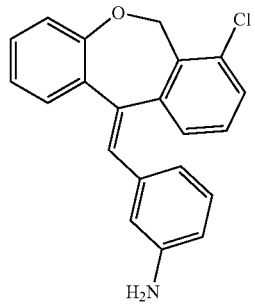

Prepare the title compound by SnCl$_2$ reduction of 7-chloro-11-(3-nitro-benzylidene)-6,11-dihydro-dibenzo[b,e]oxepine (from Example 272) to provide 900 mg (98%) of product. MS m/z: 334.1 (m$^+$+1).

EXAMPLE 274

N-[3-(7-Chloro-6H-dibenzo[b,e]oxepin-11-ylidenemethyl)-phenyl]-methanesulfonamide

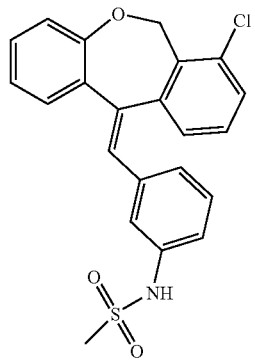

Following procedures essentially as described in Example 90, the title compound is prepared from 3-(7-chloro-6H-dibenzo[b,e]oxepin-11-ylidenemethyl)-phenylamine and methanesulfonyl chloride. Elute on silica gel with 15% ethyl acetate:toluene gave 530 mg product (86%). $^1$H NMR (400 MHz, CDCl$_3$) δ 7.463-7.443 (d, 1H), 7.358-7.337 (d, 1H), 7.230-7.155 (m, 2H), 7.116-7.077 (t, 1H), 7.016-6.840 (m, 7H), 6.264 (s, 1H), 5.563 (s, 2H), 2.88 (s, 3H) MS m/z: 410.1 (M$^-$−1).

Section 2

PREPARATION 30

1-{2-[4-(2,8-Dimethoxy-10,11-dihydro-dibenzo[a,d]cyclohepten-5-ylidenemethyl)-phenoxy]-ethyl}-piperidine

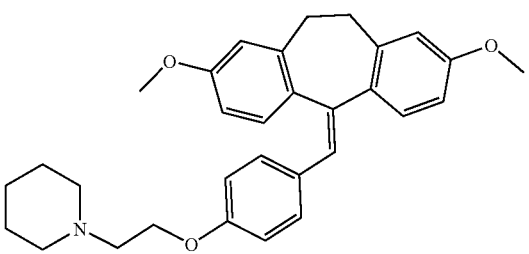

Mix 5-bromomethylene-2,8-dimethoxy-10,11-dihydro-5H-dibenzo[a,d]cycloheptene (270 mg, 0.78 mmol) and 1-[2-

(phenoxy-4-boronic acid)-ethyl]-piperidine (580 mg, 2.35 mmol) in 1,4-dioxane (8 mL) and aqueous sodium carbonate (2.0 M, 2 mL). Sparge solution with $N_2$ for 15 min, then add $Pd(Ph_3P)_4$ (140 mg, 0.12 mmol) and heat to 85° C. for 2 h. Cool reaction mixture to room temperature, dilute with dichloromethane (100 mL), and wash organic once with saturated aqueous ammonium chloride. Dry ($MgSO_4$) and concentrate organics to a brown oil. Chromatography on silica gel (40 g), eluting with 5:1 dichloromethane:methanol affords 180 mg (50%) of the title compound as a light brown oil. MS (ES) 470 (M+H); TLC $R_f$=0.40 (5:1 dichloromethane:methanol).

EXAMPLE 275

5-[4-(2-Piperidin-1-yl-ethoxy)-benzylidene]-10,11-dihydro-5H-dibenzo[a,d]cycloheptene-2,8-diol hydrochloride

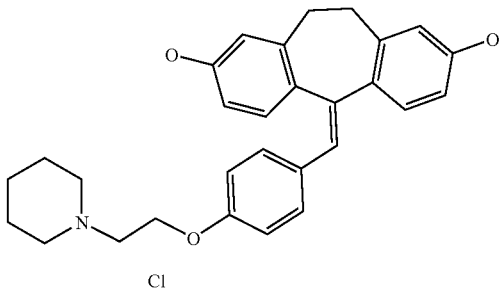

Mix 1-{2-[4-(2,8-dimethoxy-10,11-dihydro-dibenzo[a,d]cyclohepten-5-ylidenemethyl)-phenoxy]-ethyl}-piperidine (180 mg, 0.38 mmol) and ethereal hydrogen chloride (1.0 M, 1 mL) in dichloromethane (5 mL). Concentrate under reduced pressure. Dilute residue with dichloromethane (5 mL) and cool to 0° C. Add boron tribromide (100 uL, 1.14 mmol) and allow to warm to ambient temperature. Dilute with dichloromethane (50 mL) and saturated aqueous sodium bicarbonate (10 mL). Separate organics, dry over ($MgSO_4$), and concentrate to a brown oil. Chromatography on silica gel (40 g), eluting with 5:1 dichloromethane:methanol yields the product as a light brown oil. React with ethereal hydrogen chloride (1.0 M, 1 mL) in dichloromethane (5 mL). Concentrate under reduced pressure. Isolate the hydrochloride salt which weighs 70 mg (50%) MS (ES) 442 (M+H); TLC $R_f$=0.35 (5:1 dichloromethane:methanol); $^1$H-NMR (DMSO) δ 1.29-1.40 (br m, 2H), 1.83-1.60 (br m, 4H), 2.59-3.26 (br m, 8H), 3.36-3.48 (br m, 2H), 4.30 (br s, 2H); 6.42 (dd, J=8.3, 5.9 Hz, 1H), 6.47 (d, J=2.3 Hz, 1H), 6.57 (dd, J=8.4, 2.7 Hz, 1 H), 6.59 (s, 1H), 6.63 (d, J=8.3 Hz, 1H), 6.70 (d, J=2.3 Hz, 1H), 6.77 (d, J=9.0 Hz, 2H), 6.94 (d, J=8.9 Hz, 2H), 7.22 (d, J=8.4 Hz, 1H), 9.27 (s, 1H), 9.34 (s, 1H), 10.08 (br s, 1H).

EXAMPLE 276

5-[4-(2-Piperidin-1-yl-ethoxy)-benzyl]-10,11-dihydro-5H-dibenzo[a,d]cycloheptene-2,8-diol hydrochloride

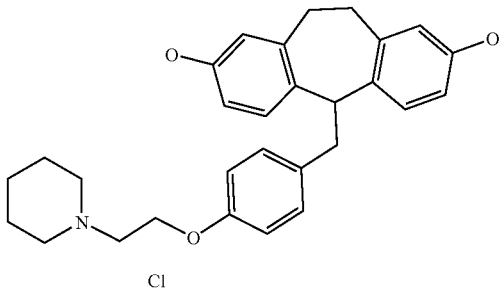

Mix 5-[4-(2-piperidin-1-yl-ethoxy)-benzylidene]-10,11-dihydro-5H-dibenzo[a,d]cycloheptene-2,8-diol (25 mg, 0.06 mmol) and 10% palladium on carbon (10 mg) in ethanol (5 mL). Place under ambient hydrogen atmosphere. Stir overnight. Filter through Celite and concentrate under reduced pressure. Chromatography on silica gel (40 g), eluting with 5:1 dichloromethane:methanol yields the product as a light brown oil. React with ethereal hydrogen chloride (1.0 M, 1 mL) in dichloromethane (5 mL). Concentrate under reduced pressure. Isolate the hydrochloride salt which weighs 25 mg (95%) MS (ES) 444 (M+H); TLC $R_f$=0.35 (5:1 dichloromethane:methanol).

Section 7 (derivatives of Formula I wherein R8 is not hydrogen and the bridge depicted by —X—Y— contains either a heteroatom or heteroatom containing group at either the X or Y position or both X and Y are $CH_2$.)

PREPARATION 31

1-[2-(5-Methylene-10,11-dihydro-5H-dibenzo[a,d]cyclohepten-2-yloxy)-ethyl]-piperidine

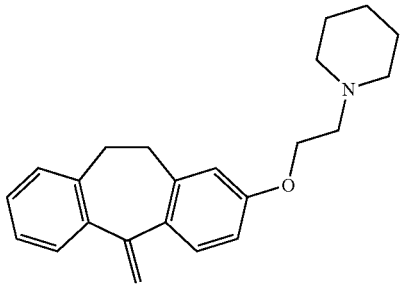

Dissolve 5-methylene-10,11-dihydro-5H-dibenzo[a,d]cyclohepten-2-ol (200 mg, 0.90 mmol) in dimethylformamide (5 mL). Add sodium hydride (90 mg, 2.25 mmol) followed by 2-chloro-ethyl-1-piperidine hydrochloride (190 mg, 1.03 mmol). Stir at room temperature overnight. Dilute with dichloromethane (50 mL) and saturated aqueous ammonium chloride (15 mL). Separate organic, dry over magnesium sulfate, filter and concentrate under reduced pressure. Chromatograph the residue on silica gel (40 g), eluting with 5:1 dichloromethane:methanol. Isolate the product as a light brown oil which weighs 300 mg (100%) MS (ES) 334 (M+H); TLC $R_f$=0.45 (5:1 dichloromethane:methanol).

PREPARATION 32

1-[2-(5-Bromomethylene-10,11-dihydro-5H-dibenzo[a,d]cyclohepten-2-yloxy)-ethyl]-piperidine

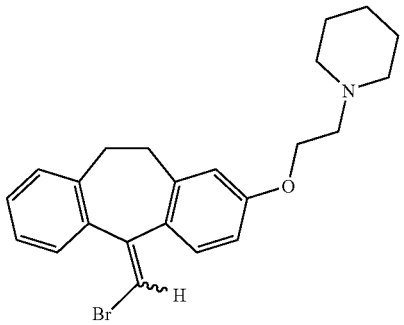

Dissolve 1-[2-(5-methylene-10,11-dihydro-5H-dibenzo[a,d]cyclohepten-2-yloxy)-ethyl]-piperidine (360 mg, 1.08 mmol) in dichloromethane (15 mL). Add dimethylaminopyridinium tribromide (390 mg, 1.08 mmol). Stir at room temperature for 30 min. Dilute with dichloromethane (50 mL) and 10% aqueous sodium thiosulfite (15 mL). Separate organic, dry over magnesium sulfate, filter and concentrate under reduced pressure. Chromatograph the residue on silica gel (40 g), eluting with 5:1 dichloromethane:methanol. Isolate the product as a light brown oil which weighs 210 mg (47%) MS (ES) 414 (M+H); TLC R$_f$=0.48 (5:1 dichloromethane:methanol).

EXAMPLE 277

4-[2-(2-Piperidin-1-yl-ethoxy)-10,11-dihydro-dibenzo[a,d]cyclohepten-5-ylidenemethyl]-phenol hydrochloride

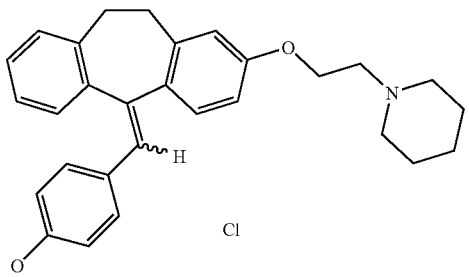

Mix 1-[2-(5-bromomethylene-10,11-dihydro-5H-dibenzo [a,d]cyclohepten-2-yloxy)-ethyl]-piperidine (210 mg, 0.51 mmol) and 4-hydroxyphenylboronic acid (110 mg, 0.76 mmol) in 1,4-dioxane (7 mL) and aqueous sodium carbonate (2.0 M, 4 mL). Sparge solution with N$_2$ for 15 min, then add Pd(Ph$_3$P)$_4$ (60 mg, 0.05 mmol) and heat to 85° C. for 2 h. Cool reaction mixture to room temperature, dilute with dichloromethane (100 mL), and wash organic once with saturated aqueous ammonium chloride. Dry (MgSO$_4$) and concentrate organics to a brown oil. Chromatograph the residue on silica gel (40 g), eluting with 5:1 dichloromethane:methanol. Isolate the product as a light brown oil. React with ethereal hydrogen chloride (1.0 M, 1 mL) in dichloromethane (5 mL). Concentrate under reduced pressure. Isolate the hydrochloride salt which weighs 110 mg (47%) MS (ES) 426 (M+H); TLC R$_f$=0.40 (5:1 dichloromethane:methanol). NMR data is reported for the free base of the major olefin isomer: $^1$H-NMR (CDCl$_3$) δ 1.42-1.48 (br m, 2H), 1.58-1.65 (br m, 4H), 2.49-2.58 (br m, 4H), 2.70-3.50 (br m, 4H), 2.77 (t, J=6.2 Hz, 2H), 4.70 (t, J=6.3 Hz, 2H); 6.49-6.58 (m, 4H), 6.64 (s, 1H), 6.76 (d, J=9.0 Hz, 2H), 6.98-7.04 (m, 2H), 7.18 (dt, J=7.4, 1.8 Hz, 1H), 7.25 (d, J=7.5 Hz, 1H), 7.32 (d, J=8.7 Hz, 1H).

ADDITIONAL EXAMPLES

The following additional preparations and examples further illustrate the invention and represent typical synthesis for the compounds of Formula I, including any novel compounds, as described generally above.

Additional preparations for, and examples of compounds of Formula I having substitution on the "C" ring but not on the "A" or "B" rings. (Section 1 as represented by original Examples 1-160)

EXAMPLE 278

5-(3-Methylsulfanyl-benzylidene)-10,11-dihydro-5H-dibenzo[a,d]cycloheptene

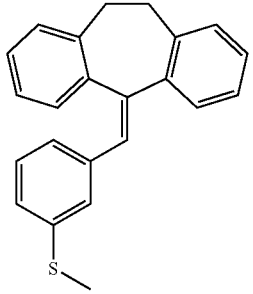

Following procedures as described in Example 219, mix 5-bromomethylene-10,11-dihydro-5H-dibenzo[a,d]cycloheptene (1 equivalent), 4,4,5,5-tetramethyl-2-(3-methylsulfanyl-phenyl)-[1,3,2]dioxaborolane (1.25 equivalents), 2N Na$_2$CO$_3$ (2 equivalents) and tetrakistriphenylphosphine palladium (0.05 equivalents)in a suitable solvent. Purify the product by silica gel chromatography to obtain a 79% yield of the title compound. MS(ES)=329(+)

EXAMPLE 279

5-(3-Methanesulfonyl-benzylidene)-10,11-dihydro-5H-dibenzo[a,d]cycloheptene

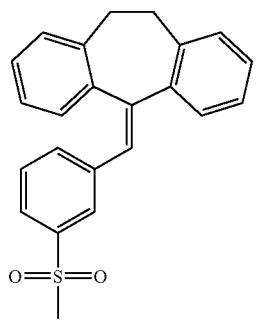

Mix 5-(3-methylsulfanyl-benzylidene)-10,11dihydro-5H-dibenzo[a,d]cycloheptene (1 equivalent) and sodium perborate hydrate (2.2 equivalents) in 50:50 dichloromethane/glacial acetic acid and stir at room temperature for 18 hours. Then warm to 45° C. for four hours. Partition between dichloromethane and 0.1N NaOH. Dry and evaporate the organic layer. Purify the product by silica gel chromatography to obtain a 72% yield of the title compound. MS(ES)=361(+)

Examples 280-288 contained in Table II, herein, provide yet additional examples of compounds of Formula I having substitution on the "C" ring, but not on the "A" or "B" rings. These examples, which further illustrate the present invention are prepared according to the procedures as described generally in the Schemes and literature references described above.

Additional preparations for, and examples of compounds of Formula I having having substitution on both the "C" ring and the "A" and/or "B" rings. (Section 2 as represented by original Examples 161-215)

PREPARATION 33

E- and Z-5-Bromomethylene-2-chloro-10,11-dihydro-5H-dibenzo[a,d]cycloheptene

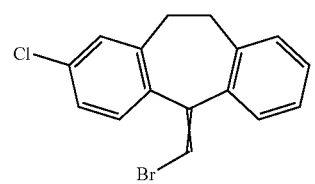

Cool a mixture of 2.8 equiv of bromomethyltriphenylphosphonium bromide (prepared as described in G. Vassilikogiannakis, M. Hatzimarinaki, M. Orfanapoulos *J. Org. Chem.*, 65, 8180) in THF (0.5 M) to −78° C. and add 2.8 equiv of LiHMDS-THF dropwise to give a bright yellow mixture. Stir for 1 h at −78° C. and then 10 min at 0° C. Recool the mixture to −78° C. and add 2-chloro-10,11-dihydro-dibenzo[a,d]cyclohepten-5-one. Allow the dark mixture to warm to room temperature and stir for 3.5 h before adding saturated, aqueous saturated ammonium chloride and diluting with pentane. Filter through celite, concentrate filtrate and concentrate under reduced pressure. Purify by column chromatography (1% to 2% to 3% to 5% EtOAc:hexanes) to give title compound (30%) as a 1:1 mixture of geometric isomers: GC-MS (GRAD60-280° C.) t=7.23 (90%).

MS (1): 320 (M+).

EXAMPLE 289

3-(2-Chloro-10,11-dihydro-dibenzo[a,d]cyclohepten-5-ylidenemethyl)-phenylamine

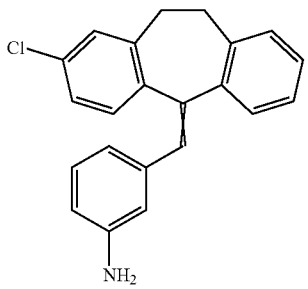

Following procedures essentially as described in Example 219, and using 5-bromomethylene-2-chloro-10,11-dihydro-5H-dibenzo[a,d]cycloheptene and 3-aminophenylboronic acid, a mixture of the E and Z isomers of the title compound is prepared.

PREPARATION 34

5-Methylene-10,11-dihydro-5H-dibenzo[a,d]cyclohepten-2-ol

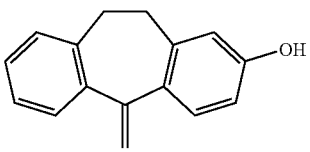

Prepared from commercially available 2-hydroxy-10,11-dihydro-dibenzo[a,d]cyclohepten-5-one following procedures essentially as described in Preparation 23. MS (ES−) 221.

PREPARATION 35

5-Bromomethylene-10,11-dihydro-5H-dibenzo[a,d]cyclohepten-2-ol

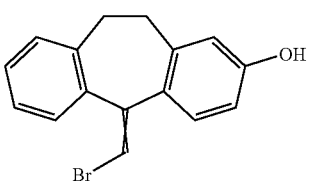

Prepared from 5-methylene-10,11-dihydro-5H-dibenzo[a,d]cyclohepten-2-ol using procedures essentially as described in Preparation 24. MS (ES−) 301.

Examples 290-435 contained in Table II, herein, provide yet additional examples of compounds of Formula I having substitution on both the "C" ring and the "A" and/or "B" rings. These examples, which further illustrate the present invention are prepared according to the procedures as described generally in the Schemes and literature references described above.

Additional preparations for, and examples of compounds of Formula I wherein the "C" ring represents a heterocyclic or benzofused heterocyclic ring. (Section 3 as represented by original Examples 216-237)

PREPARATION 36

1-(2-morpholin-4-yl-ethyl)-5-(4,4,5,5-tetramethyl-[1,3,2]dioxaborolan-2-yl)-1,3-dihydro-benzoimidazol-2-one Following procedures as described in Scheme IX.

Step A: Preparation of (4-bromo-2-nitro-phenyl)-(2-morpholin-4-yl-ethyl)-amine

Mix 5-bromo-2-fluoro-nitrobenzene (10 g, 45 mmol) and 4-(2-aminoethyl)morpholine (11.8 mL, 90 mmol) in THF (100 mL). Stir at room temperature for 18 h. Remove the THF under reduced pressure and partition the residue between water (200 mL) and ethyl acetate (200 mL). Dry the organic layer (MgSO4) and concentrate to give 15.3 g (100%) title compound. HPLC (ISO80-10M) t=1.83 min (94%), MS (S) 331 (M+1).

Step B: Preparation of 4-bromo-N1-(2-morpholinyl-ethyl)-benzene-1,2-diamine

Dissolve (4-bromo-2-nitro-phenyl)-(2-morpholin-4-yl-ethyl)-amine (15.3 g, 46.4 mmol) in ethyl acetate (1 L) and add 5% Pt/C (sulfided) (382 mg). Place the slurry under 60 psi hydrogen gas at room temperature of 8 h. Filter and concentrate to give 23 g crude product as a dark red oil. Purify using a short plug of silica gel and 10% 2N NH3 in MeOH/dichloromethane to give 13.5 g of a brown oil. HPLC (ISO60-10M) t=1.46 (94%), MS (ES) 301 (M+1).

Step C: Preparation of 5-bromo-1-(2-morpholin-4-yl-ethyl)-1,3-dihydro-benzoimidazol-2-one In a 500-mL round-bottomed flask, mix 4-bromo-N1-(2-morpholin-4-yl-ethyl)-benzene-1,2-diamine 13.25 g, 44.1 mmol), NaHCO3 (5.4 g, 66.2 mmol), water (50 mL) and methanol (250 mL). Slowly add phenyl chloroformate (8.3 mL,66.2 mmol). Stirr the reaction for 1 h at room temperature and then add 5N NaOH (20 mL) and stir overnight at room temperature. Collect the solid by vacuum filtration and wash with methanol. HPLC (ISO60-10M) t=1.42 (97%), MS (ES) 326 (M+1).

Step D: Preparation of 1-(2-morpholin-4-yl-ethyl)-5-(4,4,5,5-tetramethyl-[1,3,2]dioxaborolan-2-yl)-1,3-dihydro-benzoimidazol-2-one Under a blanket of nitrogen, cool a THF (150 mL) solution of 5-bromo-1-(2-morpholin-4-yl-ethyl)-1,3-dihydro-benzoimidazol-2-one (7.5 g, 20 mmol) to 5° C. and add 3N ethylmagnesium bromide (8 mL, 24 mmol). After ½ h, cool the reaction to −72° C. and slowly add 1.7M t-BuLi (170 mL, 100 mmol). Allow the reaction to warm to −55° C., add trimethyl borate (80 mmol) and allow the reaction to stir at room temperature overnight. Add 5N HCl (50 mL) and stir for 4 h. Adjust the pH to 6-7 and extract the crude boronic acid into ethyl acetate. Dry (MgSO$_4$) and concentrate to give 10.4 g crude product. Slurry with toluene (500 mL) and add pinacol (64 mmol). Heat briefly and then stir overnight. Add ethyl acetate and aqueous NaHCO3. Wash the organic extract with water and evaporate the dried (MgSO4) organic layer to give 5.0 g (67%) title boronic ester as a white solid. LC/MS (ISO70-10M) 374 (M+1). Recrystallize from ethyl acetate/hexane.

$^1$H NMR (CDCl$_3$) d 1.34 (s,12H), 2.55 (br s,4H), 2.70 (br s, 2H), 3.68 (br s,4H), 4.02 (br s,2H), 7.03 (s,1H), 7.52 (s, 1H), 7.56 (d, 1H), 8.78 (br s, 1).

PREPARATION 37

5-(4,4,5,5-Tetramethyl-[1,3,2]dioxaborolan-2-yl)-1, 3-dihydro-benzoimidazol-2-one 5-Bromo-1,3-dihydro-benzoimidazol-2-one (20.0 g, 93.9 mmol) is dissolved in argon purged anhydrous DMF (150 mL). To this solution is added bis(pinacolato)diboron (28.6 g, 113 mmol), KOAc (27.6 g, 282 mmol), and PdCl$_2$(dppf), 1:1 complex with CH$_2$Cl$_2$ (7.67 g, 9.40 mmol). The reaction is heated to 95° C. overnight with mechanical stirring then cooled to room temperature and diluted with brine (500 mL) and EtOAc (750 mL). The mixture is filtered to remove a dark brown solid, which is washed thoroughly with EtOAc. The layers are separated and the organics washed with water (3×500 mL), then dried (MgSO$_4$), filtered and evaporated under reduced pressure. Trituration with 1:1 CH$_2$Cl$_2$/hexanes affords the product (10.9 g, 44%).

R$_f$ 0.52 (silica gel, 85:15 CH$_2$Cl$_2$/MeOH); mp 313-315° C. (dec); $^1$H NMR (300 MHz, DMSO-d$_6$) ◻1.27 (s, 12 H), 6.92 (d, J=7.7 Hz, 1H), 7.17 (s, 1H), 7.28 (d, J=7.7 Hz, 1H), 10.62 (s, 1H), 10.74 (s, 1H); APCI MS m/z 261 [C$_{13}$H$_{17}$BN$_2$O$_3$+H]$^+$; HPLC=98.3%, t$_R$=18.3 min; Analysis for C$_{13}$H$_{17}$BN$_2$O$_3$: C, 57.07; H, 6.82; N, 10.24. Found: C, 56.69; H, 6.44; N, 10.21.

HPLC conditions:

Waters Symmetry C18 column (4.6 mm×250 mm); 95:5 to 0:100 water/MeCN; 1.0 mL/min (25 min), ◻=254 nm

EXAMPLE 436

5-(2,8-difluoro-10,11-dihydro-dibenzo[a,d]cyclohepten-5-ylidenemethyl)-1-(2-morpholin-4-yl-ethyl)-1, 3-dihydro-benzoimidazol-2-one

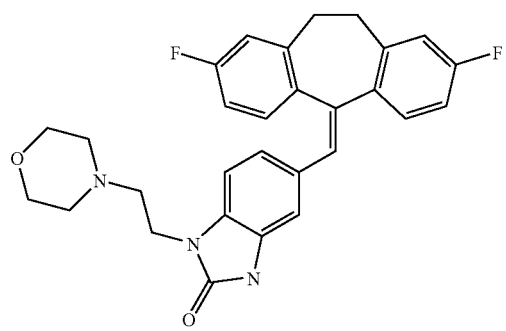

Following procedures essentially as described in Example 219, mix 1-(2-morpholin-4yl-ethyl)-5-(4,4,5,5-tetramethyl-[1,3,2]dioxaborolan-2-yl)-1,3-dihydro-benzoimidazol-2-one (520 mg, 1.4 mmol), 5-bromomethylene-2,8-difluoro-10,11-dihydro-5H-dibenzo[a,d]cycloheptene (510 mg, 1.6 mmol)(prepared using a procedure essentially as described for the 2,8-dichloro derivative in Example 182), 2N Na$_2$CO$_3$ (1 mL), dioxane (10 mL) and (Ph$_3$P)$_4$Pd (67 mg, 0.06 mmol). Purify the crude product by column chromatography using MeOH/ethyl acetate to give 310 mg colorless oil that solidified upon drying, HPLC (ISO80-10M) t=2.03 (97%). MS (ES) 488 (M+1), 486 (M−1). H NMR 10.69 (s, 1H), 7.49 (dd, 1H, J=8.4, 6.2 Hz), 7.22 (dd, 1H, J=9.7, 2.2 Hz), 7.02 (td, 1H, J=12.0, 4.2 Hz), 6.97-6.83 (m, 4H), 6.81 (s, 1H), 6.72 (d, 1H, J=7.9 Hz), 6.56 (s, 1H), 3.80 (t, 2H, J=6.2 Hz), 3.47 (t, 4H, J=4.2 Hz), 3.31 (s, 2H), 2.90 (s, 2H), 2.48 (m, 2H), 2.38 (s, 4H).

EXAMPLE 437

5-(2,8-difluoro-10,11-dihydro-dibenzo[a,d]cyclohepten-5-ylidenemethyl)-1,3-dihydro-benzoimidazol-2-one

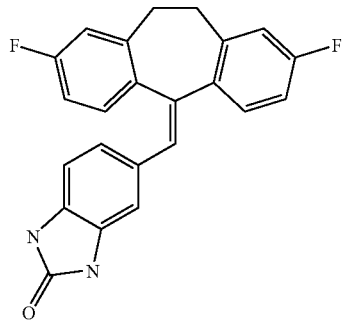

Following procedures essentially as described in Example 219, mix 5-(4,4,5,5-tetramethyl-[1,3,2]dioxaborolan-2-yl)-1,3-dihydro-benzoimidazol-2-one (535 mg, 2.06 mmol) (prepared from 5-bromo-1,3-dihydro-benzoimidazol-2-one (Preparation 27) according to the procedure reported by M Murata, T Takashi, S Watanabe and Y Yusuru, J. Org. Chem.; 65 (1) 164-168 (2000)), 5-bromomethylene-2,8-difluoro-10, 11-dihydro-5H-dibenzo[a,d]cycloheptene (550 mg, 1.71 mmol), 2N Na$_2$CO$_3$ (2 mL), dioxane (14 mL) and (Ph$_3$P)$_4$Pd (200 mg, 0.17 mmol). Purify the crude product by column chromatography using dichloromethane/ethyl acetate to give 285 mg white solid, mp 257° C. HPLC (ISO80-10M) t=2.62 (97%), MS (ES) 373 (M−1). H NMR 10.55 (s, 1H), 10.45 (s, 1H), 7.48 (dd, 1H, J=8.4, 6.2 Hz), 7.21 (dd, 1H, J=9.7, 2.2 Hz), 7.01 (td, 1H, J=12.2, 4.2 Hz), 6.94 (dd, 1H, J10.1, 2.2 Hz), 6.90 (d, 2H, J=6.2 Hz), 6.85 (dd, 1H, J=8.6, 2.4 Hz), 6.78 (s, 1H), 6.72 (d, 1H, J=8.4 Hz), 6.67 (d, 1H, J=7.9 Hz), 6.51 (s, 1H), 3.30 (s, 2H), 2.89 (s, 2H), 6.90 (d, 1H, J=6.2 Hz).

EXAMPLE 438

5-(2,8-difluoro-10,11-dihydro-dibenzo[a,d]cyclohepten-5-ylidenemethyl)-1-(3-morpholin-4-yl-propyl)-1, 3-dihydro-benzoimidazol-2-one

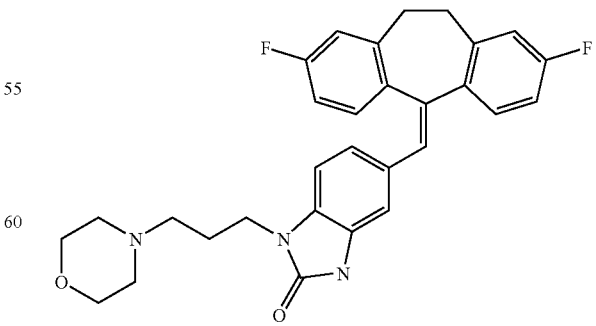

Following procedures essentially as described in Example 219, mix 1-(2-morpholin-4-yl-propyl)-5-(4,4,5,5-tetramethyl-[1,3,2]dioxaborolan-2-yl)-1,3-dihydro-benzoimidazol-2-one (458 mg, 1.18 mmol), 5-bromomethylene-2,8-difluoro-10,11-dihydro-5H-dibenzo[a,d]cycloheptene (400 mg, 1.25 mmol), 2N Na$_2$CO$_3$ (1.3 mL), dioxane (8 mL) and Ph$_3$P)$_4$Pd (45 mg, 0.04 mmol). Purify the crude product by column chromatography using 2% 2N NH$_3$ in MeOH/dichloromethane to give 170 mg title compound as a white foam.

HPLC (ISO80-10M) t=1.86 (98%), MS (ES) 502 (M+1), 500 (M−1). H NMR 8.38 (s, 1H), 7.42 (dd, 1H, J=8.4, 5.7 Hz), 7.01 (dd, 1H, J=9.2, 2.6 Hz), 6.95 (dd, 1H, J=8.4, 5.7 Hz), 6.91 (dd, 1H, J=8.4, 2.6 Hz), 6.85 (d, 1H, J=8.4 Hz), 6.80 (dd, 1H, J=9.7, 2.2 Hz), 6.71 (dd, 1H, J=8.6, 2.4 Hz), 6.64 (s, 1H), 3.89 (t, 2H, J=6.8 Hz), 3.68 (s, 4H), 3.59-2.71 (m, 4H), 1.60 (s, 2H), 1.94 (s, 2H), 2.40 (s, 4H), 6.76 (m, 2H).

Examples 439-474 contained in Table II, herein, provide yet additional examples of compounds of Formula I wherein the "C" ring represents a heterocyclic or benzofused heterocyclic ring. These examples, which further illustrate the present invention are prepared according to the procedures as described generally in the Schemes and literature references described above.

Additional preparations for, and examples of compounds of Formula I wherein the "A" and/or "B" ring represents a heterocyclic ring. (Section 4 as represented by original Examples 238-254)

PREPARATION 38

4-Methylene-9,10-dihydro-4H-1-thia-benzo[f]azulene

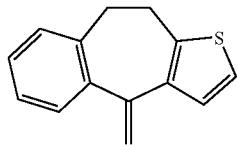

Following procedures as described in Scheme X:
Add 3 equiv of a 0.5 M solution of Tebbe reagent in toluene to a solution (−40° C.) 9,10-dihydro-1-thia-benzo[f]azulene-4-one (prepared as described in P. Bollinger, P. Cooper.; H. U. Gubler, A. Leutwiler, T. Payne Helv. Chim. Acta (1990), 73, 1197) and 3 equiv of pyridine in THF (0.1 M) under Ar. Stir the resulting dark red mixture for 2 h then allow to warm to 0° C. over ca. 30 min period before diluting with diethyl ether. Carefully add 5 N sodium hydroxide until bubbling ceases, add solid Na$_2$SO$_4$, and then stir for 1 h. Filter the mixture through Celite®, and concentrate the filtrate by rotary evaporation. Purify the crude residue by column chromatography (hexanes) to give the title compound as white crystals (56%): HPLC (ISO80-20M) t=1.903 (98%). MS (APCI): 213 (M+1). $^1$H NMR (CDCl$_3$) δ 3.07-3.12 (m, 2 H), 3.14-3.17 (m, 2 H), 5.32 (s, 1 H), 5.63 (s, 1 H), 7.05 (app d, J=5.4 Hz, 1 H), 7.08 (d, J=5.4 Hz, 1 H), 7.19-7.26 (m, 3 H), 7.35 (dd, J=7.6 Hz, 1.6 Hz, 1 H).

EXAMPLE 475 AND EXAMPLE 476

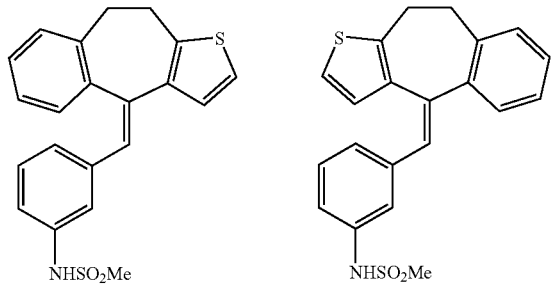

Following procedures essentially as described in Preparation 24 followed by procedures essentially as described in Example 219, and using 4-methylene-9,10-dihydro-4H-1-thia-benzo[f]azulene, the title compounds are made.

EXAMPLE 477

3-(9,10-Dihydro-1-thia-benzo[f]azulen-4-ylidenemethyl)-phenylamine

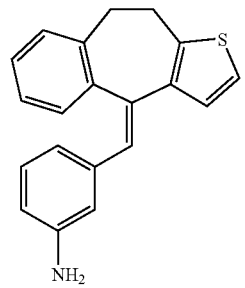

4-Methylene-9,10-dihydro-4H-1-thia-benzo[f]azulene is converted to the vinyl bromide as in Preparation 24 and the vinyl bromide coupled with 3-aminophenylboronic acid using the procedures essentially as described in Example 219.

EXAMPLE 478

3-(7-Chloro-9,10-dihydro-1-thia-benzo[f]azulen-4-ylidenemethyl)-phenylamine

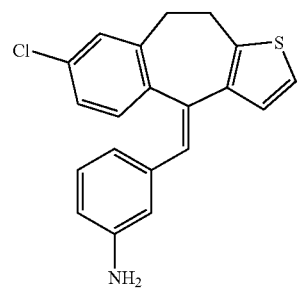

7-chloro-9,10-dihydro-benzo[4,5]cyclohepta[1,2-b] thiophen-4-one (prepared as described in Bastian et al, Helv. Chim. Acta; 49 214-234 (1966)) is converted to the title compound following procedures as described in Scheme VII.

EXAMPLE 479

3-(2-Chloro-9,10dihydro-1-thia-benzo[f]azulen-4-ylidenemethyl)-phenylamine

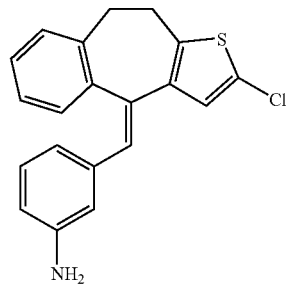

Add 2.2 equiv of n-BuLi-hexanes dropwise to a solution of 3-(9,10-dihydro-1-thia-benzo[f]azulen-4-ylidenemethyl)-phenylamine in THF (0.1 M) at 0° C. under Ar. Stir the resultant dark solution for 1 h before adding 2.5 equiv of hexachloroethane in THF. Stir for 2 h, quench with excess water, and acidify to neutral pH. Extract the aqueous layer with diethyl ether (3×) and then dry (MgSO$_4$) and concentrate the combined organic layers under reduced pressure. Purify the crude residue by column chromatography (0% to 2% to 20% EtOAc:hexanes) to give title compound as an oil (22%) along with recovered starting material: HPLC (ISO80-20A) t=1.903 (90%). MS (APCI): 338 (M+1).

EXAMPLE 480

3-(2,7-Dichloro-9,10-dihydro-1-thia-benzo[f]azulen-4-ylidenemethyl)-phenylamine

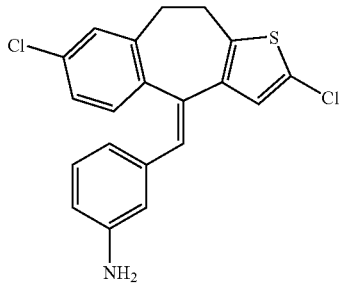

As in Example 553 (above), using 3-(7-chloro-9,10-dihydro-1-thia-benzo[f]azulen-4-ylidenemethyl)-phenylamine, n-BuLi in hexanes, THF, and hexachloroethane. Purify the crude residue by column chromatography (5% to 20% to 30% EtOAc:hexanes) to give title compound as an oil (21%) along with recovered starting material: $^1$H NMR (CDCl$_3$, 400 MHz) δ 2.06-3.02 (m, 4 H), 3.53 (br s, 2 H), 6.32 (s, 1 H), 6.38 (d, J=7.2 Hz, 1 H), 6.48 (dd, J=7.2 Hz, 1.6 Hz, 1 H), 6.79 (s, 1 H), 6.93-6.96 (m, 3 H), 7.02 (dd, J=8.2 Hz, 2.2 Hz, 1 H), 7.27 (d, J=8.2 Hz, 1 H). TLC R$_f$=0.55 (30% EtOAc:hexanes).

EXAMPLE 481

N-[3-(2-Chloro-9,10-dihydro-1-thia-benzo[f]azulen-4-ylidenemethyl)-phenyl]-methanesulfonamide

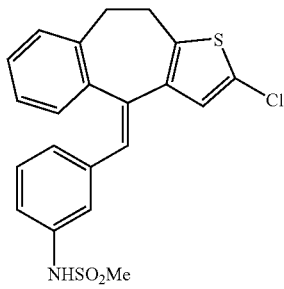

Following procedures essentially as described in Example 90 and using 3-(2-chloro-9,10-dihydro-1-thia-benzo[f]azulen-4-ylidenemethyl)-phenylamine, the title compound is prepared.

EXAMPLE 482

N-[3-(2,7-Dichloro-9,10-dihydro-1-thia-benzo[f]azulen-4-ylidenemethyl)-phenyl]-methanesulfonamide

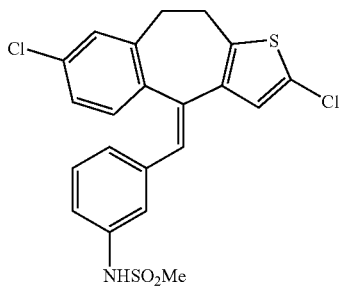

Following procedures essentially as described in Example 90 and using 3-(2,7dichloro-9,10-dihydro-1-thia-benzo[f]azulen-4-ylidenemethyl)-phenylamine, the title compound is prepared.

PREPARATION 39

2-Methyl-4-methylene-9,10-dihydro-4H-3-thia-1-aza-benzo[f]azulene

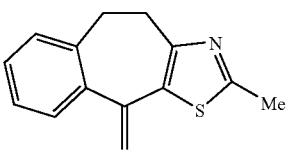

Add 1.2 equiv of n-BuLi-hexanes dropwise to a solution of 4-methylene-9,10-dihydro-4H-3-thia-1-aza-benzo[f]azulene (prepared from 9,10-dihydro-3-thia-1-aza-benzo[f]azulen-4-one (see Scheme XIII(b) as in Preparation 23) in THF (0.08 M) at −78° C. under Ar. Stir the resultant dark green solution for 5 min before adding 1.2 equiv of iodomethane in THF. Allow to warm and stir at room temperature for 18 h before quenching with excess water. Separate layers and extract the aqueous layer with diethyl ether (3×) and then dry (MgSO$_4$) and concentrate the combined organic layers under reduced pressure. Use in the next step without further purification: $^1$H NMR (CDCl$_3$, 400 MHz) δ 2.60 (s, 3 H), 3.03-3.13 (m, 4 H), 5.34 (s, 1 H), 5.53 (s, 1 H), 7.20-7.28 (m, 3 H), 7.33 (m, J=7.2 Hz, 1 H). TLC R$_f$=0.30 (10% EtOAc:hexanes).

EXAMPLE 483(a)

N-[3-(2-Methyl-9,10-dihydro-3-thia-1-aza-benzo[f]azulen-4-ylidenemethyl)-phenyl]-methanesulfonamide (E-isomer); and

EXAMPLE 483(b)

N-[3-(2-Methyl-9,10-dihydro-3-thia-1-aza-benzo[f]azulen-4-ylidenemethyl)-phenyl]-methanesulfonamide (Z-isomer)

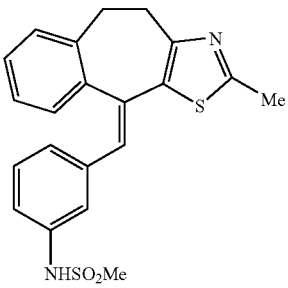

E Isomer

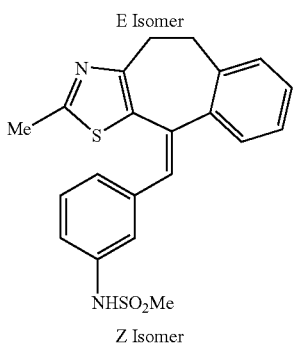

Z Isomer

Following procedures essentially as described in Preparation 24 followed by procedures essentially as described in Example 219, and using 2-methyl-4-methylene-9,10-dihydro-4H-3-thia-1-aza-benzo[f]azulene and 3-methanesulfonylaminophenylboronic acid, the title compounds are made.

PREPARATION 40

3-Chloro-2-oxo-5-phenyl-pentanoic acid methyl ester

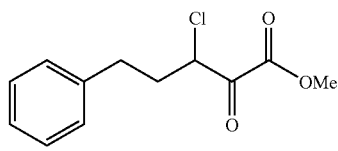

Charge a flask with equimolar methyl dichloroacetate and 3-phenyl-prionaldehyde in diethyl ether (3.0 M). Cool the solution to 0° C. and add 1.1 equiv of sodium methoxide in methanol (2.8 M) over a 1 h period. Vigorously stir the mixture for 2 h at 0 C and then allow to warm to room temperature before adding brine. Separate layers and dry (MgSO$_4$) and concentrate organic layer to give the crude residue in 92% yield. GC-MS (GRAD60-280° C.) t=13.01 (90%). MS (EI): 240 (M−).

PREPARATION 41

2-Amino-5-phenethyl-thiazole-4-carboxylic acid methyl ester

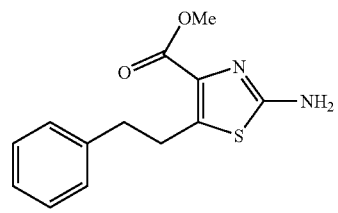

Reflux equimolar 3-chloro-2-oxo-5-phenyl-pentanoic acid methyl ester and thiourea in MeOH (1.0 M) for 4 h. Basify with ammonia-MeOH and add brine. Extract with ethyl acetate (4×). Wash combined organic layers with brine, dry (MgSO$_4$), and concentrate under reduced pressure to give (91%) of title compound. HPLC (GRAD80-100M) t=2.193 (95%). MS (APCI): 263 (M+1).

PREPARATION 42

5-Phenethyl-thiazole-4-carboxylic acid methyl ester

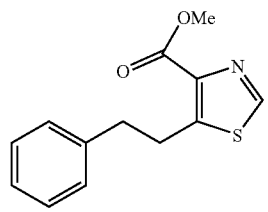

Reflux one equiv of 2-amino-5-phenethyl-thiazole-4-carboxylic acid methyl ester and 3 equiv of isoamyl nitrite in THF (0.13M) for 3 h. Evaporate volatile components to give 55% yield of title compound. BPLC (GRAD80-100M) t=2.410 (99%). MS (APCI): 248 (M+1).

PREPARATION 43

9,10-Dihydro-1-thia-3-aza-benzo[f]azulen-4-one

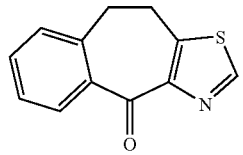

Rapidly stir and heat a thick slurry of 5-phenethyl-thiazole-4-carboxylic acid methyl ester and polyphosphoric acid (PPA) at 140° C. for 24 h and then 150° C. for 5 h. Carefully add hot mixture to ice-cold aqueous sodium hydroxide. Extract well with EtOAc (4×). Wash combined organic layers with brine, dry (MgSO$_4$), and concentrate under reduced pressure. Purify the crude residue by column chromatography (10% to 50% EtOAc:hexanes) to give title compound as a brown solid (37%). HPLC (GRAD80-100M) t=2.088 (99%). MS (APCI): 216 (M+1).

PREPARATION 44

9,10-Dihydro-3-thia-1-aza-benzo[f]azulen-4-one

To a room temperature solution of 2-amino-9,10-dihydro-3-thia-1-aza-benzo[f]azulen-4-one (5.31 g, 23.1 mmol) in DMF (50 mL) is added isoamyl nitrite (5.95 g, 50.8 mmol) and the reaction stirred for 30 min. The reaction mixture is heated to 80° C. for 2 h, and then cooled to room temperature. The solvent is removed under reduced pressure and ice-cold H$_2$O (100 mL) is added. The aqueous layer is extracted with EtOAc (2×150 mL) and the combined organic layers are dried (MgSO$_4$), filtered and the solvent removed under reduced pressure. The dark red oil is subjected to flash chromatography (silica gel, 75:25 Hex/EtOAc) to afford the slightly impure product as an orange-red solid. The product is further purified by trituration using Hex/EtOAc (90:10) to afford the title compound (2.59 g, 52%) as an orange solid: R$_f$ 0.33 (1:1 EtOAc/Hex); mp 83-86° C.; $^1$H NMR (300 MHz, CDCl$_3$) δ8.89 (s, 1H), 7.96 (dd, J=1.2, 7.7 Hz, 1H), 7.50 (dt, J=1.4, 7.4 Hz, 1H), 7.37 (m, 1H), 7.30 (d, J=7.5 Hz, 1H), 3.36 (m, 2H), 3.24 (m, 2H); ESI MS m/z 216 [C$_{12}$H$_9$NOS+H]$^+$. Anal. Calcd for C$_{12}$H$_9$NOS: C, 66.95; H, 4.21; N, 6.51. Found: C, 66.81; H, 3.99; N, 6.48.

PREPARATION 45

7-Fluoro-9,10-dihydro-3-thia-1-aza-benzo[f]azulen-4-one; and

5-Fluoro-9,10-dihydro-3-thia-1-aza-benzo[f]azulen-4-one

To a room temperature solution of a 85:15 mixture of 2-amino-7-fluoro-9,10-dihydro-3-thia-1-aza-benzo[f]azulen-4-one and 2-amino-5-fluoro-9,10-dihydro-3-thia-1-aza-benzo[f]azulen-4-one (6.00 g, 24.2 mmol) in DMF (80 mL) is added t-butyl nitrite (5.48 g, 53.2 mmol). The reaction mixture is then heated to 60° C. for 2 h (gas evolution maybe observed after 5-10 min of heating), then cooled to room temperature. The solvent is removed under reduced pressure and ice-cold H$_2$O (100 mL) and EtOAc (700 mL) are added. The organic layer is washed with saturated aqueous NaHCO$_3$ (100 mL) and saturated aqueous NaCl (100 mL). The organic layer is dried (MgSO$_4$), filtered and concentrated under reduced pressure. The resulting red oil is subjected to flash chromatography (silica gel, 80:20 to 70:30 Hex/EtOAc) to afford the products (3.16 g, 56%) as a partially separable mixture of 5- and 7-fluoro regioisomers. The fractions obtained as a mixture (1.19 g) contain some of the minor isomer (~3:7 5-fluoro/7-fluoro):

$^1$H NMR of 5-fluoro isomer, subtracted from the mixture (300 MHz, CDCl$_3$) □ 8.88 (s, 1H), 7.41 (m, 1H), 7.12-6.98 (m, 2H), 3.32 (m, 2H), 3.39-3.19 (m, 2H).

The fractions obtained pure (1.97 g) contain only the major isomer (7-fluoro) which is isolated as an orange solid: R$_f$ 0.52 (1:1 EtOAc/Hex); mp 122-125° C.; $^1$H NMR (300 MHz, CDCl$_3$) □ 8.89 (s, 1H), 8.02 (dd, J=8.7, 6.0 Hz, 1H), 7.06 (m, 1H), 7.00 (dd, J=9.1, 2.5 Hz, 1H), 3.37 (m, 2H), 3.22 (m, 2H); APCI MS m/z 232 [C$_{12}$H$_8$FNOS—H]$^-$. Anal. Calcd for C$_{12}$H$_8$FNOS: C, 61.79; H, 3.46; N, 6.00. Found: C, 61.70; H, 3.43; N, 6.04.

PREPARATION 46

4-Methylene-9,10-dihydro-4H-1-thia-3-aza-benzo[f]azulene

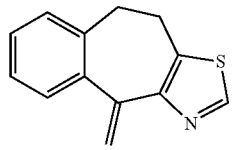

Following procedures essentially as described in Preparation 23, and using 9,10-dihydro-1-thia-3-aza-benzo[f]azulen-4-one, the title compound is made.

EXAMPLE 484(a)

N-[3-(9,10-Dihydro-1-thia-3-aza-benzo[f]azulen-4-ylidenemethyl)-phenyl]-methanesulfonamide (E isomer) and EXAMPLE 484(b)

N-[3-(9,10-Dihydro-1-thia-3-aza-benzo[f]azulen-4-ylidenemethyl)-phenyl]-methanesulfonamide (Z isomer)

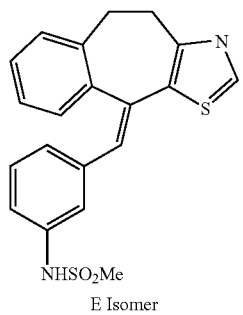 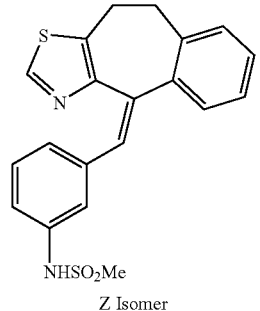

E Isomer     Z Isomer

Following procedures essentially as described in Preparation 24 followed by procedures essentially as described in Example 219, and using the product of Preparation 46 and 3-methanesulfonylaminophenylboronic acid, the title compounds are made.

PREPARATION 47

E-11-(4,4,5,5-Tetramethyl-[1,3,2]dioxaborolan-2-ylmethylene)-6,11-dihydro-5H-benzo[d]pyrrolo[1,2-a]azepine and Z-11-(4,4,5,5-Tetramethyl-[1,3,2]dioxaborolan-2-ylmethylene)-6,11-dihydro-5H-benzo[d]pyrrolo[1,2-a]azepine

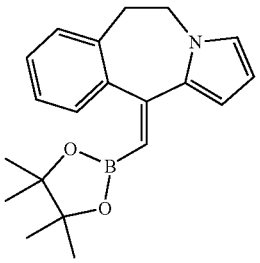 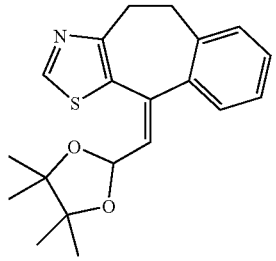

E Isomer     Z Isomer

Add one equiv of 5,6-dihydro-benzo[d]pyrrolo[1,2-a]azepin-11-one (prepared as described in Y. Girard, J. G. Atkinson, P. C. Belanger, J. J. Fuentes, J. Rokach, C. S. Rooney, D. C. Remy, C. A. Hunt *J. Org. Chem.* 1983, 48, 3220) in THF to a solution of 2.5 equiv of pinicol lithio (trimethylsilyl)methaneboronate (as described in D. S. Matteson, D. Majumder *Organometallics* 1983, 2, 230), 1 equiv TMEDA, 2.5 equiv of tetramethylpiperidine (TMP), and THF at −78° C. Allow the solution to warm to room temperature and stir for 3.5 h before quenching with excess water. Extract well with Et$_2$O (4×). Dry (MgSO$_4$) and concentrate under reduced pressure. Purify the crude residue by column chromatography (5% to 10% EtOAc:hexanes) to give pure E-isomer (45%) and Z-isomer (24%). E-isomer: HPLC (GRAD80-100M) t=4.340 (99%). MS (APCI): 322 (M+1).

Z-isomer (24%) BPLC (GRAD80-100M) t=4.423 (99%). MS (APCI): 322 (M+1).

EXAMPLE 485(a)

N-[3-(5,6-Dihydro-benzo[d]pyrrolo[1,2-a]azepin-11-ylidenemethyl)-phenyl]-methanesulfonamide (E-isomer) and EXAMPLE 485(b)

N-[3-(5,6-Dihydro-benzo[d]pyrrolo[1,2-a]azepin-11-ylidenemethyl)-phenyl]-methanesulfonamide (Z-isomer)

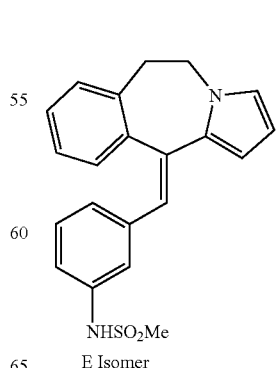 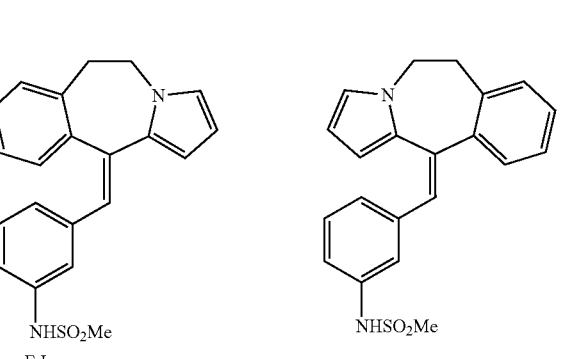

E Isomer     Z Isomer

Following procedures essentially as described in Example 219, and using E- and Z-11-(4,4,5,5-tetramethyl-[1,3,2]dioxaborolan-2-ylmethylene)-6,11-dihydro-5H-benzo[d]pyrrolo[1,2-a]azepine and N-(3-iodo-phenyl)-methanesulfonamide, the E and Z isomers of the title compound are prepared.

PREPARATION 48

2-[2-(3-Fluoro-phenyl)-ethyl]-nicotinic acid

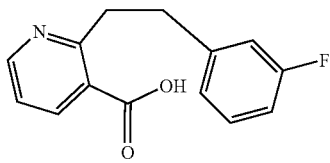

Dissolve diisopropylamine (3.8 mL, 27.3 mmol) in dry tetrahydrofuran (75 mL). Chill the resulting mixture to −78° C. and add butyl lithium (1.6M solution in hexanes, 17.1 mL, 27.3 mmol). Warm the reaction mixture to 0° C. and add a fine slurry of 2-methyl-nicotinic acid (1.5 g, 10.9 mmol) in THF (25 mL) portionwise during 10 min. Stir the resulting slurry for 1 h, then add 3-fluorobenzyl bromide (2.0 mL, 16.4 mmol) and stir 5 min. Quench the reaction with water (100 mL). Extract the reaction mixture with diethyl ether (100 mL). Adjust the pH of the aqueous layer to 3.1 with concentrated aqueous hydrochloric acid solution. Treat the resulting slurry with ethyl acetate and stir to dissolve all solids. Separate the layers and extract the aqueous layer with ethyl acetate. Concentrate the combined extracts to dryness. LCMS (APCI-pos): 244.1 (M+H).

PREPARATION 49

8-Fluoro-10,11-dihydro-benzo[4,5]cyclohepta[1,2-b]pyridin-5-one

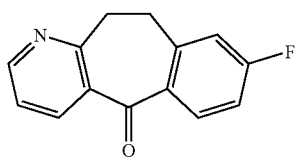

Combine crude 2-[2-(3-fluoro-phenyl)-ethyl]-nicotinic acid (2.06 g, 15.0 mmol) and polyphosphoric acid (100 g) and heat the mixture to 160° C. for 6 h. Allow slow cooling of the reaction mixture over 12 h, then reheat the mixture to 160° C. and pour it into ice (200 g). Complete the transfer using water and adjust the pH of the aqueous mixture to ~8.0 with 50% aqueous sodium hydroxide solution. Extract the product with methylene chloride. Dry the combined organic extracts with magnesium sulfate, filter and concentrate. Purify the crude product via flash chromatography (25% ethyl acetate/hexanes to 50% ethyl acetate/hexanes) to provide 1.54 mg (81%) of purified product. LCMS (APCI-pos): 228.1 (M+H). $^1$HNMR (CDCl$_3$, 400 MHz): δ8.63 (dd, 1H), 8.39 (dd, 1H), 8.01 (dd, 1H), 7.31 (dd, 1H), 7.02 (dt, 1H), 6.95 (dd, 1H), 3.46-3.43 (m, 2H), 3.23-3.21 (m, 2H). (Literature reference: *Journal of Heterocyclic Chemistry* 1971, 73).

PREPARATION 50

8-Fluoro-5-methylene-10,11-dihydro-benzo[4,5]cyclohepta[1,2-b]pyridine

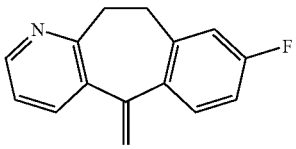

Chill a mixture of 8-fluoro-10,11-dihydro-benzo[4,5]cyclohepta[1,2-b]pyridin-5-one (1.3 g, 5.7 mmol) and dry tetrahydrofuran (50 mL) to 0° C. Treat this mixture with methyl magnesium bromide(3.0M solution in diethyl ether, 5.7 mL, 17.2 mmol). Remove cooling and stir the admixture at room temperature for 15 min. Quench the reaction, while cooling with an ice-water bath, by adding saturated aqueous ammonium chloride solution (50 mL). Separate the layers and extract the aqueous layer with methylene chloride (2×50 mL). Dry the combined organic layers with magnesium sulfate, filter and concentrate to provide the intermediate product as a thick crude oil.

Without further purification, dissolve this residue in a solution of sulfuric acid in acetic acid (3% by volume, 50 mL) and stir the resulting mixture at room temperature for 12-18 h. Concentrate the reaction mixture to remove excess solvent and dissolve the resulting orange residue in 1N aqueous sodium hydroxide solution (25 mL) and ethyl acetate (50 mL). Adjust the pH of the resulting mixture to 8 with 5N aqueous sodium hydroxide solution. Separate the layers and extract the aqueous layer with ethyl acetate (2×50 mL). Dry the combined organic layers with magnesium sulfate, filter and concentrate to 1.3 g (91%) of the title product as an orange-brown oil. LCMS: 226.1 (M+H).

PREPARATION 51

(E+Z)-5-Bromomethylene-8-fluoro-10,11-dihydro-benzo[4,5]cyclohepta[1,2-b]pyridine

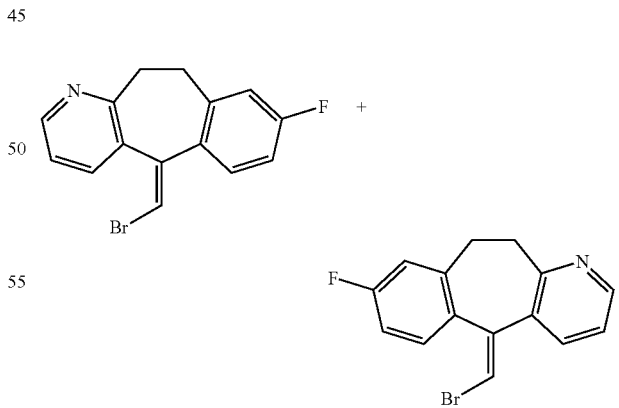

Make the title compounds according to Preparation 24, beginning with 8-fluoro-5-methylene-10,11-dihydro-benzo[4,5]cyclohepta[1,2-b]pyridine (1.1 g, 5.1 mmol). After workup and purification and separation by flash chromatography (25% ethyl acetate/hexanes to 50% ethyl acetate/hexanes) isolate 700 mg (44%/o) of (E)-5-bromomethylene-10, 11-dihydro-8-fluoro-benzo[4,5]cyclohepta[1,2-b]pyridine and 550 mg (34%/o) of (Z)-5-bromomethylene-10,11-dihydro-8-fluoro-benzo[4,5]cyclohepta[1,2-b]pyridine. For (Z)-5-bromomethylene-10,11-dihydro-8-fluoro-benzo[4,5]cyclohepta[1,2-b]pyridine, LCMS (APCI-pos): 304, 305, 306, 307. $^1$HNMR (CDCl$_3$, 400 MHz): δ8.45 (dd, 1H), 7.69 (dd, 1H), 7.18 (dd, 1H), 7.13 (dd, 1H), 6.87-6.83 (m, 2H), 6.61 (s, 1H), 3.6-2.4 (m, 4H). For (E)-5-bromomethylene-10,11-dihydro-benzo[4,5]cyclohepta[1,2-b]pyridine, LCMS (APCI-pos): 304, 305, 306, 307. $^1$HNMR (CDCl$_3$, 400 MHz): δ8.45 (dd, 1H), 7.56 (dd, 1H), 7.25 (dd, 1H), 7.09 (dd, 1H), 6.99 (dd, 1H), 6.92 (dt, 1H), 6.69 (s, 1H), 3.6-2.8 (m, 4H).

EXAMPLE 486

(E)-N-[3-(8-fluoro-10,11-dihydro-benzo[4,5]cyclohepta[1,2-b]pyridin-5-ylidenemethyl)-phenyl]-methanesulfonamide

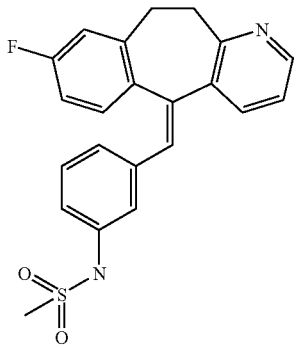

Following procedures essentially as desctribed in Example 219, beginning with (E)-5-bromomethylene-8-fluoro-10,11-dihydro-benzo[4,5]cyclohepta[1,2-b]pyridine (200 mg, 0.66 mmol). After work-up, purify the crude product by flash chromatography (50% ethyl acetate/hexanes to 75% ethyl acetate/hexanes) to provide 197 mg (76%) of purified product. LCMS (APCI-pos): 395.1 (M+H). LCMS (APCI-neg): 393.0 (M–H); Purity by LCMS (W Area percent) 99%. $^1$HNMR (d6-DMSO, 400 MHz): δ9.62 (s, 1H), 8.41 (dd, 1H), 7.90 (dd, 1H), 7.28-7.24 (m, 2H), 7.14 (t, 1H), 6.96-6.87 (m, 5H), 6.75 (d, 1H), 3.6-2.9 (m, 4H), 2.79 (s, 3H).

EXAMPLE 487

(E)-5-(8-Fluoro-10,11-dihydro-benzo[4,5]cyclohepta[1,2-b]pyridin-5-ylidenemethyl)-1,3-dihydro-benzoimidazol-2-one

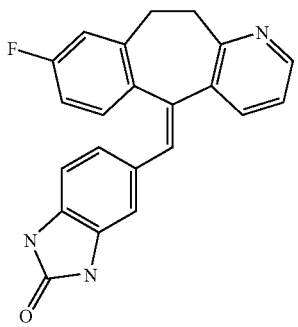

Following procedures essentially as desctribed in Example 219, beginning with (E)-5-bromomethylene-8-fluoro-10,11-dihydro-benzo[4,5]cyclohepta[1,2-b]pyridine (100 mg, 0.33 mmol) and 5-(4,4,5,5-tetramethyl-[1,3,2]dioxaborolan-2-yl)-1,3-dihydro-benzoimidazol-2-one (111 mg, 0.43 mmol). After work-up, purify the crude product by flash chromatography (100% ethyl acetate to 10% ethanol/ethyl acetate) to provide 70 mg (60%) of purified product. LCMS (APCI-pos): 358.0 (M+H). LCMS (APCI-neg): 356.0 (M–H). Purity by LCMS (UV Area percent): 99%. $^1$HNMR (d6-DMSO, 400 MHz): δ10.56 (s, 1H), 10/46 (s, 1H), 8.38 (dd, 1H), 7.88 (dd, 1H), 7.28 (dd, 1H), 7.23 (dd, 1H), 6.96-6.90 (m, 2H), 6.89 (s, 1H), 6.73 (d, 1H), 6.68 (d, 1H), 6.52 (s, 1H), 3.5-3.3 (m, 2H), 3.1-2.9 (m, 2H).

PREPARATION 52

2-(3-Fluoro-5-nitro-phenyl)-4,4,5,5-tetramethyl-[1,3,2]dioxaborolane

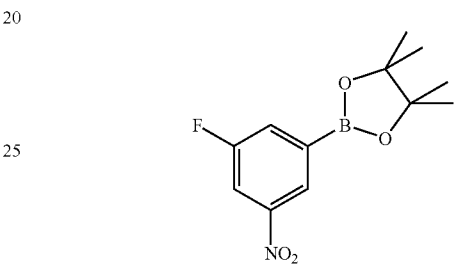

Make according to literature precedent (*Journal of Organic Chemistry* 1995, 60, 7508) beginning with 1-fluoro-3-iodo-5-nitrobenzene (1.0 g, 3.7 mmol). Purify the crude product by flash chromatography (1:3-4% acetic acid in tetrahydrofuran/hexanes) and combine product fractions. Strip to dryness and add 50 mL ethanol and strip to dryness to provide 945 mg (94%) of purified product. Purity by GCMS: 80%, mass 267.0. $^1$HNMR (CDCl$_3$, 400 MHz): δ8.43 (bs, 1H), 7.98 (dt, 1H), 7.80 (dd, 1H), 1.36 (s, 12H)

PREPARATION 53

3-Fluoro-5-(4,4,5,5-tetramethyl-[1,3,2]dioxaborolan-2-yl)-phenylamine

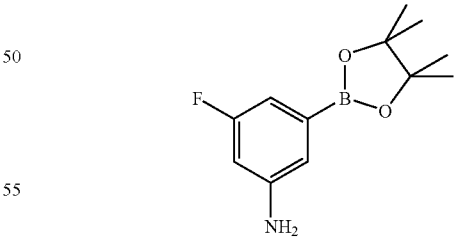

Combine 1-fluoro-3-iodo-5-nitrobenzene 2-(3-Fluoro-5-nitro-phenyl)-4,4,5,5-tetramethyl-[1,3,2]dioxaborolane (940 mg, 3.5 mmol), 5% palladium on carbon (~60% H$_2$O, 200 mg), and anhydrous ethanol (25 mL). Purge and fill the reaction vessel with hydrogen three times. Stir the reaction mixture under 1 atm of hydrogen. When the reaction is complete by LCMS, filter the reaction mixture through celite to remove the catalyst and wash the filter cake with ethanol. Strip to dryness and purify the crude product by flash chromatography (25% ethyl acetate/hexanes) and combine product fractions. Strip to dryness to provide the crude product. LCMS (APCI-pos): mass 238.2 (M+1), Purity by LCMS (UV area percent): 85%. $^1$HNMR (CDCl$_3$, 400 MHz): δ6.88-6.83 (m, 2H), 6.47-6.43 (m, 1H), 3.55-3.9 (bs, 2H), 1.32 (s, 12H)

PREPARATION 54

N-[3-Fluoro-5-(4,4,5,5-tetramethyl-[1,3,2]dioxaborolan-2-yl)-phenyl]-methanesulfonamide

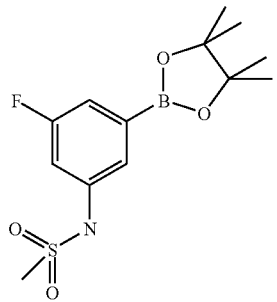

Combine 3-fluoro-5-(4,4,5,5-tetramethyl-[1,3,2]dioxaborolan-2-yl)-phenylamine (610 mg, 2.6 mmol), methanesulfonyl chloride (240 μL, 3.09 mmol) in pyridine (25 mL). Stir the reaction mixture under nitrogen for 18-24 h. Strip to dryness and partition the crude product between methylene chloride (100 mL) and brine (100 mL). Separate the layers and dry the organic layer with magnesium sulfate. Purify the crude product by crystallization (methylene chloride/hexanes) to provide 625 mg of purified product.

LCMS (APCI-pos): mass 333.1 (M+H$_2$O), Purity by LCMS (UV area percent): 99%.

$^1$HNMR (CDCl$_3$, 400 MHz): δ7.31-7.20 (m, 3H), 6.44 (s, 1H), 3.03 (s, 3H), 1.34 (s, 12H).

EXAMPLE 488

(E)-N-[3-Fluoro-5-(8-fluoro-10,11-dihydro-benzo[4,5]cyclohepta[1,2-b]pyridin-5-ylidenemethyl)-phenyl]-methanesulfonamide

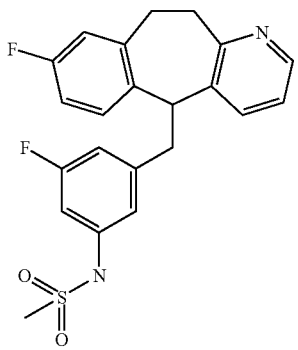

Following procedures essentially as desctribed in Example 219, beginning with (E)-5-bromomethylene-8-fluoro-10,11-dihydro-benzo[4,5]cyclohepta[1,2-b]pyridine (50 mg, 0.16 mmol) and N-[3-fluoro-5-(4,4,5,5-tetramethyl-[1,3,2]dioxaborolan-2-yl)-phenyl]-methanesulfonamide (62 mg, 0.20 mmol). After work-up, purify the crude product by flash chromatography (50% ethyl acetate/hexanes to 75% ethyl acetate/hexanes) to provide 44 mg (65%) of purified product. LCMS (APCI-pos): 413.0 (M+H). LCMS (APCI-neg): 411.0 (M−H). Purity by LCMS 1 Area percent) 98%. $^1$HNMR (d6-DMSO, 400 MHz): δ9.91 (s, 1H), 8.42 (dd, 1H), 7.91 (dd, 1H), 7.29-7.25 (m, 2H), 6.92 (s, 2H), 6.90 (d, 1H), 6.77-6.74 (m, 2H), 6.52-6.49(m, 1H), 3.4-2.8 (m, 4H), 2.87 (s, 3H).

Examples 489-601 contained in Table 11, herein, provide yet additional examples of compounds of Formula I wherein the "A" and/or "B" ring represents a heterocyclic ring.

These examples, which further illustrate the present invention are prepared according to the procedures as described generally in the Schemes and literature references described above.

Examples 602-606 contained in Table II, herein, provide yet additional examples of compounds of Formula I wherein the bridge depicted by —X—Y— represents a fused cyclopropyl structure. (Section 5 as represented by original Examples 255-260). These examples, which further illustrate the present invention are prepared according to the procedures as described generally in the Schemes and literature references described above.

Additional preparations for, and examples of compounds of Formula I wherein the bridge depicted by —X—Y— contains a heteroatom or heteroatom containing group at either the X or Y position. (Section 6 as represented by original Examples 261-274)

PREPARATION 55

3,8-difluoro-6H-dibenzo[b,e]oxepin-11-one

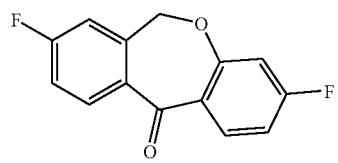

Prepare starting ketones for oxepine derivatives as described by M Kurokawa, F Sato, Y Masuda, T Yoshida and Y Ochi, Chem. Pharm. Bull., 39; 10; (1991) 2564-5273.

EXAMPLE 607

5-(3-Fluoro-6H-dibenzo[b,e]oxepin-11-ylidenemethyl)-1-(2-morpholin-4-yl-ethyl)-1,3-dihydro-benzoimidazol-2-one

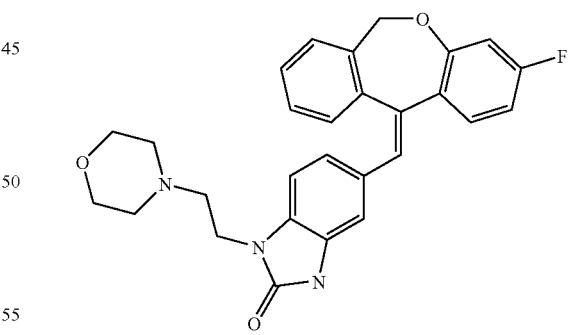

Following procedures essentially as described in Example 219, mix 1-(2-morpholinyl-4-yl-ethyl)-5-(4,4,5,5-tetramethyl-[1,3,2]dioxaborolan-2-yl)-1,3-dihydro-benzoimidazol-2-one (330 mg, 1.1 mmol), 11-bromomethylene-3-fluoro-6,11-dihydro-dibenzo[b,e]oxepine (E-isomer, 300 mg, 1.03 mmol)(prepared following procedures essentially as described in Preparations 55, 23, and 24), 2N Na$_2$CO$_3$ (1.4 mL), dioxane (10 mL) and (Ph$_3$P)$_4$Pd (44 mg, 0.04 mmol). Recrystallize the crude product from toluene and then further purify by using an SCX column by eluting with 1/1 MeOH/dichloromethane then 1/1 2N NH$_3$ MeOH/dichloromethane.

Obtain 51 mg of title compound as a white solid, HPLC (ISO80-10M) t=1.82(99%). MS (ES) 472 (M+1), 470 (M−1). H NMR (MSO-d$_6$)δ10.72 (s, 1H), 7.57 (m, 2H), 7.35 (t, 1H, J=7.5 Hz), 7.23 (t, 1H, J=7.5 Hz), 7.00 (d, 1H, J=7.4 Hz), 6.97 (s, 1H), 6.93 (d, 1H, J=8.4 Hz), 6.79 (td, 1H, J=11.9, 4.3 Hz), 6.73 (d, 1H, J=8.4 Hz), 6.60 (m, 2H), 5.31 (d, 2H, J=225.4 Hz), 3.80 (t, 2H, J=6.4 Hz), 3.46 (t, 4H, J=4.4 Hz), 2.48 (t, 3H, J=6.2 Hz), 2.38 (s, 4H), 2.48 (t, 2H, J=6.2 Hz).

EXAMPLE 608

5-(3-fluoro-6H-dibenzo[b,e]oxepin-11-ylidenem-ethyl)-1-(3-morpholin-4-yl-propyl)-1,3-dihydro-benzoimidazol-2-one

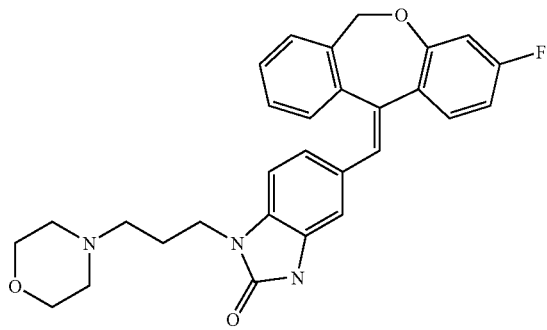

Following procedures essentially as described in Example 219, mix 1-(2-morpholin-4-yl-propyl)-5-(4,4,5,5-tetram-ethyl-[1,3,2]dioxaborolan-2-yl)-1,3-dihydro-benzoimida-zol-2-one (205 mg, 0.53 mmol)(prepared following procedures essentially as described in Preparation 36), 11-bromomethylene-3-fluoro-6,11-dihydro-dibenzo[b,e]ox-epine (E-isomer, 150 mg, 0.5 mmol), 2N Na$_2$CO$_3$ (0.5 mL), dioxane (5 mL) and (Ph$_3$P)$_4$Pd (53 mg, 0.046 mmol). Purify the crude product by column chromatography using 2N NH$_3$ in MeOH/dichloromethane. Triturate the product obtained (192 mg) with hexane to give 170 mg pure title compound, HPLC (ISO80-10M) t=1.72 (100%). MS (ES) 486 (M+1), 484 (M−1). H NMR (DMSO-d$_6$)10.68 (s, 1H), 7.57 (m, 2H), 7.35 (t, 1H, J=7.5 Hz), 7.22 (t, 1H, J=7.7 Hz), 6.96 (m, 3H), 6.78 (td, 1H, J=12.0, 4.2 Hz), 6.71 (d, 1H, J=7.5 Hz), 6.60 (m, 2H), 5.31 (br d, 2H), 3.72 (t, 2H, J=6.6 Hz), 3.46 (t, 4H, J=4.2 Hz), 2.48 (m, 4H), 1.71 (m, 2H), 2.20 (m, 6H).

EXAMPLE 609

1-cyclopropyl-5-(3-fluoro-6H-dibenzo[b,e]oxepin-11-ylidenemethyl)-1,3-dihydro-benzoimidazol-2-one

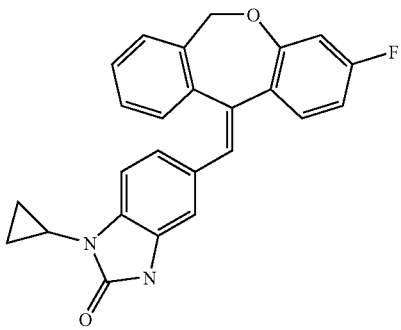

Following procedures essentially as described in Example 219, mix 1-cyclopropyl-2-oxo-2,3-dihydro-1H-benzoimida-zole-5-boronic acid (120 mg, 0.55 mmol) (prepared essentially as described in Preparation 36), 11-bromomethylene-3-fluoro-6,11-dihydro-dibenzo[b,e]oxepine (E and Z mixture, 177 mg, 0.58 mmol), 2N Na$_2$CO$_3$ (0.7 mL), dioxane (8 mL) and (Ph$_3$P)$_4$Pd (38 mg, 0.033 mmol). Purify the crude product by column chromatography using THF/hexane to give 65 mg title compound as a gray powder.

HPLC (ISO80-10M) t=3.53 (93%), MS (ES) 399 (M+1), 397 (M−1). H NMR 10.58 (s, 1H), 7.58 (m, 3H), 7.35 (t, 1H, J=7.5 Hz), 7.23 (t, 1H, J=7.5 Hz), 6.96 (m, 3H), 7.58 (m, 2H), 6.80 (dd, 1H, J=7.9, 2.6 Hz), 6.75 (d, 1H, J=7.5 Hz), 6.60 (dd, 1H, J=10.6, 2.2 Hz), 6.57 (s, 1H), 5.84-4.79 (m, 2H), 2.75 (m, 1H), 0.93 (m, 2H), 0.77 (m, 2H).

EXAMPLE 610

5-(3-fluoro-6H-dibenzo[b,e]oxepin-11-ylidenem-ethyl)-1-(2-morpholin-4yl-ethyl)-1,3-dihydro-ben-zoimidazol-2-one

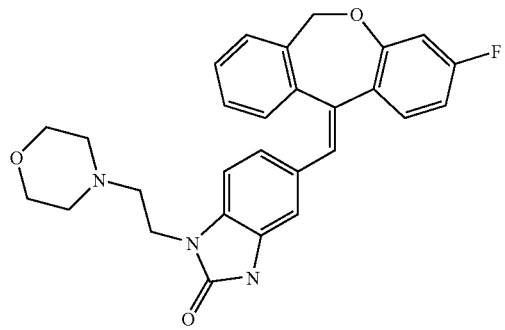

Following procedures essentially as described in Example 219, mix 1-(2-morpholin-4-yl-ethyl)-5-(4,4,5,5-tetramethyl-[1,3,2]dioxaborolan-2-yl)-1,3-dihydro-benzoimidazol-2-one (300 mg, 1.03 mmol), 11-bromomethylene-3-fluoro-6,11-dihydro-dibenzo[b,e]oxepine (E isomer, 330 mg, 1.08 mmol), 2N Na$_2$CO$_3$ (1.4 mL), dioxane (10 mL) and (Ph$_3$P)$_4$Pd (44 mg, 0.038 mmol). Purify the crude product by column chromatography using 40% THF/hexane to yield 80 mg title compound as a pale yellow powder. HPLC (ISO80-10M) t=1.84 (96%), MS (ES) 472 (M+1), 470 (M−1). H NMR (DMSO-d$_6$)10.72 (s, 1H), 7.57 (m, 2H), 7.35 (t, 1H, J=7.5 Hz), 7.23 (t, 1H, J=7.5 Hz), 7.00 (d, 1H, J=7.5 Hz), 6.97 (s, 1H), 6.93 (d, 1H, J=8.4 Hz), 6.79 (td, 1H, J=11.9, 4.3 Hz), 6.73 (d, 1H, J=8.4 Hz), 6.60 (m, 2H), 5.82-4.79 (m, 2H), 3.80 (t, 2H, J=6.4 Hz), 3.46 (t, 4H, J=4.4 Hz), 2.48 (m, 2H), 2.38 (s, 4H).

EXAMPLE 611

5-(3-Fluoro-6H-dibenzo[b,e]oxepin-11-ylidenem-ethyl)-1,3-dihydro-benzoimidazol-2-one

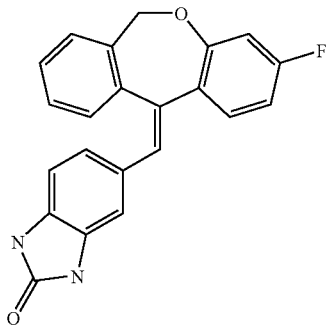

Following procedures essentially as described in Example 219, using 11-bromomethylene-3-fluoro-6,11-dihydro-dibenzo[b,e]oxepine (E-isomer, 1.05 eq.) and 5-(4,4,5,5-tet-ramethyl-[1,3,2]dioxaborolan-2-yl)-1,3-dihydro-benzoimi-dazol-2-one (1 eq.). Purify crude product on silica gel, eluting with 60% to 100% ethyl acetate/CHCl$_3$ to afford a light yellow solid. Triturate with acetone to afford the title compound as a white solid. HPLC (ISO60-10) t=4.09 min, 100%; MS [ES] 357 (M–H), 359 M+H); ¹H-NMR (DMSO-d₆) δ 10.56 (s, 1H), 10.46 (s, 1H), 7.56 (m, 2H), 7.35 (t, 1H, J=7.5 Hz), 7.23 (t, 1H, J=7.5 Hz), 6.99 (d, 1H, J=7.5 Hz), 6.94 (s, 1H), 6.78 (td, 1H, J=12.0, 4.2 Hz), 6.71 (d, 1H, J=8.4 Hz), 6.66 (d, 1H, J=8.4 Hz), 6.59 (dd, 1H, J=10.6, 2.6 Hz), 6.57 (s, 1H), 5.83-4.71 (br d, 2H).

EXAMPLE 612

5-(3-Fluoro-6H-dibenzo[b,e]oxepin-11-ylidenem-ethyl)-1-isopropyl-1,3-dihydro-benzoimidazol-2-one

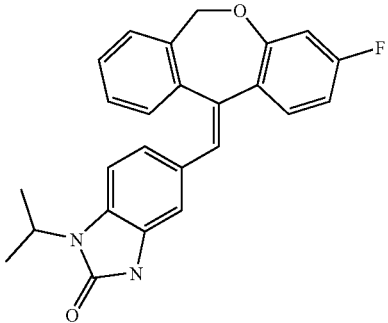

Following procedures essentially as described in Example 219, mix 11-bromomethylene-3-fluoro-6,11-dihydro-dibenzo[b,e]oxepine (150 mg, 0.493 mmol), 1-isopropyl-2-oxo-2,3-dihydro-1H-benzoimidazole-5-boronic acid (103 mg, 0.468 mmol)(prepared according to Scheme IX by using isopropylamine in Step A), Na₂CO₃ (2M in water, 620 □L, 1.23 mmol), dioxane (4 mL), and Pd(PPh₃)₄ (29 mg, 0.025 mmol). Purify the crude product on silica gel (24 g), eluting with 25% to 50% THF/hexanes to afford 130 mg (69%) of the title compound as a yellow foam. HPLC (ISO80-10) t=3.86 min, 98%; MS [ES] 399 (M–H); ¹H-NMR (CDCl₃) δ 9.10 (s, 1H), 7.44 (m, 2H), 7.32 (t, 1H, J=7.5 Hz), 7.22 (t, 1H, J=7.5 Hz), 7.11 (d, 1H, J=7.5 Hz), 6.93 (d, 1H, J=8.4 Hz), 6.86 (s, 1H), 6.75 (d, 1H, J=8.4 Hz), 6.69 (s, 1H), 6.66 (td, 1H, J=11.7, 4.1 Hz), 6.52 (dd, 1H, J=10.3, 2.4 Hz), 5.92-4.73 (m, 2H), 4.66 (m, 1H), 1.51 (d, 6H, J=7.0 Hz).

EXAMPLE 613

5-(3,8-Difluoro-6H-dibenzo[b,e]oxepin-11-yliden-emethyl)-1,3-dihydro-benzoimidazol-2-one

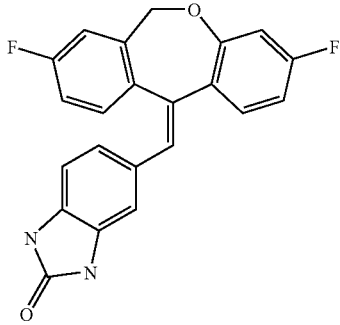

Following procedures essentially as described in Example 219, mix 11-bromomethylene-3,8-difluoro-6,11-dihydro-dibenzo[b,e]oxepine (E-isomer, 326 mg, 1.0 mmol), 5-(4,4,5,5-tetramethyl-[1,3,2]dioxaborolan-2-yl)-1,3-dihydro-benzoimidazol-2-one (250 mg, 0.961 mmol), Na₂CO₃ (2M in water, 1.20 mL, 2.40 mmol), dioxane (7 mL), and Pd(PPh₃)₄ (58 mg, 0.051 mmol). Purify the crude product on silica gel (12 g) eluting with 50% to 70% THF/hexanes to afford two lots of yellow solid weighing 180 mg and 151 mg. Dissolve the 180 mg lot in boiling MeOH (20 mL), concentrate to 10 mL and cool to –26° C. to precipitate 165 mg (46%) of the title compound as a white solid. Repeat the recrystallization on the 151 mg lot to afford 98 mg (27%) of the title compound as a white solid. HPLC (ISO80-10) t=2.38 min, 97%; MS [ES] 375 (M–H), 377 (M+H); ¹H-NMR (DMSO-d₆) δ 10.57 (s, 1H), 10.46 (s, 1H), 7.57 (dd, 1H, J=8.4, 7.0 Hz), 7.49 (dd, 1H, J=9.2, 2.6 Hz), 7.08 (td, 1H, J=12.5, 4.3 Hz), 7.01 (d, 1H, J=5.7 Hz), 6.97 (s, 1H), 6.79 (td, 1H, J=12.0, 4.2 Hz), 6.73 (d, 1H, J=8.4 Hz), 6.67 (d, 1H, J=8.4 Hz), 6.61 (dd, 1H, J=10.6, 2.6 Hz), 6.52 (s, 1H), 5.78-4.78 (br d, 2H).

EXAMPLE 614

5-(3-Chloro-6H-dibenzo[b,e]oxepin-11-ylidenem-ethyl)-1,3-dihydro-benzoimidazol-2-one

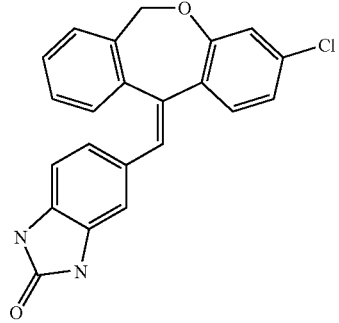

Following procedures essentially as described in Example 219, mix 11-bromomethylene-3-chloro-6,11-dihydro-dibenzo[b,e]oxepine (E-isomer, 40 mg, 0.124 mmol) (prepared essentially as described in Preparation 55), 5-(4,4,5,5-tetramethyl-[1,3,2]dioxaborolan-2-yl)-1,3-dihydro-benzoimidazol-2-one (31 mg, 0.118 mmol), Na₂CO₃ (2M in water, 148 □L, 0.295 mmol), dioxane (1 mL), and Pd(PPh₃)₄ (7 mg, 0.006 mmol). Purify the crude product on silica gel (12 g) eluting with 2% to 5% (2M NH₃/MeOH)/CH₂Cl₂ to afford 31 mg (69%) of the title compound as a white solid. HPLC (ISO80-10) t=2.85min, 99%; MS [ES] 373 (M–H); ¹H-NMR (DMSO-d₆) δ10.57 (s, 1H), 10.47 (s, 1H), 7.56 (dd, 2H, J=7.8, 6.1 Hz), 7.35 (t, 1H, J=7.5 Hz), 7.24 (t, 1H, J=7.7 Hz), 6.98 (m, 3H), 6.82 (d, 1H, J=4.4 Hz), 6.69 (m, 2H), 6.57 (s, 1H), 5.89-4.79 (br d, 2H).

EXAMPLE 615

5-(3,7-Difluoro-6H-dibenzo[b,e]oxepin-11-yliden-emethyl)-1-(2-morpholin-4-yl-ethyl)-1,3-dihydro-benzoimidazol-2-one

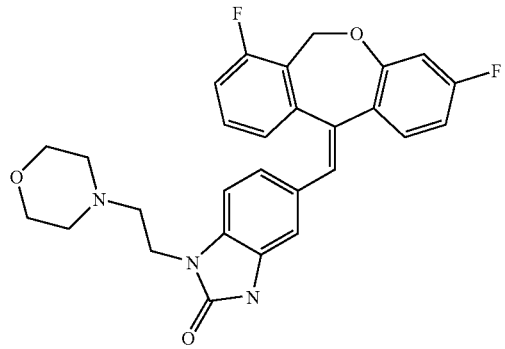

Following procedures essentially as described in Example 219, mix 11-bromomethylene-3,7-difluoro-6,11-dihydro-dibenzo[b,e]oxepine (E-isomer, 200 mg, 0.619 mmol) (prepared essentially as described in Preparation 55), 1-(2-morpholin-4-yl-ethyl)-5-(4,4,5,5-tetramethyl-[1,3,2]dioxaborolan-2-yl)-1,3-dihydro-benzoimidazol-2-one (220 mg, 0.589 mmol), Na$_2$CO$_3$ (2M in water, 736 □L, 1.47 mmol), dioxane (4 mL), and Pd(PPh$_3$)$_4$ (36 mg, 0.031 mmol). Purify the crude product on silica gel (64 g) eluting with 2% (2M NH$_3$/MeOH)/CH$_2$Cl$_2$ to afford 191 mg (66%) of the title compound as a white foam. HPLC (ISO80-10) t=1.95 min, 98%; MS [ES] 488 (M−H), 490 (M+H); $^1$H-NMR (DMSO-d$_6$) δ 10.69 (s, 1H), 7.58 (dd, 1H, J=8.8, 7.0 Hz), 7.24 (m, 2H), 7.02 (s, 1H), 6.96 (d, 1H, J=8.4 Hz), 6.80 (m, 3H), 6.64 (m, 2H), 5.56-5.20 (br d, 2H), 3.81 (t, 2H, J=6.4 Hz), 3.46 (t, 4H, 4.4 Hz), 2.48 (m, 2H), 2.37 (s, 4H).

EXAMPLE 616

5-(3,7-Difluoro-6H-dibenzo[b,e]oxepin-11-ylidenemethyl)-1,3-dihydro-benzoimidazol-2-one

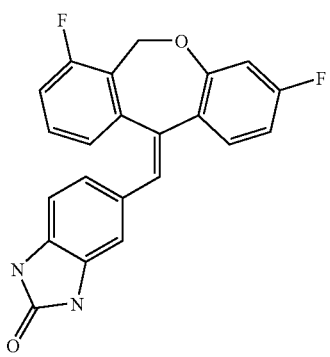

Following procedures essentially as described in Example 219, mix 11-bromomethylene-3,7-difluoro-6,11-dihydro-dibenzo[b,e]oxepine (E-isomer, 68 mg, 0.21 mmol), 5-(4,4,5,5-tetramethyl-[1,3,2]dioxaborolan-2-yl)-1,3-dihydro-benzoimidazol-2-one (52 mg, 0.20 mmol), Na$_2$CO$_3$ (2M in water, 251 μL, 0.503 mmol), dioxane (2 mL), and Pd(PPh$_3$)$_4$ (12 mg, 0.010 mmol). Purify on silica gel (12 g) eluting with THF to afford a brown solid. Triturate with acetone to afford 56 mg (74%) of the title compound as a white solid. HPLC (ISO80-10) t=2.42 min, 96%; MS [ES] 375 (M−H); $^1$H-NMR (DMSO-d$_6$) δ 10.58 (s, 1H), 10.46 (s, 1H), 7.57 (dd, 1H, J=8.8, 7.0 Hz), 7.24 (m, 2H), 7.00 (s, 1H), 6.81 (m, 2H), 6.72 (m, 2H), 6.64 (dd, 1H, J=10.6, 2.6 Hz), 6.59 (s, 1H), 5.55-5.19 (br d, 2H).

EXAMPLE 617

5-(3,8-Difluoro-6H-dibenzo[b,e]oxepin-11-ylidenemethyl)-1-(2-morpholin-4-yl-ethyl)-1,3-dihydro-benzoimidazol-2-one

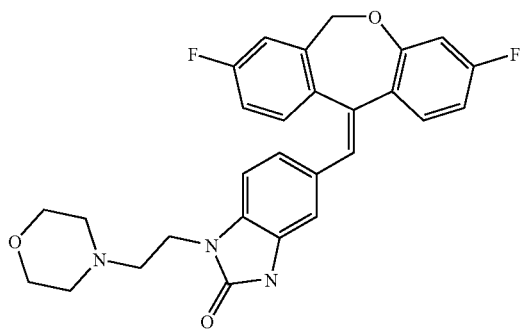

Following procedures essentially as described in Example 219, mix 11-bromomethylene-3,8-difluoro-6,11-dihydro-dibenzo[b,e]oxepine (E-isomer, 40 mg, 0.12 mmol), 1-(2-morpholin-4-yl-ethyl)-5-(4,4,5,5-tetramethyl-[1,3,2]dioxaborolan-2-yl)-1,3-dihydro-benzoimidazol-2-one (44 mg, 0.12 mmol), Na$_2$CO$_3$ (2M in water, 155 μL, 0.310 mmol), dioxane (1 mL), and Pd(PPh$_3$)$_4$ (7 mg, 0.006 mmol). Purify on silica gel (12 g), eluting with 2% to 5% (2M NH$_3$/MeOH)/CH$_2$Cl$_2$ to afford 45 mg (78%) of the title compound as a white foam. HPLC (ISO80-10) t=1.86 min, 99%; MS [ES] 488 (M−H), 490 (M+H); $^1$H-NMR (DMSO-d$_6$) δ 10.70 (s, 1H), 7.59 (dd, 1H, J=8.5, 7.1 Hz), 7.51 (dd, 1H, J=8.8, 2.6 Hz), 7.08 (td, 1H, J12.5, 4.3 Hz), 7.01 (m, 2H), 6.96 (d, 1H, J=7.9 Hz), 6.80 (td, 1H, J=12.0, 4.2 Hz), 6.73 (d, 1H, J=7.9 Hz), 6.62 (dd, 1H, J=10.3, 2.4 Hz), 6.58 (s, 1H), 5.72-4.85 (br d, 2H), 3.81 (t, 2H, J=6.4 Hz), 3.47 (t, 4H, J=4.4 Hz), 2.48 (m, 2H), 2.38 (s, 4H).

PREPARATION 56

8-Fluoro-11H-10-oxa-1-aza-dibenzo[a,d]cyclohepten-5-one

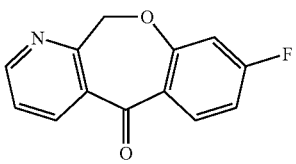

Prepare according to literature precedent: *Journal of Medicinal Chemistry* 1990, 33, 3095.

PREPARATION 57

8-Fluoro-5-methylene-5,11-dihydro-10-oxa-1-aza-dibenzo[a,d]cycloheptene

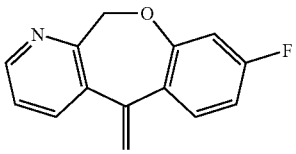

Combine 8-fluoro-11H-10-oxa-1-aza-dibenzo[a,d]cyclohepten-5-one (567 mg, 2.47 mmol) and anhydrous tetrahydrofuran (25 mL). Chill the solution to 0° C. and add Tebbe reagent (0.5M/L solution in toluene, 5.4 mL, 2.72 mmol). Remove cooling and stir the admixture for 10 min. Quench the reaction by adding saturated aqueous Rochelle's salt solution (75 mL). Stir the biphasic mixture rapidly for 10 min, then separate the layers and extract the aqueous layer with ethyl acetate. Dry the combined organic layers with magnesium sulfate, filter and strip. Purify the crude product by flash chromatography (25% ethyl acetate/hexanes) to provide 416 mg(74%) of purified product. LCMS (APCI-pos): 228.1 (M+H). LCMS (APCI-neg): 226.9 (M−H).

PREPARATION 58

(E+Z)-5-Bromomethylene-8-fluoro-5,11-dihydro-10-oxa-1-aza-dibenzo[a,d]cycloheptene

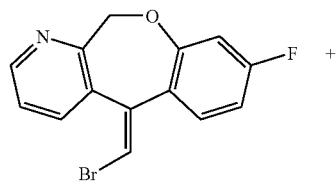 +

-continued

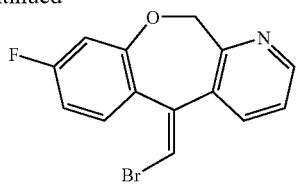

Make the title compounds according to procedures essentially as described in Preparation 24, beginning with 8-fluoro-5-methylene-5,11-dihydro-10-oxa-1-aza-dibenzo[a,d]cycloheptene (416 mg, 1.83 mmol). After workup and purification and separation by flash chromatography (25% ethyl acetate/hexanes) isolate 383 mg (68%) of (E)-5-bromomethylene-8-fluoro-5,11-dihydro-10-oxa-1-aza-dibenzo[a,d]cycloheptene and 125 mg (23%) of (Z)-5-bromomethylene-8-fluoro-5,11-dihydro-10-oxa-1-aza-dibenzo[a,d]cycloheptene. For (E)-5-bromomethylene-8-fluoro-5,11-dihydro-10-oxa-1-aza-dibenzo[a,d]cycloheptene, LCMS (APCI-pos): 306, 308. $^1$HNMR (d6-DMSO, 400 MHz): δ8.55 (d, 1H), 7.86 (d, 1H), 7.49 (dd, 1H), 7.40 (dd, 1H), 7.25 (s, 1H), 6.84 (dt, 1H), 6.73 (dd, 1H), 5.23 (bs, 2H). For (Z)-5-bromomethylene-8-fluoro-5,11-dihydro-10-oxa-1-aza-dibenzo[a,d]cycloheptene, LCMS (APCI-pos): 306, 308. $^1$HNMR (d6-DMSO, 400 MHz): δ8.50 (dd, 1H), 7.81 (d, 1H), 7.50 (dd, 1H), 7.40 (dd, 1H), 7.09 (s, 1H), 6.99-6.93 (m, 2H), 5.22 (bs, 2H).

EXAMPLE 618

(E)-5-(8-Fluoro-11H-10-oxa-1-aza-dibenzo[a,d]cyclohepten-5-ylidenemethyl)-1-(2-morpholin-4-yl-ethyl)-1,3-dihydro-benzoimidazol-2-one

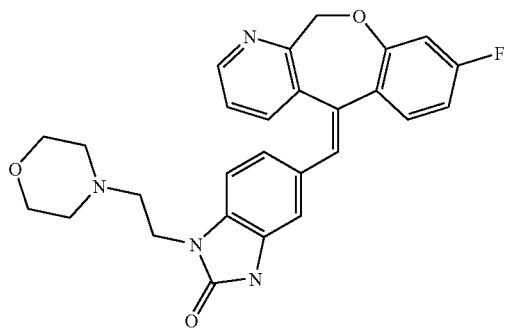

Following procedures essentially as described in Example 219, beginning with (E)-5-bromomethylene-8-fluoro-5,11-dihydro-10-oxa-1-aza-dibenzo[a,d]cycloheptene (192 mg, 0.63 mmol) and 1-(2-morpholinyl-ethyl)-5-(dihyroxyborolan-2-yl)-1,3-dihydro-benzoimidazol-2-one (219 mg, 0.75 mmol). Partition the reaction mixture between ethyl acetate (50 mL) and 1N aqueous hydrochloric acid solution (50 mL). Separate the layers and extract the aqueous layer with methylene chloride (2×50 mL). Combine the organic layers and extract with 1N aqueous hydrochloric acid solution (50 mL). Adjust the pH of the combined aqueous layers to 8.0 with 5N aqueous sodium hydroxide solution, and extract the product with ethyl acetate (3×50 mL). Purify the crude product by flash chromatography (25% ethanol/ethyl acetate) to provide 115 mg (39%) of purified product.

LCMS (APCI-pos): 473.1 (M+H). Purity by LCMS (UV Area percent) 98%. $^1$HNMR (d6-DMSO, 400 MHz): δ10.70 (s, 1H), 8.51 (d, 1H), 7.64 (t, 1H), 7.39 (d, 1H), 7.27 (dd, 1H), 7.09 (s, 1H), 6.97 (d, 1H), 6.85 (dt, 1H), 6.73 (d, 1H), 6.69 (dd, 1H), 6.61 (s, 1H), 5.5-5.3 (bs, 2H), 3.81 (t, 2H), 3.30 (s, 4H), 2.48 (s, 4H), 2.34 (bs, 2H).

EXAMPLE 630

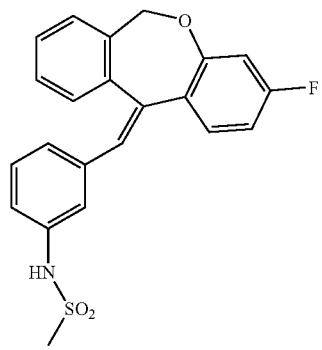

A. Preparation of 2-[2-(3-nitrophenylethynyl)]benzyl alcohol

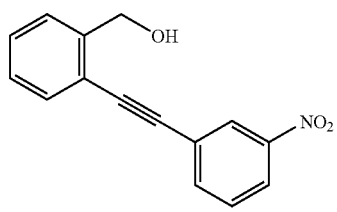

2-ethynylbenzyl alcohol (1.65 g, 12.5 mmol), PdCl$_2$(PPh$_3$)$_2$ (437 mg, 0.623 mmol), CuI (237 mg, 1.25 mmol) are successively added to a solution of 3-iodonitrobenzene (3.1 g, 12.5 mmol) in 62 mL of Et$_3$N at rt. The reaction mixture is stirred at rt for 1 h. Water (100 mL) is added followed by EtOAc (100 mL). The layers are separated and the aqueous layer extracted with additional 100 mL of EtOAc. The combined organic layer is dried and concentrated to give a dark yellow residue. The residue is purified by column chromatography to give 2 as a yellow solid (2.59 g, 10.25 mmol, 82% yield). $^1$H NMR (300 MHz, CDCl$_3$) δ 8.37 (m, 1 H), 8.21 (m, 1 H), 7.82 (m, 1 H), 7.60-7.32 (m, 5 H), 4.94 (d, J=5.9 Hz, 2 H), 1.97 (t, J=2.3 Hz, 1 H). Yu, H. RG6-R6H-070.

B. Preparation of:

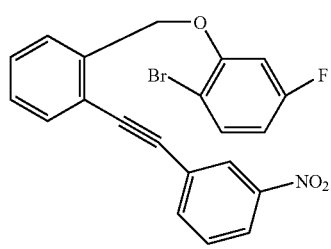

To a mixture of 2-bromo-5-fluorophenol (3.77 g, 19.8 mmol) and the alkyne from Step A, above (5.0 g, 19.8 mmol) in 125 mL of anhydrous THF is added triphenylphosphine (7.8 g, 29.6 mmol) at rt. The reaction mixture is cooled to 0° C. and diisopropylazodicarboxylate (5.99 g, 29.6 mmol) is added dropwise under $N_2$. The reaction mixture is warmed up to rt and stirred at rt for 2 h. 200 mL of water is added followed by 200 mL of EtOAc. The layers are separated and the aqueous layer further extracted with 200 mL of EtOAc. The combined organic layer is dried and concentrated to give a brown residue. The residue is purified by column chromatography (5% EtOAc/hexane) to give the product (6.70 g, 15.7 mmol, 79% yield) as an off-white solid.

$^1$H NMR (300 MHz, $CDCl_3$) δ 8.30 (m, 1 H), 8.20 (m, 1 H), 7.78 (m, 1 H), 7.69-7.35 (m, 6 H), 6.78 (m, 1 H), 6.61 (m, 1 H), 5.18 (s, 2H). Yu, H, RG6-R6H-087.

C. Preparation of:

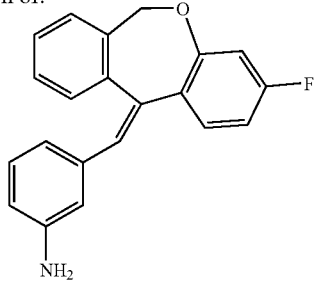

A mixture of the product of Step B, above (56 mg, 0.131 mmol), Pd $(OAc)_2$ (3 mg, 0.013 mmol) and tri-O-tolylphosphine (8.0 mg, 0.026 mmol) in 0.7 mL of acetonitrile is stirred under $N_2$ at rt. Formic acid (96%, 18.2 mmol, 0.394 mmol) is added dropwise followed by piperidine (45 mg, 0.526 mmol). The reaction mixture is heated at 70° C. overnight. TLC shows starting material still remains. Additional Pd $(OAc)_2$ (3 mg, 0.013 mmol), tri-O-tolylphosphine (8.0 mg, 0.026 mmol), formic acid (96%, 18.2 mmol, 0.394 mmol) and piperidine (45 mg, 0.526 mmol) are added in this sequence. The reaction mixture is heated at 70° C. for additional 4 h with until no starting observed by TLC. The reaction mixture is concentrated to a black residue and purified through 5 g of silica gel to give the aniline product (17 mg, 0.054 mmol, 41% yield) as a beige solid. H NMR (300 MHz, $CDCl_3$) δ 7.42 (m, 2 H), 7.31 (dt, J=9.6 Hz, J=1.3 Hz, 1 H), 7.21 (dt, J=9.6 Hz, J=1.3 Hz, 1 H), 7.11 (m, 1 H), 6.93 (t,J=9.6 Hz, 1 H), 6.78 (s, 1 H), 6.65 (m, 1 H), 6.53-6.29 (m, 4 H), 3.46 (bs, 2 H). Yu, H. RG6-R6H-074.

D. Preparation of Final Title Compound:

To a mixture of the aniline of Step C (1.0 mg, 0.0132 mmol) in 0.1 mL of methylene chloride is added pyridine (0.3 mg, 0.0038 mmol) followed by methanesulfonylchloride (0.4 mg, 0.0035 mmol) at rt under $N_2$. The reaction mixture is stirred at rt for 2 h. The reaction mixture is concentrated to dry and the residue is purified by column chromatogrphy to give Title Compound as a solid. $^1$H NMR (300 MHz, $CDCl_3$) δ 7.44 (m, 2 H), 7.32 (t, J=7.5 Hz, 1 H), 7.17 (m, 2 H), 7.00 (m, 2 H), 6.87 (m, 2 H), 6.78 (m, 1 H), 6.67 (dt, J=11.7 Hz, J=4.1 Hz, 1 H), 6.53 (dd, J=10.6 Hz, J=2.5 Hz, 1 H), 6.07 (s, 1H), 2.81 (s, 3 H).

Examples 619-751 contained in Table II, herein, provide yet additional examples of compounds of Formula I wherein the bridge depicted by —X—Y— contains a heteroatom or heteroatom containing group at either the X or Y position. These examples, which further illustrate the present invention are prepared according to the procedures as described generally in the Schemes and literature references described above.

Additional preparations for, and examples of compounds of Formula I wherein R8 is other than hydrogen and the bridge depicted by —X—Y— contains either a heteroatom or heteroatom containing group at either the X or Y position or both X and Y are $CH_2$. (Section 7)

EXAMPLE 752

N-{3-[1-(8-Methoxy-6,11-dihydro-dibenzo[b,e]oxepin-11-yl)-ethyl]-phenyl}-methanesulfonamide

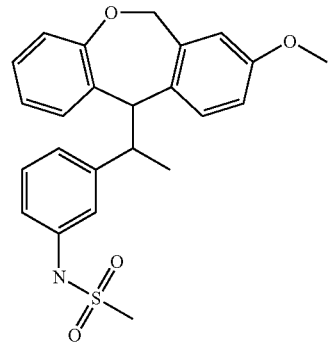

Mix N-{3-[1-(8-methoxy-6H-dibenzo[b,e]oxepin-1-ylidene)-ethyl]-phenyl}-methanesulfonamide (prepared essentially a sdescribed in Example 271) (1.0 eq) with 10% Pd/C (65.2 weight %) in EtOH and heat at 60° C. overnight under 500 psi hydrogen. Remove the solvent and purify by chromatography (ISCO Combi Flash, 3/1 hexane/ethyl acetate) to give 29% of the title compound as a racemic mixture. HPLC (Xterra C18 2.1×50 μm 3.5 μM, 5-100% acetonitrile with 0.2% formic acid.) t=4.55 (100%). MS (ES) 424 (M+1), 422 (M−1).

PREPARATION 59

(10,11-dihydro-dibenzo[a,d]cyclohepten-5-ylidine)-acetic acid ethyl ester

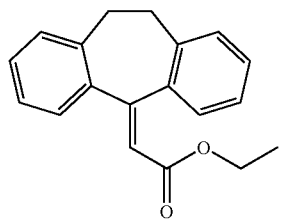

Prepared as described in Bergmann, E. D., Solomonovici, A., *Synthesis*, 1970, 183-189.

PREPARATION 60

Bromo-(10,11-dihydro-dibenzo[a,d]cyclohepten-5-ylidine)-acetic acid ethyl ester

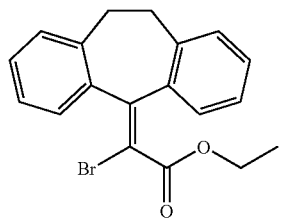

Dissolve (10,11-dihydro-dibenzo[a,d]cyclohepten-5-ylidine)-acetic acid ethyl ester (1 equivalent) in a suitable dry solvent and chill to 0° C. under a dry atmosphere. Add bromine (1.05 equivalents) dropwise and stir at 0° C. for 20 minutes. Remove the ice bath and stir at room temperature for three hours. Return to the ice bath and add potassium tert-butoxide (1.1.equivalents) and stir for one hour. Quench the mixture with aqueous $Na_2SO_3$ and partition between dichloromethane and water and dry the organic layer over anhydrous sodium sulfate. Purify the residue obtained after evaporation by silica gel chromatography to yield 71% of the title compound.

EXAMPLE 753

(10,11-Dihydro-dibenzo[a,d]cyclohepten-5-ylidene)-(3-methanesulfonylamino-phenyl)-acetic acid ethy lester

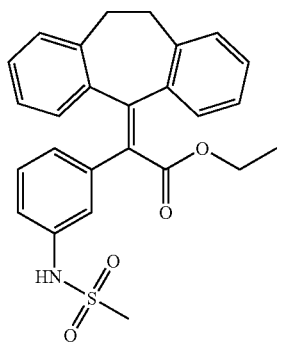

Following procedures essentially as described in Example 219, mix bromo-(10,11-dihydro-dibenzo[a,d]cyclohepten-5-ylidine)-acetic acid ethyl ester (1 equivalent), N-[3-(4,4,5,5-tetramethyl-[1,3,2]dioxaborolan-2-yl)-phenyl]-methanesulfonamide (1.25 equivalents), 2N $Na_2CO_3$ (2 equivalents) and tetrakrisphenylphosphine palladium (0.05 equivalents)in a suitable solvent. Purify the product by silica gel chromatography to obtain a 78% yield of the title compound. MS(ES)=446(+)

EXAMPLE 754

(10,11-Dihydro-dibenzo[a,d]cyclohepten-5-ylidene)-(3-methanesulfonylamino-phenyl)-acetic acid

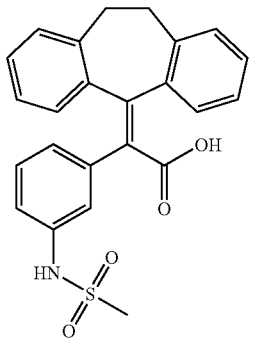

Treat (10,11-dihydro-dibenzo[a,d]cyclohepten-5-ylidene)-(3-methanesulfonylamino-phenyl)-acetic acid ethyl ester with a 50:50 mixture of 1N NaOH and ethanol and heat under reflux conditions for 14 hours. Acidify with 1N HCl and collect the solid by filtration and dry. Purify by reverse phase HPLC to obtain a 20% yield of the title compound. MS(ES)=437(+$NH_3$)

EXAMPLE 755

N-{3-[1-(10,11-Dihydro-dibenzo[a,d]cyclohepten-5-ylidene)-2-hydroxy-ethyl]-phenyl}-methanesulfonamide

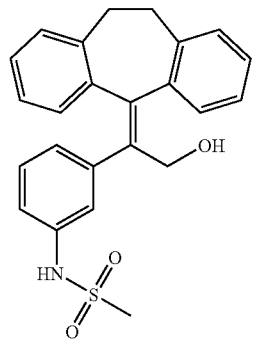

Treat (10,11-dihydro-dibenzo[a,d]cyclohepten-5-ylidene)-(3-methansulfonylamino-phenyl)-acetic acid ethyl ester (1 equivalent) with lithium aluminum hydride (2 equivalents) in a suitable dry solvent and stir at room temperature for four hours. Quench by the dropwise addition of water and partition between dichloromethane and water. Dry the organic layer over anhydrous sodium sulfate and evaporate. Purify the crude residue by silica gel chromatography to obtain a 33% yield on the title compound.
MS(ES)=404(+)

PREPARATION 61

(2-Chloro-10,11-dihydro-dibenzo[a,d]cyclohepten-5-ylidene)-acetic acid methyl ester

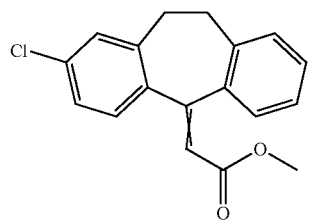

Title compound is prepared from 2-chloro-10,11-dihydro-dibenzo[a,d]cyclohepten-5-one as described in Bergmann, E. D., Solomonovici, A., *Synthesis*, 1970, 183-189.

PREPARATION 62

2-(2-Chloro-10,11-dihydro-dibenzo[a,d]cyclohepten-5-ylidene)-ethanol

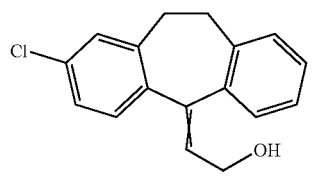

Dissolve (2-chloro-10,11-dihydro-dibenzo[a,d]cyclohepten-5-ylidene)acetic acid methyl ester (1 equivalent) in a suitable dry solvent and cool to 0° C. under a dry atmosphere. Add 1M diisobutylaluminum hydride solution in toluene (3 equivalents) dropwise and stir the mixture for one hour. Quench with aqueous citric acid solution and partition between water and ethyl acetate. Dry and evaporate the organic layer to obtain the title compound in 87% yield.

PREPARATION 63

2-Chloro-5-(2-methoxy-ethylidene)-10,11-dihydro-5H-dibenzo[a,d]cycloheptene

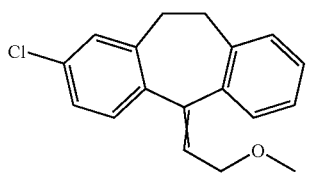

Treat 2-(2-chloro-10,11-dihydro-dibenzo[a,d]cyclohepten-5-ylidene)-ethanol (1 equivalent) with sodium hydride (2 equivalents) in a suitable dry solvent at 0° C. and stir for 15 minutes. Add dimethyl sulfate dropwise (2 equivalents) and stir at 0° C. for one hour. Quench with aqueous citric acid solution and partition between water and ethyl acetate. Dry and evaporate the organic layer. Purify the residue by silica gel chromatography to give the title compound in 82% yield

PREPARATION 64

5-(1-Bromo-2-methoxy-ethylidene)-2-chloro-10,11-dihydro-5H-dibenzo[a,d]cycloheptene

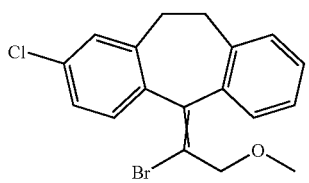

Treat 2-chloro-5-(2-methoxy-ethylidene)-10,11-dihydro-5H-dibenzo[a,d]cycloheptene essentially as described in Preparation 24 to give the title compound in 43% yield.

EXAMPLE 756

N-{3-[1-(2-Chloro-10,11-dihydro-dibenzo[a,d]cyclohepten-5-ylidene)-2-methoxy-ethyl]-phenyl}-methanesulfonamide

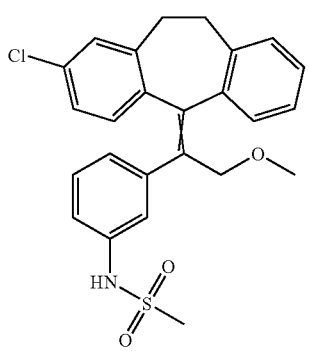

Following procedures essentially as described in Example 219, mix 5-(1-bromo-2-methoxy-ethylidene)-2-chloro-10,11-dihydro-5H-dibenzo[a,d]cycloheptene (1 equivalent), N-[3-(4,4,5,5-tetramethyl-[1,3,2]dioxaborolan-2-yl)-phenyl]-methanesulfonamide (1.25 equivalents), 2N Na$_2$CO$_3$ (2 equivalents) and tetrakistriphenylphosphine palladium (0.65 equivalents) in a suitable solvent. Purify the product by silica gel chromatography to obtain a 62% yield of the title compound.

MS(ES)=452(−)

PREPARATION 65

11-Fluoromethylene-6,11-dihydro-dibenzo[b,e]oxepine

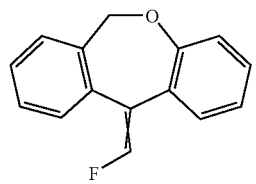

Dissolve 11-Bromomethylene-6,11-dihydro-dibenzo[b,e]oxepine (1 eq.) in dry THF (0.1 M). Cool the solution to −78 C in a dry ice/acetone bath. Slowly add s-butyl lithium (1.2 eq., 1.3 M in cyclohexane) to the above solution. Stir the dark brown solution at −78 C. for two hours. Add a solution of N-fluorobenzene sulfonimide (1.2 eq.) in dry THF (0.4 M) over 2 minutes. Remove the cold bath and allow the reaction mixture to warm to ambient temperature. Stir the reaction mixture at room temperature for 1 hour. Quench the reaction with water. Wash the resulting mixture with saturated aqueous NaHCO$_3$.

Separate the organic phase and dry over sodium sulfate. Filter the mixture and concentrate under reduced pressure to afford a crude product. Purify the crude product by chromatography on silica gel, eluting with 30% CH$_2$Cl$_2$ in hexanes. MS (E)=226 (M).

PREPARATION 66

11-Bromo-fluoro-methylene-6,11-dihydro-dibenzo[b,e]oxepine

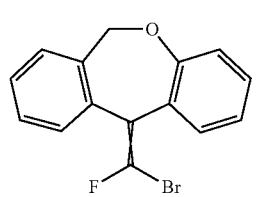

Dissolve 11-Fluoromethylene-6,11-dihydro-dibenzo[b,e] oxepine in methylene chloride (0.2 M). Add (4-Dimethylamino)pyridinium tribromide (1.05 eq.). Stir the mixture at ambient temperature for 2 hours. Wash the resulting solution with aqueous sodium disulfite, dry with sodium sulfate and concentrate the filtrate. Purify the crude product by silica gel chromatography using 30% methylene chloride in hexanes. MS(EI)=304/306 (M).

Examples 757-843 contained in Table II, herein, provide yet additional examples of compounds of Formula I wherein R8 is other than hydrogen and the bridge depicted by —X—Y— contains either a heteroatom or heteroatom containing group at either the X or Y position or both X and Y are $CH_2$. These examples, which further illustrate the present invention are prepared according to the procedures as described generally in the Schemes and literature references described above.

As stated, Table II, below provides formulae and physical data for additional compounds of Formula I. In the table, the heading "Example No." refers to the example number of the compound, "Structure" refers to the chemical formula of the particular compound, "MS Data" refers to the mass spectroscopy data generated for the particular compound, and "HPLC" refers to the high pressure liquid-chromatography data generated for the particular compound. Some of the entries in the Table do not contain either MS Data or HPLC values, instead the designation "NMR" appears in the MS Data column. For these Examples, nuclear magnetic resonance data are provided below.

EXAMPLE 621

1H NMR (400 MHz, CDCl3) 8.02 (d, 1H, J=5), 7.97 (s, 1H), 7.50 (dd, 1H, J=5, 1), 7.42 (d, 1H, J=5.2), 7.35 (t, 1H, J=9.7, 5), 7.28 (m, 2H), 7.14 (t, 1H, J=9.7, 5), 7.02 (m, 2H), 6.91 (m, 2H), 5.6 (s, 2H).

EXAMPLE 658

1H NMR(CDCl3, 400 MHz) δ 8.03 (d, J=8.56 Hz, 1H), 7.50-6.97 (m, 12H), 6.79 (bs, 1H), 5.70 (d, –J=12.80 Hz, 1H), 4.84 (d, –J=12.80 Hz, 1H), 3.48 (bs, 3H), 2.73 (bs, 3H)

EXAMPLE 659

1H NMR(d6-DMSO, 400 MHz) δ 9.58 (bs, 1H), 8.09 (d, J=2.20 Hz, 1H), 7.75 (dd, J=8.35 Hz, 2.20 Hz, 1H), 7.58 (d, J=6.59 Hz, 1H), 7.34 (dt. J=7.47 Hz, 1.32 Hz, 1H), 7.23 (dt. J=7.47 Hz, 1.32 Hz, 1H), 7.05 (s, 1H), 7.00-6.94 (m, 3H), 6.87 (d, J=8.79 Hz, 1H), 6.78 (d, J=7.91 Hz, 1H), 5.65 (vbs, 1H), 5.13 (vbs, 1H), 3.30 (bs, 3H), 2.78 (s, 3H)

EXAMPLE 660

1H NMR(CDCl3, 400 MHz) δ 7.76-7.72 (m, 2H), 7.44-7.41 (m, 2H), 7.35-7.34 (m, 2H), 7.26-7.17 (m, 2H), 7.06-7.04 (m, 1H), 6.88 (d, J=8.79 Hz, 1H), 6.28 (bs, 1H), 5.58 (vbs, 2H), 3.72 (s, 3H), 2.83 (s, 3H)

EXAMPLE 670

1H NMR(CDCl3, 400 MHz) δ 7.45-7.09 (m, 9H), 6.75-6.72 (m, 1H), 6.65-6.61 (m, 2H), 6.38 (bs, 1H), 5.43 (vbs, 2H), 3.87 (s, 3H), 2.88 (s, 3H)

EXAMPLE 671

1H NMR(CDCl3, 400 MHz) δ 7.48-7.46 (m, 1H), 7.34-6.63 (m, 12H), 5.75 (vbs, 1H), 5.10 (m, 1H), 2.83 (s, 3H)

EXAMPLE 672

1H NMR(CDCl3, 300 MHz) δ 7.47-7.06 (m, 8H), 6.86-6.82 (m, 2H), 6.73-6.67 (m, 2H), 6.54-6.52 (m, 1H), 5.31 (vbs, 2H), 2.89 (s, 3H)

EXAMPLE 673

1H NMR(CDCl3, 300 MHz) δ 7.45 (d, J=7.58 Hz, 1H), 7.32 (dt, J=7.42, 1.32, 1H), 7.22-7.14 (m, 3H), 7.04-6.98 (m, 2H), 6.92-6.86, (m, 3H), 6.80-6.73 (m, 2H), 6.47 (bs, 1H), 5.25 (vbs, 2H), 2.81 (s, 3H)

EXAMPLE 675

1H NMR(CDCl3, 300 MHz) δ 7.47-6.81 (m, 1H), 5.63 (vbs, 1H), 5.05 (vbs, 1H), 2.82 (s, 3H), 2.18 (s, 1.5H) 2.14 (s, 1.5H)

EXAMPLE 676

1H NMR(CDCl3, 400 MHz) δ 7.41-7.15 (m, 10H), 6.76 (s, 1H), 6.61 (s, 1H), 6.48 (bs, 1H), 5.30 (vbs, 2H), 2.90 (s, 3H), 2.06 (s, 3H)

EXAMPLE 677

1H NMR(CDCl3, 400 MHz) δ 7.63-6.84 (m, 13H), 5.60 (vbs, 1H), 4.95 (vbs, 1H), 2.81 (s, 3H), 2.32 (s, 3H).

EXAMPLE 679

1H NMR(CDCl3, 400 MHz) δ 7.64 (s, 1H), 7.44 (d, J=7.47 Hz, 1H), 7.39-7.28 (m, 2H), 7.19-7.12 (m, 2H), 7.01-6.98 (m, 2H), 6.91-6.83 (m, 4H), 6.70 (s, 1H), 5.57 (vbs, 1H), 5.00 (vbs, 1H), 2.82 (s, 3H), 2.30 (s, 3H).

EXAMPLE 681

1H NMR(CDCl3, 400 MHz) δ 7.45-7.26 (m, 5H), 7.21-7.17 (m, 2H), 7.09 (dd, J=7.91 Hz, 1.32 Hz, 1H), 7.05 (dd, J=8.79 Hz, 2.63 Hz, 1H), 6.98 (d, J=2.64 Hz, 1H), 6.83 (d, J=8.79 Hz, 1H), 6.65 (s, 1H), 6.41 (bs, 1H), 5.33 (vbs, 2H), 2.90 (s, 3H).

EXAMPLE 682

1H NMR(CDCl3, 400 MHz) δ 7.46-7.44 (m, 2H), 7.32 (dt, J=7.47 Hz, 1.32 Hz, 2H), 7.21-7.10 (m, 3H), 7.03-6.98 (m, 2H), 6.91-6.88 (m, 2H), 6.80 (s, 1H), 6.75 (d, J=8.79 Hz, 1H), 6.40 (bs, 1H), 5.63 (vbs, 1H), 4.93 (vbs, 1H), 2.82 (s, 3H).

| Example No. | Structure | MS Data | HPLC | Section |
|---|---|---|---|---|
| 278 | 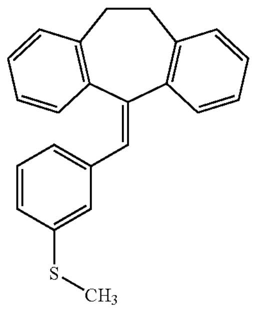 | ES 329 (+) | NA | 1 |
| 279 | 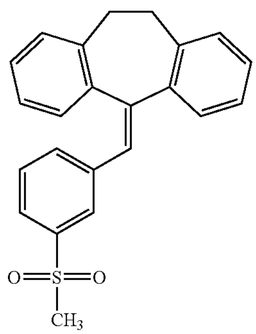 | ES 361 (+) | NA | 1 |
| 280 | 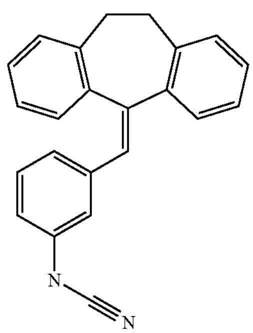 | ES 321 (−)/323 (+) | (GRAD) t = 3.392 (95%) | 1 |
| 281 | 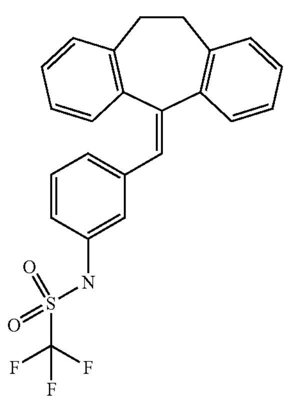 | ES 428 (−) | (ISO80-10) t = 5.59 (100%) | 1 |

-continued

| Example No. | Structure | MS Data | HPLC | Section |
|---|---|---|---|---|
| 282 | 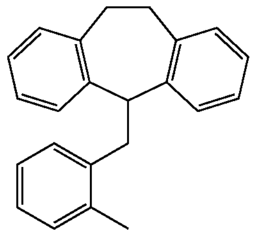 | EA; C23H22<br>th; C, 91.45 H, 7.41<br>fd; C, 91.99 H, 7.39 | t = 2.96 (97.4%) | 1 |
| 283 | 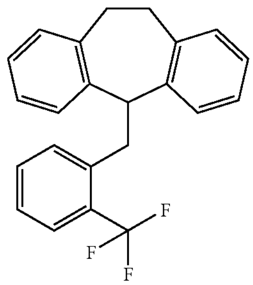 | TOF MS El+ = 352 | EA; C23H19F3<br>th; C, 78.39 H, 5.43<br>fd; C, 78.84 H, 5.11 | 1 |
| 284 | 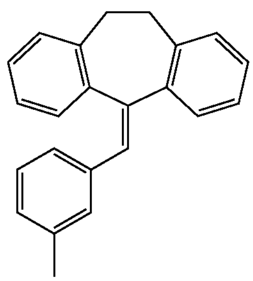 | TOF MS El+= 298 | NA | 1 |
| 285 | 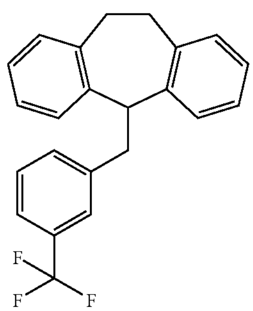 | TOF MS El+ = 352 | NA | 1 |
| 286 | 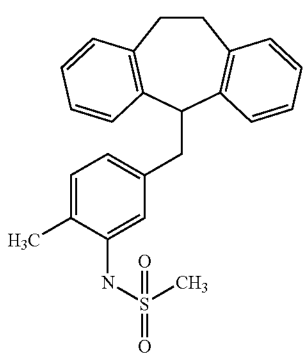 | ES 391 (+) | t =5.05 min (100%) | 1 |

-continued
| Example No. | Structure | MS Data | HPLC | Section |
|---|---|---|---|---|
| 287 | 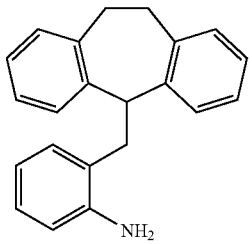 | m/z = 300 (M + 1) | ISO60-10.M, ret time =14.15 min.; 100% | 1 |
| 288 | 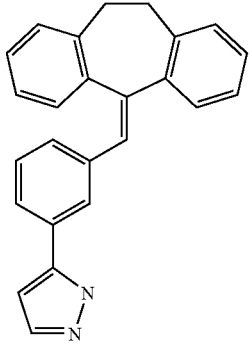 | ES 347 (−) /349 (+) | (ISO90-10) t = 3.15 (99%) | 1 |
| 289 | 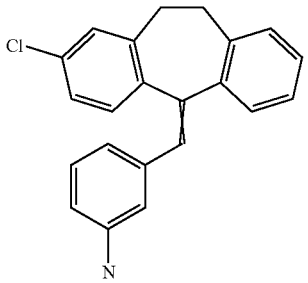 | NA | NA | 2 |
| 290 | 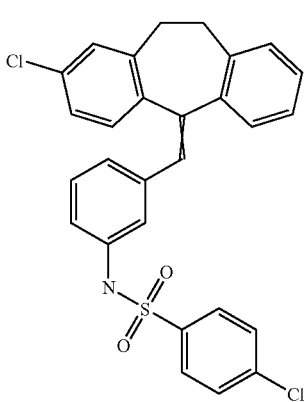 | APCI 506 (+) | GRAD 80-100M t = 6.048 (100%) | 2 |

-continued
| Example No. | Structure | MS Data | HPLC | Section |
|---|---|---|---|---|
| 291 | 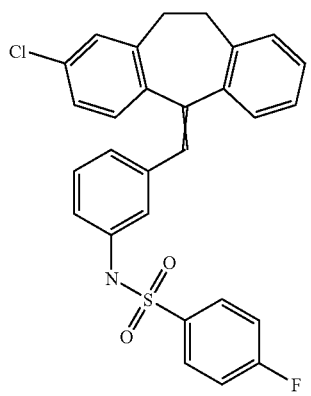 | APCI 490 (+) | GRAD 80-100M t = 5.638 (100%) | 2 |
| 292 | 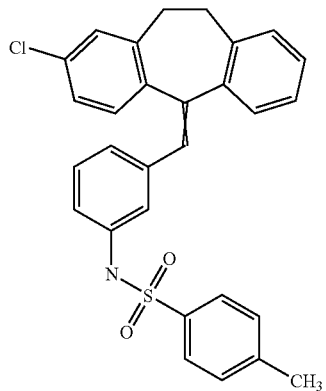 | APCI 486 (+)/484 (−) | GRAD 80-100M t = 5.638 (100%) | 2 |
| 293 | 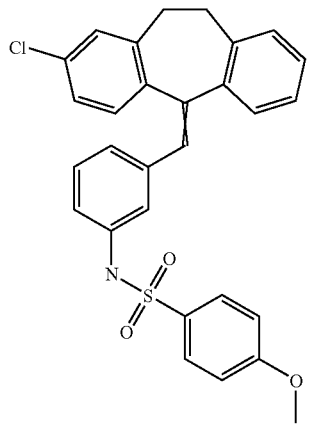 | APCI 502 (+)/500 (−) | GRAD 80-100M t = 5.464 (100%) | 2 |

-continued

| Example No. | Structure | MS Data | HPLC | Section |
|---|---|---|---|---|
| 294 | 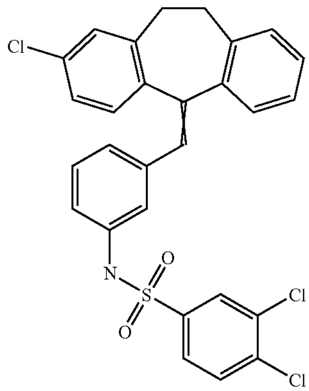 | APCI 542 (+)/540 (−) | GRAD 80-100M t = 6.221 (100%) | 2 |
| 295 | 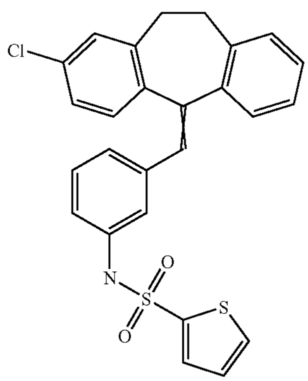 | APCI 478 (+) | GRAD 80-100M t = 5.200 (100%) | 2 |
| 296 | 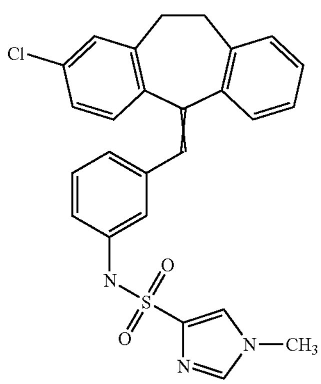 | APCI 476 (+) | GRAD 80-100M t = 3.876 (100%) | 2 |
| 297 | 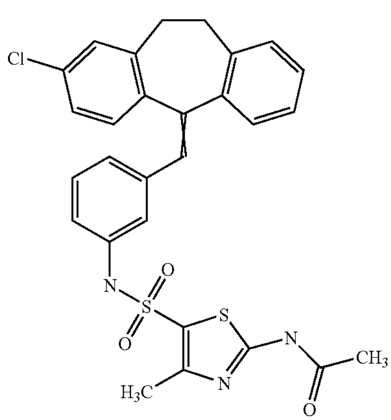 | APCI 550 (+) | GRAD 80-100M t1 = 4.316 (50%) t2 = 4.553 (50%) ISOMERMIX | 2 |

-continued

| Example No. | Structure | MS Data | HPLC | Section |
|---|---|---|---|---|
| 298 | 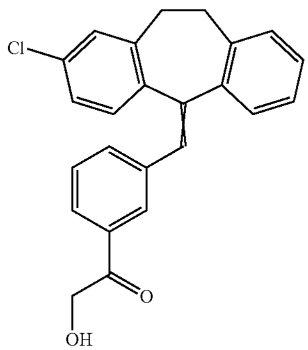 | APCI 374 (+) | GRAD 80-100M t1 = 5.210 (50%) t2 = 5.340 (50%) ISOMERMIX | 2 |
| 299 | 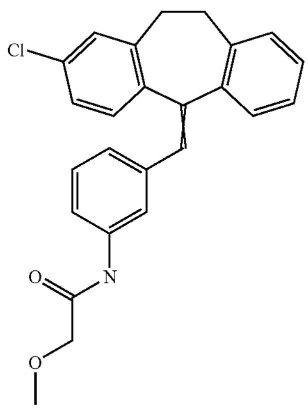 | APCI 404 (+) | GRAD 80-100M t = 5.343 (100%) | 2 |
| 300 | 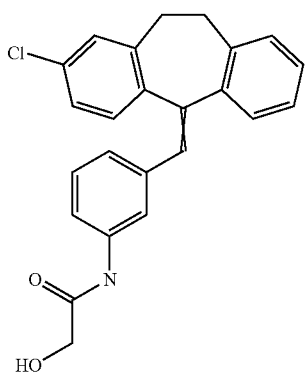 | APCI 392 (+) | GRAD 80-100M t = 5.282 (95%) | 2 |
| 301 | 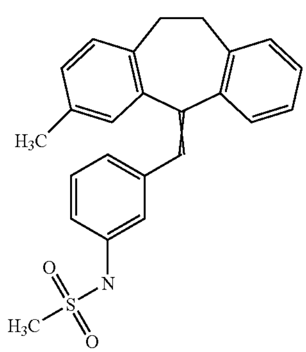 | ES 388 (−)/390 (+) | (GRAD) t = 3.477 (99%) | 2 |

-continued
| Example No. | Structure | MS Data | HPLC | Section |
|---|---|---|---|---|
| 302 | 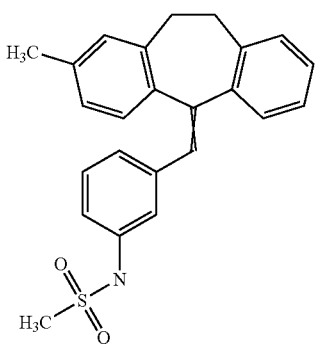 | ES 388 (−)/390 (+) | (GRAD) t = 3.488 (97%) | 2 |
| 303 | 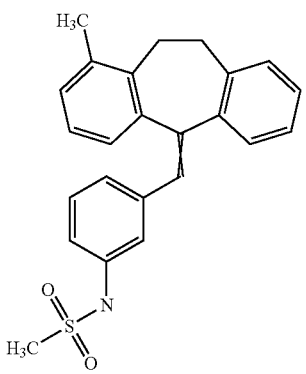 | ES 388 (−)/390 (+) | (GRAD) t = 3.435 (97%) | 2 |
| 304 | 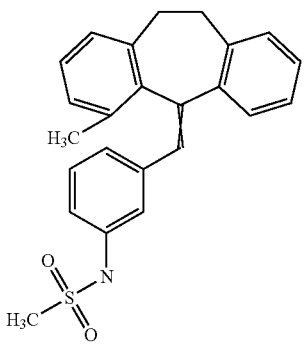 | ES 388 (−)/390 (+) | (GRAD) t = 3.424 (100%) | 2 |
| 305 | 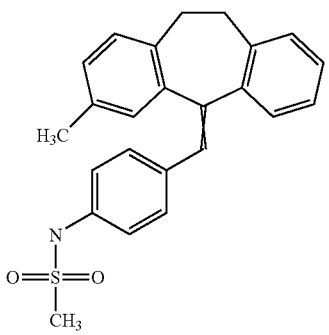 | ES 388 (−)/390 (+) | (GRAD) t = 3.531 (100%) | 2 |

-continued
| Example No. | Structure | MS Data | HPLC | Section |
|---|---|---|---|---|
| 306 | 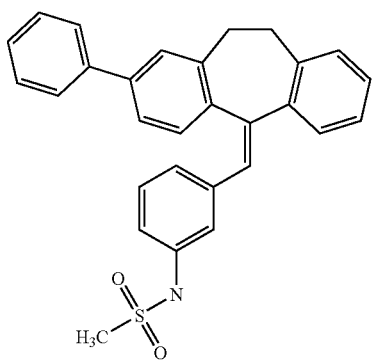 | ES 450 (−)/452 (+) | (GRAD) t = 3.712 (96%) | 2 |
| 307 | 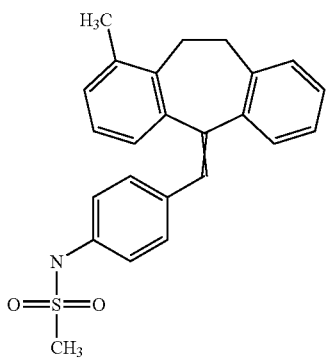 | ES 388 (−)/390 (+) | (GRAD) t = 3.467 (99%) | 2 |
| 308 | 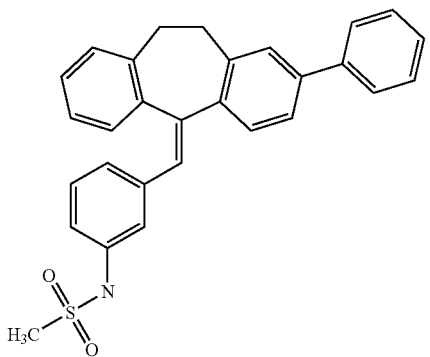 | ES 450 (−)/452 (+) | (GRAD) t = 3.744 (100%) | 2 |
| 309 | 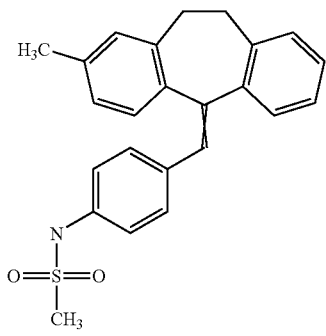 | ES 388 (−)/390 (+) | (GRAD) t = 3.531 (94%) | 2 |

-continued
| Example No. | Structure | MS Data | HPLC | Section |
|---|---|---|---|---|
| 310 | 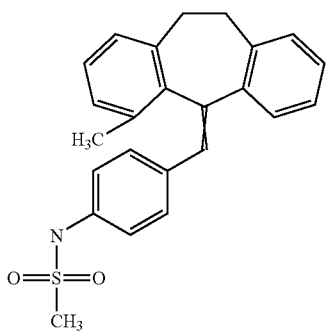 | ES 388 (−)/390 (+) | (GRAD) t = 3.445 (100%) | 2 |
| 311 | 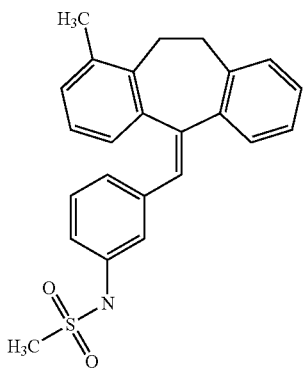 | ES 388 (−)/390 (+) | (GRAD) t = 8.790 (100%) | 2 |
| 312 | 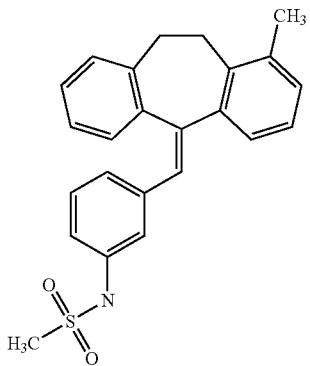 | ES 388 (−)/390 (+) | (GRAD) t = 11.057 (100%) | 2 |
| 313 | 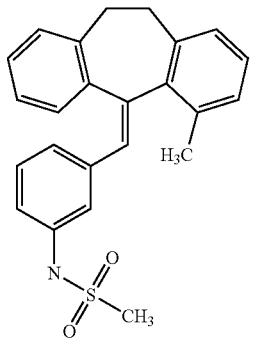 | ES 388 (−)/390 (+) | (GRAD) t = 8.128 (100%) | 2 |

-continued

| Example No. | Structure | MS Data | HPLC | Section |
|---|---|---|---|---|
| 314 | 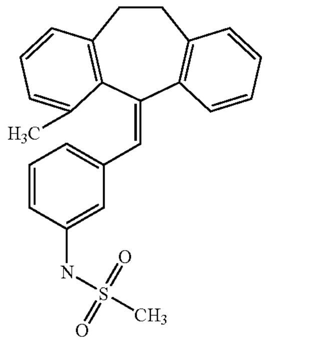 | ES 388 (−)/390 (+) | (GRAD) t = 9.738 (100%) | 2 |
| 315 | 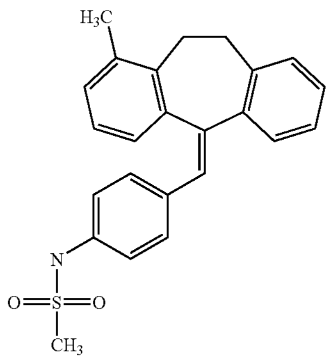 | ES 388 (−)/390 (+) | (GRAD) t = 7.626 (97%) | 2 |
| 316 | 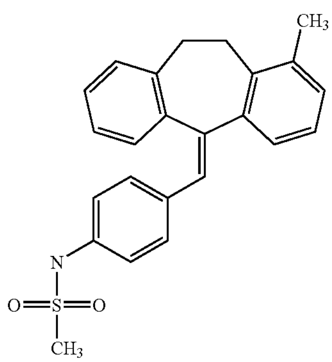 | ES 388 (−)/390 (+) | (GRAD) t = 6.508 (99%) | 2 |
| 317 | 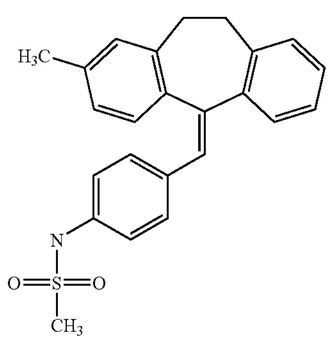 | ES 388 (−)/390 (+) | (GRAD) t = 4.790 (99%) | 2 |

| Example No. | Structure | MS Data | HPLC | Section |
|---|---|---|---|---|
| 318 | 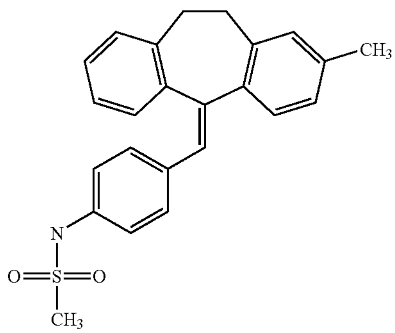 | ES 388 (−)/390 (+) | (GRAD) t = 4.932 (100%) | 2 |
| 319 | 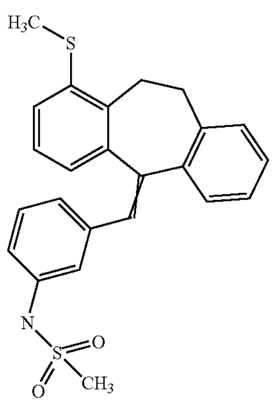 | ES 420 (−)/422 (+) | (GRAD) t = 3.424 (100%) | 2 |
| 320 | 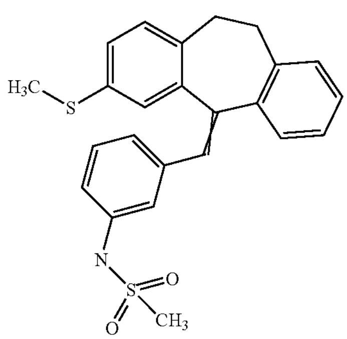 | ES 420 (−)/422 (+) | (GRAD) t = 3.424 (100%) | 2 |
| 321 | 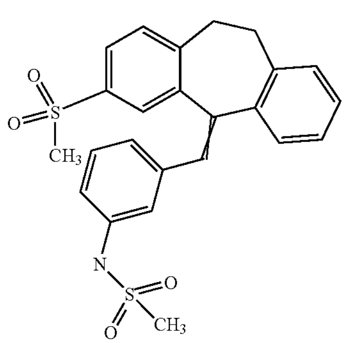 | ES 452 (−)/454 (+) | (GRAD) t = 2.779 (100%) | 2 |

-continued

| Example No. | Structure | MS Data | HPLC | Section |
|---|---|---|---|---|
| 322 | 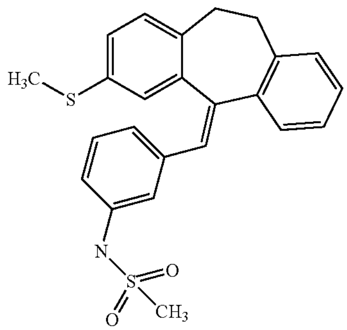 | ES 420 (−)/422 (+) | (GRAD) t = 6.50 (100%) | 2 |
| 323 | 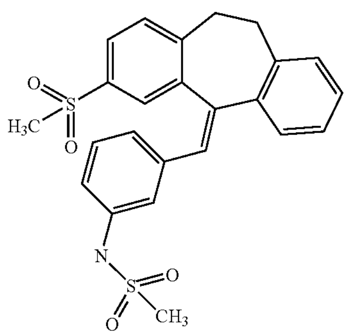 | ES 452 (−)/454 (+) | (GRAD) t = 13.40 (100%) | 2 |
| 324 | 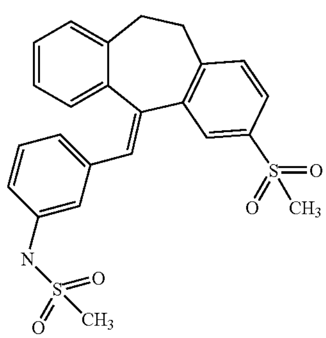 | ES 452 (−)/454 (+) | (GRAD) t = 17.90 (100%) | 2 |
| 325 | 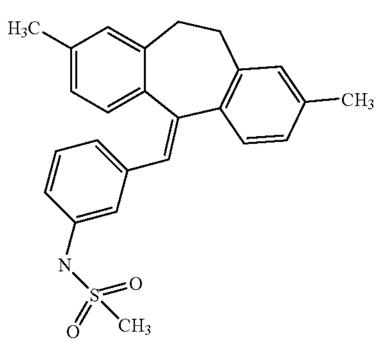 | ES 402 (+)/404 (−) | NA | 2 |

-continued

| Example No. | Structure | MS Data | HPLC | Section |
|---|---|---|---|---|
| 326 | 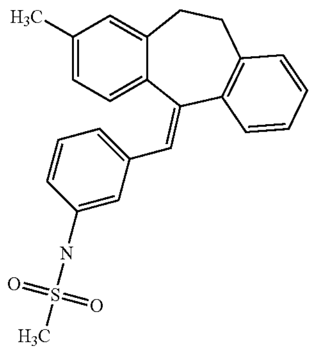 | ES 388 (−)/390 (+) | (GRAD) t = 3.381 (97%) | 2 |
| 327 | 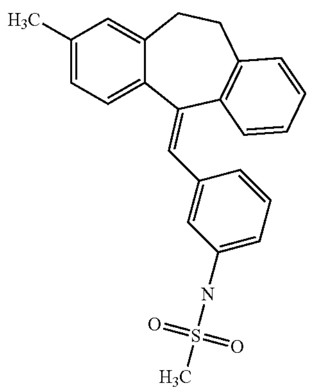 | ES 388 (−)/390 (+) | (GRAD) t = 3.413 (97%) | 2 |
| 328 | 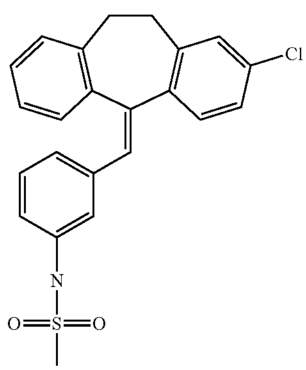 | ES− = 390.3, ES+ = 392.2 | NA | 2 |
| 329 | 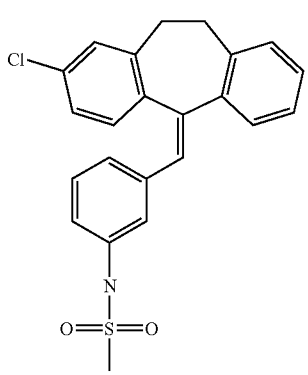 | ES− = 390.3, ES+ = 392.2 | NA | 2 |

-continued

| Example No. | Structure | MS Data | HPLC | Section |
|---|---|---|---|---|
| 330 | 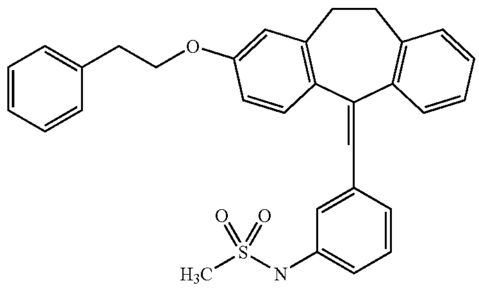 | ES− = 494 (Mixture) | NA | 2 |
| 331 | 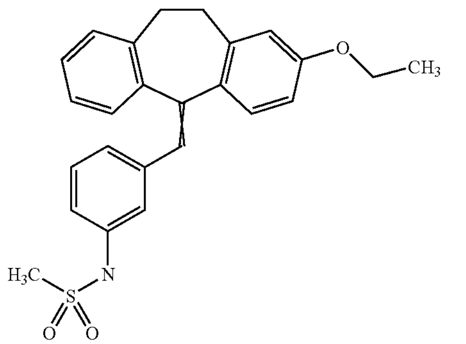 | ES− = 418 | NA | 2 |
| 332 | 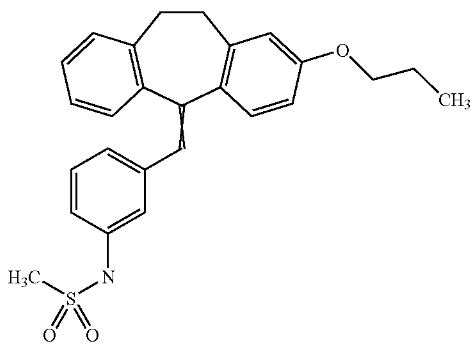 | ES− = 432 | NA | 2 |
| 333 | 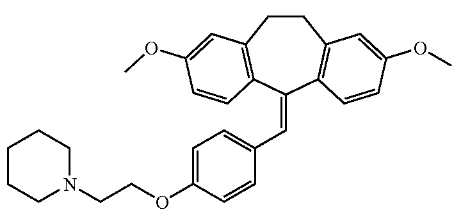 | ES 470 (+) | t = 1.40 | 2 |
| 334 | 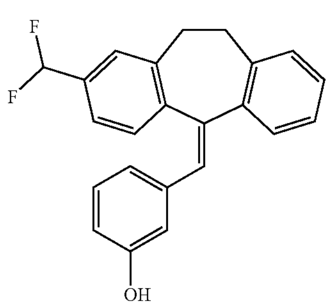 | ES 347 (−) | (ISO80-10) t = 3.41 (96%) | 2 |

-continued
| Example No. | Structure | MS Data | HPLC | Section |
|---|---|---|---|---|
| 335 | 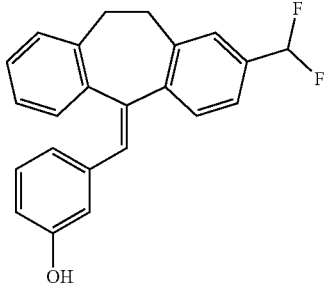 | ES 347 (−) | (ISO80-10) t = 3.74 (99%) | 2 |
| 336 | 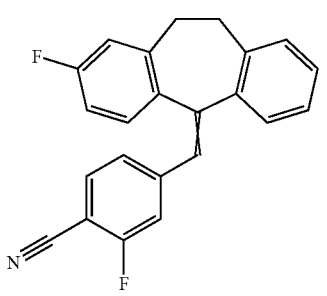 | EI 343 | (ISO80-10) t = 7.08 (47%), 7.31 (52%) | 2 |
| 337 | 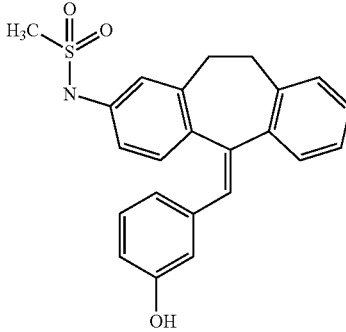 | ES 390 (−)/392 (+) | (ISO80-10) t = 2.40 (93%) | 2 |
| 338 | 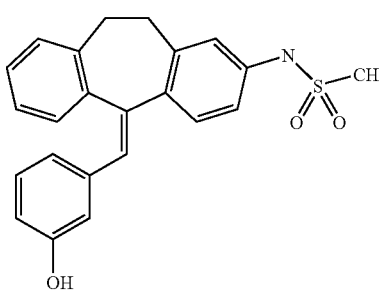 | ES 390 (−) | (ISO80-10) t = 2.01 (92%) | 2 |
| 339 | 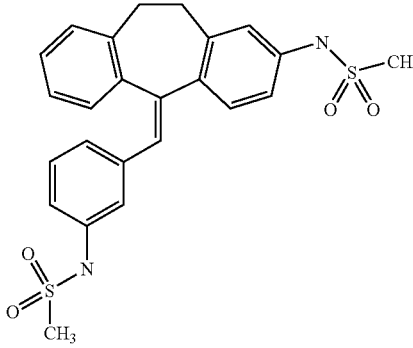 | ES 467 (−) | (ISO80-10) t = 1.90 (82%) | 2 |

-continued
| Example No. | Structure | MS Data | HPLC | Section |
|---|---|---|---|---|
| 340 | 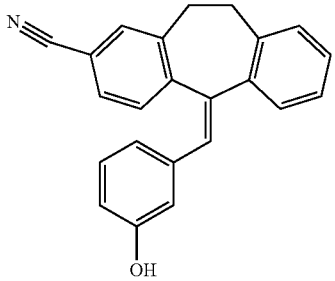 | ES 322 (−) | (ISO80-10) t = 3.43 (98%) | 2 |
| 341 | 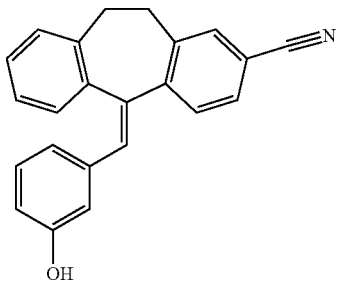 | ES 322 (−) | (ISO80-10) t = 3.09 (96%) | 2 |
| 342 | 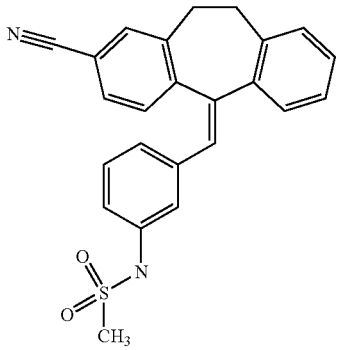 | ES 399 (−)/401 (+) | (ISO80-10) t = 3.12 (98%) | 2 |
| 343 | 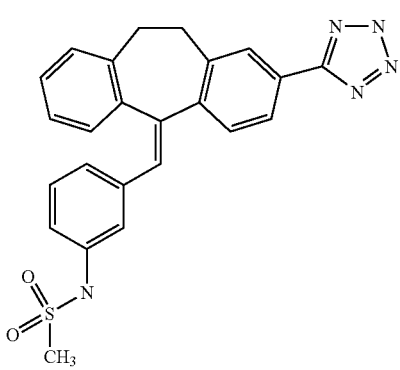 | ES 442 (−)/444 (+) | (ISO80-10) t = 1.88 (98%) | 2 |

-continued

| Example No. | Structure | MS Data | HPLC | Section |
|---|---|---|---|---|
| 344 | 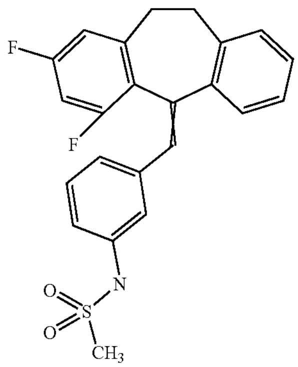 | ES 410 (−)/412 (+) | (ISO70-10) t = 5.73 (75%), 5.98 (25%) | 2 |
| 345 | 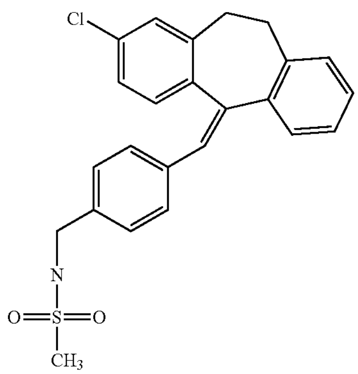 | ES 422 (−)/424 (+) | (GRAD 5-100) t = 5.52 | 2 |
| 346 | 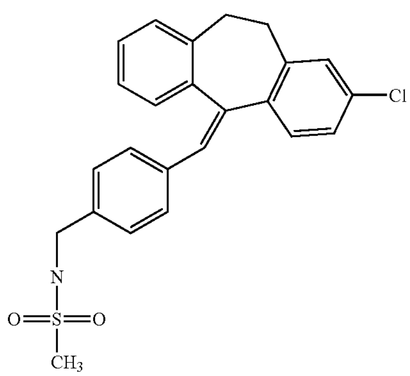 | ES 422 (−)/424 (+) | (GRAD 5-100) t = 5.71 | 2 |
| 347 | 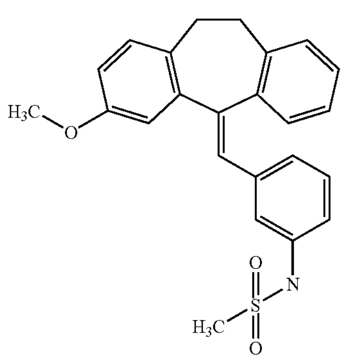 | ES 406 (+) | NA | 2 |

-continued

| Example No. | Structure | MS Data | HPLC | Section |
|---|---|---|---|---|
| 348 | 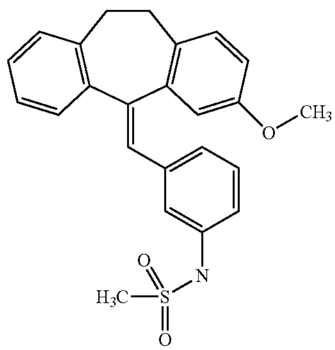 | ES 406 (+) | NA | 2 |
| 349 | 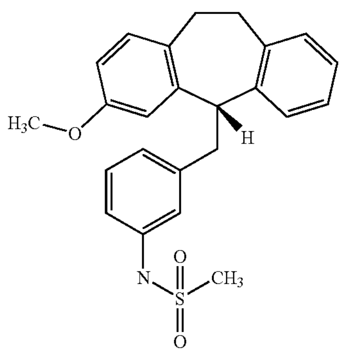 | ES 407 (+) | t = 4.89 min | 2 |
| 350 | 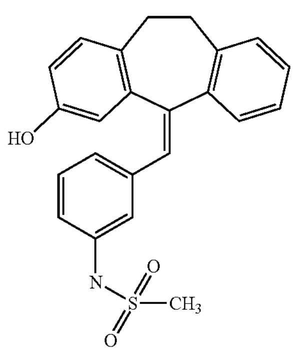 | ES 392 (+) | t = 4.46 min (100%) | 2 |
| 351 | 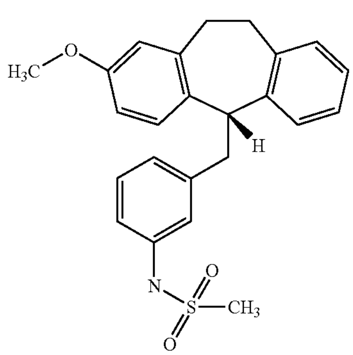 | ES 407 (+) | t = 4.80 min (100%) | 2 |

-continued
| Example No. | Structure | MS Data | HPLC | Section |
|---|---|---|---|---|
| 352 | 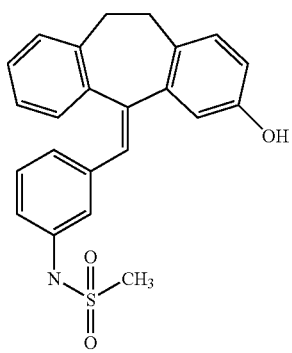 | ES 392 (+) | t = 4.24 min (100%) | 2 |
| 353 | 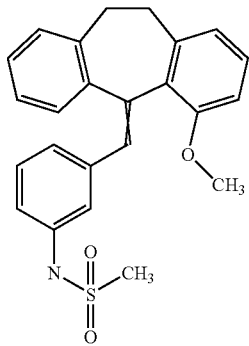 | ES 405 (+) | t = 5.85 min (100%) | 2 |
| 354 | 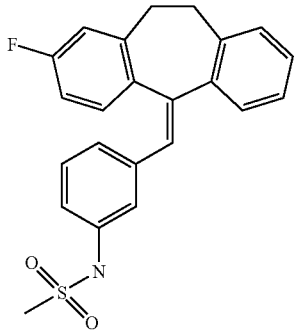 | ES 392 (−) | (ISO60-15M)<br>t = 11.22 (100%) | 2 |
| 355 | 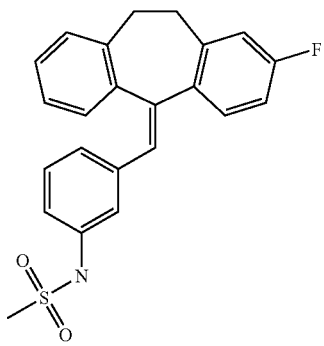 | ES 392 (−) | (ISO60-15M) t = 10.90 (96%) | 2 |

-continued

| Example No. | Structure | MS Data | HPLC | Section |
|---|---|---|---|---|
| 356 | 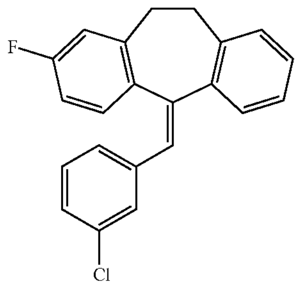 | ES 315 (−) | (ISO80-10M) t = 4.02 (94%) | 2 |
| 357 | 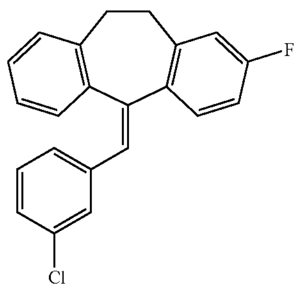 | ES 315 (−) | (ISO80-10M) t = 3.86 (95%) | 2 |
| 358 | 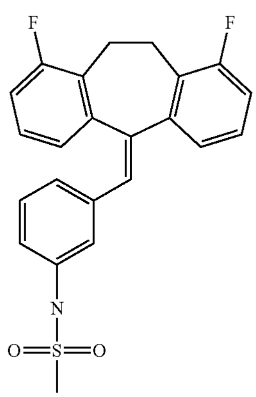 | ES 410 (−) | (ISO90-10M) t = 2.64 (92%) | 2 |
| 359 | 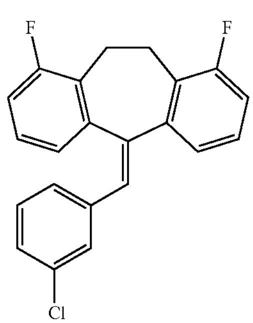 | ES 333 (−) | (ISO90-10M) t = 2.90 (98%) | 2 |

-continued

| Example No. | Structure | MS Data | HPLC | Section |
|---|---|---|---|---|
| 360 | 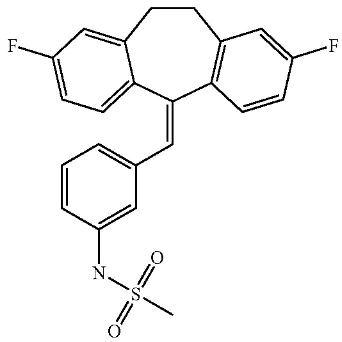 | ES 410 (−) | (ISO80-10M) t = 3.56 (99%) | 2 |
| 361 | 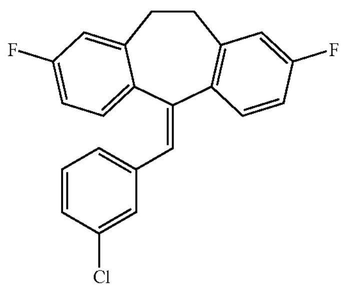 | ES 333 (−) | (ISO90-10M) t = 2.63 (99%) | 2 |
| 362 | 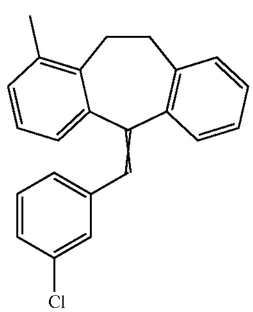 | ES 311 (−) | (ISO90-10M) t = 2.94 (92%) | 2 |
| 363 | 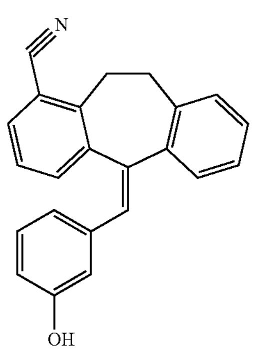 | ES 322 (−) | (ISO80-10M) t = 3.40 (96%) | 2 |

-continued

| Example No. | Structure | MS Data | HPLC | Section |
|---|---|---|---|---|
| 364 | 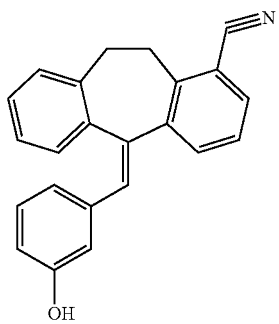 | ES 322 (−) | (ISO80-10M) t = 3.10 (99%) | 2 |
| 365 | 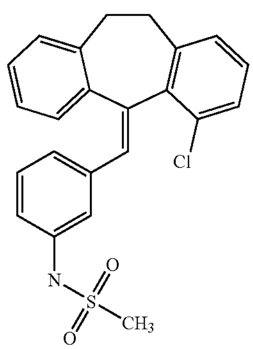 | ES 408 (−) | (ISO80-10M) t = 4.15 (90%) | 2 |
| 366 | 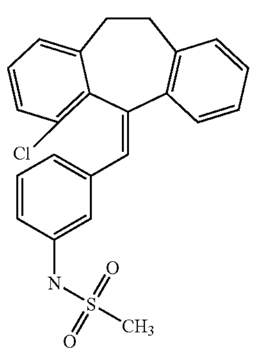 | ES 408 (−)/410 (+) | (ISO80-10M) t = 3.81 (100%) | 2 |
| 367 | 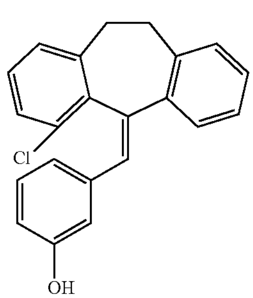 | ES 331 (−)/333 (+) | (ISO80-10M) t = 4.10 (99%) | 2 |

-continued

| Example No. | Structure | MS Data | HPLC | Section |
|---|---|---|---|---|
| 368 | 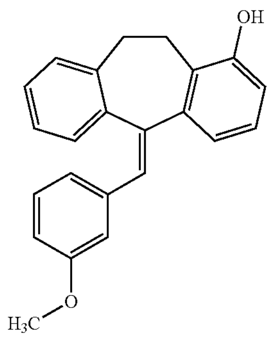 | ES 327 (−)/329 (+) | (ISO80-10M) t = 3.66 (100%) | 2 |
| 369 | 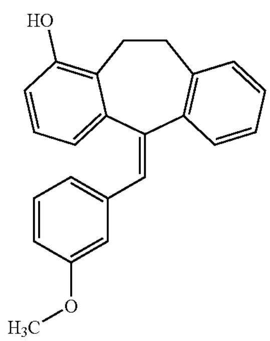 | ES 327 (−)/329 (+) | (ISO80-10M) t = 4.15 (99%) | 2 |
| 370 | 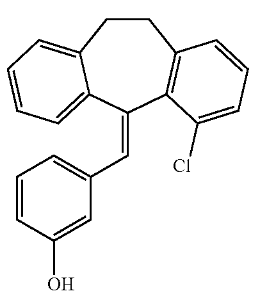 | ES 332 (−)/334 (+) | (ISO80-10M) t = 4.53 (99%) | 2 |
| 371 | 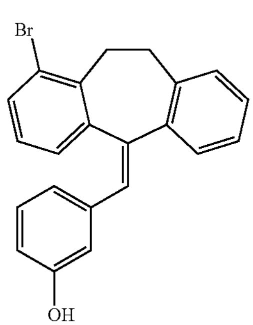 | ES 377 (−) | (ISO80-10M) t = 5.93 (96%) | 2 |

-continued
| Example No. | Structure | MS Data | HPLC | Section |
|---|---|---|---|---|
| 372 | 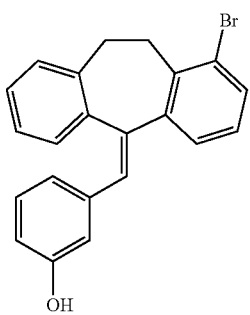 | ES 377 (−) | (ISO80-10M) t = 6.28 (95%) | 2 |
| 373 | 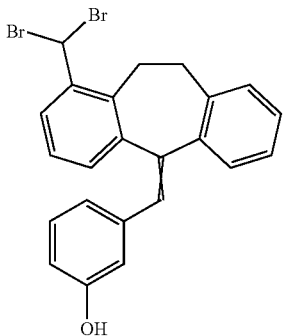 | ES 467 (−) | (ISO80-10M) t = 5.26 (95%) | 2 |
| 374 | 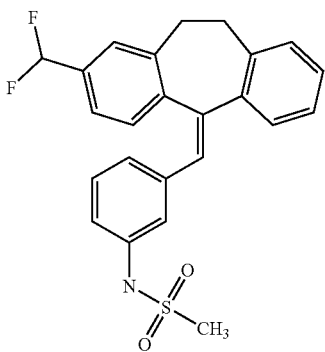 | ES 424 (−) | (ISO80-10M) t = 3.45 (92%) | 2 |
| 375 | 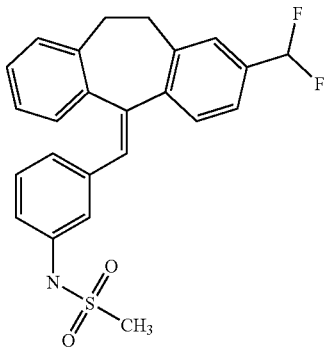 | ES 424 (−) | (ISO80-10M) t = 3.06 (94%) | 2 |

-continued
| Example No. | Structure | MS Data | HPLC | Section |
|---|---|---|---|---|
| 376 | 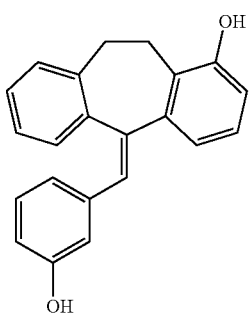 | ES 313 (−)/315 (+) | (ISO80-10M) t = 2.15 (99%) | 2 |
| 377 | 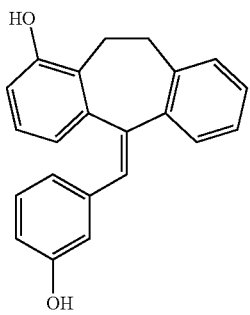 | ES 313 (−)/315 (+) | (ISO80-10M) t = 2.50 (98%) | 2 |
| 378 | 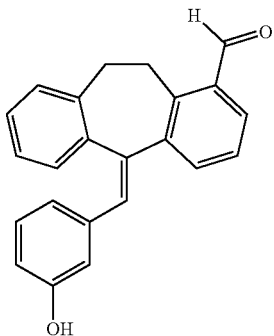 | ES 325 (−) | (ISO80-10M) t = 3.00 (93%) | 2 |
| 379 | 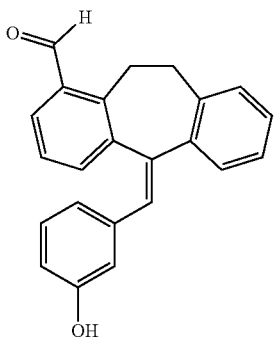 | ES 325 (−) | (ISO80-10M) t = 3.22 (94%) | 2 |

-continued
| Example No. | Structure | MS Data | HPLC | Section |
|---|---|---|---|---|
| 380 | 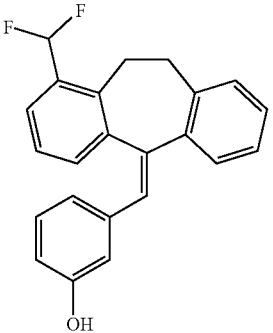 | ES 347 (−) | (ISO80-10M) t = 3.48 (89%) | 2 |
| 381 | 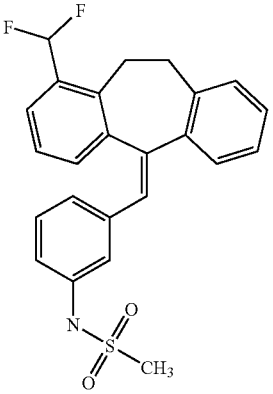 | ES 424 (−) | (ISO80-10M) t = 3.44 (92%) | 2 |
| 382 | 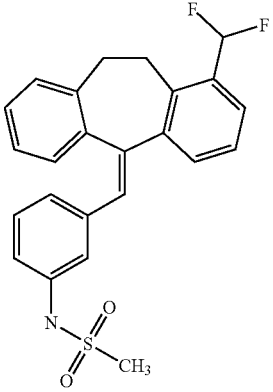 | ES 424 (−) | (ISO80-10M) t = 3.16 (93%) | 2 |
| 383 | 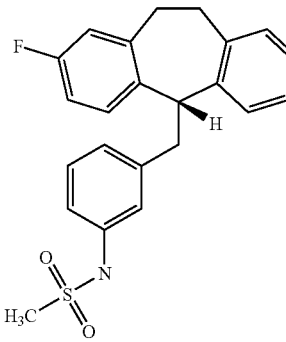 | ES 394 (−) | (ISO60-15M) t = 10.37 (99%) | 2 |

-continued
| Example No. | Structure | MS Data | HPLC | Section |
|---|---|---|---|---|
| 384 | 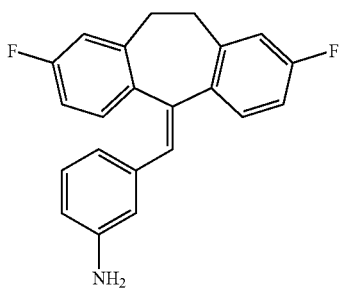 | ES 334 (+) | (ISO80-10M) t = 4.14 (98%) | 2 |
| 385 | 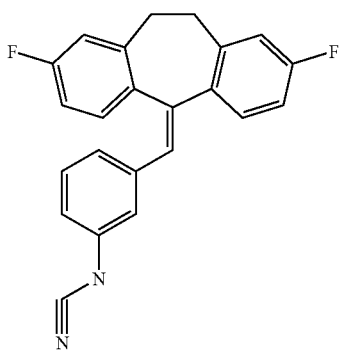 | ES 357 (−) | (ISO80-10M) t = 3.93 (89%) | 2 |
| 386 | 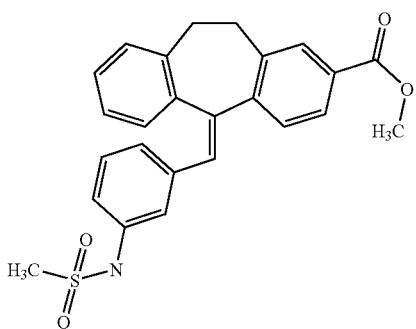 | ES 4.32 (−) | (ISO80-10M) t = 3.21 (91%) | 2 |
| 387 | 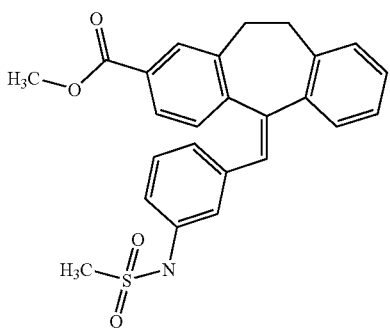 | ES 432 (−) | (ISO80-10M) t = 3.49 (94%) | 2 |

-continued

| Example No. | Structure | MS Data | HPLC | Section |
|---|---|---|---|---|
| 388 | 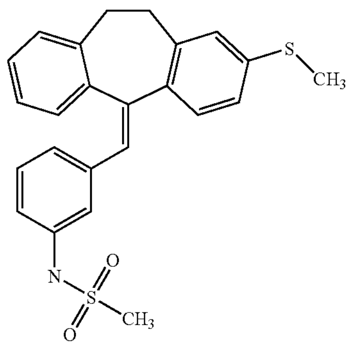 | NA | (ISO80-10M) t = 3.20 (95%) | 2 |
| 389 | 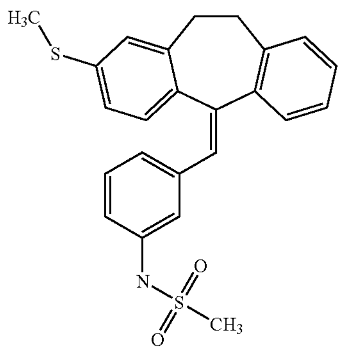 | NA | (ISO80-10M) t = 4.08 (93%) | 2 |
| 390 | 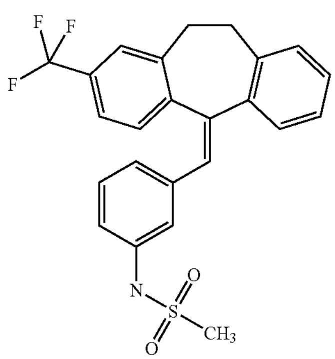 | ES 442 (−) | (ISO80-10M) t = 4.39 (99%) | 2 |
| 391 | 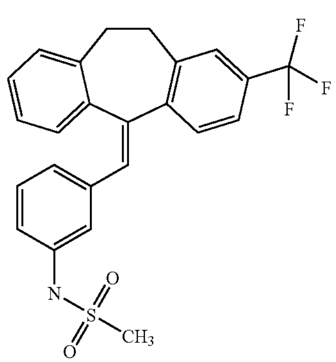 | ES 442 (−) | (ISO80-10M) t = 4.39 (93%) | 2 |

-continued
| Example No. | Structure | MS Data | HPLC | Section |
|---|---|---|---|---|
| 392 | 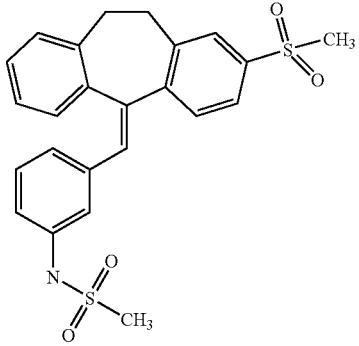 | ES 452 (−) | (ISO80-10M) t = 2.07 (93%) | 2 |
| 393 | 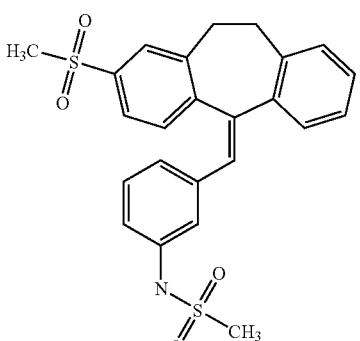 | ES 452 (−) | (ISOS0-10M) t = 2.43 (99%) | 2 |
| 394 | 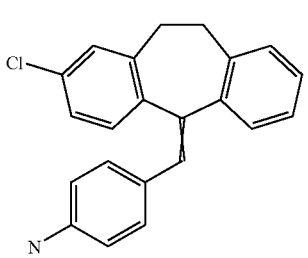 | 332 (ES+)<br>330 (ES−) | NA | 2 |
| 395 | 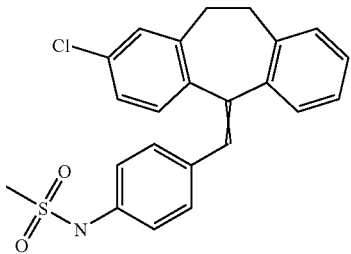 | 408 (ES−) | NA | 2 |
| 396 | 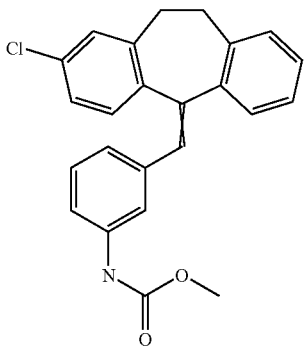 | 390 (ES−)<br>388 (ES+) | NA | 2 |

-continued

| Example No. | Structure | MS Data | HPLC | Section |
|---|---|---|---|---|
| 397 | 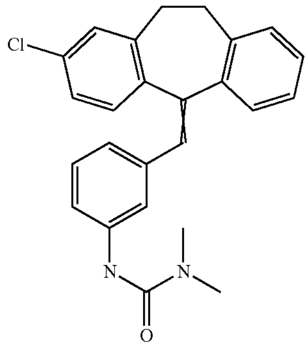 | 402 (EI+) | NA | 2 |
| 398 | 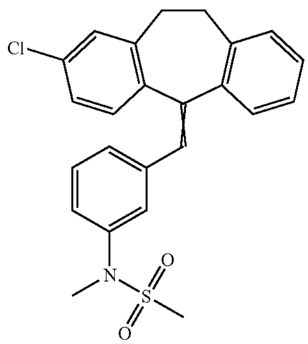 | MS(ES+) = 424. | NA | 2 |
| 399 | 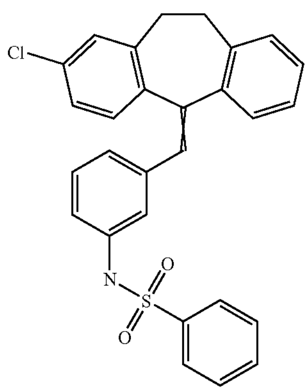 | 470/472 (ES−) | NA | 2 |
| 400 | 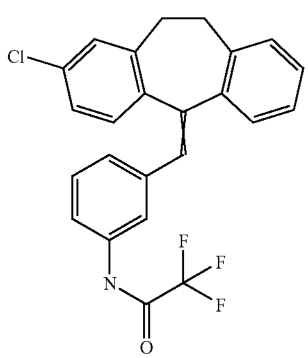 | 426 (ES−) | NA | 2 |

-continued

| Example No. | Structure | MS Data | HPLC | Section |
|---|---|---|---|---|
| 401 | 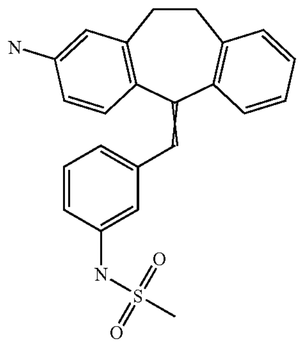 | 389 (ES−) | NA | 2 |
| 402 | 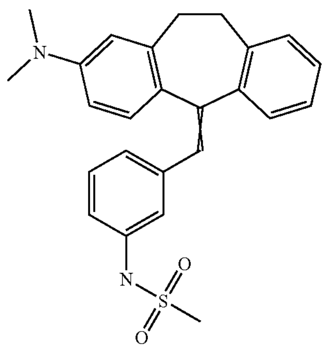 | 419 (ES+) | NA | 2 |
| 403 | 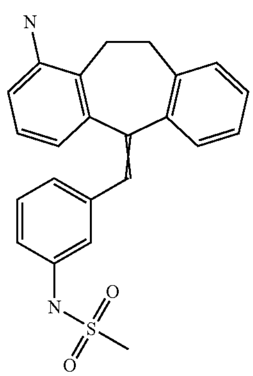 | Isomers separated NA | NA | 2 |
| 404 | 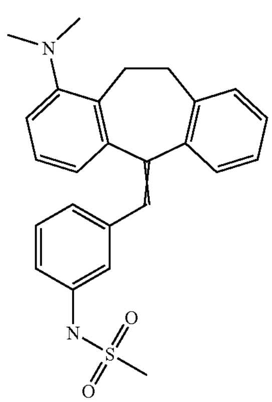 | 419 (ES+) | NA | 2 |

-continued

| Example No. | Structure | MS Data | HPLC | Section |
|---|---|---|---|---|
| 405 | 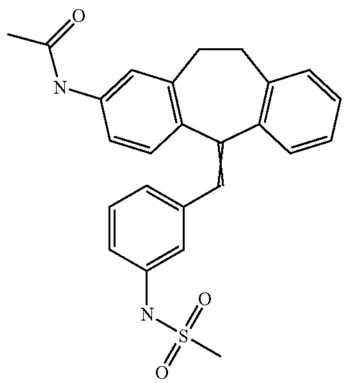 | 433 (ES+) | NA | 2 |
| 406 | 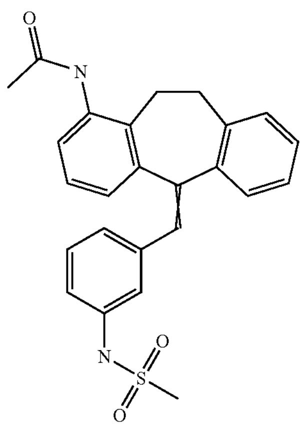 | 433 (ES+) | NA | 2 |
| 407 | 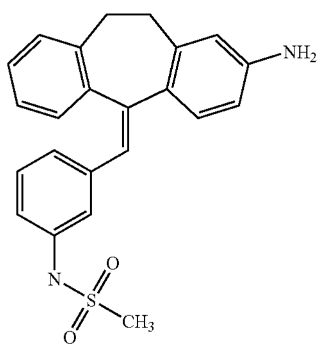 | 391 (ES+) | NA | 2 |
| 408 | 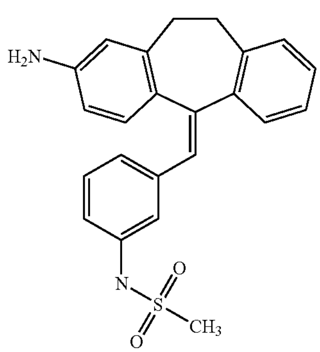 | 391 (ES+) | NA | 2 |

-continued

| Example No. | Structure | MS Data | HPLC | Section |
|---|---|---|---|---|
| 409 | 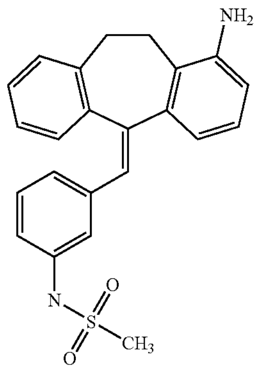 | 391 (ES+) | NA | 2 |
| 410 | 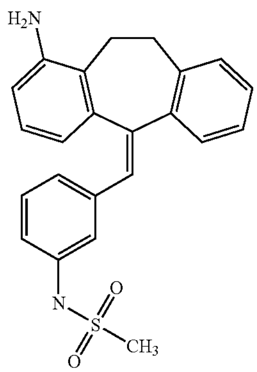 | 391 (ES+) | NA | 2 |
| 411 | 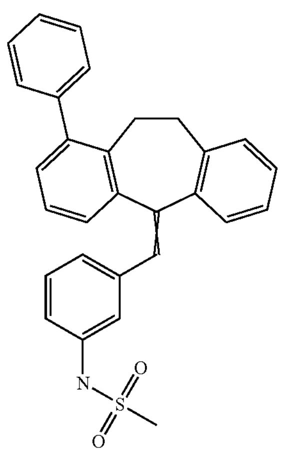 | 450 (ES−) | NA | 2 |
| 412 | 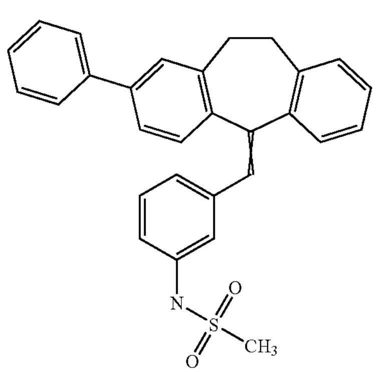 | 450 (ES−) | NA | 2 |

-continued
| Example No. | Structure | MS Data | HPLC | Section |
|---|---|---|---|---|
| 413 | 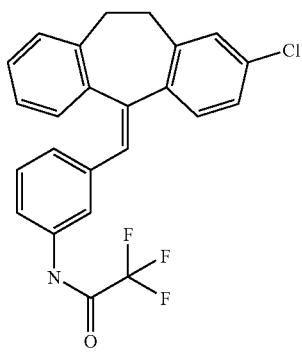 | 426/428 (ES−) | 100% | 2 |
| 414 | 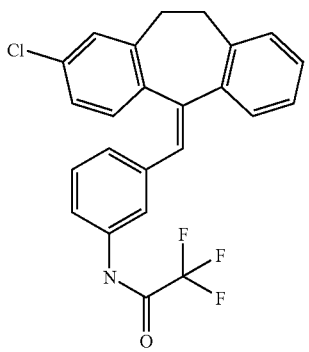 | 426/428 (ES−) | 100% | 2 |
| 415 | 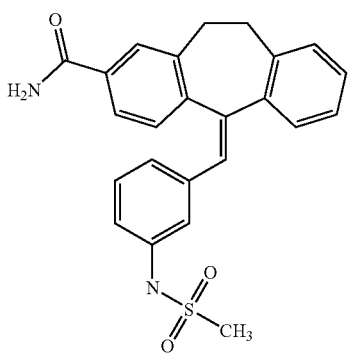 | 419 (ES+) | 93% | 2 |
| 416 | 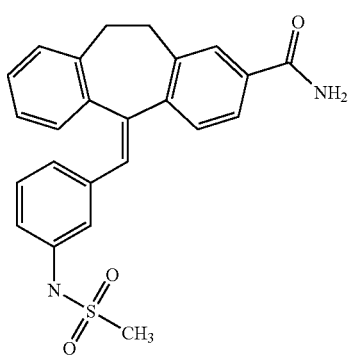 | 419 (ES+) | 97% | 2 |

-continued

| Example No. | Structure | MS Data | HPLC | Section |
|---|---|---|---|---|
| 417 | 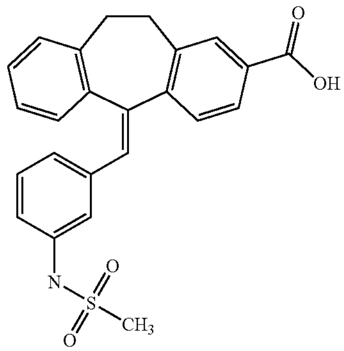 | 418 (ES−) | NA | 2 |
| 418 | 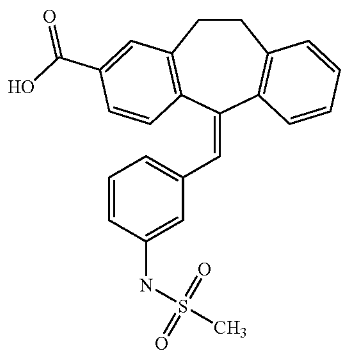 | 418 (ES−) | NA | 2 |
| 419 | 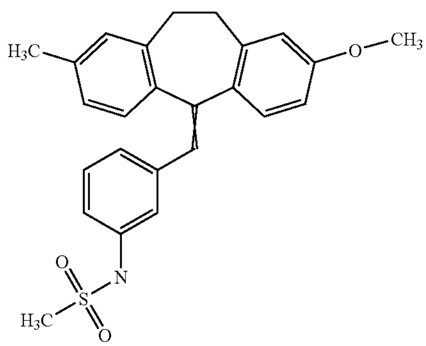 | ES 420 (+) | (GRAD) t = 3.30 (97%) | 2 |
| 420 | 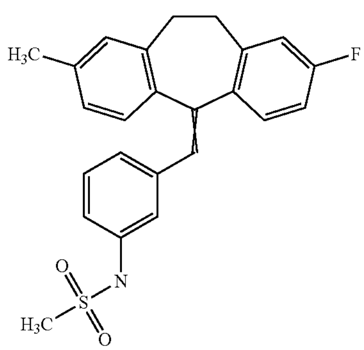 | ES 408 (+) | (GRAD) t = 3.49 (100%) | 2 |

-continued

| Example No. | Structure | MS Data | HPLC | Section |
|---|---|---|---|---|
| 421 | 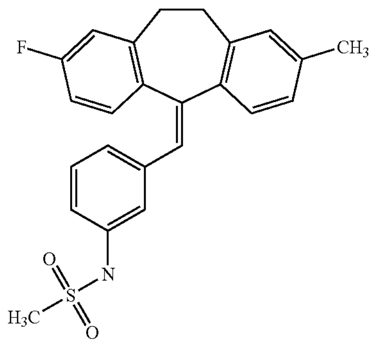 | NA | (GRAD) t = 3.49 (100%) | 2 |
| 422 | 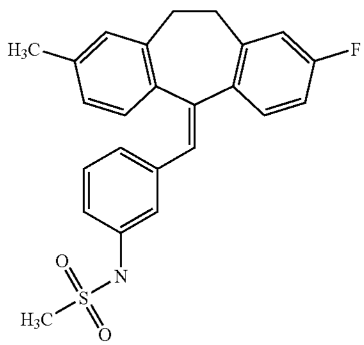 | N/A | (GRAD) t = 3.46 (98.4%) | 2 |
| 423 | 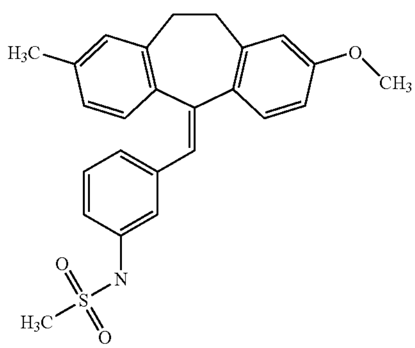 | ES 418 (−)/420 (+) | (GRAD) t = 2.48 (100%) | 2 |
| 424 | 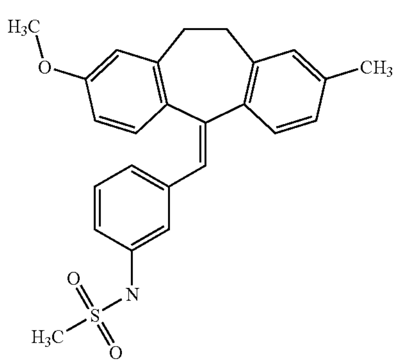 | ES 418 (−)/420 (+) | (GRAD) t = 2.46 (100%) | 2 |

-continued

| Example No. | Structure | MS Data | HPLC | Section |
|---|---|---|---|---|
| 425 | 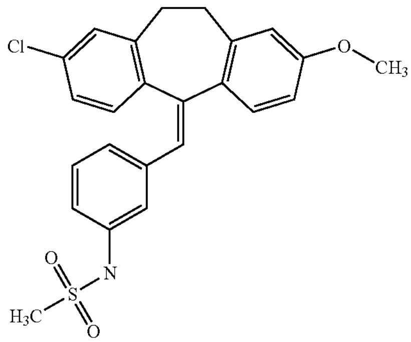 | ES 438 (−)/440 (+) | (GRAD) t = 2.74 (100%) | 2 |
| 426 | 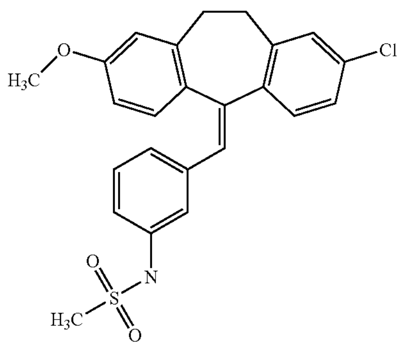 | ES 438 (−)/440 (+) | NA | 2 |
| 427 | 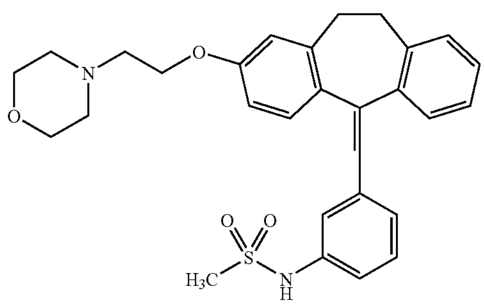 | ES− = 504, ES+ = 505 (E Isomer) | NA | 2 |
| 428 | 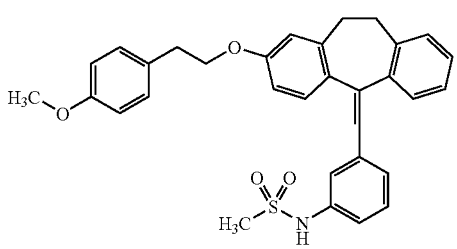 | ES− = 524 (E Isomer) | NA | 2 |
| 429 | 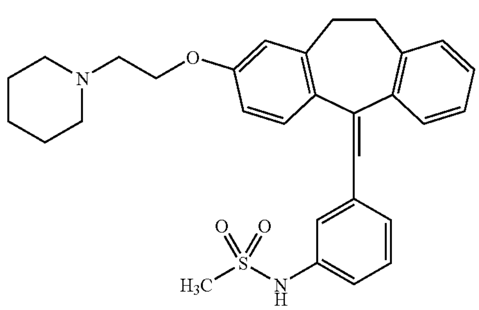 | ES− = 501, ES+ = 503 (E Isomer) | NA | 2 |

-continued
| Example No. | Structure | MS Data | HPLC | Section |
|---|---|---|---|---|
| 430 | 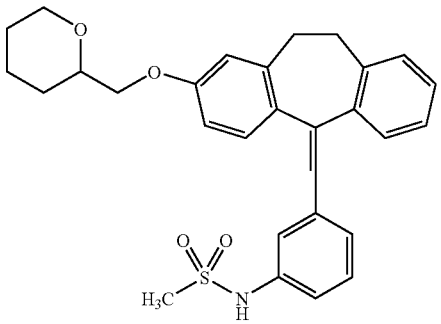 | ES− = 488, ES+ = 490 (E Isomer) | NA | 2 |
| 431 | 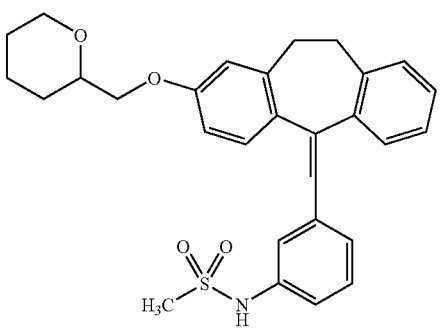 | ES− = 488, ES+ = 490 (Z Isomer) | NA | 2 |
| 432 | 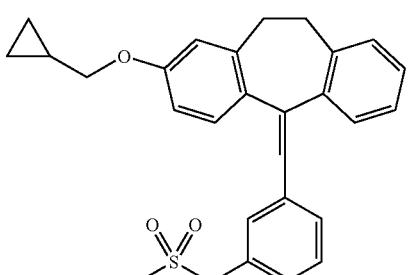 | ES− = 444 (E Isomer) | NA | 2 |
| 433 | 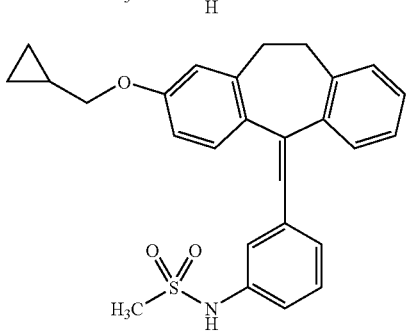 | ES− = 444 (Z Isomer) | NA | 2 |
| 434 | 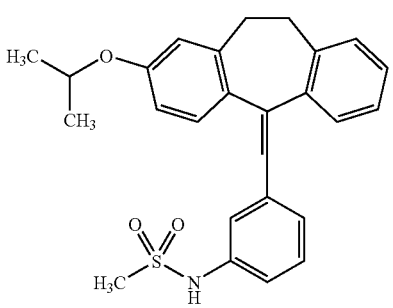 | ES− = 432 (E Isomer) | NA | 2 |

-continued

| Example No. | Structure | MS Data | HPLC | Section |
|---|---|---|---|---|
| 435 | 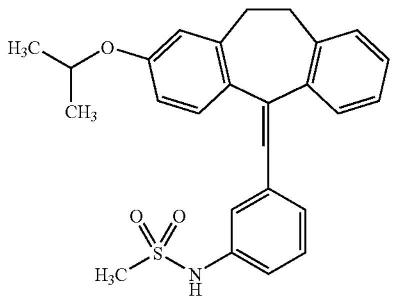 | ES− = 432 (Mixture) | NA | 2 |
| 436 | 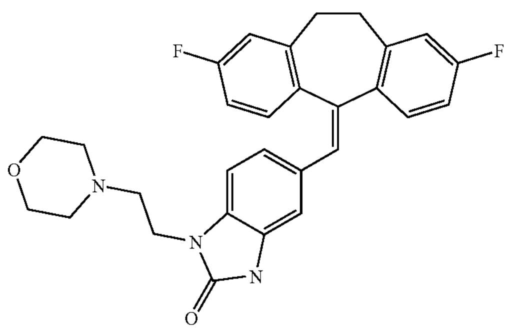 | ES 488 (+) | (ISO80-10M) t = 2.03 (97%) | 3 |
| 437 | 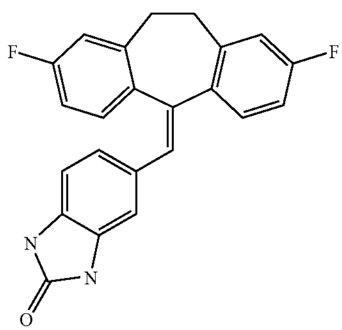 | ES 373 (−) | (ISO80-10M) t = 2.62 (97%) | 3 |
| 439 | 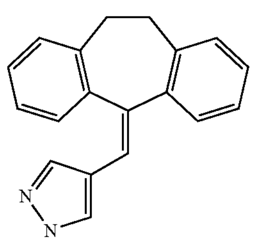 | ES 271 (−)/273 (+) | (ISO90-10) t = 2.55 (98%) | 3 |
| 440 | 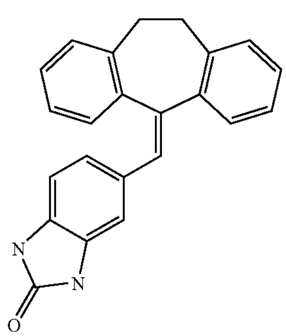 | ES 337 (−)/339 (+) | (ISO90-10) t = 2.32 (93%) | 3 |

-continued

| Example No. | Structure | MS Data | HPLC | Section |
|---|---|---|---|---|
| 441 | 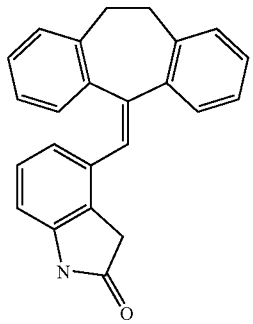 | ES 338 (+) | (ISO80-10) t = 3.61 (96%) | 3 |
| 442 | 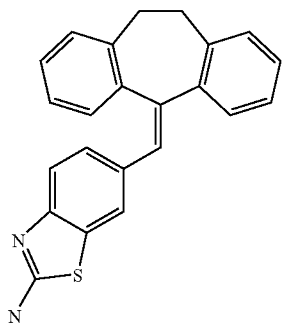 | ES 353 (−)/355 (+) | (ISO80-10) t = 4.03 (98%) | 3 |
| 443 | 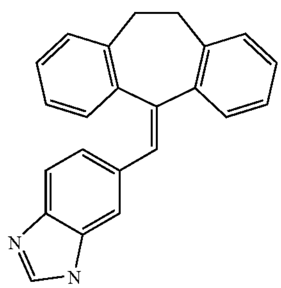 | ES 321 (−)/323 (+) | (ISO80-10) t = 2.39 (99%) | 3 |
| 444 | 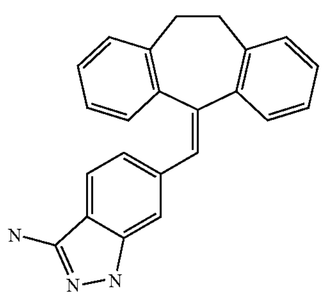 | ES 336 (−)/338 (+) | (ISO80-10) t = 2.85 (98%) | 3 |
| 445 | 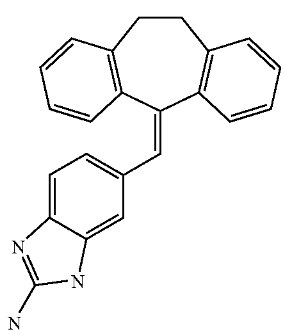 | ES 336 (−)/338 (+) | (ISO80-10) t = 1.96 (100%) | 3 |

-continued

| Example No. | Structure | MS Data | HPLC | Section |
|---|---|---|---|---|
| 446 | 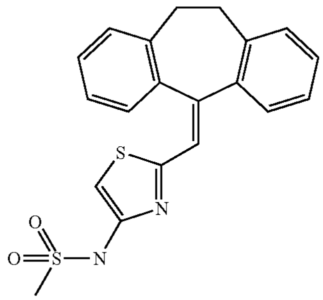 | ES 381 (−)/383 (+) | (ISO80-10) t = 2.99 (98%) | 3 |
| 447 | 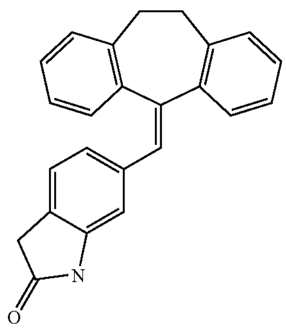 | ES 336 (−)/338 (+) | (ISO80-10) t = 3.68 (91%) | 3 |
| 448 | 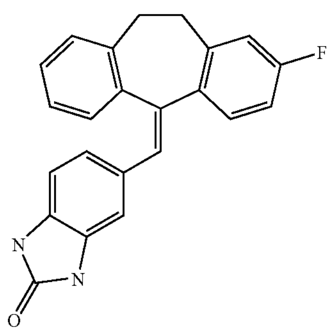 | ES 355 (−)/357 (+) | (ISO80-10) t = 2.64 (78%) | 3 |
| 449 | 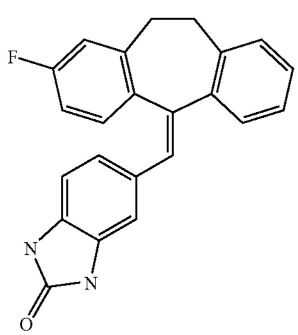 | ES 355 (−)/357 (+) | (ISO80-10) t = 2.74 (94%) | 3 |

-continued

| Example No. | Structure | MS Data | HPLC | Section |
|---|---|---|---|---|
| 450 | 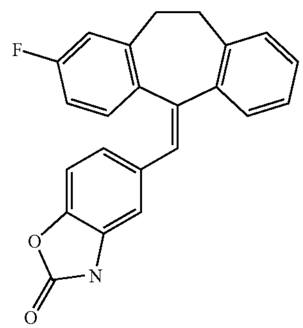 | ES 356 (−) | (ISO80-10) t = 3.93 (92%) | 3 |
| 451 | 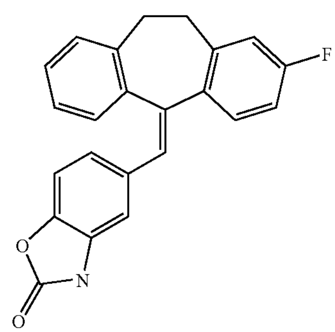 | ES 356 (−)/358 (+) | (ISO80-10) t = 3.81 (92%) | 3 |
| 452 | 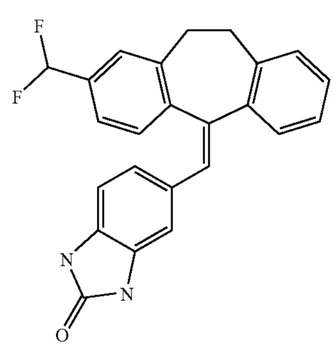 | ES 387 (−)/389 (+) | (ISO80-10) t = 2.58 (96%) | 3 |
| 453 | 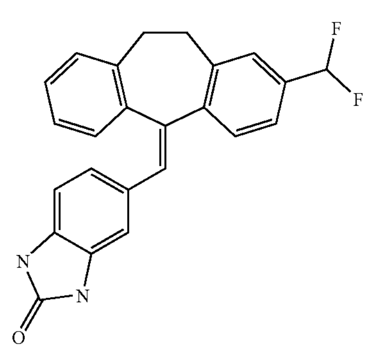 | ES 387 (−)/389 (+) | (ISO80-10) t = 2.40 (96%) | 3 |

-continued

| Example No. | Structure | MS Data | HPLC | Section |
|---|---|---|---|---|
| 454 | 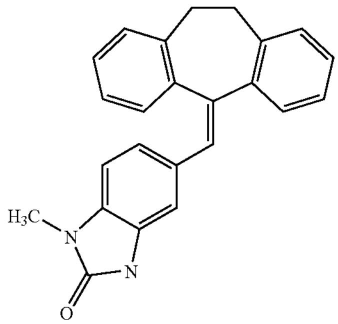 | ES 351 (−)/353 (+) | (ISO80-10) t = 3.78 (100%) | 3 |
| 455 | 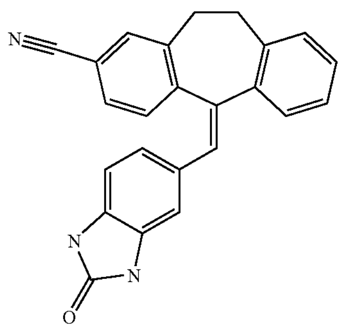 | ES 362 (−)/364 (+) | (ISO80-10) t = 2.41 (84%) | 3 |
| 456 | 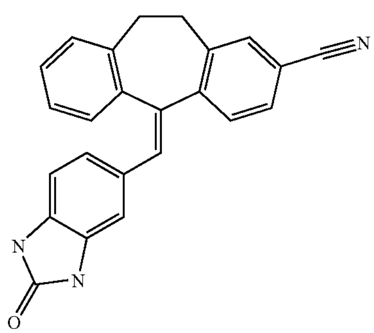 | ES 362 (−)/364 (+) | (ISO80-10) t = 2.22 (88%) | 3 |
| 457 | 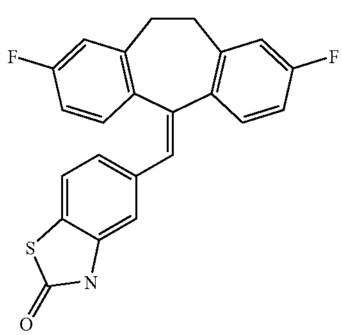 | ES 390 (−)/392 (+) | (ISO80-10) t = 4.71 (96%) | 3 |

-continued

| Example No. | Structure | MS Data | HPLC | Section |
|---|---|---|---|---|
| 458 | 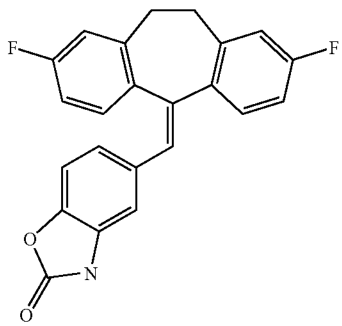 | ES 374 (−) | (ISO80-10) t = 3.69 (95%) | 3 |
| 459 | 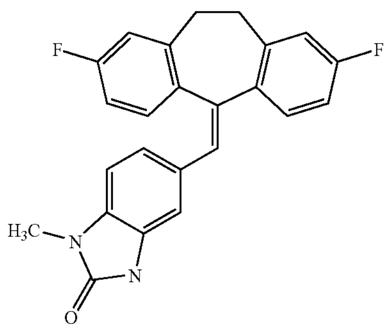 | ES 387 (−)/389 (+) | (ISO80-10) t = 3.72 (95%) | 3 |
| 460 | 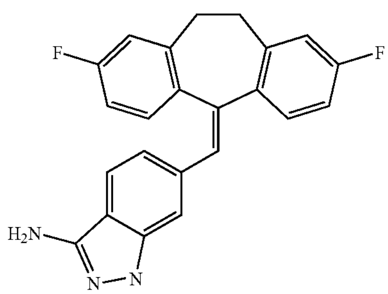 | ES 372 (−)/374 (+) | (ISO80-10) t = 2.89 (83%) | 3 |
| 461 | 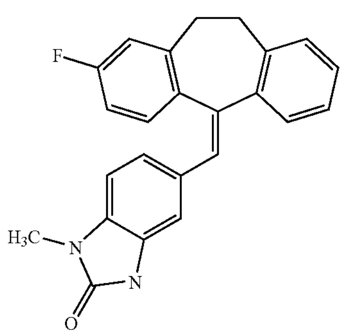 | ES 369 (−)/371 (+) | (ISO80-10) t = 3.73 (100%) | 3 |

-continued

| Example No. | Structure | MS Data | HPLC | Section |
|---|---|---|---|---|
| 462 | 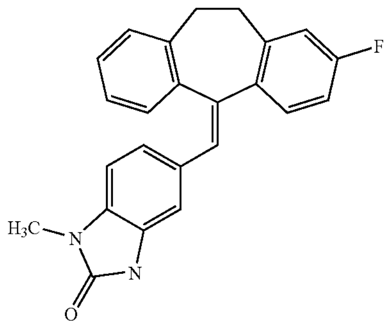 | ES 369 (−)/371 (+) | (ISO80-10) t = 3.64 (99%) | 3 |
| 463 | 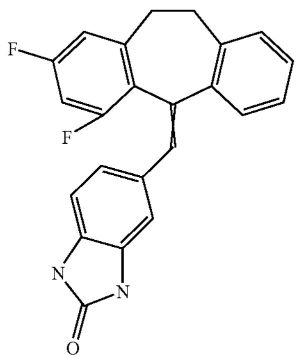 | ES 373 (−) | (ISO70-10) t = 3.54 (78%), 3.64 (22%) | 3 |
| 464 | 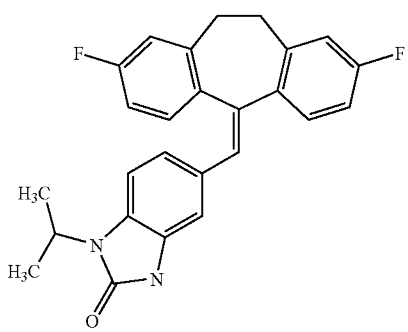 | ES 415 (−)/417 (+) | (ISO80-10) t = 4.81 (97%) | 3 |
| 465 | 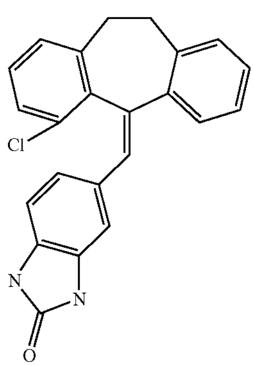 | ES 371 (−)/373 (+) | (ISO80-10M) t = 2.95 (93%) | 3 |

-continued

| Example No. | Structure | MS Data | HPLC | Section |
|---|---|---|---|---|
| 466 | 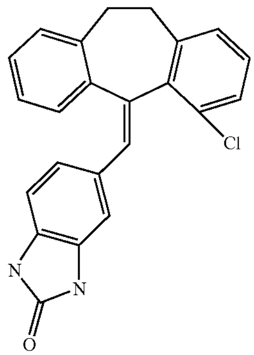 | ES 371 (−)/373 (+) | (ISO80-10M) t = 2.73 (94%) | 3 |
| 467 | 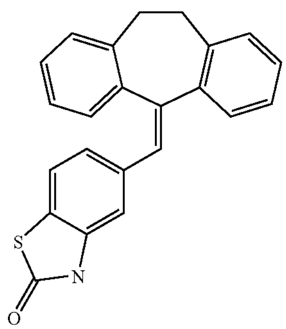 | ES 354 (−) | (ISO80-10M) t = 4.87 (100%) | 3 |
| 468 | 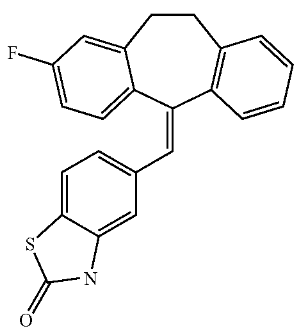 | ES 372 (−)/374 (+) | (ISO80-10M) t = 5.10 (99%) | 3 |
| 469 | 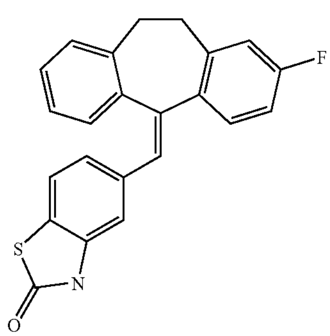 | ES 372 (−)/374 (+) | (ISO80-10M) t = 4.97 (99%) | 3 |

-continued

| Example No. | Structure | MS Data | HPLC | Section |
|---|---|---|---|---|
| 470 | 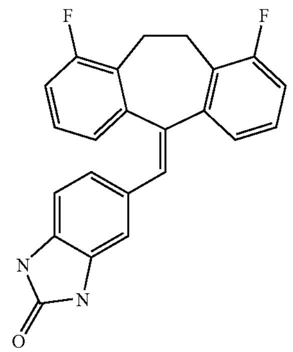 | ES 373 (−)/375 (+) | (ISO80-10M) t = 2.93 (96%) | 3 |
| 471 | 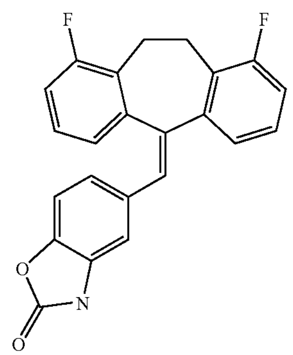 | ES 374 (−)/376 (+) | (ISO80-10M) t = 4.28 (93%) | 3 |
| 472 | 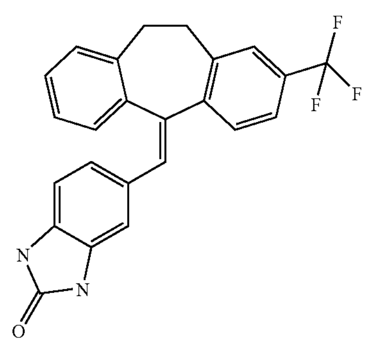 | ES 405 (−) | (ISO80-10M) t = 3.31 (97%) | 3 |
| 473 | 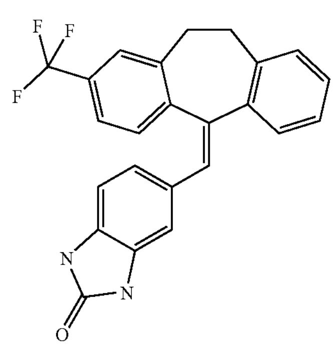 | ES 405 (−) | (ISO80-10M) t = 3.30 (94%) | 3 |

-continued

| Example No. | Structure | MS Data | HPLC | Section |
|---|---|---|---|---|
| 474 | 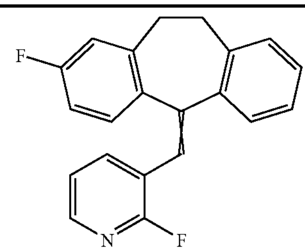 | m/z = 320 (M + 1) | ISO80-10.M, ret time = 5.63, 5.73 min.; 98.2% | 3 |
| 475 | 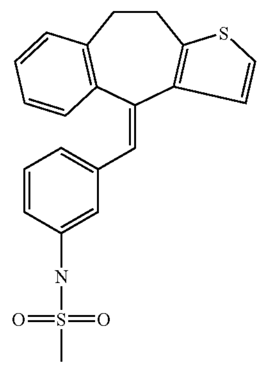 | APCI 382 (+) | ISO 80:100M t = 3.047 (95%) | 4 |
| 476 | 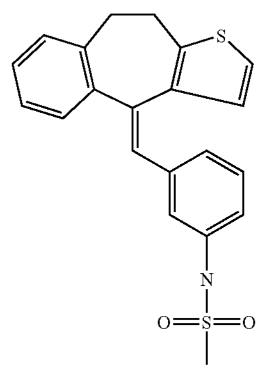 | APCI 382 (+) | ISO 80:100M t = 3.310 (95%) | 4 |
| 477 | 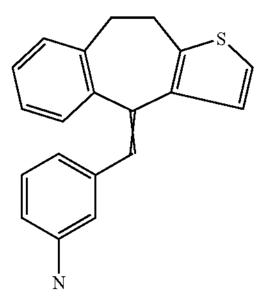 | APCI 304 (+) | GRAD 80-100M t = 4.037 (98%) | 4 |
| 478 | 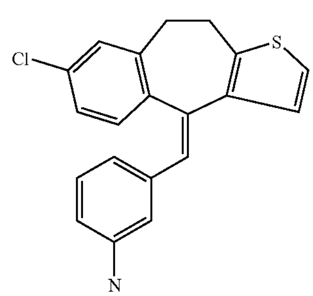 | EI 337 | GRAD 60-280 t = 24.21 (98%) | 4 |

-continued

| Example No. | Structure | MS Data | HPLC | Section |
|---|---|---|---|---|
| 481 | 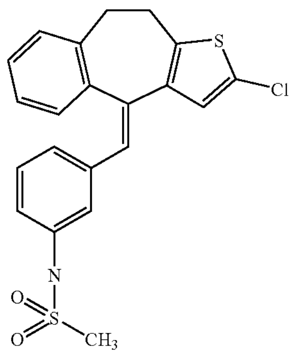 | APCI 416 (+) | GRAD 80-100M t = 1.852 (100%) | 4 |
| 482 | 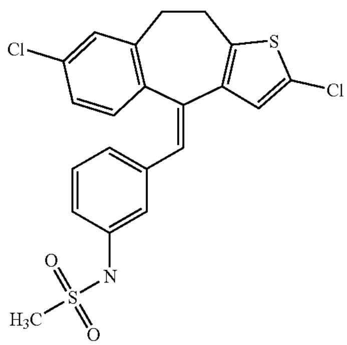 | APCI 450 (+) | GRAD 80-100M t = 5.466 (100%) | 4 |
| 483(a) | 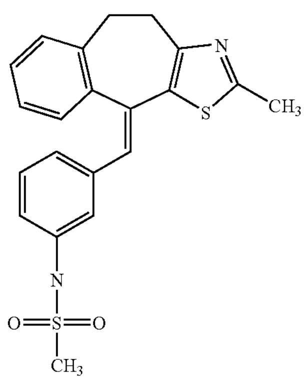 | APCI 397 (+) | GRAD 80-100M t = 2.799 (95%) | 4 |
| 483(b) | 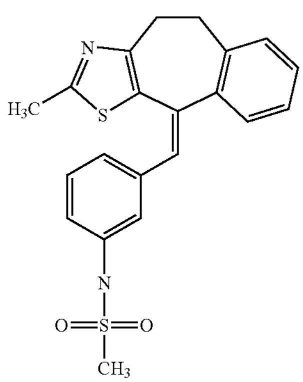 | APCI 397 (+) | GRAD 80-100M t = 2.598 (95%) | 4 |

-continued
| Example No. | Structure | MS Data | HPLC | Section |
|---|---|---|---|---|
| 484(a) | 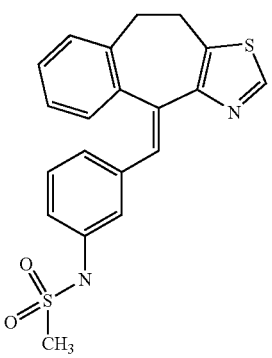 | APCI 383 (+) | GRAD 80-100M t = 2.128 (100%) | 4 |
| 484(b) | 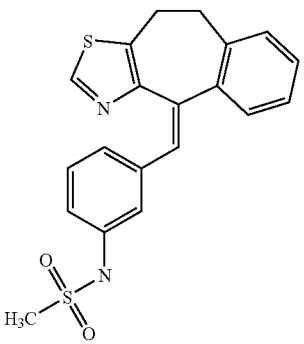 | APCI 383 (+) | GRAD 80-100M t = 2.219 (98%) | 4 |
| 485(a) | 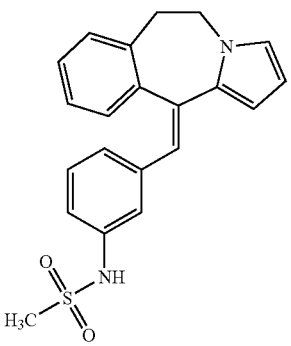 | APCI 365 (+) | GRAD 80-100M t = 2.823 (99%) | 4 |
| 486 | 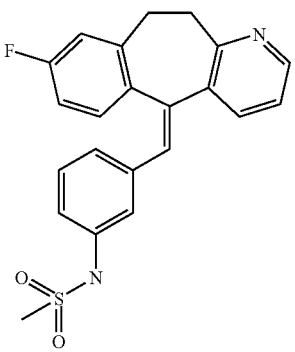 | 395.1 (APCI-pos) 393.0 (APCI-neg) | 98% | 4 |

-continued

| Example No. | Structure | MS Data | HPLC | Section |
|---|---|---|---|---|
| 487 | 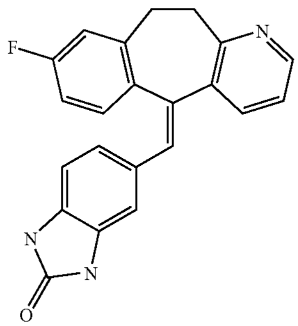 | 358.0 (APCI-pos)<br>356.0 (APCI-neg) | 98% | 4 |
| 488 | 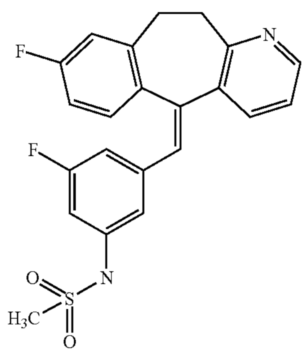 | 413.0 (APCI-pos)<br>411.0 (APCI-neg) | 98% | 4 |
| 489 | 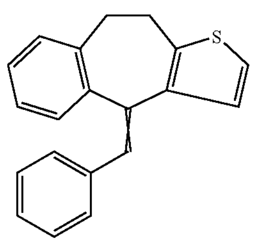 | APCI<br>289 (+) | GRAD 80-100M<br>t = 5.7550 (100%) | 4 |
| 490 | 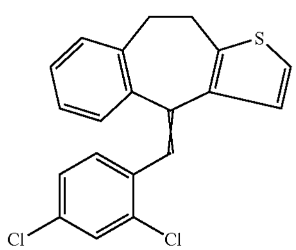 | NA | NA | 4 |
| 491 | 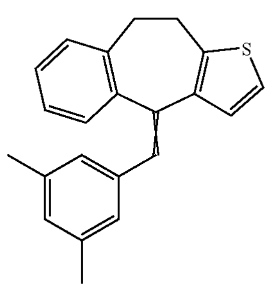 | EI<br>316 | GRAD 60-280<br>t1 23.09 (33%)<br>t2 23.25 (66%)<br>ISOMERICMIX | 4 |

-continued

| Example No. | Structure | MS Data | HPLC | Section |
|---|---|---|---|---|
| 492 | 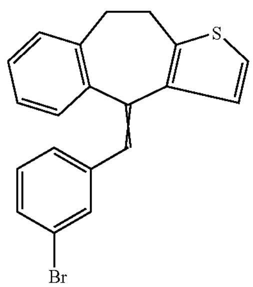 | EI 364 | GRAD 60-280 t1 20.4 (20%) t2 20.6 (80%) ISOMERICMIX | 4 |
| 493 | 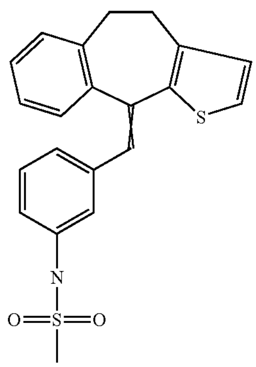 | APCI 382 (+) | ISO 70:30M t = 4.351 (95%) | 4 |
| 494 | 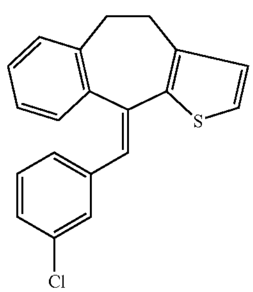 | APCI 303 (+) | ISO 80:20M t = 3.892 (95%) | 4 |
| 495 | 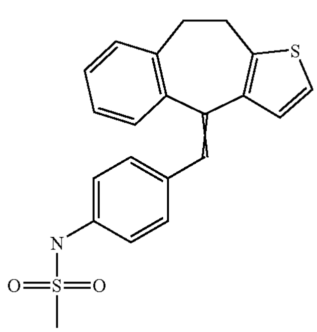 | APCI 382 (+) | ISO 80:20M t = 3.413 (95%) | 4 |

-continued

| Example No. | Structure | MS Data | HPLC | Section |
|---|---|---|---|---|
| 496 | 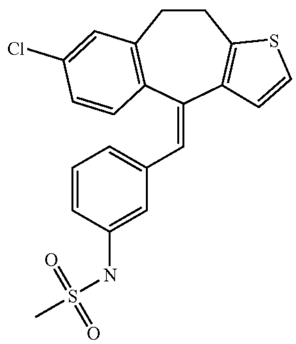 | APCI 416 (+) | ISO 80:20 A t = 3.527 (95%) | 4 |
| 497 | 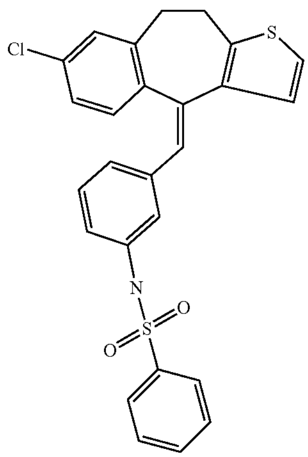 | APCI 440 (+) | ISO 80:100 A t = 6.922 (95%) | 4 |
| 498 | 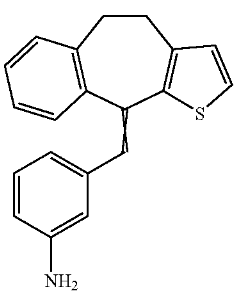 | EI 303 | GRAD 60-280 21.15 (98%) | 4 |
| 499 | 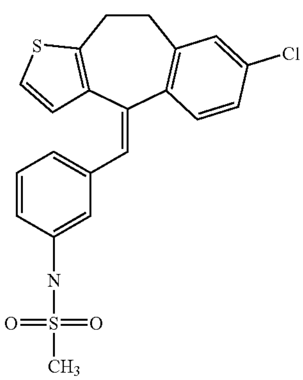 | APCI 416 (+) | ISO 80-20 A t = 6.910 (99%) | 4 |

-continued
| Example No. | Structure | MS Data | HPLC | Section |
|---|---|---|---|---|
| 500 | 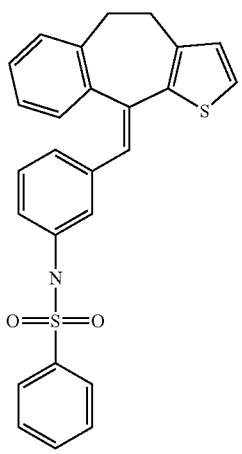 | APCI 440 (+) | ISO 80-20 A t = 6.922 (95%) | 4 |
| 501 | 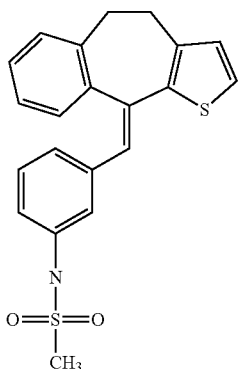 | APCI 382 (+) | ISO 80-20 A t = 5.438 (99%) | 4 |
| 502 | 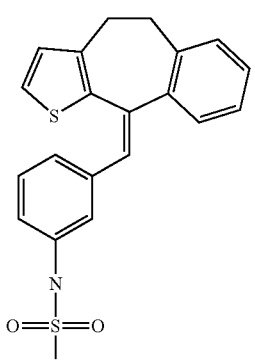 | APCI 382 (+) | ISO 80-20 A t = 5.430 (95%) | 4 |

-continued
| Example No. | Structure | MS Data | HPLC | Section |
|---|---|---|---|---|
| 503 | 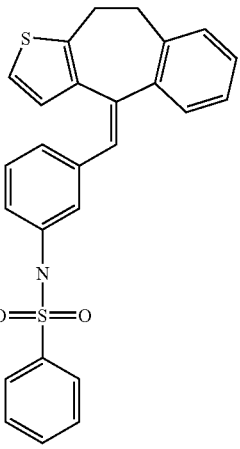 | APCI 444 (+) | ISO 80-20 A t = 6.682 (95%) | 4 |
| 504 | 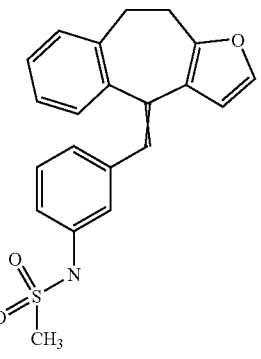 | APCI 366 (+) | GRAD 80-100M t = 3.038 (50%) t = 3.336 (50%) ISOMERICMIX | 4 |
| 505 | 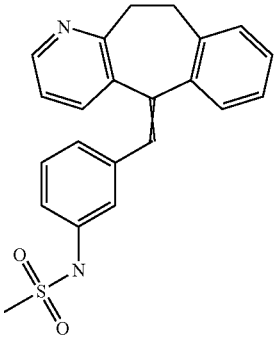 | 377.1 (APCI-pos) 375.0 (APCI-neg) | 95% | 4 |
| 506 | 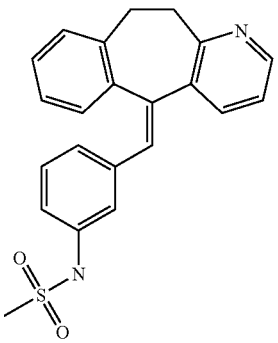 | 377.1 (APCI-pos) 375.0 (APCI-neg) | 95% | 4 |

-continued

| Example No. | Structure | MS Data | HPLC | Section |
|---|---|---|---|---|
| 507 | 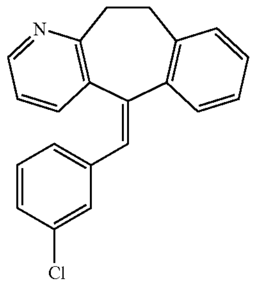 | 300.1 (APCI-pos) | 95% | 4 |
| 508 | 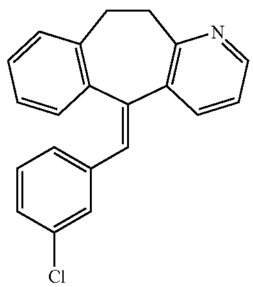 | 300.1 (APCI-pos) | 95% | 4 |
| 509 | 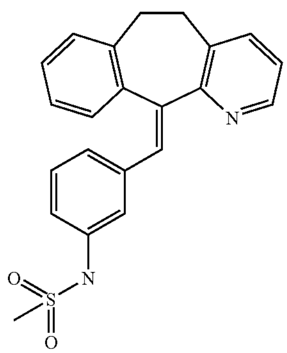 | 377.1 (APCI-pos)<br>375. (APCI-neg) | 98% | 4 |
| 510 | 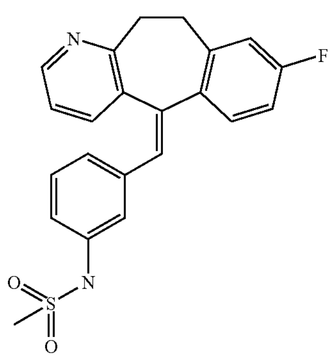 | 395.1 (APCI-pos)<br>393.0 (APCI-neg) | 99% | 4 |
| 511 | 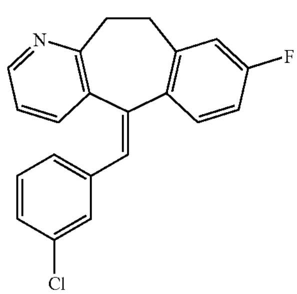 | 318.0 (APCI-pos) | 95% | 4 |

-continued
| Example No. | Structure | MS Data | HPLC | Section |
|---|---|---|---|---|
| 512 | 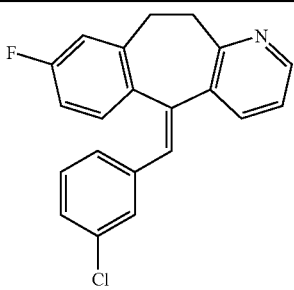 | 318.0 (APCI-pos) | 95% | 4 |
| 513 | 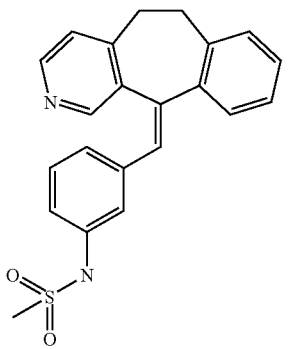 | 377.1 (APCI-pos)<br>375. (APCI-neg) | 96% | 4 |
| 514 | 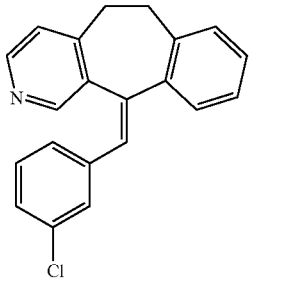 | 300.1 (APCI-pos) | 95% | 4 |
| 515 | 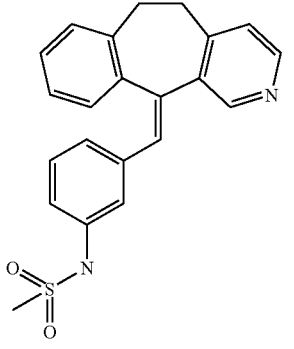 | 377.1 (APCI-pos)<br>375. (APCI-neg) | 85% | 4 |
| 516 | 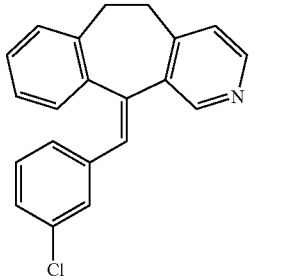 | 300.1 (APCI-pos) | 85% | 4 |

-continued
| Example No. | Structure | MS Data | HPLC | Section |
|---|---|---|---|---|
| 517 | 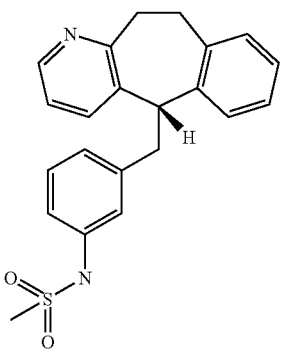 | 379.0 (APCI-pos) | 85% | 4 |
| 518 | 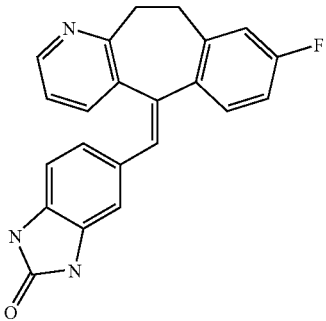 | 358.0 (APCI-pos)<br>356.0 (APCI-neg) | 98% | 4 |
| 519 | 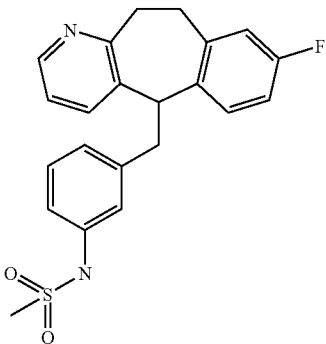 | 397.0 (APCI-pos) | 98% | 4 |
| 520 | 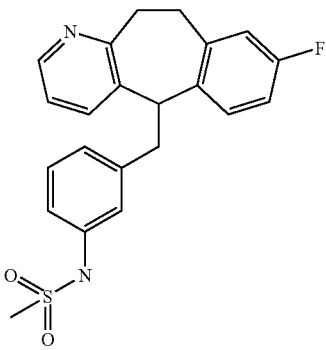 | 397.0 (APCI-pos) | 98% | 4 |

-continued
| Example No. | Structure | MS Data | HPLC | Section |
|---|---|---|---|---|
| 521 | 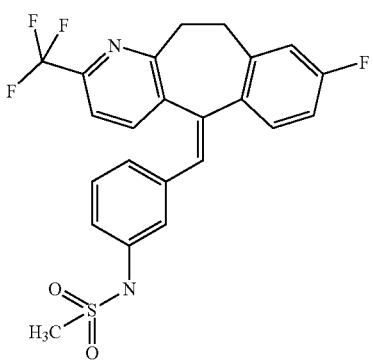 | 463.0 (APCI-pos)<br>461.0 (APCI-neg) | 98% | 4 |
| 522 | 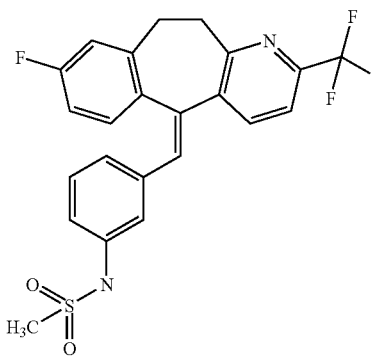 | 463.0 (APCI-pos)<br>461.0 (APCI-neg) | 95% | 4 |
| 524 | 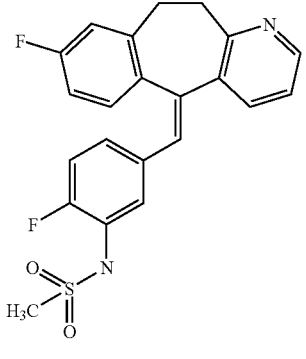 | 413.0 (APCI-pos)<br>411.0 (APCI-neg) | 95% | 4 |
| 525 | 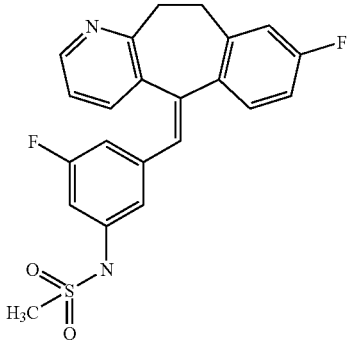 | 413.0 (APCI-pos)<br>411.0 (APCI-neg) | 98% | 4 |

-continued

| Example No. | Structure | MS Data | HPLC | Section |
|---|---|---|---|---|
| 526 | 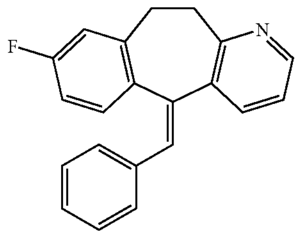 | 302.1 (APCI-pos) | 98% | 4 |
| 527 | 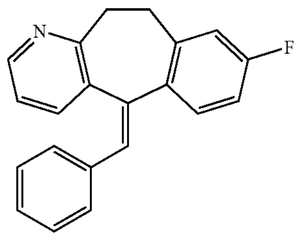 | 302.1 (APCI-pos) | 98% | 4 |
| 528 | 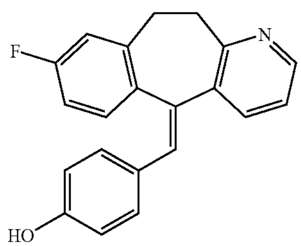 | 318.0 (APCI-pos)<br>316.0 (APCI-neg) | 98% | 4 |
| 529 | 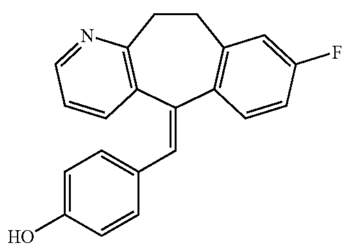 | 318.0 (APCI-pos)<br>316.0 (APCI-neg) | 98% | 4 |
| 530 | 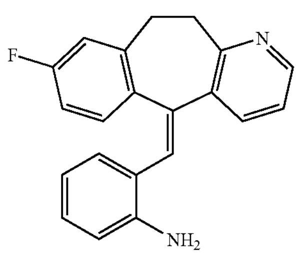 | 317.1 (APCI-pos) | 95% | 4 |
| 531 | 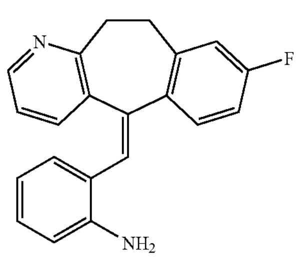 | 317.1 (APCI-pos) | 98% | 4 |

-continued

| Example No. | Structure | MS Data | HPLC | Section |
|---|---|---|---|---|
| 532 | 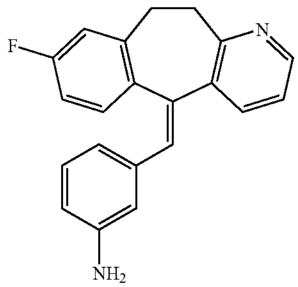 | 317.1 (APCI-pos) | 95% | 4 |
| 533 | 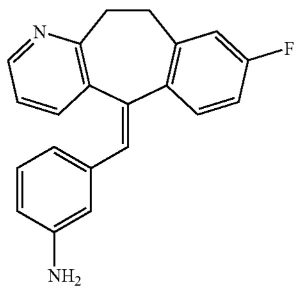 | 317.1 (APCI-pos) | 90% | 4 |
| 534 | 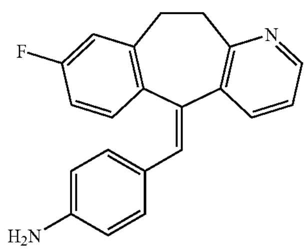 | 317.1 (APCI-pos) | 95% | 4 |
| 535 | 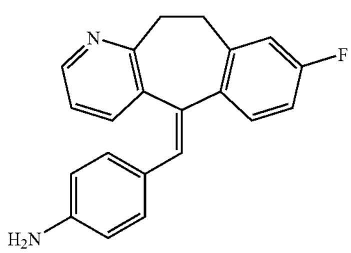 | 317.1 (APCI-pos) | 95% | 4 |
| 536 | 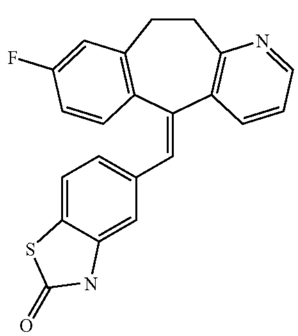 | 375.0 (APCI-pos)<br>373.0 (APCI-neg) | 95% | 4 |

-continued

| Example No. | Structure | MS Data | HPLC | Section |
|---|---|---|---|---|
| 537 | 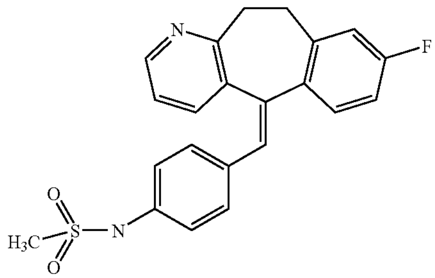 | 395.0 (APCI-pos) | 95% | 4 |
| 538 | 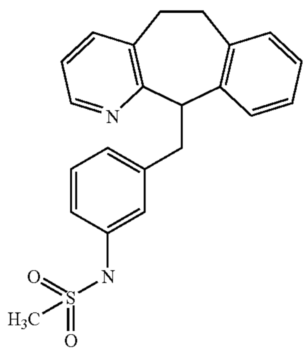 | 377.1 (APCI-pos) | 95% | 4 |
| 539 | 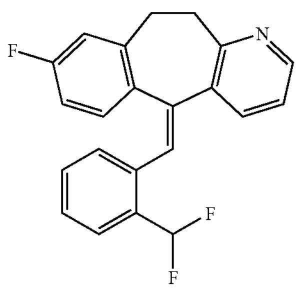 | 352.0 (APCI-pos) | 98% | 4 |
| 540 | 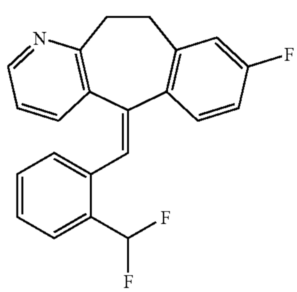 | 352.0 (APCI-pos) | 99% | 4 |
| 541 | 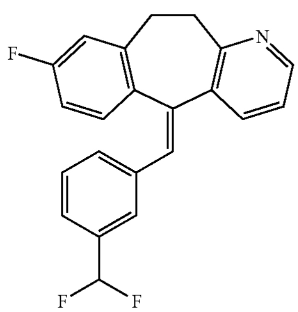 | 352.0 (APCI-pos) | 98% | 4 |

-continued

| Example No. | Structure | MS Data | HPLC | Section |
|---|---|---|---|---|
| 542 | 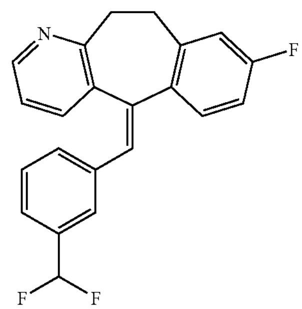 | 352.0 (APCI-pos) | 98% | 4 |
| 543 | 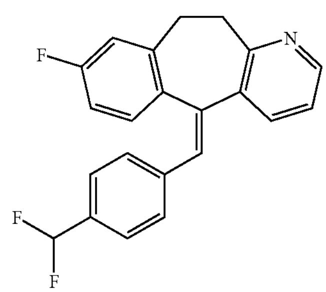 | 352.0 (APCI-pos) | 98% | 4 |
| 544 | 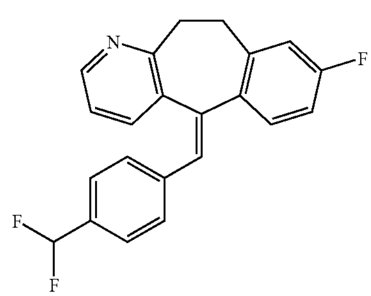 | 352.0 (APCI-pos) | 95% | 4 |
| 545 | 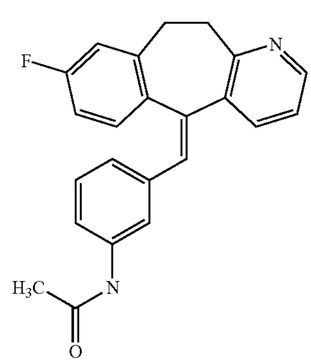 | 359.1 (APCI-pos) | 98% | 4 |

-continued
| Example No. | Structure | MS Data | HPLC | Section |
|---|---|---|---|---|
| 546 | 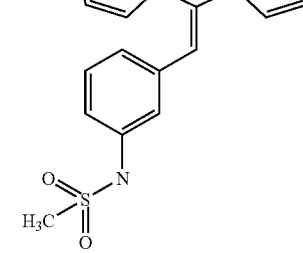 | 420.0 (APCI-pos)<br>417.9 (APCI-neg) | 99% | 4 |
| 547 | 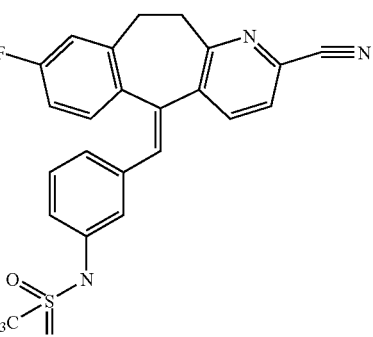 | 420.0 (APCI-pos) | 98% | 4 |
| 548 | 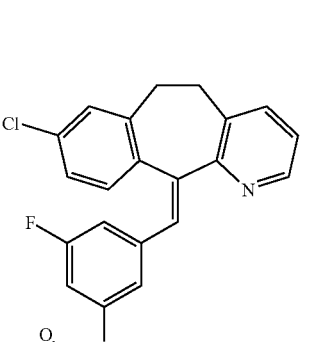 | ES 427 (−)/429 (+) | (ISO80-10) t = 2.66 (99%) | 4 |
| 549 | 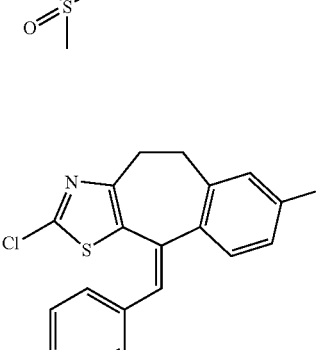 | ES 396 (−)/398 (+) | (ISO80-10) t = 2.49 (96%) | 4 |

-continued

| Example No. | Structure | MS Data | HPLC | Section |
|---|---|---|---|---|
| 550 | 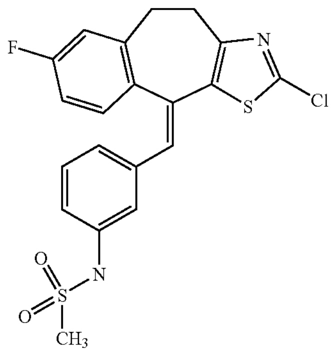 | ES 433 (−)/435 (+) | (ISO80-10) t = 3.75 (92%) | 4 |
| 551 | 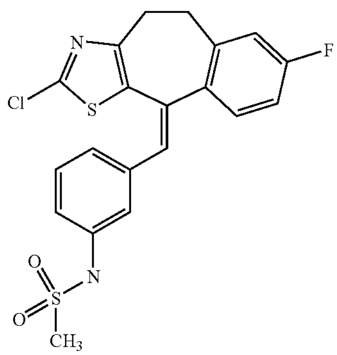 | ES 433 (−)/435 (+) | (ISO80-10) t = 3.48 (92%) | 4 |
| 552 | 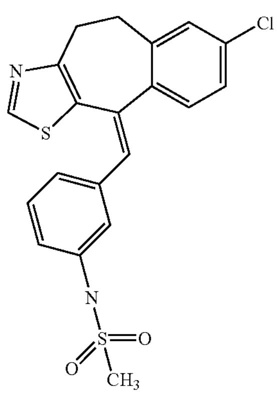 | APCI 417 (+) | (GRAD 80-100) t = 1.31 (96%) | 4 |
| 553 | 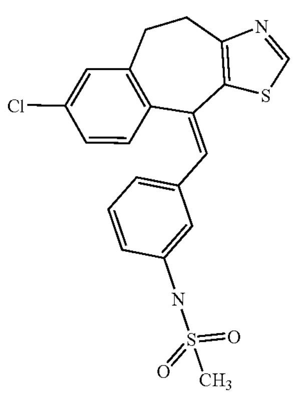 | ES 417 (+) | (GRAD 70-100) t = 2.10 (95%) | 4 |

-continued
| Example No. | Structure | MS Data | HPLC | Section |
|---|---|---|---|---|
| 554 | 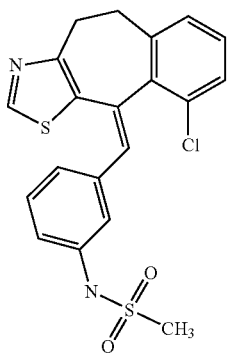 | ES 417 (+) | NA | 4 |
| 555 | 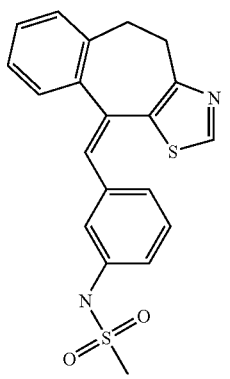 | ES 382 (−)/384 (+) | (ISO60-10M) t = 4.31 (98%) | 4 |
| 556 | 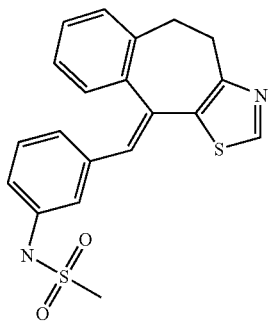 | ES 382 (−)/384 (+) | NA | 4 |
| 557 | 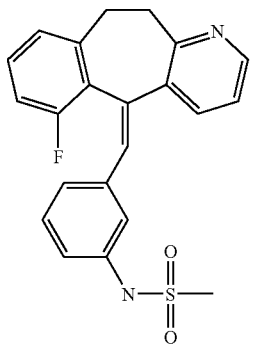 | ES 393 (−)/395 (+) | (ISO60-10M) t = 2.09 (98%) | 4 |

-continued

| Example No. | Structure | MS Data | HPLC | Section |
|---|---|---|---|---|
| 558 | 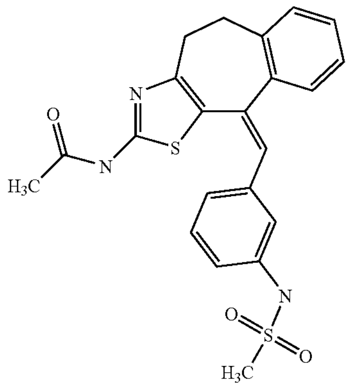 | ES 438 (−)/440 (+) | (ISO60-10M) t = 3.40 (98%) | 4 |
| 559 | 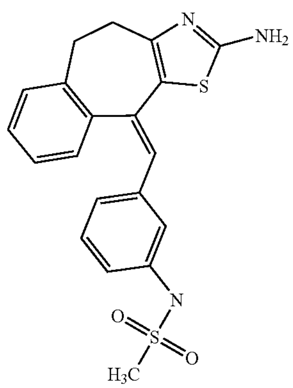 | ES 396 (−)/398 (+) | (ISO40-10M) t = 2.45 (92%) | 4 |
| 560 | 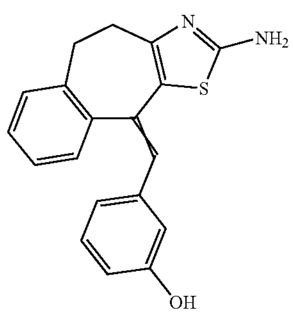 | ES 319 (−)/321 (+) | NA | 4 |
| 561 | 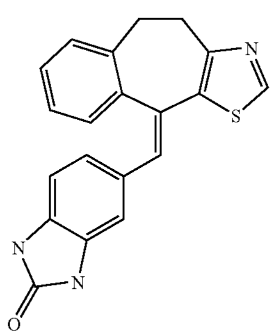 | ES 344 (−)/346 (+) | (ISO60-10M) t = 2.46 (94%) | 4 |

-continued

| Example No. | Structure | MS Data | HPLC | Section |
|---|---|---|---|---|
| 562 | 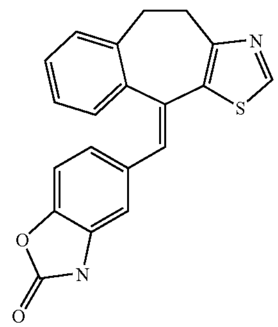 | ES 345 (−)/347 (+) | (ISO60-10M) t = 4.23 (88%) | 4 |
| 563 | 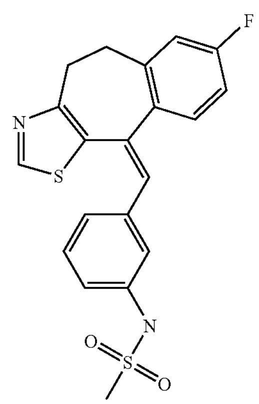 | ES 399 (−)/401 (+) | (ISO80-10M) t = 2.42 (100%) | 4 |
| 564 | 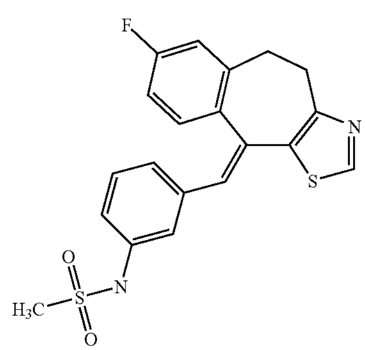 | ES 399 (−)/401 (+) | (ISO80-10M) t = 2.42 (91%) | 4 |
| 565 | 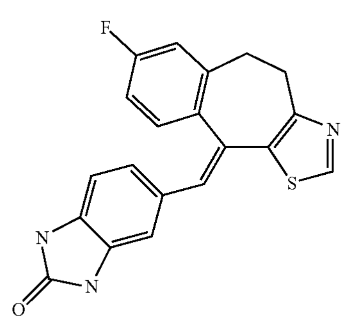 | ES 362 (−)/364 (+) | (ISO80-10M) t = 1.98 (94%) | 4 |

-continued

| Example No. | Structure | MS Data | HPLC | Section |
|---|---|---|---|---|
| 566 | 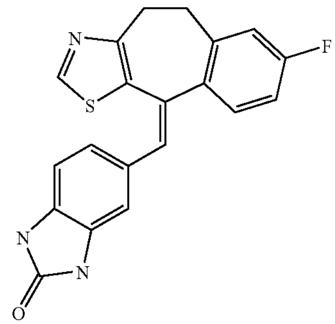 | ES 362 (−)/364 (+) | (ISO60-10M) t = 2.55 (97%) | 4 |
| 567 | 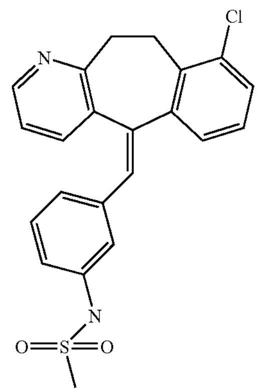 | APCI 411, 413 (+) | LCMS(ISO8O20M) t = 2.60 | 4 |
| 568 | 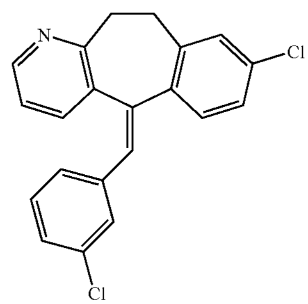 | APCI 334, 336 (+) | LCMS(ISO8O20M) t = 3.28 | 4 |
| 569 | 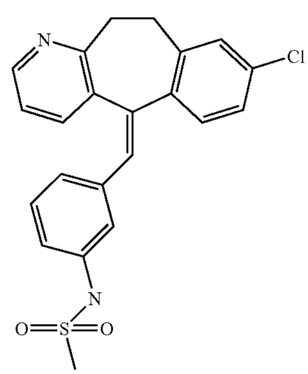 | APCI 411 ,413 (+)/ 409, 411 (−) | LCMS(ISO8020M) t = 2.56 | 4 |

-continued

| Example No. | Structure | MS Data | HPLC | Section |
|---|---|---|---|---|
| 570 | 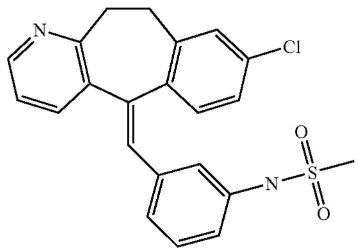 | ES 411, 413 (+)/409, 411 (−) | LCMS(ISO8020M) t = 1.94 | 4 |
| 571 | 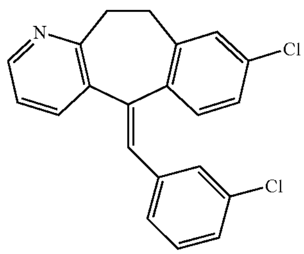 | ES 334, 336 (+)/332, 334 (−) | LCMS(ISO8020M) t = 2.40 | 4 |
| 572 | 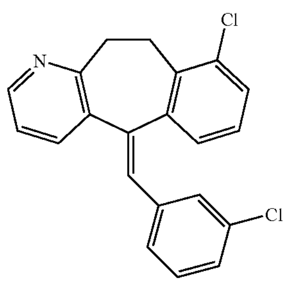 | ES 334, 336 (+)/332, 334 (−) | LCMS(ISO8020M) t = 2.91 | 4 |
| 573 | 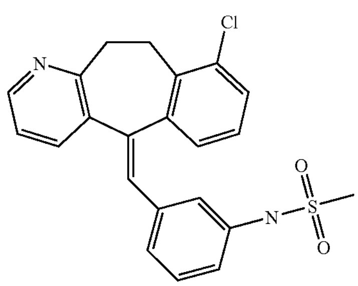 | ES 411, 413 (+)/409, 411 (−) | LCMS(ISO8020M) t = 2.05 | 4 |
| 574 | 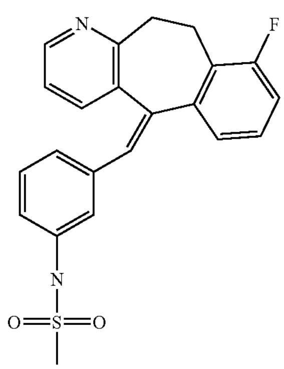 | APCI 395 (+) | LCMS(ISO7030M) t = 6.44 | 4 |

-continued
| Example No. | Structure | MS Data | HPLC | Section |
|---|---|---|---|---|
| 575 | 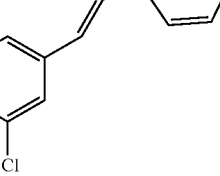 | APCI 318 (+) | LCMS(ISO7030M) t = 8.96 | 4 |
| 576 | 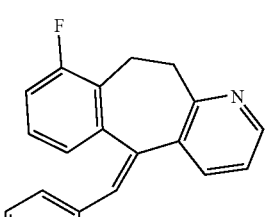 | APCI 395 (+) | LCMS(ISO7030M) t = 4.51 | 4 |
| 577 | 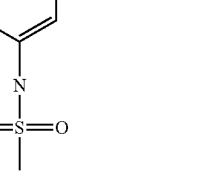 | APCI 318 (+) | LCMS(ISO7030M) t = 6.54 | 4 |
| 578 | 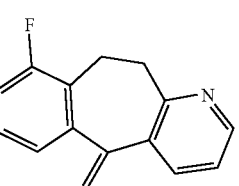 | APCI 320 (+) | LCMS(GRA80100M) t = 4.48 | 4 |
| 579 | 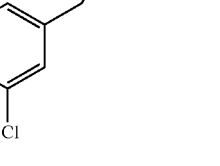 | APCI 320 (+) | LCMS(GRA80100M) t = 4.05 | 4 |

-continued

| Example No. | Structure | MS Data | HPLC | Section |
|---|---|---|---|---|
| 580 | 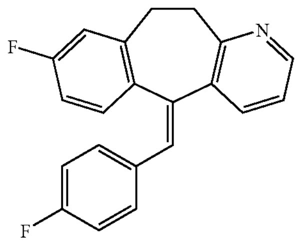 | APCI 320 (+) | LCMS(GRA80100M) t = 4.33 | 4 |
| 581 | 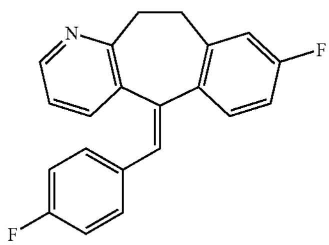 | APCI 320 (+) | LCMS(GRA80100) t = 4.32 | 4 |
| 582 | 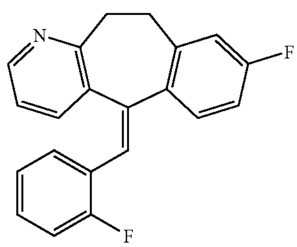 | APCI 320 (+) | LCMS(GRA80100) t = 4.58 | 4 |
| 583 | 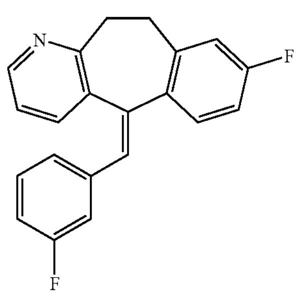 | APCI 320 (+) | LCMS(GRA80100M) t = 4.24 | 4 |
| 584 | 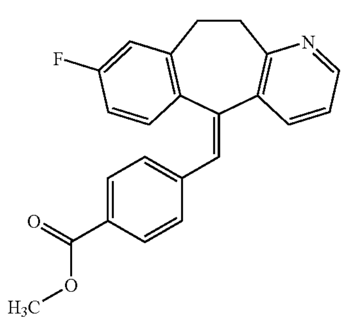 | APCI 360 (+) | LCMS(GRA80100M) t = 3.76 | 4 |

-continued

| Example No. | Structure | MS Data | HPLC | Section |
|---|---|---|---|---|
| 585 | 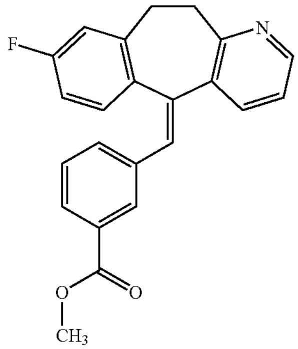 | APCI 360 (+) | LCMS(GRA80100) t = 3.54 | 4 |
| 586 | 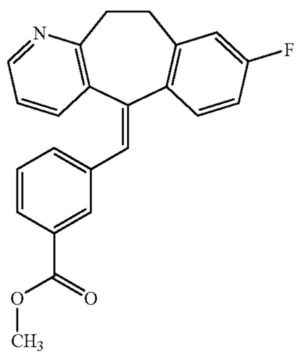 | APCI 360 (+) | LCMS(GRA80100M) t = 3.82 | 4 |
| 587 | 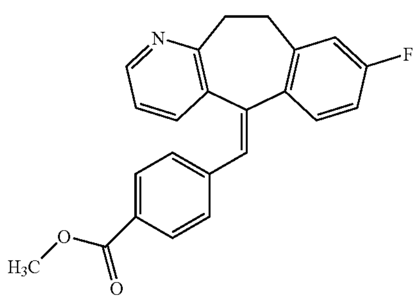 | APCI 360 (+) | LCMS(GRA80100M) t = 3.77 | 4 |
| 588 | 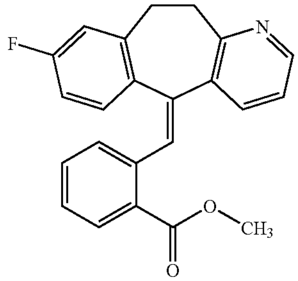 | APCI 360 (+) | LCMS(GRA80100M) t = 4.26 | 4 |

-continued

| Example No. | Structure | MS Data | HPLC | Section |
|---|---|---|---|---|
| 589 | 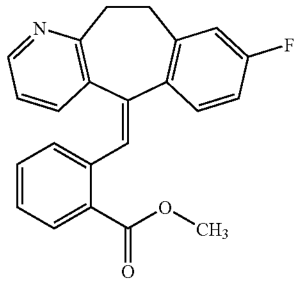 | APCI 360 (+) | LCMS(GRA80100M) t = 3.95 | 4 |
| 590 | 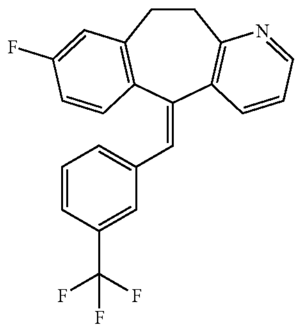 | APCI 370 (+) | LCMS(GRA80100M) t = 4.70 | 4 |
| 591 | 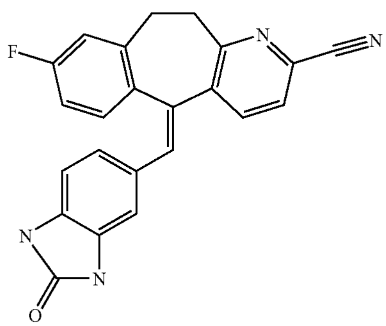 | APCI 383 (+)/381 (−) | LCMS(GRA80100M) t = 1.98 | 4 |
| 592 | 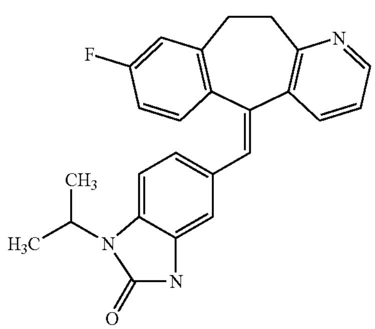 | APCI 400 (+)/398 (−) | LCMS(GRA80100M) t = 3.08 | 4 |

-continued

| Example No. | Structure | MS Data | HPLC | Section |
|---|---|---|---|---|
| 593 | 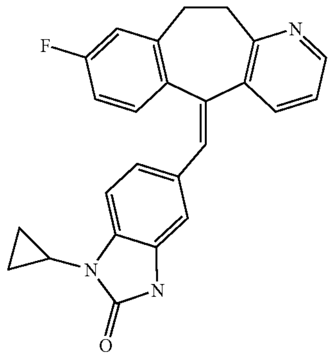 | APCI 398 (+)/396 (−) | LCMS(GRA80100M) t = 2.97 | 4 |
| 594 | 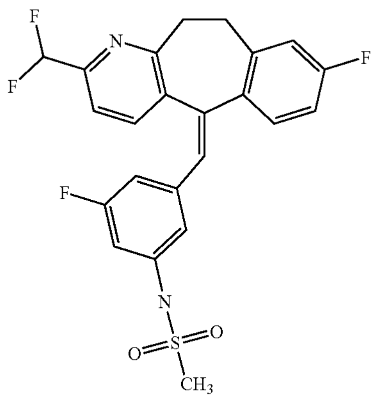 | APCI 461 (−) | LCMS(ISO7030M) t = 6.52 | 4 |
| 595 | 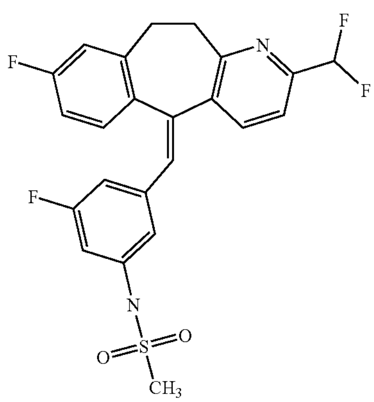 | APCI 463 (+)/461 (−) | LCMS(ISO7030M) t = 6.52 | 4 |
| 596 | 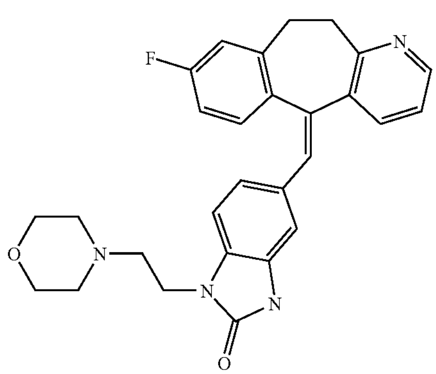 | APCI 471 (+)/469 (−) | LCMS(ISO8020M) t = 2.41 | 4 |

| Example No. | Structure | MS Data | HPLC | Section |
|---|---|---|---|---|
| 597 | 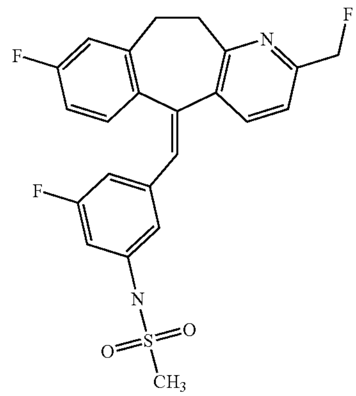 | APCI 445 (+)/443 (−) | LCMS(ISO7030M) t = 5.49 | 4 |
| 598 | 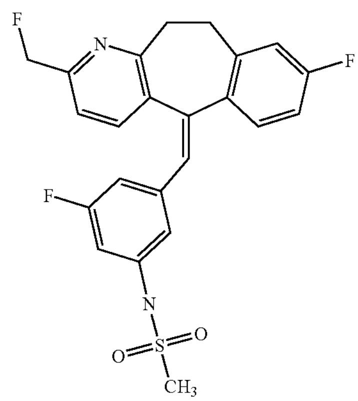 | APCI 445 (+)/443 (−) | LCMS(ISO7030M) t = 7.35 | 4 |
| 599 | 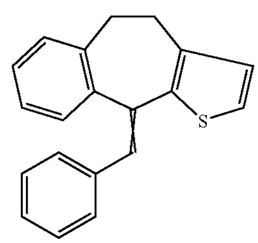 | EI 286 | GRAD60-280 17.84 (95%) | 4 |
| 600 | 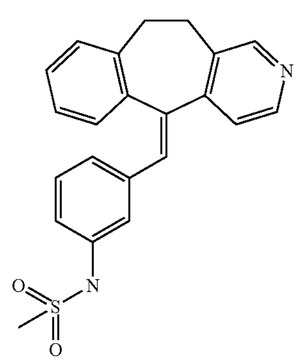 | APCI 377 (+) | 90% | 4 |

-continued

| Example No. | Structure | MS Data | HPLC | Section |
|---|---|---|---|---|
| 601 | 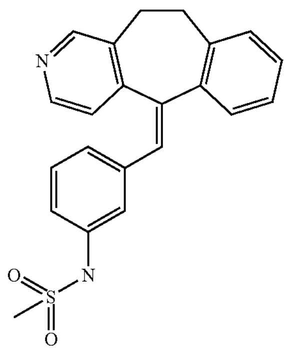 | APCI 377 (+) | 90% | 4 |
| 602 | 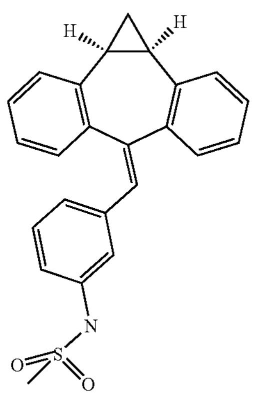 | ES 386(−)/388 (+) | LCMS(ISO8020M) t = 3.04 | 5 |
| 603 | 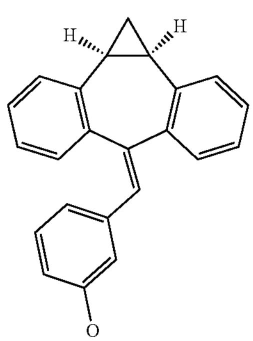 | ES 311 (+) | LCMS(ISO8020M) t = 3.79 | 5 |
| 604 | 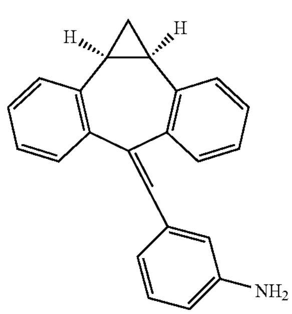 | APCI 310 (+) | LCMS(GRA80100M) t = 3.60 | 5 |

| Example No. | Structure | MS Data | HPLC | Section |
|---|---|---|---|---|
| 605 | 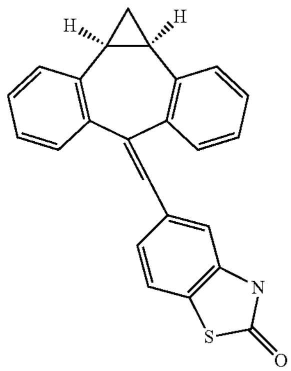 | APCI 368 (+) | LCMS(GRA80100M) t = 4.96 | 5 |
| 606 | 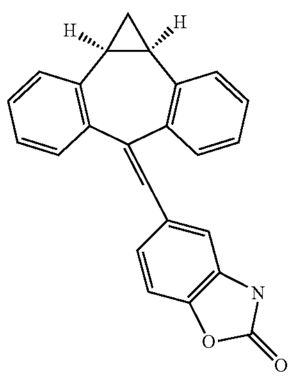 | APCI 352 (+) | LCMS(GRA80100M) t = 4.28 | 5 |
| 607 | 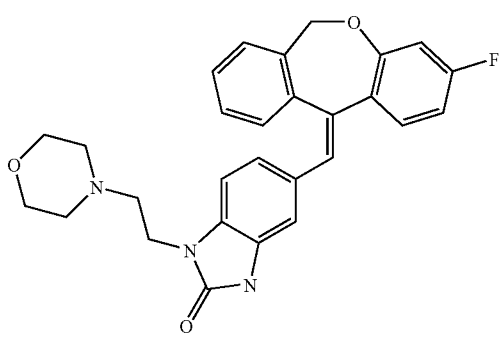 | ES 471 (−)/473 (+) | (ISO80-10M) t = 1.79 (98%) | 6 |
| 608 | 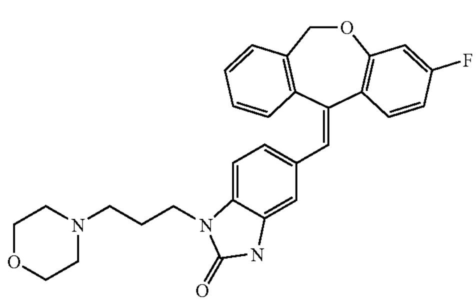 | ES 484 (−)/486 (+) | (ISO80-10M) t = 1.72 (100%) | 6 |

-continued

| Example No. | Structure | MS Data | HPLC | Section |
|---|---|---|---|---|
| 609 | 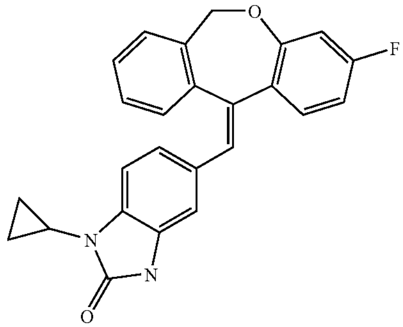 | ES 397 (−)/399 (+) | (ISO80-10M) t = 3.68 (93%) | 6 |
| 611 | 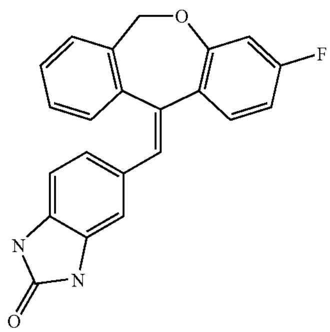 | ES 357 (−) | (ISO60-10) t = 3.94 (93%) | 6 |
| 612 | 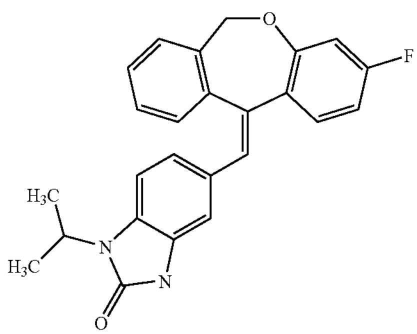 | ES 399 (−)/401 (+) | (ISO80-10) t = 3.74 (96%) | 6 |
| 613 | 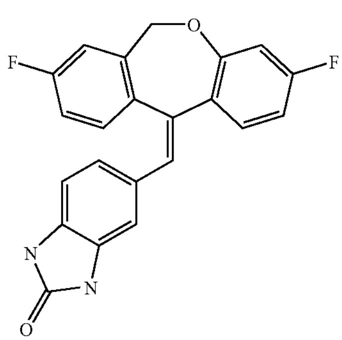 | ES 375 (−) | (ISO80-10) t = 2.38 (98%) | 6 |

-continued

| Example No. | Structure | MS Data | HPLC | Section |
|---|---|---|---|---|
| 614 | 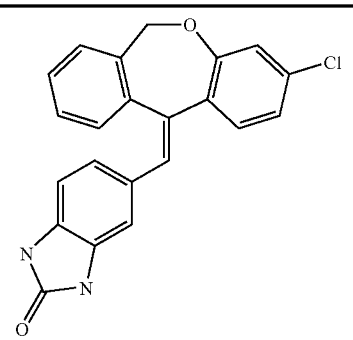 | ES 373 (−) | (ISO80-10) t = 2.85 (99%) | 6 |
| 617 | 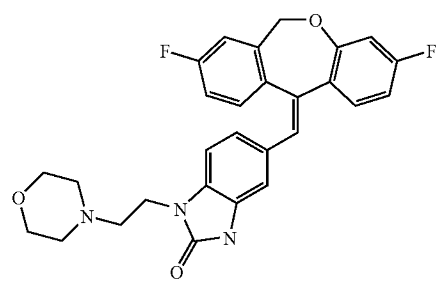 | ES 488 (−)/490 (+) | (ISO80-10) t = 1.86 (99%) | 6 |
| 618 | 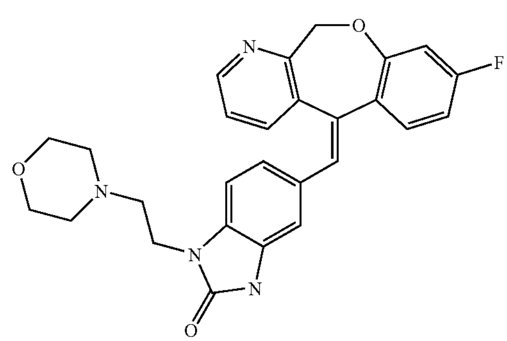 | 473.1 (APCI-pos) | 95% | 6 |
| 619 | 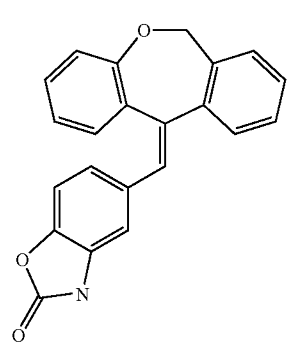 | ES 340 (−)/342 (+) | (ISO80-10) t = 2.98 (95%) | 6 |

-continued
| Example No. | Structure | MS Data | HPLC | Section |
|---|---|---|---|---|
| 620 | 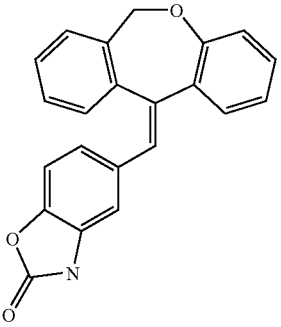 | ES 340 (−)/342 (+) | (ISO80-10) t = 2.96 (92%) | 6 |
| 621 | 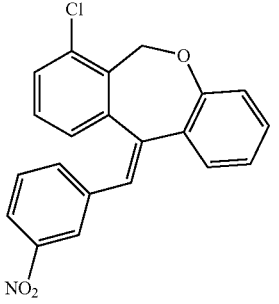 | NMR | NA | 6 |
| 622 | 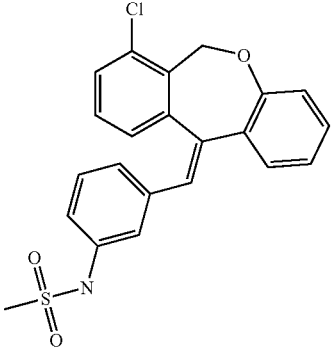 | ES 410 (−) | NA | 6 |
| 623 | 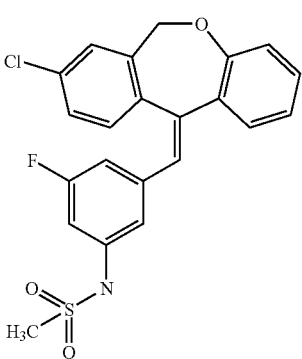 | 430.0 (APCI-pos) 427.9, 428.9, 429.9 (APCI-neg) | 95% | 6 |

-continued
| Example No. | Structure | MS Data | HPLC | Section |
|---|---|---|---|---|
| 624 | 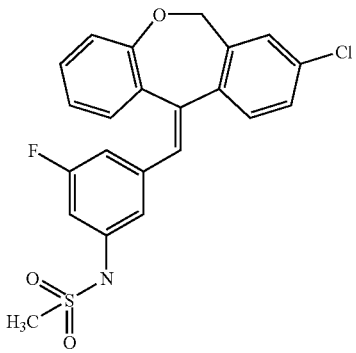 | 430.0 (APCI-pos) 427.9, 428.9, 429.9 (APCI-neg) | 95% | 6 |
| 625 | 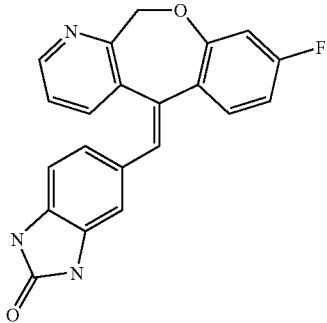 | 360.0 (APCI-pos) | 99% | 6 |
| 626 | 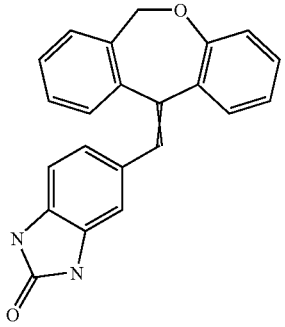 | ES 339 (−) | (ISO80-10) t = 2.21 (96%) | 6 |
| 627 | 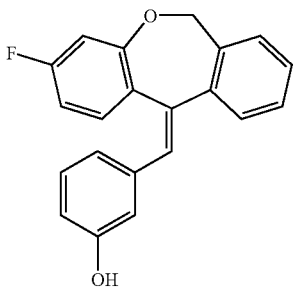 | ES 317 (−)/319 (+) | (ISO80-10) t = 3.33 (96%) | 6 |

-continued

| Example No. | Structure | MS Data | HPLC | Section |
|---|---|---|---|---|
| 628 | 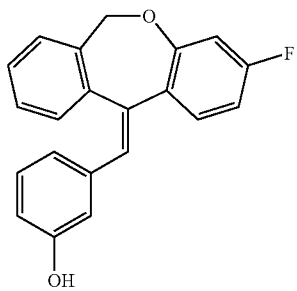 | ES 317 (−)/319 (+) | (ISO80-10) t = 3.21 (96%) | 6 |
| 629 | 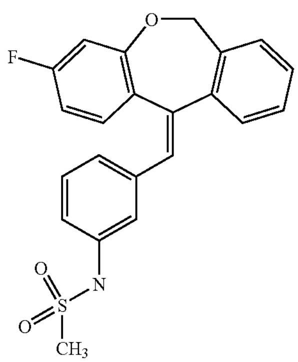 | ES 394 (−)/396 (+) | (ISO80-10) t = 8.44 (90%) | 6 |
| 630 | 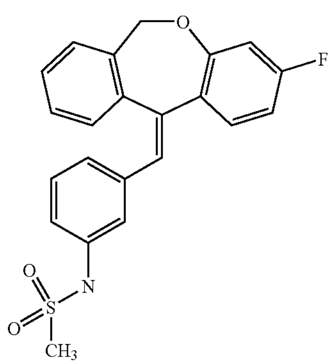 | ES 394 (−)/396 (+) | (ISO60-10) t = 8.06 (97%) | 6 |
| 631 | 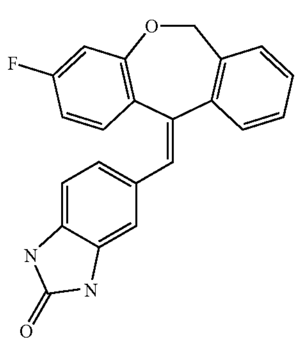 | ES 357 (−) | (ISO60-10) t = 4.30 (95%) | 6 |

-continued
| Example No. | Structure | MS Data | HPLC | Section |
|---|---|---|---|---|
| 632 | 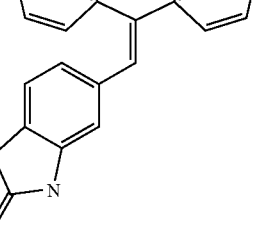 | ES 358 (−)/360 (+) | (ISO80-10) t = 3.11 (90%) | 6 |
| 633 | 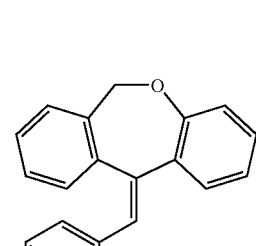 | ES 358 (−) | (ISO80-10) t = 3.04 (92%) | 6 |
| 634 | 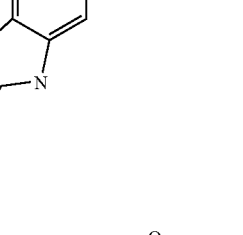 | ES 371 (−)/373 (+) | (ISO80-10) t = 3.11 (92%) | 6 |
| 635 | 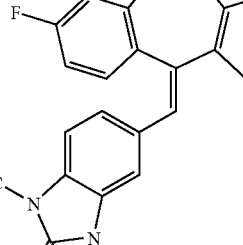 | ES 371 (−)/373 (+) | (ISO80-10) t = 3.00 (92%) | 6 |

-continued

| Example No. | Structure | MS Data | HPLC | Section |
|---|---|---|---|---|
| 636 | 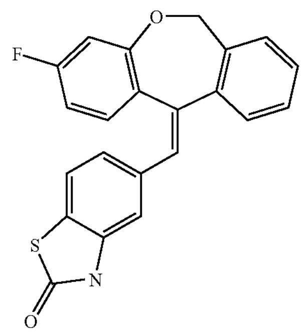 | ES 374 (−) | (ISO80-10) t = 3.91 (97%) | 6 |
| 637 | 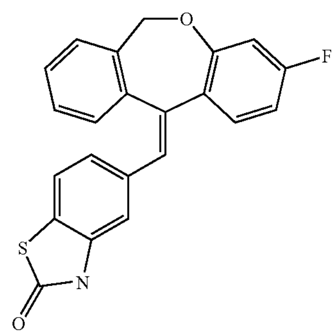 | ES 374 (−) | (ISO80-10) t = 3.65 (93%) | 6 |
| 638 | 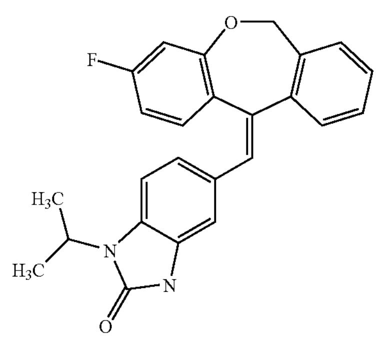 | ES 399 (−)/401 (+) | (ISO80-10) t = 3.91 (94%) | 6 |
| 639 | 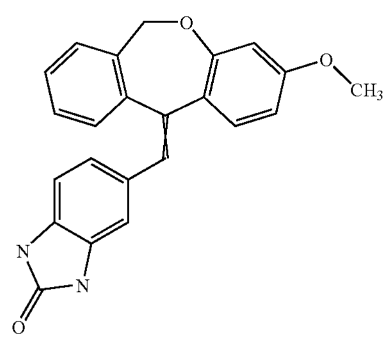 | ES 369 (−) | (ISO70-10) t = 2.15 (75%), 2.25 (15%) | 6 |

-continued

| Example No. | Structure | MS Data | HPLC | Section |
|---|---|---|---|---|
| 640 | 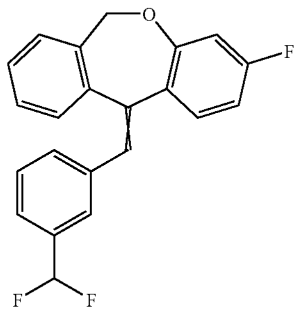 | EI 352 | (ISO80-10) t = 5.64 (100%) | 6 |
| 641 | 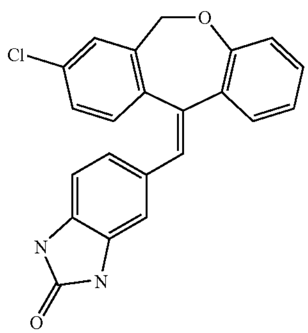 | ES 373 (−) | (ISO80-10) t = 2.68 (99%) | 6 |
| 642 | 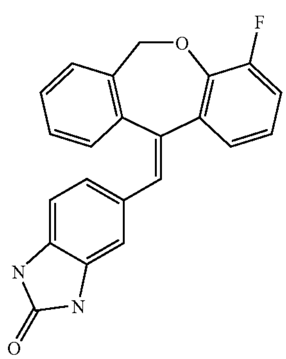 | ES 357 (−) | (ISO80-10) t = 2.15 (99%) | 6 |
| 643 | 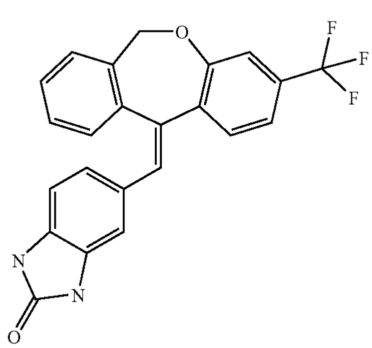 | ES 407 (−) | (ISO80-10) t = 2.82 (99%) | 6 |

-continued

| Example No. | Structure | MS Data | HPLC | Section |
|---|---|---|---|---|
| 644 | 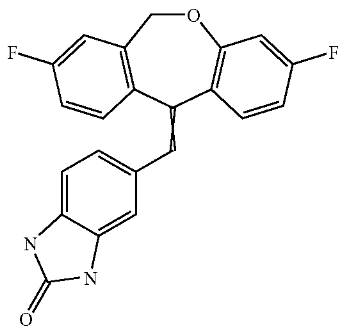 | ES 375 (−) | (ISO80-10) t = 2.36 (96%) | 6 |
| 645 | 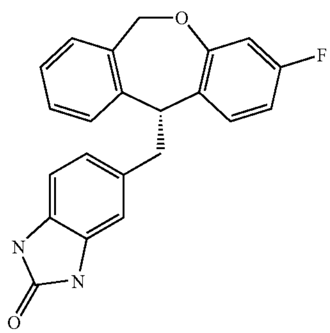 | ES 359 (−) | (ISO60-10) t = 3.71 (100%) | 6 |
| 646 | 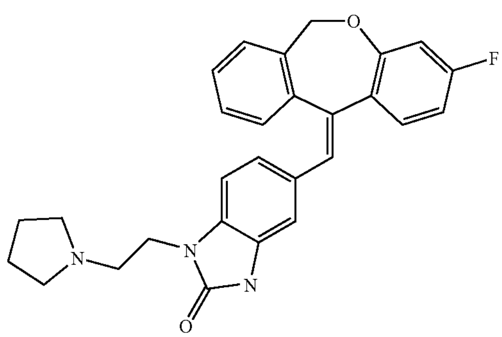 | ES 454 (−)/456 (+) | (ISO80-10) t = 1.75 (98%) | 6 |
| 647 | 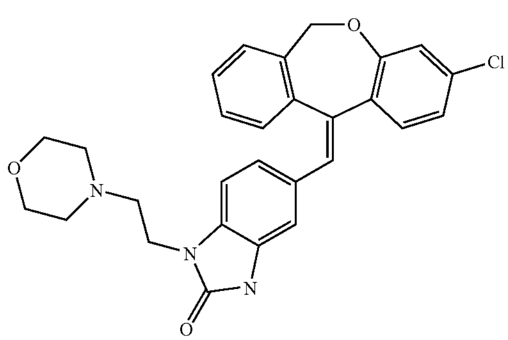 | ES 486 (−)/488 (+) | (ISO80-10) t = 2.07 (95%) | 6 |

-continued

| Example No. | Structure | MS Data | HPLC | Section |
|---|---|---|---|---|
| 648 | 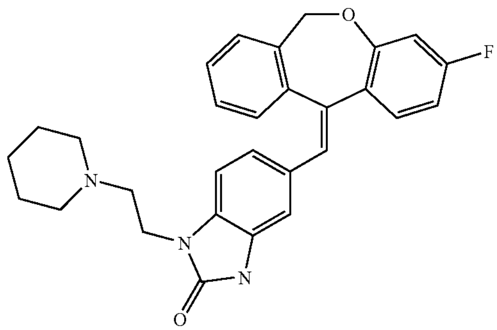 | ES 470 (+) | (ISO80-10) t = 1.80 (96%) | 6 |
| 649 | 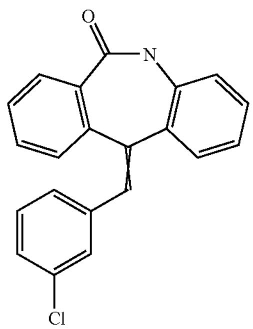 | ES 313.9 (+) | NA | 6 |
| 650 | 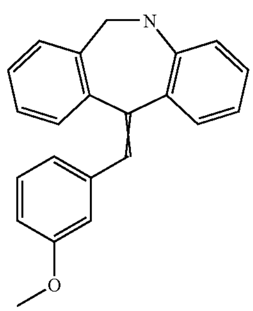 | ES 314.0 (+) | NA | 6 |
| 651 | 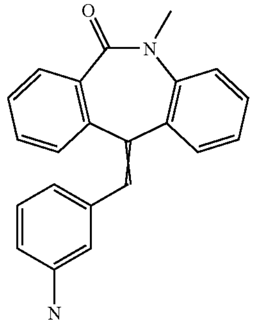 | ES 327.0 (+) | NA | 6 |

-continued

| Example No. | Structure | MS Data | HPLC | Section |
|---|---|---|---|---|
| 652 | 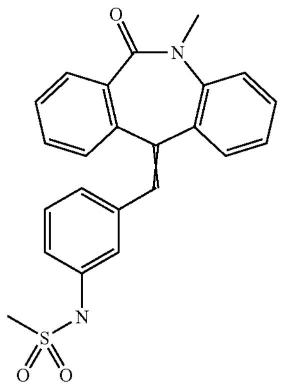 | ES 405.0 (+) | NA | 6 |
| 653 | 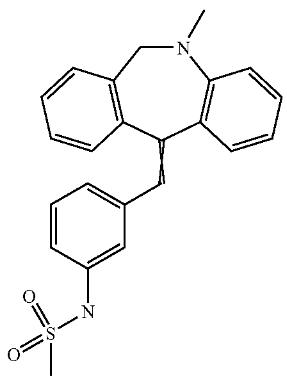 | ES 391.0 (+) | NA | 6 |
| 654 | 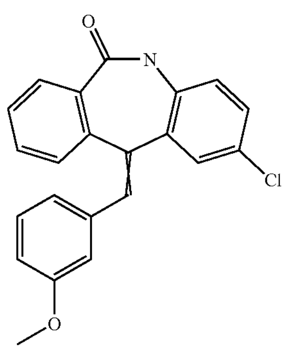 | ES 361.0 (+) | NA | 6 |
| 655 | 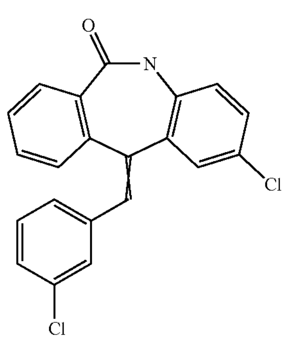 | ES 347.9 (+) | NA | 6 |

-continued

| Example No. | Structure | MS Data | HPLC | Section |
|---|---|---|---|---|
| 656 | 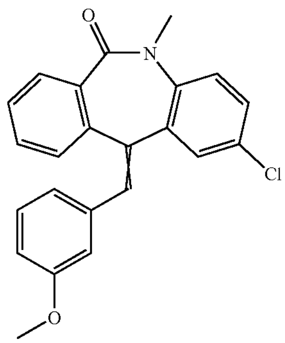 | ES 375.9 (+) | NA | 6 |
| 657 | 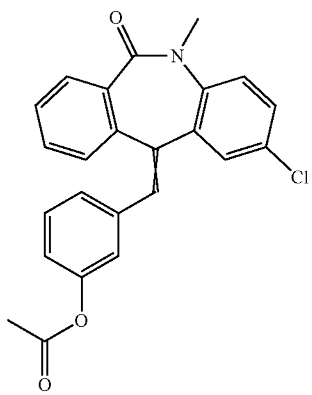 | ES 389.9 (+) | NA | 6 |
| 658 | 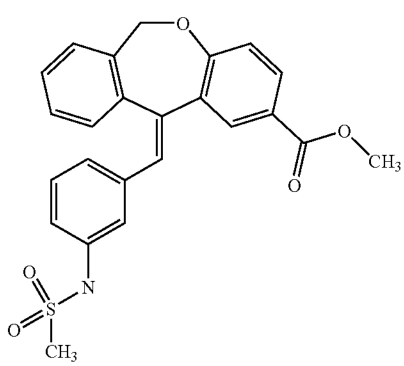 | NMR | NA | 6 |
| 659 | 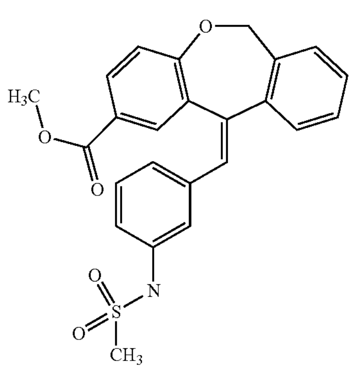 | NMR | NA | 6 |

| Example No. | Structure | MS Data | HPLC | Section |
|---|---|---|---|---|
| 660 | 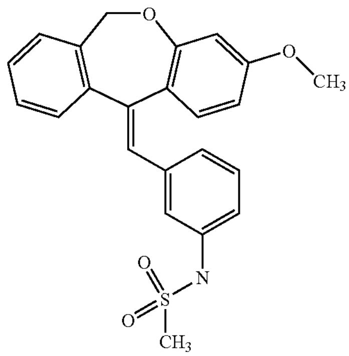 | ES 406.1 (+) | NA | 6 |
| 661 | 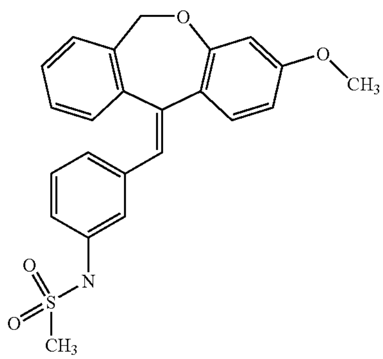 | ES 406.1 (+) | NA | 6 |
| 662 | 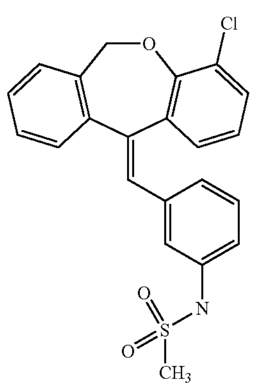 | ES 410.0 (+) | NA | 6 |
| 663 | 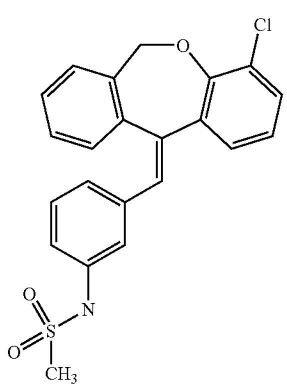 | ES 410.0 (+) | NA | 6 |

-continued

| Example No. | Structure | MS Data | HPLC | Section |
|---|---|---|---|---|
| 664 | 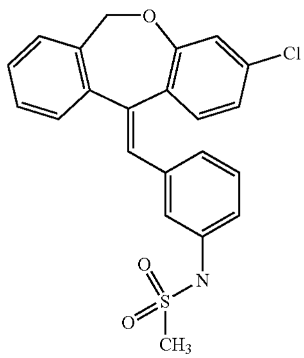 | ES 410.0 (+) | NA | 6 |
| 665 | 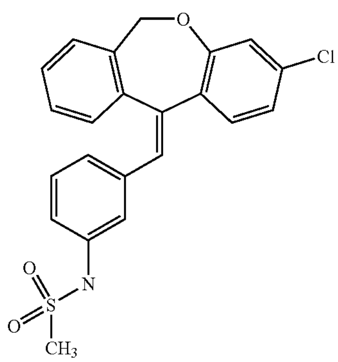 | NA | >95% (254 nM) | 6 |
| 666 | 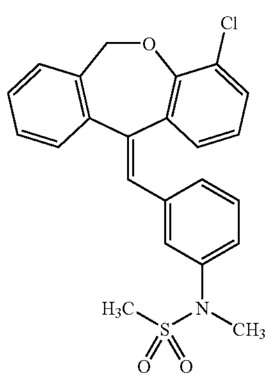 | NA | >99% (254 nM) | 6 |
| 667 | 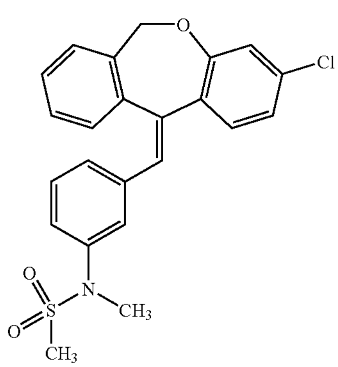 | ES 424 (−) | NA | 6 |

-continued

| Example No. | Structure | MS Data | HPLC | Section |
|---|---|---|---|---|
| 668 | 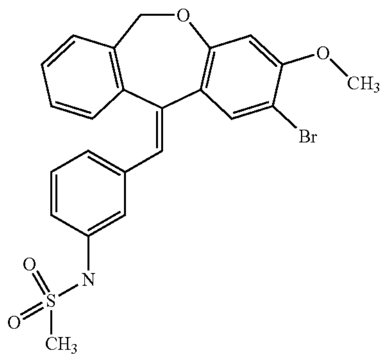 | ES 486 (+) | NA | 6 |
| 669 | 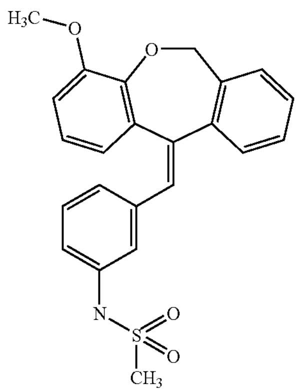 | NMR | NA | 6 |
| 670 | 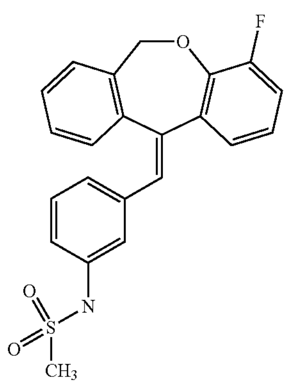 | NMR | NA | 6 |
| 671 | 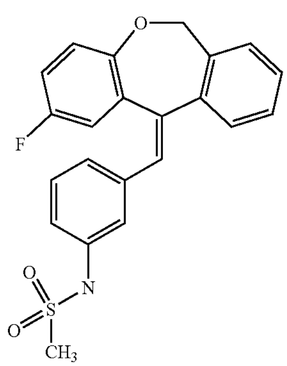 | NMR | NA | 6 |

-continued

| Example No. | Structure | MS Data | HPLC | Section |
|---|---|---|---|---|
| 672 | 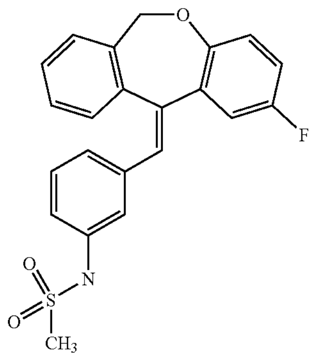 | NMR | NA | 6 |
| 673 | 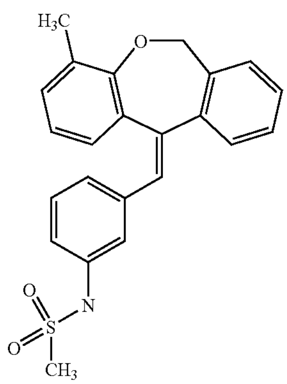 | ES 390.1 (−) | NA | 6 |
| 674 | 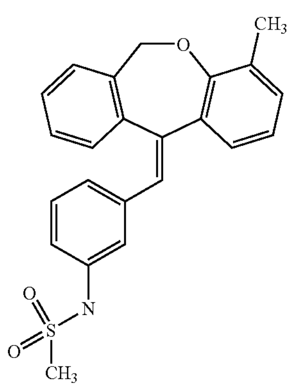 | NMR | NA | 6 |
| 675 | 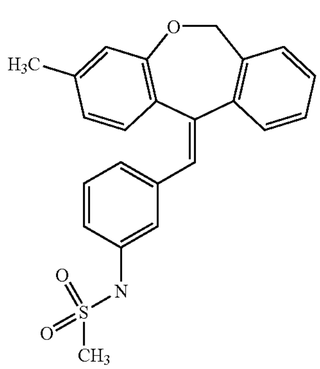 | NMR | NA | 6 |

-continued
| Example No. | Structure | MS Data | HPLC | Section |
|---|---|---|---|---|
| 676 | 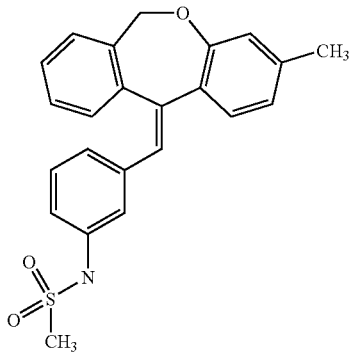 | NMR | NA | 6 |
| 677 | 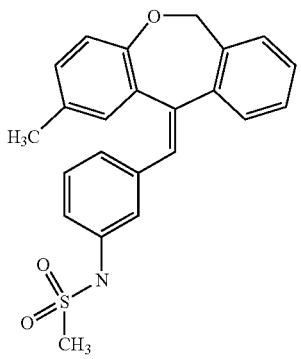 | ES 390.1 (−) | NA | 6 |
| 678 | 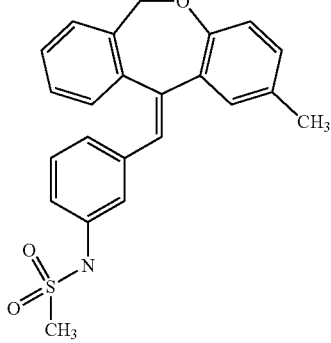 | NMR | NA | 6 |
| 679 | 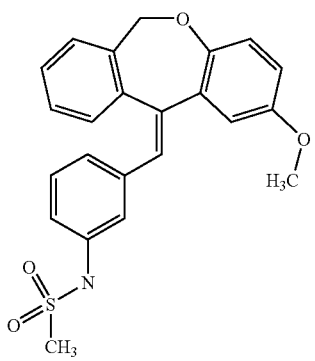 | ES 406.5 (−) | NA | 6 |

| Example No. | Structure | MS Data | HPLC | Section |
|---|---|---|---|---|
| 680 | 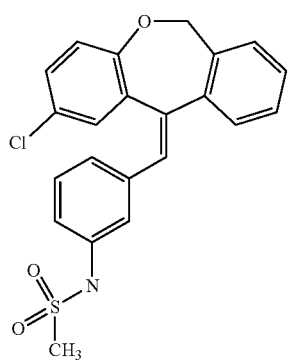 | NMR | NA | 6 |
| 681 | 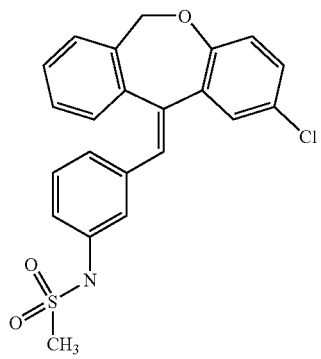 | NMR | NA | 6 |
| 682 | 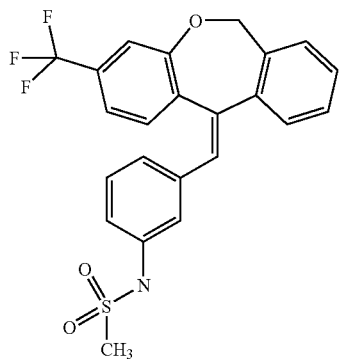 | ES 444.1 (−) | NA | 6 |
| 683 | 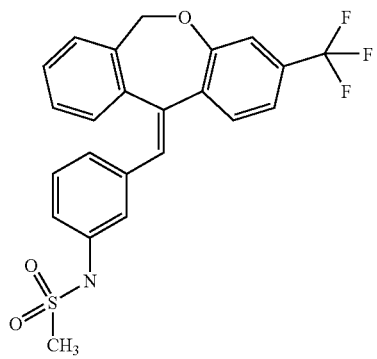 | ES 444.1 (−) | NA | 6 |

-continued

| Example No. | Structure | MS Data | HPLC | Section |
|---|---|---|---|---|
| 684 | 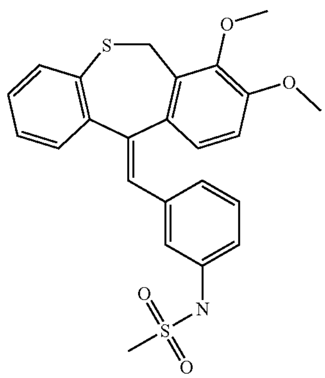 | Cl = 453.93 | t = 3.24 min (100%) | 6 |
| 685 | 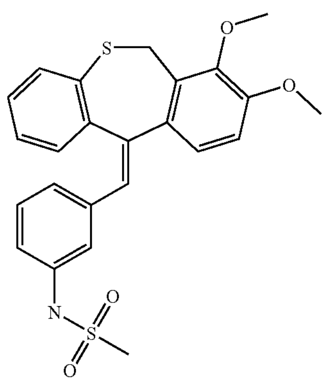 | Cl = 454 | t = 3.18 min (100%) | 6 |
| 686 | 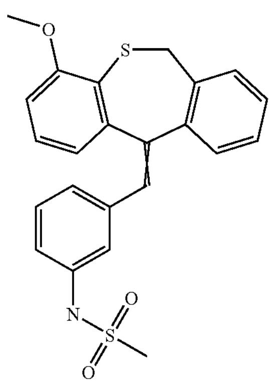 | Cl = 424 | t = 2.24 min (64%)<br>t = 2.29 min (34%) | 6 |
| 687 | 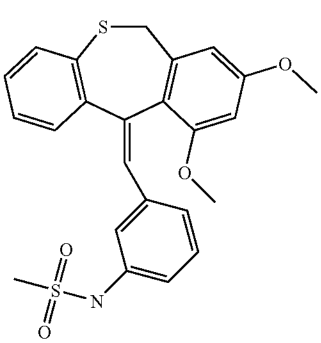 | Cl = 454 | t = 3.18 min (100%) | 6 |

-continued

| Example No. | Structure | MS Data | HPLC | Section |
|---|---|---|---|---|
| 688 | 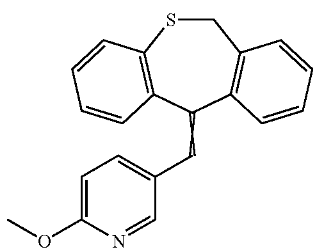 | ES 332 (+) | t = 2.66 min (99%) | 6 |
| 689 | 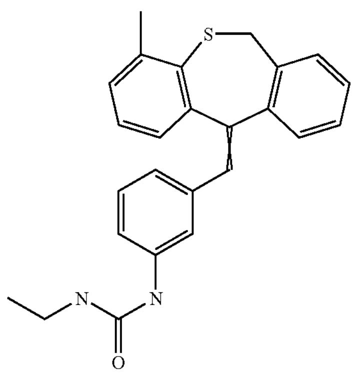 | APCI = 401 | t = 3.88 min (92%) | 6 |
| 690 | 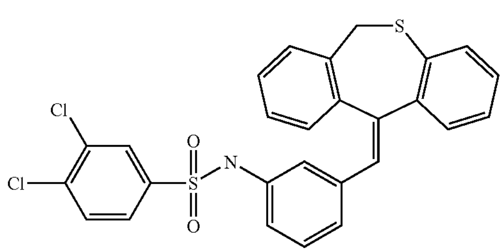 | ES 522 (+) | t = 3.93 min (98%) | 6 |
| 691 | 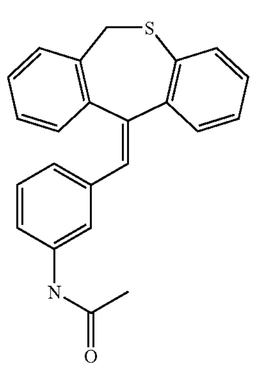 | ES 356 (−) | t = 3.3 min (100) | 6 |

-continued
| Example No. | Structure | MS Data | HPLC | Section |
|---|---|---|---|---|
| 692 | 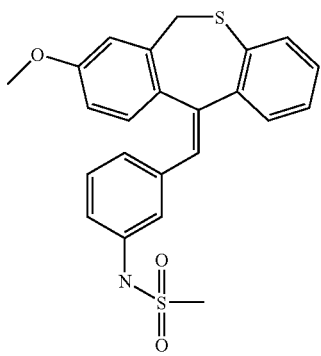 | APCI = 424 | t = 3.29 min (100%) | 6 |
| 693 | 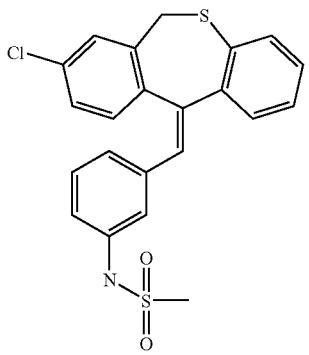 | APCI = 410 | t = 2.97 min (100%) | 6 |
| 694 | 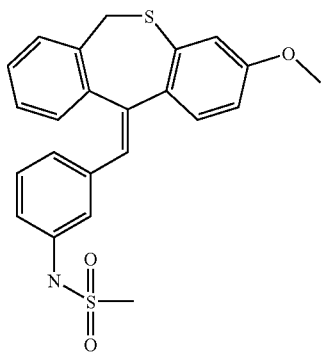 | APCI = 424 | t = 3.25 min (100%) | 6 |
| 695 | 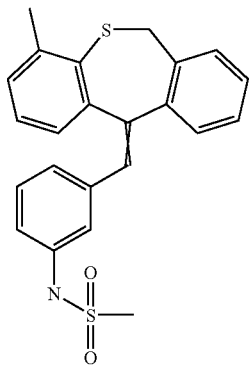 | APCI = 408 | t = 5.64 min (24%)<br>t = 5.87 min (76%) | 6 |

-continued

| Example No. | Structure | MS Data | HPLC | Section |
|---|---|---|---|---|
| 696 | 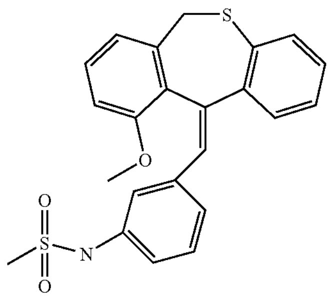 | APCI = 424 | t = 3.12 min (100%) | 6 |
| 697 | 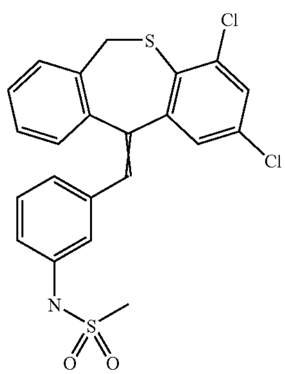 | APCI = 462 | t = 4.3 min | 6 |
| 698 | 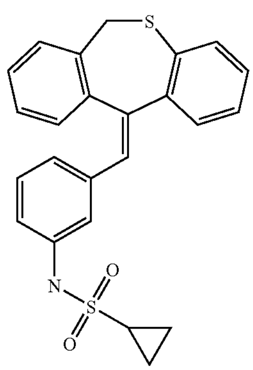 | ES 418 (−) | t = 3.36 min (100%) | 6 |
| 699 | 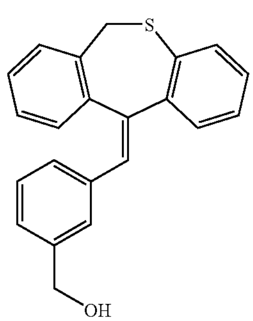 | APCI 313 | t = 3.66 min (100%) | 6 |

-continued

| Example No. | Structure | MS Data | HPLC | Section |
|---|---|---|---|---|
| 700 | 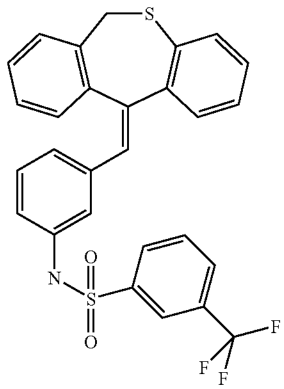 | ES 522 (−) | t = 3.75 min (97%) | 6 |
| 701 | 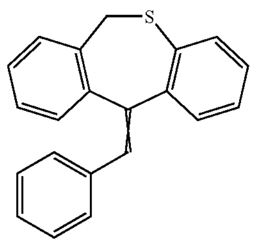 | APCI 301 | t = 4.43 min | 6 |
| 702 | 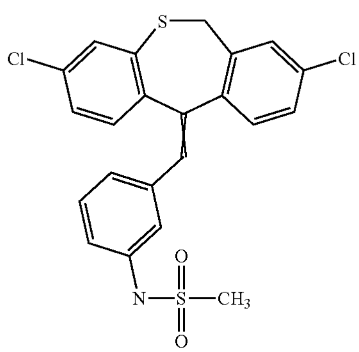 | APCI = 464 | t = 3.69 min (98%) | 6 |
| 703 | 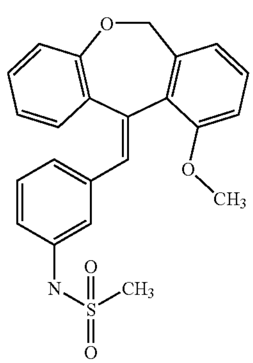 | ES 407 (+) | t = 4.42 min (100%) | 6 |

-continued

| Example No. | Structure | MS Data | HPLC | Section |
|---|---|---|---|---|
| 704 | 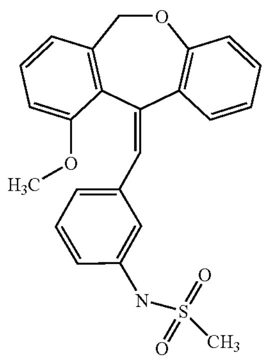 | ES 407 (+) | t = 4.39 min (100%) | 6 |
| 705 | 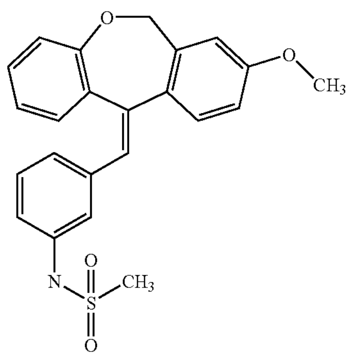 | ES 407 (+) | t = 4.47 min (100%) | 6 |
| 706 | 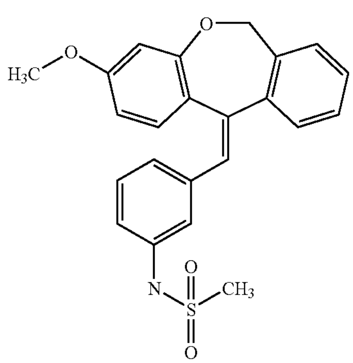 | ES 407 (+) | t = 4.53 min (100%) | 6 |
| 707 | 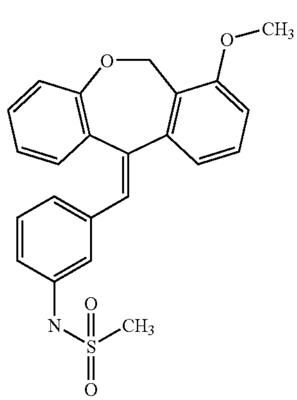 | ES 407 (+) | t = 4.61 min (100%) | 6 |

-continued
| Example No. | Structure | MS Data | HPLC | Section |
|---|---|---|---|---|
| 708 | 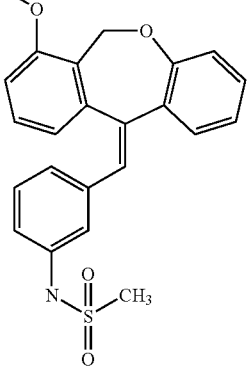 | ES 407 (+) | t = 4.61 min (100%) | 6 |
| 709 | 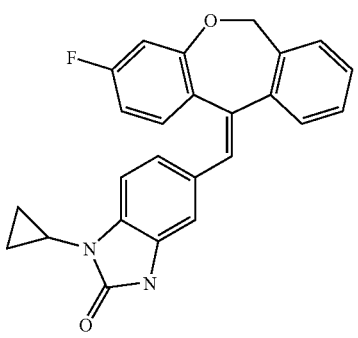 | ES 397 (−)/399 (+) | (ISO80-10M) t = 3.53 (93%) | 6 |
| 710 | 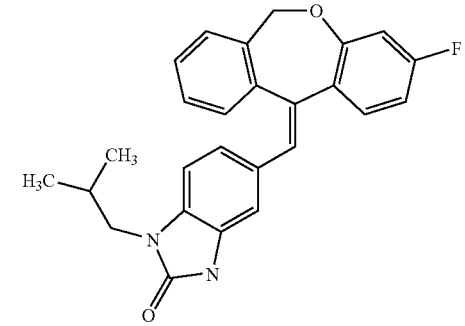 | ES 413 (−)/415 (+) | (ISO80-10M) t = 4.59 (95%) | 6 |
| 711 | 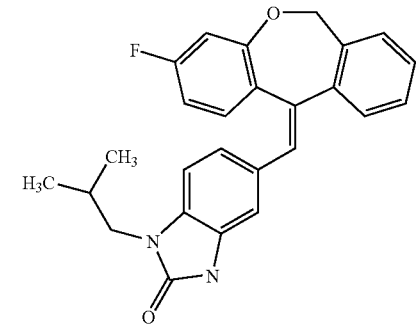 | ES 413 (−)/415 (+) | (ISO80-10M) t = 4.82 (95%) | 6 |

-continued

| Example No. | Structure | MS Data | HPLC | Section |
|---|---|---|---|---|
| 712 | 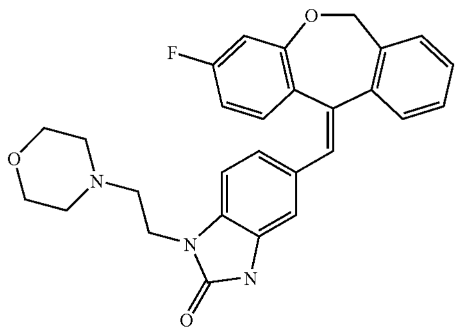 | ES 471 (−)/ 473 (+) | (ISO80-10M) t = 1.82 (97%) | 6 |
| 713 | 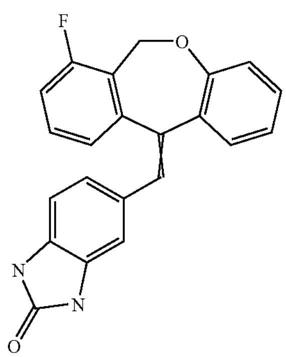 | ES 357 (−) | (ISO80-10M) t = 2.39 (97%) | 6 |
| 714 | 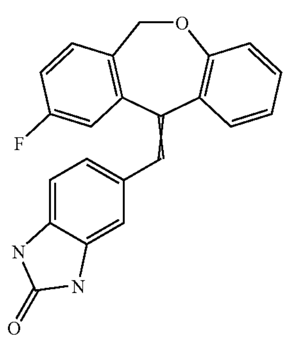 | ES 357 (−) | (ISO80-10M) t = 2.26 (100%) | 6 |
| 715 | 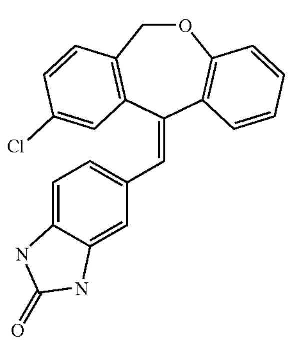 | ES 374 (−) | (ISO80-10M) t = 2.57 (97%) | 6 |

-continued

| Example No. | Structure | MS Data | HPLC | Section |
|---|---|---|---|---|
| 716 | 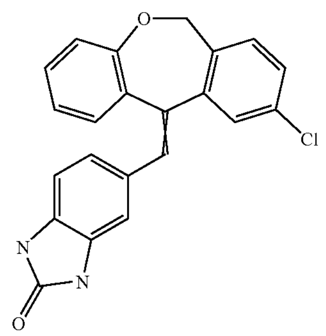 | ES 374 (−) | (ISO80-10M) t = 2.77 (94%) | 6 |
| 717 | 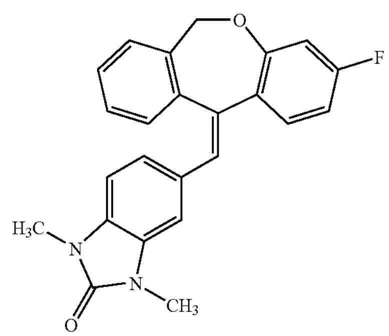 | ES 387 (+) | (ISO80-10M) t = 4.68 (92%) | 6 |
| 718 | 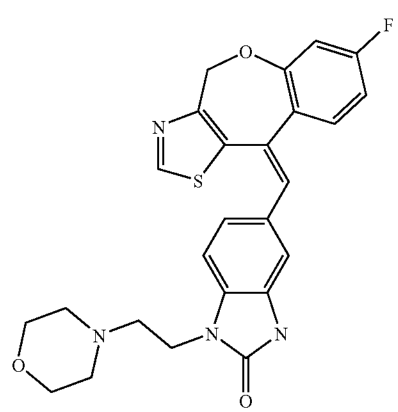 | ES 477 (−)/479 (+) | (ISO60-10M) t = 1.64 (94%) | 6 |
| 719 | 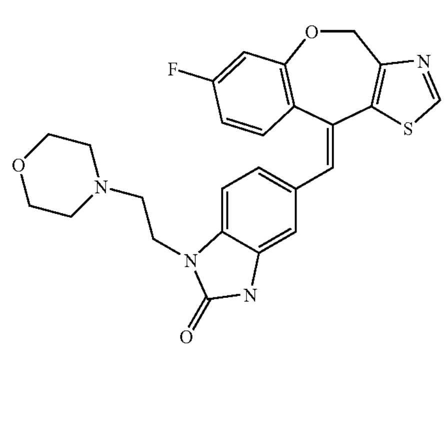 | ES 477 (−)/479 (+) | (ISO60-10M) t = 1.51 (88%) | 6 |

-continued
| Example No. | Structure | MS Data | HPLC | Section |
|---|---|---|---|---|
| 720 | 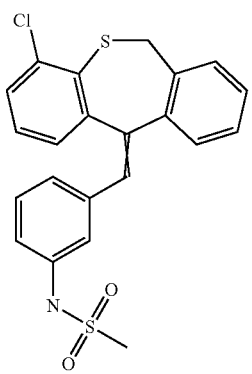 | APCI 428 | t = 3.41 min (93%) | 6 |
| 721 | 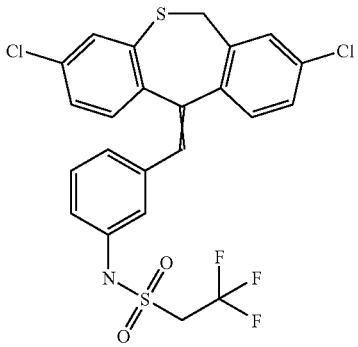 | 530 | 96% (220 nm) | 6 |
| 722 | 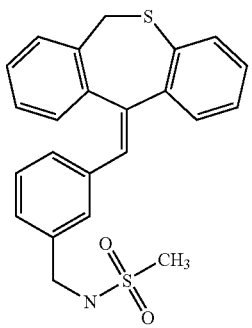 | 406 (ES−) | NA | 6 |
| 723 | 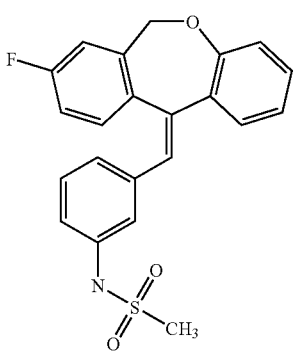 | 394 (ES−) | 100% | 6 |

-continued

| Example No. | Structure | MS Data | HPLC | Section |
|---|---|---|---|---|
| 724 | 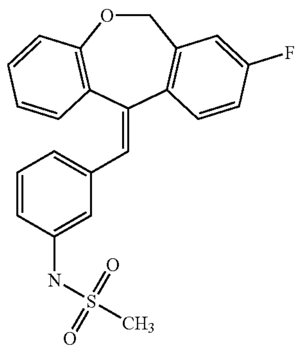 | 394 (ES−) | 94.80% | 6 |
| 725 | 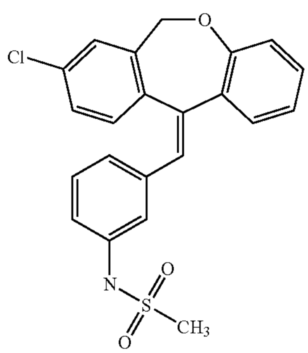 | 410 (ES−) | NA | 6 |
| 726 | 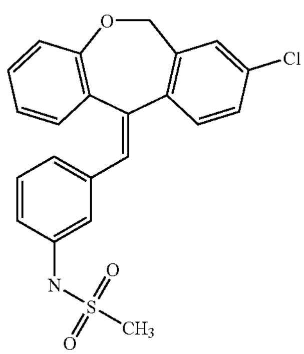 | 410 (ES−) | NA | 6 |
| 727 | 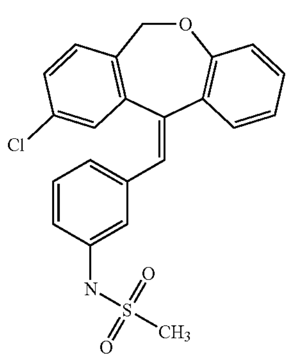 | 410/412 (ES−) | NA | 6 |

-continued
| Example No. | Structure | MS Data | HPLC | Section |
|---|---|---|---|---|
| 728 | 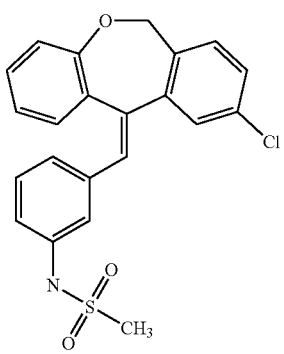 | 410/412 (ES−) | NA | 6 |
| 729 | 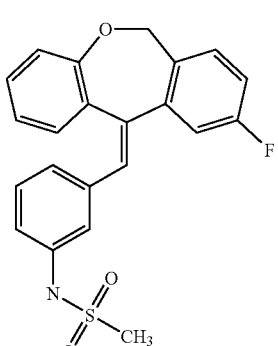 | 394 (ES−) | NA | 6 |
| 730 | 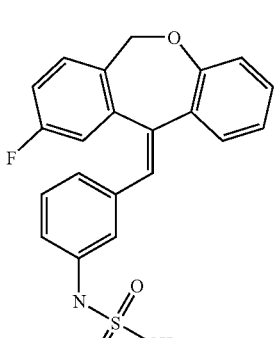 | 394 (ES−) | NA | 6 |
| 731 | 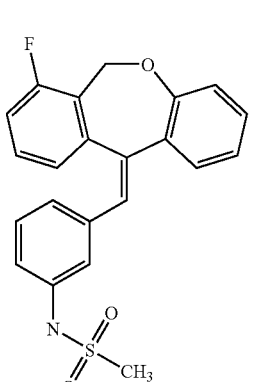 | 394 (ES−) | NA | 6 |

-continued

| Example No. | Structure | MS Data | HPLC | Section |
|---|---|---|---|---|
| 732 | 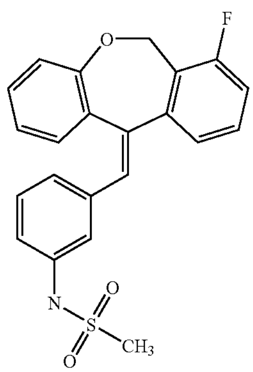 | 394 (ES−) | NA | 6 |
| 733 | 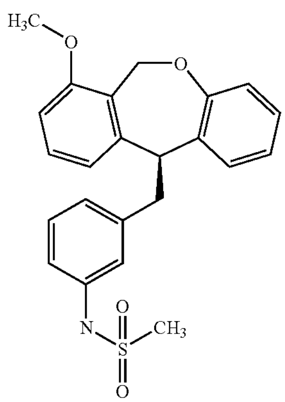 | ES 408 (−)/410 (+) | t = 4.58 (100%) | 6 |
| 734 | 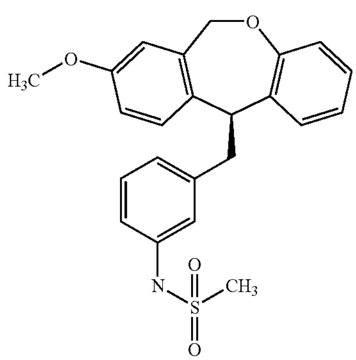 | ES 408 (−)/409 (+) | t = 4.39 (100%) | 6 |
| 735 | 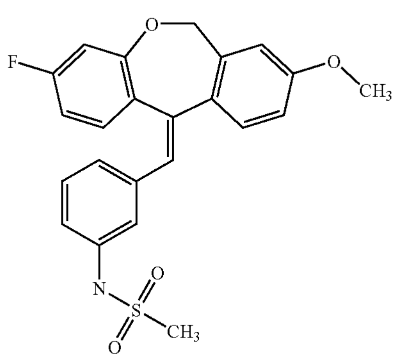 | ES 424 (−)/426 (+) | t = 4.58 (100%) | 6 |

-continued

| Example No. | Structure | MS Data | HPLC | Section |
|---|---|---|---|---|
| 736 | 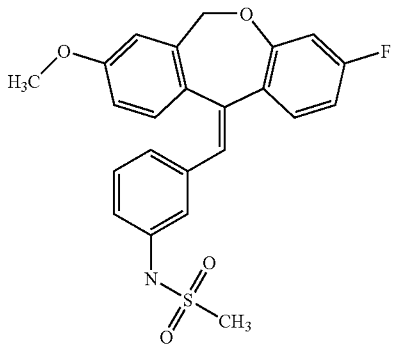 | ES 424 (−)/426 (+) | t = 4.62 (100%) | 6 |
| 737 | 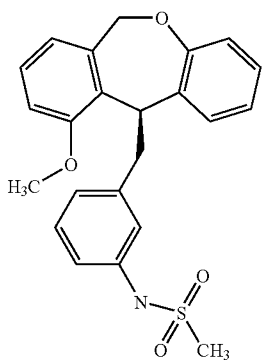 | ES 408 (−)/410 (+) | t = 4.49 (67%) | 6 |
| 738 | 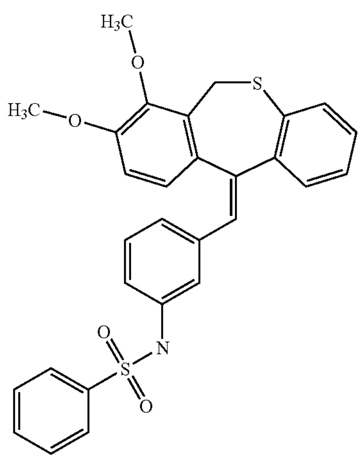 | ES 514 (−)/516 (+) | (GRAD) t = 3.49 (100%) | 6 |
| 739 | 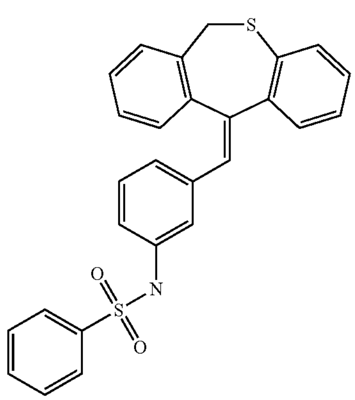 | ES 454 (−)/456 (+) | (GRAD) t = 3.44 (100%) | 6 |

-continued
| Example No. | Structure | MS Data | HPLC | Section |
|---|---|---|---|---|
| 740 | 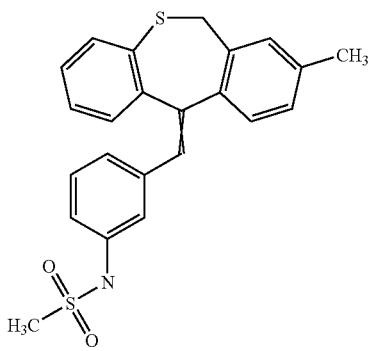 | ES 406 (−)/408 (+) | (GRAD) t = 3.29 (97%) | 6 |
| 741 | 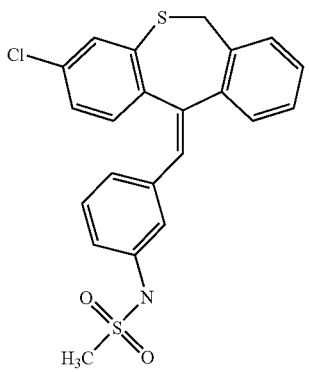 | ES 426 (−)/428 (+) | (GRAD) t = 2.49 (85%) | 6 |
| 742 | 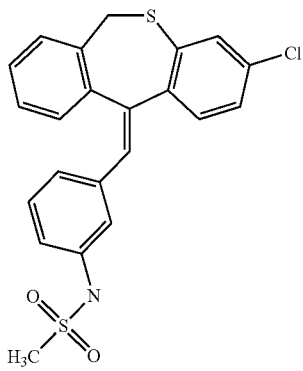 | ES 426 (−) | (GRAD) t = 2.49 (100%) | 6 |
| 743 | 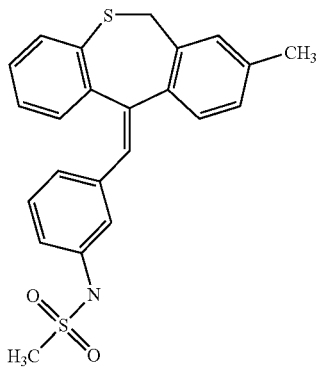 | ES 406 (−)/408 (+) | (GRAD) t = 2.43 (100%) | 6 |

-continued
| Example No. | Structure | MS Data | HPLC | Section |
|---|---|---|---|---|
| 744 | 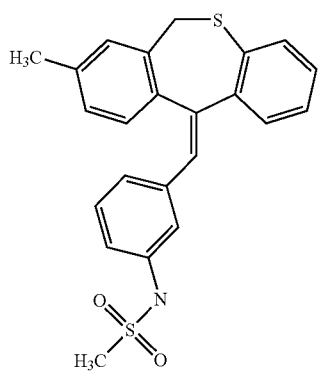 | ES 406 (−)/408 (+) | (GRAD) t = 2.41 (100%) | 6 |
| 745 | 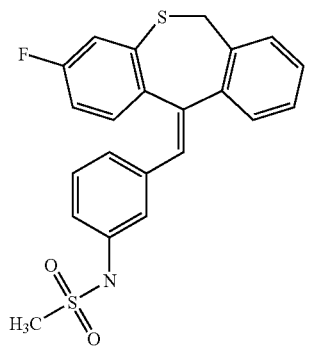 | ES 410 (−)/412 (+) | (GRAD) t = 2.36 (100%) | 6 |
| 746 | 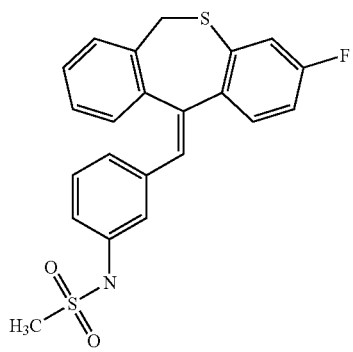 | ES 410 (−)/412 (+) | (GRAD) t = 2.36 (91%) | 6 |
| 747 | 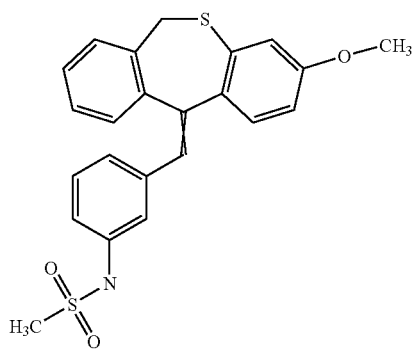 | ES 422 (−)/424 (+) | (GRAD) t = 2.34 (100%) | 6 |

-continued
| Example No. | Structure | MS Data | HPLC | Section |
|---|---|---|---|---|
| 748 | 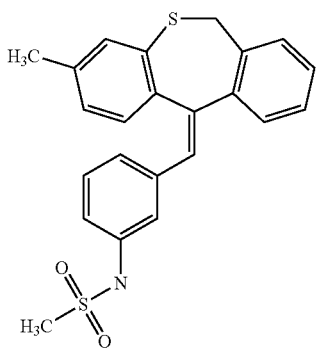 | ES 406 (−)/408 (+) | (GRAD) t = 2.59 (95%) | 6 |
| 749 | 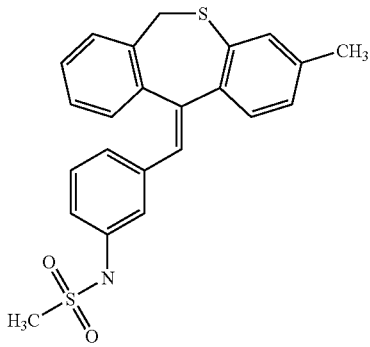 | ES 406 (−)/408 (+) | (GRAD) t = 2.61 (100%) | 6 |
| 750 | 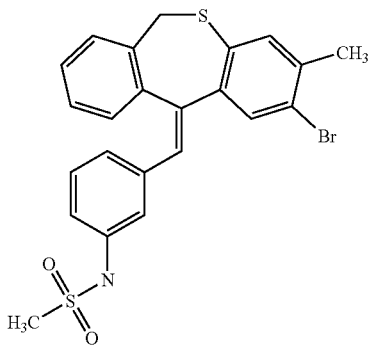 | ES 406 (−)/408 (+) | (GRAD) t = 2.77 (100%) | 6 |
| 752 | 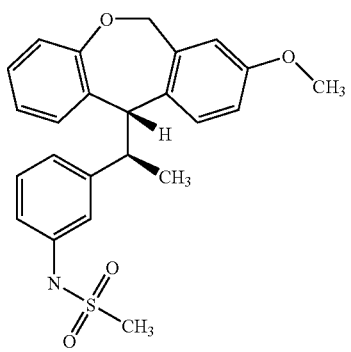 | ES 424 (−)/422 (+) | t = 4.55 (100%)<br>t = 6.571 (100%) | 7 |

-continued
| Example No. | Structure | MS Data | HPLC | Section |
|---|---|---|---|---|
| 753 | 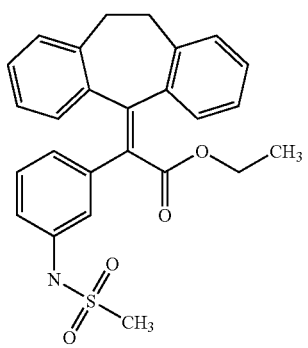 | ES 446 (+) | NA | 7 |
| 754 | 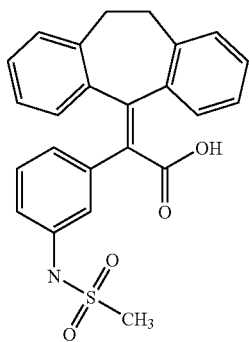 | ES 437 (+NH3) | NA | 7 |
| 755 | 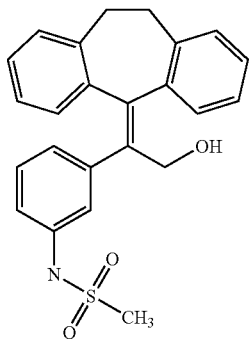 | ES 404 (+) | NA | 7 |
| 756 | 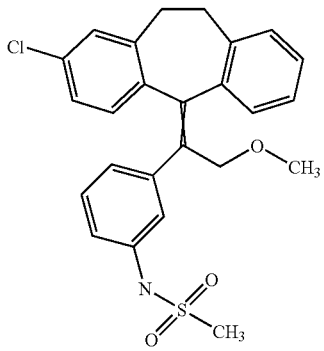 | ES 452 (−) | NA | 7 |

-continued

| Example No. | Structure | MS Data | HPLC | Section |
|---|---|---|---|---|
| 758 | 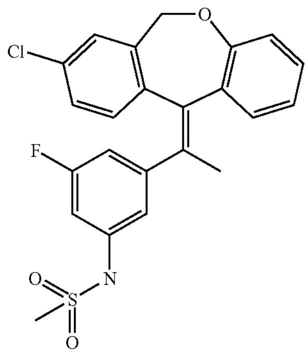 | APCI 444 (+) | 95% | 7 |
| 759 | 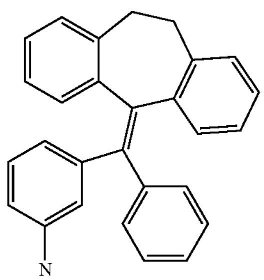 | ES 364 (+) | NA | 7 |
| 760 | 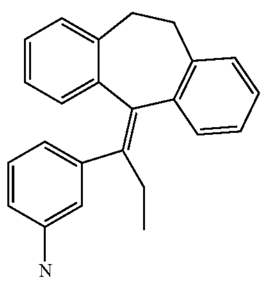 | ES 326 (+) | NA | 7 |
| 761 | 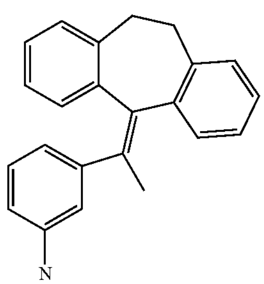 | ES 312 (+) | NA | 7 |
| 762 | 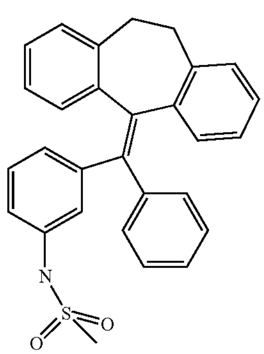 | ES 450 (−) | NA | 7 |

-continued

| Example No. | Structure | MS Data | HPLC | Section |
|---|---|---|---|---|
| 763 | 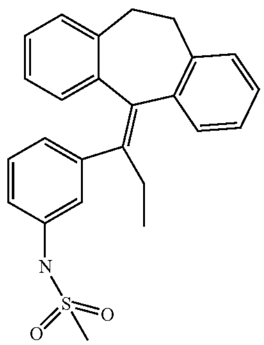 | ES 402 (−) | NA | 7 |
| 764 | 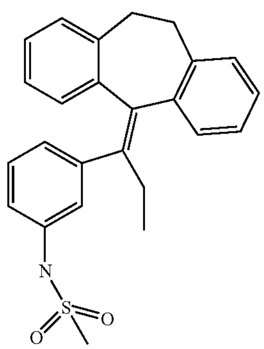 | ES 402 (−) | NA | 7 |
| 765 | 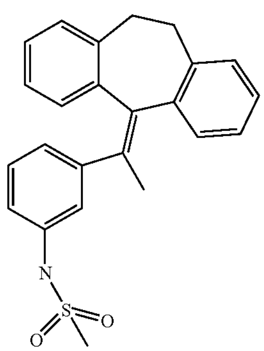 | ES 388 (−) | NA | 7 |
| 766 | 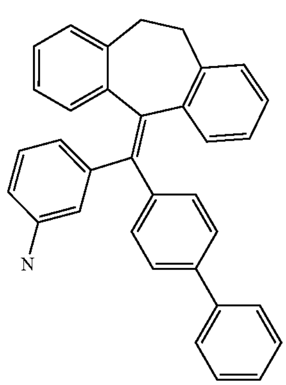 | ES 450 (+) | NA | 7 |

-continued

| Example No. | Structure | MS Data | HPLC | Section |
|---|---|---|---|---|
| 767 | 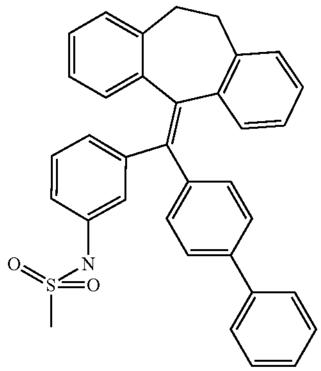 | ES 526 (−) | NA | 7 |
| 768 | 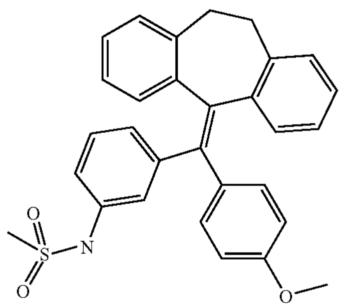 | ES 480 (−) | NA | 7 |
| 769 | 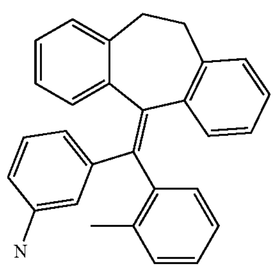 | ES 388 (+) | NA | 7 |
| 770 | 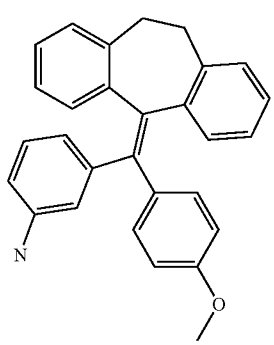 | ES 464 (+) | NA | 7 |

-continued

| Example No. | Structure | MS Data | HPLC | Section |
|---|---|---|---|---|
| 771 | 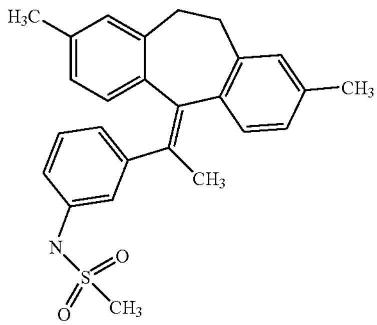 | ES 416 (−)/418 (+) | (GRAD) t = 3.648 (98%) | 7 |
| 772 | 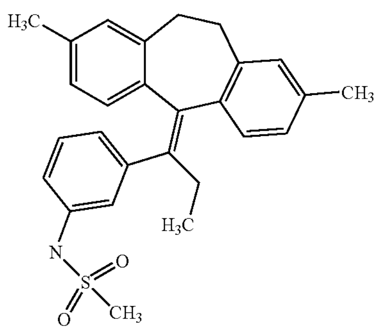 | ES 430 (−)/432 (+) | (GRAD) t = 3.733 (98%) | 7 |
| 773 | 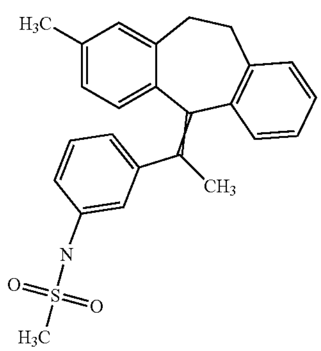 | ES 402 (−)/404 (+) | (GRAD) t = 3.445 (100%) | 7 |
| 774 | 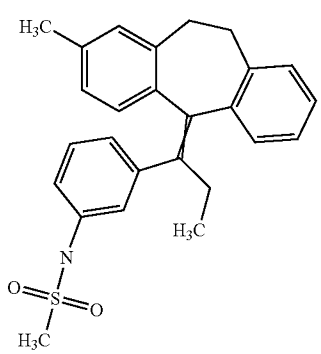 | ES 416 (−)/418 (+) | (GRAD) t = 3.541 (100%) | 7 |

-continued

| Example No. | Structure | MS Data | HPLC | Section |
|---|---|---|---|---|
| 775 | 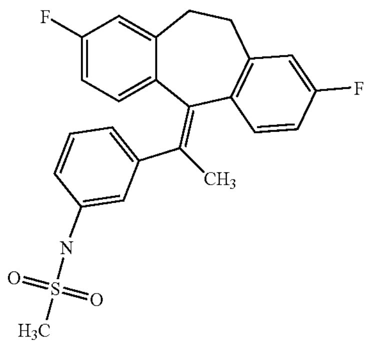 | ES 424 (−)/443 (+NH4) | (GRAD) t = 3.349 (100%) | 7 |
| 776 | 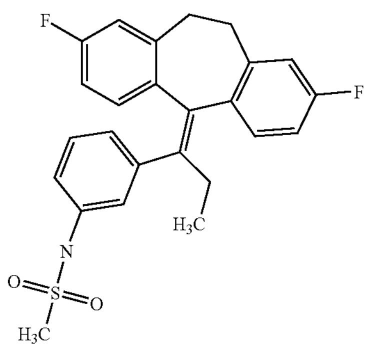 | ES 438 (−)/440 (+) | (GRAD) t = 3.456 (100%) | 7 |
| 777 | 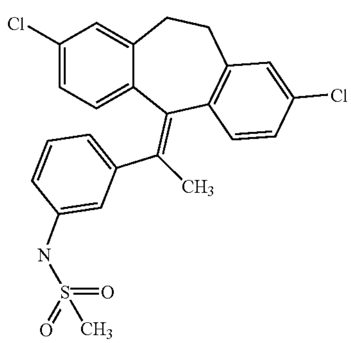 | ES 456 (−)/475 (+NH4) | (GRAD) t = 3.733 (99%) | 7 |
| 778 | 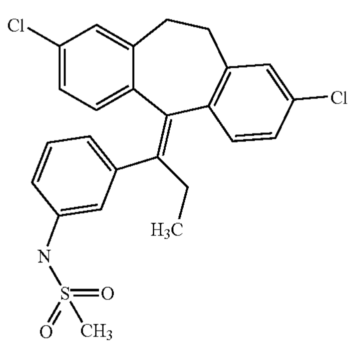 | ES 470 (−)/489 (+NH4) | (GRAD) t = 3.819 (95%) | 7 |

-continued

| Example No. | Structure | MS Data | HPLC | Section |
|---|---|---|---|---|
| 779 | 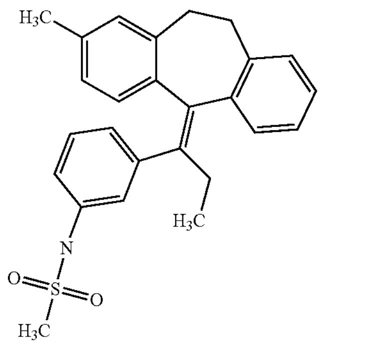 | ES 416 (−)/435 (+NH4) | (GRAD) t = 3.552 (100%) | 7 |
| 780 | 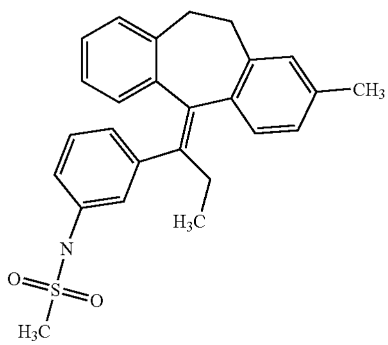 | ES 416 (−)/435 (+NH4) | (GRAD) t = 3.595 (97%) | 7 |
| 781 | 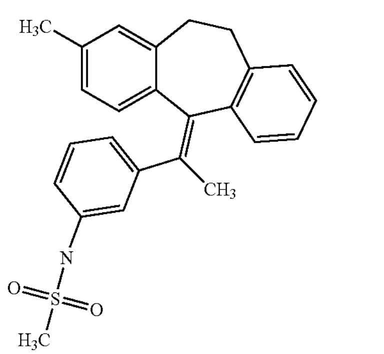 | ES 402 (−)/412 (+NH4) | (GRAD) t = 3.477 (100%) | 7 |
| 782 | 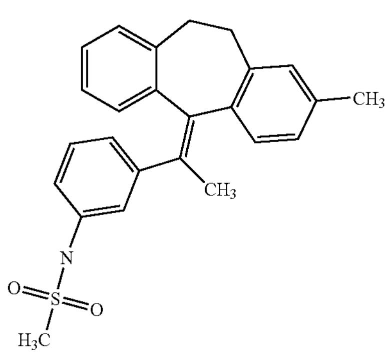 | ES 402 (−)/412 (+NH4) | (GRAD) t = 3.509 (100%) | 7 |

-continued
| Example No. | Structure | MS Data | HPLC | Section |
|---|---|---|---|---|
| 783 | 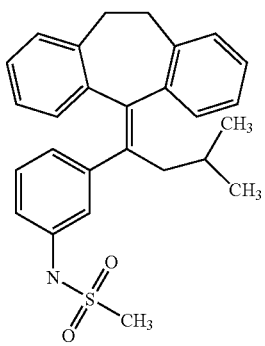 | ES 430 (−) | NA | 7 |
| 784 | 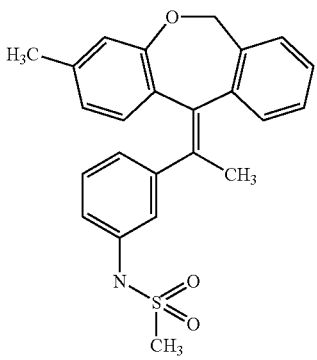 | ES 404.1 (−) | NA | 7 |
| 785 | 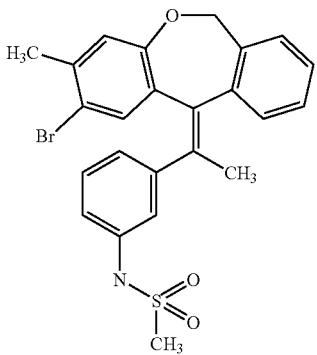 | ES 482.0 (−) | NA | 7 |
| 786 | 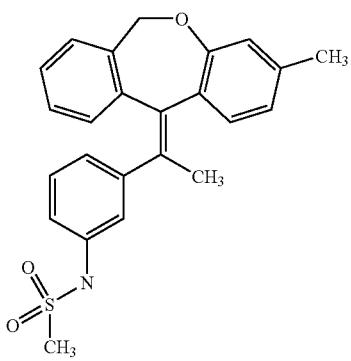 | ES 404.1 (−) | NA | 7 |

-continued
| Example No. | Structure | MS Data | HPLC | Section |
|---|---|---|---|---|
| 787 | 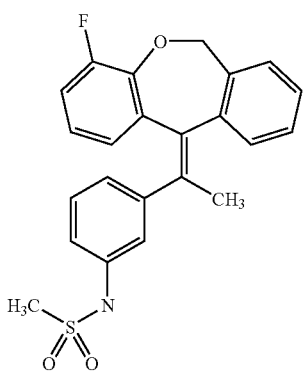 | ES 408.0 (−) | NA | 7 |
| 788 | 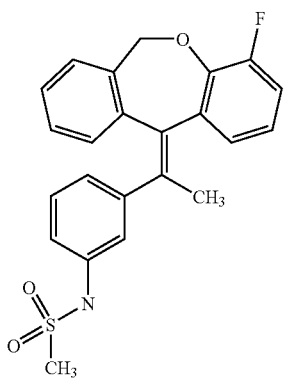 | ES 408.0 (−) | NA | 7 |
| 789 | 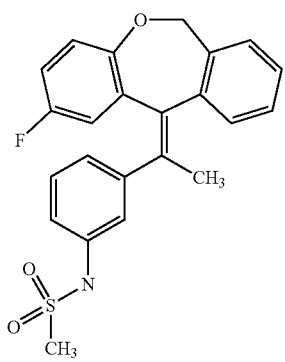 | ES 408.0 (−) | NA | 7 |
| 790 | 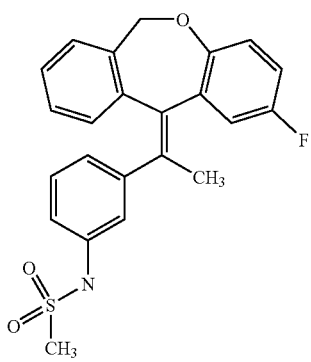 | ES 408.0 (−) | NA | 7 |

-continued

| Example No. | Structure | MS Data | HPLC | Section |
|---|---|---|---|---|
| 791 | 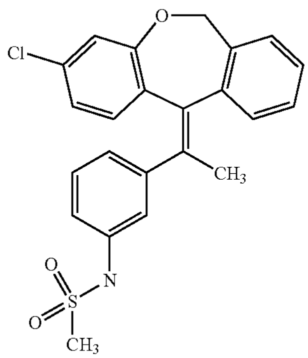 | ES 424.0 (−) | NA | 7 |
| 792 | 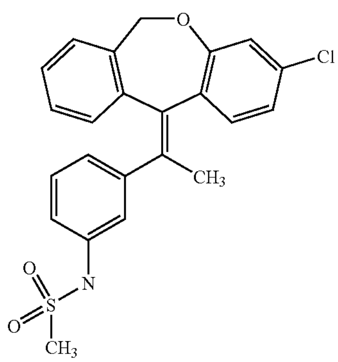 | ES 424.0 (−) | NA | 7 |
| 793 | 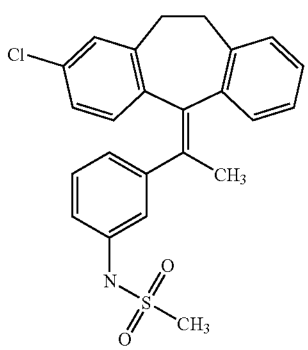 | 422/424 (ES−) | 100% | 7 |
| 794 | 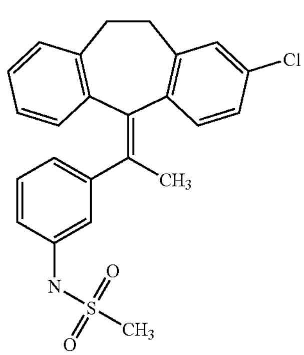 | 422/424 (ES−) | 99.60% | 7 |

-continued
| Example No. | Structure | MS Data | HPLC | Section |
|---|---|---|---|---|
| 795 | 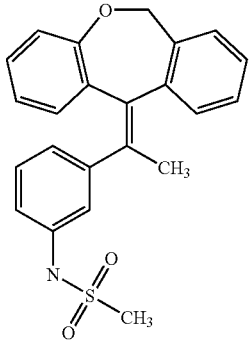 | 390 (ES−) | 99.80% | 7 |
| 796 | 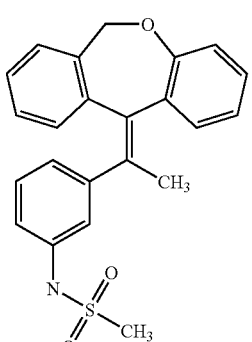 | 390 (ES−) | 100% | 7 |
| 797 | 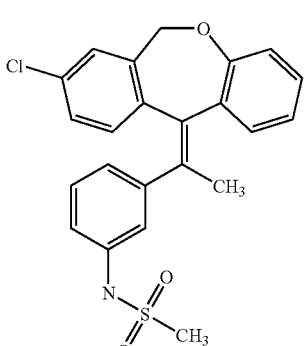 | 424/426 (ES−) | NA | 7 |
| 798 | 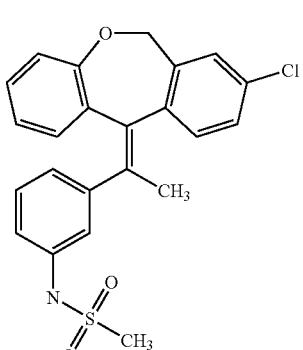 | 424/426 (ES−) | NA | 7 |

-continued

| Example No. | Structure | MS Data | HPLC | Section |
|---|---|---|---|---|
| 799 | 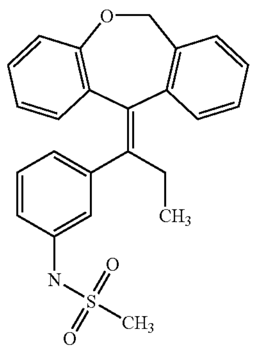 | 404 (ES−) | 99.70% | 7 |
| 800 | 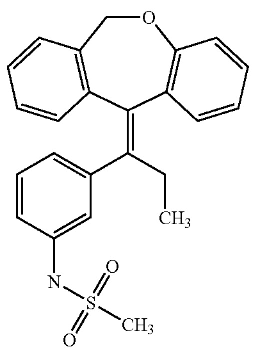 | 404 (ES−) | 97.40% | 7 |
| 801 | 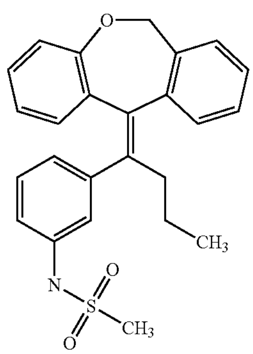 | 418 (ES−) | NA | 7 |
| 802 | 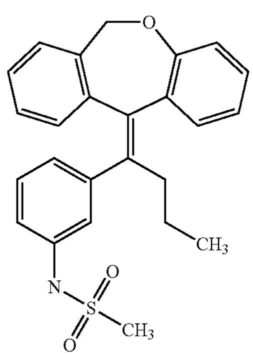 | 418 (ES−) | NA | 7 |

-continued

| Example No. | Structure | MS Data | HPLC | Section |
|---|---|---|---|---|
| 803 | 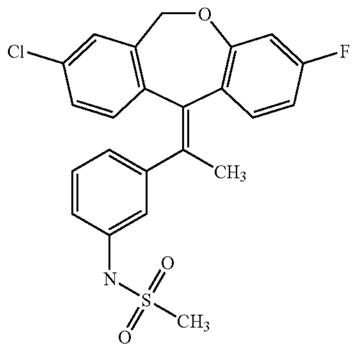 | 442/444 (ES−) | NA | 7 |
| 804 | 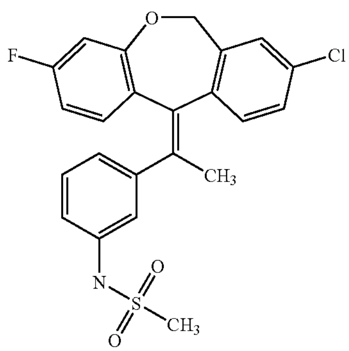 | 442/444 (ES−) | NA | 7 |
| 805 | 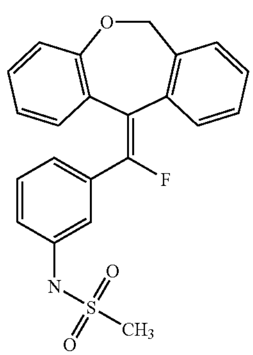 | MS(ES+) = 424. | NA | 7 |
| 806 | 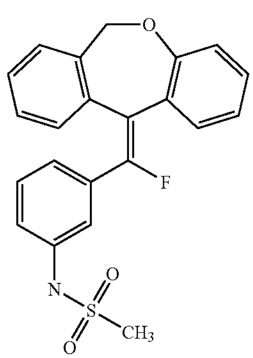 | 394 (ES−) | NA | 7 |

-continued
| Example No. | Structure | MS Data | HPLC | Section |
|---|---|---|---|---|
| 807 | 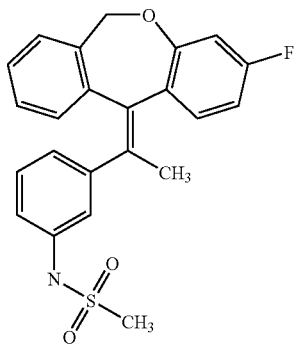 | 408 (ES−) | NA | 7 |
| 808 | 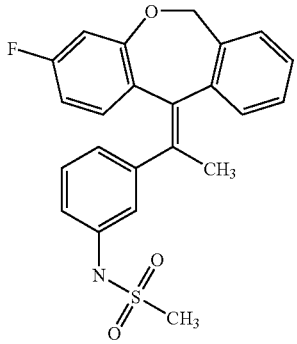 | 408 (ES−) | NA | 7 |
| 809 | 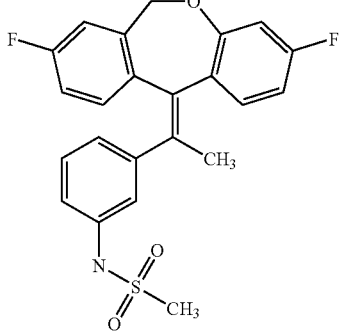 | 426 (ES−) | NA | 7 |
| 810 | 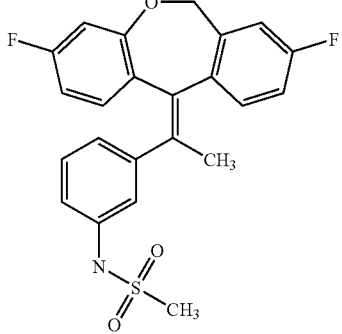 | 426 (ES−) | NA | 7 |

-continued

| Example No. | Structure | MS Data | HPLC | Section |
|---|---|---|---|---|
| 811 | 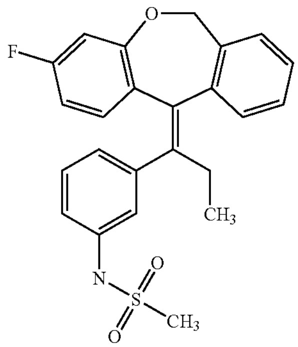 | 422 (ES−) | NA | 7 |
| 812 | 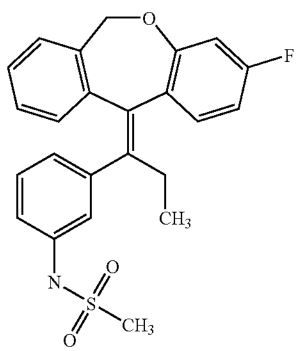 | 422 (ES−) | NA | 7 |
| 813 | 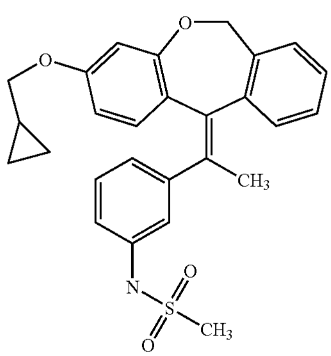 | MS(ES−) = 460. | NA | 7 |
| 814 | 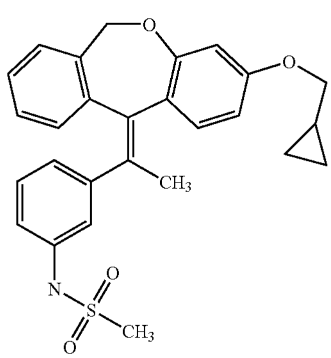 | 460 (ES−) | NA | 7 |

-continued

| Example No. | Structure | MS Data | HPLC | Section |
|---|---|---|---|---|
| 815 | 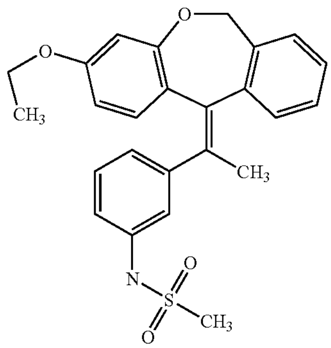 | 434 (ES−) | NA | 7 |
| 816 | 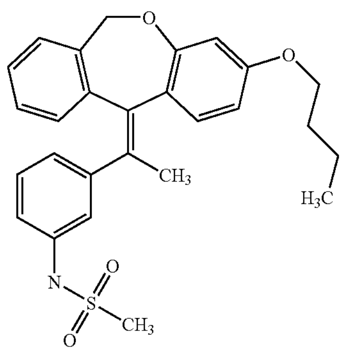 | 462 (ES−) | NA | 7 |
| 817 | 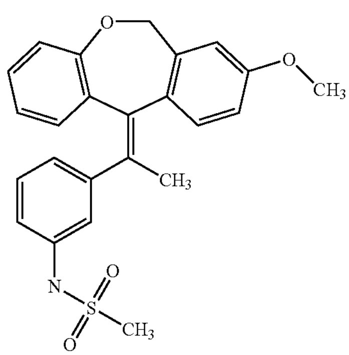 | ES 420 (−)/422 (+) | t = 4.50 (100%) | 7 |
| 818 | 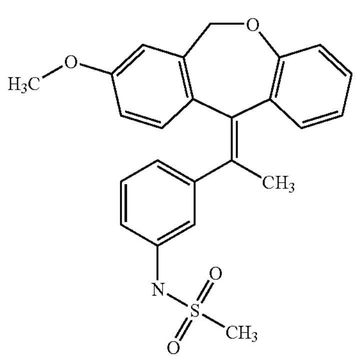 | ES 420 (−)/422 (+) | t = 4.57 (100%) | 7 |

-continued
| Example No. | Structure | MS Data | HPLC | Section |
|---|---|---|---|---|
| 819 | 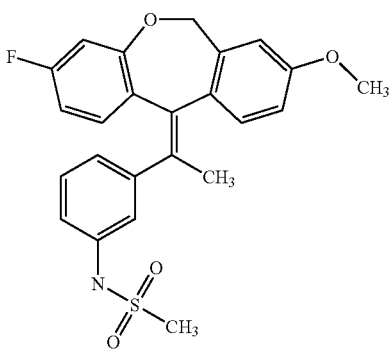 | ES 438 (−)/440 (+) | t = 4.63 (100%) | 7 |
| 820 | 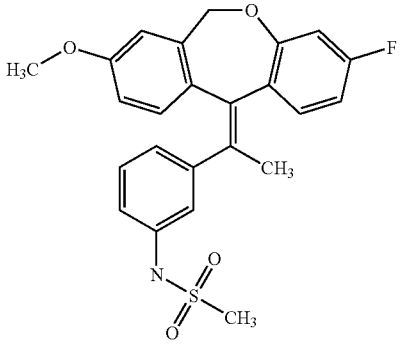 | ES 438 (−)/440 (+) | t = 4.69 (100%) | 7 |
| 821 | 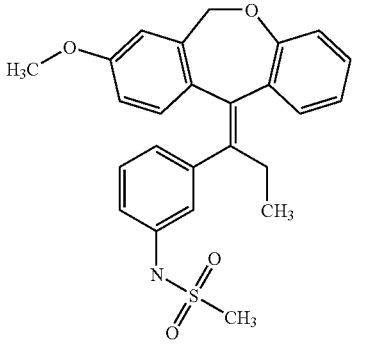 | ES 434 (−)/436 (+) | t = 4.77 (100%) | 7 |
| 822 | 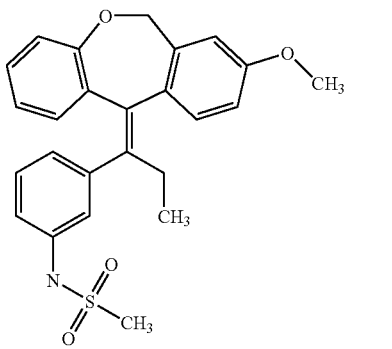 | ES 434 (−)/436 (+) | t = 4.68 (100%) | 7 |

-continued
| Example No. | Structure | MS Data | HPLC | Section |
|---|---|---|---|---|
| 823 | 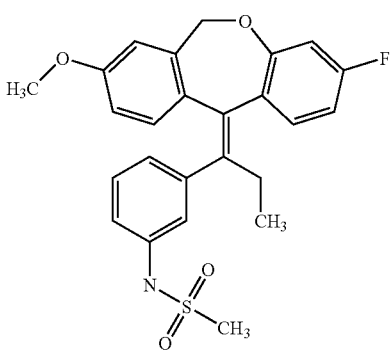 | ES 452 (−)/454 (+) | t = 4.84 (100%) | 7 |
| 824 | 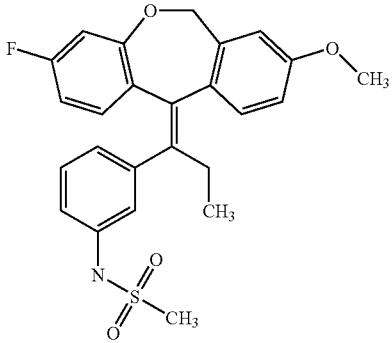 | ES 452 (−)/454 (+) | t = 4.74 (100%) | 7 |
| 825 | 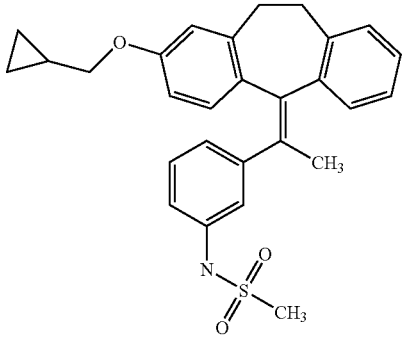 | ES 458 (−)/460 (+) | t = 5.30 (100%) | 7 |
| 826 | 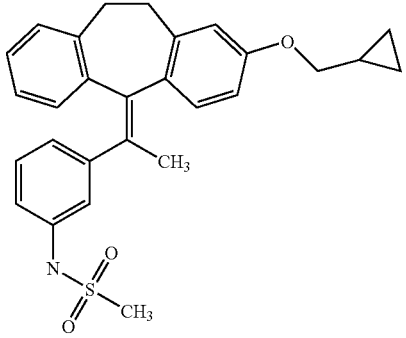 | ES 458 (−)/460 (+) | t = 5.27 (100%) | 7 |

-continued

| Example No. | Structure | MS Data | HPLC | Section |
|---|---|---|---|---|
| 827 | 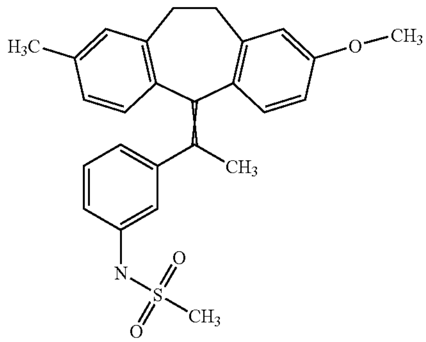 | NA | (GRAD) t = 3.40 (86%) | 7 |
| 828 | 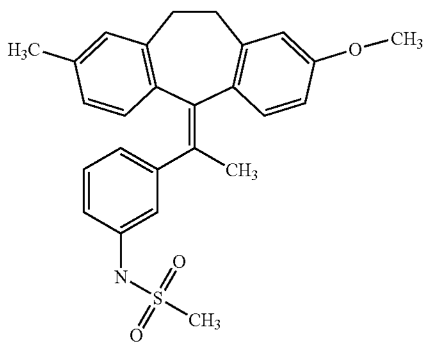 | ES 432 (−) | (GRAD) t = 3.35 (98.8%) | 7 |
| 829 | 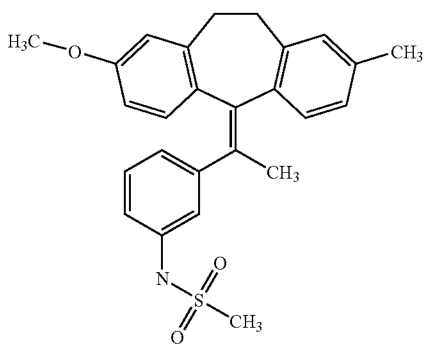 | ES 432 (−) | (GRAD) t = 3.48 (97%) | 7 |
| 830 | 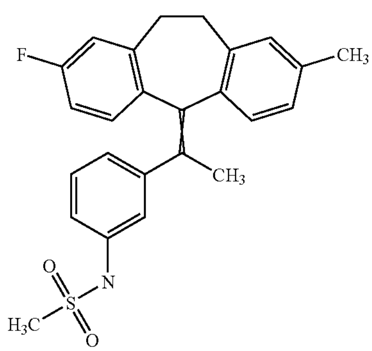 | NA | (GRAD) t = 3.53 (100%) | 7 |

-continued
| Example No. | Structure | MS Data | HPLC | Section |
|---|---|---|---|---|
| 831 | 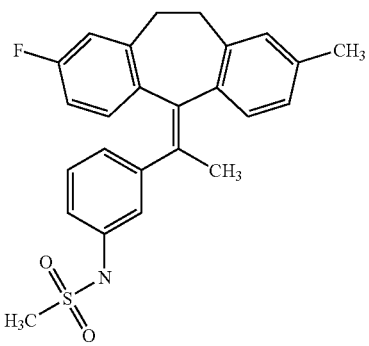 | NA | (GRAD) t = 3.52 (100%) | 7 |
| 832 | 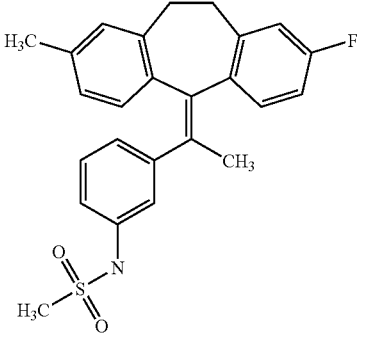 | NA | (GRAD) t = 3.48 (100%) | 7 |
| 833 | 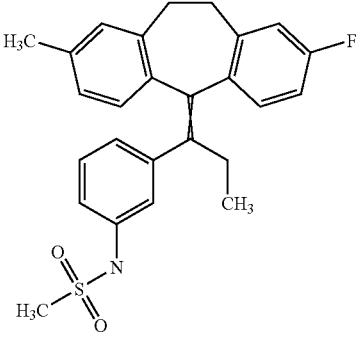 | ES 434 (−) | (GRAD) t = 2.54 (96%) | 7 |
| 834 | 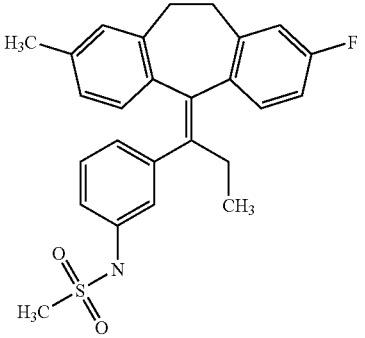 | ES 434 (−) | (GRAD) t = 2.54 (96%) | 7 |

-continued

| Example No. | Structure | MS Data | HPLC | Section |
|---|---|---|---|---|
| 835 | 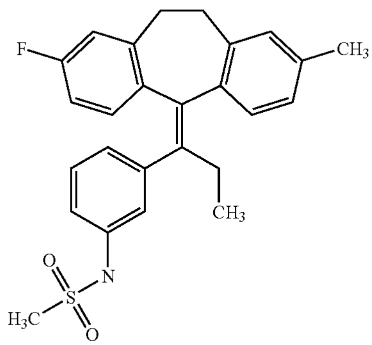 | ES 434 (−) | NA | 7 |
| 836 | 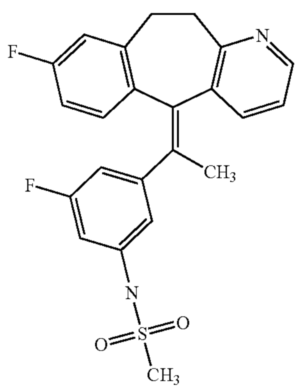 | APCI 427 (+)/425 (−) | LCMS(ISO7030M) t = 4.88 | 7 |
| 837 | 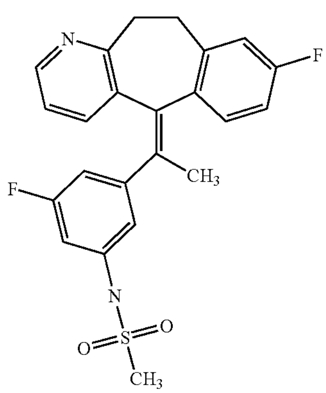 | APCI 427(+)/425 (−) | LCMS(ISO7030M) t = 6.89 | 7 |
| 838 | 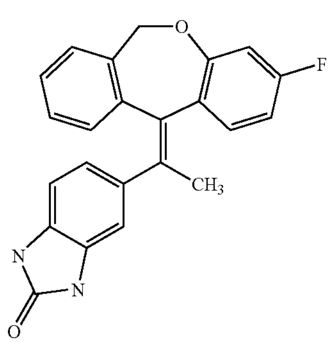 | 373.0 (APCI-pos) | 95% | 7 |

US 7,411,072 B2
537                                                                                              538
-continued
| Example No. | Structure | MS Data | HPLC | Section |
|---|---|---|---|---|
| 839 | 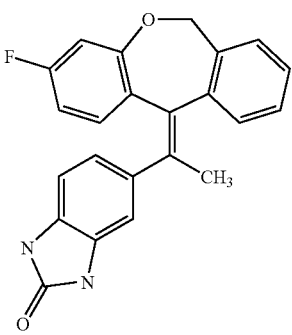 | 373.0 (APCI-pos) | 95% | 7 |
| 840 | 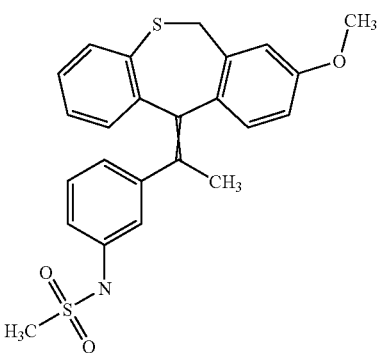 | ES 436 (−)/438 (+) | (GRAD) t = 2.35 (100%) | 7 |
| 841 | 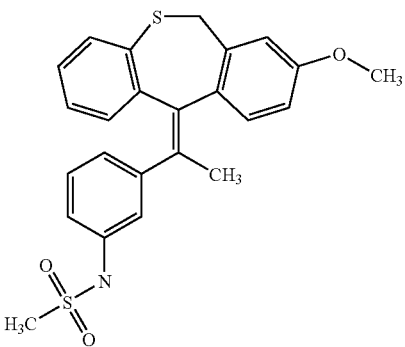 | ES 436 (−)/438 (+) | (GRAD) t = 2.54 (100%) | 7 |
| 842 | 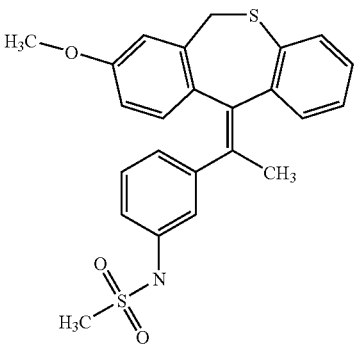 | ES 436 (−)/438 (+) | (GRAD) t = 2.54 (100%) | 7 |

-continued
| Example No. | Structure | MS Data | HPLC | Section |
|---|---|---|---|---|
| 843 | 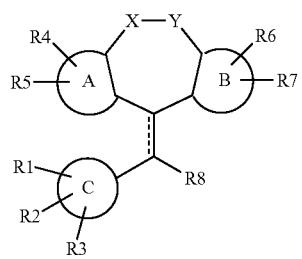 | MS (ES−) 434 | NA | 7 |
What we claim:
1. A compound of Formula I:
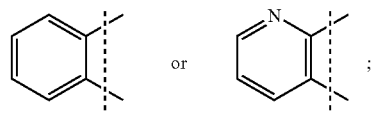
Formula 1
wherein,
"A" represents
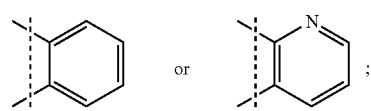 or ;
"B" represents
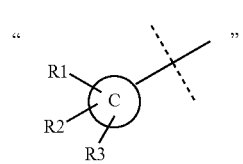 or ;
and
"  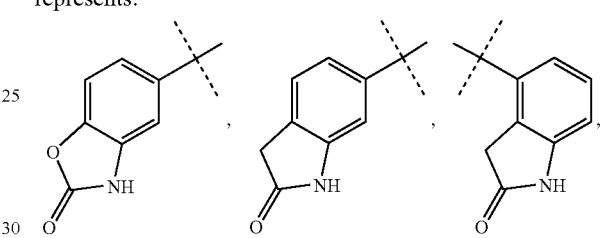  "
represents:
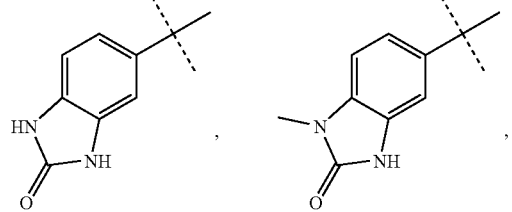,
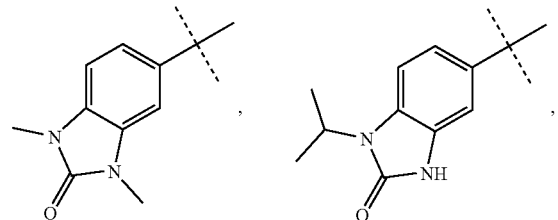,
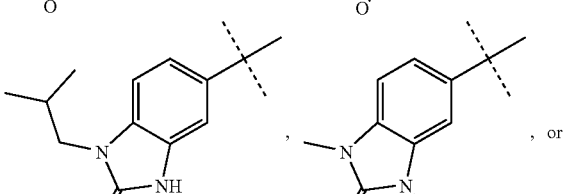,
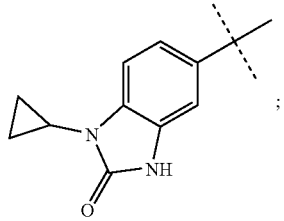;
X and Y together represent —CH$_2$—CH$_2$—, —CH$_2$—O—, or —O—CH$_2$—;
"═" represents a double bond;

$R^4$-$R^7$ each independently represent hydrogen, hydroxy, halo, $(C_1$-$C_6)$alkyl, or $(C_1$-$C_6)$alkoxy; and $R^8$ represents hydrogen or $(C_1$-$C_6)$alkyl;

or a pharmaceutically acceptable salt thereof.

2. The compound according to claim 1 which is selected from the group consisting of

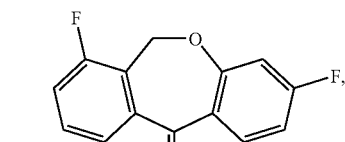

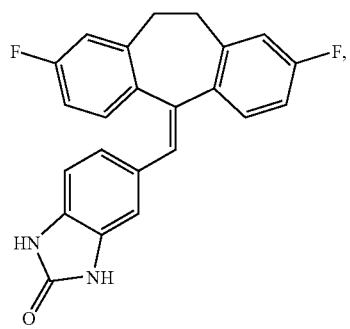

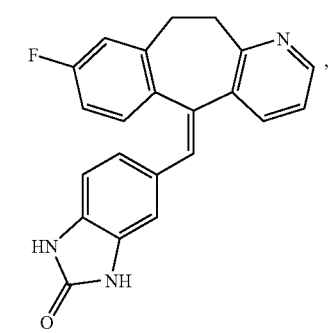

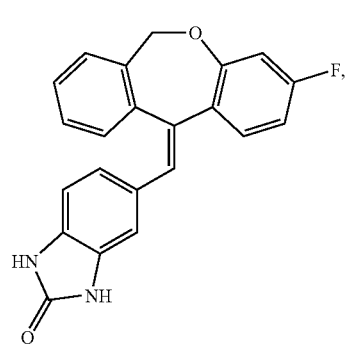

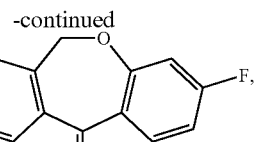

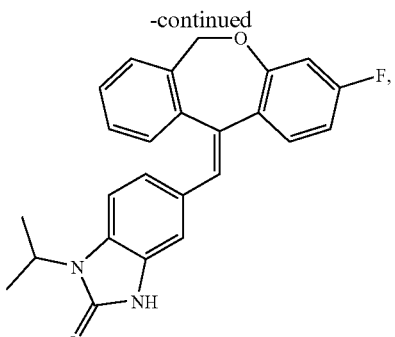

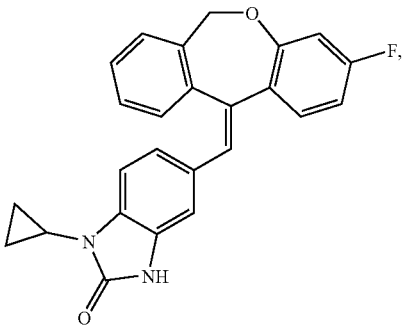

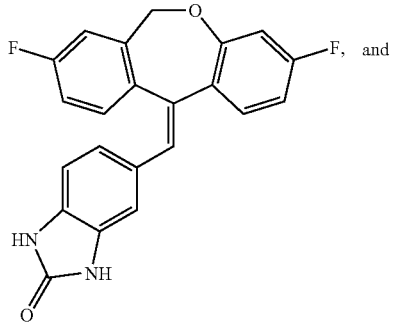

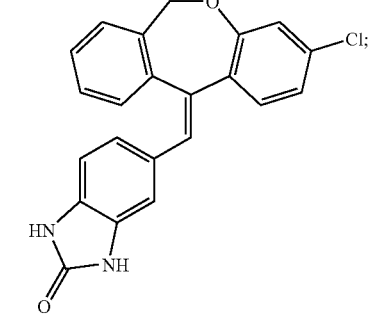

or a pharmaceutically acceptable salt thereof.

3. The compound according to claim 2 selected from

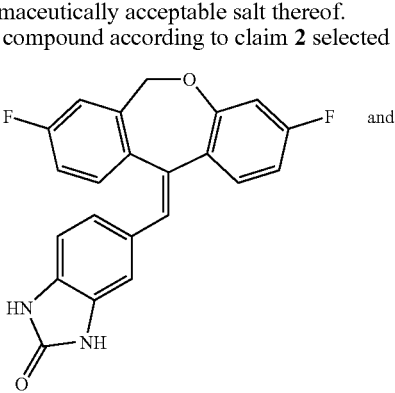

-continued

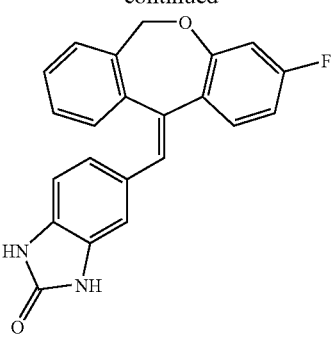

or a pharmaceutically acceptable salt thereof.

4. The compound according to claim 3 which is

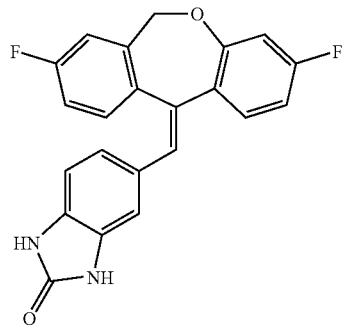

or a pharmaceutically acceptable salt thereof.

5. The compound according to claim 3 which is

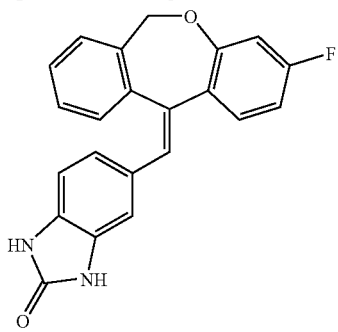

or a pharmaceutically acceptable salt thereof.

6. A pharmaceutical composition comprising a compound according to claim 1, or a pharmaceutically acceptable salt thereof, in combination with a pharmaceutically acceptable carrier, diluent or excipient.

7. A pharmaceutical composition according to claim 6 comprising a compound which is

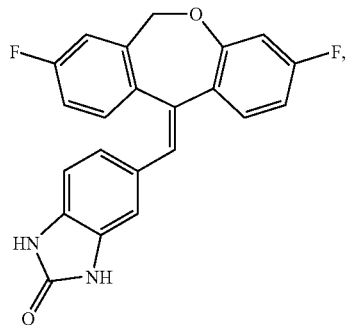

or a pharmaceutically acceptable salt thereof, in combination with a pharmaceutically acceptable carrier, diluent or excipient.

* * * * *